US011871767B2

United States Patent
Embree et al.

(10) Patent No.: US 11,871,767 B2
(45) Date of Patent: Jan. 16, 2024

(54) MICROBIAL COMPOSITIONS AND METHODS FOR RUMINANT HEALTH AND PERFORMANCE

(71) Applicant: Native Microbials, Inc., San Diego, CA (US)

(72) Inventors: Mallory Embree, San Diego, CA (US); Cameron Martino, San Diego, CA (US); Norman Pitt, San Diego, CA (US); Jordan Embree, San Diego, CA (US); Corey Dodge, Encinitas, CA (US)

(73) Assignee: Native Microbials, Inc., San Diego, CA (US)

( * ) Notice: Subject to any disclaimer, the term of this patent is extended or adjusted under 35 U.S.C. 154(b) by 0 days.

(21) Appl. No.: 17/354,306

(22) Filed: Jun. 22, 2021

(65) Prior Publication Data

US 2022/0386646 A1 Dec. 8, 2022

Related U.S. Application Data

(63) Continuation of application No. 15/965,661, filed on Apr. 27, 2018, now Pat. No. 11,044,924.

(60) Provisional application No. 62/578,188, filed on Oct. 27, 2017, provisional application No. 62/491,845, filed on Apr. 28, 2017.

(51) Int. Cl.
| | |
|---|---|
| *A23K 10/18* | (2016.01) |
| *A61K 35/74* | (2015.01) |
| *A61P 1/04* | (2006.01) |
| *A23K 50/10* | (2016.01) |

(52) U.S. Cl.
CPC .............. *A23K 10/18* (2016.05); *A23K 50/10* (2016.05); *A61K 35/74* (2013.01); *A61P 1/04* (2018.01)

(58) Field of Classification Search
CPC ........... A23K 10/18; A23K 50/10; A61P 1/04; A61K 35/74
See application file for complete search history.

(56) References Cited

U.S. PATENT DOCUMENTS

| | | | |
|---|---|---|---|
| 3,484,243 A | 12/1969 | Anderson et al. | |
| 4,559,298 A | 12/1985 | Fahy | |
| 4,647,536 A | 3/1987 | Mosbach et al. | |
| 5,104,662 A | 4/1992 | Kalsta et al. | |
| 5,290,765 A | 3/1994 | Wettlaufer et al. | |
| 5,534,271 A | 7/1996 | Ware et al. | |
| 5,605,793 A | 2/1997 | Stemmer | |
| 5,733,568 A | 3/1998 | Ford | |
| 5,741,508 A | 4/1998 | Katsumi et al. | |
| 5,837,458 A | 11/1998 | Minshull et al. | |
| 6,090,416 A | 7/2000 | Iritani et al. | |
| 6,210,891 B1 | 4/2001 | Nyren et al. | |
| 6,214,337 B1 | 4/2001 | Hayen et al. | |
| 6,258,568 B1 | 7/2001 | Nyren | |
| 6,274,320 B1 | 8/2001 | Rothberg et al. | |
| 6,841,168 B1 | 11/2005 | Worrall | |
| 7,427,408 B2 | 9/2008 | Merritt et al. | |
| 7,488,503 B1 | 2/2009 | Porzio et al. | |
| 7,998,502 B2 | 8/2011 | Harel | |
| 8,071,295 B2 | 12/2011 | Ashby | |
| 8,097,245 B2 | 1/2012 | Harel et al. | |
| 8,114,396 B2 | 2/2012 | Horn et al. | |
| 8,345,010 B2 | 1/2013 | Fitzgibbon et al. | |
| 8,349,252 B2 | 1/2013 | Elliot et al. | |
| 8,449,916 B1 * | 5/2013 | Bellaire | A61K 9/5146 977/906 |
| 8,460,726 B2 | 6/2013 | Harel et al. | |
| 8,906,668 B2 | 12/2014 | Henn et al. | |
| 9,011,834 B1 | 4/2015 | Mckenzie et al. | |
| 9,028,841 B2 | 5/2015 | Henn et al. | |
| 9,050,358 B2 | 6/2015 | Borody | |
| 9,113,636 B2 | 8/2015 | Von Maltzahn et al. | |
| 9,179,694 B2 | 11/2015 | Porter et al. | |
| 9,180,147 B2 | 11/2015 | Mckenzie et al. | |
| 9,206,680 B2 | 12/2015 | Ashby et al. | |
| 9,288,995 B2 | 3/2016 | Von Maltzahn et al. | |
| 9,295,263 B2 | 3/2016 | Von Maltzahn et al. | |
| 9,404,162 B2 | 8/2016 | Boileau et al. | |
| 9,446,080 B2 | 9/2016 | Mckenzie et al. | |
| 9,469,835 B2 | 10/2016 | Bronshtein | |
| 9,532,572 B2 | 1/2017 | Mckenzie et al. | |
| 9,532,573 B2 | 1/2017 | Von Maltzahn et al. | |

(Continued)

FOREIGN PATENT DOCUMENTS

| | | |
|---|---|---|
| AU | 76290/98 A | 1/1999 |
| AU | 753327 B2 | 10/2002 |

(Continued)

OTHER PUBLICATIONS

U.S. Appl. No. 16/920,997 (Year: 2020).*
"Vitamin", Wikipedia, https://en.wikipedia.org/wiki/Vitamin (Year: 2022).*
"Vitamin B6", Wikipedia, https://en.wikipedia.org/wiki/Vitamin_B (Year: 2022).*
Watanabe et al., "Vitamin B12 sources and microbial interaction", Exp Biol Med (Maywood). Jan. 2018; 243(2): 148-158. Published online Dec. 7, 2017 (Year: 2017).*

(Continued)

*Primary Examiner* — Ruth A Davis
(74) *Attorney, Agent, or Firm* — COOLEY LLP

(57) ABSTRACT

The disclosure relates to isolated microorganisms—including novel strains of the microorganisms—microbial ensembles, and compositions comprising the same. Furthermore, the disclosure teaches methods of utilizing the described microorganisms, microbial compositions, and compositions comprising the same, in methods for modulating the agricultural production of ruminants. In particular aspects, the disclosure provides methods of increasing feed efficiency, and methods of decreasing acidosis.

28 Claims, 36 Drawing Sheets

Specification includes a Sequence Listing.

(56) References Cited

U.S. PATENT DOCUMENTS

| | | | |
|---|---|---|---|
| 9,533,014 B2 | 1/2017 | Henn et al. | |
| 9,540,676 B1 | 1/2017 | Zengler et al. | |
| 9,562,271 B2 | 2/2017 | Neely | |
| 9,622,485 B2 | 4/2017 | Von Maltzahn et al. | |
| 9,642,881 B2 | 5/2017 | Honda et al. | |
| 9,649,345 B2 | 5/2017 | Honda et al. | |
| 9,700,586 B2 | 7/2017 | Bicalho et al. | |
| 9,901,605 B2 | 2/2018 | Garner et al. | |
| 9,903,002 B2 | 2/2018 | Zeng et al. | |
| 9,909,180 B2 | 3/2018 | Quake et al. | |
| 9,938,558 B2 | 4/2018 | Embree et al. | |
| 9,993,507 B2* | 6/2018 | Embree | A23K 20/158 |
| 10,293,006 B2 | 5/2019 | Embree et al. | |
| 10,398,154 B2 | 9/2019 | Embree et al. | |
| 10,448,657 B2 | 10/2019 | Embree et al. | |
| 10,448,658 B2 | 10/2019 | Embree et al. | |
| 10,645,952 B2 | 5/2020 | Embree et al. | |
| 10,701,955 B2 | 7/2020 | Embree et al. | |
| 10,966,437 B2 | 4/2021 | Embree et al. | |
| 11,044,924 B2 | 6/2021 | Embree et al. | |
| 11,291,219 B2 | 4/2022 | Embree et al. | |
| 2005/0079244 A1 | 4/2005 | Giffard et al. | |
| 2005/0106554 A1 | 5/2005 | Palecek et al. | |
| 2005/0158699 A1 | 7/2005 | Kadkake et al. | |
| 2005/0239706 A1 | 10/2005 | Backhed et al. | |
| 2006/0127530 A1 | 6/2006 | Axelrod | |
| 2008/0299098 A1 | 12/2008 | Se et al. | |
| 2009/0280098 A1 | 11/2009 | Tabata et al. | |
| 2011/0280840 A1 | 11/2011 | Blaser et al. | |
| 2012/0149584 A1 | 6/2012 | Olle et al. | |
| 2012/0282675 A1 | 11/2012 | Kim et al. | |
| 2013/0330307 A1 | 12/2013 | Millan | |
| 2014/0171339 A1 | 6/2014 | Keku et al. | |
| 2015/0093360 A1 | 4/2015 | McKenzie et al. | |
| 2015/0213193 A1 | 7/2015 | Apte et al. | |
| 2015/0216817 A1 | 8/2015 | Luhman | |
| 2015/0218614 A1 | 8/2015 | Henderson et al. | |
| 2015/0267163 A1 | 9/2015 | Liao et al. | |
| 2015/0376609 A1 | 12/2015 | Hindson et al. | |
| 2016/0040119 A1 | 2/2016 | Hashman | |
| 2016/0113974 A1 | 4/2016 | Jones et al. | |
| 2016/0143961 A1 | 5/2016 | Berry et al. | |
| 2016/0376627 A1 | 12/2016 | Zengler et al. | |
| 2017/0107557 A1 | 4/2017 | Embree et al. | |
| 2017/0196921 A1 | 7/2017 | Embree et al. | |
| 2017/0196922 A1 | 7/2017 | Embree et al. | |
| 2017/0224745 A1* | 8/2017 | Dart | A23K 10/18 |
| 2017/0260584 A1 | 9/2017 | Zheng et al. | |
| 2017/0342457 A1 | 11/2017 | Embree et al. | |
| 2018/0030516 A1 | 2/2018 | Nawana et al. | |
| 2018/0044712 A1 | 2/2018 | Embree et al. | |
| 2018/0051310 A1 | 2/2018 | Hallock et al. | |
| 2018/0051327 A1 | 2/2018 | Blainey et al. | |
| 2018/0070825 A1 | 3/2018 | Apte et al. | |
| 2018/0080065 A1 | 3/2018 | Jain | |
| 2018/0223325 A1 | 8/2018 | Embree et al. | |
| 2018/0310592 A1 | 11/2018 | Embree et al. | |
| 2018/0325966 A1 | 11/2018 | Embree et al. | |
| 2019/0200642 A1 | 7/2019 | Embree et al. | |
| 2019/0281861 A1 | 9/2019 | Embree et al. | |
| 2019/0357571 A1 | 11/2019 | Embree et al. | |
| 2020/0037633 A1 | 2/2020 | Embree et al. | |
| 2020/0123588 A1* | 4/2020 | Mizrahi | A23K 50/10 |
| 2020/0275680 A1 | 9/2020 | Oh et al. | |
| 2020/0305462 A1 | 10/2020 | Embree et al. | |
| 2020/0315212 A1 | 10/2020 | Watson et al. | |
| 2021/0037853 A1 | 2/2021 | Embree et al. | |
| 2021/0177006 A1 | 6/2021 | Embree et al. | |
| 2022/0287330 A1 | 9/2022 | Embree et al. | |
| 2023/0139325 A1 | 5/2023 | Embree et al. | |

FOREIGN PATENT DOCUMENTS

| | | |
|---|---|---|
| CN | 1703968 A | 12/2005 |
| CN | 101519638 A | 9/2009 |
| CN | 102533621 A | 7/2012 |
| CN | 103053860 B | 3/2014 |
| CN | 104814278 A | 8/2015 |
| CN | 107173587 A | 9/2017 |
| EP | 0553444 B1 | 3/1998 |
| EP | 0664671 B1 | 9/2002 |
| KR | 20110124976 A | 11/2011 |
| KR | 1020130127784 B1 | 11/2013 |
| RU | 2 458 527 C1 | 8/2012 |
| WO | WO 1993/025232 A1 | 12/1993 |
| WO | WO 2001/012779 A1 | 2/2001 |
| WO | WO 2006/117019 A1 | 11/2006 |
| WO | WO 2008/076975 A1 | 6/2008 |
| WO | WO 2010/015580 A1 | 2/2010 |
| WO | WO 2010/062909 A1 | 6/2010 |
| WO | WO 2010/111347 A2 | 9/2010 |
| WO | WO 2010/111565 A2 | 9/2010 |
| WO | WO 2010/138522 A2 | 12/2010 |
| WO | WO 2011/075138 A1 | 6/2011 |
| WO | WO 2011/094469 A2 | 8/2011 |
| WO | WO 2012/077038 A1 | 6/2012 |
| WO | WO 2012/122522 A2 | 9/2012 |
| WO | WO 2014/141274 A1 | 9/2014 |
| WO | WO 2015/023461 A2 | 2/2015 |
| WO | WO 2015/068054 A1 | 5/2015 |
| WO | WO 2016/007544 A1 | 1/2016 |
| WO | WO 2016/127956 A1 | 8/2016 |
| WO | WO 2016/153247 A1 | 9/2016 |
| WO | WO 2016/210251 A1 | 12/2016 |
| WO | WO 2017/120495 A1 | 7/2017 |
| WO | WO 2017/131821 A1 | 8/2017 |
| WO | WO 2017/181203 A1 | 10/2017 |
| WO | WO 2018/126026 A1 | 7/2018 |
| WO | WO 2018/126033 A1 | 7/2018 |
| WO | WO 2018/126036 A1 | 7/2018 |
| WO | WO 2018/201049 A1 | 11/2018 |
| WO | WO-2020176834 A1 | 9/2020 |
| WO | WO 2021/202804 A1 | 10/2021 |
| WO | WO-2022081992 A1 | 4/2022 |
| WO | WO-2022226367 A1 | 10/2022 |

OTHER PUBLICATIONS https://www.thecattlesite.com/articles/3941/when-dairy-cows-become-beef-cows/, "When Dairy Cows Become Beef Cows", The Cattle Site, Jun. 2014 (Year: 2014).*

Abu-Tarboush, et al., "Evaluation of diet containing lactobacilli on performance, fecal coliform, and lactobacilli of young dairy calves." Animal Feed Science and Technology (1996); 57;1-2: 39-49.

Adams, Rachel: Incorporating quantity into microbiome analysis; (https://iwww.microbe.net/2017 /11/20/incorporating-quantity-into-microbiome-analysis/); printed Dec. 13, 2017, 6 pages.

Aikman, P.C., et al., "Rumen pH and fermentation characteristics in dairy cows supplemented with Megasphaera elsdenii NCIMB 41125 in early lactation." Journal of Dairy Science (2011); 94.6: 2840-2849.

Almeida, Elionor RP, et al., "Transgenic expression of two marker genes under the control of an *Arabidopsis* rbcS promoter: Sequences encoding the Rubisco transit peptide increase expression levels." Molecular and General Genetics MGG (1989); 218.1: 78-86.

Anderson, et al., "Rumen bacterial communities can be acclimated faster to high concentrate diets than currently implemented feedlot programs." Journal of Applied Microbiology (2016); 120 (3): 588-599.

Bauman, et al., "Nutrigenomics, Rumen-Derived Bioactive Fatty Acids, and the Regulation of Milk Fat Synthesis," Annual Review of Nutrition (2011); 31: 299-319.

Belk, et al., "Tissue-specific activity of pentose cycle oxidative enzymes during feeder lamb development" Journal of Animal Science (1993); 71: 1796-1804.

Bennett, et al., "Toward the $1000 human genome," Pharmacogenomics (2005); 6(4):373-382.

Bentley, et al., "Accurate whole genome sequencing using reversible terminator chemistry," Nature (2008); 456: 53-59.

Beye et al., "Careful use of 16S rRNA gene sequence similarity values for the identification of *Mycobacterium* species," New Microbe and New Infect 2018; 22: 24-29.

(56) References Cited

OTHER PUBLICATIONS

Blondel, et al., "Fast unfolding of communities in large networks," Journal of Statistical Mechanics: Theory and Experiment, (2008); P10008.

Borling, "Feed improvement by energy efficient storage using Pichia anomala inoculated ensiled cereal grain," Master thesis 2010:1, Uppsala BioCenter Department of Microbiology Faculty of Natural Resources and Agriculture Sciences Swedish University of Agricultural Sciences, ISSN 1101-8151, 25 pages.

Boyd, J., "Effects of the addition of direct-fed microbials and glycerol to the diet of lactating dairy cows on milk yield and apparent efficiency of yield." Journal of Dairy Science (2011); 94.9: 4616-4622.

Breiman, L., "Random Forests." Machine Learning (2001); 45 (1): 5-32.

Bremges et al., "Deeply sequenced metagenome and metatranscriptome of a biogas-producing microbial community from an agricultural production-scale biogas plant," GigaScience (2015) 4:33, 6 pages.

Bretonnière, Cedric, et al. "MIC score, a new tool to compare bacterial susceptibility to antibiotics application to the comparison of susceptibility to different penems of clinical strains of Pseudomonas aeruginosa." The Journal of Antibiotics 6911 (2016): 806-810. Published online Mar. 30, 2016.

Brown, et al., "Adaptation of beef cattle to high-concentrate diets: Performance and ruminal metabolism." Journal of Animal Science (2006); 84 (E. Suppl): E25-E33.

Burgain, et al., "Encapsulation of probiotic living cells: From laboratory scale to industrial applications." Journal of Food Engineering (2011); 104 (4): 467-483.

Cacite, F., and Weimer, P. J., "Ruminal dosing with Megasphaera elsdenii and strain persistence are associated with milk fat depression in Holstein cows." J. Anim. Sci. 1611 (2016); 94, E-Suppl. 5/J. Dairy Sci. vol. 99, E-Suppl. 1, p. 784, 1 page.

Caporaso et al., "Ultra-high-throughput microbial community analysis on the Illumina HiSeq and MiSeq platforms," The ISME Journal (2012); 6: 1621-1624.

Chambers, et al., "A cross-platform toolkit for mass spectrometry and proteomics." Nat Biotechnol. (2012); 30 (10): 918-920.

Chi et al., "Increase in antioxidant enzyme activity, stress tolerance and biocontrol efficacy of Pichia kudriavzevii with the transition from a yeast-like to biofilm morphology." Biological Control, 90: 113-119 (2015).

Chiquette, J., et al. "Prevotella bryantii 25A used as a probiotic in early-lactation dairy cows: effect on ruminal fermentation characteristics, milk production, and milk composition." Journal of Dairy Science (2008); 91.9: 3536-3543.

Chiquette, J., et al. "Use of Prevotella bryantii 25A and a commercial probiotic during subacute acidosis challenge in midlactation dairy cows." Journal of Dairy Science (2012); 95.10: 5985-5995.

Clarke, K.R., "Non-parametric multivariate analyses of changes in community structure." Australian Journal of Ecology (1993); 18 (1): 117-143.

Clasquin, et al., "LC-MS Data Processing with MAVEN: A Metabolomic Analysis and Visualization Engine." Curr. Protoc. Bioinform. (2012); 37 (1): 14.11.1-14.11.23.

Colby, S. R. "Calculating synergistic and antagonistic responses of herbicide combinations." Weeds (1967); 15(1): 20-22.

Cole, et al., "Ribosomal Database Project: data and tools for high throughput rRNA analysis." Nucleic Acids Research (2014); 42 (D1): D633-D642.

Cori, et al., "The role of glucose-1-phosphate in the formation of blood sugar and synthesis of glycogen in the liver." Journal of Biological Chemistry (1939); 129: 629-639.

Coulon, Jean-Baptiste, et al. "Effect of mastitis and related-germ on milk yield and composition during naturally-occurring udder infections in dairy cows." Animal Research (2002); 51.05: 383-393.

Count your blessings: Quantitative microbiome profiling; Vib (The Flanders Institute for Biotechnology); Public Release: Nov. 15, 2017 https://www.eurekalert.org/pub_releases/2017-11/vfi-cyb11417.php); printed Dec. 13, 2017, 1 page.

Crameri, Andreas, et al. "DNA shuffling of a family of genes from diverse species accelerates directed evolution." Nature (1998); 391.6664: 288-291.

Crameri, Andreas, et al. "Molecular evolution of an arsenate detoxification pathway by DNA shuffling." Nature Biotechnology (1997); 15.5: 436-438.

Dannemiler, K.C., et al., "Combining real-time PCR and next-generation DNA sequencing to provide quantitative comparisons of fungal aerosol populations." Atmospheric Environment (2014); 84: 113-121.

DDBJ Blast search results; using blastn program with default parameters; query Seq Id No. 28 from U.S. Appl. No. 16/655,776 specification; limited to bct database; conducted on Feb. 19, 2020, 831 pages.

De Almeida et al., "Aerobic fungi in the rumen fluid from dairy cattle fed different sources of forage," R. Bras. Zootec., 2012, vol. 41, No. 11, pp. 2336-2342.

De Menezes, Alexandre B., et al. "Microbiome analysis of dairy cows fed pasture or total mixed ration diets." FEMS Microbiology Ecology (2011); 78.2: 256-265.

Dosogne, Hilde, et al. "Differential leukocyte count method for bovine low somatic cell count milk." Journal of Dairy Science (2003); 86.3: 828-834.

Doto and Liu, "Effects of direct-fed microbials and their combinations with yeast culture on in vitro rumen termentation characteristics," Journal of Animal and Feed Sciences, 2011, 20, 259-271.

Edgar and Flyvberg, "Error filtering, pair assembly and error correction for next-generation sequencing reads." Bioinformatics (2015); 31 (21): 3476-3482.

Edgar, "SINTAX: a simple non-Bayesian taxonomy classifier for 16S and ITS sequences." BioRxiv (2016); 074161, 20 pages.

Edgar, R., "Updating the 97% identity threshold for 16S ribosomal RNA OTUs," Bioinformatics, 34(14), 2018, 2371-2375.

Embree, Mallory, et al. "Networks of energetic and metabolic interactions define dynamics in microbial communities." Proceedings of the National Academy of Sciences (2015); 112.50: 15450-15455.

Extended European Search Report for European Application No. 17736448.6 dated Aug. 21, 2019, 11 pages.

Fadrosh et al., "An improved dual-indexing approach for multiplexed 16S rRNA gene sequencing on the Illumina MiSeq platform," Microbiome (2014); 2:6, 7 pages.

Falkowski et al., "Primary production of the biosphere: integrating terrestrial and oceanic components," Science (1998); 281(5374): 237-240.

Fernando, et al., "Rumen Microbial Population Dynamics during Adaptation to a High-Grain Diet." Applied and Environmental Microbiology (2010); 76 (22): 7482-7490.

Final Office Action in U.S. Appl. No. 15/400,436, dated Jan. 28, 2019, 5 pages.

Final Office Action in U.S. Appl. No. 16/029,398, dated Jun. 26, 2019, 8 pages.

Final Office Action in U.S. Appl. No. 15/965,661 dated May 14, 2020, 12 pages.

Final Office Action in U.S. Appl. No. 15/400,436, dated Dec. 13, 2017, 11 pages.

Final Office Action in U.S. Appl. No. 15/400,484, dated Dec. 13, 2017, 8 pages.

Flores, et al., "Temporal variability is a personalized feature of the human microbiome." Genome Biology (2014); 15: 531, 13 pages.

Gbassi et al. "Probiotic Encapsulation Technology: From Microencapsulation to Release into the Gut," Pharmaceutics, 2012, 4, 149-163.

GenBank Accession No. EU556330 "Issatchenkia orientalis 18S ribosomal RNA gene, partial sequence; internal transcribed spacer 1, complete sequence; and 5.8S ribosomal RNA gene, partial sequence" Apr. 5, 2008, 1 page.

GenBank Accession No. EU663567 "Issatchenkia orientalis 5.8S ribosomal RNA gene, partial sequence; internal transcribed spacer 2, complete sequence; and 28S ribosomal RNA gene, partial sequence" May 17, 2008, 1 page.

(56) References Cited

OTHER PUBLICATIONS

GenBank Accession No. JF629154 Uncultured bacterium clone GDIC21K01DL4MU 16S ribosomal RNA gene, partial sequence, Aug. 3, 2011 [online]. (Retrieved online Aug. 14, 2018], 1 page.
Gray, Nathan; A revolution in microbiome analysis? Novel method offers 'true' quantitative analysis of gut bacteria; Nov. 17, 2017; New methods to measure and accurately quantify the levels of gut bacteria in stool samples could be a revolution for researchers and companies looking to link our gut bacteria make up to specific issues of health and disease. 3 pages, (https://www.nutraingredients.com/Article/2017/11/17/A-revolution-inmicrobiome-analysis-Novel-method-offers-true-quantitative-analysis-of-gut-bacteria); printed Dec. 13. 2017.
Gröhn, Y. T., et al. "Effect of Pathogen-Specific Clinical Mastitis on Milk Yield in Dairy Cows." Journal of Dairy Science (2004); 87.10: 3358-3374.
Hammer, et al., "Past: Paleontological Statistics Software Package for Education and Data Analysis." Palaeontologia Electronica (2001); 4 (1): 1-9.
Higginbotham, G. E., and Bath, D. L. "Evaluation of Lactobacillus Fermentation Cultures in Calf Feeding Systems." Journal of Dairy Science (1993); 76.2: 615-620.
Hippe et al., "Phylogenetic analysis of Formivibrio citricus, Propionivibrio dicarboxylicus, Anaerobiospirillum thomasii, Succinimonas amylolytica and Succinivibrio dextrinosolvens and proposal of Succinivibrionaceae fam. nov.," International Journal of Systematic Bacteriology (1999), 49, 779- 782.
Huhtanen, Pekka, et al. "Effect of increasing ruminal butyrate on milk yield and blood constituents in dairy cows fed a grass silage-based diet." Journal of Dairy Science (1993); 76.4: 1114-1124.
Human Microbiome Project Consortium. "Structure, function and diversity of the healthy human microbiome." Nature (2012); 486(7402): 207-214.
Hungate, "The Rumen Microbial Ecosystem." Annual Review of Ecology and Systematics (1975); 6: 39-66.
Ingolia et al., "Genome-wide analysis in vivo of translation with nucleotide resolution using ribosome profiling," Science (2009); 324(5924): 218-223.
Ingolia, N.T., "Ribosome profiling: new views of translation, from single codons to genome scale," Nat Rev Genet. (2014); 15(3): 205-213.
International Patent Application No. PCT/US2016/039221, International Preliminary Report on Patentability dated Dec. 26, 2017, 11 pages.
International Patent Application No. PCT/US2016/039221, International Search Report and Written Opinion dated Sep. 23, 2016, 14 pages.
International Search Report and Written Opinion, dated Feb. 28, 2018, for PCT International Application No. PCT/US2018/068753, 11 pages.
International Search Report and Written Opinion, dated Feb. 28, 2018, for PCT International Application No. PCT/US2018/068758, 9 pages.
International Search Report and Written Opinion, dated Jun. 7, 2017, for PCT International Application No. PCT/US2017/012573, 18 pages.
International Search Report and Written Opinion, dated Mar. 22, 2018, for PCT International Application No. PCT/US2017/068740, 16 pages.
International Search Report and Written Opinion, dated Sep. 6, 2018, for PCT International Application No. PCT/US2018/029953, 17 pages.
International Search Report for PCT/US2017/028015, dated Sep. 5, 2017, 7 pages.
Japanese Office Action for Japanese Application No. 2018-535389 dated Oct. 7, 2020, 15 pages (with English translation).
Jewell et al., "Ruminal Bacterial Community Composition in Dairy Cows is Dynamic over the Course of Two Lactations and Correlates with Feed Efficiency," Applied and Environmental Microbiology (2015); 81(14): 4697-4710.
Jin, G. L. et al., "Effect of Microbial Additives on Metabolic Characteristics in Sheep and Milking Performance of Lactating Dairy Cows," J. Anim. Sci. & Technol. (Kor.), 2007, 49(6):819-828. (with English abstract).
Jones, Jonathan D.G., et al. "High level expression of introduced chimaeric genes in regenerated transformed plants." The EMBO Journal (1985); 4.10: 2411-2418.
Kamphorst, et al., "Liquid Chromatography-High Resolution Mass Spectrometry Analysis of Fatty Acid Metabolism." Anal. Chem. (2011); 83 (23): 9114-9122.
Kim, Y. J., et al. "The enrichment of a ruminal bacterium (*Megasphaera elsdenii* YJ-4) that produces the trans-10, cis-12 isomer of conjugated linoleic acid." Journal of Applied Microbiology (2002); 92.5: 976-982.
Koch, et al., "Efficiency of Feed Use in Beef Cattle." Journal of Animal Science (1963); 22: 486-494.
Kõljalg, Urmas, et al. "UNITE: a database providing web-based methods for the molecular identification of ectomycorrhizal fungi." New Phytologist (2005); 166.3: 1063-1068.
Kozawa, M., "Probiotics for animal use in Japan," Rev. sci. tech. Off. int. Epiz., 1989, 8(2), 517-531.
Krysl and Hess, "Influence of supplementation on behavior of grazing cattle." Journal of Animal Science (1993); 71 (9): 2546-2555.
Laliotis, et al., "Cloning, characterization and computational analysis of the 5' regulatory region of ovine glucose 6-phosphate dehydrogenase gene." Comparative Biochemistry and Physiology, Part B (2007); 147 (4): 627-634.
Lan, Yemin, et al. "Using the RDP classifier to predict taxonomic novelty and reduce the search space for finding novel organisms." PLoS One (2012); 7.3: e32491, 15 pages.
Lane, et al., "16S/23S rRNA Sequencing," Nucleic Acid Techniques in Bacterial Systematics, Chapter 6, pp. 115-175, 1991.
Lange et al., "Cost-efficient high-throughput HLA typing by MiSeq amplicon sequencing," BMC Genomics (2014); 15:63, 11 pages.
Laporte-Uribe, J.A., "The role of dissolved carbon dioxide in both the decline in rumen pH and nutritional diseases in ruminants." Animal Feed Science and Technology (2016); 219: 268-279.
Lee et al., "Nonradioactive Method To Study Genetic Profiles of Natural Bacterial Communities by PCR-Single-Strand-Conformation Polymorphism," Applied and Environmental Microbiology (1996); 62 (9): 3112-3120.
Lee, K., et al., "Antiobesity effect of trans-10, cis-12-conjugated linoleic acid-producing Lactobacillus plantarum PL62 on diet-induced obese mice." Journal of Applied Microbiology (2007); 103.4: 1140-1146.
Li et al., "Quantifying absolute protein synthesis rates reveals principles underlying allocation of cellular resources," Cell (2013);157 (3): 624-635.
Li, M., et al. "Uncultured Bacterium Clone SJTU_A3_11_21 16S Ribosomal RNA Gene, Partial Sequence." GenBank Accession No. EF403757.1. Submitted Jan. 26, 2007; downloaded from internet <https://www.ncbi.nlm.nih.gov/nucleotide/126114074?report=genbank&log$=nuclalign&blast_rank=1&RID=G57ADV19015> on Apr. 27, 2017, 1 page.
Lowe, Susan E., et al., "Growth of anaerobic rumen fungi on defined and semi-defined media lacking rumen fluid." Journal of General Microbiology (1985); 131.9: 2225-2229.
Lu, et al., "Metabolomic Analysis via Reversed-Phase Ion-Pairing Liquid Chromatography Coupled to a Stand Alone Orbitrap Mass Spectrometer." Analytical Chemistry (2010); 82 (8): 3212-3221.
Lund, A., "Yeasts and Moulds in the Bovine Rumen," Journal of General Microbiology (1974), 81, 453-462.
Mardis, Elaine R., "Next Generation DNA Sequencing Methods," Annu. Rev. Genomics Hum. Genet. (2008); 9: 387-402.
Margulies et al., "Genome sequencing in microfabricated high-density picolitre reactors," Nature (2005); 437: 376-380.
Massol-Deya, A.A. et al., "Bacterial community fingerprinting of amplified 16S and 16-23S ribosomal DNA gene sequences and restriction endonuclease analysis (ARDRA)." Molecular Microbial Ecology Manual, 1995, vol. 3.3.2. Kluwer Academic Publishers, Dordrecht, pp. 1-8.

(56) References Cited

OTHER PUBLICATIONS

Maurice et al., "Xenobiotics Shape the Physiology and Gene Expression of the Active Human Guy Microbiome," Cell, 152, Jan. 17, 2013, pp. 39-50.
McGilliard, M. L., and Stallings, C.C. "Increase in milk yield of commercial dairy herds fed a microbial and enzyme supplement." Journal of Dairy Science (1998); 81.5: 1353-1357.
Mitra et al., "Analysis of the intestinal microbiota using Solid 16S rRNA gene sequencing and SOLiD shotgun sequencing," BMC Genomics (2013); 14(Suppl 5):S16, 11 pages.
Mohammed, R., et al., "Changes in ruminal bacterial community composition following feeding of alfalfa ensiled with a lactic acid bacterial inoculant." Journal of Dairy Science (2012); 95.1: 328-339.
Moore, Jeffrey C., et al. "Strategies for the in vitro evolution of protein function: enzyme evolution by random recombination of improved sequences." Journal of Molecular Biology (1997); 272.3: 336-347.
Morgante, et al., "Blood gas analyses, ruminal and blood pH, urine and faecal pH in dairy cows during subacute ruminal acidosis." Comparative Clinical Pathology (2009); 18 (3): 229-232.
Muck, R., "Recent advances in silage microbiology," Agricultural and Food Science (2013) 22:3-15.
Musselman, et al., "CoA protects against the deleterious effects of caloric overload in *Drosophila*." Journal of Lipid Research (2016); 57: 380-387.
Muyzer, et al., "Profiling of complex microbial populations by denaturing gradient gel electrophoresis analysis of polymerase chain reaction-amplified genes coding for 16S rRNA." Applied and Environmental Microbiology (1993); 59 (3): 695-700.
Myer, et al., "Rumen Microbiome from Steers Differing in Feed Efficiency." PLOS One (2015); 10 (6): e0129174, 17 pages.
NCBI Blast Nucleotide Sequence search results; using blastn program with default parameters; query SEQ Id No. 28 from U.S. Appl. No. 16/655,776 specification; limited to Clostridium butyricum (taxid:1492); conducted on Feb. 19, 2020, 45 pages.
Nissan Gosei Kogyo Co., Ltd., "Bovine Probiotics and Prebiotics," Nissan News, Mar. 2011, Issue 73, pp. 1-2, retrieved from http://www.nissangosei.co.jp/nissan/073.pdf.
Non-Final Office Action in U.S. Appl. No. 15/349,829 dated May 4, 2018, 13 pages.
Non-Final Office Action in U.S. Appl. No. 15/392,913 dated Oct. 16, 2018, 16 pages.
Non-Final Office Action in U.S. Appl. No. 15/948,965 dated Jun. 26, 2018, 25 pages.
Non-Final Office Action in U.S. Appl. No. 15/965,661 dated Dec. 30, 2019, 36 pages.
Non-Final Office Action in U.S. Appl. No. 16/029,398 dated Feb. 26, 2019, 9 pages.
Non-Final Office Action in U.S. Appl. No. 16/206,098 dated Aug. 8, 2019, 35 pages.
Non-Final Office Action in U.S. Appl. No. 16/207,811 dated Jul. 29, 2019, 32 pages.
Non-Final Office Action in U.S. Appl. No. 16/655,776 dated Jan. 15, 2020, 22 pages.
Non-Final Office Action in U.S. Appl. No. 15/217,575, dated Oct. 12, 2016, 11 pages.
Non-Final Office Action in U.S. Appl. No. 15/400,436, dated Aug. 31, 2018, 9 pages.
Non-Final Office Action in U.S. Appl. No. 15/400,436, dated Mar. 30, 2017, 9 pages.
Non-Final Office Action in U.S. Appl. No. 15/400,436, dated May 18, 2017, 15 pages.
Non-Final Office Action in U.S. Appl. No. 15/400,484, dated Apr. 4, 2017, 6 pages.
Non-Final Office Action in U.S. Appl. No. 15/400,484, dated May 30, 2017, 16 pages.
Non-Final Office Action in U.S. Appl. No. 15/965,661 dated Sep. 17, 2020, 12 pages.
Non-Final Office Action in U.S. Appl. No. 16/534,481, dated Sep. 23, 2019, 13 pages.
Non-Final Office Action in U.S. Appl. No. 16/871,290, dated Jun. 18, 2020, 13 pages.
Notice of Allowance in U.S. Appl. No. 15/392,913 dated Apr. 19, 2018, 9 pages.
Notice of Allowance in U.S. Appl. No. 15/400,484, dated Apr. 2, 2018, 4 pages.
Notice of Allowance in U.S. Appl. No. 15/400,484, dated Apr. 27, 2018, 2 pages.
Notice of Allowance in U.S. Appl. No. 15/400,484, dated Feb. 13, 2018, 4 pages.
Notice of Allowance in U.S. Appl. No. 15/400,484, dated Jan. 16, 2018, 8 pages.
Notice of Allowance in U.S. Appl. No. 15/400,484, dated Jan. 25, 2018, 2 pages.
Notice of Allowance in U.S. Appl. No. 15/217,575, dated Nov. 8, 2016, 13 pages.
Okine and Mathison, "Effects of feed intake on particle distribution, passage of digesta, and extent of digestion in the gastrointestinal tract of cattle." Journal of Animal Science (1991); 69 (8): 3435-3445.
Palmonari et al., "pH dynamics and bacterial community composition in the rumen of lactating dairy cows," J. Dairy Sci. (2010); 93(1): 279-287.
Partial Supplementary European Search Report for European Application No. 18792045.9 dated Mar. 30, 2021.
Peckham et al., "SOLiD™ Sequencing and 2-Base Encoding," San Diego, CA: American Society of Human Genetics, Poster No. 2624 (2007), 1 page.
Petrenko et al., "MetAnnotate: function-specific taxonomic profiling and comparison of metagenomes," BMC Biology (2015) 13:92, 8 pages.
Petri, Renee M., et al., "Characterization of the core rumen microbiome in cattle during transition from forage to concentrate as well as during and after an acidotic challenge." PLoS One (2013); 8.12: e83424, 15 pages.
Pool-Zobel et al., "Overview of Experimental Data on Reduction of Colorectal Cancer Risk by Inulin-Type Fructans," J. Nutr. (2007); 137: 2580S-2584S.
Qiu, Yu, et al., "Characterizing the interplay between multiple levels of organization within bacterial sigma factor regulatory networks." Nature Communications (2013); 4: 1755 (pp. 1-10).
Raeth-Knight, M. L., et al., "Effect of direct-fed microbials on performance, diet digestibility, and rumen characteristics of Holstein dairy cows." Journal of Dairy Science (2007); 90.4: 1802-1809.
Ragaller, et al., "Pantothenic acid in ruminant nutrition: a review." Journal of Animal Physiology and Animal Nutrition (2011); 95 (1): 6-16.
Ramirez-Farias et al., "Effect of inulin on the human gut microbiota: stimulation of Bifidobacterium adolescentis and Faecalibacterium prausnitzii," Br J Nutr (2009); 101(4): 541-550.
Ranjard et al., "Sampling strategy in molecular microbial ecology: influence of soil sample size on DNA fingerprinting analysis of fungal and bacterial communities," Environmental Microbiology 5(11); 1111-1120 (2003).
Restriction / Election Requirement in U.S. Appl. No. 16/029,398 dated Sep. 18, 2018, 9 pages.
Restriction / Election Requirement in U.S. Appl. No. 16/207,811 dated Feb. 12, 2019, 6 pages.
Rigobelo et al., "Protective Effect of Probiotics Strains in Ruminants," Submitted: Jan. 26, 2012 Reviewed: May 22, 2012 Published: Oct. 3, 2012, published by INTEC Open source, 20 pages, downloaded from: https://www.intechopen.com/books/probiotic-in-animals/protective-effect-of-probiotics-strains-in-ruminants.
Rook, J. A. F., and Balch, C.C. "The effects of intraruminal infusions of acetic, propionic and butyric acids on the yield and composition of the milk of the cow." British Journal of Nutrition (1961); 15.03: 361-369.
Ross, et al., "High throughput whole rumen metagenome profiling using untargeted massively parallel sequencing." BMC Genetics (2012); 13:53, 14 pages.

(56) References Cited

OTHER PUBLICATIONS

Rossi-Tamisier et al., "Cautionary tale of using 16S rRNA gene sequence similarity values in identification of human-associated bacterial species," International Journal of Systematic and Evolutionary Microbiology (2015), 65, 1929-1934.
Ruminobacter, MicrobeWiki, Aug. 6, 2010, 3 pages, retrieved from https://microbewiki.kenyon.edu/index.php/Ruminobacter.
San Miguel et al., "Effects of organochlorines on microbial diversity and community structure in Phragmites australis rhizosphere," Appl Microbiol Biotechnol (2014); 98(9): 4257-4266.
Sandri et al., "Microbial biodiversity of the liquid fraction of rumen content from lactating cows," Animal (2014); 8(4): 572-579.
Sanger et al., "DNA sequencing with chain-terminating inhibitors," Proc Natl. Acad. Sci. USA (1977); 74(12): 5463-5467.
Santos and Thompson, "The Family Succinivibrionaceae," The Prokaryotes—Gammaproteobacteria (Eds. E. Rosenberg et al.), 2014, Springer-Verlag Berlin Heidelberg, pp. 639-648.
Scheinert et al., "Molecular differentiation of bacteria by PCR amplification of the 16-23S rRNA spacer," J Microbiol Meth (1996); 26: 103-117.
Schloss, Patrick D., et al., "Assessing and improving methods used in operational taxonomic unit-based approaches for 16S rRNA gene sequence analysis." Applied and Environmental Microbiology (2011); 77.10: 3219-3226.
Schogor, Ana L.B., et al., "Ruminal *Prevotella* spp. may play an important role in the conversion of plant lignans into human health beneficial antioxidants." PLoS One (2014); 9.4: e87949. 10 pages.
Schwieger et al.,"A New Approach To Utilize PCR-Single-Strand-Conformation Polymorphism for the 16S rRNA Gene-Based Microbial Community Analysis," Applied and Environmental Microbiology (1998); 64(12): 4870-4876.
Segata et al., "Computational meta'omics for microbial community studies," Molecular Systems Biology 9:666 (2013), 15 pages.
Segata, Nicola, et al., "Metagenomic biomarker discovery and explanation." Genome Biology (2011); 12:R60, 18 pages.
Seymour, et al., "Relationships between rumen volatile fatty acid concentrations and milk production in dairy cows: a literature study." Animal Feed Science and Technology (2005); 119 (Issues 1-2): 155-169.
Shabat, et al., "Specific microbiome-dependent mechanisms underlie the energy harvest efficiency of ruminants." The ISME Journal (2016); 10 (12): 2958-2972.
Shanks, Orin C., et al., "Community structures of fecal bacteria in cattle from different animal feeding operations." Applied and Environmental Microbiology (2011); 77.9; 2992-3001.
Shi, et al., "Regression analysis for microbiome compositional data." The Annals of Applied Statistics (2016); 10 (2): 1019-1040.
Shi, et al., Integrated metatranscriptomic and metagenomics analyses of stratified microbial assemblages in the open ocean, The ISME Journal (2011) 5, 999-1013.
Sirisan, V., et al. "Isolation, identification and growth determination of lactic acid-utilizing yeasts from the ruminal fluid of dairy cattle." Letters in Applied Microbiology (2013); 57.2: 102-107.
Smith, et al., "The effect of pantothenate deficiency in mice on their metabolic response to fast and exercise." Metabolism (1987); 36 (2): 115-121.
Song, et al., "Comparison of co-expression measures: mutual information, correlation, and model based indices." BMC Bioinformatics (2012); 13: 328, pp. 1-21.
Stemmer, Willem P. "DNA shuffling by random fragmentation and reassembly: in vitro recombination for molecular evolution." Proceedings of the National Academy of Sciences (1994); 91.22: 10747-10751.
Stemmer, Willem PC. "Rapid evolution of a protein in vitro by DNA shuffling." Nature (1994); 370.6488: 389-391.
Stewart, R., et al., "Compendium of 4,941 rumen metagenome-assembled genomes for rumen microbiome biology and enzyme discovery," Nature Biotechnology, Aug. 2019, vol. 37, pp. 953-961.

Tajima, et al., "Diet-Dependent Shifts in the Bacterial Population of the Rumen Revealed with Real-Time PCR." Appl. Environ. Microbiol. (2001); 67 (6): 2766-2774.
Tao, N., et al. "Variations in bovine milk oligosaccharides during early and middle lactation stages analyzed by high-performance liquid chromatography-chip/mass spectrometry." Journal of Dairy Science (2009); 92.7: 2991-3001.
Tashiro, Yukihiro, et al. "High butanol production by Clostridium saccharoperbutylacetonicum N1-4 in fed-batch culture with pH-stat continuous butyric acid and glucose feeding method." Journal of Bioscience and Bioengineering (2004); 98.4: 263-268.
Van Houtert, M. F. J. "The production and metabolism of volatile fatty acids by ruminants fed roughages: A review." Animal Feed Science and Technology (1993); 43(3): 189-225.
Vandamme, Peter, et al., "Polyphasic taxonomy, a consensus approach to bacterial systematics." Microbiological Reviews (1996); 60.2: 407-438.
Vandeputte, D, et al., "Quantitative microbiome profiling links gut community variation to microbial load." Nature (2017); 551 (7681): 507.
Vineetha, P. G., et al., "Screening of Lactobacillus isolates from gastrointestinal tract of guinea fowl for probiotic qualities using in vitro tests to select species-specific probiotic candidates." British poultry science 57.4 (2016): 474-482.
Wagg et al., "Soil biodiversity and soil community composition determine ecosystem multifunctionality." Proceedings of the National Academy of Sciences (2014); 111(14): 5266-5270.
Whittaker, "Evolution and Measurement of Species Diversity." Taxon (May 1972), 21 (2/3): 213-251.
Written Opinion for PCT/US2017/028015, dated Sep. 5, 2017, 10 pages.
Yarza, Pablo, et al., "Uniting the classification of cultured and uncultured bacteria and archaea using 16S rRNA gene sequences." Nature Reviews Microbiology (2014); 12.9: 635-645.
Zebeli, Qendrim, et al., "Intraruminal administration of Megasphaera elsdenii modulated rumen fermentation profile in mid-lactation dairy cows." Journal of Dairy Research (2012); 79.01; 16-25.
Zhang, Ji-Hu, et al., "Directed evolution of a fucosidase from a galactosidase by DNA shuffling and screening." Proceedings of the National Academy of Sciences USA (1997); 94.9: 4504-4509.
Zhou et al., "High-Throughput Metagenomic Technologies for Complex Microbial Community Analysis: Open and Closed formats." MBio (2015); 6(1): e02288-14, 17 pages.
Bandarupalli et al., "Identification of a Candidate Starch Utilizing Strain of Prevotella albensis from Bovine Rumen," Microorganisms 2020, 8, 2005, 13 pages.
Chiquette, J. et al., "Repeated ruminal dosing of Ruminococcus flavefaciens NJ along with a probiotic mixture in forage or concentrate-fed dairy cows: Effect on ruminal fermentation, cellulolytic populations and in sacco digestibility," Can. J. Anim. Sci. (2007) 87: 237-249.
Extended European Search Report for European Application No. 18792045.9 dated Jul. 30, 2021.
GenBank Accession No. AB507707.1, Uncultured bacterium gene for 16S rRNA, partial sequence, clone: CNSL-118, Apr. 3, 2013, 1 page.
GenBank Accession No. KY229916.1, Clostridiales bacterium JS109 16S ribosomal RNA gene, partial sequence, Apr. 1, 2017, 1 page.
Serna-cock and Vallejo-castillo, "Probiotic encapsulation," African Journal of Microbiology Research, Oct. 2013, 7(40): 4743-4753.
Šimůnek Jr, et al., "Characterization of a xylanolytic bacterial strain C10 isolated from the rumen of a red deer (*Cervus elaphus*) closely related of the recently described species *Actinomyces succiniciruminis*, A. glycerinitolerans, and A. ruminicola," Folia Microbiologica (2018) 63:391-399.
Weimer et al., "Effect of Diet on Populations of Three Species of Ruminal Cellulolytic Bacteria in Lactating Dairy Cows," J Dairy Sci, 1999, 82:122-134.
Whitford et al., "Phylogenetic Analysis of Rumen Bacteria by Comparative Sequence Analysis of Cloned 16S rRNA Genes[8]," Anaerobe (1998) 4, 153-163, Article No. an980155.

(56) References Cited

OTHER PUBLICATIONS

Zigová and Šturdik, "Advances in biotechnological production of butyric acid," Journal of Industrial Microbiology & Biotechnology (2000) 24, 153-160.

GenBank Accession No. CP039381.1, *Ruminococcus* sp. JE7A12 chromosome, complete genome, May 22, 2019, 1 page.

GenBank Accession No. MK761171.1, *Ruminococcus* sp. JE7A12 16S ribosomal RNA gene, partial sequence, May 22, 2019, 1 page.

International Search Report and Written Opinion of the International Searching Authority, dated Aug. 4, 2021, for PCT International Application No. PCT/US2021/025264, 13 pages.

Final Office Action in U.S. Appl. No. 17/178,552 dated Oct. 18, 2021.

Avgustin et al., "Phenotypic Diversity among Ruminai Isolates of Prevotella ruminicola: Proposal of *Prevotella brevis* sp. nov., *Prevotella bryantii* sp. nov., and *Prevotella albensis* sp. nov. and Redefinition of Prevotella ruminicola," Int J Syst Bacteriol, Apr. 1997, vol. 47, No. 2, pp. 284-288.

Chassard et al., "*Ruminococcus champanellensis* sp. nov., a cellulose-degrading bacterium from human gut microbiota," International Journal of Systematic and Evolutionary Microbiology (2012), 62, 138-143.

Deatherage and Barrick, "Identification of mutations in laboratory-evolved microbes from next-generation sequencing data using breseq," Methods Mol. Biol. (2014) 1151: 165-188.

Domingo et al., "*Ruminococcus gauvreauii* sp. nov., a glycopeptide-resistant species isolated from a human faecal specimen," International Journal of Systematic and Evolutionary Microbiology (2008), 58, 1393-1397.

Ezaki, T, "Ruminococcus," Bergey's Manual of Systematics of Archaea and Bacteria, 2015, p. 1-5.

Goris et al., "DNA-DNA hybridization values and their relationship to whole-genome sequence similarities," Int J Syst Evol Microbiol. (2007), 57, 81-91.

Jain et al., "Nanopore sequencing and assembly of a human genome with ultra-long reads," Nature Biotechnology, Apr. 2018, 36(4): 338-345.

Jones et al., "Manual of Methods for General Bacteriology," Journal of Clinical Pathology, 1981, vol. 34, p. 1069.

Kumar et al., "Mega X: Molecular Evolutionary Genetics Analysis across Computing Platforms," Mol. Biol. Evol. 2018, 35(6):1547-1549.

Langmead B., "Fast Gapped-Read Alignment with Bowtie 2," Nature Methods, 2012, vol. 9(4), pp. 357-359.

Liu et al., "Reclassification of Clostridium coccoides, Ruminococcus hansenii, Ruminococcus hydrogenotrophicus, Ruminococcus luti, Ruminococcus productus and Ruminococcus schinkii as *Blautia coccoides* gen. nov., comb. nov., *Blautia hansenii* comb. nov., *Blautia hydrogenotrophica* comb. nov., *Blautia luti* comb. nov., *Blautia producta* comb. nov., *Blautia schinkii* comb. nov. and description of *Blautia wexlerae* sp. nov., isolated from human faeces," International Journal of Systematic and Evolutionary Microbiology. 2008. p. 1896-1902.

Mukhopadhya et al., "Sporulation capability and amylosome conservation among diverse human colonic and rumen isolates of the keystone starch-degrader Ruminococcus bromii," Environmental Microbiology (2018) 20(1), 324-336.

Non-Final Office Action for U.S. Appl. No. 16/920,997 dated Jan. 20, 2023, 24 pages.

Richter et al., "Shifting the genomic gold standard for the prokaryotic species definition," PNAS, Nov. 10, 2009, vol. 10, No. 45, 19126-19131.

Segata et al., "PhyloPhlAn is a new method for improved phylogenetic and taxonomic placement of microbes," Nature Communications, (2013) 4:2304, 11 pages.

Sijpesteijn, A.K., "Cellulose-decomposing bacteria from the rumen of cattle," Antonie van Leeuwenhoek (1949) 15, 49-52.

Sijpesteijn, A.K., "On Ruminococcus flavefaciens, a Cellulose-decomposing Bacterium from the Rumen of Sheep and Cattle," J Gen Microbiol. 1951, 5, 869-879.

Valldecabres et al., "Effects of rumen-native microbial feed supplementation on milk yield, composition, and feed efficiency in lactating dairy cows," Journal of Animal Science, 2022, 100, 1-10.

Yoon et al., "A large-scale evaluation of algorithms to calculate average nucleotide identity," Antonie van Leeuwenhoek, (2017) vol. 110, pp. 1281-1286.

Restriction / Election Requirement in U.S. Appl. No. 16/920,997 dated Sep. 19, 2022, 6 pages.

Allen-Vercoe et al., "*Anaerostipes hadrus* comb. nov., a dominant species within the human colonic microbiota; reclassification of Eubacterium hadrum Moore et al. 1976.," Anaerobe, Oct. 2012, 18(5):523-529.

Barco et al., A Genus Definition for Bacteria and Archaea Based on a Standard Genome Relatedness Index. MBio, Jan./Feb. 2020 vol. 11, Issue 1, e02475-19, 20 pages.

Biddle et al., "Untangling the Genetic Basis of Fibrolytic Specialization by Lachnospiraceae and Ruminococcaceae in Diverse Gut Communities," Diversity, 2013, 5, 627-640.

Cai and Dong, *Cellulosilyticum ruminicola* gen. nov., sp. nov., isolated from the rumen of yak, and reclassification of Clostridium lentocellum as *Cellulosilyticum lentocellum* comb. nov., International Journal of Systematic and Evolutionary Microbiology (2010), 60, 845-849.

Creevey et al., "Determining the culturability of the rumen bacterial microbiome," Microbial Biotechnology(2014)7(5), 467-479.

Dehority, Pectin-fermenting Bacteria Isolated from the Bovine Rumen, Journal of Bacteriology, Jul. 1969, vol. 99, No. 1, pp. 189-196.

Downes et al., "*Shuttleworthia satelles* gen. nov., sp. nov., isolated from the human oral cavity," International Journal of Systematic and Evolutionary Microbiology (2002), 52, 1469-1475.

Duncan et al., "Acetate Utilization and Butyryl Coenzyme A (CoA):Acetate-CoA Transferase in Butyrate-Producing Bacteria from the Human Large Intestine," Applied and Environmental Microbiology. 2002, vol. 68, No. 10, pp. 5186-5190.

Duncan et al. "Human colonic microbiota Associated with diet, obesity and weight loss," International Journal of Obesity (2008) 32, 1720-1724.

Frank, D. C., et al., "Molecular-phylogenetic characterization of microbial community imbalances in human inflammatory bowel diseases," Proc. Natl. Acad. Sci. USA., (2007), 104 (34): p. 13780-5.

Gagen et al., Hydrogenotrophic culture enrichment reveals rumen Lachnospiraceae and Ruminococcaceae acetogens and hydrogen-responsive Bacteroidetes from pasture-fed cattle, FEMS Microbiology Letters, Jul. 2015, vol. 362, No. 14, fnv104, 8 pages.

GenBank Accession No. AB507640, Uncultured bacterium gene for 16S rRNA, partial sequence. clone: CNSL-51., Apr. 13, 2013, 2 pages.

Gosalbes et al., "Metatranscriptomic Approach to Analyze the Functional Human Gut Microbiota," PLoS One, Mar. 2011, 6(3):e17447, 9 pages.

Henderson et al. Rumen microbial community composition varies with diet and host, but a core microbiome is found across a wide geographical range Scientific Reports (2015) vol. 5, Article 14567, 15 pages.

International Preliminary Report on Patentability for International Application No. PCT/US2021/055210 dated Apr. 27, 2023, 7 pages.

International Search Report and Written Opinion for Application No. PCT/US2021/055210, dated Mar. 10, 2022, 11 pages.

International Search Report and Written Opinion for Application No. PCT/US2022/026037, dated Sep. 16, 2022, 12 pages.

Kittelmann et al., "Simultaneous Amplicon Sequencing to Explore Co-Occurrence Patterns of Bacterial, Archaeal and Eukaryotic Microorganisms in Rumen Microbial Communities," PLoS One. Feb. 2013, 8(2):e47879, 11 pages.

Kopecný J, et al., "*Butyrivibrio hungatei* sp. nov. and *Pseudobutyrivibrio xylanivorans* sp. nov., butyrate-producing bacteria from the rumen," Int J Syst Evol Microbiol. (2003) 53, 201-209.

Li and Guan, Metatranscriptomic Profiling Reveals Linkages between the Active Rumen Microbiome and Feed Efficiency in Beef Cattle. Appl Environ Microbiol 83(9):e00061-17, 16 pages, May 2017.

(56) References Cited

OTHER PUBLICATIONS

Ludwig et al., "Revised road map to the phylum Firmicutes," in: De Vos P et al. (editors). Bergey's Manual® of Systematic Bacteriology: Volume Three The Firmicutes. New York, NY: Springer New York; 2009. p. 1-13 (39 total pages).

Meehan and Beiko, A Phylogenomic View of Ecological Specialization in the Lachnospiraceae, a Family of Digestive Tract-Associated Bacteria, Genome Biol Evol. Mar. 2014;6(3):703-13.

Moon et al., "Reclassification of Clostridium proteoclasticum as *Butyrivibrio proteoclasticus* comb. nov., a butyrateproducing ruminal bacterium," Int J Syst Evol Microbiol, 2008, 58, 2041-2045.

Non-Final Office Action for U.S. Appl. No. 17/678,634 dated Jun. 14, 2023, 8 pages.

Qin et al., "A Proposed Genus Boundary for the Prokaryotes Based on Genomic Insights," Journal of Bacteriology, Jun. 15, 2014, vol. 196, No. 12, 2210-2215.

Rosero JA, et al., "Reclassification of Eubacterium rectale (Hauduroy et al. 1937) Prévot 1938 in a new genus *Agathobacter* gen. nov. as *Agathobacter rectalis* comb. nov., and description of *Agathobacter ruminis* sp. nov., isolated from the rumen contents of sheep and cows," International Journal of Systematic and Evolutionary Microbiology, 2016, vol. 66, 768-773.

Sakamoto et al., *Faecalimonas umbilicata* gen. nov., sp. nov., isolated from human faeces, and reclassification of Eubacterium contortum, Eubacterium fissicatena and Clostridium oroticum as *Faecalicatena contorta* gen. nov., comb. nov., *Faecalicatena fissicatena* comb. nov. and *Faecalicatena orotica comb. nov.*, Int J Syst Evol Microbiol 2017;67:1219-1227.

Seshadri et al., Cultivation and sequencing of rumen microbiome members from the Hungate1000 Collection, Nature Biotechnology, Apr. 2018, vol. 36, No. 4, 359-367.

Shetty et al., Reclassification of Eubacterium hallii as *Anaerobutyricum hallii* gen. nov., comb. nov., and description of *Anaerobutyricum soehngenii* sp. nov., a butyrate and propionate-producing bacterium from infant faeces, Int J Syst Evol Microbiol 2018;68:3741-3746.

Stackebrandt et al., "Phylogenetic basis for a taxonomic dissection of the genus Clostridium," FEMS Immunol Med Microbial. (1999) 24:253-258.

Stackebrandt, "The Family Lachnospiraceae," The Prokaryotes—Firmicutes and Tenericutes, E. Rosenberg et al. (eds.), 2014, pp. 197-201.

Tap et al., "Towards the human intestinal microbiota phylogenetic core," Environ Microbiol. (2009) 11(10), 2574-2584.

Thoetkiattikul et al., "Comparative Analysis of Microbial Profiles in Cow Rumen Fed with Different Dietary Fiber by Tagged 16S rRNA Gene Pyrosequencing," Current Microbiology, 2013, 67, 130-137.

Tong et al., Illumina sequencing analysis of the ruminal microbiota in high-yield and low-yield lactating dairy cows, PLoS One. (2018) 13(11):e0198225, 15 pages.

Turnbaugh et al., An obesity-associated gut microbiome with increased capacity for energy harvest, Nature, 2006, 444, 1027-1031.

Van Gylswyk et al., "*Pseudobutyrivibrio ruminis* gen. nov., sp. nov., a Butyrate-Producing Bacterium from the Rumen That Closely Resembles Butyrivibrio fibrisolvens in Phenotype," Int J Syst Evol Microbiol., Apr. 1996, vol. 46, No. 2, pp. 559-563.

Whitford et al., "*Lachnobacterium bovis gen. nov.*, sp. nov., a novel bacterium isolated from the rumen and faeces of cattle," International Journal of Systematic and Evolutionary Microbiology (2001), 51, 1977-1981.

Willems and Collins, Butyrivibrio, Bergey's Manual of Systematics of Archaea and Bacteria, 2015, 1-20 https://doi.org/10.1002/9781118960608.gbm00640.

Yang et al., "Alfalfa Intervention Alters Rumen Microbial Community Development in Hu Lambs During Early Life," Frontiers in Microbiology, Mar. 2018, vol. 9, Article 574, 13 pages.

Yutin and Galperin, A genomic update on clostridial phylogeny: Gram-negative spore formers and other misplaced clostridia: Genomics update. Environmental Microbiology (2013)15(10), 2631-2641.

Zhang et al., "Corn oil supplementation enhances hydrogen use for biohydrogenation, inhibits methanogenesis, and alters fermentation pathways and the microbial community in the rumen of goats," Journal of Animal Science, 2019, vol. 97, No. 12, 4999-5008.

\* cited by examiner

FIG. 6

Ruminal VFA concentrations and pH of Black Angus steers between high- and low-RFI[1] at week 10

| VFA (mM) | High-RFI | Low-RFI | SEM | P-value2 |
|---|---|---|---|---|
| Acetate | 16.90 | 19.27 | 1.032 | 0.257 |
| Propionate | 2.10 | 2.23 | 0.149 | 0.667 |
| Butyrate | 6.99 | 7.63 | 0.010 | 0.525 |
| Isobutyrate | 0.09 | 0.13 | 0.492 | 0.038 |
| Valerate3 | 0.41 | 0.97 | 0.164 | 0.093 |
| Acetate:propionate | 7.86 | 8.62 | 0.868 | 0.109 |
| pH | 6.93 | 6.97 | 0.392 | 0.732 |

Week 1        Week 5

MICROBIAL COMPOSITIONS AND METHODS FOR RUMINANT HEALTH AND PERFORMANCE

CROSS-REFERENCE TO RELATED APPLICATIONS

This application is a Continuation of U.S. application Ser. No. 15/965,661, filed Apr. 27, 2018, now U.S. Pat. No. 11,044,924, which claims the benefit of priority to U.S. Provisional Application No. 62/491,845, filed Apr. 28, 2017; and U.S. Provisional Application No. 62/578,188, filed Oct. 27, 2017; each of which is herein incorporated by reference in its entirety.

FIELD

The present disclosure relates to isolated and biologically pure microorganisms that have applications, inter alia, in the farming of beef cattle. The disclosed microorganisms can be utilized in their isolated and biologically pure states, as well as being formulated into compositions. Furthermore, the disclosure provides a microbial ensemble, containing at least two members of the disclosed microorganisms, as well as methods of utilizing said microbial ensemble. Furthermore, the disclosure provides for methods of modulating the rumen microbiome.

STATEMENT REGARDING SEQUENCE LISTING

The sequence listing associated with this application is provided in text format in lieu of a paper copy, and is hereby incorporated by reference into the specification. The name of the text file containing the sequence listing is ASBI_005_04US_SeqList_ST25.txt. The text file is 4,652,612 bytes, was created on Jun. 22, 2021, and is being submitted electronically via EFS-Web.

BACKGROUND

The global population is predicted to increase to over 9 billion people by the year 2050 with a concurrent reduction in the quantity of land, water, and other natural resources available per capita. Projections indicate that the average domestic income will also increase, with the projected rise in the GDP of China and India. The desire for a diet richer in animal-source proteins rises in tandem with increasing income, thus the global livestock sector will be charged with the challenge of producing more animal products using fewer resources. The Food and Agriculture Organization of the United Nations predict that 70% more food will have to be produced, yet the area of arable land available will decrease. It is clear that the food output per unit of resource input will have to increase considerably in order to support the rise in population.

Over recent decades the farm industry has seen fast growth in the meat sector. As more of the world's population ascends into the middle class demand for protein—including beef—is expected to remain robust for years to come. Worldwide beef production tops 59 million tons per annum.

Beef and products thereof are predominantly utilized in the preparation of foodstuffs in many different forms. There have been many strategies to improve beef production through nutritional modulations, hormone treatments, changes in animal management, and selective breeding; however, the need for more efficient production of edible beef foodstuffs per animal is required. Current animal feeding and handling practices, for example, often induce microbial dysbiosis in the rumen that ultimately leads to incidences of sub-acute acidosis or bloat, hindering the efficiency of production, increasing feed costs, and/or increasing a reliance on chemistry based treatments, such as antibiotics.

Identifying compositions and methods for sustainably increasing beef production while balancing animal health and wellbeing have become imperative to satisfy the needs of everyday humans in an expanding population. Increasing the worldwide production of beef by scaling up the total number of beef cattle on farms would not only be economically infeasible for many parts of the world, but would further result in negative environmental consequences as the beef sector's growth and trends towards intensification and concentration have already given rise to a number of environmental concerns, led predominantly by the production of far more waste than can be managed by land disposal.

Population densities of beef cattle, particularly feedlot cattle, on large farms are often accompanied by an increased incidence of microbial pathogens that place the beef yield at risk, and further place the ultimate consumer of the beef at risk in instances of zoonotic pathogens and/or the blooming of organisms in the rumen that lead to incidences of subacute acidosis (ruminal subacute acidosis) or bloat, which further hinders the productivity of feedlot operations. Considering the widespread occurrence of many zoonotic pathogens, it is unlikely that beef can be completely protected from exposure. Research has focused on investigative means of increasing resistance to colonization in beef cattle exposed to these pathogens.

Thus, meeting global beef yield expectations, by simply scaling up current high-input agricultural systems—utilized in most of the developed world—is simply not feasible.

There is therefore an urgent need in the art for improved methods of increasing beef production, while also mitigating the colonization and spread of microbial pathogens and further increasing the desirable aspects of beef.

SUMMARY OF THE DISCLOSURE

In some aspects, the present disclosure provides isolated microbes, including novel strains of microbes, presented in Table 1 and/or Table 2.

In other aspects, the present disclosure provides isolated whole microbial cultures of the microbes identified in Table 1 and Table 2. These cultures may comprise microbes at various concentrations.

In some aspects, the disclosure provides for utilizing one or more microbes selected from Table 1 and/or Table 2 to increase a phenotypic trait of interest in beef cattle.

In some embodiments, a microbial composition comprises at least two microbial strains selected from Table 1 and/or Table 2. In another embodiment, a microbial composition is provided, said composition comprising at least one microbial strain selected from Table 1 and/or Table 2. In a further embodiment, a microbial composition comprises at least two microbial strains, wherein the at least two microbial strains comprise a 16S rRNA sequence encoded by sequences selected from SEQ ID NOs:1-5993

In some embodiments, the disclosure is drawn to a ruminant supplement capable of treating or preventing acidosis or bloat in a ruminant, comprising: a) a purified population of bacteria selected from any one or more bacteria comprising a 16S nucleic acid sequence that is at least about 97% identical to any one of SEQ ID NO:1-5993:

and b) a carrier suitable for ruminant administration; wherein the purified population of bacteria of a) is present in the supplement in an amount effective to treat or prevent acidosis or bloat in a ruminant administered the supplement, as compared to a ruminant not administered the supplement.

In some embodiments, the ruminant supplement capable of treating or preventing acidosis or bloat in a ruminant, comprising: a) a purified population of bacteria selected from: (i) *Succinivibrio* bacteria with a 16S nucleic acid sequence that is at least about 97% identical to SEQ ID NO:75, (ii) *Prevotella* bacteria with a 16S nucleic acid sequence that is at least about 97% identical to SEQ ID NO:86, and/or (iii) *Bacteroides* bacteria with a 16S nucleic acid sequence that is at least about 97% identical to SEQ ID NO:13; and b) a carrier suitable for ruminant administration; wherein the purified population of bacteria of a) is present in the supplement in an amount effective to treat or prevent acidosis or bloat in a ruminant administered the supplement, as compared to a ruminant not administered the supplement.

On some embodiments, the at least one of the bacteria are selected from: (i) *Succinivibrio* bacteria with a 16S nucleic acid sequence that is at least about 97% identical to SEQ ID NO:75, (ii)*Prevotella* bacteria with a 16S nucleic acid sequence that is at least about 97% identical to SEQ ID NO:86, and/or (iii) *Bacteroides* bacteria with a 16S nucleic acid sequence that is at least about 97% identical to SEQ ID NO:13

In one embodiment the purified population of bacteria is selected from: (i) *Succinivibrio* bacteria with a 16S nucleic acid sequence that is at least about 99% identical to SEQ ID NO:75, (ii) *Prevotella* bacteria with a 16S nucleic acid sequence that is at least about 99% identical to SEQ ID NO:86, and/or (iii) *Bacteroides* bacteria with a 16S nucleic acid sequence that is at least about 99% identical to SEQ ID NO:13.

In one embodiment, purified population of bacteria is selected from: (i) *Succinivibrio* bacteria with a 16S nucleic acid sequence comprising SEQ ID NO:75, (ii) *Prevotella* bacteria with a 16S nucleic acid sequence comprising SEQ ID NO:86, and/or (iii) *Bacteroides* bacteria with a 16S nucleic acid sequence comprising SEQ ID NO:13.

In one embodiment, the purified population of bacteria is selected from: (i) *Succinivibrio* bacteria deposited as B-67550. (ii) *Prevotella* bacteria deposited as B-67552, and/or (iii) *Bacteroides* bacteria deposited as B-67555.

In one embodiment the purified population of bacteria comprises bacteria with a 16S nucleic acid sequence that is at least about 97% identical to a nucleic acid sequence selected from the group consisting of SEQ ID NO:1-5993.

In one embodiment, the ruminant supplement further comprising a purified population of bacteria that comprises bacteria with a 16S nucleic acid sequence that is at least about 99% identical to a nucleic acid sequence selected from the group consisting of SEQ ID NO:1-5993.

In one embodiment, the ruminant supplement further comprising a purified population of bacteria that comprises bacteria with a 16S nucleic acid sequence comprising a nucleic acid sequence selected from the group consisting of SEQ ID NO:1-5993.

In one embodiment the purified population of bacteria are encapsulated in one or more of a polymer, carbohydrate, sugar, plastic, glass, polysaccharide, lipid, wax, oil, fatty acid, or glyceride.

In one embodiment, the encapsulated bacteria are vitrified. In one embodiment, the encapsulated bacteria are further encapsulated in a wax. In one embodiment, the purified population of bacteria are in the form of spores. In one embodiment, the spores are spray dried. In one embodiment, the ruminant supplement is formulated as a tablet, capsule, pill, feed additive, food ingredient, food additive, food preparation, food supplement, consumable solution, consumable spray additive, consumable solid, consumable gel, injection, bolus, or combinations thereof.

In some embodiments, the disclosure is drawn to a method for treating or preventing acidosis or bloat in a ruminant, comprising: administering to a ruminant an effective amount of a ruminant supplement comprising: a) a purified population of bacteria selected from: (i) *Succinivibrio* bacteria with a 16S nucleic acid sequence that is at least about 97% identical to SEQ ID NO:75, (ii) *Prevotella* bacteria with a 16S nucleic acid sequence that is at least about 97% identical to SEQ ID NO:86, and/or (iii) *Bacteroides* bacteria with a 16S nucleic acid sequence that is at least about 97% identical to SEQ ID NO:13; and b) a carrier suitable for ruminant administration; wherein the purified population of bacteria of a) is present in the supplement in an amount effective to treat or prevent acidosis or bloat in a ruminant administered the supplement, as compared to a ruminant not administered the supplement.

In some embodiments, at least one of the bacteria are selected from: (i) *Succinivibrio* bacteria with a 16S nucleic acid sequence that is at least about 97% identical to SEQ ID NO:75, (ii)*Prevotella* bacteria with a 16S nucleic acid sequence that is at least about 97% identical to SEQ ID NO:86, and/or (iii) *Bacteroides* bacteria with a 16S nucleic acid sequence that is at least about 97% identical to SEQ ID NO:13.

In some embodiments, the purified population of bacteria is selected from: (i) *Succinivibrio* bacteria with a 16S nucleic acid sequence that is at least about 99% identical to SEQ ID NO:75, (ii)*Prevotella* bacteria with a 16S nucleic acid sequence that is at least about 99% identical to SEQ ID NO:86, and/or (iii) *Bacteroides* bacteria with a 16S nucleic acid sequence that is at least about 99% identical to SEQ ID NO:13.

In some embodiments, the purified population of bacteria is selected from: (i) *Succinivibrio* bacteria with a 16S nucleic acid sequence comprising SEQ ID NO:75, (ii) *Prevotella* bacteria with a 16S nucleic acid sequence comprising SEQ ID NO:86, and/or (iii) *Bacteroides* bacteria with a 16S nucleic acid sequence comprising SEQ ID NO:13.

In some embodiments, the purified population of bacteria is selected from: (i) *Succinivibrio* bacteria deposited as B-67550. (ii) *Prevotella* bacteria deposited as B-67552, and/or (iii) *Bacteroides* bacteria deposited as B-67555.

In some embodiments, the ruminant supplement further comprises a purified population of bacteria that comprises bacteria with a 16S nucleic acid sequence that is at least about 97% identical to a nucleic acid sequence selected from the group consisting of SEQ ID NO:1-5993.

In some embodiments, the ruminant supplement further comprises a purified population of bacteria that comprises bacteria with a 16S nucleic acid sequence that is at least about 99% identical to a nucleic acid sequence selected from the group consisting of SEQ ID NO:1-5993.

In some embodiments, the ruminant supplement further comprises a purified population of bacteria that comprises bacteria with a 16S nucleic acid sequence comprising a nucleic acid sequence selected from the group consisting of SEQ ID NO:1-5993.

In some embodiments, the purified population of bacteria are encapsulated in one or more of a polymer, carbohydrate, sugar, sugar alcohol, surfactant, plastic, glass, polysaccharide, lipid, wax, oil, fatty acid, amino acid, or glyceride.

In one embodiment, the encapsulated bacteria are vitrified. In one embodiment, the encapsulated bacteria are further encapsulated in a wax, fat, fatty acid, fatty alcohol, or glyceride. In one embodiment, the purified population of bacteria are in the form of spores. In one embodiment, the spores are spray dried. In one embodiment, the supplement is formulated as a tablet, capsule, pill, feed additive, food ingredient, food additive, food preparation, food supplement, consumable solution, consumable spray additive, consumable solid, consumable gel, injection, bolus, or combinations thereof.

In one embodiment, the ruminant is administered to a ruminant orally. In one embodiment, the ruminant is a cow or a steer. In one embodiment, the ruminant is fed a step-up diet. In one embodiment, the ruminant is fed a finishing diet.

The ruminant supplement of claim 36, wherein the purified population of bacteria is selected from: (i) *Succinivibrio* bacteria with a 16S nucleic acid sequence that is at least about 99% identical to SEQ ID NO:75, (ii) *Prevotella* bacteria with a 16S nucleic acid sequence that is at least about 99% identical to SEQ ID NO:86, and/or (iii) *Bacteroides* bacteria with a 16S nucleic acid sequence that is at least about 99% identical to SEQ ID NO:13.

In some embodiments, the purified population of bacteria is selected from: (i) *Succinivibrio* bacteria with a 16S nucleic acid sequence comprising SEQ ID NO:75, (ii) *Prevotella* bacteria with a 16S nucleic acid sequence comprising SEQ ID NO:86, and/or (iii) *Bacteroides* bacteria with a 16S nucleic acid sequence comprising SEQ ID NO:13.

In some embodiments, the purified population of bacteria is selected from (i) *Succinivibrio* bacteria deposited as B-67550, (ii) *Prevotella* bacteria deposited as B-67552, and/or (iii) *Bacteroides* bacteria deposited as B-67555.

In some embodiments, the ruminant supplement further comprises a purified population of bacteria that comprises bacteria with a 16S nucleic acid sequence that is at least about 97% identical to a nucleic acid sequence selected from the group consisting of SEQ ID NO:1-5993.

In some embodiments, the ruminant supplement further comprises a purified population of bacteria that comprises bacteria with a 16S nucleic acid sequence that is at least about 99% identical to a nucleic acid sequence selected from the group consisting of SEQ ID NO:1-5993.

In some embodiments, the ruminant supplement further comprises a purified population of bacteria that comprises bacteria with a 16S nucleic acid sequence comprising a nucleic acid sequence selected from the group consisting of SEQ ID NO:1-5993.

In some embodiments, the purified population of bacteria are encapsulated in one or more of a polymer, carbohydrate, sugar, sugar alcohol, surfactant, plastic, glass, polysaccharide, lipid, wax, oil, fatty acid, amino acid, or glyceride. In some embodiment, the encapsulated bacteria are vitrified. In one embodiment, the encapsulated bacteria are further encapsulated in a wax, fat, fatty acid, fatty alcohol, or glyceride.

In one embodiment, the purified population of bacteria are in the form of spores. In one embodiment, the spores are spray dried. In one embodiment, the ruminant supplement is formulated as a tablet, capsule, pill, feed additive, food ingredient, food additive, food preparation, food supplement, consumable solution, consumable spray additive, consumable solid, consumable gel, injection, bolus, or combinations thereof.

In some embodiments, the disclosure is drawn to a method of decreasing the amount of carbon dioxide and/or carbonic acid in the rumen of a ruminant, comprising: administering to a ruminant an effective amount of a ruminant supplement comprising: a) a purified population of bacteria selected from any one or more bacteria comprising a 16S nucleic acid sequence that is at least about 97% identical to any one of SEQ ID NO:1-5993; and b) a carrier suitable for ruminant administration; wherein the purified population of bacteria of a) is present in the supplement in an amount effective to decrease the amount of carbon dioxide and/or carbonic acid in the rumen of a ruminant administered the supplement, as compared to a ruminant not administered the supplement.

In some embodiments, the disclosure is drawn to a method of decreasing the amount of carbon dioxide and/or carbonic acid in the rumen of a ruminant, comprising: administering to a ruminant an effective amount of a ruminant supplement comprising: a) a purified population of bacteria selected from: (i) *Succinivibrio* bacteria with a 16S nucleic acid sequence that is at least about 97% identical to SEQ ID NO:75, (ii) *Prevotella* bacteria with a 16S nucleic acid sequence that is at least about 97% identical to SEQ ID NO:86, and/or (iii) *Bacteroides* bacteria with a 16S nucleic acid sequence that is at least about 97% identical to SEQ ID NO:13; and b) a carrier suitable for ruminant administration; wherein the purified population of bacteria of a) is present in the supplement in an amount effective to decrease the amount of carbon dioxide and/or carbonic acid in the rumen of a ruminant administered the supplement, as compared to a ruminant not administered the supplement.

In one embodiment, at least one of the bacteria are selected from: (i) *Succinivibrio* bacteria with a 16S nucleic acid sequence that is at least about 97% identical to SEQ ID NO:75, (ii) *Prevotella* bacteria with a 16S nucleic acid sequence that is at least about 97% identical to SEQ ID NO:86, and/or (iii) *Bacteroides* bacteria with a 16S nucleic acid sequence that is at least about 97% identical to SEQ ID NO:13.

In one embodiment, the purified population of bacteria is selected from: (i) *Succinivibrio* bacteria with a 16S nucleic acid sequence that is at least about 99% identical to SEQ ID NO:75, (ii)*Prevotella* bacteria with a 16S nucleic acid sequence that is at least about 99% identical to SEQ ID NO:86, and/or (iii) *Bacteroides* bacteria with a 16S nucleic acid sequence that is at least about 99% identical to SEQ ID NO:13.

In one embodiment, the purified population of bacteria is selected from: (i) *Succinivibrio* bacteria with a 16S nucleic acid sequence comprising SEQ ID NO:75, (ii) *Prevotella* bacteria with a 16S nucleic acid sequence comprising SEQ ID NO:86, and/or (iii) *Bacteroides* bacteria with a 16S nucleic acid sequence comprising SEQ ID NO:13.

In one embodiment, the purified population of bacteria is selected from: (i) *Succinivibrio* bacteria deposited as B-67550. (ii) *Prevotella* bacteria deposited as B-67552, and/or (iii) *Bacteroides* bacteria deposited as B-67555.

In one embodiment, the ruminant supplement further comprises a purified population of bacteria that comprises bacteria with a 16S nucleic acid sequence that is at least about 97% identical to a nucleic acid sequence selected from the group consisting of SEQ ID NO:1-5993.

In one embodiment, the ruminant supplement further comprises a purified population of bacteria that comprises bacteria with a 16S nucleic acid sequence that is at least about 99% identical to a nucleic acid sequence selected from the group consisting of SEQ ID NO:1-5993.

In one embodiment, the ruminant supplement further comprises a purified population of bacteria that comprises bacteria with a 16S nucleic acid sequence comprising a nucleic acid sequence selected from the group consisting of SEQ ID NO:1-5993.

In one embodiment, the purified population of bacteria are encapsulated in one or more of a polymer, carbohydrate, sugar, sugar alcohol, surfactant, plastic, glass, polysaccharide, lipid, wax, oil, fatty acid, amino acid, or glyceride.

In one embodiment, the encapsulated bacteria are vitrified. In one embodiment, the encapsulated bacteria are further encapsulated in a wax, fat, fatty acid, fatty alcohol, or glyceride. The method of claim 51, wherein the purified population of bacteria are in the form of spores. The method of claim 62, wherein the spores are spray dried.

In one embodiment, the ruminant supplement is formulated as a tablet, capsule, pill, feed additive, food ingredient, food additive, food preparation, food supplement, consumable solution, consumable spray additive, consumable solid, consumable gel, injection, bolus, or combinations thereof.

In one embodiment, the ruminant is administered to a ruminant orally. In one embodiment, the ruminant is a cow or a steer. In one embodiment, the ruminant is fed a step-up diet. In one embodiment, the ruminant is fed a finishing diet.

In one embodiment, the disclosure is drawn to a ruminant supplement capable of increasing the amount of meat marbling in a ruminant, comprising: a) a purified population of bacteria selected from any one or more bacteria comprising a 16S nucleic acid sequence that is at least about 97% identical to any one of SEQ ID NO:1-5993: and b) a carrier suitable for ruminant administration; wherein the purified population of bacteria of a) is present in the supplement in an amount effective to increase the amount of meat marbling in the ruminant administered the supplement, as compared to a ruminant not administered the supplement.

In one embodiment, the disclosure is drawn to a ruminant supplement capable of increasing the amount of meat marbling in a ruminant, comprising: a) a purified population of bacteria selected from: (i) *Succinivibrio* bacteria with a 16S nucleic acid sequence that is at least about 97% identical to SEQ ID NO:75, (ii) *Prevotella* bacteria with a 16S nucleic acid sequence that is at least about 97% identical to SEQ ID NO:86, and/or (iii) *Bacteroides* bacteria with a 16S nucleic acid sequence that is at least about 97% identical to SEQ ID NO:13; and b) a carrier suitable for ruminant administration; wherein the purified population of bacteria of a) is present in the supplement in an amount effective to increase the amount of meat marbling in the ruminant administered the supplement, as compared to a ruminant not administered the supplement.

In one embodiment, the least one of the bacteria are selected from: (i) *Succinivibrio* bacteria with a 16S nucleic acid sequence that is at least about 97% identical to SEQ ID NO:75, (ii) *Prevotella* bacteria with a 16S nucleic acid sequence that is at least about 97% identical to SEQ ID NO:86, and/or (iii) *Bacteroides* bacteria with a 16S nucleic acid sequence that is at least about 97% identical to SEQ ID NO:13.

In one embodiment, the purified population of bacteria is selected from: (i) *Succinivibrio* bacteria with a 16S nucleic acid sequence that is at least about 99% identical to SEQ ID NO:75, (ii)*Prevotella* bacteria with a 16S nucleic acid sequence that is at least about 99% identical to SEQ ID NO:86, and/or (iii) *Bacteroides* bacteria with a 16S nucleic acid sequence that is at least about 99% identical to SEQ ID NO:13.

In one embodiment, the purified population of bacteria is selected from: (i) *Succinivibrio* bacteria with a 16S nucleic acid sequence comprising SEQ ID NO:75, (ii) *Prevotella* bacteria with a 16S nucleic acid sequence comprising SEQ ID NO:86, and/or (iii) *Bacteroides* bacteria with a 16S nucleic acid sequence comprising SEQ ID NO:13.

In one embodiment, the purified population of bacteria is selected from: (i) *Succinivibrio* bacteria deposited as B-67550, (ii) *Prevotella* bacteria deposited as B-67552, and/or (iii) *Bacteroides* bacteria deposited as B-67555.

In one embodiment, the rumen supplement further comprises a purified population of bacteria that comprises bacteria with a 16S nucleic acid sequence that is at least about 97% identical to a nucleic acid sequence selected from the group consisting of SEQ ID NO:1-5993.

In one embodiment, the rumen supplement further comprises a purified population of bacteria that comprises bacteria with a 16S nucleic acid sequence that is at least about 99% identical to a nucleic acid sequence selected from the group consisting of SEQ ID NO:1-5993.

In one embodiment, the rumen supplement further comprising a purified population of bacteria that comprises bacteria with a 16S nucleic acid sequence comprising a nucleic acid sequence selected from the group consisting of SEQ ID NO:1-5993.

In one embodiment, the purified population of bacteria are encapsulated in one or more of a polymer, carbohydrate, sugar, sugar alcohol, surfactant, plastic, glass, polysaccharide, lipid, wax, oil, fatty acid, amino acid, or glyceride.

In one embodiment, the encapsulated bacteria are vitrified. In one embodiment, the encapsulated bacteria are further encapsulated in a wax, fat, fatty acid, fatty alcohol, or glyceride. In one embodiment, the purified population of bacteria are in the form of spores. In one embodiment, the spores are spray dried.

In one embodiment, the rumen supplement is formulated as a tablet, capsule, pill, feed additive, food ingredient, food additive, food preparation, food supplement, consumable solution, consumable spray additive, consumable solid, consumable gel, injection, bolus, or combinations thereof.

In some embodiments, the disclosure is drawn to a method increasing the amount of meat marbling in a ruminant, comprising: administering to a ruminant an effective amount of a ruminant supplement comprising: a) a purified population of bacteria selected from any one or more bacteria comprising a 16S nucleic acid sequence that is at least about 97% identical to any one of SEQ ID NO:1-5993; and b) a carrier suitable for ruminant administration; wherein the purified population of bacteria of a) is present in the supplement in an amount effective to increase the amount of meat marbling in the ruminant administered the supplement, as compared to a ruminant not administered the supplement.

In some embodiments, the disclosure is drawn to a method increasing the amount of meat marbling in a ruminant, comprising: administering to a ruminant an effective amount of a ruminant supplement comprising: a) a purified population of bacteria selected from: (i) *Succinivibrio* bacteria with a 16S nucleic acid sequence that is at least about 97% identical to SEQ ID NO:75, (ii)*Prevotella* bacteria with a 16S nucleic acid sequence that is at least about 97% identical to SEQ ID NO:86, and/or (iii) *Bacteroides* bacteria with a 16S nucleic acid sequence that is at least about 97% identical to SEQ ID NO:13; and b) a carrier suitable for ruminant administration; wherein the purified population of bacteria of a) is present in the supplement in an amount effective to increase the amount of meat marbling in the ruminant administered the supplement, as compared to a ruminant not administered the supplement.

In one embodiment, at least one of the bacteria are selected from: (i) *Succinivibrio* bacteria with a 16S nucleic acid sequence that is at least about 97% identical to SEQ ID NO:75, (ii) *Prevotella* bacteria with a 16S nucleic acid sequence that is at least about 97% identical to SEQ ID NO:86, and/or (iii) *Bacteroides* bacteria with a 16S nucleic acid sequence that is at least about 97% identical to SEQ ID NO:13.

In one embodiment, the purified population of bacteria is selected from: (i) *Succinivibrio* bacteria with a 16S nucleic acid sequence that is at least about 99% identical to SEQ ID NO:75, (ii) *Prevotella* bacteria with a 16S nucleic acid sequence that is at least about 99% identical to SEQ ID NO:86, and/or (iii) *Bacteroides* bacteria with a 16S nucleic acid sequence that is at least about 99% identical to SEQ ID NO:13.

In one embodiment, the purified population of bacteria is selected from: (i) *Succinivibrio* bacteria with a 16S nucleic acid sequence comprising SEQ ID NO:75, (ii) *Prevotella* bacteria with a 16S nucleic acid sequence comprising SEQ ID NO:86, and/or (iii) *Bacteroides* bacteria with a 16S nucleic acid sequence comprising SEQ ID NO:13.

In one embodiment, the purified population of bacteria is selected from: (i) *Succinivibrio* bacteria deposited as B-67550, (ii) *Prevotella* bacteria deposited as B-67552, and/or (iii) *Bacteroides* bacteria deposited as B-67555.

In one embodiment, the ruminant supplement further comprises a purified population of bacteria that comprises bacteria with a 16S nucleic acid sequence that is at least about 97% identical to a nucleic acid sequence selected from the group consisting of SEQ ID NO:5993.

In one embodiment, the ruminant supplement further comprises a purified population of bacteria that comprises bacteria with a 16S nucleic acid sequence that is at least about 99% identical to a nucleic acid sequence selected from the group consisting of SEQ ID NO:5993.

In one embodiment, the ruminant supplement further comprises a purified population of bacteria that comprises bacteria with a 16S nucleic acid sequence comprising a nucleic acid sequence selected from the group consisting of SEQ ID NO:1-5993.

In one embodiment, the purified population of bacteria are encapsulated in one or more of a polymer, carbohydrate, sugar, sugar alcohol, surfactant, plastic, glass, polysaccharide, lipid, wax, oil, fatty acid, amino acid, or glyceride.

In one embodiment, the encapsulated bacteria are vitrified. In one embodiment, the encapsulated bacteria are further encapsulated in a wax. On one embodiment, the purified population of bacteria are in the form of spores. In one embodiment, the spores are spray dried.

In one embodiment, the ruminant supplement is formulated as a tablet, capsule, pill, feed additive, food ingredient, food additive, food preparation, food supplement, consumable solution, consumable spray additive, consumable solid, consumable gel, injection, bolus, or combinations thereof. In one embodiment, the ruminant supplement is administered to a ruminant orally. In one embodiment, the ruminant is a cow or a steer. In one embodiment, the ruminant is fed a step-up diet. In one embodiment the ruminant is fed a finishing diet. In one embodiment, the increase in meat marbling is an increase of at least 10%.

In some embodiments, the disclosure is drawn to a ruminant supplement capable of increasing feed efficiency in a ruminant, comprising: a) a purified population of bacteria selected from any one or more bacteria comprising a 16S nucleic acid sequence that is at least about 97% identical to any one of SEQ ID NO:1-5993: and b) a carrier suitable for ruminant administration; wherein the purified population of bacteria of a) is present in the supplement in an amount effective to increase feed efficiency in a ruminant administered the supplement, as compared to a ruminant not administered the supplement.

In some embodiments, the disclosure is drawn to a ruminant supplement capable of increasing feed efficiency in a ruminant, comprising: a) a purified population of bacteria selected from: (i) *Succinivibrio* bacteria with a 16S nucleic acid sequence that is at least about 97% identical to SEQ ID NO:75, (ii) *Prevotella* bacteria with a 16S nucleic acid sequence that is at least about 97% identical to SEQ ID NO:86, and/or (iii) *Bacteroides* bacteria with a 16S nucleic acid sequence that is at least about 97% identical to SEQ ID NO:13; and b) a carrier suitable for ruminant administration; wherein the purified population of bacteria of a) is present in the supplement in an amount effective to increase feed efficiency in a ruminant administered the supplement, as compared to a ruminant not administered the supplement.

In some embodiments, the at least one of the bacteria are selected from: (i) *Succinivibrio* bacteria with a 16S nucleic acid sequence that is at least about 97% identical to SEQ ID NO:75, (ii)*Prevotella* bacteria with a 16S nucleic acid sequence that is at least about 97% identical to SEQ ID NO:86, and/or (iii) *Bacteroides* bacteria with a 16S nucleic acid sequence that is at least about 97% identical to SEQ ID NO:13.

In some embodiments, the disclosure is drawn to a method for increasing feed efficiency in a ruminant, comprising: administering to a ruminant an effective amount of a ruminant supplement comprising: a) a purified population of bacteria selected from any one or more bacteria comprising a 16S nucleic acid sequence that is at least about 97% identical to any one of SEQ ID NO:1-5993; and b) a carrier suitable for ruminant administration; wherein the purified population of bacteria of a) is present in the supplement in an amount effective to increase feed efficiency in a ruminant administered the supplement, as compared to a ruminant not administered the supplement.

In some embodiments, the method increasing feed efficiency in a ruminant comprises: administering to a ruminant an effective amount of a ruminant supplement comprising: a) a purified population of bacteria selected from: (i) *Succinivibrio* bacteria with a 16S nucleic acid sequence that is at least about 97% identical to SEQ ID NO:75, (ii) *Prevotella* bacteria with a 16S nucleic acid sequence that is at least about 97% identical to SEQ ID NO:86, and/or (iii) *Bacteroides* bacteria with a 16S nucleic acid sequence that is at least about 97% identical to SEQ ID NO:13; and b) a carrier suitable for ruminant administration; wherein the purified population of bacteria of a) is present in the supplement in an amount effective to increase feed efficiency in a ruminant administered the supplement, as compared to a ruminant not administered the supplement.

In some embodiments, the at least one of the bacteria are selected from: (i) *Succinivibrio* bacteria with a 16S nucleic acid sequence that is at least about 97% identical to SEQ ID NO:75, (ii) *Prevotella* bacteria with a 16S nucleic acid sequence that is at least about 97% identical to SEQ ID NO:86, and/or (iii) *Bacteroides* bacteria with a 16S nucleic acid sequence that is at least about 97% identical to SEQ ID NO:13.

In some embodiments, the ruminant supplement capable of increasing performance in a ruminant, comprising: a) a purified population of bacteria selected from any one or more bacteria comprising a 16S nucleic acid sequence that is at least about 97% identical to any one of SEQ ID NO:1-5993: and b) a carrier suitable for ruminant administration; wherein the purified population of bacteria of a) is present in the supplement in an amount effective to increase performance in a ruminant administered the supplement, as compared to a ruminant not administered the supplement.

In some embodiments, the ruminant supplement capable of increasing performance in a ruminant, comprising: a) a purified population of bacteria selected from: (i) *Succinivibrio* bacteria with a 16S nucleic acid sequence that is at least about 97% identical to SEQ ID NO:75, (ii) *Prevotella* bacteria with a 16S nucleic acid sequence that is at least about 97% identical to SEQ ID NO:86, and/or (iii) *Bacteroides* bacteria with a 16S nucleic acid sequence that is at least about 97% identical to SEQ ID NO:13; and b) a carrier suitable for ruminant administration; wherein the purified population of bacteria of a) is present in the supplement in an amount effective to increase performance in a ruminant administered the supplement, as compared to a ruminant not administered the supplement.

In some embodiments, at least one of the bacteria are selected from: (i) *Succinivibrio* bacteria with a 16S nucleic acid sequence that is at least about 97% identical to SEQ ID NO:75, (ii)*Prevotella* bacteria with a 16S nucleic acid sequence that is at least about 97% identical to SEQ ID NO:86, and/or (iii) *Bacteroides* bacteria with a 16S nucleic acid sequence that is at least about 97% identical to SEQ ID NO:13.

In some embodiments, the disclosure is drawn to a ruminant supplement capable of reducing methane production and emission in a ruminant, comprising: a) a purified population of bacteria selected from any one or more bacteria comprising a 16S nucleic acid sequence that is at least about 97% identical to any one of SEQ ID NO:1-5993: and b) a carrier suitable for ruminant administration; wherein the purified population of bacteria of a) is present in the supplement in an amount effective to reduce methane production and emission in a ruminant administered the supplement, as compared to a ruminant not administered the supplement.

In some embodiments, the disclosure is drawn to a ruminant supplement capable of reducing methane production and emission in a ruminant, comprising: a) a purified population of bacteria selected from: (i) *Succinivibrio* bacteria with a 16S nucleic acid sequence that is at least about 97% identical to SEQ ID NO:75, (ii) *Prevotella* bacteria with a 16S nucleic acid sequence that is at least about 97% identical to SEQ ID NO:86, and/or (iii) *Bacteroides* bacteria with a 16S nucleic acid sequence that is at least about 97% identical to SEQ ID NO:13; and b) a carrier suitable for ruminant administration; wherein the purified population of bacteria of a) is present in the supplement in anamount effective to reduce methane production and emission in a ruminant administered the supplement, as compared to a ruminant not administered the supplement.

In some embodiments, at least one of the bacteria are selected from: (i) *Succinivibrio* bacteria with a 16S nucleic acid sequence that is at least about 97% identical to SEQ ID NO:75, (ii)*Prevotella* bacteria with a 16S nucleic acid sequence that is at least about 97% identical to SEQ ID NO:86, and/or (iii) *Bacteroides* bacteria with a 16S nucleic acid sequence that is at least about 97% identical to SEQ ID NO:13.

In some embodiments, the disclosure is drawn to a ruminant supplement capable of reducing methane production and emission in a ruminant, comprising: a) a purified population of bacteria selected from any one or more bacteria comprising a 16S nucleic acid sequence that is at least about 97% identical to any one of SEQ ID NO:1-5993: and b) a carrier suitable for ruminant administration; wherein the purified population of bacteria of a) is present in the supplement in an amount effective to reduce methane production and emission in a ruminant administered the supplement, as compared to a ruminant not administered the supplement.

In some embodiments, the disclosure is drawn to a ruminant supplement capable of reducing methane production and emission in a ruminant, comprising: a) a purified population of bacteria selected from: (i) *Succinivibrio* bacteria with a 16S nucleic acid sequence that is at least about 97% identical to SEQ ID NO:75, (ii) *Prevotella* bacteria with a 16S nucleic acid sequence that is at least about 97% identical to SEQ ID NO:86, and/or (iii) *Bacteroides* bacteria with a 16S nucleic acid sequence that is at least about 97% identical to SEQ ID NO:13; and b) a carrier suitable for ruminant administration; wherein the purified population of bacteria of a) is present in the supplement in an amount effective to reduce methane production and emission in a ruminant administered the supplement, as compared to a ruminant not administered the supplement.

In some embodiments, the at least one of the bacteria are selected from: (i) *Succinivibrio* bacteria with a 16S nucleic acid sequence that is at least about 97% identical to SEQ ID NO:75, (ii)*Prevotella* bacteria with a 16S nucleic acid sequence that is at least about 97% identical to SEQ ID NO:86, and/or (iii) *Bacteroides* bacteria with a 16S nucleic acid sequence that is at least about 97% identical to SEQ ID NO:13.

In some embodiments, the microbes are administered with a prebiotic, a vitamin, or a mineral. In some embodiments, the microbes are administered with vitamin B or a precursor thereof.

Budapest Treaty on the International Recognition of the Deposit of Microorganisms for the Purpose of Patent Procedures The microorganisms described in this application were deposited with (1) the American Type Culture Collection (ATCC®), located at 10801 University Blvd., Manassas, VA 20110, USA; and the United States Department of Agriculture (USDA) Agricultural Research Service (ARS) Culture Collection (NRRL®), located at 1815 N. University St., Peoria, IL 61604, USA The deposits were made under the terms of the Budapest Treaty on the International Recognition of the Deposit of Microorganisms for the Purposes of Patent Procedure. The ATCC and NRRL accession numbers for the aforementioned Budapest Treaty deposits are provided in Table 1. The Accession numbers and corresponding dates of deposit for the microorganisms described in this application are separately provided in Table 2.

The strains designated in the below table have been deposited in the labs of Ascus Biosciences, Inc. since at least Apr. 22, 2017, and August 2017.

In Table 1, the closest predicted hits for taxonomy of the microbes are listed in columns 2, and 5. Column 2 is the top taxonomic hit predicted by BLAST, and column 5 is the top taxonomic hit for genus+species predicted by BLAST. The strains designated in the below table have been deposited in the labs of Ascus Biosciences, Inc. since at least Apr. 22, 2017, and August, 2017.

TABLE 1

Microbes of the present disclosure, including bacteria (1-190).

| Predicted Closest Taxa of Isolated Microbes | BLAST Taxonomic Top Hit w/Genus + Species | BLAST % Ident. | Query Cover | Strain Designation | Sequence Identifier for Associated Marker | MIC Score |
|---|---|---|---|---|---|---|
| 1. *Prevotella* (genus) | *Prevotella ruminicola* | 93% | 98% | Ascusbbf_6176 | SEQ ID NO: 1 | 1 |
| 2. *Prevotella* (genus) | *Prevotella loescheii* | 88% | 99% | Ascusbbf_22143 | SEQ ID NO: 2 | 1 |
| 3. *Prevotella* (genus) | *Prevotella ruminicola* | 91% | 100% | Ascusbbf_4883 | SEQ ID NO: 3 | 0.97095 |
| 4. *Selenomonas* (genus) | *Selenomonas ruminantium* | 93% | 95% | Ascusbbf_13543 | SEQ ID NO: 4 | 0.97095 |
| 5. *Clostridium* XIVa (Cluster) | *Oscillibacter valericigenes* | 92% | 100% | Ascusbbf_152 | SEQ ID NO: 5 | 0.88129 |
| 6. *Clostridium* XIVa (Cluster) | *Oscillibacter valericigenes* | | | Ascusbbf_152A | SEQ ID NO: 5398 | 0.88129 |
| 7. *Prevotella* (genus) | *Prevotella ruminicola* | 94% | 100% | Ascusbbf_707 | SEQ ID NO: 6 | 0.88129 |
| 8. *Fibrobacter* (genus) | *Fibrobacter intestinalis* | 99% | 100% | Ascusbbf_1238 | SEQ ID NO: 7 | 0.88129 |
| 9. *Prevotella* (genus) | *Prevotella ruminicola* | 89% | 100% | Ascusbbf_5588 | SEQ ID NO: 8 | 0.88129 |
| 10. *Saccharofermentans* (genus) | *Saccharofermentans acetigenes* | 86% | 100% | Ascusbbf_4691 | SEQ ID NO: 9 | 0.88129 |
| 11. *Saccharofermentans* (genus) | *Saccharofermentans acetigenes* | | | Ascusbbf_4691C | SEQ ID NO: 5425 | 0.88129 |
| 12. *Saccharofermentans* (genus) | *Intestinimonas butyriciproducens* | 86% | 100% | Ascusbbf_59499 | SEQ ID NO: 10 | 0.88129 |
| 13. *Bacillus* (genus) | *Brevibacillus brevis* | 86% | 89% | Ascusbbf_9770 | SEQ ID NO: 11 | 0.88129 |
| 14. *Spirochaeta* (genus) | *Treponema parvum* | 88% | 92% | Ascusbbf_123632 | SEQ ID NO: 12 | 0.88129 |
| 15. *Bacteroides* (genus) | *Bacteroides xylanisolvens* | 99% | 97% | Ascusbbf_14146 | SEQ ID NO: 13 | 0.78606 |
| 16. *Lachnospiracea incertae sedis* (genus) | *Desulfotomaculum* sp. | 94% | 100% | Ascusbbf_1103 | SEQ ID NO: 14 | 0.67032 |
| 17. *Clostridium* XIVa (Cluster) | *Lachnoclostridium pacaense* | 89% | 100% | Ascusbbf_498 | SEQ ID NO: 15 | 0.66823 |
| 18. *Prevotella* (genus) | *Prevotella oralis* | 89% | 100% | Ascusbbf_13717 | SEQ ID NO: 16 | 0.65415 |
| 19. *Prevotella* (genus) | *Prevotella oralis* | | | Ascusbbf_13717A | SEQ ID NO: 5450 | 0.65415 |
| 20. *Clostridium* XIVa (Cluster) | *Coprococcus catus* | 90% | 97% | Ascusbbf_876 | SEQ ID NO: 17 | 0.65106 |
| 21. *Bacteroides* (genus) | *Bacteroides uniformis* | 89% | 100% | Ascusbbf_612 | SEQ ID NO: 18 | 0.65002 |
| 22. *Selenomonas* (genus) | *Selenomonas ruminantium* | 97% | 100% | Ascusbbf_4936 | SEQ ID NO: 19 | 0.63816 |
| 23. *Selenomonas* (genus) | *Selenomonas ruminantium* | | | Ascusbbf_4936A | SEQ ID NO: 5460 | 0.63816 |
| 24. *Prevotella* (genus) | *Prevotella oulorum* | 92% | 100% | Ascusbbf_6809 | SEQ ID NO: 20 | 0.6337 |
| 25. *Clostridium* XIVa (Cluster) | *Clostridium aminophilum* | 91% | 100% | Ascusbbf_113152 | SEQ ID NO: 21 | 0.63008 |
| 26. *Clostridium* XIVa (Cluster) | *Clostridium aminophilum* | | | Ascusbbf_113152A | SEQ ID NO: 5462 | 0.63008 |
| 27. *Ruminococcus* (genus) | *Ruminococcus bromii* | 99% | 96% | Ascusbbf_18 | SEQ ID NO: 22 | 0.62713 |
| 28. *Prevotella* (genus) | *Prevotella ruminicola* | 94% | 100% | Ascusbbf_9031 | SEQ ID NO: 23 | 0.62075 |
| 29. *Spirochaeta* (genus) | *Treponema brennaborense* | 86% | 98% | Ascusbbf_11823 | SEQ ID NO: 24 | 0.61287 |
| 30. *Butyricimonas* (genus) | *Porphyromonadaceae* | 87% | 98% | Ascusbbf_1007 | SEQ ID NO: 25 | 0.60495 |
| 31. *Butyricimonas* (genus) | *Porphyromonadaceae* | | | Ascusbbf_1007A | SEQ ID NO: 5473 | 0.60495 |
| 32. *Prevotella* (genus) | *Prevotella baroniae* | 87% | 99% | Ascusbbf_24422 | SEQ ID NO: 26 | 0.59156 |
| 33. *Prevotella* (genus) | *Prevotella baroniae* | | | Ascusbbf_24422A | SEQ ID NO: 5474 | 0.59156 |
| 34. *Olsenella* (genus) | *Olsenella umbonata* | 99% | 100% | Ascusbbf_951 | SEQ ID NO: 27 | 0.59007 |
| 35. *Clostridium* XIVa (Cluster) | [*Clostridium*] *symbiosum* | 96% | 100% | Ascusbbf_80169 | SEQ ID NO: 28 | 0.58852 |
| 36. *Spirochaeta* (genus) | *Treponema bryantii* | 90% | 97% | Ascusbbf_5699 | SEQ ID NO: 29 | 0.58423 |
| 37. *Spirochaeta* (genus) | *Treponema bryantii* | | | Ascusbbf_5699B | SEQ ID NO: 5483 | 0.58423 |
| 38. *Prevotella* (genus) | *Prevotella ruminicola* | 91% | 100% | Ascusbbf_130 | SEQ ID NO: 30 | 0.58333 |
| 39. *Acidaminococcus* (genus) | *Acidaminococcus fermentans* | 95% | 100% | Ascusbbf_10109 | SEQ ID NO: 31 | 0.58267 |
| 40. *Parabacteroides* (genus) | *Culturomica massiliensis* | 86% | 89% | Ascusbbf_29797 | SEQ ID NO: 32 | 0.58241 |
| 41. *Parabacteroides* (genus) | *Culturomica massiliensis* | | | Ascusbbf_29797A | SEQ ID NO: 5502 | 0.58241 |
| 42. *Clostridium sensu stricto* (genus) | *Christensenella timonensis* | 86% | 99% | Ascusbbf_24410 | SEQ ID NO: 33 | 0.58142 |
| 43. *Oribacterium* (genus) | *Oribacterium sinus* | 91% | 99% | Ascusbbf_54068 | SEQ ID NO: 34 | 0.58113 |
| 44. *Clostridium* XIVa (Cluster) | [*Clostridium*] *bolteae* | 93% | 100% | Ascusbbf_7003 | SEQ ID NO: 35 | 0.58059 |
| 45. *Pseudoflavonifractor* (genus) | *Intestinimonas butyriciproducens* | 89% | 100% | Ascusbbf_23 | SEQ ID NO: 36 | 0.57785 |
| 46. *Prevotella* (genus) | *Prevotella ruminicola* | 90% | 100% | Ascusbbf_1697 | SEQ ID NO: 37 | 0.57337 |
| 47. *Prevotella* (genus) | *Prevotella ruminicola* | | | Ascusbbf_1697B | SEQ ID NO: 5511 | 0.57337 |
| 48. *Treponema* (genus) | *Treponema zioleckii* | 99% | 99% | Ascusbbf_24513 | SEQ ID NO: 38 | 0.5696 |
| 49. *Prevotella* (genus) | *Prevotella oralis* | 89% | 100% | Ascusbbf_7586 | SEQ ID NO: 39 | 0.56896 |
| 50. *Butyricimonas* (genus) | *Barnesiella viscericola* | 85% | 91% | Ascusbbf_27854 | SEQ ID NO: 40 | 0.56657 |

TABLE 1-continued

Microbes of the present disclosure, including bacteria (1-190).

| Predicted Closest Taxa of Isolated Microbes | BLAST Taxonomic Top Hit w/Genus + Species | BLAST % Ident. | Query Cover | Strain Designation | Sequence Identifier for Associated Marker | MIC Score |
| --- | --- | --- | --- | --- | --- | --- |
| 51. *Saccharofermentans* (genus) | *Oscillibacter valericigenes* | 87% | 100% | Ascusbbf_1034 | SEQ ID NO: 41 | 0.56476 |
| 52. *Saccharofermentans* (genus) | *Oscillibacter valericigenes* | | | Ascusbbf_1034A | SEQ ID NO: 5517 | 0.56476 |
| 53. *Butyricimonas* (genus) | *Butyricimonas virosa* | 82% | 100% | Ascusbbf_23134 | SEQ ID NO: 42 | 0.56219 |
| 54. *Butyricimonas* (genus) | *Butyricimonas virosa* | | | Ascusbbf_23134A | SEQ ID NO: 5519 | 0.56219 |
| 55. *Rhodobacter* (genus) | *Gemmobacter intermedius* | 99% | 87% | Ascusbbf_7027 | SEQ ID NO: 43 | 0.56127 |
| 56. *Prevotella* (genus) | *Butyricimonas virosa* | 84% | 92% | Ascusbbf_43679 | SEQ ID NO: 44 | 0.56056 |
| 57. *Fluviicola* (genus) | *Anaerocella delicata* | 85% | 87% | Ascusbbf_63954 | SEQ ID NO: 45 | 0.55952 |
| 58. *Fluviicola* (genus) | *Anaerocella delicata* | | | Ascusbbf_63954A | SEQ ID NO: 5526 | 0.55952 |
| 59. *Succiniclasticum* (genus) | *Succiniclasticum ruminis* | 95% | 95% | Ascusbbf_1517 | SEQ ID NO: 46 | 0.55908 |
| 60. *Solobacterium* (genus) | *Solobacterium moorei* | 91% | 99% | Ascusbbf_104 | SEQ ID NO: 47 | 0.55759 |
| 61. *Clostridium* XIVa (Cluster) | [*Clostridium*] *lavalense* | 90% | 100% | Ascusbbf_148 | SEQ ID NO: 48 | 0.55551 |
| 62. *Prevotella* (genus) | *Prevotella bryantii* | 99% | 100% | Ascusbbf_944 | SEQ ID NO: 49 | 0.55265 |
| 63. *Lachnospiracea incertae sedis* (genus) | *Eubacterium oxidoreducens* | 90% | 100% | Ascusbbf_76009 | SEQ ID NO: 50 | 0.55253 |
| 64. *Veillonella* (genus) | *Holdemania filiformis* | 84% | 96% | Ascusbbf_23033 | SEQ ID NO: 51 | 0.55253 |
| 65. *Cellulosimicrobium* (genus) | *Cellulosimicrobium cellulans* | 95% | 100% | Ascusbbf_20389 | SEQ ID NO: 52 | 0.55131 |
| 66. *Cupriavidus* (genus) | *Sutterella wadsworthensis* | 92% | 100% | Ascusbbf_2600 | SEQ ID NO: 53 | 0.54892 |
| 67. *Bacteroides* (genus) | *Paraprevotella xylaniphila* | 86% | 92% | Ascusbbf_8118 | SEQ ID NO: 54 | 0.54888 |
| 68. *Prevotella* (genus) | *Prevotella ruminicola* | 92% | 100% | Ascusbbf_201 | SEQ ID NO: 55 | 0.54656 |
| 69. *Prevotella* (genus) | *Prevotella ruminicola* | | | Ascusbbf_20IK | SEQ ID NO: 5576 | 0.54656 |
| 70. *Spirochaeta* (genus) | *Treponema saccharophilum* | 88% | 100% | Ascusbbf_6315 | SEQ ID NO: 56 | 0.54535 |
| 71. *Megasphaera* (genus) | *Megasphaera elsdenii* | 99% | 100% | Ascusbbf_10712 | SEQ ID NO: 57 | 0.54494 |
| 72. *Megasphaera* (genus) | *Megasphaera elsdenii* | | | Ascusbbf_10712E | SEQ ID NO: 5582 | 0.54494 |
| 73. *Succinivibrio* (genus) | *Succinivibrio dextrinosolvens* | 90% | 99% | Ascusbbf_6012 | SEQ ID NO: 58 | 0.54428 |
| 74. *Succinivibrio* (genus) | *Succinivibrio dextrinosolvens* | | | Ascusbbf_6012C | SEQ ID NO: 5589 | 0.54428 |
| 75. *Spirochaeta* (genus) | *Treponema bryantii* | 98% | 99% | Ascusbbf_2297 | SEQ ID NO: 59 | 0.54413 |
| 76. *Spirochaeta* (genus) | *Treponema bryantii* | | | Ascusbbf_2297G | SEQ ID NO: 5598 | 0.54413 |
| 77. *Bacteroides* (genus) | *Bacteroides uniformis* | 89% | 100% | Ascusbbf_9540 | SEQ ID NO: 60 | 0.54383 |
| 78. *Oscillibacter* (genus) | *Oscillibacter valericigenes* | 94% | 100% | Ascusbbf_873 | SEQ ID NO: 61 | 0.54374 |
| 79. *Prevotella* (genus) | *Prevotella dentalis* | 83% | 95% | Ascusbbf_87102 | SEQ ID NO: 62 | 0.54356 |
| 80. *Pseudomonas* (genus) | *Pseudomonas pertucinogena* | 98% | 99% | Ascusbbf_77105 | SEQ ID NO: 63 | 0.54356 |
| 81. *Corynebacterium* (genus) | *Corynebacterium marinum* | 99% | 100% | Ascusbbf_269 | SEQ ID NO: 64 | 0.54206 |
| 82. *Adlercreutzia* (genus) | *Raoultibacter massiliensis* | 92% | 100% | Ascusbbf_41015 | SEQ ID NO: 65 | 0.54192 |
| 83. *Adlercreutzia* (genus) | *Raoultibacter massiliensis* | | | Ascusbbf_41015A | SEQ ID NO: 5614 | 0.54192 |
| 84. *Acidaminococcus* (genus) | *Acidaminococcus fermentans* | 98% | 97% | Ascusbbf_32877 | SEQ ID NO: 66 | 0.54166 |
| 85. *Acidaminococcus* (genus) | *Acidaminococcus fermentans* | | | Ascusbbf_32877A | SEQ ID NO: 5619 | 0.54166 |
| 86. *Dorea* (genus) | *Dorea longicatena* | 99% | 100% | Ascusbbf_57294 | SEQ ID NO: 67 | 0.53443 |
| 87. *Dorea* (genus) | *Dorea longicatena* | | | Ascusbbf_57294B | SEQ ID NO: 5621 | 0.53443 |
| 88. *Roseburia* (genus) | *Howardella ureilytica* | 88% | 98% | Ascusbbf_27932 | SEQ ID NO: 68 | 0.53375 |
| 89. *Anaerovibrio* (genus) | *Anaerovibrio lipolyticus* | 95% | 97% | Ascusbbf_22558 | SEQ ID NO: 69 | 0.53353 |
| 90. *Anaerovibrio* (genus) | *Anaerovibrio lipolyticus* | | | Ascusbbf_22558B | SEQ ID NO: 5627 | 0.53353 |
| 91. *Bacteroides* (genus) | *Bacteroides helcogenes* | 88% | 100% | Ascusbbf_983757 | SEQ ID NO: 70 | 0.5317 |
| 92. *Bacteroides* (genus) | *Bacteroides helcogenes* | | | Ascusbbf_983757B | SEQ ID NO: 5629 | 0.5317 |
| 93. *Clostridium* XIVa (Cluster) | *Clostridium aminophilum* | 98% | 100% | Ascusbbf_52330 | SEQ ID NO: 71 | 0.53133 |
| 94. *Clostridium* XIVa (Cluster) | *Clostridium aminophilum* | | | Ascusbbf_52330A | SEQ ID NO: 5631 | 0.53133 |
| 95. *Sporosarcina* (genus) | *Lactobacillus floricola* | 79% | 97% | Ascusbbf_88445 | SEQ ID NO: 72 | 0.53069 |
| 96. *Streptomyces* (genus) | *Streptomyces albus* | 99% | 100% | Ascusbbf_4111 | SEQ ID NO: 73 | 0.53006 |
| 97. *Syntrophococcus* (genus) | *Syntrophococcus sucromutans* | 93% | 100% | Ascusbbf_1085 | SEQ ID NO: 74 | 0.5294 |

TABLE 1-continued

Microbes of the present disclosure, including bacteria (1-190).

| Predicted Closest Taxa of Isolated Microbes | BLAST Taxonomic Top Hit w/Genus + Species | BLAST % Ident. | Query Cover | Strain Designation | Sequence Identifier for Associated Marker | MIC Score |
|---|---|---|---|---|---|---|
| 98. Succinivibrio (genus) | Succinivibrio dextrinosolvens | 99% | 99% | Ascusbbf_154 | SEQ ID NO: 75 | 0.52737 |
| 99. Selenomonas (genus) | Selenomonas bovis | 99% | 100% | Ascusbbf_1010 | SEQ ID NO: 76 | 0.527 |
| 100. Parabacteroides (genus) | Megasphaera indica | 99% | 99% | Ascusbbf_5575 | SEQ ID NO: 77 | 0.52675 |
| 101. Parabacteroides (genus) | Megasphaera indica | | | Ascusbbf_5575B | SEQ ID NO: 5663 | 0.52675 |
| 102. Prevotella (genus) | Prevotella oris | 82% | 100% | Ascusbbf_775 | SEQ ID NO: 78 | 0.52672 |
| 103. Prevotella (genus) | Prevotella oris | | | Ascusbbf_775A | SEQ ID NO: 5670 | 0.52672 |
| 104. Butyrivibrio (genus) | Butyrivibrio fibrisolvens | 96% | 100% | Ascusbbf_19348 | SEQ ID NO: 79 | 0.52608 |
| 105. Clostridium sensu stricto (genus) | Clostridium beijerinckii | 99% | 100% | Ascusbbf_24302 | SEQ ID NO: 80 | 0.52361 |
| 106. Succinivibrio (genus) | Succinivibrio dextrinosolvens | 99% | 97% | Ascusbbf_1 | SEQ ID NO: 81 | 0.51924 |
| 107. Lachnobacterium (genus) | Lachnobacterium bovis | 99% | 99% | Ascusbbf_52548 | SEQ ID NO: 82 | 0.51683 |
| 108. Clostridium IV (Cluster) | Clostridiales bacterium | 93% | 100% | Ascusbbf_50658 | SEQ ID NO: 83 | 0.51263 |
| 109. Lachnospiracea incertae sedis (genus) | Lachnospira pectinoschiza | 89% | 100% | Ascusbbf_850 | SEQ ID NO: 84 | 0.5088 |
| 110. Parabacteroides (genus) | Parabacteroides distasonis | 84% | 100% | Ascusbbf_25259 | SEQ ID NO: 85 | 0.50691 |
| 111. Prevotella (genus) | Prevotella albensis | 98% | 100% | Ascusbbf_4 | SEQ ID NO: 86 | 0.50464 |
| 112. Bacteroides (genus) | Bacteroides uniformis | 89% | 100% | Ascusbbf_5131 | SEQ ID NO: 87 | 0.49238 |
| 113. Clostridium IV (Cluster) | Caproiciproducens galactitolivorans | 89% | 95% | Ascusbbf_8600 | SEQ ID NO: 88 | 0.47814 |
| 114. Clostridium IV (Cluster) | Caproiciproducens galactitolivorans | | | Ascusbbf_8600B | SEQ ID NO: 5726 | 0.47814 |
| 115. Pyramidobacter (genus) | Rarimicrobium hominis | 92% | 94% | Ascusbbf_1273 | SEQ ID NO: 89 | 0.46972 |
| 116. Ruminococcus (genus) | Ruminococcus flavefaciens | 98% | 99% | Ascusbbf_39159 | SEQ ID NO: 90 | 0.46727 |
| 117. Coprococcus (genus) | Eubacterium oxidoreducens | 89% | 100% | Ascusbbf_9751 | SEQ ID NO: 91 | 0.4618 |
| 118. Ruminobacter (genus) | Ruminobacter amylophilus | 99% | 100% | Ascusbbf_318 | SEQ ID NO: 92 | 0.45953 |
| 119. Thermobifida (genus) | Thermobifida fusca | 99% | 100% | Ascusbbf_7046 | SEQ ID NO: 93 | 0.45752 |
| 120. Papillibacter (genus) | Oscillibacter valericigenes | 86% | 100% | Ascusbbf_25993 | SEQ ID NO: 94 | 0.45023 |
| 121. Rhodobacter (genus) | Rhodobacter gluconicum | 95% | 99% | Ascusbbf_7027 | SEQ ID NO: 95 | 0.56127 |
| 122. Prevotella (genus) | Gabonibacter massiliensis | 87% | 76% | Ascusbbf_1372985 | SEQ ID NO: 96 | 0.55953 |
| 123. Prevotella (genus) | Gabonibacter massiliensis | | | Ascusbbf_1372985F | SEQ ID NO: 5746 | 0.55953 |
| 124. Aquamarina atlantica (genus + species) | Gabonibacter massiliensis | 89% | 76% | Ascusbbf_23253 | SEQ ID NO: 97 | 0.50683 |
| 125. Aquamarina pacifica (genus + species) | Gabonibacter massiliensis | 86% | 87% | Ascusbbf_121971 | SEQ ID NO: 98 | 0.42 |
| 126. Aquamarina pacifica (genus + species) | Gabonibacter massiliensis | | | Ascusbbf_121971A | SEQ ID NO: 5757 | 0.42 |
| 127. Treponema bryantii (genus + species) | Treponema bryantii | 98% | 94% | Ascusbbf_5251 | SEQ ID NO: 99 | 0.56738 |
| 128. Treponema bryantii (genus + species) | Treponema bryantii | | | Ascusbbf_5251G | SEQ ID NO: 5764 | 0.56738 |
| 129. Actinomyces turicensis (genus + species) | Actinomyces turicensis | 85% | 100% | Ascusbbf_6716 | SEQ ID NO: 100 | 0.5201 |
| 130. Prevotella (genus) | Prevotella oulorum | 92% | 99% | Ascusbbf_100 | SEQ ID NO: 101 | 0.53729 |
| 131. Staphylococcus (genus) | Paenibacillus hemerocallicola | 84% | 84% | Ascusbbf_20584 | SEQ ID NO: 102 | 0.52104 |
| 132. Prevotella (genus) | Prevotella ruminicola | 88% | 100% | Ascusbbf_4317 | SEQ ID NO: 103 | 0.55564 |
| 133. Prevotella (genus) | Prevotella ruminicola | | | Ascusbbf_4317D | SEQ ID NO: 5777 | 0.55564 |
| 134. Prevotella (genus) | Prevotella ruminicola | 90% | 93% | Ascusbbf_6 | SEQ ID NO: 104 | 0.46763 |
| 135. Mogibacterium (genus) | Mogibacterium pumilum | 91% | 100% | Ascusbbf_19022 | SEQ ID NO: 105 | 0.47803 |
| 136. Pseudobutyribibrio (genus) | Pseudobutyrivibrio ruminis | 99% | 100% | Ascusbbf_2624 | SEQ ID NO: 106 | 0.52337 |
| 137. Pseudobutyribibrio (genus) | Pseudobutyrivibrio ruminis | | | Ascusbbf_2624D | SEQ ID NO: 5797 | 0.52337 |
| 138. Fluviicola (genus) | Fluviicola taffensis | 84% | 90% | Ascusbbf_3427 | SEQ ID NO: 107 | 0.50515 |
| 139. Fluviicola (genus) | Fluviicola taffensis | | | Ascusbbf_3427B | SEQ ID NO: 5802 | 0.50515 |
| 140. Prevotella (genus) | Prevotella ruminicola | 92% | 100% | Ascusbbf_5005 | SEQ ID NO: 108 | 0.57034 |
| 141. Prevotella (genus) | Prevotella ruminicola | 100% | 100% | Ascusbbf_69 | SEQ ID NO: 109 | 0.50536 |

TABLE 1-continued

Microbes of the present disclosure, including bacteria (1-190).

| Predicted Closest Taxa of Isolated Microbes | BLAST Taxonomic Top Hit w/Genus + Species | BLAST % Ident. | Query Cover | Strain Designation | Sequence Identifier for Associated Marker | MIC Score |
|---|---|---|---|---|---|---|
| 142. *Succiniclasticum* (genus) | *Succiniclasticum ruminis* | 90% | 90% | Ascusbbf_8082 | SEQ ID NO: 110 | 0.50084 |
| 143. *Prevotella* (genus) | *Prevotella ruminicola* | 94% | 100% | Ascusbbf_95 | SEQ ID NO: 111 | 0.53509 |
| 144. *Clostridium* XIVa (cluster) | *Butyrivibrio fibrisolvens* | 89% | 100% | Ascusbbf_1136 | SEQ ID NO: 112 | 0.50966 |
| 145. *Asteroleplasma* (genus) | *Asteroleplasma anaerobium* | 98% | 100% | Ascusbbf_2770 | SEQ ID NO: 113 | 0.51006 |
| 146. *Turicibacter* (genus) | *Turicibacter sanguinis* | 98% | 100% | Ascusbbf_1629 | SEQ ID NO: 114 | 0.51632 |
| 147. *Prevotella* (genus) | *Bacteroides caecicola* | 85% | 99% | Ascusbbf_1821 | SEQ ID NO: 115 | 0.53784 |
| 148. *Prevotella* (genus) | *Prevotella ruminicola* | 95% | 100% | Ascusbbf_56782 | SEQ ID NO: 116 | 0.5317 |
| 149. *Olsenella* (genus) | *Olsenella scatoligenes* | 99% | 100% | Ascusbbf_92 | SEQ ID NO: 117 | 0.46089 |
| 150. *Prevotella* (genus) | *Prevotella ruminicola* | 94% | 99% | Ascusbbf_118 | SEQ ID NO: 118 | 0.6108 |
| 151. *Prevotella* (genus) | *Prevotella ruminicola* | | | Ascusbbf_118B | SEQ ID NO: 5868 | 0.6108 |
| 152. *Aggregatibacter* (genus) | *Prevotella ruminicola* | 87% | 44% | Ascusbbf_5429 | SEQ ID NO: 119 | 0.57983 |
| 153. *Aggregatibacter* (genus) | *Prevotella ruminicola* | | | Ascusbbf_5429C | SEQ ID NO: 5872 | 0.57983 |
| 154. *Ruminobacter* (genus) | *Ruminobacter amylophilus* | 86% | 88% | Ascusbbf_3 | SEQ ID NO: 120 | 0.56323 |
| 155. *Prevotella* (genus) | *Prevotella ruminicola* | 91% | 99% | Ascusbbf_10576 | SEQ ID NO: 121 | 0.56208 |
| 156. *Prevotella* (genus) | *Prevotella ruminicola* | 93% | 98% | Ascusbbf_729 | SEQ ID NO: 122 | 0.54949 |
| 157. *Prevotella* (genus) | *Prevotella ruminicola* | 92% | 100% | Ascusbbf_201 | SEQ ID NO: 123 | 0.54656 |
| 158. *Prevotella* (genus) | *Prevotella ruminicola* | 91% | 99% | Ascusbbf_416 | SEQ ID NO: 124 | 0.53816 |
| 159. *Prevotella* (genus) | *Prevotella ruminicola* | 94% | 99% | Ascusbbf_15806 | SEQ ID NO: 125 | 0.52527 |
| 160. *Clostridium* XIVa (cluster) | *Clostridium aminophilum* | 94% | 100% | Ascusbbf_6115 | SEQ ID NO: 126 | 0.52278 |
| 161. *Anaerovibrio* (genus) | *Anaerovibrio lipolyticus* | 95% | 97% | Ascusbbf_1325058 | SEQ ID NO: 127 | 0.52183 |
| 162. *Prevotella* (genus) | *Prevotella buccalis* | 91% | 100% | Ascusbbf_28350 | SEQ ID NO: 128 | 0.51744 |
| 163. *Parabacteroides* (genus) | *Muribaculum intestinale* | 93% | 100% | Ascusbbf_372 | SEQ ID NO: 129 | 0.51572 |
| 164. *Phascolarctobacterium* (genus) | *Phascolarctobacterium succinatutens* | 96% | 93% | Ascusbbf_667 | SEQ ID NO: 130 | 0.51381 |
| 165. *Phascolarctobacterium* (genus) | *Phascolarctobacterium succinatutens* | | | Ascusbbf_667A | SEQ ID NO: 5930 | 0.51381 |
| 166. *Bacteroides* (genus) | *Bacteroides coprophilus* | 83% | 100% | Ascusbbf_1207 | SEQ ID NO: 131 | 0.51075 |
| 167. *Lachnospiracea incertae sedis* (genus) | *Coprococcus catus* | 92% | 97% | Ascusbbf_3875 | SEQ ID NO: 132 | 0.47237 |
| 168. *Clostridium* XIVa (cluster) | *Clostridium aminophilum* | 90% | 100% | Ascusbbf_72889 | SEQ ID NO: 133 | 0.46531 |
| 169. *Clostridium* XIVa (cluster) | *Clostridium aminophilum* | | | Ascusbbf_72889B | SEQ ID NO: 5947 | 0.46531 |
| 170. *Parabacteroides* (genus) | *Barnesiella viscericola* | 85% | 94% | Ascusbbf_106863 | SEQ ID NO: 134 | 0.45152 |
| 171. *Parabacteroides* (genus) | *Barnesiella viscericola* | | | Ascusbbf_106863B | SEQ ID NO: 5949 | 0.45152 |
| 172. *Prevotella* (genus) | *Prevotella ruminicola* | 94% | 97% | Ascusbbf_120 | SEQ ID NO: 135 | 0.53376 |
| 173. *Prevotella* (genus) | *Prevotella ruminicola* | 93% | 99% | Ascusbbf_930 | SEQ ID NO: 136 | 0.51321 |
| 174. *Bacteroides* (genus) | *Bacteroides uniformis* | 89% | 100% | Ascusbbf_915 | SEQ ID NO: 5369 | 0.54396 |
| 175. *Bacteroides* (genus) | *Bacteroides uniformis* | | | Ascusbbf_915A | SEQ ID NO: 5955 | 0.54396 |
| 176. *Prevotella* (genus) | *Prevotella ruminicola* | 88% | 98% | Ascusbbf_8941 | SEQ ID NO: 5370 | 0.5328 |
| 177. *Prevotella* (genus) | *Prevotella ruminicola* | | | Ascusbbf_8941A | SEQ ID NO: 5956 | 0.5328 |
| 178. *Anaerovibrio* | *Anaerovibrio lipolyticus* | 96% | 97% | Ascusbbf_8480 | SEQ ID NO: 5371 | 0.48193 |
| 179. *Anaerovibrio* | *Anaerovibrio lipolyticus* | | | Ascusbbf_8480A | SEQ ID NO: 5989 | 0.48193 |
| 180. *Prevotella* (genus) | *Prevotella ruminicola* | 92% | 98% | Ascusbbf_374 | SEQ ID NO: 5372 | 0.52368 |
| 181. *Prevotella* (genus) | *Prevotella ruminicola* | | | Ascusbbf_374C | SEQ ID NO: 5991 | 0.52368 |
| 182. *Prevotella* (genus) | *Prevotella brevis* | 92% | 100% | Ascusbbf_6906 | SEQ ID NO: 5373 | 0.4889 |
| 183. *Prevotella* (genus) | *Prevotella ruminicola* | 94% | 99% | Ascusbbf_721 | SEQ ID NO: 5374 | 0.88129 |
| 184. *Syntrophococcus* (genus) | *Syntrophococcus sucromutans* | 93% | 100% | Ascusbbf_3819 | SEQ ID NO: 5375 | 0.45798 |
| 185. *Syntrophococcus* (genus) | *Syntrophococcus sucromutans* | | | Ascusbbf_3819A | SEQ ID NO: 5971 | 0.45798 |
| 186. *Bacteroides* (genus) | *Bacteroides coprocola* | 87% | 100% | Ascusbbf_4323 | SEQ ID NO: 5376 | 0.50634 |
| 187. *Bacteroides* (genus) | *Bacteroides coprocola* | | | Ascusbbf_4323B | SEQ ID NO: 5973 | 0.50634 |
| 188. *Prevotella* (genus) | *Prevotella ruminicola* | 91% | 100% | Ascusbbf_6087 | SEQ ID NO: 5377 | 0.52954 |
| 189. *Prevotella* (genus) | *Prevotella ruminicola* | | | Ascusbbf_6087B | SEQ ID NO: 5977 | 0.52954 |
| 190. *Saccharofermentans* (genus) | *Christensenella timonensis* | 86% | 99% | Ascusbbf_8414 | SEQ ID NO: 5378 | 0.52719 |

TABLE 2

Deposited Microbes of the present disclosure

| Strain Designation | SEQ ID No: | Deposit Accession # |
|---|---|---|
| Ascusbbf_6176A | 5379 | PTA-125041, PTA-125042, PTA-125049, PTA-125050, PTA-125051, PTA-125052 |
| Ascusbbf_6176B | 5380 | PTA-125041, PTA-125042, PTA-125049, PTA-125050, PTA-125051, PTA-125052 |
| Ascusbbf_6176C | 5381 | PTA-125041, PTA-125049, PTA-125050 |
| Ascusbbf_6176D | 5382 | PTA-125049, PTA-125051, PTA-125052 |
| Ascusbbf_6176E | 5383 | PTA-125049, PTA-125051, PTA-125052 |
| Ascusbbf_6176F | 5384 | PTA-125049 |
| Ascusbbf_6176G | 5385 | PTA-125049, PTA-125050, PTA-125051, PTA-125052 |
| Ascusbbf_6176H | 5386 | PTA-125049, PTA-125051, PTA-125052 |
| Ascusbbf_6176I | 5387 | PTA-125050, PTA-125051, PTA-125052 |
| Ascusbbf_4883A | 5388 | PTA-125042, PTA-125049 |
| Ascusbbf_4883B | 5389 | PTA-125041, PTA-125051 |
| Ascusbbf_4883C | 5390 | PTA-125049, PTA-125050, PTA-125051 |
| Ascusbbf_4883D | 5391 | PTA-125049, PTA-125050, PTA-125051 |
| Ascusbbf_4883E | 5392 | PTA-125050 |
| Ascusbbf_13543A | 5393 | PTA-125033 |
| Ascusbbf_13543B | 5394 | PTA-125041, PTA-125050 |
| Ascusbbf_13543C | 5395 | PTA-125041, PTA-125042, PTA-125050, PTA-125051 |
| Ascusbbf_13543D | 5396 | PTA-125041, PTA-125050 |
| Ascusbbf_13543E | 5397 | PTA-125033, PTA-125041, PTA-125042, PTA-125051, PTA-125052 |
| Ascusbbf_152A | 5398 | PTA-125051 |
| Ascusbbf_152B | 5399 | PTA-125051 |
| Ascusbbf_152C | 5400 | PTA-125051 |
| Ascusbbf_707A | 5401 | PTA-125049, PTA-125050, PTA-125051, PTA-125052 |
| Ascusbbf_707B | 5402 | PTA-125049, PTA-125050, PTA-125051, PTA-125052 |
| Ascusbbf_707C | 5403 | PTA-125049, PTA-125050 |
| Ascusbbf_707D | 5404 | PTA-125049, PTA-125051, PTA-125052 |
| Ascusbbf_707E | 5405 | PTA-125049, PTA-125051, PTA-125052 |
| Ascusbbf_707F | 5406 | PTA-125049, PTA-125050, PTA-125051, PTA-125052 |
| Ascusbbf_707G | 5407 | PTA-125049, PTA-125050, PTA-125051, PTA-125052 |
| Ascusbbf_707H | 5408 | PTA-125049, PTA-125050, PTA-125051, PTA-125052 |
| Ascusbbf_707I | 5409 | PTA-125051 |
| Ascusbbf_707J | 5410 | PTA-125051 |
| Ascusbbf_1238A | 5411 | PTA-125033, PTA-125040, PTA-125041, PTA-125050, PTA-125051, PTA-125052 |
| Ascusbbf_1238B | 5412 | PTA-125040, PTA-125041, PTA-125051, PTA-125052 |
| Ascusbbf_1238C | 5413 | PTA-125033, PTA-125040, PTA-125041, PTA-125042, PTA-125050, PTA-125051, PTA-125052 |
| Ascusbbf_1238D | 5414 | PTA-125033, PTA-125051, PTA-125052 |
| Ascusbbf_5588A | 5415 | PTA-125040, PTA-125041, PTA-125042, PTA-125049, PTA-125050 |
| Ascusbbf_5588B | 5416 | PTA-125040, PTA-125042 |
| Ascusbbf_5588C | 5417 | PTA-125040, PTA-125041, PTA-125042, PTA-125049, PTA-125050, PTA-125051 |
| Ascusbbf_5588D | 5418 | PTA-125040, PTA-125041, PTA-125042, PTA-125049, PTA-125050, PTA-125051, PTA-125052 |
| Ascusbbf_5588E | 5419 | PTA-125042 |
| Ascusbbf_5588F | 5420 | PTA-125042 |
| Ascusbbf_5588G | 5421 | PTA-125042 |
| Ascusbbf_5588H | 5422 | PTA-125049, PTA-125051 |
| Ascusbbf_4691A | 5423 | PTA-125050, PTA-125051 |
| Ascusbbf_4691B | 5424 | PTA-125051, PTA-125052 |
| Ascusbbf_4691C | 5425 | PTA-125051 |
| Ascusbbf_9770A | 5426 | PTA-125041, PTA-125042, PTA-125049, PTA-125050 |
| Ascusbbf_9770B | 5427 | PTA-125041, PTA-125049, PTA-125050 |
| Ascusbbf_9770C | 5428 | PTA-125049, PTA-125051, PTA-125052 |
| Ascusbbf_9770D | 5429 | PTA-125049, PTA-125050 |
| Ascusbbf_9770E | 5430 | PTA-125049, PTA-125050 |
| Ascusbbf_9770F | 5431 | PTA-125049, PTA-125050 |
| Ascusbbf_9770G | 5432 | PTA-125049, PTA-125050 |
| Ascusbbf_9770H | 5433 | PTA-125049, PTA-125050, PTA-125051 |
| Ascusbbf_14146A | 5434 | PTA-124942, PTA-125033, PTA-125041, PTA-125042, PTA-125051, PTA-125052, B-67555 |
| Ascusbbf_14146B | 5435 | PTA-125033, PTA-125041, PTA-125042, PTA-125051, PTA-125052 |
| Ascusbbf_14146C | 5436 | PTA-125041 |
| Ascusbbf_14146D | 5437 | PTA-125033, PTA-125041, PTA-125042, PTA-125051, PTA-125052 |
| Ascusbbf_14146E | 5438 | PTA-125033, PTA-125041 |
| Ascusbbf_14146F | 5439 | PTA-125041 |
| Ascusbbf_14146G | 5440 | PTA-125042, PTA-125051, PTA-125052 |
| Ascusbbf_1103A | 5441 | PTA-125033, PTA-125041 |
| Ascusbbf_1103B | 5442 | PTA-125041, PTA-125051, PTA-125052 |
| Ascusbbf_1103C | 5443 | PTA-125041, PTA-125051, PTA-125052 |
| Ascusbbf_1103D | 5444 | PTA-125041, PTA-125042, PTA-125051 |
| Ascusbbf_1103E | 5445 | PTA-125041, PTA-125051, PTA-125052 |
| Ascusbbf_1103F | 5446 | PTA-125051, PTA-125052 |
| Ascusbbf_1103G | 5447 | PTA-125051, PTA-125052 |
| Ascusbbf_1103H | 5448 | PTA-125051, PTA-125052 |
| Ascusbbf_1103I | 5449 | PTA-125051 |
| Ascusbbf_13717A | 5450 | PTA-125051, PTA-125052 |
| Ascusbbf_13717B | 5451 | PTA-125051 |
| Ascusbbf_13717C | 5452 | PTA-125051 |
| Ascusbbf_876A | 5453 | PTA-124942, PTA-125042 |
| Ascusbbf_876B | 5454 | PTA-125042 |
| Ascusbbf_876C | 5455 | PTA-125033, PTA-125040, PTA-125041, PTA-125042, PTA-125050 |
| Ascusbbf_876D | 5456 | PTA-125033, PTA-125040, PTA-125041, PTA-125042, PTA-125050, PTA-125052 |
| Ascusbbf_876E | 5457 | B-67553 |
| Ascusbbf_876F | 5458 | PTA-125033, PTA-125040, PTA-125041, PTA-125042, PTA-125050, PTA-125052 |
| Ascusbbf_876G | 5459 | PTA-125033, PTA-125042 |
| Ascusbbf_4936A | 5460 | PTA-125041, PTA-125050 |
| Ascusbbf_4936B | 5461 | PTA-125041 |
| Ascusbbf_113152A | 5462 | PTA-125050 |
| Ascusbbf_9031A | 5463 | PTA-125049 |
| Ascusbbf_9031B | 5464 | PTA-125049 |
| Ascusbbf_9031C | 5465 | PTA-125049 |
| Ascusbbf_9031D | 5466 | PTA-125049, PTA-125050 |
| Ascusbbf_9031E | 5467 | PTA-125049, PTA-125050 |
| Ascusbbf_9031F | 5468 | PTA-125049, PTA-125050 |
| Ascusbbf_9031G | 5469 | PTA-125050 |
| Ascusbbf_11823A | 5470 | PTA-125041 |
| Ascusbbf_11823B | 5471 | PTA-125041, PTA-125042, PTA-125049 |

TABLE 2-continued

Deposited Microbes of the present disclosure

| Strain Designation | SEQ ID No: | Deposit Accession # |
|---|---|---|
| Ascusbbf_11823C | 5472 | PTA-125050 |
| Ascusbbf_1007A | 5473 | PTA-125041 |
| Ascusbbf_24422A | 5474 | PTA-125051, PTA-125052 |
| Ascusbbf_951A | 5475 | PTA-124942, PTA-125042 |
| Ascusbbf_951B | 5476 | PTA-125033, PTA-125040, PTA-125041, PTA-125042, PTA-125049, PTA-125050, PTA-125051, PTA-125052 |
| Ascusbbf_951C | 5477 | PTA-125033, PTA-125040, PTA-125041, PTA-125042, PTA-125049, PTA-125050, PTA-125051, PTA-125052 |
| Ascusbbf_951D | 5478 | PTA-125033, PTA-125040, PTA-125041, PTA-125042, PTA-125049 |
| Ascusbbf_951E | 5479 | PTA-125033, PTA-125042, PTA-125051, PTA-125052 |
| Ascusbbf_951F | 5480 | PTA-125033 |
| Ascusbbf_951G | 5481 | PTA-125033 |
| Ascusbbf_5699A | 5482 | PTA-125049, PTA-125050 |
| Ascusbbf_5699B | 5483 | PTA-125049, PTA-125050 |
| Ascusbbf_5699C | 5484 | PTA-125049, PTA-125050 |
| Ascusbbf_5699D | 5485 | PTA-125050, PTA-125051 |
| Ascusbbf_130A | 5486 | PTA-125049, PTA-125050, PTA-125051, PTA-125052 |
| Ascusbbf_130B | 5487 | PTA-125049 |
| Ascusbbf_130C | 5488 | PTA-125049, PTA-125050 |
| Ascusbbf_130D | 5489 | PTA-125049, PTA-125050 |
| Ascusbbf_130E | 5490 | PTA-125049 |
| Ascusbbf_130F | 5491 | PTA-125049, PTA-125050 |
| Ascusbbf_130G | 5492 | PTA-125051 |
| Ascusbbf_10109A | 5493 | PTA-124942 |
| Ascusbbf_10109B | 5494 | PTA-124942 |
| Ascusbbf_10109C | 5495 | PTA-125033, PTA-125049 |
| Ascusbbf_10109D | 5496 | PTA-125049 |
| Ascusbbf_10109E | 5497 | PTA-125049, PTA-125050 |
| Ascusbbf_10109F | 5498 | PTA-125049 |
| Ascusbbf_10109G | 5499 | PTA-125049, PTA-125052 |
| Ascusbbf_10109H | 5500 | PTA-125049, PTA-125050 |
| Ascusbbf_10109I | 5501 | PTA-125050 |
| Ascusbbf_29797A | 5502 | PTA-125051 |
| Ascusbbf_54068A | 5503 | PTA-124942 |
| Ascusbbf_54068B | 5504 | PTA-125033 |
| Ascusbbf_54068C | 5505 | PTA-125033, PTA-125040, PTA-125041, PTA-125042, PTA-125049 |
| Ascusbbf_54068D | 5506 | PTA-125033, PTA-125041, PTA-125042, PTA-125049, PTA-125050 |
| Ascusbbf_7003A | 5507 | PTA-124942 |
| Ascusbbf_7003C | 5508 | PTA-125033 |
| Ascusbbf_23A | 5509 | PTA-125051, PTA-125052 |
| Ascusbbf_1697A | 5510 | PTA-125049 |
| Ascusbbf_1697B | 5511 | PTA-125050 |
| Ascusbbf_1697C | 5512 | PTA-125050 |
| Ascusbbf_7586A | 5513 | PTA-125041 |
| Ascusbbf_7586B | 5514 | PTA-125041, PTA-125042, PTA-125050 |
| Ascusbbf_7586C | 5515 | PTA-125041, PTA-125042, PTA-125050 |
| Ascusbbf_7586D | 5516 | PTA-125042 |
| Ascusbbf_1034A | 5517 | PTA-125051, PTA-125052 |
| Ascusbbf_1034B | 5518 | PTA-125051 |
| Ascusbbf_23134A | 5519 | PTA-125049 |
| Ascusbbf_43679A | 5520 | PTA-125040, PTA-125041, PTA-125050 |
| Ascusbbf_43679B | 5521 | PTA-125041 |
| Ascusbbf_43679C | 5522 | PTA-125041 |
| Ascusbbf_43679D | 5523 | PTA-125041 |
| Ascusbbf_43679E | 5524 | PTA-125041, PTA-125050 |
| Ascusbbf_43679F | 5525 | PTA-125050 |
| Ascusbbf_63954A | 5526 | PTA-125049 |
| Ascusbbf_1517A | 5527 | PTA-125033, PTA-125040, PTA-125041, PTA-125042, PTA-125051, PTA-125052 |
| Ascusbbf_1517B | 5528 | PTA-125040, PTA-125041, PTA-125042, PTA-125051, PTA-125052 |
| Ascusbbf_1517C | 5529 | PTA-125040, PTA-125042, PTA-125049, PTA-125050, PTA-125051 |
| Ascusbbf_1517D | 5530 | PTA-125033, PTA-125040, PTA-125042, PTA-125049, PTA-125050, PTA-125051, PTA-125052 |
| Ascusbbf_1517E | 5531 | PTA-125033, PTA-125041, PTA-125050 |
| Ascusbbf_1517F | 5532 | PTA-125042 |
| Ascusbbf_1517G | 5533 | PTA-125042 |
| Ascusbbf_1517H | 5534 | PTA-125042 |
| Ascusbbf_1517I | 5535 | PTA-125049 |
| Ascusbbf_104A | 5536 | PTA-124942 |
| Ascusbbf_104B | 5537 | PTA-125040, PTA-125042, PTA-125049, PTA-125050 |
| Ascusbbf_104C | 5538 | PTA-125040, PTA-125042, PTA-125049, PTA-125050 |
| Ascusbbf_104D | 5539 | PTA-125040 |
| Ascusbbf_104E | 5540 | PTA-125040, PTA-125041, PTA-125042 |
| Ascusbbf_104F | 5541 | PTA-125033, PTA-125042 |
| Ascusbbf_104G | 5542 | PTA-125050 |
| Ascusbbf_104H | 5543 | PTA-125042 |
| Ascusbbf_104I | 5544 | PTA-125042 |
| Ascusbbf_148A | 5545 | PTA-125049, PTA-125051, PTA-125052 |
| Ascusbbf_148B | 5546 | PTA-125049, PTA-125051 |
| Ascusbbf_148C | 5547 | PTA-125049, PTA-125050, PTA-125051, PTA-125052 |
| Ascusbbf_148D | 5548 | PTA-125051, PTA-125052 |
| Ascusbbf_148E | 5549 | PTA-125051, PTA-125052 |
| Ascusbbf_148F | 5550 | PTA-125051, PTA-125052 |
| Ascusbbf_148G | 5551 | PTA-125051 |
| Ascusbbf_148H | 5552 | PTA-125051 |
| Ascusbbf_944A | 5553 | PTA-124942 |
| Ascusbbf_944B | 5554 | PTA-125041, PTA-125049, PTA-125051, PTA-125052 |
| Ascusbbf_944C | 5555 | PTA-125049, PTA-125051 |
| Ascusbbf_944D | 5556 | PTA-125049, PTA-125050 |
| Ascusbbf_944E | 5557 | PTA-125049 |
| Ascusbbf_944F | 5558 | PTA-125049 |
| Ascusbbf_944G | 5559 | PTA-125049, PTA-125051, PTA-125052 |
| Ascusbbf_23033A | 5560 | PTA-125051, PTA-125052 |
| Ascusbbf_23033B | 5561 | PTA-125051, PTA-125052 |
| Ascusbbf_23033C | 5562 | PTA-125051, PTA-125052 |
| Ascusbbf_23033D | 5563 | PTA-125051 |
| Ascusbbf_2600A | 5564 | PTA-124942 |
| Ascusbbf_2600B | 5565 | PTA-125033, PTA-125040, PTA-125041, PTA-125042 |
| Ascusbbf_2600C | 5566 | PTA-125033, PTA-125040, PTA-125041, PTA-125042 |
| Ascusbbf_2600D | 5567 | PTA-125041 |
| Ascusbbf_2600E | 5568 | PTA-125033, PTA-125041 |
| Ascusbbf_2600F | 5569 | PTA-125033, PTA-125041 |
| Ascusbbf_2600G | 5570 | PTA-125041 |
| Ascusbbf_2600H | 5571 | PTA-125042 |
| Ascusbbf_8118A | 5572 | PTA-125051, PTA-125052 |
| Ascusbbf_8118B | 5573 | PTA-125051 |
| Ascusbbf_201A | 5574 | PTA-125042 |
| Ascusbbf_201J | 5575 | PTA-125033, PTA-125042, PTA-125049 |
| Ascusbbf_201K | 5576 | PTA-125042, PTA-125049, PTA-125051, PTA-125052 |
| Ascusbbf_201L | 5577 | PTA-125042, PTA-125052 |
| Ascusbbf_10712A | 5578 | PTA-124942, PTA-125033, PTA-125042, PTA-125050 |
| Ascusbbf_10712B | 5579 | PTA-124942 |
| Ascusbbf_10712C | 5580 | PTA-125033, PTA-125042, PTA-125049 |
| Ascusbbf_10712D | 5581 | PTA-125033, PTA-125042 |
| Ascusbbf_10712E | 5582 | PTA-125042, PTA-125049 |

TABLE 2-continued

Deposited Microbes of the present disclosure

| Strain Designation | SEQ ID No: | Deposit Accession # |
|---|---|---|
| Ascusbbf_10712F | 5583 | PTA-125033, PTA-125042, PTA-125050 |
| Ascusbbf_10712G | 5584 | PTA-125033, PTA-125042, PTA-125049, PTA-125050, PTA-125052 |
| Ascusbbf_10712H | 5585 | PTA-125033, PTA-125042, PTA-125049, PTA-125050, PTA-125052 |
| Ascusbbf_10712I | 5586 | PTA-125042, PTA-125050 |
| Ascusbbf_6012A | 5587 | PTA-124942 |
| Ascusbbf_6012B | 5588 | PTA-125040, PTA-125041, PTA-125049, PTA-125050 |
| Ascusbbf_6012C | 5589 | PTA-125040, PTA-125041, PTA-125049, PTA-125050 |
| Ascusbbf_6012D | 5590 | PTA-125041, PTA-125049 |
| Ascusbbf_6012E | 5591 | PTA-125041 |
| Ascusbbf_2297A | 5592 | PTA-125049, PTA-125050, PTA-125051 |
| Ascusbbf_2297B | 5593 | PTA-125049, PTA-125051 |
| Ascusbbf_2297C | 5594 | PTA-125049, PTA-125051, PTA-125052 |
| Ascusbbf_2297D | 5595 | PTA-125049, PTA-125051, PTA-125052 |
| Ascusbbf_2297E | 5596 | PTA-125049, PTA-125051, PTA-125052 |
| Ascusbbf_2297F | 5597 | PTA-125051, PTA-125052 |
| Ascusbbf_2297G | 5598 | PTA-125051, PTA-125052 |
| Ascusbbf_2297H | 5599 | PTA-125051 |
| Ascusbbf_873A | 5600 | PTA-125033 |
| Ascusbbf_873B | 5601 | PTA-125033, PTA-125041, PTA-125042, PTA-125049, PTA-125050, PTA-125052 |
| Ascusbbf_873C | 5602 | PTA-125040, PTA-125041, PTA-125042, PTA-125050 |
| Ascusbbf_873D | 5603 | PTA-125041, PTA-125042, PTA-125050 |
| Ascusbbf_873E | 5604 | PTA-125033, PTA-125041, PTA-125042, PTA-125049, PTA-125050 |
| Ascusbbf_873F | 5605 | PTA-125033, PTA-125041, PTA-125042, PTA-125052 |
| Ascusbbf_873G | 5606 | PTA-125042 |
| Ascusbbf_269A | 5607 | PTA-125033, PTA-125041, PTA-125042, PTA-125050 |
| Ascusbbf_269B | 5608 | PTA-125033 |
| Ascusbbf_269C | 5609 | PTA-125033, PTA-125042 |
| Ascusbbf_269D | 5610 | PTA-125041, PTA-125050 |
| Ascusbbf_269E | 5611 | PTA-125033, PTA-125041, PTA-125050 |
| Ascusbbf_269F | 5612 | PTA-125033 |
| Ascusbbf_269G | 5613 | PTA-125033 |
| Ascusbbf_41015A | 5614 | PTA-125033, PTA-125041, PTA-125050 |
| Ascusbbf_41015B | 5615 | PTA-125033 |
| Ascusbbf_41015C | 5616 | PTA-125041 |
| Ascusbbf_41015D | 5617 | PTA-125042 |
| Ascusbbf_41015E | 5618 | PTA-125042 |
| Ascusbbf_32877A | 5619 | PTA-124942 |
| Ascusbbf_57294A | 5620 | PTA-124942, PTA-125041 |
| Ascusbbf_57294B | 5621 | PTA-125033, PTA-125050 |
| Ascusbbf_57294C | 5622 | PTA-125033, PTA-125052 |
| Ascusbbf_27932A | 5623 | PTA-125040 |
| Ascusbbf_27932B | 5624 | PTA-125040, PTA-125041, PTA-125050 |
| Ascusbbf_27932C | 5625 | PTA-125040, PTA-125049, PTA-125052 |
| Ascusbbf_22558A | 5626 | PTA-125051 |
| Ascusbbf_22558B | 5627 | PTA-125051 |
| Ascusbbf_983757A | 5628 | PTA-125051, PTA-125052 |
| Ascusbbf_983757B | 5629 | PTA-125051, PTA-125052 |
| Ascusbbf_983757C | 5630 | PTA-125051, PTA-125052 |
| Ascusbbf_52330A | 5631 | PTA-125033 |
| Ascusbbf_1085A | 5632 | PTA-124942, PTA-125033, PTA-125041, PTA-125049, PTA-125050 |
| Ascusbbf_1085B | 5633 | PTA-125033, PTA-125042, PTA-125050, PTA-125051, B-67554 |
| Ascusbbf_1085C | 5634 | PTA-125033, PTA-125040, PTA-125041, PTA-125042, PTA-125049, PTA-125050, PTA-125051, PTA-125052 |
| Ascusbbf_1085D | 5635 | PTA-125040, PTA-125041, PTA-125042, PTA-125049, PTA-125050, PTA-125052 |
| Ascusbbf_1085E | 5636 | PTA-125033, PTA-125040, PTA-125041, PTA-125042, PTA-125049, PTA-125050, PTA-125052 |
| Ascusbbf_1085F | 5637 | PTA-125033, PTA-125049, PTA-125051, PTA-125052 |
| Ascusbbf_1085G | 5638 | PTA-125033, PTA-125050 |
| Ascusbbf_1085H | 5639 | PTA-125033, PTA-125050 |
| Ascusbbf_1085I | 5640 | PTA-125033, PTA-125050 |
| Ascusbbf_1085J | 5641 | PTA-125033, PTA-125042 |
| Ascusbbf_1085K | 5642 | PTA-125042 |
| Ascusbbf_154A | 5643 | PTA-124942 |
| Ascusbbf_154B | 5644 | PTA-125042, PTA-125049, PTA-125050, PTA-125051, B-67550 |
| Ascusbbf_154D | 5645 | PTA-125040, PTA-125041, PTA-125042, PTA-125051 |
| Ascusbbf_154E | 5646 | PTA-125040, PTA-125041, PTA-125049, PTA-125050, PTA-125052 |
| Ascusbbf_154F | 5647 | PTA-125033, PTA-125040, PTA-125041, PTA-125042, PTA-125049, PTA-125050, PTA-125052 |
| Ascusbbf_154G | 5648 | PTA-125033, PTA-125041, PTA-125042, PTA-125049, PTA-125050, PTA-125051, PTA-125052 |
| Ascusbbf_154H | 5649 | PTA-125049, PTA-125050 |
| Ascusbbf_154I | 5650 | PTA-125049, PTA-125050 |
| Ascusbbf_154M | 5651 | PTA-125042 |
| Ascusbbf_1010A | 5652 | PTA-124942 |
| Ascusbbf_1010B | 5653 | PTA-125033, PTA-125040, PTA-125041, PTA-125042, PTA-125049, PTA-125050, PTA-125051, PTA-125052 |
| Ascusbbf_1010C | 5654 | PTA-125040, PTA-125041, PTA-125042, PTA-125049, PTA-125050, PTA-125051, PTA-125052 |
| Ascusbbf_1010D | 5655 | PTA-125033, PTA-125040, PTA-125041, PTA-125042, PTA-125049, PTA-125050, PTA-125051, PTA-125052 |
| Ascusbbf_1010E | 5656 | PTA-125033, PTA-125040, PTA-125041, PTA-125042, PTA-125052 |
| Ascusbbf_1010F | 5657 | PTA-125033, PTA-125040, PTA-125041, PTA-125052 |
| Ascusbbf_1010G | 5658 | PTA-125033, PTA-125040, PTA-125041, PTA-125042, PTA-125049, PTA-125050, PTA-125051, PTA-125052 |
| Ascusbbf_1010H | 5659 | PTA-125033, PTA-125041 |
| Ascusbbf_1010I | 5660 | PTA-125033, PTA-125041, PTA-125051 |
| Ascusbbf_1010J | 5661 | PTA-125041, PTA-125050, PTA-125052 |
| Ascusbbf_5575A | 5662 | PTA-124942 |
| Ascusbbf_5575B | 5663 | PTA-124942 |
| Ascusbbf_5575C | 5664 | PTA-125033, PTA-125042, PTA-125050 |
| Ascusbbf_5575D | 5665 | PTA-125042, PTA-125050 |
| Ascusbbf_5575E | 5666 | PTA-125033, PTA-125042, PTA-125049, PTA-125052 |

TABLE 2-continued

Deposited Microbes of the present disclosure

| Strain Designation | SEQ ID No: | Deposit Accession # |
|---|---|---|
| Ascusbbf_5575F | 5667 | PTA-125033, PTA-125042, PTA-125049 |
| Ascusbbf_5575G | 5668 | PTA-125033, PTA-125042, PTA-125049, PTA-125050 |
| Ascusbbf_5575H | 5669 | PTA-125033, PTA-125042, PTA-125050 |
| Ascusbbf_775A | 5670 | PTA-125049, PTA-125050, PTA-125051, PTA-125052 |
| Ascusbbf_775B | 5671 | PTA-125051 |
| Ascusbbf_24302A | 5672 | PTA-125041, PTA-125050, B-67551 |
| Ascusbbf_24302B | 5673 | PTA-125033, PTA-125040, PTA-125041, PTA-125049 |
| Ascusbbf_24302C | 5674 | PTA-125033, PTA-125040, PTA-125041, PTA-125051, PTA-125052 |
| Ascusbbf_24302D | 5675 | PTA-125041, PTA-125049 |
| Ascusbbf_24302E | 5676 | PTA-125033, PTA-125041, PTA-125052 |
| Ascusbbf_24302F | 5677 | PTA-125033, PTA-125041, PTA-125042, PTA-125049, PTA-125050, PTA-125052 |
| Ascusbbf_24302G | 5678 | PTA-125033, PTA-125041, PTA-125049, PTA-125050, PTA-125051, PTA-125052 |
| Ascusbbf_24302H | 5679 | PTA-125041, PTA-125052 |
| Ascusbbf_24302I | 5680 | PTA-125041, PTA-125050, PTA-125051, PTA-125052 |
| Ascusbbf_24302J | 5681 | PTA-125051, PTA-125052 |
| Ascusbbf_1A | 5682 | PTA-125040, PTA-125041, PTA-125042, PTA-125052 |
| Ascusbbf_1B | 5683 | PTA-125040, PTA-125041, PTA-125042, PTA-125049, PTA-125050, PTA-125052 |
| Ascusbbf_1C | 5684 | PTA-125040, PTA-125041, PTA-125042, PTA-125050 |
| Ascusbbf_1D | 5685 | PTA-125033, PTA-125040, PTA-125041, PTA-125042, PTA-125049, PTA-125050, PTA-125051, PTA-125052 |
| Ascusbbf_1E | 5686 | PTA-125033, PTA-125040, PTA-125042 |
| Ascusbbf_1F | 5687 | PTA-125033, PTA-125040, PTA-125041, PTA-125042, PTA-125050, PTA-125051, PTA-125052 |
| Ascusbbf_1G | 5688 | PTA-125033, PTA-125040, PTA-125041, PTA-125042, PTA-125049, PTA-125050, PTA-125052 |
| Ascusbbf_1H | 5689 | PTA-125033, PTA-125040, PTA-125041, PTA-125050 |
| Ascusbbf_1I | 5690 | PTA-125033, PTA-125040, PTA-125041, PTA-125042, PTA-125050, PTA-125052 |
| Ascusbbf_1J | 5691 | PTA-125033, PTA-125040, PTA-125041, PTA-125042, PTA-125049, PTA-125050 |
| Ascusbbf_1K | 5692 | PTA-125041, PTA-125042, PTA-125049, PTA-125050 |
| Ascusbbf_52548A | 5693 | PTA-125051, PTA-125052 |
| Ascusbbf_52548B | 5694 | PTA-125051, PTA-125052 |
| Ascusbbf_50658A | 5695 | PTA-125050 |
| Ascusbbf_850A | 5696 | PTA-124942 |
| Ascusbbf_850B | 5697 | PTA-125033 |
| Ascusbbf_850C | 5698 | PTA-125033, PTA-125040, PTA-125041, PTA-125049, PTA-125050 |
| Ascusbbf_850D | 5699 | PTA-125040 |
| Ascusbbf_850E | 5700 | PTA-125040, PTA-125041, PTA-125042, PTA-125049, PTA-125050 |
| Ascusbbf_850F | 5701 | PTA-125033, PTA-125040, PTA-125041, PTA-125042, PTA-125049, PTA-125050 |
| Ascusbbf_850G | 5702 | PTA-125033, PTA-125040, PTA-125041, PTA-125049, PTA-125050 |
| Ascusbbf_850H | 5703 | PTA-125033, PTA-125041, PTA-125050 |
| Ascusbbf_850I | 5704 | PTA-125033, PTA-125050 |
| Ascusbbf_850J | 5705 | PTA-125033, PTA-125042 |
| Ascusbbf_4A | 5706 | PTA-124942 |
| Ascusbbf_4B | 5707 | PTA-125040, PTA-125041, PTA-125042, PTA-125049, PTA-125050, PTA-125052 |
| Ascusbbf_4C | 5708 | PTA-125041, PTA-125051 |
| Ascusbbf_4D | 5709 | PTA-125040, PTA-125041, PTA-125042, PTA-125050, PTA-125051, PTA-125052, B-67552 |
| Ascusbbf_4E | 5710 | PTA-125040, PTA-125041, PTA-125050, PTA-125052 |
| Ascusbbf_4F | 5711 | PTA-125033, PTA-125040, PTA-125041, PTA-125042, PTA-125050, PTA-125051, PTA-125052 |
| Ascusbbf_4G | 5712 | PTA-125041, PTA-125042, PTA-125049, PTA-125050, PTA-125051, PTA-125052 |
| Ascusbbf_4H | 5713 | PTA-125041, PTA-125042, PTA-125049, PTA-125050, PTA-125051, PTA-125052 |
| Ascusbbf_4I | 5714 | PTA-125041, PTA-125049, PTA-125050, PTA-125052 |
| Ascusbbf_4J | 5715 | PTA-125041, PTA-125050 |
| Ascusbbf_4K | 5716 | PTA-125051 |
| Ascusbbf_5131A | 5717 | PTA-125049, PTA-125050, PTA-125051 |
| Ascusbbf_5131B | 5718 | PTA-125049, PTA-125051 |
| Ascusbbf_5131C | 5719 | PTA-125049, PTA-125051 |
| Ascusbbf_5131D | 5720 | PTA-125049, PTA-125051 |
| Ascusbbf_5131E | 5721 | PTA-125051, PTA-125052 |
| Ascusbbf_5131F | 5722 | PTA-125051 |
| Ascusbbf_5131G | 5723 | PTA-125051 |
| Ascusbbf_5131H | 5724 | PTA-125051 |
| Ascusbbf_8600A | 5725 | PTA-125051 |
| Ascusbbf_8600B | 5726 | PTA-125051 |
| Ascusbbf_1273A | 5727 | PTA-125049, PTA-125051, PTA-125052 |
| Ascusbbf_1273B | 5728 | PTA-125051 |
| Ascusbbf_1273C | 5729 | PTA-125051 |
| Ascusbbf_1273D | 5730 | PTA-125051 |
| Ascusbbf_39159A | 5731 | PTA-125041 |
| Ascusbbf_39159B | 5732 | PTA-125041 |
| Ascusbbf_39159C | 5733 | PTA-125050 |
| Ascusbbf_39159D | 5734 | PTA-125042 |
| Ascusbbf_318A | 5735 | PTA-125049, PTA-125050 |
| Ascusbbf_318B | 5736 | PTA-125049 |
| Ascusbbf_318C | 5737 | PTA-125049, PTA-125050 |
| Ascusbbf_318D | 5738 | PTA-125042, PTA-125050, PTA-125051 |
| Ascusbbf_318E | 5739 | PTA-125042, PTA-125050, PTA-125051, PTA-125052 |
| Ascusbbf_7046A | 5740 | PTA-125050 |
| Ascusbbf_1372985A | 5741 | PTA-124942, PTA-125041 |
| Ascusbbf_1372985B | 5742 | PTA-125033, PTA-125041, PTA-125042 |
| Ascusbbf_1372985C | 5743 | PTA-125033, PTA-125041 |
| Ascusbbf_1372985D | 5744 | PTA-125040, PTA-125041, PTA-125042, PTA-125049, PTA-125050 |
| Ascusbbf_1372985E | 5745 | PTA-125040, PTA-125041, PTA-125049, PTA-125050 |
| Ascusbbf_1372985F | 5746 | PTA-125041 |
| Ascusbbf_1372985G | 5980 | PTA-125033, PTA-125041 |
| Ascusbbf_1372985H | 5981 | PTA-125033, PTA-125041 |
| Ascusbbf_1372985I | 5747 | PTA-125033, PTA-125041 |
| Ascusbbf_1372985J | 5982 | PTA-125033, PTA-125041, PTA-125042, PTA-125051, PTA-125052 |

TABLE 2-continued

Deposited Microbes of the present disclosure

| Strain Designation | SEQ ID No: | Deposit Accession # |
|---|---|---|
| Ascusbbf_1372985K | 5983 | PTA-125033, PTA-125041, PTA-125050, PTA-125051 |
| Ascusbbf_1372985L | 5748 | PTA-125041 |
| Ascusbbf_1372985M | 5749 | PTA-125041 |
| Ascusbbf_1372985N | 5750 | PTA-125041 |
| Ascusbbf_1372985O | 5751 | PTA-125041 |
| Ascusbbf_1372985P | 5752 | PTA-125041 |
| Ascusbbf_1372985Q | 5753 | PTA-125041 |
| Ascusbbf_1372985R | 5754 | PTA-125041 |
| Ascusbbf_1372985S | 5755 | PTA-125041, PTA-125049, PTA-125050 |
| Ascusbbf_1372985T | 5756 | PTA-125041, PTA-125049, PTA-125050 |
| Ascusbbf_121971A | 5757 | PTA-125041 |
| Ascusbbf_5251A | 5758 | PTA-125041, PTA-125049, PTA-125050 |
| Ascusbbf_5251B | 5759 | PTA-125033, PTA-125041 |
| Ascusbbf_5251C | 5760 | PTA-125041, PTA-125049, PTA-125050, PTA-125051 |
| Ascusbbf_5251D | 5761 | PTA-125033, PTA-125041, PTA-125049 |
| Ascusbbf_5251E | 5762 | PTA-125049, PTA-125050, PTA-125051 |
| Ascusbbf_5251F | 5763 | PTA-125051, PTA-125052 |
| Ascusbbf_5251G | 5764 | PTA-125051 |
| Ascusbbf_100A | 5765 | PTA-125033, PTA-125049, PTA-125050, PTA-125052 |
| Ascusbbf_100B | 5766 | PTA-125040, PTA-125042 |
| Ascusbbf_100C | 5767 | PTA-125033, PTA-125040, PTA-125041, PTA-125042, PTA-125049, PTA-125050, PTA-125052 |
| Ascusbbf_100D | 5768 | PTA-125033, PTA-125040, PTA-125041, PTA-125050 |
| Ascusbbf_100E | 5769 | PTA-125033, PTA-125040, PTA-125041, PTA-125042, PTA-125049, PTA-125050 |
| Ascusbbf_100F | 5770 | PTA-125041 |
| Ascusbbf_100G | 5771 | PTA-125042 |
| Ascusbbf_20584A | 5772 | PTA-125049 |
| Ascusbbf_20584B | 5773 | PTA-125051, PTA-125052 |
| Ascusbbf_4317A | 5774 | PTA-125041 |
| Ascusbbf_4317B | 5775 | PTA-125041 |
| Ascusbbf_4317C | 5776 | PTA-125042 |
| Ascusbbf_4317D | 5777 | PTA-125051, PTA-125052 |
| Ascusbbf_4317E | 5778 | PTA-125051, PTA-125052 |
| Ascusbbf_6A | 5779 | PTA-125040, PTA-125041, PTA-125049, PTA-125050, PTA-125052 |
| Ascusbbf_6B | 5780 | PTA-125040, PTA-125041, PTA-125042, PTA-125049, PTA-125050, PTA-125052 |
| Ascusbbf_6C | 5781 | PTA-125040, PTA-125041, PTA-125042, PTA-125049, PTA-125050, PTA-125052 |
| Ascusbbf_6D | 5782 | PTA-125040, PTA-125041, PTA-125050, PTA-125052 |
| Ascusbbf_6E | 5783 | PTA-125040, PTA-125041, PTA-125042, PTA-125050, PTA-125052 |
| Ascusbbf_6F | 5784 | PTA-125040, PTA-125052 |
| Ascusbbf_6G | 5785 | PTA-125040, PTA-125041, PTA-125042, PTA-125049, PTA-125050, PTA-125052 |
| Ascusbbf_6H | 5786 | PTA-125041, PTA-125042, PTA-125050 |
| Ascusbbf_6I | 5787 | PTA-125041, PTA-125050 |
| Ascusbbf_6J | 5788 | PTA-125041, PTA-125050 |
| Ascusbbf_6K | 5789 | PTA-125042 |
| Ascusbbf_6L | 5790 | PTA-125042 |
| Ascusbbf_19022A | 5791 | PTA-125033, PTA-125040, PTA-125041 |
| Ascusbbf_19022B | 5792 | PTA-125040, PTA-125041, PTA-125042, PTA-125050 |
| Ascusbbf_19022C | 5793 | PTA-125042, PTA-125052 |
| Ascusbbf_2624A | 5794 | PTA-125033, PTA-125041, PTA-125042, PTA-125051, PTA-125052 |
| Ascusbbf_2624B | 5795 | PTA-125041, PTA-125042, PTA-125050, PTA-125051, PTA-125052 |
| Ascusbbf_2624C | 5796 | PTA-125042, PTA-125051, PTA-125052 |
| Ascusbbf_2624D | 5797 | PTA-125042, PTA-125051, PTA-125052 |
| Ascusbbf_2624E | 5798 | PTA-125042, PTA-125051, PTA-125052 |
| Ascusbbf_2624F | 5799 | PTA-125051, PTA-125052 |
| Ascusbbf_2624G | 5800 | PTA-125051 |
| Ascusbbf_3427A | 5801 | PTA-125041, PTA-125049, PTA-125050 |
| Ascusbbf_3427B | 5802 | PTA-125041, PTA-125042, PTA-125049, PTA-125050, PTA-125051, PTA-125052 |
| Ascusbbf_3427C | 5803 | PTA-125042, PTA-125049, PTA-125050, PTA-125051 |
| Ascusbbf_3427D | 5804 | PTA-125050 |
| Ascusbbf_3427E | 5805 | PTA-125052 |
| Ascusbbf_5005A | 5806 | PTA-125049, PTA-125050, PTA-125051 |
| Ascusbbf_5005B | 5807 | PTA-125050 |
| Ascusbbf_69A | 5808 | PTA-125033, PTA-125040, PTA-125041, PTA-125042, PTA-125049, PTA-125050, PTA-125051, PTA-125052 |
| Ascusbbf_69B | 5809 | PTA-125033, PTA-125040, PTA-125041, PTA-125042, PTA-125049, PTA-125050, PTA-125051, PTA-125052 |
| Ascusbbf_69C | 5810 | PTA-125033, PTA-125040, PTA-125041, PTA-125042, PTA-125049, PTA-125050, PTA-125051, PTA-125052 |
| Ascusbbf_69D | 5811 | PTA-125033, PTA-125040, PTA-125041, PTA-125049, PTA-125050, PTA-125051, PTA-125052 |
| Ascusbbf_69E | 5812 | PTA-125033, PTA-125040, PTA-125041, PTA-125042, PTA-125049, PTA-125050, PTA-125051, PTA-125052 |
| Ascusbbf_69F | 5813 | PTA-125033, PTA-125040, PTA-125041, PTA-125042, PTA-125049, PTA-125050, PTA-125051, PTA-125052 |
| Ascusbbf_69G | 5814 | PTA 125033, PTA-125041, PTA-125042, PTA-125049, PTA-125050, PTA-125051, PTA-125052 |
| Ascusbbf_69H | 5815 | PTA-125033, PTA-125041, PTA-125042, PTA-125049, PTA-125050, PTA-125051, PTA-125052 |
| Ascusbbf_69I | 5816 | PTA-125033, PTA-125041, PTA-125042, PTA-125049, PTA-125051, PTA-125052 |
| Ascusbbf_69J | 5817 | PTA-125033, PTA-125042, PTA-125051, PTA-125052 |
| Ascusbbf_8082A | 5818 | PTA-125033, PTA-125040, PTA-125041, PTA-125042, PTA-125050, PTA-125052 |
| Ascusbbf_8082B | 5819 | PTA-125040, PTA-125041, PTA-125042, PTA-125050 |
| Ascusbbf_8082C | 5820 | PTA-125033, PTA-125040, PTA-125041, PTA-125042, PTA-125050, PTA-125052 |
| Ascusbbf_8082D | 5821 | PTA-125033, PTA-125040, PTA-125041, PTA-125042, PTA-125050, PTA-125052 |
| Ascusbbf_8082E | 5822 | PTA-125033, PTA-125041 |

TABLE 2-continued

Deposited Microbes of the present disclosure

| Strain Designation | SEQ ID No: | Deposit Accession # |
|---|---|---|
| Ascusbbf_8082F | 5823 | PTA-125033, PTA-125041, PTA-125042 |
| Ascusbbf_8082G | 5824 | PTA-125033, PTA-125042 |
| Ascusbbf_8082H | 5825 | PTA-125033, PTA-125042 |
| Ascusbbf_8082I | 5826 | PTA-125033 |
| Ascusbbf_95A | 5827 | PTA-125049, PTA-125050 |
| Ascusbbf_95B | 5828 | PTA-125049, PTA-125050, PTA-125051, PTA-125052 |
| Ascusbbf_95C | 5829 | PTA-125049, PTA-125050 |
| Ascusbbf_95D | 5830 | PTA-125049, PTA-125050, PTA-125051, PTA-125052 |
| Ascusbbf_95E | 5831 | PTA-125051, PTA-125052 |
| Ascusbbf_95F | 5832 | PTA-125051, PTA-125052 |
| Ascusbbf_95G | 5833 | PTA-125051, PTA-125052 |
| Ascusbbf_95H | 5834 | PTA-125051 |
| Ascusbbf_1136A | 5835 | PTA-125040, PTA-125041, PTA-125042, PTA-125049, PTA-125050 |
| Ascusbbf_1136B | 5836 | PTA-125040, PTA-125041, PTA-125042, PTA-125049, PTA-125050, PTA-125052 |
| Ascusbbf_1136C | 5837 | PTA-125033, PTA-125040, PTA-125041, PTA-125042, PTA-125049, PTA-125050 |
| Ascusbbf_1136D | 5838 | PTA-125040, PTA-125041, PTA-125042, PTA-125049, PTA-125050, PTA-125052 |
| Ascusbbf_1136E | 5839 | PTA-125040, PTA-125041, PTA-125049, PTA-125050 |
| Ascusbbf_1136F | 5840 | PTA-125042 |
| Ascusbbf_2770A | 5841 | PTA-125042, PTA-125049, PTA-125050, PTA-125051 |
| Ascusbbf_2770B | 5842 | PTA-125049, PTA-125050 |
| Ascusbbf_2770C | 5843 | PTA-125049 |
| Ascusbbf_1629A | 5844 | PTA-125033 |
| Ascusbbf_1629B | 5845 | PTA-125040, PTA-125041 |
| Ascusbbf_1629C | 5846 | PTA-125040, PTA-125041, PTA-125042, PTA-125049, PTA-125050 |
| Ascusbbf_1629D | 5847 | PTA-125033, PTA-125040, PTA-125041, PTA-125049, PTA-125050 |
| Ascusbbf_1629E | 5848 | PTA-125041, PTA-125050 |
| Ascusbbf_1629F | 5849 | PTA-125050 |
| Ascusbbf_1629G | 5850 | PTA-125050 |
| Ascusbbf_1821A | 5851 | PTA-125049 |
| Ascusbbf_1821B | 5852 | PTA-125049, PTA-125050 |
| Ascusbbf_1821C | 5853 | PTA-125049, PTA-125050 |
| Ascusbbf_1821D | 5854 | PTA-125049, PTA-125050 |
| Ascusbbf_56782A | 5855 | PTA-125033, PTA-125041, PTA-125042, PTA-125049, PTA-125050, PTA-125051 |
| Ascusbbf_56782B | 5856 | PTA-125051 |
| Ascusbbf_56782C | 5857 | PTA-125051 |
| Ascusbbf_92A | 5858 | PTA-125040, PTA-125050 |
| Ascusbbf_92B | 5859 | PTA-125040, PTA-125041, PTA-125049, PTA-125050 |
| Ascusbbf_92C | 5860 | PTA-125040, PTA-125050 |
| Ascusbbf_92D | 5861 | PTA-125040, PTA-125041, PTA-125050, PTA-125052 |
| Ascusbbf_92E | 5862 | PTA-125040 |
| Ascusbbf_92F | 5863 | PTA-125040, PTA-125049, PTA-125050 |
| Ascusbbf_92G | 5984 | PTA-125041, PTA-125042 |
| Ascusbbf_92H | 5864 | PTA-125041, PTA-125049 |
| Ascusbbf_92I | 5985 | PTA-125041 |
| Ascusbbf_92J | 5986 | PTA-125041 |
| Ascusbbf_92K | 5865 | PTA-125041, PTA-125051, PTA-125052 |
| Ascusbbf_92L | 5866 | PTA-125050 |
| Ascusbbf_118A | 5867 | PTA-125049, PTA-125051 |
| Ascusbbf_118B | 5868 | PTA-125051, PTA-125052 |
| Ascusbbf_118C | 5869 | PTA-125051 |
| Ascusbbf_5429A | 5870 | PTA-125040, PTA-125041, PTA-125049, PTA-125050, PTA-125052 |
| Ascusbbf_5429B | 5871 | PTA-125040, PTA-125041, PTA-125049, PTA-125050, PTA-125052 |
| Ascusbbf_5429C | 5872 | PTA-125033, PTA-125042 |
| Ascusbbf_5429D | 5873 | PTA-125049 |
| Ascusbbf_3A | 5874 | PTA-125033, PTA-125040, PTA-125041, PTA-125049, PTA-125050, PTA-125052 |
| Ascusbbf_3B | 5875 | PTA-125040, PTA-125041, PTA-125049, PTA-125050, PTA-125052 |
| Ascusbbf_3C | 5876 | PTA-125040, PTA-125041, PTA-125049, PTA-125050 |
| Ascusbbf_3D | 5877 | PTA-125040 |
| Ascusbbf_3E | 5878 | PTA-125042 |
| Ascusbbf_3F | 5879 | PTA-125042 |
| Ascusbbf_3G | 5880 | PTA-125050 |
| Ascusbbf_10576A | 5881 | PTA-125049, PTA-125050, PTA-125051 |
| Ascusbbf_10576B | 5882 | PTA-125049, PTA-125050, PTA-125051, PTA-125052 |
| Ascusbbf_10576C | 5883 | PTA-125049, PTA-125050, PTA-125051 |
| Ascusbbf_10576D | 5884 | PTA-125049 |
| Ascusbbf_10576E | 5885 | PTA-125051 |
| Ascusbbf_729A | 5886 | PTA-125049, PTA-125051 |
| Ascusbbf_729B | 5887 | PTA-125051, PTA-125052 |
| Ascusbbf_729C | 5888 | PTA-125051 |
| Ascusbbf_729D | 5889 | PTA-125051 |
| Ascusbbf_729E | 5890 | PTA-125051 |
| Ascusbbf_729F | 5891 | PTA-125051 |
| Ascusbbf_201A | 5892 | PTA-125042 |
| Ascusbbf_201B | 5893 | PTA-125041, PTA-125042, PTA-125050, PTA-125051, PTA-125052 |
| Ascusbbf_201C | 5894 | PTA-125033 |
| Ascusbbf_201D | 5895 | PTA-125033, PTA-125041, PTA-125042, PTA-125051, PTA-125052 |
| Ascusbbf_201E | 5896 | PTA-125040, PTA-125041 |
| Ascusbbf_201F | 5897 | PTA-125040 |
| Ascusbbf_201G | 5898 | PTA-125033, PTA-125041, PTA-125050 |
| Ascusbbf_201H | 5899 | PTA-125033, PTA-125041, PTA-125042, PTA-125050 |
| Ascusbbf_201I | 5900 | PTA-125033, PTA-125041, PTA-125042, PTA-125050, PTA-125051, PTA-125052 |
| Ascusbbf_416A | 5901 | PTA-125049 |
| Ascusbbf_416B | 5902 | PTA-125049, PTA-125051, PTA-125052 |
| Ascusbbf_416C | 5903 | PTA-125049, PTA-125050 |
| Ascusbbf_416D | 5904 | PTA-125049, PTA-125050 |
| Ascusbbf_416E | 5905 | PTA-125049 |
| Ascusbbf_416F | 5906 | PTA-125049, PTA-125051 |
| Ascusbbf_416G | 5907 | PTA-125050 |
| Ascusbbf_15806A | 5908 | PTA-125049 |
| Ascusbbf_15806B | 5909 | PTA-125049, PTA-125051, PTA-125052 |
| Ascusbbf_6115A | 5910 | PTA-125033, PTA-125041 |
| Ascusbbf_6115B | 5911 | PTA-125041, PTA-125050 |
| Ascusbbf_6115C | 5912 | PTA-125041, PTA-125050 |
| Ascusbbf_6115D | 5913 | PTA-125041 |
| Ascusbbf_1325058A | 5914 | PTA-125041, PTA-125049, PTA-125051 |
| Ascusbbf_1325058B | 5915 | PTA-125041, PTA-125042, PTA-125049, PTA-125050, PTA-125051 |
| Ascusbbf_1325058C | 5916 | PTA-125049 |
| Ascusbbf_1325058D | 5917 | PTA-125049 |
| Ascusbbf_1325058E | 5918 | PTA-125050 |
| Ascusbbf_1325058F | 5919 | PTA-125051 |
| Ascusbbf_28350A | 5920 | PTA-125041, PTA-125050 |
| Ascusbbf_28350B | 5921 | PTA-125041, PTA-125050 |
| Ascusbbf_28350C | 5922 | PTA-125041, PTA-125050 |

TABLE 2-continued

Deposited Microbes of the present disclosure

| Strain Designation | SEQ ID No: | Deposit Accession # |
|---|---|---|
| Ascusbbf_372A | 5923 | PTA-125033, PTA-125040, PTA-125041, PTA-125042, PTA-125049, PTA-125050, PTA-125052 |
| Ascusbbf_372B | 5924 | PTA-125033 |
| Ascusbbf_372C | 5925 | PTA-125040, PTA-125041, PTA-125049, PTA-125050 |
| Ascusbbf_372D | 5926 | PTA-125033, PTA-125040, PTA-125041 |
| Ascusbbf_372E | 5927 | PTA-125033, PTA-125040, PTA-125041, PTA-125042, PTA-125049, PTA-125050 |
| Ascusbbf_372F | 5928 | PTA-125033, PTA-125041, PTA-125050 |
| Ascusbbf_372G | 5929 | PTA-125033, PTA-125042 |
| Ascusbbf_667A | 5930 | PTA-125042, PTA-125049, PTA-125050, PTA-125052 |
| Ascusbbf_667B | 5931 | PTA-125042, PTA-125049 |
| Ascusbbf_1207A | 5932 | PTA-125033, PTA-125042, PTA-125049, PTA-125050 |
| Ascusbbf_1207B | 5933 | PTA-125033, PTA-125042 |
| Ascusbbf_1207C | 5934 | PTA-125033 |
| Ascusbbf_1207D | 5935 | PTA-125040, PTA-125041 |
| Ascusbbf_1207E | 5936 | PTA-125040, PTA-125041 |
| Ascusbbf_1207F | 5937 | PTA-125040, PTA-125041, PTA-125042 |
| Ascusbbf_1207G | 5938 | PTA-125033, PTA-125040, PTA-125041, PTA-125042, PTA-125049, PTA-125050, PTA-125052 |
| Ascusbbf_1207H | 5939 | PTA-125033, PTA-125040 |
| Ascusbbf_1207I | 5940 | PTA-125033, PTA-125040, PTA-125041, PTA-125049, PTA-125050 |
| Ascusbbf_1207J | 5941 | PTA-125033, PTA-125042, PTA-125049 |
| Ascusbbf_3875A | 5942 | PTA-125033, PTA-125041, PTA-125042 |
| Ascusbbf_3875B | 5943 | PTA-125040, PTA-125042 |
| Ascusbbf_3875C | 5944 | PTA-125033, PTA-125041 |
| Ascusbbf_3875D | 5945 | PTA-125041 |
| Ascusbbf_72889A | 5946 | PTA-125051, PTA-125052 |
| Ascusbbf_72889B | 5947 | PTA-125051, PTA-125052 |
| Ascusbbf_106863A | 5948 | PTA-125051, PTA-125052 |
| Ascusbbf_106863B | 5949 | PTA-125051 |
| Ascusbbf_120A | 5987 | PTA-125051 |
| Ascusbbf_120B | 5950 | PTA-125051 |
| Ascusbbf_120C | 5951 | PTA-125051 |
| Ascusbbf_1207K | 5952 | PTA-125033, PTA-125049, PTA-125050 |
| Ascusbbf_1207L | 5953 | PTA-125049 |
| Ascusbbf_930A | 5954 | PTA-125051, PTA-125052 |
| Ascusbbf_930B | 5988 | PTA-125051 |
| Ascusbbf_915A | 5955 | PTA-125051 |
| Ascusbbf_8941A | 5956 | PTA-125051, PTA-125052 |
| Ascusbbf_8480A | 5989 | PTA-125051, PTA-125052 |
| Ascusbbf_8480B | 5957 | PTA-125051 |
| Ascusbbf_374A | 5990 | PTA-125051, PTA-125052 |
| Ascusbbf_374B | 5958 | PTA-125051, PTA-125052 |
| Ascusbbf_374C | 5991 | PTA-125051, PTA-125052 |
| Ascusbbf_6906A | 5959 | PTA-125051, PTA-125052 |
| Ascusbbf_6906B | 5960 | PTA-125051, PTA-125052 |
| Ascusbbf_6906C | 5992 | PTA-125051, PTA-125052 |
| Ascusbbf_6906D | 5961 | PTA-125051 |
| Ascusbbf_6906E | 5962 | PTA-125051 |
| Ascusbbf_69K | 5963 | PTA-125033, PTA-125042 |
| Ascusbbf_69L | 5993 | PTA-125033, PTA-125042 |
| Ascusbbf_69M | 5964 | PTA-125033, PTA-125042 |
| Ascusbbf_69N | 5965 | PTA-125033, PTA-125042 |
| Ascusbbf_69O | 5966 | PTA-125033, PTA-125042 |
| Ascusbbf_69P | 5967 | PTA-125033 |
| Ascusbbf_721A | 5968 | PTA-125051, PTA-125052 |
| Ascusbbf_721B | 5969 | PTA-125051, PTA-125052 |
| Ascusbbf_721C | 5970 | PTA-125051, PTA-125052 |
| Ascusbbf_3819A | 5971 | PTA-125051 |
| Ascusbbf_4323A | 5972 | PTA-125051, PTA-125052 |
| Ascusbbf_4323B | 5973 | PTA-125051, PTA-125052 |
| Ascusbbf_4323C | 5974 | PTA-125051, PTA-125052 |
| Ascusbbf_4323D | 5975 | PTA-125051 |
| Ascusbbf_6087A | 5976 | PTA-125051, PTA-125052 |
| Ascusbbf_6087B | 5977 | PTA-125051, PTA-125052 |
| Ascusbbf_6087C | 5978 | PTA-125051 |
| Ascusbbf_8414A | 5979 | PTA-125051 |

BRIEF DESCRIPTION OF THE FIGURES

FIG. 6 depicts the average ruminal VFA concentrations of high-RFI and low-RFI steers. More efficient animals tended to have a higher production of VFAs.

In FIG. 21 reveals the comparison as to how much the microbial community changes week to week between high RFI animals and low RFI animals. The figure indicates that in week 4 the amount of change in the microbial communities is important to the RFI.

DETAILED DESCRIPTION

Definitions

Figure 1:
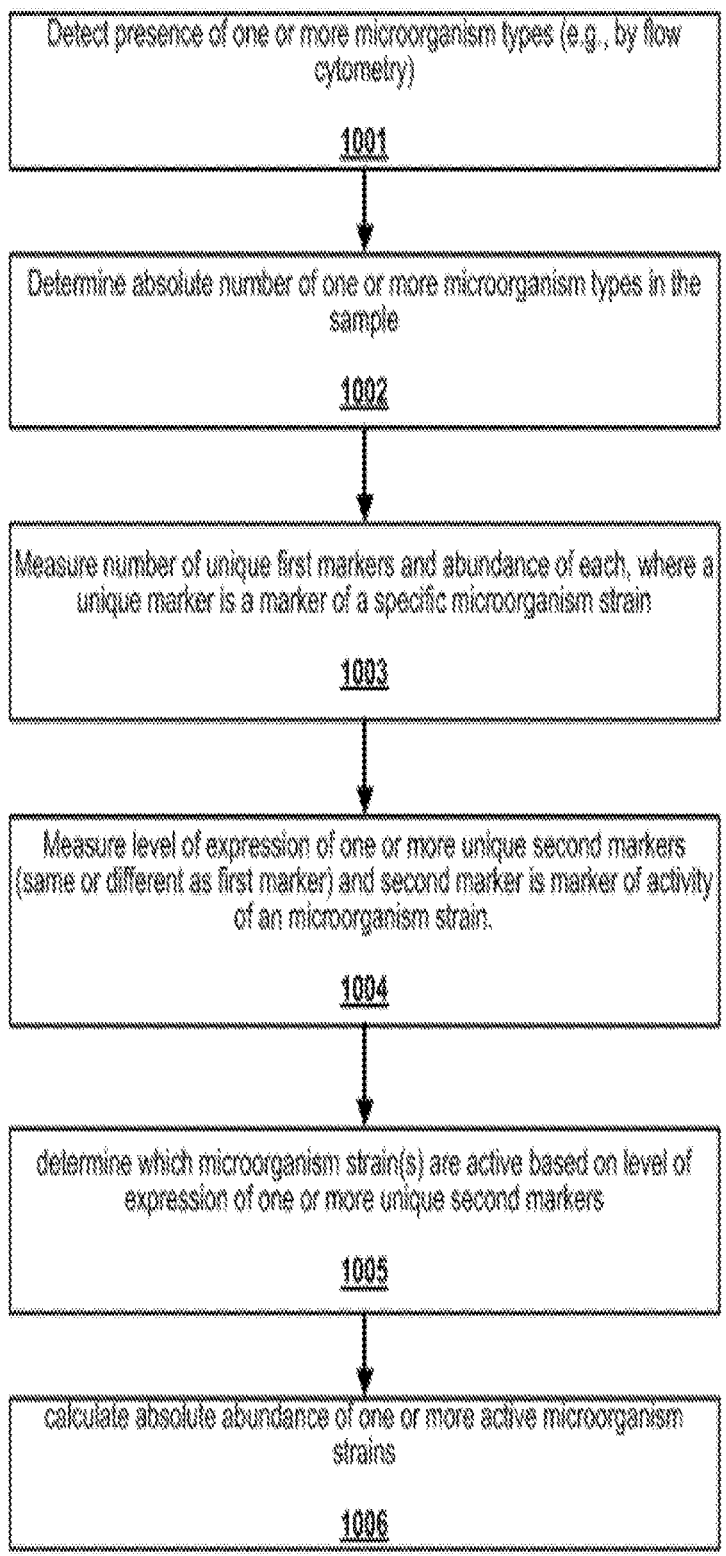
FIG. 1 shows a general workflow of one embodiment of the method for determining the absolute abundance of one or more active microorganism strains.

While the following terms are believed to be well understood by one of ordinary skill in the art, the following definitions are set forth to facilitate explanation of the presently disclosed subject matter.

The term "a" or "an" may refer to one or more of that entity, i.e. can refer to plural referents. As such, the terms "a" or "an", "one or more" and "at least one" are used interchangeably herein. In addition, reference to "an element" by the indefinite article "a" or "an" does not exclude the possibility that more than one of the elements is present, unless the context clearly requires that there is one and only one of the elements.

Reference throughout this specification to "one embodiment", "an embodiment", "one aspect", or "an aspect" means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics can be combined in any suitable manner in one or more embodiments.

As used herein, in particular embodiments, the terms "about" or "approximately" when preceding a numerical value indicates the value plus or minus a range of 10%.

As used herein the terms "microorganism" or "microbe" should be taken broadly. These terms are used interchangeably and include, but are not limited to, the two prokaryotic domains, Bacteria and Archaea, eukaryotic fungi and protozoa, as well as viruses. In some embodiments, the disclosure refers to the "microbes" of Table 1 and/or Table 2, or the "microbes" incorporated by reference. This characterization can refer to not only the predicted taxonomic microbial identifiers of the table, but also the identified strains of the microbes listed in the table.

The term "microbial community" means a group of microbes comprising two or more species or strains. Unlike microbial ensemble, a microbial community does not have to be carrying out a common function, or does not have to be participating in, or leading to, or correlating with, a recognizable parameter, such as a phenotypic trait of interest (e.g. increased feed efficiency in beef cattle).

As used herein, "isolate," "isolated," "isolated microbe," and like terms, are intended to mean that the one or more microorganisms has been separated from at least one of the materials with which it is associated in a particular environment (for example soil, water, animal tissue).

Microbes of the present disclosure may include spores and/or vegetative cells. In some embodiments, microbes of the present disclosure include microbes in a viable but non-culturable (VBNC) state, or a quiescent state. See Liao and Zhao (US Publication US2015267163A1). In some embodiments, microbes of the present disclosure include microbes in a biofilm. See Merritt et al. (U.S. Pat. No. 7,427,408).

Thus, an "isolated microbe" does not exist in its naturally occurring environment; rather, it is through the various techniques described herein that the microbe has been removed from its natural setting and placed into a non-naturally occurring state of existence. Thus, the isolated strain or isolated microbe may exist as, for example, a biologically pure culture, or as spores (or other forms of the strain) in association with an acceptable carrier.

As used herein, "spore" or "spores" refer to structures produced by bacteria and fungi that are adapted for survival and dispersal. Spores are generally characterized as dormant structures; however, spores are capable of differentiation through the process of germination. Germination is the differentiation of spores into vegetative cells that are capable of metabolic activity, growth, and reproduction. The germination of a single spore results in a single fungal or bacterial vegetative cell. Fungal spores are units of asexual reproduction, and in some cases are necessary structures in fungal life cycles. Bacterial spores are structures for surviving conditions that may ordinarily be nonconductive to the survival or growth of vegetative cells.

As used herein, "microbial composition" refers to a composition comprising one or more microbes of the present disclosure, wherein a microbial composition, in some embodiments, is administered to animals of the present disclosure.

As used herein, "carrier", "acceptable carrier", or "pharmaceutical carrier" refers to a diluent, adjuvant, excipient, or vehicle with which the compound is administered. Such carriers can be sterile liquids, such as water and oils, including those of petroleum, animal, vegetable, or synthetic origin; such as peanut oil, soybean oil, mineral oil, sesame oil, and the like. Water or aqueous solution saline solutions and aqueous dextrose and glycerol solutions are preferably employed as carriers, in some embodiments as injectable solutions. In some embodiments, gelling agents are employed as carriers. Alternatively, the carrier can be a solid dosage form carrier, including but not limited to one or more of a binder (for compressed pills), a glidant, an encapsulating agent, a flavorant, and a colorant. The choice of carrier can be selected with regard to the intended route of administration and standard pharmaceutical practice. See Hardee and Baggo (1998. Development and Formulation of Veterinary Dosage Forms. $2^{nd}$ Ed. CRC Press. 504 pg.); E. W. Martin (1970. Remington's Pharmaceutical Sciences. $17^{th}$ Ed. Mack Pub. Co.); and Blaser et al. (US Publication US20110280840A1).

In some aspects, carriers may be granular in structure, such as sand or sand particles. In further aspects, the carriers may be dry, as opposed to a moist or wet carrier. In some aspects, carriers can be nutritive substances and/or prebiotic substances selected from fructo-oligosaccharides, inulins, isomalto-oligosaccharides, lactitol, lactosucruse, lactulose, pyrodextrines, soy oligosaccharides, transgalacto-oligosaccharides, xylo-oligosaccharides, trace minerals, and vitamins. In some aspects, carriers can be in solid or liquid form. In some aspects, carriers can be zeolites, calcium carbonate, magnesium carbonate, silicon dioxide, ground corn, trehalose, chitosan, shellac, albumin, starch, skim-milk powder, sweet-whey powder, maltodextrin, lactose, and inulin. In some aspects, a carrier is water or physiological saline.

The term "bioensemble," "microbial ensemble," or "synthetic ensemble" refers to a composition comprising one or more active microbes identified by methods, systems, and/or apparatuses of the present disclosure and that do not naturally exist in a naturally occurring environment and/or at ratios or amounts that do not exist in nature. A bioensemble is a subset of a microbial community of individual microbial species, or strains of a species, which can be described as carrying out a common function, or can be described as participating in, or leading to, or correlating with, a recognizable parameter, such as a phenotypic trait of interest (e.g. increased feed efficiency in feedlot cattle). The bioensemble may comprise two or more species, or strains of a species, of microbes. In some instances, the microbes coexist within the community symbiotically.

In certain aspects of the disclosure, the isolated microbes exist as isolated and biologically pure cultures. It will be appreciated by one of skill in the art, that an isolated and biologically pure culture of a particular microbe, denotes that said culture is substantially free (within scientific reason) of other living organisms and contains only the individual microbe in question. The culture can contain varying concentrations of said microbe. The present disclosure notes that isolated and biologically pure microbes often "necessarily differ from less pure or impure materials." See, e.g. In re Bergstrom, 427 F.2d 1394, (CCPA 1970)(discussing purified prostaglandins), see also, In re Bergy, 596 F.2d 952 (CCPA 1979)(discussing purified microbes), see also, Parke-Davis & Co. v. H. K. Mulford & Co., 189 F. 95 (S.D.N.Y. 1911) (Learned Hand discussing purified adrenaline), aff'd in part, rev'd in part, 196 F. 496 (2d Cir. 1912), each of which are incorporated herein by reference. Furthermore, in some aspects, the disclosure provides for certain quantitative measures of the concentration, or purity limitations, that must be found within an isolated and biologically pure microbial culture. The presence of these purity values, in certain embodiments, is a further attribute that distinguishes the presently disclosed microbes from those microbes existing in a natural state. See, e.g., Merck & Co. v. Olin Mathieson Chemical Corp., 253 F.2d 156 (4th Cir. 1958) (discussing purity limitations for vitamin B12 produced by microbes), incorporated herein by reference.

As used herein, "individual isolates" should be taken to mean a composition, or culture, comprising a predominance of a single genera, species, or strain, of microorganism, following separation from one or more other microorganisms. The phrase should not be taken to indicate the extent to which the microorganism has been isolated or purified. However, "individual isolates" can comprise substantially only one genus, species, or strain, of microorganism.

As used herein, "microbiome" refers to the collection of microorganisms that inhabit the digestive tract or gastrointestinal tract of an animal (including the rumen if said animal is a ruminant) and the microorganism's physical environment (i.e. the microbiome has a biotic and physical component). The microbiome is fluid and may be modulated by numerous naturally occurring and artificial conditions (e.g., change in diet, disease, antimicrobial agents, influx of additional microorganisms, etc.). The modulation of the microbiome of a rumen that can be achieved via administration of the compositions of the disclosure, can take the form of: (a) increasing or decreasing a particular Family, Genus, Species, or functional grouping of microbe (i.e. alteration of the biotic component of the rumen microbiome) and/or (b) increasing or decreasing volatile fatty acids in the rumen, increasing or decreasing rumen pH, increasing or decreasing any other physical parameter important for rumen health (i.e. alteration of the abiotic component of the rumen microbiome).

As used herein, "probiotic" refers to a substantially pure microbe (i.e., a single isolate) or a mixture of desired microbes, and may also include any additional components that can be administered to beef cattle for restoring microbiota. Probiotics or microbial inoculant compositions of the disclosure may be administered with an agent to allow the microbes to survive the environment of the gastrointestinal tract, i.e., to resist low pH and to grow in the gastrointestinal environment. In some embodiments, the present compositions (e.g., microbial compositions) are probiotics in some aspects.

As used herein, "prebiotic" refers to an agent that increases the number and/or activity of one or more desired microbes. Non-limiting examples of prebiotics that may be useful in the methods of the present disclosure include fructooligosaccharides (e.g., oligofructose, inulin, inulin-type fructans), galactooligosaccharides, amino acids, alcohols, and mixtures thereof. See Ramirez-Farias et al. (2008. *Br. J. Nutr.* 4:1-10) and Pool-Zobel and Sauer (2007. *J. Nutr.* 137:2580-2584 and supplemental).

The term "growth medium" as used herein, is any medium which is suitable to support growth of a microbe. By way of example, the media may be natural or artificial including gastrin supplemental agar, LB media, blood serum, and tissue culture gels. It should be appreciated that the media may be used alone or in combination with one or more other media. It may also be used with or without the addition of exogenous nutrients.

The term "relative abundance" as used herein, is the number or percentage of a microbe present in the gastrointestinal tract or other organ system, relative to the number or percentage of total microbes present in said tract or organ system. The relative abundance may also be determined for particular types of microbes such as bacteria, fungi, viruses, and/or protozoa, relative to the total number or percentage of bacteria, fungi, viruses, and/or protozoa present. In one embodiment, relative abundance is determined by PCR. In another embodiment, relative abundance is determined by colony forming unit assays (cfu) or plaque forming unit assays (pfu) performed on samples from the gastrointestinal tract or other organ system of interest.

The medium may be amended or enriched with additional compounds or components, for example, a component which may assist in the interaction and/or selection of specific groups of microorganisms. For example, antibiotics (such as penicillin) or sterilants (for example, quaternary ammonium salts and oxidizing agents) could be present and/or the physical conditions (such as salinity, nutrients (for example organic and inorganic minerals (such as phosphorus, nitrogenous salts, ammonia, potassium and micronutrients such as cobalt and magnesium), pH, and/or temperature), methionine, prebiotics, ionophores, and beta glucans could be amended.

As used herein, the term "ruminant" includes mammals that are capable of acquiring nutrients from plant-based food by fermenting it in a specialized stomach (rumen) prior to digestion, principally through microbial actions. Ruminants included cattle, goats, sheep, giraffes, yaks, deer, antelope, and others.

As used herein, the term "bovid" includes any member of family Bovidae, which include hoofed mammals such as antelope, sheep, goats, and cattle, among others.

As used herein, the term "steer" includes any member, species, variant, or hybrid of *Bos indicus, Bos taurus indicus*, or *Bos taurus taurus*. The term "steer" further includes reference to cow (mature female), steer (castrated male), heifer (immature female not having born offspring), bull (mature uncastrated male), and calve (immature males or females).

As used herein, the terms "beef cattle" and "feedlot cattle" are used synonymously to refer to cattle that are grown and utilized for the production of beef. Said cattle of the present disclosure include varieties such as the following: Africander, Angus, Aubrac, Barzona, Bazadaise, Beef Shorthorn, Beefalo, Beefmaster, Belgian Blue, Belmont Red, Belted Galloway, Black Angus, Blonde d'Aquitaine, Bonsmara, Boran, Bradford, Brahman, Brahmousin, Brangus, British White, Buelingo, Canchim, Caracu, Charolais, Chianina, Composite, Corriente, Devon, Dexter, Drakensberger, Droughtmaster, English Longhorn, Galloway, Gelbvieh, Gloucester, Hays Converter, Hereford, Highland, Holstein, Hybridmaster, Limousin, Lincoln Red, Lowline, Luing, Maine-Anjou, Rouge des Pres, Marchigiana, Miniature Hereford, Mirandesa, Mongolian, Murray Grey, Nelore, Nguni, Parthenais, Piemontese, Pinzgauer, Red Angus, Red Poll, Retinta, Romagnola, Salers, Sanganer, Santa Cruz, Santa Gertrudis, Senepol, Shetland, Simbrah, Simmental, South Devon, Speckle Park, Square Meaters, Sussex, Tarentaise, Texas Longhorn, Tuli, Wagyu, Watusi, Welsh Black, Whitebred Shorthorn, and Zebu; or hybrids and/or crosses thereof.

As used herein, "dairy cattle" or "dairy cows" are used synonymously to refer to cows that are grown and utilized for the production of milk.

As used herein, "performance" should be taken to be increased weight gain, improved feed efficiency, improved residual feed intake, improved feed intake.

As used herein, "improved" should be taken broadly to encompass improvement of a characteristic of interest, as compared to a control group, or as compared to a known average quantity associated with the characteristic in question. For example, "improved" feed efficiency associated with application of a beneficial microbe, or microbial ensemble, of the disclosure can be demonstrated by comparing the feed efficiency of beef cattle treated by the microbes taught herein to the feed efficiency of beef cattle not treated. In the present disclosure, "improved" does not necessarily demand that the data be statistically significant (i.e. $p<0.05$); rather, any quantifiable difference demonstrating that one value (e.g. the average treatment value) is different from another (e.g. the average control value) can rise to the level of "improved."

As used herein, "inhibiting and suppressing" and like terms should not be construed to require complete inhibition or suppression, although this may be desired in some embodiments.

The term "marker" or "unique marker" as used herein is an indicator of unique microorganism type, microorganism strain or activity of a microorganism strain. A marker can be measured in biological samples and includes without limitation, a nucleic acid-based marker such as a ribosomal RNA gene, a peptide- or protein-based marker, and/or a metabolite or other small molecule marker.

The term "metabolite" as used herein is an intermediate or product of metabolism. A metabolite in one embodiment is a small molecule. Metabolites have various functions, including in fuel, structural, signaling, stimulatory and inhibitory effects on enzymes, as a cofactor to an enzyme, in defense, and in interactions with other organisms (such as pigments, odorants and pheromones). A primary metabolite is directly involved in normal growth, development and reproduction. A secondary metabolite is not directly involved in these processes but usually has an important ecological function. Examples of metabolites include but are not limited to antibiotics and pigments such as resins and terpenes, etc. Some antibiotics use primary metabolites as precursors, such as actinomycin which is created from the primary metabolite, tryptophan. Metabolites, as used herein, include small, hydrophilic carbohydrates; large, hydrophobic lipids and complex natural compounds.

As used herein, the term "genotype" refers to the genetic makeup of an individual cell, cell culture, tissue, organism, or group of organisms.

As used herein, the term "allele(s)" means any of one or more alternative forms of a gene, all of which alleles relate to at least one trait or characteristic. In a diploid cell, the two alleles of a given gene occupy corresponding loci on a pair of homologous chromosomes. Since the present disclosure, in embodiments, relates to QTLs, i.e. genomic regions that may comprise one or more genes or regulatory sequences, it is in some instances more accurate to refer to "haplotype" (i.e. an allele of a chromosomal segment) instead of "allele", however, in those instances, the term "allele" should be understood to comprise the term "haplotype". Alleles are considered identical when they express a similar phenotype. Differences in sequence are possible but not important as long as they do not influence phenotype.

As used herein, the term "locus" (loci plural) means a specific place or places or a site on a chromosome where for example a gene or genetic marker is found.

As used herein, the term "genetically linked" refers to two or more traits that are co-inherited at a high rate during breeding such that they are difficult to separate through crossing.

A "recombination" or "recombination event" as used herein refers to a chromosomal crossing over or independent assortment. The term "recombinant" refers to an organism having a new genetic makeup arising as a result of a recombination event.

As used herein, the term "molecular marker" or "genetic marker" refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), insertion mutations, microsatellite markers (SSRs), sequence-characterized amplified regions (SCARs), cleaved amplified polymorphic sequence (CAPS) markers or isozyme markers or combinations of the markers described herein which defines a specific genetic and chromosomal location. Markers further include polynucleotide sequences encoding 16S or 18S rRNA, and internal transcribed spacer (ITS) sequences, which are sequences found between small-subunit and large-subunit rRNA genes that have proven to be especially useful in elucidating relationships or distinctions among when compared against one another. Mapping of molecular markers in the vicinity of an allele is a procedure which can be performed by the average person skilled in molecular-biological techniques.

The primary structure of major rRNA subunit 16S comprise a particular combination of conserved, variable, and hypervariable regions that evolve at different rates and enable the resolution of both very ancient lineages such as domains, and more modern lineages such as genera. The secondary structure of the 16S subunit include approximately 50 helices which result in base pairing of about 67% of the residues. These highly conserved secondary structural features are of great functional importance and can be used to ensure positional homology in multiple sequence alignments and phylogenetic analysis. Over the previous few decades, the 16S rRNA gene has become the most sequenced taxonomic marker and is the cornerstone for the current systematic classification of bacteria and archaea (Yarza et al. 2014. Nature Rev. Micro. 12:635-45).

A sequence identity of 94.5% or lower for two 16S rRNA genes is strong evidence for distinct genera, 86.5% or lower is strong evidence for distinct families, 82% or lower is strong evidence for distinct orders, 78.5% is strong evidence for distinct classes, and 75% or lower is strong evidence for distinct phyla. The comparative analysis of 16S rRNA gene sequences enables the establishment of taxonomic thresholds that are useful not only for the classification of cultured microorganisms but also for the classification of the many environmental sequences. Yarza et al. 2014. Nature Rev. Micro. 12:635-45).

As used herein, the term "trait" refers to a characteristic or phenotype. For example, in the context of some embodiments of the present disclosure; efficiency of feed utilization, particularly with corn-intensive diets; amount of feces produced; susceptibility to gut pathogens; and a decrease in mortality rates; among others. Desirable traits may also include other characteristics, including but not limited to: an increase in weight; an increase in average daily weight gain; an increase of musculature; an increase of fatty acid concentration in the gastrointestinal tract; an improved efficiency in feed utilization and digestibility; an increase in polysaccharide and lignin degradation; an increase in fat, starch, and/or protein digestion; an increase in fatty acid concentration in the rumen; pH balance in the rumen, an increase in vitamin availability; an increase in mineral availability; an increase in amino acid availability; a reduction in methane and/or nitrous oxide emissions; a reduction in manure production; an improved dry matter intake; an improved efficiency of nitrogen utilization; an improved efficiency of phosphorous utilization; an increased resistance to colonization of pathogenic microbes that colonize cattle; reduced mortality; increased production of antimicrobials; increased clearance of pathogenic microbes; increased resistance to colonization of pathogenic microbes that colonize cattle; increased resistance to colonization of pathogenic microbes that infect humans; reduced incidence of acidosis or bloat; increased meat marbling, increased or decreased red coloring of meat, increased or decreased texture/coarseness of meat; increased amount of USDA Prime, USDA Choice, and USDA Select quality meat per animal, increased in the number of animals producing USDA Prime, USDA Choice, and USDA Select quality meat; increase or reduced concentration or presence of volatile compounds in the meat; reduced prevalence of acidosis or bloat; reduced body temperature; and any combination thereof; wherein said increase or reduction is determined by comparing against an animal not having been administered said composition.

A trait may be inherited in a dominant or recessive manner, or in a partial or incomplete-dominant manner. A trait may be monogenic (i.e. determined by a single locus)

or polygenic (i.e. determined by more than one locus) or may also result from the interaction of one or more genes with the environment.

In the context of this disclosure, traits may also result from the interaction of one or more beef cattle genes and one or more microorganism genes.

As used herein, the term "homozygous" means a genetic condition existing when two identical alleles reside at a specific locus, but are positioned individually on corresponding pairs of homologous chromosomes in the cell of a diploid organism. Conversely, as used herein, the term "heterozygous" means a genetic condition existing when two different alleles reside at a specific locus, but are positioned individually on corresponding pairs of homologous chromosomes in the cell of a diploid organism.

As used herein, the term "phenotype" refers to the observable characteristics of an individual cell, cell culture, organism (e.g., cattle), or group of organisms which results from the interaction between that individual's genetic makeup (i.e., genotype) and the environment.

As used herein, the term "chimeric" or "recombinant" when describing a nucleic acid sequence or a protein sequence refers to a nucleic acid, or a protein sequence, that links at least two heterologous polynucleotides, or two heterologous polypeptides, into a single macromolecule, or that re-arranges one or more elements of at least one natural nucleic acid or protein sequence. For example, the term "recombinant" can refer to an artificial combination of two otherwise separated segments of sequence, e.g., by chemical synthesis or by the manipulation of isolated segments of nucleic acids by genetic engineering techniques.

As used herein, a "synthetic nucleotide sequence" or "synthetic polynucleotide sequence" is a nucleotide sequence that is not known to occur in nature or that is not naturally occurring. Generally, such a synthetic nucleotide sequence will comprise at least one nucleotide difference when compared to any other naturally occurring nucleotide sequence.

As used herein, the term "nucleic acid" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. It also includes modified nucleic acids such as methylated and/or capped nucleic acids, nucleic acids containing modified bases, backbone modifications, and the like. The terms "nucleic acid" and "nucleotide sequence" are used interchangeably.

As used herein, the term "gene" refers to any segment of DNA associated with a biological function. Thus, genes include, but are not limited to, coding sequences and/or the regulatory sequences required for their expression. Genes can also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "homologous" or "homologue" or "ortholog" is known in the art and refers to related sequences that share a common ancestor or family member and are determined based on the degree of sequence identity. The terms "homology," "homologous," "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant disclosure such as deletion or insertion of one or more nucleotides that do not substantially alter the functional properties of the resulting nucleic acid fragment relative to the initial, unmodified fragment. It is therefore understood, as those skilled in the art will appreciate, that the disclosure encompasses more than the specific exemplary sequences. These terms describe the relationship between a gene found in one species, subspecies, variety, cultivar or strain and the corresponding or equivalent gene in another species, subspecies, variety, cultivar or strain. For purposes of this disclosure homologous sequences are compared. "Homologous sequences" or "homologues" or "orthologs" are thought, believed, or known to be functionally related. A functional relationship may be indicated in any one of a number of ways, including, but not limited to: (a) degree of sequence identity and/or (b) the same or similar biological function. Preferably, both (a) and (b) are indicated. Homology can be determined using software programs readily available in the art, such as those discussed in Current Protocols in Molecular Biology (F. M. Ausubel et al., eds., 1987) Supplement 30, section 7.718, Table 7.71. Some alignment programs are MacVector (Oxford Molecular Ltd, Oxford, U.K.), ALIGN Plus (Scientific and Educational Software, Pennsylvania) and AlignX (Vector NTI, Invitrogen, Carlsbad, CA). Another alignment program is Sequencher (Gene Codes, Ann Arbor, Michigan), using default parameters.

As used herein, the term "nucleotide change" refers to, e.g., nucleotide substitution, deletion, and/or insertion, as is well understood in the art. For example, mutations contain alterations that produce silent substitutions, additions, or deletions, but do not alter the properties or activities of the encoded protein or how the proteins are made.

As used herein, the term "protein modification" refers to, e.g., amino acid substitution, amino acid modification, deletion, and/or insertion, as is well understood in the art.

As used herein, the term "at least a portion" or "fragment" of a nucleic acid or polypeptide means a portion having the minimal size characteristics of such sequences, or any larger fragment of the full length molecule, up to and including the full length molecule. A fragment of a polynucleotide of the disclosure may encode a biologically active portion of a genetic regulatory element. A biologically active portion of a genetic regulatory element can be prepared by isolating a portion of one of the polynucleotides of the disclosure that comprises the genetic regulatory element and assessing activity as described herein. Similarly, a portion of a polypeptide may be 4 amino acids, 5 amino acids, 6 amino acids, 7 amino acids, and so on, going up to the full length polypeptide. The length of the portion to be used will depend on the particular application. A portion of a nucleic acid useful as a hybridization probe may be as short as 12 nucleotides; in some embodiments, it is 20 nucleotides. A portion of a polypeptide useful as an epitope may be as short as 4 amino acids. A portion of a polypeptide that performs the function of the full-length polypeptide would generally be longer than 4 amino acids.

Variant polynucleotides also encompass sequences derived from a mutagenic and recombinogenic procedure such as DNA shuffling. Strategies for such DNA shuffling are known in the art. See, for example, Stemmer (1994) PNAS 91:10747-10751; Stemmer (1994) Nature 370:389-391; Crameri et al. (1997) Nature Biotech. 15:436-438; Moore et al. (1997) J. Mol. Biol. 272:336-347; Zhang et al. (1997) PNAS 94:4504-4509; Crameri et al. (1998) Nature 391:288-291; and U.S. Pat. Nos. 5,605,793 and 5,837,458. For PCR amplifications of the polynucleotides disclosed herein, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) Molecular Cloning: A Laboratory Manual (2nd ed., Cold Spring Harbor Laboratory Press, Plainview, New York). See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). Known methods of PCR include, but are not limited to, methods using paired primers, nested primers, single specific primers, degenerate primers, gene-specific primers, vector-specific primers, partially-mismatched primers, and the like.

The term "primer" as used herein refers to an oligonucleotide which is capable of annealing to the amplification target allowing a DNA polymerase to attach, thereby serving as a point of initiation of DNA synthesis when placed under conditions in which synthesis of primer extension product is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxyribonucleotide. The primer must be sufficiently long to prime the synthesis of extension products in the presence of the agent for polymerization. The exact lengths of the primers will depend on many factors, including temperature and composition (A/T vs. G/C content) of primer. A pair of bi-directional primers consists of one forward and one reverse primer as commonly used in the art of DNA amplification such as in PCR amplification.

The terms "stringency" or "stringent hybridization conditions" refer to hybridization conditions that affect the stability of hybrids, e.g., temperature, salt concentration, pH, formamide concentration and the like. These conditions are empirically optimized to maximize specific binding and minimize non-specific binding of primer or probe to its target nucleic acid sequence. The terms as used include reference to conditions under which a probe or primer will hybridize to its target sequence, to a detectably greater degree than other sequences (e.g. at least 2-fold over background). Stringent conditions are sequence dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength and pH) at which 50% of a complementary target sequence hybridizes to a perfectly matched probe or primer. Typically, stringent conditions will be those in which the salt concentration is less than about 1.0 M Na+ ion, typically about 0.01 to 1.0 M Na+ion concentration (or other salts) at pH 7.0 to 8.3 and the temperature is at least about 30° C. for short probes or primers (e.g. 10 to 50 nucleotides) and at least about 60° C. for long probes or primers (e.g. greater than 50 nucleotides). Stringent conditions may also be achieved with the addition of destabilizing agents such as formamide. Exemplary low stringent conditions or "conditions of reduced stringency" include hybridization with a buffer solution of 30% formamide, 1 M NaCl, 1% SDS at 37° C. and a wash in 2×SSC at 40° C. Exemplary high stringency conditions include hybridization in 50% formamide, 1M NaCl, 1% SDS at 37° C., and a wash in 0.1×SSC at 60° C. Hybridization procedures are well known in the art and are described by e.g. Ausubel et al., 1998 and Sambrook et al., 2001. In some embodiments, stringent conditions are hybridization in 0.25 M Na2HPO4 buffer (pH 7.2) containing 1 mM Na2EDTA, 0.5-20% sodium dodecyl sulfate at 45° C., such as 0.5%, 1%, 2%, 3%, 4%, 5%, 6%, 7%, 8%, 9%, 10%, 11%, 12%, 13%, 14%, 15%, 16%, 17%, 18%, 19% or 20%, followed by a wash in 5×SSC, containing 0.1% (w/v) sodium dodecyl sulfate, at 55° C. to 65° C.

As used herein, "promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity.

As used herein, a "constitutive promoter" is a promoter which is active under most conditions and/or during most development stages. There are several advantages to using constitutive promoters in expression vectors used in biotechnology, such as: high level of production of proteins used to select transgenic cells or organisms; high level of expression of reporter proteins or scorable markers, allowing easy detection and quantification; high level of production of a transcription factor that is part of a regulatory transcription system; production of compounds that requires ubiquitous activity in the organism; and production of compounds that are required during all stages of development. Non-limiting exemplary constitutive promoters include, CaMV 35S promoter, opine promoters, ubiquitin promoter, alcohol dehydrogenase promoter, etc.

As used herein, a "non-constitutive promoter" is a promoter which is active under certain conditions, in certain types of cells, and/or during certain development stages. For example, tissue specific, tissue preferred, cell type specific, cell type preferred, inducible promoters, and promoters under development control are non-constitutive promoters. Examples of promoters under developmental control include promoters that preferentially initiate transcription in certain tissues.

As used herein, "inducible" or "repressible" promoter is a promoter which is under chemical or environmental factors control. Examples of environmental conditions that may affect transcription by inducible promoters include anaerobic conditions, certain chemicals, the presence of light, acidic or basic conditions, etc.

As used herein, a "tissue specific" promoter is a promoter that initiates transcription only in certain tissues. Unlike constitutive expression of genes, tissue-specific expression is the result of several interacting levels of gene regulation. As such, in the art sometimes it is preferable to use promoters from homologous or closely related species to achieve efficient and reliable expression of transgenes in particular tissues. This is one of the main reasons for the large amount of tissue-specific promoters isolated from particular tissues found in both scientific and patent literature.

As used herein, the term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the disclosure can be operably linked, either directly or indirectly, 5' to the target mRNA, or 3' to the target mRNA, or within the target mRNA, or a first complementary region is 5' and its complement is 3' to the target mRNA.

As used herein, the phrases "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such construct may be used by itself or may be used in conjunction with a vector. If a vector is used then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the disclosure. The skilled artisan will also recognize that different independent transformation events will result in different levels and patterns of expression (Jones et al., (1985) EMBO J. 4:2411-2418; De Almeida et al., (1989) Mol. Gen. Genetics 218:78-86), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others. Vectors can be plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. As used herein, the term "expression" refers to the production of a functional end-product e.g., an mRNA or a protein (precursor or mature).

In some embodiments, the cell or organism has at least one heterologous trait. As used herein, the term "heterologous trait" refers to a phenotype imparted to a transformed host cell or transgenic organism by an exogenous DNA segment, heterologous polynucleotide or heterologous nucleic acid. Various changes in phenotype are of interest to the present disclosure, including but not limited to increasing yield of an economically important trait (e.g., weight, etc.) and the like. These results can be achieved by providing expression of heterologous products or increased expression of endogenous products in organisms using the methods and compositions of the present disclosure.

As used herein, the term "MIC" means maximal information coefficient. MIC is a type of nonparamentric network analysis that identifies a score (MIC score) between active microbial strains of the present disclosure and at least one measured metadata (e.g., milk fat). Further, U.S. application Ser. No. 15/217,575, filed on Jul. 22, 2016 (issued as U.S. Pat. No. 9,540,676 on Jan. 10, 2017) is hereby incorporated by reference in its entirety.

Figure 2:
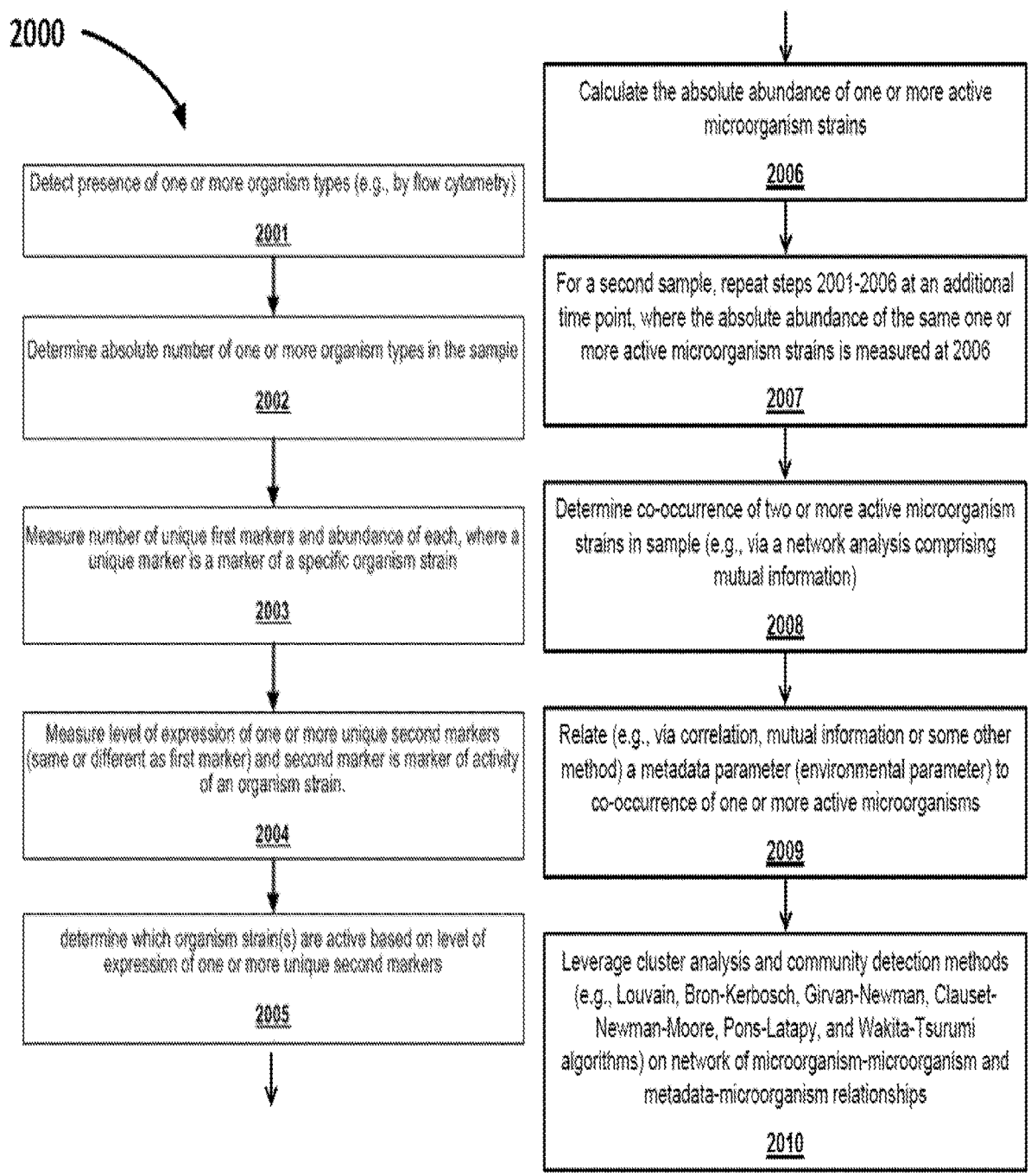
FIG. 2 shows a general workflow of one embodiment of a method for determining the co-occurrence of one or more, or two or more, active microorganism strains in a sample with one or more metadata (environmental) parameters, followed by leveraging cluster analysis and community detection methods on the network of determined relationships.

The maximal information coefficient (MIC) is then calculated between strains and metadata 3021a, and between strains 3021b; as seen in FIG. 2. Results are pooled to create a list of all relationships and their corresponding MIC scores 3022. If the relationship scores below a given threshold 3023, the relationship is deemed/identified as irrelevant 3023b. If the relationship is above a given threshold 3023, the relationship deemed/identified as relevant 2023a, and is further subject to network analysis 3024. The following code fragment shows an exemplary methodology for such analysis, according to one embodiment:

```
Read total list of relationships file as links
threshold = 0.8
for i in range(len(links)):
    if links >= threshold
        multiplier[i] = 1
    else
        multiplier[i] = 0
    end if
links_temp = multiplier*links
final_links = links_temp[links_temp != 0]
savetxt(output_file,final_links)
output_file.close( )
```

In some embodiments, the compositions of the present disclosure comprise one or more bacteria and/or one or more fungi that have a MIC score of at least about 0.1, at least about 0.15, at least about 0.2, at least about 0.25, at least about 0.3, at least about 0.35, at least about 0.4, at least about 0.45, at least about 0.5, at least about 0.55, at least about 0.6, at least about 0.65, at least about 0.7, at least about 0.75, at least about 0.80, at least about 0.85, at least about 0.9, or at least about 0.95.

In some embodiments, the compositions of the present disclosure comprise one or more bacteria and/or one or more fungi that have a MIC score of at least 0.1, at least 0.15, at least 0.2, at least 0.25, at least 0.3, at least 0.35, at least 0.4, at least 0.45, at least 0.5, at least 0.55, at least 0.6, at least 0.65, at least 0.7, at least 0.75, at least 0.80, at least 0.85, at least 0.9, or at least 0.95.

Based on the output of the network analysis, active strains are selected 3025 for preparing products (e.g., ensembles, aggregates, and/or other synthetic groupings) containing the selected strains. The output of the network analysis can also be used to inform the selection of strains for further product composition testing.

The use of thresholds is discussed above for analyses and determinations. Thresholds can be, depending on the implementation and application: (1) empirically determined (e.g., based on distribution levels, setting a cutoff at a number that removes a specified or significant portion of low level reads); (2) any non-zero value; (3) percentage/percentile based; (4) only strains whose normalized second marker (i.e., activity) reads is greater than normalized first marker (cell count) reads; (5) log 2 fold change between activity and quantity or cell count; (6) normalized second marker (activity) reads is greater than mean second marker (activity) reads for entire sample (and/or sample set); and/or any magnitude threshold described above in addition to a statistical threshold (i.e., significance testing). The following example provides thresholding detail for distributions of RNA-based second marker measurements with respect to DNA-based first marker measurements, according to one embodiment.

As used herein "shelf-stable" refers to a functional attribute and new utility acquired by the microbes formulated according to the disclosure, which enable said microbes to exist in a useful/active state outside of their natural environment in the rumen (i.e. a markedly different characteristic). Thus, shelf-stable is a functional attribute created by the formulations/compositions of the disclosure and denoting that the microbe formulated into a shelf-stable composition can exist outside the rumen and under ambient conditions for a period of time that can be determined depending upon the particular formulation utilized, but in general means that the microbes can be formulated to exist in a composition that is stable under ambient conditions for at least a few days and generally at least one week. Accordingly, a "shelf-stable ruminant supplement" is a composition comprising one or more microbes of the disclosure, said microbes formulated in a composition, such that the composition is stable under ambient conditions for at least one week, meaning that the microbes comprised in the composition (e.g. whole cell, spore, or lysed cell) are able to impart one or more beneficial phenotypic properties to a ruminant when administered (e.g. increased milk yield, improved milk compositional characteristics, improved rumen health, and/or modulation of the rumen microbiome).

Feedlot Cattle vs. Dairy Cows

The instant subject matter is distinct over the subject matter of prior Ascus Biosciences, Inc. applications. The 16S sequences of the microbes of the instant disclosure are believed to be distinct over those of any prior Ascus Biosciences, Inc. applications. One of ordinary skill in the art would be aware that the diet of a dairy cow would be distinct from that of a steer on a beef feedlot. The steer on the beef feedlot would be fed a high-energy high-grain diet in order to quickly increase the rate of weight gain and to increase the maximum weight prior to rendering. The cow on the dairy farm would be fed a different diet that is optimized for the production of milk with little consideration for rapid weight gain or highest maximum weight. The two diets would result in the rumen of the animals in the two environments to yield drastically different microbiota. Thus, the microorganisms in the rumen of the dairy cow and that of the feedlot steer are expected to be different from one another.

Isolated Microbes

In some aspects, the present disclosure provides isolated microbes, including novel strains of microbes, presented in Table 1 and Table 2.

In other aspects, the present disclosure provides isolated whole microbial cultures of the microbes identified in Table 1 and Table 2. These cultures may comprise microbes at various concentrations.

In some aspects, the disclosure provides for utilizing one or more microbes selected from Table 1 and Table 2 to increase a phenotypic trait of interest in beef cattle.

In some embodiments, the disclosure provides isolated microbial species belonging to taxonomic families of Prevotellaceae, Veillonellaceae, Ruminococcaceae, Fibrobacteraceae, Bacillaceae 1, Spirochaetaceae, Bacteroidaceae, Lachnospiraceae, Porphyromonadaceae, Coriobacteriaceae, Acidaminococcaceae, Clostridiaceae 1, Rhodobacteraceae, Cryomorphaceae, Erysipelotrichaceae, Promicromonosporaceae, Burkholderiaceae, Succinivibrionaceae, Pseudomonadaceae, Corynebacteriaceae, Planococcaceae, Streptomycetaceae, Synergistaceae, Nocardiopsaceae, Flavobacteriaceae, Propionibacteriaceae, Staphylococcaceae, Clostridiales incertae sedis XIII, Anaeroplasmataceae, Pasteurellaceae, Caulobacteraceae, and Sphingomonadaceae.

In further embodiments, isolated microbial species may be selected from genera of *Fibrobacter, Saccharofermentans, Bacillus, Spirochaeta, Bacteroides, Lachnospiracea incertae sedis, Clostridium XLVa, Ruminococcus, Butyricimonas, Olsenella, Acidaminococcus, Parabacteroides, Clostridum sensu stricto, Oribacterium, Pseudoflavonifractor, Treponema, Rhodobacter, Fluviicola, Succiniclasticum, Solobacterium, Veillonella, Cellulosimicrobium, Cupriavidus, Megasphaera, Succinivibrio, Oscillibacter, Pseudomonas, Corynebacterium, Adlercreutzia, Dorea, Roseburia, Anaerovibrio, Sporosarcina, Streptomyces, Syntrophococcus, Butyrivibrio, Lachnobacterium, Pyramidobacter, Coprococcus, Ruminobacter, Thermobifidia, Papillibacter, Aquimarina, Propioniciclava, Staphylococcus, Mogibacterium, Pseudobutyrivibrio, Asteroleplasma, Turicibacter, Aggregatibacter, Brevundimonas, Phascolarctobacterium,* and *Sphingobium.*

Furthermore, the disclosure relates to microbes having characteristics substantially similar to that of a microbe identified in Table 1 and/or Table 2.

The isolated microbial species, and novel strains of said species, identified in the present disclosure, are able to impart beneficial properties or traits to beef cattle production.

For instance, the isolated microbes described in Table 1 and Table 2, or microbial ensemble of said microbes, are able to increase feed efficiency. The increase can be quantitatively measured, for example, by measuring the effect that said microbial application has upon the modulation of feed efficiency.

In some embodiments, the isolated microbial strains are microbes of the present disclosure that have been genetically modified. In some embodiments, the genetically modified or recombinant microbes comprise polynucleotide sequences which do not naturally occur in said microbes. In some embodiments, the microbes may comprise heterologous polynucleotides. In further embodiments, the heterologous polynucleotides may be operably linked to one or more polynucleotides native to the microbes.

In some embodiments, the heterologous polynucleotides may be reporter genes or selectable markers. In some embodiments, reporter genes may be selected from any of the family of fluorescence proteins (e.g., GFP, RFP, YFP, and the like), β-galactosidase, luciferase. In some embodiments, selectable markers may be selected from neomycin phosphotransferase, hygromycin phosphotransferase, aminoglycoside adenyltransferase, dihydrofolate reductase, acetolactase synthase, bromoxynil nitrilase, β-glucuronidase, dihydrogolate reductase, and chloramphenicol acetyltransferase. In some embodiments, the heterologous polynucleotide may be operably linked to one or more promoter.

In some embodiments the isolated microbial strains express transgenic or native polypeptides selected from cellulases (endocellulases, exocellulases, glucosidases), pectinases, amylases, amylopectinases, ligninases, and phytases.

The isolated microbes of Table 2 represent variants of the microbes recited in Table 1. The microbes of Table 2, comprise the reference strains, and the microbes of Table 1 comprise the variants thereof. Generally, the variants of Table 2 comprise 16S rRNA sequences that share at least about 97% sequence identity with the 16S rRNA of the corresponding reference strain in Table B. For example, strains Asbusbbf_873A to Asbusbbf_873G (Table 2 correspond to variants of the reference strain Ascusbbf_873 (Table 1), wherein the 16S rRNA of the variants share at least about 97% sequence identity with that of the reference strain.

Microbial Compositions

In some aspects, the disclosure provides microbial compositions comprising a combination of at least any two microbes selected from amongst the microbes identified in Table 1 and Table 2.

In certain embodiments, the compositions of the present disclosure comprise two microbes, or three microbes, or four microbes, or five microbes, or six microbes, or seven microbes, or eight microbes, or nine microbes, or ten or more microbes. Said microbes of the compositions are different microbial species, or different strains of a microbial species.

In some embodiments, the disclosure provides microbial compositions, comprising: at least one or at least two isolated microbial species belonging to genera of: *Fibrobacter, Saccharofermentans, Bacillus, Spirochaeta, Bacteroides, Lachnospiracea incertae sedis, Clostridium XLVa, Ruminococcus, Butyricimonas, Olsenella, Acidaminococcus, Parabacteroides, Clostridum sensu stricto, Oribacterium, Pseudoflavonifractor, Treponema, Rhodobacter, Fluviicola, Succiniclasticum, Solobacterium, Veillonella, Cellulosimicrobium, Cupriavidus, Megasphaera, Succinivibrio, Oscillibacter, Pseudomonas, Corynebacterium, Adlercreutzia, Dorea, Roseburia, Anaerovibrio, Sporosarcina, Streptomyces, Syntrophococcus, Butyrivibrio, Lachnobacterium, Pyramidobacter, Coprococcus, Ruminobacter, Thermobifidia, Papillibacter, Aquimarina, Propioniciclava, Staphylococcus, Mogibacterium, Pseudobutyrivibrio, Asteroleplasma, Turicibacter, Aggregatibacter, Brevundimonas, Phascolarctobacterium*, and *Sphingobium*. Particular novel strains of species of these aforementioned genera can be found in Table 1 and Table 2.

In some embodiments, the disclosure provides microbial compositions, comprising: at least one or at least two isolated microbial species belonging to the family of: Prevotellaceae, Veillonellaceae, Ruminococcaceae, Fibrobacteraceae, Bacillaceae 1, Spirochaetaceae, Bacteroidaceae, Lachnospiraceae, Porphyromonadaceae, Coriobacteriaceae, Acidaminococcaceae, Clostridiaceae 1, Rhodobacteraceae, Cryomorphaceae, Erysipelotrichaceae, Promicromonosporaceae, Burkholderiaceae, Succinivibrionaceae, Pseudomonadaceae, Corynebacteriaceae, Planococcaceae, Streptomycetaceae, Synergistaceae, Nocardiopsaceae, Flavobacteriaceae, Propionibacteriaceae, Staphylococcaceae, Clostridiales incertae sedis XIII, Anaeroplasmataceae, Pasteurellaceae, Caulobacteraceae, and Sphingomonadaceae.

Particular novel strains of species of these aforementioned genera can be found in Table 1 and Table 2.

In particular aspects, the disclosure provides microbial compositions, comprising species as grouped in Tables 3-9. With respect to Tables 3-9, the letters A through I represent a non-limiting selection of microbes of the present disclosure, defined as:

A=Strain designation Ascusbbf_154 identified in Table 1;
B=Strain designation Ascusbbf_4 identified in Table 1;
C=Strain designation Ascusbbf_14146 identified in Table 1;
D=Strain designation Ascusbbf_876 identified in Table 1;
E=Strain designation Ascusbbf_24302 identified in Table 1;
F=Strain designation Ascusbbf_1085 identified in Table 1;
G=Strain designation Ascusbbf_1 identified in Table 1;
H=Strain designation Ascusbbf_6176 identified in Table 1; and
I=Strain designation Ascusbbf_3427 identified in Table 1.

TABLE 3

Eight and Nine Strain Compositions

| | | | | | |
|---|---|---|---|---|---|
| A, B, C, D, E, F, G, H | A, B, C, D, E, F, G, I | A, B, C, D, E, F, H, I | A, B, C, D, E, G, H, I | A, B, C, D, F, G, H, I | A, B, C, E, F, G, H, I |
| A, B, D, E, F, G, H, I | A, C, D, E, F, G, H, I | B, C, D, E, F, G, H, I | A, B, C, D, E, F, G, H, I | | |

TABLE 4

Seven Strain Compositions

| | | | | | |
|---|---|---|---|---|---|
| A, B, C, D, E, F, G | A, B, C, D, E, F, H | A, B, C, D, E, F, I | A, B, C, D, E, G, H | A, B, C, D, E, G, I | A, B, C, D, E, H, I |
| A, B, C, D, F, G, H | A, B, C, D, F, G, I | A, B, C, D, F, H, I | A, B, C, D, G, H, I | A, B, C, E, F, G, H | A, B, C, E, F, G, I |
| A, B, C, E, F, H, I | A, B, C, E, G, H, I | A, B, C, F, G, H, I | A, B, D, E, F, G, H | A, B, D, E, F, G, I | A, B, D, E, F, H, I |
| A, B, D, E, G, H, I | A, B, D, F, G, H, I | A, B, E, F, G, H, I | A, C, D, E, F, G, H | A, C, D, E, F, G, I | A, C, D, E, F, H, I |
| A, C, D, E, G, H, I | A, C, D, F, G, H, I | A, C, E, F, G, H, I | A, D, E, F, G, H, I | B, C, D, E, F, G, H | B, C, D, E, F, G, I |
| B, C, D, E, F, H, I | B, C, D, E, G, H, I | B, C, D, F, G, H, I | B, C, E, F, G, H, I | B, D, E, F, G, H, I | C, D, E, F, G, H, I |

TABLE 5

Six Strain Compositions

| | | | | | | |
|---|---|---|---|---|---|---|
| A, B, C, D, E, F | A, B, C, D, E, G | A, B, C, D, E, H | A, B, C, D, E, I | A, B, C, D, F, G | A, B, C, D, F, H | A, B, C, D, F, I |
| A, B, C, D, G, H | A, B, C, D, G, I | A, B, C, D, H, I | A, B, C, E, F, G | A, B, C, E, F, H | A, B, C, E, F, I | A, B, C, E, G, H |
| A, B, C, E, G, I | A, B, C, E, H, I | A, B, C, F, G, H | A, B, C, F, G, I | A, B, C, F, H, I | A, B, C, G, H, I | A, B, D, E, F, G |
| A, B, D, E, F, H | A, B, D, E, F, I | A, B, D, E, G, H | A, B, D, E, G, I | A, B, D, E, H, I | A, B, D, F, G, H | A, B, D, F, G, I |
| D, E, F, G, H, I | C, E, F, G, H, I | A, B, D, F, H, I | A, B, D, G, H, I | A, B, E, F, G, H | A, B, E, F, G, I | A, B, E, F, H, I |
| A, B, E, G, H, I | A, B, F, G, H, I | A, C, D, E, F, G | A, C, D, E, F, H | A, C, D, E, F, I | A, C, D, E, G, H | A, C, D, E, G, I |
| A, C, D, E, H, I | A, C, D, F, G, H | A, C, D, F, G, I | A, C, D, F, H, I | A, C, D, G, H, I | A, C, E, F, G, H | A, C, E, F, G, I |

TABLE 5-continued

Six Strain Compositions

| | | | | | | |
|---|---|---|---|---|---|---|
| A, C, E, F, H, I | A, C, E, G, H, I | A, C, F, G, H, I | A, D, E, F, G, H | A, D, E, F, G, I | A, D, E, F, H, I | A, D, E, G, H, I |
| A, D, F, G, H, I | A, E, F, G, H, I | B, C, D, E, F, G | B, C, D, E, F, H | B, C, D, E, F, I | B, C, D, E, G, H | B, C, D, E, G, I |
| B, C, D, E, H, I | B, C, D, F, G, H | B, C, D, F, G, I | B, C, D, F, H, I | B, C, D, G, H, I | B, C, E, F, G, H | B, C, E, F, G, I |
| B, C, E, F, H, I | B, C, E, G, H, I | B, C, F, G, H, I | B, D, E, F, G, H | B, D, E, F, G, I | B, D, E, F, H, I | B, D, E, G, H, I |
| B, D, F, G, H, I | B, E, F, G, H, I | C, D, E, F, G, H | C, D, E, F, G, I | C, D, E, F, H, I | C, D, E, G, H, I | C, D, F, G, H, I |

TABLE 6

Five Strain Compositions

| | | | | | | | |
|---|---|---|---|---|---|---|---|
| A, B, C, D, E | A, B, C, D, F | A, B, C, D, G | A, B, C, D, H | A, B, C, D, I | A, B, C, E, F | A, B, C, E, G | A, B, C, E, H |
| A, B, C, F, H | A, B, C, F, G | A, B, C, F, I | A, B, C, G, H | A, B, C, G, I | A, B, C, H, I | A, B, D, E, F | A, B, D, E, G |
| A, B, D, E, I | A, B, D, F, G | A, B, D, F, H | A, B, D, F, I | A, B, D, G, H | A, B, D, G, I | A, B, D, H, I | A, B, E, F, G |
| A, B, E, F, I | A, B, E, G, H | A, B, E, G, I | A, B, E, H, I | A, B, F, G, H | A, B, F, G, I | A, B, F, H, I | A, B, G, H, I |
| A, C, D, E, G | A, C, D, E, H | A, C, D, E, I | A, C, D, F, H | A, C, D, F, I | A, C, D, G, H | A, C, D, G, I | A, C, D, H, I |
| A, C, E, F, G | A, C, E, F, H | A, C, E, F, I | A, C, E, G, H | A, C, E, G, I | A, C, E, H, I | A, C, F, G, H | A, C, F, G, I |
| A, C, G, H, I | A, D, E, F, G | A, D, E, F, H | A, D, E, F, I | A, D, E, G, H | A, D, E, G, I | A, D, E, H, I | A, D, F, G, H |
| A, D, F, H, I | A, D, G, H, I | A, E, F, G, H | A, E, F, G, I | A, E, F, H, I | A, E, G, H, I | A, F, G, H, I | B, C, D, E, F |
| B, C, D, E, H | B, C, D, E, I | B, C, D, F, G | B, C, D, F, H | B, C, D, F, I | B, C, D, G, H | B, C, D, G, I | B, C, D, H, I |
| B, C, E, F, H | B, C, E, F, I | B, C, E, G, H | B, C, E, G, I | B, C, E, H, I | B, C, F, G, H | B, C, F, G, I | B, C, F, H, I |
| B, D, E, F, G | B, D, E, F, H | B, D, E, F, I | B, D, E, G, H | B, D, E, G, I | B, D, E, H, I | B, D, F, G, H | B, D, F, G, I |
| B, D, G, H, I | B, E, F, G, H | B, E, F, G, I | B, E, F, H, I | B, E, G, H, I | B, F, G, H, I | C, D, E, F, G | C, D, E, F, H |
| C, D, E, G, H | C, D, E, G, I | C, D, E, H, I | C, D, F, G, H | C, D, F, G, I | C, D, F, H, I | C, D, G, H, I | C, E, F, G, H |
| C, E, F, H, I | C, E, G, H, I | C, F, G, H, I | D, E, F, G, H | D, E, F, G, I | D, E, F, H, I | D, E, G, H, I | D, F, G, H, I |
| A, B, C, E, I | A, B, D, E, H | A, B, E, F, H | A, C, D, E, F | A, C, D, H, I | A, C, F, H, I | A, D, F, G, I | B, C, D, E, G |
| B, C, E, F, G | B, C, G, H, I | B, D, F, H, I | C, D, E, F, I | C, E, F, G, I | E, F, G, H, I | | |

TABLE 7

Four Strain Compositions

| | | | | | | | |
|---|---|---|---|---|---|---|---|
| A, B, C, D | A, B, C, E | A, B, C, F | A, B, C, G | A, B, C, H | A, B, C, I | A, B, D, E | A, B, D, F | D, G, H, I |
| A, B, D, G | A, B, D, H | A, B, D, I | A, B, E, F | A, B, E, G | A, B, E, H | A, B, E, I | A, B, F, G | E, F, G, H |
| A, B, F, H | A, D, F, H | A, D, F, I | A, D, G, H | A, D, G, I | A, D, H, I | A, E, F, G | A, E, F, H | E, F, G, I |
| A, B, F, I | A, B, G, H | A, B, G, I | A, B, H, I | A, C, D, E | A, C, D, F | A, C, D, G | A, C, D, H | E, F, H, I |
| A, C, D, I | A, C, E, F | A, C, E, G | A, C, E, H | A, C, E, I | A, C, F, G | A, C, F, H | A, C, F, I | E, G, H, I |
| A, C, G, H | A, C, G, I | A, C, H, I | A, D, E, F | A, D, E, G | A, D, E, H | A, D, E, I | A, D, F, G | F, G, H, I |
| A, E, F, I | A, E, G, H | A, E, G, I | A, E, H, I | A, F, G, H | A, F, G, I | A, F, H, I | A, G, H, I | D, E, F, H |
| B, C, D, E | B, C, D, F | B, C, D, G | B, C, D, H | B, C, D, I | B, C, E, F | B, C, E, G | B, C, E, H | D, E, F, I |
| B, C, E, I | B, C, F, G | B, C, F, H | B, C, F, I | B, C, G, H | B, C, G, I | B, C, H, I | B, D, E, F | D, E, G, H |
| B, D, E, G | B, D, E, H | B, D, E, I | B, D, F, G | B, D, F, H | B, D, F, I | B, D, G, H | B, D, G, I | D, E, G, I |
| B, D, H, I | B, E, F, G | B, E, F, H | B, E, F, I | B, E, G, H | B, E, G, I | B, E, H, I | B, F, G, H | D, E, H, I |
| B, F, G, I | B, F, H, I | B, G, H, I | C, D, E, F | C, D, E, G | C, D, E, H | C, D, E, I | C, D, F, G | D, F, G, H |
| C, D, F, H | C, D, F, I | C, D, G, H | C, D, G, I | C, D, H, I | C, E, F, G | C, E, F, H | C, E, F, I | D, F, G, I |
| C, E, G, H | C, E, G, I | C, E, H, I | C, F, G, H | C, F, G, I | C, F, H, I | C, G, H, I | D, E, F, G | D, F, H, I |

TABLE 8

Three Strain Compositions

| | | | | | | | | | |
|---|---|---|---|---|---|---|---|---|---|
| A, B, C | A, B, D | A, B, E | A, B, F | A, B, G | A, B, H | A, B, I | A, C, D | A, C, E | G, H, I | E, F, H |
| A, C, F | A, C, G | A, C, H | A, C, I | A, D, E | A, D, F | A, D, G | A, D, H | A, D, I | F, H, I | E, F, G |
| A, E, F | A, E, G | A, E, H | A, E, I | A, F, G | A, F, H | A, F, I | A, G, H | A, G, I | F, G, I | D, H, I |
| A, H, I | B, C, D | B, C, E | B, C, F | B, C, G | B, C, H | B, C, I | B, D, E | B, D, F | F, G, H | D, G, I |
| B, D, G | B, D, H | B, D, I | B, E, F | B, E, G | B, E, H | B, F, G | B, F, H | E, H, I | E, F, I |
| B, F, I | B, G, H | B, G, I | B, H, I | C, D, E | C, D, F | C, D, G | C, D, H | C, D, I | E, G, I | D, G, H |
| C, E, F | C, E, G | C, E, H | C, E, I | C, F, G | C, F, H | C, F, I | C, G, H | C, G, I | E, G, H | D, F, I |
| C, H, I | D, E, F | D, E, G | D, E, H | D, E, I | D, F, G | D, F, H | | | | |

TABLE 9

Two Strain Compositions

| | | | | | | | | | | | | | | | |
|---|---|---|---|---|---|---|---|---|---|---|---|---|---|---|---|
| A, B | A, C | A, D | A, E | A, F | A, G | A, H | A, I | B, C | B, D | B, E | B, F | B, G | B, H | B, I | C, D |
| C, E | C, F | C, G | C, H | C, I | D, E | D, F | D, G | D, H | D, I | E, F | E, G | E, H | E, I | F, G | F, H |
| F, I | G, H | G, I | H, I | | | | | | | | | | | | |

In some embodiments, the microbial compositions may be selected from any member group from Tables 3-9.

Isolated Microbes—Source Material

In particular embodiments, the microbes of the present compositions are not naturally found in association with the same animal. In some aspects, the microbial species forming the microbial community are all found in association with animals from the same geographic location. In other aspects, each microbial species forming the composition is from a different geographic location. A geographic location can be defined based upon the predominant soil type in a region, the predominant climate in a region, the predominant plant community present in a region, the predominant plant community present in a region, the distance between regions, the average rainfall in a region, among others.

In some embodiments, the microbes of the present compositions are not naturally found in association with the same species of animal. In some embodiments, the microbes of the present compositions are found in the same species of animal, but separated by geographic region.

In a particular embodiment, at least one microbial species that is a member of the microbial community derived by the disclosed method is native to, or was acquired from, a geographic region at least about 1 m, 10 m, 100 m, 1 km, 10 km, 100 km, 1,000 km, 10,000 km, 20,000 km, 30,000 km, or 40,000 km from the location of the plant upon which a phenotypic trait is to be increased based upon the taught methods.

The microbes of the present disclosure were obtained, among other places, at various locales in the United States from the gastrointestinal tract of beef cattle.

Isolated Microbes—Microbial Culture Techniques

The microbes of Table 1 and Table 2 were matched to their nearest taxonomic groups by utilizing classification tools of the Ribosomal Database Project (RDP) for 16s rRNA sequences and the User-friendly Nordic ITS Ectomycorrhiza (UNITE) database for ITS rRNA sequences. Examples of matching microbes to their nearest taxa may be found in Lan et al. (2012. *PLOS one.* 7(3):e32491), Schloss and Westcott (2011. *Appl. Environ. Microbiol.* 77(10):3219-3226), and Koljalg et al. (2005. *New Phytologist.* 166(3): 1063-1068).

The isolation, identification, and culturing of the microbes of the present disclosure can be effected using standard microbiological techniques. Examples of such techniques may be found in Gerhardt, P. (ed.) Methods for General and Molecular Microbiology. American Society for Microbiology, Washington, D.C. (1994) and Lennette, E. H. (ed.) Manual of Clinical Microbiology, Third Edition. American Society for Microbiology, Washington, D.C. (1980), each of which is incorporated by reference.

Isolation can be effected by streaking the specimen on a solid medium (e.g., nutrient agar plates) to obtain a single colony, which is characterized by the phenotypic traits described hereinabove (e.g., Gram positive/negative, capable of forming spores aerobically/anaerobically, cellular morphology, carbon source metabolism, acid/base production, enzyme secretion, metabolic secretions, etc.) and to reduce the likelihood of working with a culture which has become contaminated.

For example, for microbes of the disclosure, biologically pure isolates can be obtained through repeated subculture of biological samples, each subculture followed by streaking onto solid media to obtain individual colonies or colony forming units. Methods of preparing, thawing, and growing lyophilized bacteria are commonly known, for example, Gherna, R. L. and C. A. Reddy. 2007. Culture Preservation, p 1019-1033. In C. A. Reddy, T. J. Beveridge, J. A. Breznak, G. A. Marzluf, T. M. Schmidt, and L. R. Snyder, eds. American Society for Microbiology, Washington, D.C., 1033 pages; herein incorporated by reference. Thus freeze dried liquid formulations and cultures stored long term at −70° C. in solutions containing glycerol are contemplated for use in providing formulations of the present disclosure.

The microbes of the disclosure can be propagated in a liquid medium under aerobic conditions, or alternatively anaerobic conditions. Medium for growing the bacterial strains of the present disclosure includes a carbon source, a nitrogen source, and inorganic salts, as well as specially required substances such as vitamins, amino acids, nucleic acids and the like. Examples of suitable carbon sources which can be used for growing the microbes include, but are not limited to, starch, peptone, yeast extract, amino acids, sugars such as glucose, arabinose, mannose, glucosamine, maltose, and the like; salts of organic acids such as acetic acid, fumaric acid, adipic acid, propionic acid, citric acid, gluconic acid, malic acid, pyruvic acid, malonic acid and the like; alcohols such as ethanol and glycerol and the like; oil or fat such as soybean oil, rice bran oil, olive oil, corn oil, sesame oil. The amount of the carbon source added varies according to the kind of carbon source and is typically between 1 to 100 gram(s) per liter of medium. Preferably, glucose, starch, and/or peptone is contained in the medium as a major carbon source, at a concentration of 0.1-5% (W/V). Examples of suitable nitrogen sources which can be used for growing the bacterial strains of the present disclosure include, but are not limited to, amino acids, yeast extract, tryptone, beef extract, peptone, potassium nitrate, ammonium nitrate, ammonium chloride, ammonium sulfate, ammonium phosphate, ammonia or combinations thereof. The amount of nitrogen source varies according to the type of nitrogen source, typically between 0.1 to 30 gram per liter of medium. The inorganic salts, potassium dihydrogen phosphate, dipotassium hydrogen phosphate, disodium hydrogen phosphate, magnesium sulfate, magnesium chloride, ferric sulfate, ferrous sulfate, ferric chloride, ferrous chloride, manganous sulfate, manganous chloride, zinc sulfate, zinc chloride, cupric sulfate, calcium chloride, sodium chloride, calcium carbonate, sodium carbonate can be used alone or in combination. The amount of inorganic acid varies according to the kind of the inorganic salt, typically between 0.001 to 10 gram per liter of medium. Examples of specially required substances include, but are not limited to, vitamins, nucleic acids, yeast extract, peptone, meat extract, malt extract, dried yeast and combinations thereof. Cultivation can be effected at a temperature, which allows the growth of the microbial strains, essentially, between 20° C. and 46° C. In some aspects, a temperature range is 30° C.-39° C. For optimal growth, in some embodiments, the medium can be adjusted to pH 6.0-7.4. It will be appreciated that commercially available media may also be used to culture the microbial strains, such as Nutrient Broth or Nutrient Agar available from Difco, Detroit, MI It will be appreciated that cultivation time may differ depending on the type of culture medium used and the concentration of sugar as a major carbon source.

In some aspects, cultivation lasts between 24-96 hours. Microbial cells thus obtained are isolated using methods, which are well known in the art. Examples include, but are not limited to, membrane filtration and centrifugal separation. The pH may be adjusted using sodium hydroxide and the like and the culture may be dried using a freeze dryer, until the water content becomes equal to 4% or less. Microbial co-cultures may be obtained by propagating each strain as described hereinabove. In some aspects, microbial multi-strain cultures may be obtained by propagating two or more of the strains described hereinabove. It will be appreciated that the microbial strains may be cultured together when compatible culture conditions can be employed.

Isolated Microbes—Microbial Strains

Microbes can be distinguished into a genus based on polyphasic taxonomy, which incorporates all available phenotypic and genotypic data into a consensus classification (Vandamme et al. 1996. Polyphasic taxonomy, a consensus approach to bacterial systematics. *Microbiol Rev* 1996, 60:407-438). One accepted genotypic method for defining species is based on overall genomic relatedness, such that strains which share approximately 70% or more relatedness using DNA-DNA hybridization, with 5° C. or less $\Delta T_m$ (the difference in the melting temperature between homologous and heterologous hybrids), under standard conditions, are considered to be members of the same species. Thus, populations that share greater than the aforementioned 70% threshold can be considered to be variants of the same species. Another accepted genotypic method for defining species is to isolate marker genes of the present disclosure, sequence these genes, and align these sequenced genes from multiple isolates or variants. The microbes are interpreted as belonging to the same species if one or more of the sequenced genes share at least 97% sequence identity.

The 16S or 18S rRNA sequences or ITS sequences are often used for making distinctions between species and strains, in that if one of the aforementioned sequences shares less than a specified % sequence identity from a reference sequence, then the two organisms from which the sequences were obtained are said to be of different species or strains.

Thus, one could consider microbes to be of the same species, if they share at least 80%, 85%, 90%, 95%, 97%, 98%, or 99% sequence identity across the 16S or 18S rRNA sequence, or the ITS1 or ITS2 sequence.

Further, one could define microbial strains of a species, as those that share at least 80%, 85%, 90%, 95%, 97%, 98%, or 99% sequence identity across the 16S or 18S rRNA sequence, or the ITS1 or ITS2 sequence.

In one embodiment, microbial strains of the present disclosure include those that comprise polynucleotide sequences that share at least 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity with any one of SEQ ID NOs:1-5,993. In a further embodiment, microbial strains of the present disclosure include those that comprise polynucleotide sequences that share at least 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity with any one of SEQ ID NOs:1-5,993.

Comparisons may also be made with 23S rRNA sequences against reference sequences.

Unculturable microbes often cannot be assigned to a definite species in the absence of a phenotype determination, the microbes can be given a *candidatus* designation within a genus provided their 16S or 18S rRNA sequences or ITS sequences subscribes to the principles of identity with known species.

One approach is to observe the distribution of a large number of strains of closely related species in sequence space and to identify clusters of strains that are well resolved from other clusters. This approach has been developed by using the concatenated sequences of multiple core (housekeeping) genes to assess clustering patterns, and has been called multilocus sequence analysis (MLSA) or multilocus sequence phylogenetic analysis. MLSA has been used successfully to explore clustering patterns among large numbers of strains assigned to very closely related species by current taxonomic methods, to look at the relationships between small numbers of strains within a genus, or within a broader taxonomic grouping, and to address specific taxonomic questions. More generally, the method can be used to ask whether bacterial species exist—that is, to observe whether large populations of similar strains invariably fall into well-resolved clusters, or whether in some cases there is a genetic continuum in which clear separation into clusters is not observed.

In order to more accurately make a determination of genera, a determination of phenotypic traits, such as morphological, biochemical, and physiological characteristics are made for comparison with a reference genus archetype. The colony morphology can include color, shape, pigmentation, production of slime, etc. Features of the cell are described as to shape, size, Gram reaction, extracellular material, presence of endospores, flagella presence and location, motility, and inclusion bodies. Biochemical and physiological features describe growth of the organism at different ranges of temperature, pH, salinity and atmospheric conditions, growth in presence of different sole carbon and nitrogen sources. One of ordinary skill in the art would be reasonably apprised as to the phenotypic traits that define the genera of the present disclosure.

In one embodiment, the microbes taught herein were identified utilizing 16S rRNA gene sequences and ITS sequences. It is known in the art that 16S rRNA contains hypervariable regions that can provide species/strain-specific signature sequences useful for bacterial identification, and that ITS sequences can also provide species/strain-specific signature sequences useful for fungal identification.

Phylogenetic analysis using the rRNA genes and/or ITS sequences are used to define "substantially similar" species belonging to common genera and also to define "substantially similar" strains of a given taxonomic species. Furthermore, physiological and/or biochemical properties of the isolates can be utilized to highlight both minor and significant differences between strains that could lead to advantageous behavior in beef cattle.

Compositions of the present disclosure may include combinations of fungal spores and bacterial spores, fungal spores and bacterial vegetative cells, fungal vegetative cells and bacterial spores, fungal vegetative cells and bacterial vegetative cells. In some embodiments, compositions of the present disclosure comprise bacteria only in the form of spores. In some embodiments, compositions of the present disclosure comprise bacteria only in the form of vegetative cells. In some embodiments, compositions of the present disclosure comprise bacteria in the absence of fungi. In some embodiments, compositions of the present disclosure comprise fungi in the absence of bacteria. In some embodiments, compositions of the present disclosure comprise VBNC bacteria and/or fungi. In some embodiments, compositions of the present disclosure comprise bacteria and/or fungi in a quiescent state. In some embodiments, compositions of the present disclosure include dormant bacteria and/or fungi.

Bacterial spores may include endospores and akinetes. Fungal spores may include statismospores, ballistospores, autospores, aplanospores, zoospores, mitospores, megaspores, microspores, meiospores, chlamydospores, urediniospores, teliospores, oospores, carpospores, tetraspores, sporangiospores, zygospores, ascospores, basidiospores, ascospores, and asciospores.

In some embodiments, spores of the composition germinate upon administration to animals of the present disclosure. In some embodiments, spores of the composition germinate only upon administration to animals of the present disclosure.

Microbial Compositions

In some embodiments, the microbes of the disclosure are combined into microbial compositions.

In some embodiments, the microbial compositions include cattle feed, such as grain and grain byproducts (barley, maize, oats, sorghum, wheat, distillers grains, sweet bran, and the like); roughage (alfalfa, silage, fescue, clover, ryegrass, and the like); starches (tapioca and the like); protein (oilseed cakes, vegetable wastes, corn by-products, wheat by-products, and the like); liquid feeds (condensed corn distillers solubles, molasses, tallow, yellow grease, corn oil, and the like); or non-nitrogen protein. In some embodiments, the microbial compositions include vitamins and/or metabolites thereof, minerals, urea, trace elements, emulsifiers, aromatizing products, binders, colorants, odorants, thickening agents, antibiotics, and the like. In some embodiments, the microbial compositions include one or more of an ionophore; vaccine, antibiotic; antihelmintic; virucide; nematicide; amino acids such as methionine, glutamine, valine, glycine, cysteine, homocysteine, aspartic acid, and arginine; fish oil; oregano; carnitine, pantoate, pantothenate, aspartate, and biologically active molecules such as enzymes.

In some embodiments, the vitamins include vitamin B5, B1, B2, B3, B6, B9, B12, H, C, A, D, E, or K; and combinations thereof. In some embodiments, the microbial compositions include microbes that synthesize vitamin B5, B1, B2, B3, B6, B9, B12, H, C, A, D, E, and/or K. In some embodiments, the microbial compositions include microbes that synthesize vitamin B5. In some embodiments, the metabolites of vitamin B5, B1, B2, B3, B6, B9, B12, H, C, A, D, E, or K are contemplated as one or more components of a microbial composition of the present disclosure. In one embodiment, pantothenate is a component of a microbial composition of the present disclosure. In one embodiment, a component of a microbial composition of the present disclosure includes one or more precursors utilized by mammalian or microbial biosynthesis of vitamins.

In some embodiments, the microbial compositions of the present disclosure are solid. Where solid compositions are used, it may be desired to include one or more carrier materials including, but not limited to: mineral earths such as silicas, talc, kaolin, limestone, chalk, clay, dolomite, diatomaceous earth; calcium sulfate; magnesium sulfate; magnesium oxide; zeolites, calcium carbonate; magnesium carbonate; trehalose; chitosan; shellac; albumins; starch; skim milk powder; sweet whey powder; maltodextrin; lactose; inulin; dextrose; and products of vegetable origin such as cereal meals, tree bark meal, wood meal, and nutshell meal.

In some embodiments, the microbial compositions of the present disclosure are liquid. In further embodiments, the liquid comprises a solvent that may include water or an alcohol or a saline or carbohydrate solution, and other animal-safe solvents. In some embodiments, the microbial compositions of the present disclosure include binders such as animal-safe polymers, carboxymethylcellulose, starch, polyvinyl alcohol, and the like.

In some embodiments, the microbial compositions of the present disclosure comprise thickening agents such as silica, clay, natural extracts of seeds or seaweed, synthetic derivatives of cellulose, guar gum, locust bean gum, alginates, and methylcelluloses. In some embodiments, the microbial compositions comprise anti-settling agents such as modified starches, polyvinyl alcohol, xanthan gum, and the like.

In some embodiments, the microbial compositions of the present disclosure comprise colorants including organic chromophores classified as nitroso; nitro; azo, including monoazo, bisazo and polyazo; acridine, anthraquinone, azine, diphenylmethane, indamine, indophenol, methine, oxazine, phthalocyanine, thiazine, thiazole, triarylmethane, xanthene. In some embodiments, the microbial compositions of the present disclosure comprise trace nutrients such as salts of iron, manganese, boron, copper, cobalt, molybdenum and zinc. In some embodiments, the microbial compositions comprise dyes, both natural and artificial. In some embodiments, the dye is green in color.

In some embodiments, the microbial compositions of the present disclosure comprise an animal-safe virucide, parasiticide, bacteriocide, fungicide, or nematicide.

In some embodiments, microbial compositions of the present disclosure comprise saccharides (e.g., monosaccharides, disaccharides, trisaccharides, polysaccharides, oligosaccharides, and the like), polymeric saccharides, lipids, polymeric lipids, lipopolysaccharides, proteins, polymeric proteins, lipoproteins, nucleic acids, nucleic acid polymers, silica, inorganic salts and combinations thereof. In a further embodiment, microbial compositions comprise polymers of agar, agarose, gelrite, gellan gum, and the like. In some embodiments, microbial compositions comprise plastic capsules, emulsions (e.g., water and oil), membranes, and artificial membranes. In some embodiments, emulsions or linked polymer solutions may comprise microbial compositions of the present disclosure. See Harel and Bennett (U.S. Pat. No. 8,460,726 B2).

In some embodiments, microbial compositions of the present disclosure comprise one or more exygen scavengers, denitrifies, nitrifiers, heavy metal chelators, and/or dechlorinators; and combinations thereof. In one embodiment, the one or more exygen scavengers, denitrifiers, nitrifiers, heavy metal chelators, and/or dechlorinators are not chemically active once the microbial compositions are mixed with food and/or water to be administered to the animal. In one embodiment, the one or more oxygen scavengers, denitrifiers, nitrifiers, heavy metal chelators, and/or dechlorinators are not chemically active when administered to the animal.

In some embodiments, microbial compositions of the present disclosure occur in a solid form (e.g., dispersed lyophilized spores) or a liquid form (microbes interspersed in a storage medium). In some embodiments, microbial compositions of the present disclosure are added in dry form to a liquid to a liquid to form a suspension immediately prior to administration In some embodiments, microbial compositions of the present disclosure comprise one or more preservatives. The preservatives may be in liquid or gas formulations. The preservatives may be selected from one or more of monosaccharide, disaccharide, trisaccharide, polysaccharide, acetic acid, ascorbic acid, calcium ascorbate, erythorbic acid, iso-ascorbic acid, erythrobic acid, potassium nitrate, sodium ascorbate, sodium erythorbate, sodium iso-ascorbate, sodium nitrate, sodium nitrite, nitrogen, benzoic acid, calcium sorbate, ethyl lauroyl arginate, methyl-p-hydroxy benzoate, methyl paraben, potassium acetate, potassium benzoiate, potassium bisulphite, potassium diacetate, potassium lactate, potassium metabisulphite, potassium sorbate, propyl-p-hydroxy benzoate, propyl paraben, sodium acetate, sodium benzoate, sodium bisulphite, sodium nitrite, sodium diacetate, sodium lactate, sodium metabisulphite, sodium salt of methyl-p-hydroxy benzoic acid, sodium salt of propyl-p-hydroxy benzoic acid, sodium sulphate, sodium sulfite, sodium dithionite, sulphurous acid, calcium propionate, dimethyl dicarbonate, natamycin, potassium sorbate, potassium bisulfite, potassium metabisulfite, propionic acid, sodium diacetate, sodium propionate, sodium sorbate, sorbic acid, ascorbic acid, ascorbyl palmitate, ascorbyl stearate, butylated hydro-xyanisole, butylated hydroxytoluene (BHT), butylated hydroxyl anisole (BHA), citric acid, citric acid esters of mono- and/or diglycerides, L-cysteine, L-cysteine hydrochloride, gum guaiacum, gum guaiac, lecithin, lecithin citrate, monoglyceride citrate, monoisopropyl citrate, propyl gallate, sodium metabisulphite, tartaric acid, tertiary butyl hydroquinone, stannous chloride, thiodipropionic acid, dilauryl thiodipropionate, distearyl thiodipropionate, ethoxyquin, sulfur dioxide, formic acid, or tocopherol(s).

In some embodiments, microbial compositions of the present disclosure comprise one or more oxygen scavengers, denitrifiers, nitrifiers, heavy metal chelators, and/or dechlorinators; and combinations thereof. In one embodiment, the one or more oxygen scavengers, denitrifiers, nitrifiers, heavy metal chelators, and/or dechlorinators are not chemically active once the microbial compositions are mixed with food and/or water to be administered to the beef cattle. In one embodiment, the one or more oxygen scavengers, denitrifiers, nitrifiers, heavy metal chelators, and/or dechlorinators are not chemically active when administered to the beef cattle.

In some embodiments, microbial compositions of the present disclosure include bacterial and/or fungal cells in spore form, vegetative cell form, and/or lysed cell form. In one embodiment, the lysed cell form acts as a mycotoxin binder, e.g. mycotoxins binding to dead cells.

In some embodiments, the microbial compositions are shelf stable in a refrigerator (35-40° F.) for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 days. In some embodiments, the microbial compositions are shelf stable in a refrigerator (35-40° F.) for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 weeks.

In some embodiments, the microbial compositions are shelf stable at room temperature (68-72° F.) or between 50-77° F. for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 days. In some embodiments, the microbial compositions are shelf stable at room temperature (68-72° F.) or between 50-77° F. for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 weeks.

In some embodiments, the microbial compositions are shelf stable at −23-35° F. for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 days. In some embodiments, the microbial compositions are shelf stable at −23-35° F. for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 weeks.

In some embodiments, the microbial compositions are shelf stable at 77-100° F. for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 days. In some embodiments, the microbial compositions are shelf stable at 77-100° F. for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 weeks.

In some embodiments, the microbial compositions are shelf stable at 101-213° F. for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 days. In some embodiments, the microbial compositions are shelf stable at 101-213° F. for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 weeks.

In some embodiments, the microbial compositions of the present disclosure are shelf stable at refrigeration temperatures (35-40° F.), at room temperature (68-72° F.), between 50-77° F., between −23-35° F., between 70-100° F., or between 101-213° F. for a period of about 1 to 100, about 1 to 95, about 1 to 90, about 1 to 85, about 1 to 80, about 1 to 75, about 1 to 70, about 1 to 65, about 1 to 60, about 1 to 55, about 1 to 50, about 1 to 45, about 1 to 40, about 1 to 35, about 1 to 30, about 1 to 25, about 1 to 20, about 1 to 15, about 1 to 10, about 1 to 5, about 5 to 100, about 5 to 95, about 5 to 90, about 5 to 85, about 5 to 80, about 5 to 75, about 5 to 70, about 5 to 65, about 5 to 60, about 5 to 55, about 5 to 50, about 5 to 45, about 5 to 40, about 5 to 35, about 5 to 30, about 5 to 25, about 5 to 20, about 5 to 15, about 5 to 10, about 10 to 100, about 10 to 95, about 10 to 90, about 10 to 85, about 10 to 80, about 10 to 75, about 10 to 70, about 10 to 65, about 10 to 60, about 10 to 55, about 10 to 50, about 10 to 45, about 10 to 40, about 10 to 35, about 10 to 30, about 10 to 25, about 10 to 20, about 10 to 15, about 15 to 100, about 15 to 95, about 15 to 90, about 15 to 85, about 15 to 80, about 15 to 75, about 15 to 70, about 15 to 65, about 15 to 60, about 15 to 55, about 15 to 50, about 15 to 45, about 15 to 40, about 15 to 35, about 15 to 30, about 15 to 25, about 15 to 20, about 20 to 100, about 20 to 95, about 20 to 90, about 20 to 85, about 20 to 80, about 20 to 75, about 20 to 70, about 20 to 65, about 20 to 60, about 20 to 55, about 20 to 50, about 20 to 45, about 20 to 40, about 20 to 35, about 20 to 30, about 20 to 25, about 25 to 100, about 25 to 95, about 25 to 90, about 25 to 85, about 25 to 80, about 25 to 75, about 25 to 70, about 25 to 65, about 25 to 60, about 25 to 55, about 25 to 50, about 25 to 45, about 25 to 40, about 25 to 35, about 25 to 30, about 30 to 100, about 30 to 95, about 30 to 90, about 30 to 85, about 30 to 80, about 30 to 75, about 30 to 70, about 30 to 65, about 30 to 60, about 30 to 55, about 30 to 50, about 30 to 45, about 30 to 40, about 30 to 35, about 35 to 100, about 35 to 95, about 35 to 90, about 35 to 85, about 35 to 80, about 35 to 75, about 35 to 70, about 35 to 65, about 35 to 60, about 35 to 55, about 35 to 50, about 35 to 45, about 35 to 40, about 40 to 100, about 40 to 95, about 40 to 90, about 40 to 85, about 40 to 80, about 40 to 75, about 40 to 70, about 40 to 65, about 40 to 60, about 40 to 55, about 40 to 50, about 40 to 45, about 45 to 100, about 45 to 95, about 45 to 90, about 45 to 85, about 45 to 80, about 45 to 75, about 45 to 70, about 45 to 65, about 45 to 60, about 45 to 55, about 45 to 50, about 50 to 100, about 50 to 95, about 50 to 90, about 50 to 85, about 50 to 80, about 50 to 75, about 50 to 70, about 50 to 65, about 50 to 60, about 50 to 55, about 55 to 100, about 55 to 95, about 55 to 90, about 55 to 85, about 55 to 80, about 55 to 75, about 55 to 70, about 55 to 65, about 55 to 60, about 60 to 100, about 60 to 95, about 60 to 90, about 60 to 85, about 60 to 80, about 60 to 75, about 60 to 70, about 60 to 65, about 65 to 100, about 65 to 95, about 65 to 90, about 65 to 85, about 65 to 80, about 65 to 75, about 65 to 70, about 70 to 100, about 70 to 95, about 70 to 90, about 70 to 85, about 70 to 80, about 70 to 75, about 75 to 100, about 75 to 95, about 75 to 90, about 75 to 85, about 75 to 80, about 80 to 100, about 80 to 95, about 80 to 90, about 80 to 85, about 85 to 100, about 85 to 95, about 85 to 90, about 90 to 100, about 90 to 95, or 95 to 100 weeks In some embodiments, the microbial compositions of the present disclosure are shelf stable at refrigeration temperatures (35-40° F.), at room temperature (68-72° F.), between 50-77° F., between −23-35° F., between 70-100° F., or between 101-213° F. for a period of 1 to 100, 1 to 95, 1 to 90, 1 to 85, 1 to 80, 1 to 75, 1 to 70, 1 to 65, 1 to 60, 1 to 55, 1 to 50, 1 to 45, 1 to 40, 1 to 35, 1 to 30, 1 to 25, 1 to 20, 1 to 15, 1 to 10, 1 to 5, 5 to 100, 5 to 95, 5 to 90, 5 to 85, 5 to 80, 5 to 75, 5 to 70, 5 to 65, 5 to 60, 5 to 55, 5 to 50, 5 to 45, 5 to 40, 5 to 35, 5 to 30, 5 to 25, 5 to 20, 5 to 15, 5 to 10, 10 to 100, 10 to 95, 10 to 90, 10 to 85, 10 to 80, 10 to 75, 10 to 70, 10 to 65, 10 to 60, 10 to 55, 10 to 50, 10 to 45, 10 to 40, 10 to 35, 10 to 30, 10 to 25, 10 to 20, 10 to 15, 15 to 100, 15 to 95, 15 to 90, 15 to 85, 15 to 80, 15 to 75, 15 to 70, 15 to 65, 15 to 60, 15 to 55, 15 to 50, 15 to 45, 15 to 40, 15 to 35, 15 to 30, 15 to 25, 15 to 20, 20 to 100, 20 to 95, 20 to 90, 20 to 85, 20 to 80, 20 to 75, 20 to 70, 20 to 65, 20 to 60, 20 to 55, 20 to 50, 20 to 45, 20 to 40, 20 to 35, 20 to 30, 20 to 25, 25 to 100, 25 to 95, 25 to 90, 25 to 85, 25 to 80, 25 to 75, 25 to 70, 25 to 65, 25 to 60, 25 to 55, 25 to 50, 25 to 45, 25 to 40, 25 to 35, 25 to 30, 30 to 100, 30 to 95, 30 to 90, 30 to 85, 30 to 80, 30 to 75, 30 to 70, 30 to 65, 30 to 60, 30 to 55, 30 to 50, 30 to 45, 30 to 40, 30 to 35, 35 to 100, 35 to 95, 35 to 90, 35 to 85, 35 to 80, 35 to 75, 35 to 70, 35 to 65, 35 to 60, 35 to 55, 35 to 50, 35 to 45, 35 to 40, 40 to 100, 40 to 95, 40 to 90, 40 to 85, 40 to 80, 40 to 75, 40 to 70, 40 to 65, 40 to 60, 40 to 55, 40 to 50, 40 to 45, 45 to 100, 45 to 95, 45 to 90, 45 to 85, 45 to 80, 45 to 75, 45 to 70, 45 to 65, 45 to 60, 45 to 55, 45 to 50, 50 to 100, 50 to 95, 50 to 90, 50 to 85, 50 to 80, 50 to 75, 50 to 70, 50 to 65, 50 to 60, 50 to 55, 55 to 100, 55 to 95, 55 to 90, 55 to 85, 55 to 80, 55 to 75, 55 to 70, 55 to 65, 55 to 60, 60 to 100, 60 to 95, 60 to 90, 60 to 85, 60 to 80, 60 to 75, 60 to 70, 60 to 65, 65 to 100, 65 to 95, 65 to 90, 65 to 85, 65 to 80, 65 to 75, 65 to 70, 70 to 100, 70 to 95, 70 to 90, 70 to 85, 70 to 80, 70 to 75, 75 to 100, 75 to 95, 75 to 90, 75 to 85, 75 to 80, 80 to 100, 80 to 95, 80 to 90, 80 to 85, 85 to 100, 85 to 95, 85 to 90, 90 to 100, 90 to 95, or 95 to 100 weeks.

In some embodiments, the microbial compositions of the present disclosure are shelf stable at refrigeration temperatures (35-40° F.), at room temperature (68-72° F.), between 50-77° F., between −23-35° F., between 70-100° F., or between 101-213° F. for a period of about 1 to 36, about 1 to 34, about 1 to 32, about 1 to 30, about 1 to 28, about 1 to 26, about 1 to 24, about 1 to 22, about 1 to 20, about 1 to 18, about 1 to 16, about 1 to 14, about 1 to 12, about 1 to 10, about 1 to 8, about 1 to 6, about 1 one 4, about 1 to 2, about 4 to 36, about 4 to 34, about 4 to 32, about 4 to 30, about 4 to 28, about 4 to 26, about 4 to 24, about 4 to 22, about 4 to 20, about 4 to 18, about 4 to 16, about 4 to 14, about 4 to 12, about 4 to 10, about 4 to 8, about 4 to 6, about 6 to 36, about 6 to 34, about 6 to 32, about 6 to 30, about 6 to 28, about 6 to 26, about 6 to 24, about 6 to 22, about 6 to 20, about 6 to 18, about 6 to 16, about 6 to 14, about 6 to 12, about 6 to 10, about 6 to 8, about 8 to 36, about 8 to 34, about 8 to 32, about 8 to 30, about 8 to 28, about 8 to 26, about 8 to 24, about 8 to 22, about 8 to 20, about 8 to 18, about 8 to 16, about 8 to 14, about 8 to 12, about 8 to 10, about 10 to 36, about 10 to 34, about 10 to 32, about 10 to 30, about 10 to 28, about 10 to 26, about 10 to 24, about 10 to 22, about 10 to 20, about 10 to 18, about 10 to 16, about 10 to 14, about 10 to 12, about 12 to 36, about 12 to 34, about 12 to 32, about 12 to 30, about 12 to 28, about 12 to 26, about 12 to 24, about 12 to 22, about 12 to 20, about 12 to 18, about 12 to 16, about 12 to 14, about 14 to 36, about 14 to 34, about 14 to 32, about 14 to 30, about 14 to 28, about 14 to 26, about 14 to 24, about 14 to 22, about 14 to 20, about 14 to 18, about 14 to 16, about 16 to 36, about 16 to 34, about 16 to 32, about 16 to 30, about 16 to 28, about 16 to 26, about 16 to 24, about 16 to 22, about 16 to 20, about 16 to 18, about 18 to 36, about 18 to 34, about 18 to 32, about 18 to 30, about 18 to 28, about 18 to 26, about 18 to 24, about 18 to 22, about 18 to 20, about 20 to 36, about 20 to 34, about 20 to 32, about 20 to 30, about 20 to 28, about 20 to 26, about 20 to 24, about 20 to 22, about 22 to 36, about 22 to 34, about 22 to 32, about 22 to 30, about 22 to 28, about 22 to 26, about 22 to 24, about 24 to 36, about 24 to 34, about 24 to 32, about 24 to 30, about 24 to 28, about 24 to 26, about 26 to 36, about 26 to 34, about 26 to 32, about 26 to 30, about 26 to 28, about 28 to 36, about 28 to 34, about 28 to 32, about 28 to 30, about 30 to 36, about 30 to 34, about 30 to 32, about 32 to 36, about 32 to 34, or about 34 to 36 months.

In some embodiments, the microbial compositions of the present disclosure are shelf stable at refrigeration temperatures (35-40° F.), at room temperature (68-72° F.), between 50-77° F., between −23-35° F., between 70-100° F., or between 101-213° F. for a period of 1 to 36 1 to 34 1 to 32 1 to 30 1 to 28 1 to 26 1 to 24 1 to 22 1 to 20 1 to 18 1 to 16 1 to 14 1 to 12 1 to 10 1 to 8 1 to 6 1 one 4 1 to 24 to 36 4 to 34 4 to 32 4 to 30 4 to 28 4 to 26 4 to 24 4 to 22 4 to 20 4 to 18 4 to 16 4 to 14 4 to 12 4 to 10 4 to 8 4 to 6 6 to 36 6 to 34 6 to 32 6 to 30 6 to 28 6 to 26 6 to 24 6 to 22 6 to 20 6 to 18 6 to 16 6 to 14 6 to 12 6 to 10 6 to 8 8 to 36 8 to 34 8 to 32 8 to 30 8 to 28 8 to 26 8 to 24 8 to 22 8 to 20 8 to 18 8 to 16 8 to 14 8 to 12 8 to 10 10 to 36 10 to 34 10 to 32 10 to 30 10 to 28 10 to 26 10 to 24 10 to 22 10 to 20 10 to 18 10 to 16 10 to 14 10 to 12 12 to 36 12 to 34 12 to 32 12 to 30 12 to 28 12 to 26 12 to 24 12 to 22 12 to 20 12 to 18 12 to 16 12 to 14 14 to 36 14 to 34 14 to 32 14 to 30 14 to 28 14 to 26 14 to 24 14 to 22 14 to 20 14 to 18 14 to 16 16 to 36 16 to 34 16 to 32 16 to 30 16 to 28 16 to 26 16 to 24 16 to 22 16 to 20 16 to 18 18 to 36 18 to 34 18 to 32 18 to 30 18 to 28 18 to 26 18 to 24 18 to 22 18 to 20 20 to 36 20 to 34 20 to 32 20 to 30 20 to 28 20 to 26 20 to 24 20 to 22 22 to 36 22 to 34 22 to 32 22 to 30 22 to 28 22 to 26 22 to 24 24 to 36 24 to 34 24 to 32 24 to 30 24 to 28 24 to 26 26 to 36 26 to 34 26 to 32 26 to 30 26 to 28 28 to 36 28 to 34 28 to 32 28 to 30 30 to 36 30 to 34 30 to 32 32 to 36 32 to 34, or about 34 to 36.

In some embodiments, the microbial compositions of the present disclosure are shelf stable at any of the disclosed temperatures and/or temperature ranges and spans of time at a relative humidity of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, or 98%.

In some embodiments, the microbial composition of the present disclosure possesses a water activity (aw) of less than 0.750, 0.700, 0.650, 0.600, 0.550, 0.500, 0.475, 0.450, 0.425, 0.400, 0.375, 0.350, 0.325, 0.300, 0.275, 0.250, 0.225, 0.200, 0.190, 0.180, 0.170, 0.160, 0.150, 0.140, 0.130, 0.120, 0.110, 0.100, 0.095, 0.090, 0.085, 0.080, 0.075, 0.070, 0.065, 0.060, 0.055, 0.050, 0.045, 0.040, 0.035, 0.030, 0.025, 0.020, 0.015, 0.010, or 0.005.

In some embodiments, the microbial composition of the present disclosure possesses a water activity (aw) of less than about 0.750, about 0.700, about 0.650, about 0.600, about 0.550, about 0.500, about 0.475, about 0.450, about 0.425, about 0.400, about 0.375, about 0.350, about 0.325, about 0.300, about 0.275, about 0.250, about 0.225, about 0.200, about 0.190, about 0.180, about 0.170, about 0.160, about 0.150, about 0.140, about 0.130, about 0.120, about 0.110, about 0.100, about 0.095, about 0.090, about 0.085, about 0.080, about 0.075, about 0.070, about 0.065, about 0.060, about 0.055, about 0.050, about 0.045, about 0.040, about 0.035, about 0.030, about 0.025, about 0.020, about 0.015, about 0.010, or about 0.005.

The water activity values are determined by the method of Saturated Aqueous Solutions (Multon, "Techniques d'Analyse E De Controle Dans Les Industries Agroalimentaires" APRIA (1981)) or by direct measurement using a viable Robotronic BT hygrometer or other hygrometer or hygroscope.

In some embodiments, the microbial composition comprises at least two different microbes, and wherein the at least two microbes are present in the composition at a ratio of 1:2, 1:3, 1:3, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:40, 1:50, 1:60, 1:100, 1:125, 1:150, 1:175, or 1:200 or the inverse thereof. In some embodiments, the microbial composition comprises at least three different microbes, and wherein the three microbes are present in the composition at a ratio of 1:2:1, 1:1:2, 2:2:1, 1:3:1, 1:1:3, 3:1:1, 3:3:1, 1:5:1, 1:1:5, 5:1:1, 5:5:1, or 1:5:5.

Encapsulation Compositions

In some embodiments, the microbes or microbial compositions of the disclosure are encapsulated in an encapsulating composition. An encapsulating composition protects the microbes from external stressors prior to entering the gastrointestinal tract of beef cattle. In some embodiments, external stressors include thermal and physical stressors associated with pelleting and extrusion. In some embodiments, external stressors include chemicals present in the compositions. Encapsulating compositions further create an environment that may be beneficial to the microbes, such as minimizing the oxidative stresses of an aerobic environment on anaerobic microbes. See Kalsta et al. (U.S. Pat. No. 5,104,662A), Ford (U.S. Pat. No. 5,733,568A), and Mosbach and Nilsson (U.S. Pat. No. 4,647,536A) for encapsulation compositions of microbes, and methods of encapsulating microbes.

In one embodiment, the compositions of the present disclosure exhibit a thermal tolerance, which is used interchangeably with heat tolerance and heat resistance. In one embodiment, thermal tolerant compositions of the present disclosure are tolerant of the high temperatures associated with feed manufacturing, mixing of feed and compositions of the present disclosure, storage in high heat environments, etc. In one embodiment, thermal tolerant compositions of the present disclosure are resistant to heat-killing and denaturation of the cell wall components and the intracellular environment.

In one embodiments, the encapsulation is a reservoir-type encapsulation. In one embodiment, the encapsulation is a matrix-type encapsulation. In one embodiment, the encapsulation is a coated matrix-type encapsulation. Burgain et al. (2011. J. Food Eng. 104:467-483) discloses numerous encapsulation embodiments and techniques, all of which are incorporated by reference.

In some embodiments, the compositions of the present disclosure are encapsulated in one or more of the following: gellan gum, xanthan gum, K-Carrageenan, cellulose acetate phthalate, chitosan, starch, milk fat, whey protein, Ca-alginate, raftilose, raftiline, pectin, saccharide, glucose, maltodextrin, gum arabic, guar, seed flour, alginate, dextrins, dextrans, celluloase, gelatin, gelatin, albumin, casein, gluten, acacia gum, tragacanth, wax, paraffin, stearic acid, monodiglycerides, and diglycerides. In some embodiments, the compositions of the present disclosure are encapsulated by one or more of a polymer, carbohydrate, sugar, plastic, glass, polysaccharide, lipid, wax, oil, fatty acid, or glyceride. In one embodiment, the microbial composition is encapsulated by glucose. In one embodiment, the microbial composition is encapsulated by a glucose-containing composition. In one embodiment, formulations of the microbial composition comprise a glucose encapsulant. In one embodiment, formulations of the microbial composition comprise a glucose-encapsulated composition.

In some embodiments, the encapsulation of the compositions of the present disclosure is carried out by an extrusion, emulsification, coating, agglomeration, lyophilization, vitrification, foam drying, preservation by vaporization, vacuum-drying, or spray-drying.

In some embodiments, the encapsulated compositions of the present disclosure are vitrified. In some embodiments, encapsulation involves a process of drying a composition of the present disclosure in the presence of a substance which forms a glassy, amorphous solid state, a process known as vitrification, and in doing so encapsulates the composition. In some embodiments, the vitrified composition is protected from degradative conditions that would typically destroy or degrade microbes. Many common substances have the property of vitrification; that is, they will form a glassy solid state under certain conditions. Among these substances are several sugars, including sucrose and maltose, and other more complex compounds, such as polyvinyl pyrolidone (PVP). As any solution dries down, the molecules in the solution can either crystalize, or they can vitrify. A solute which has an extensive asymmetry may be a superior vitrifier, because of the hindrances to nucleation of crystals during drying. A substance that inhibits the crystallization of another substance may result in the combined substances forming a superior vitrification, such as raffinose in the presence of sucrose. See U.S. Pat. Nos. 5,290,765 and 9,469,835.

In some embodiments, a microbial composition is produced that is encapsulated in a vitrified substance. The vitrified composition may be created by selecting a mixture including cells; combining said mixture with sufficient quantity of one or more vitrifying solutes to protect said mixture during drying and to inhibit destructive reactions; and drying said combination by exposing said combination to a desiccant, or desiccating conditions, at a temperature above that which said combination will freeze and below that at which said vitrifying solutes achieve the vitrified state, at approximately normal atmospheric pressure, until said combination is substantially dry.

In one embodiment, the encapsulating composition comprises microcapsules having a multiplicity of liquid cores encapsulated in a solid shell material. For purposes of the disclosure, a "multiplicity" of cores is defined as two or more.

A first category of useful fusible shell materials is that of normally solid fats, including fats which are already of suitable hardness and animal or vegetable fats and oils which are hydrogenated until their melting points are sufficiently high to serve the purposes of the present disclosure. Depending on the desired process and storage temperatures and the specific material selected, a particular fat can be either a normally solid or normally liquid material. The terms "normally solid" and "normally liquid" as used herein refer to the state of a material at desired temperatures for storing the resulting microcapsules. Since fats and hydrogenated oils do not, strictly speaking, have melting points, the term "melting point" is used herein to describe the minimum temperature at which the fusible material becomes sufficiently softened or liquid to be successfully emulsified and spray cooled, thus roughly corresponding to the maximum temperature at which the shell material has sufficient integrity to prevent release of the choline cores. "Melting point" is similarly defined herein for other materials which do not have a sharp melting point.

Specific examples of fats and oils useful herein (some of which require hardening) are as follows: animal oils and fats, such as beef tallow, mutton tallow, lamb tallow, lard or pork fat, fish oil, and sperm oil; vegetable oils, such as canola oil, cottonseed oil, peanut oil, corn oil, olive oil, soybean oil, sunflower oil, safflower oil, coconut oil, palm oil, linseed oil, tung oil, and castor oil; fatty acid monoglycerides and diglycerides; free fatty acids, such as stearic acid, palmitic acid, and oleic acid; and mixtures thereof. The above listing of oils and fats is not meant to be exhaustive, but only exemplary.

Specific examples of fatty acids include linoleic acid, γ-linoleic acid, dihomo-γ-linolenic acid, arachidonic acid, docosatetraenoic acid, vaccenic acid, nervonic acid, mead acid, erucic acid, gondoic acid, elaidic acid, oleic acid, palitoleic acid, stearidonic acid, eicosapentaenoic acid, valeric acid, caproic acid, enanthic acid, caprylic acid, pelargonic acid, capric acid, undecylic acid, lauric acid, tridecylic acid, myristic acid, pentadecylic acid, palmitic acid, margaric acid, stearic acid, nonadecyclic acid, arachidic acid, heneicosylic acid, behenic acid, tricosylic acid, lignoceric acid, pentacosylic acid, cerotic acid, heptacosylic acid, montanic acid, nonacosylic acid, melissic acid, henatriacontylic acid, lacceroic acid, psyllic acid, geddic acid, ceroplastic acid, hexatriacontylic acid, heptatriacontanoic acid, and octatriacontanoic acid.

Another category of fusible materials useful as encapsulating shell materials is that of waxes. Representative waxes contemplated for use herein are as follows: animal waxes, such as beeswax, lanolin, shell wax, and Chinese insect wax; vegetable waxes, such as carnauba, candelilla, bayberry, and sugar cane; mineral waxes, such as paraffin, microcrystalline petroleum, ozocerite, ceresin, and montan; synthetic waxes, such as low molecular weight polyolefin (e.g., CARBOWAX), and polyol ether-esters (e.g., sorbitol); Fischer-Tropsch process synthetic waxes; and mixtures thereof. Water-soluble waxes, such as CARBOWAX and sorbitol, are not contemplated herein if the core is aqueous.

Still other fusible compounds useful herein are fusible natural resins, such as rosin, balsam, shellac, and mixtures thereof.

In some embodiments, the microbes or microbial composition is embedded in a wax, such as the waxes described in the present disclosure.

In some embodiments, the microbes or microbial composition is embedded in wax balls. In some embodiments, the microbes or microbial composition is already encapsulated prior to being embedded in wax balls. In some embodiments, the wax balls are 10 microbes, 20 microns, 30 microns, 40 microns, 50 microns, 60 microns, 70 microns, 80 microns, 90 microns, 100 microns, 150 microns, 200 microns, 250 microns, 300 microns, 350 microns, 400 microns, 450 microns, 500 microns, 550 microns, 600 microns, 650 microns, 700 microns, 750 microns, 800 microns, 850 microns, 900 microns, 950 microns, or 1,000 microns.

In some embodiments, the wax balls are about 10 microbes, about 20 microns, about 30 microns, about 40 microns, about 50 microns, about 60 microns, about 70 microns, about 80 microns, about 90 microns, about 100 microns, about 150 microns, about 200 microns, about 250 microns, about 300 microns, about 350 microns, about 400 microns, about 450 microns, about 500 microns, about 550 microns, about 600 microns, about 650 microns, about 700 microns, about 750 microns, about 800 microns, about 850 microns, about 900 microns, about 950 microns, or about 1,000 microns.

In some embodiments, the wax balls are between 10-20 microns, 10-30 microns, 10-40 microns, 10-50 microns, 10-60 microns, 10-70 microns, 10-80 microns, 10-90 microns, 10-100 microns, 10-250 microns, 10-500 microns, 10-750 microns, 10-1,000 microns, 20-30 microns, 20-40 microns, 20-50 microns, 20-60 microns, 20-70 microns, 20-80 microns, 20-90 microns, 20-100 microns, 20-250 microns, 20-500 microns, 20-750 microns, 20-1,000 microns, 30-40 microns, 30-50 microns, 30-60 microns, 30-70 microns, 30-80 microns, 30-90 microns, 30-100 microns, 30-250 microns, 30-500 microns, 30-750 microns, 30-1,000 microns, 40-50 microns, 40-60 microns, 40-70 microns, 40-80 microns, 40-90 microns, 40-100 microns, 40-250 microns, 40-500 microns, 40-750 microns, 40-1,000 microns, 50-60 microns, 50-70 microns, 50-80 microns, 50-90 microns, 50-100 microns, 50-250 microns, 50-500 microns, 50-750 microns, 50-1,000 microns, 60-70 microns, 60-80 microns, 60-90 microns, 60-100 microns, 60-250 microns, 60-500 microns, 60-750 microns, 60-1,000 microns, 70-80 microns 70-90 microns, 70-90 microns, 70-100 microns, 70-250 microns, 70-500 microns, 70-750 microns, 70-1,000 microns, 80-90 microns, 80-100 microns, 80-250 microns, 80-500 microns, 80-500 microns, 80-750 microns, 80-1,000 microns, 90-100 microns, 90-250 microns, 90-500 microns, 90-750 microns, 90-1,000 microns, 100-250 microns, 100-500 microns, 100-750 microns, 100-1,000 microns, 250-500 microns, 250-750 microns, 250-1,000 microns, 500-750 microns, 500-1,000 microns, or 750-1,000 microns.

In some embodiments, the wax balls are between about 10-20 microns, about 10-30 microns, about 10-40 microns, about 10-50 microns, about 10-60 microns, about 10-70 microns, about 10-80 microns, about 10-90 microns, about 10-100 microns, about 10-250 microns, about 10-500 microns, about 10-750 microns, about 10-1,000 microns, about 20-30 microns, about 20-40 microns, about 20-50 microns, about 20-60 microns, about 20-70 microns, about 20-80 microns, about 20-90 microns, about 20-100 microns, about 20-250 microns, about 20-500 microns, about 20-750 microns, about 20-1,000 microns, about 30-40 microns, about 30-50 microns, about 30-60 microns, about 30-70 microns, about 30-80 microns, about 30-90 microns, about 30-100 microns, about 30-250 microns, about 30-500 microns, about 30-750 microns, about 30-1,000 microns, about 40-50 microns, about 40-60 microns, about 40-70 microns, about 40-80 microns, about 40-90 microns, about 40-100 microns, about 40-250 microns, about 40-500 microns, about 40-750 microns, about 40-1,000 microns, about 50-60 microns, about 50-70 microns, about 50-80 microns, about 50-90 microns, about 50-100 microns, about 50-250 microns, about 50-500 microns, about 50-750 microns, about 50-1,000 microns, about 60-70 microns, about 60-80 microns, about 60-90 microns, about 60-100 microns, about 60-250 microns, about 60-500 microns, about 60-750 microns, about 60-1,000 microns, about 70-80 microns about 70-90 microns, about 70-90 microns, about 70-100 microns, about 70-250 microns, about 70-500 microns, about 70-750 microns, about 70-1,000 microns, about 80-90 microns, about 80-100 microns, about 80-250 microns, about 80-500 microns, about 80-500 microns, about 80-750 microns, about 80-1,000 microns, about 90-100 microns, about 90-250 microns, about 90-500 microns, about 90-750 microns, about 90-1,000 microns, about 100-250 microns, about 100-500 microns, about 100-750 microns, about 100-1,000 microns, about 250-500 microns, about 250-750 microns, about 250-1,000 microns, about 500-750 microns, about 500-1,000 microns, or about 750-1,000 microns.

Various adjunct materials are contemplated for incorporation in fusible materials according to the present disclosure. For example, antioxidants, light stabilizers, dyes and lakes, flavors, essential oils, anti-caking agents, fillers, pH stabilizers, sugars (monosaccharides, disaccharides, trisaccharides, and polysaccharides) and the like can be incorporated in the fusible material in amounts which do not diminish its utility for the present disclosure.

The core material contemplated herein constitutes from about 0.1% to about 50%, about 1% to about 35%. or about 5% to about 30% by weight of the microcapsules. In some embodiments, the core material contemplated herein constitutes no more than about 30% by weight of the microcapsules. In some embodiments, the core material contemplated herein constitutes about 5% by weight of the microcapsules. The core material is contemplated as either a liquid or solid at contemplated storage temperatures of the microcapsules.

The cores may include other additives well-known in the pharmaceutical art, including edible sugars, such as sucrose, glucose, maltose, fructose, lactose, cellobiose, monosaccharides, disaccharides, trisaccharides, and polysaccharides, and mixtures thereof; artificial sweeteners, such as aspartame, saccharin, cyclamate salts, and mixtures thereof; edible acids, such as acetic acid (vinegar), citric acid, ascorbic acid, tartaric acid, and mixtures thereof; edible starches, such as corn starch; hydrolyzed vegetable protein; water-soluble vitamins, such as Vitamin C; water-soluble medicaments; water-soluble nutritional materials, such as ferrous sulfate; flavors; salts; monosodium glutamate; antimicrobial agents, such as sorbic acid; antimycotic agents, such as potassium sorbate, sorbic acid, sodium benzoate, and benzoic acid; food grade pigments and dyes; and mixtures thereof. Other potentially useful supplemental core materials will be apparent to those of ordinary skill in the art.

Emulsifying agents may be employed to assist in the formation of stable emulsions. Representative emulsifying agents include glyceryl monostearate, polysorbate esters, ethoxylated mono- and diglycerides, and mixtures thereof.

For ease of processing, and particularly to enable the successful formation of a reasonably stable emulsion, the viscosities of the core material and the shell material should be similar at the temperature at which the emulsion is formed. In particular, the ratio of the viscosity of the shell to the viscosity of the core, expressed in centipoise or comparable units, and both measured at the temperature of the emulsion, should be from about 22:1 to about 1:1, desirably from about 8:1 to about 1:1, and preferably from about 3:1 to about 1:1. A ratio of 1:1 would be ideal, but a viscosity ratio within the recited ranges is useful.

Encapsulating compositions are not limited to microcapsule compositions as disclosed above. In some embodiments encapsulating compositions encapsulate the microbial compositions in an adhesive polymer that can be natural or synthetic without toxic effect. In some embodiments, the encapsulating composition may be a matrix selected from sugar matrix, gelatin matrix, polymer matrix, silica matrix, starch matrix, foam matrix, glass/glassy matrix etc. See Pirzio et al. (U.S. Pat. No. 7,488,503). In some embodiments, the encapsulating composition may be selected from polyvinyl acetates; polyvinyl acetate copolymers; ethylene vinyl acetate (EVA) copolymers; polyvinyl alcohols; polyvinyl alcohol copolymers; celluloses, including ethylcelluloses, methylcelluloses, hydroxymethylcelluloses, hydroxypropylcelluloses and carboxymethylcellulose; polyvinylpyrolidones; polysaccharides, including starch, modified starch, dextrins, maltodextrins, alginate and chitosans; monosaccharides; fats; fatty acids, including oils; proteins, including gelatin and zeins; gum arabics; shellacs; vinylidene chloride and vinylidene chloride copolymers; calcium lignosulfonates; acrylic copolymers; polyvinylacrylates; polyethylene oxide; acrylamide polymers and copolymers; polyhydroxyethyl acrylate, methylacrylamide monomers; and polychloroprene.

In some embodiments, the encapsulating compositions comprise at least one layer of encapsulation. In some embodiments, the encapsulating compositions comprise at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 layers of encapsulation/encapsulants.

In some embodiments, the encapsulating compositions comprise at least two layers of encapsulation. In some embodiments, each layer of encapsulation confers a different characteristic to the composition. In some embodiments, no two consecutive layers confer the same characteristic. In some embodiments, at least one layer of the at least two layers of encapsulation confers thermostability, shelf stability, ultraviolet resistance, moisture resistance, hydrophobicity, hydrophilicity, lipophobicity, lipophilicity, pH stability, acid resistance, and base resistance.

In some embodiments, the encapsulating compositions comprise two layers of encapsulation; the first layer confers thermostability and/or shelf stability, and the second layer provides pH resistance.

In some embodiments, the encapsulating layers confer a timed release of the microbial composition held in the center of the encapsulating layers. In some embodiments, the greater the number of layers confers a greater amount of time before the microbial composition is exposed, post administration.

In some embodiments, the encapsulating shell of the present disclosure can be up to 10 µm, 20 µm, 30 µm, 40 µm, 50 µm, 60 µm, 70 µm, 80 µm, 90 µm, 100 µm, 110 µm, 120 µm, 130 µm, 140 µm, 150 µm, 160 µm, 170 µm, 180 µm, 190 µm, 200 µm, 210 µm, 220 µm, 230 µm, 240 µm, 250 µm, 260 µm, 270 µm, 280 µm, 290 µm, 300 µm, 310 µm, 320 µm, 330

µm, 340 µm, 350 µm, 360 µm, 370 µm, 380 µm, 390 µm, 400 µm, 410 µm, 420 µm, 430 µm, 440 µm, 450 µm, 460 µm, 470 µm, 480 µm, 490 µm, 500 µm, 510 µm, 520 µm, 530 µm, 540 µm, 550 µm, 560 µm, 570 µm, 580 µm, 590 µm, 600 µm, 610 µm, 620 µm, 630 µm, 640 µm, 650 µm, 660 µm, 670 µm, 680 µm, 690 µm, 700 µm, 710 µm, 720 µm, 730 µm, 740 µm, 750 µm, 760 µm, 770 µm, 780 µm, 790 µm, 800 µm, 810 µm, 820 µm, 830 µm, 840 µm, 850 µm, 860 µm, 870 µm, 880 µm, 890 µm, 900 µm, 910 µm, 920 µm, 930 µm, 940 µm, 950 µm, 960 µm, 970 µm, 980 µm, 990 µm, 1000 µm, 1010 µm, 1020 µm, 1030 µm, 1040 µm, 1050 µm, 1060 µm, 1070 µm, 1080 µm, 1090 µm, 1100 µm, 1110 µm, 1120 µm, 1130 µm, 1140 µm, 1150 µm, 1160 µm, 1170 µm, 1180 µm, 1190 µm, 1200 µm, 1210 µm, 1220 µm, 1230 µm, 1240 µm, 1250 µm, 1260 µm, 1270 µm, 1280 µm, 1290 µm, 1300 µm, 1310 µm, 1320 µm, 1330 µm, 1340 µm, 1350 µm, 1360 µm, 1370 µm, 1380 µm, 1390 µm, 1400 µm, 1410 µm, 1420 µm, 1430 µm, 1440 µm, 1450 µm, 1460 µm, 1470 µm, 1480 µm, 1490 µm, 1500 µm, 1510 µm, 1520 µm, 1530 µm, 1540 µm, 1550 µm, 1560 µm, 1570 µm, 1580 µm, 1590 µm, 1600 µm, 1610 µm, 1620 µm, 1630 µm, 1640 µm, 1650 µm, 1660 µm, 1670 µm, 1680 µm, 1690 µm, 1700 µm, 1710 µm, 1720 µm, 1730 µm, 1740 µm, 1750 µm, 1760 µm, 1770 µm, 1780 µm, 1790 µm, 1800 µm, 1810 µm, 1820 µm, 1830 µm, 1840 µm, 1850 µm, 1860 µm, 1870 µm, 1880 µm, 1890 µm, 1900 µm, 1910 µm, 1920 µm, 1930 µm, 1940 µm, 1950 µm, 1960 µm, 1970 µm, 1980 µm, 1990 µm, 2000 µm, 2010 µm, 2020 µm, 2030 µm, 2040 µm, 2050 µm, 2060 µm, 2070 µm, 2080 µm, 2090 µm, 2100 µm, 2110 µm, 2120 µm, 2130 µm, 2140 µm, 2150 µm, 2160 µm, 2170 µm, 2180 µm, 2190 µm, 2200 µm, 2210 µm, 2220 µm, 2230 µm, 2240 µm, 2250 µm, 2260 µm, 2270 µm, 2280 µm, 2290 µm, 2300 µm, 2310 µm, 2320 µm, 2330 µm, 2340 µm, 2350 µm, 2360 µm, 2370 µm, 2380 µm, 2390 µm, 2400 µm, 2410 µm, 2420 µm, 2430 µm, 2440 µm, 2450 µm, 2460 µm, 2470 µm, 2480 µm, 2490 µm, 2500 µm, 2510 µm, 2520 µm, 2530 µm, 2540 µm, 2550 µm, 2560 µm, 2570 µm, 2580 µm, 2590 µm, 2600 µm, 2610 µm, 2620 µm, 2630 µm, 2640 µm, 2650 µm, 2660 µm, 2670 µm, 2680 µm, 2690 µm, 2700 µm, 2710 µm, 2720 µm, 2730 µm, 2740 µm, 2750 µm, 2760 µm, 2770 µm, 2780 µm, 2790 µm, 2800 µm, 2810 µm, 2820 µm, 2830 µm, 2840 µm, 2850 µm, 2860 µm, 2870 µm, 2880 µm, 2890 µm, 2900 µm, 2910 µm, 2920 µm, 2930 µm, 2940 µm, 2950 µm, 2960 µm, 2970 µm, 2980 µm, 2990 µm, or 3000 µm thick.

In some embodiments, the encapsulation composition of the present disclosure possesses a water activity (aw) of less than 0.750, 0.700, 0.650, 0.600, 0.550, 0.500, 0.475, 0.450, 0.425, 0.400, 0.375, 0.350, 0.325, 0.300, 0.275, 0.250, 0.225, 0.200, 0.190, 0.180, 0.170, 0.160, 0.150, 0.140, 0.130, 0.120, 0.110, 0.100, 0.095, 0.090, 0.085, 0.080, 0.075, 0.070, 0.065, 0.060, 0.055, 0.050, 0.045, 0.040, 0.035, 0.030, 0.025, 0.020, 0.015, 0.010, or 0.005.

In some embodiments, the encapsulation composition of the present disclosure possesses a water activity (aw) of less than about 0.750, about 0.700, about 0.650, about 0.600, about 0.550, about 0.500, about 0.475, about 0.450, about 0.425, about 0.400, about 0.375, about 0.350, about 0.325, about 0.300, about 0.275, about 0.250, about 0.225, about 0.200, about 0.190, about 0.180, about 0.170, about 0.160, about 0.150, about 0.140, about 0.130, about 0.120, about 0.110, about 0.100, about 0.095, about 0.090, about 0.085, about 0.080, about 0.075, about 0.070, about 0.065, about 0.060, about 0.055, about 0.050, about 0.045, about 0.040, about 0.035, about 0.030, about 0.025, about 0.020, about 0.015, about 0.010, or about 0.005.

In one embodiment, the microbe(s) are first dried by spray dry, lyophilization, or foam drying along with excipients that may include one or more sugars, sugar alcohols, disaccharides, trisaccharides, polysaccharides, salts, amino acids, amino acid salts, or polymers.

In some embodiments, the microbes or compositions comprising the microbes are milled to a size of 10 microns, 20 microns, 30 microns, 40 microns, 50 microns, 60 microns, 70 microns, 80 microns, 90 microns, 100 microns, 150 microns, 200 microns, 250 microns, 300 microns, 350 microns, 400 microns, 450 microns, 500 microns, 550 microns, 600 microns, 650 microns, 700 microns, 750 microns, 800 microns, 850 microns, 900 microns, 950 microns, or 1,000 microns.

In some embodiments, the microbes or compositions comprising the microbes are milled to a size of about 10 microbes, about 20 microns, about 30 microns, about 40 microns, about 50 microns, about 60 microns, about 70 microns, about 80 microns, about 90 microns, about 100 microns, about 150 microns, about 200 microns, about 250 microns, about 300 microns, about 350 microns, about 400 microns, about 450 microns, about 500 microns, about 550 microns, about 600 microns, about 650 microns, about 700 microns, about 750 microns, about 800 microns, about 850 microns, about 900 microns, about 950 microns, or about 1,000 microns.

In some embodiments, the microbes or compositions comprising the microbes are milled to a size of between 10-20 microns, 10-30 microns, 10-40 microns, 10-50 microns, 10-60 microns, 10-70 microns, 10-80 microns, 10-90 microns, 10-100 microns, 10-250 microns, 10-500 microns, 10-750 microns, 10-1,000 microns, 20-30 microns, 20-40 microns, 20-50 microns, 20-60 microns, 20-70 microns, 20-80 microns, 20-90 microns, 20-100 microns, 20-250 microns, 20-500 microns, 20-750 microns, 20-1,000 microns, 30-40 microns, 30-50 microns, 30-60 microns, 30-70 microns, 30-80 microns, 30-90 microns, 30-100 microns, 30-250 microns, 30-500 microns, 30-750 microns, 30-1,000 microns, 40-50 microns, 40-60 microns, 40-70 microns, 40-80 microns, 40-90 microns, 40-100 microns, 40-250 microns, 40-500 microns, 40-750 microns, 40-1,000 microns, 50-60 microns, 50-70 microns, 50-80 microns, 50-90 microns, 50-100 microns, 50-250 microns, 50-500 microns, 50-750 microns, 50-1,000 microns, 60-70 microns, 60-80 microns, 60-90 microns, 60-100 microns, 60-250 microns, 60-500 microns, 60-750 microns, 60-1,000 microns, 70-80 microns 70-90 microns, 70-90 microns, 70-100 microns, 70-250 microns, 70-500 microns, 70-750 microns, 70-1,000 microns, 80-90 microns, 80-100 microns, 80-250 microns, 80-500 microns, 80-500 microns, 80-750 microns, 80-1,000 microns, 90-100 microns, 90-250 microns, 90-500 microns, 90-750 microns, 90-1,000 microns, 100-250 microns, 100-500 microns, 100-750 microns, 100-1,000 microns, 250-500 microns, 250-750 microns, 250-1,000 microns, 500-750 microns, 500-1,000 microns, or 750-1,000 microns.

In some embodiments, the microbes or compositions comprising the microbes are milled to a size of between about 10-20 microns, about 10-30 microns, about 10-40 microns, about 10-50 microns, about 10-60 microns, about 10-70 microns, about 10-80 microns, about 10-90 microns, about 10-100 microns, about 10-250 microns, about 10-500 microns, about 10-750 microns, about 10-1,000 microns, about 20-30 microns, about 20-40 microns, about 20-50 microns, about 20-60 microns, about 20-70 microns, about 20-80 microns, about 20-90 microns, about 20-100 microns, about 20-250 microns, about 20-500 microns, about 20-750 microns, about 20-1,000 microns, about 30-40 microns, about 30-50 microns, about 30-60 microns, about 30-70 microns, about 30-80 microns, about 30-90 microns, about 30-100 microns, about 30-250 microns, about 30-500 microns, about 30-750 microns, about 30-1,000 microns, about 40-50 microns, about 40-60 microns, about 40-70 microns, about 40-80 microns, about 40-90 microns, about 40-100 microns, about 40-250 microns, about 40-500 microns, about 40-750 microns, about 40-1,000 microns, about 50-60 microns, about 50-70 microns, about 50-80 microns, about 50-90 microns, about 50-100 microns, about 50-250 microns, about 50-500 microns, about 50-750 microns, about 50-1,000 microns, about 60-70 microns, about 60-80 microns, about 60-90 microns, about 60-100 microns, about 60-250 microns, about 60-500 microns, about 60-750 microns, about 60-1,000 microns, about 70-80 microns about 70-90 microns, about 70-90 microns, about 70-100 microns, about 70-250 microns, about 70-500 microns, about 70-750 microns, about 70-1,000 microns, about 80-90 microns, about 80-100 microns, about 80-250 microns, about 80-500 microns, about 80-500 microns, about 80-750 microns, about 80-1,000 microns, about 90-100 microns, about 90-250 microns, about 90-500 microns, about 90-750 microns, about 90-1,000 microns, about 100-250 microns, about 100-500 microns, about 100-750 microns, about 100-1,000 microns, about 250-500 microns, about 250-750 microns, about 250-1,000 microns, about 500-750 microns, about 500-1,000 microns, or about 750-1,000 microns.

In some embodiments, the microbes or compositions comprising the microbes are combined with a wax, fat, oil, fatty acid, or fatty alcohol, and spray congealed into beads of about 10 microbes, about 20 microns, about 30 microns, about 40 microns, about 50 microns, about 60 microns, about 70 microns, about 80 microns, about 90 microns, about 100 microns, about 150 microns, about 200 microns, about 250 microns, about 300 microns, about 350 microns, about 400 microns, about 450 microns, about 500 microns, about 550 microns, about 600 microns, about 650 microns, about 700 microns, about 750 microns, about 800 microns, about 850 microns, about 900 microns, about 950 microns, or about 1,000 microns.

In some embodiments, the microbes or compositions comprising the microbes are combined with a wax, fat, oil, fatty acid, or fatty alcohol, and spray congealed into beads of between 10-20 microns, 10-30 microns, 10-40 microns, 10-50 microns, 10-60 microns, 10-70 microns, 10-80 microns, 10-90 microns, 10-100 microns, 10-250 microns, 10-500 microns, 10-750 microns, 10-1,000 microns, 20-30 microns, 20-40 microns, 20-50 microns, 20-60 microns, 20-70 microns, 20-80 microns, 20-90 microns, 20-100 microns, 20-250 microns, 20-500 microns, 20-750 microns, 20-1,000 microns, 30-40 microns, 30-50 microns, 30-60 microns, 30-70 microns, 30-80 microns, 30-90 microns, 30-100 microns, 30-250 microns, 30-500 microns, 30-750 microns, 30-1,000 microns, 40-50 microns, 40-60 microns, 40-70 microns, 40-80 microns, 40-90 microns, 40-100 microns, 40-250 microns, 40-500 microns, 40-750 microns, 40-1,000 microns, 50-60 microns, 50-70 microns, 50-80 microns, 50-90 microns, 50-100 microns, 50-250 microns, 50-500 microns, 50-750 microns, 50-1,000 microns, 60-70 microns, 60-80 microns, 60-90 microns, 60-100 microns, 60-250 microns, 60-500 microns, 60-750 microns, 60-1,000 microns, 70-80 microns 70-90 microns, 70-90 microns, 70-100 microns, 70-250 microns, 70-500 microns, 70-750 microns, 70-1,000 microns, 80-90 microns, 80-100 microns, 80-250 microns, 80-500 microns, 80-500 microns, 80-750 microns, 80-1,000 microns, 90-100 microns, 90-250 microns, 90-500 microns, 90-750 microns, 90-1,000 microns, 100-250 microns, 100-500 microns, 100-750 microns, 100-1,000 microns, 250-500 microns, 250-750 microns, 250-1,000 microns, 500-750 microns, 500-1,000 microns, or 750-1,000 microns.

In some embodiments, the microbes or compositions comprising the microbes are combined with a wax, fat, oil, fatty acid, or fatty alcohol, and spray congealed into beads of between about 10-20 microns, about 10-30 microns, about 10-40 microns, about 10-50 microns, about 10-60 microns, about 10-70 microns, about 10-80 microns, about 10-90 microns, about 10-100 microns, about 10-250 microns, about 10-500 microns, about 10-750 microns, about 10-1,000 microns, about 20-30 microns, about 20-40 microns, about 20-50 microns, about 20-60 microns, about 20-70 microns, about 20-80 microns, about 20-90 microns, about 20-100 microns, about 20-250 microns, about 20-500 microns, about 20-750 microns, about 20-1,000 microns, about 30-40 microns, about 30-50 microns, about 30-60 microns, about 30-70 microns, about 30-80 microns, about 30-90 microns, about 30-100 microns, about 30-250 microns, about 30-500 microns, about 30-750 microns, about 30-1,000 microns, about 40-50 microns, about 40-60 microns, about 40-70 microns, about 40-80 microns, about 40-90 microns, about 40-100 microns, about 40-250 microns, about 40-500 microns, about 40-750 microns, about 40-1,000 microns, about 50-60 microns, about 50-70 microns, about 50-80 microns, about 50-90 microns, about 50-100 microns, about 50-250 microns, about 50-500 microns, about 50-750 microns, about 50-1,000 microns, about 60-70 microns, about 60-80 microns, about 60-90 microns, about 60-100 microns, about 60-250 microns, about 60-500 microns, about 60-750 microns, about 60-1,000 microns, about 70-80 microns about 70-90 microns, about 70-90 microns, about 70-100 microns, about 70-250 microns, about 70-500 microns, about 70-750 microns, about 70-1,000 microns, about 80-90 microns, about 80-100 microns, about 80-250 microns, about 80-500 microns, about 80-500 microns, about 80-750 microns, about 80-1,000 microns, about 90-100 microns, about 90-250 microns, about 90-500 microns, about 90-750 microns, about 90-1,000 microns, about 100-250 microns, about 100-500 microns, about 100-750 microns, about 100-1,000 microns, about 250-500 microns, about 250-750 microns, about 250-1,000 microns, about 500-750 microns, about 500-1,000 microns, or about 750-1,000 microns.

In some embodiments, the microbes or compositions comprising the microbes are combined with a wax, fat, oil, fatty acid, or fatty alcohol as well as a water-soluble polymer, salt, polysaccharide, sugar, polypeptide, protein, or sugar alcohol and spray congealed into beads, the size of which are described herein. In some embodiments, the water-soluble polymer, salt, polysaccharide, sugar, or sugar alcohol serves as a disintegrant. In some embodiments, the disintegrant forms pores once the beads are dispersed in the rumen of the animal.

In some embodiments, the composition of the water-soluble polymer, salt, polysaccharide, sugar, polypeptide, protein, or sugar alcohol is modified such that the disintegrant dissolves within 1, 5, 10, 15, 20, 25, 30, 35, 40, 45, 50, 55, 60 minutes of being administered. In some embodiments, the composition of the water-soluble polymer, salt, polysaccharide, sugar, polypeptide, protein, or sugar alcohol is modified such that the disintegrant dissolves within about 1, about 5, about 10, about 15, about 20, about 25, about 30, about 35, about 40, about 45, about 50, about 55, or about 60 minutes of being administered.

In some embodiments, the composition of the water-soluble polymer, salt, polysaccharide, sugar, polypeptide, protein, or sugar alcohol is modified such that the disintegrant dissolves within 1, 1.5, 2, 2.5, 3, 3.5, 4, 4.5, 5, 5.5, 6, 6.5, 7, 7.5, 8, 8.5, 9, 9.5, 10, 10.5, 11, 11.5, or 12 hours of being administered. In some embodiments, the composition of the water-soluble polymer, salt, polysaccharide, sugar, polypeptide, protein, or sugar alcohol is modified such that the disintegrant dissolves within about 1, about 1.5, about 2, about 2.5, about 3, about 3.5, about 4, about 4.5, about 5, about 5.5, about 6, about 6.5, about 7, about 7.5, about 8, about 8.5, about 9, about 9.5, about 10, about 10.5, about 11, about 11.5, or about 12 hours of being administered.

In some embodiments, the composition of the water-soluble polymer, salt, polysaccharide, sugar, polypeptide, protein, or sugar alcohol is modified such that the disintegrant dissolves at a temperature of at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50° C. In some embodiments, the composition of the water-soluble polymer, salt, polysaccharide, sugar, polypeptide, protein, or sugar alcohol is modified such that the disintegrant dissolves at a temperature of at least about 10, least about 11, least about 12, least about 13, least about 14, least about 15, least about 16, least about 17, least about 18, least about 19, least about 20, least about 21, least about 22, least about 23, least about 24, least about 25, least about 26, least about 27, least about 28, least about 29, least about 30, least about 31, least about 32, least about 33, least about 34, about 35, about 36, about 37, about 38, about 39, about 40, about 41, about 42, about 43, about 44, least about 45, least about 46, least about 47, least about 48, least about 49, or least about 50° C.

In some embodiments, the composition of the water-soluble polymer, salt, polysaccharide, sugar, polypeptide, protein, or sugar alcohol is modified such that the disintegrant dissolves at a pH of at least 3.8, 3.9, 4. 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9 or 10.0. In some embodiments, the composition of the water-soluble polymer, salt, polysaccharide, sugar, polypeptide, protein, or sugar alcohol is modified such that the disintegrant dissolves at a pH of at least about 3.8, least about 3.9, least about 4. least about 4.1, least about 4.2, least about 4.3, least about 4.4, least about 4.5, least about 4.6, least about 4.7, least about 4.8, least about 4.9, least about 5.0, least about 5.1, least about 5.2, least about 5.3, least about 5.4, least about 5.5, least about 5.6, least about 5.7, least about 5.8, least about 5.9, least about 6.0, least about 6.2, least about 6.3, least about 6.4, least about 6.5, least about 6.6, least about 6.7, least about 6.8, least about 6.9, least about 7.0, least about 7.1, least about 7.2, least about 7.3, least about 7.4, least about 7.5, least about 7.6, least about 7.7, least about 7.8, least about 7.9, least about 8.0, least about 8.1, least about 8.2, least about 8.3, least about 8.4, least about 8.5, least about 8.6, least about 8.7, least about 8.8, least about 8.9, least about 9.0, least about 9.1, least about 9.2, least about 9.3, least about 9.4, least about 9.5, least about 9.6, least about 9.7, least about 9.8, least about 9.9, or least about 10.0.

In some embodiments, the microbes or compositions comprising the microbes are coated with a polymer, a polysaccharide, sugar, sugar alcohol, gel, wax, fat, fatty alcohol, or fatty acid.

In some embodiments, the microbes or compositions comprising the microbes are coated with a polymer, a polysaccharide, sugar, sugar alcohol, gel, wax, fat, fatty alcohol, or fatty acid.

In some embodiments, the coating of the microbes or compositions comprising the microbes is modified such that the coating dissolves within 1, 5, 10, 15, 20, 25, 30, 35, 40, 45, 50, 55, 60 minutes of being administered. In some embodiments, the coating of the microbes or compositions comprising the microbes is modified such that the coating dissolves within about 1, about 5, about 10, about 15, about 20, about 25, about 30, about 35, about 40, about 45, about 50, about 55, or about 60 minutes of being administered.

In some embodiments, the coating of the microbes or compositions comprising the microbes is modified such that the coating dissolves within 1, 1.5, 2, 2.5, 3, 3.5, 4, 4.5, 5, 5.5, 6, 6.5, 7, 7.5, 8, 8.5, 9, 9.5, 10, 10.5, 11, 11.5, or 12 hours of being administered. In some embodiments, the coating of the microbes or compositions comprising the microbes is modified such that the coating dissolves within about 1, about 1.5, about 2, about 2.5, about 3, about 3.5, about 4, about 4.5, about 5, about 5.5, about 6, about 6.5, about 7, about 7.5, about 8, about 8.5, about 9, about 9.5, about 10, about 10.5, about 11, about 11.5, or about 12 hours of being administered.

In some embodiments, the coating of the microbes or compositions comprising the microbes is modified such that the coating dissolves at a temperature of at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50° C. In some embodiments, the coating of the microbes or compositions comprising the microbes is modified such that the coating dissolves at a temperature of at least about 10, least about 11, least about 12, least about 13, least about 14, least about 15, least about 16, least about 17, least about 18, least about 19, least about 20, least about 21, least about 22, least about 23, least about 24, least about 25, least about 26, least about 27, least about 28, least about 29, least about 30, least about 31, least about 32, least about 33, least about 34, about 35, about 36, about 37, about 38, about 39, about 40, about 41, about 42, about 43, about 44, least about 45, least about 46, least about 47, least about 48, least about 49, or least about 50° C.

In some embodiments, the coating of the microbes or compositions comprising the microbes is modified such that the coating dissolves at a pH of at least 3.8, 3.9, 4. 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9 or 10.0. In some embodiments, the coating of the microbes or compositions comprising the microbes is modified such that the coating dissolves at a pH of at least about 3.8, least about 3.9, least about 4. least about 4.1, least about 4.2, least about 4.3, least about 4.4, least about 4.5, least about 4.6, least about 4.7, least about 4.8, least about 4.9, least about 5.0, least about 5.1, least about 5.2, least about 5.3, least about 5.4, least about 5.5, least about 5.6, least about 5.7, least about 5.8, least about 5.9, least about 6.0, least about 6.2, least about 6.3, least about 6.4, least about 6.5, least about 6.6, least about 6.7, least about 6.8, least about 6.9, least about 7.0, least about 7.1, least about 7.2, least about 7.3, least about 7.4, least about 7.5, least about 7.6, least about 7.7, least about 7.8, least about 7.9, least about 8.0, least about 8.1, least about 8.2, least about 8.3, least about 8.4, least about 8.5, least about 8.6, least about 8.7, least about 8.8, least about 8.9, least about 9.0, least about 9.1, least about 9.2, least about 9.3, least about 9.4, least about 9.5, least about 9.6, least about 9.7, least about 9.8, least about 9.9, or least about 10.0.

Animal Feed

In some embodiments, compositions of the present disclosure are mixed with animal feed. In some embodiments, animal feed may be present in various forms such as pellets, capsules, granulated, powdered, mash, liquid, semi-liquid, or mixed rations(s).

In some embodiments, compositions of the present disclosure are mixed into the premix at the feed mill (e.g., Carghill or Western Millin), alone as a standalone premix, and/or alongside other feed additives such as MONENSIN, vitamins, etc. In one embodiment, compositions of the present disclosure are mixed into the feed itself. In one embodiment, the compositions of the present disclosure are mixed into the feed at the feed mill.

In some embodiments, feed of the present disclosure may be supplemented with water, premix or premixes, forage, beans (e.g., whole, cracked, or ground), grains (e.g., whole, cracked, or ground), bean- or grain-based oils, bean- or grain-based meals, bean- or grain-based haylage or silage, bean- or grain-based syrups, fatty acids, sugar alcohols (e.g., polyhydric alcohols), commercially available formula feeds, oyster shells and those of other bivalves, and mixtures thereof.

In some embodiments, forage encompasses hay, haylage, and silage. In some embodiments, hays include grass hays (e.g., sudangrass, orchardgrass, or the like), alfalfa hay, and clover hay. In some embodiments, haylages include grass haylages, sorghum haylage, and alfalfa haylage. In some embodiments, silages include maize, oat, wheat, alfalfa, clover, and the like.

In some embodiments, premix or premixes may be utilized in the feed. Premixes may comprise micro-ingredients such as vitamins, minerals, amino acids; chemical preservatives; pharmaceutical compositions such as antibiotics, ionophores, and other medicaments; fermentation products, and other ingredients. In some embodiments, premixes are blended into the feed.

In some embodiments, the feed may include feed concentrates such as soybean hulls, soybean oils, sugar beet pulp, molasses, high protein soybean meal, ground corn, shelled corn, cornflakes, wheat midds, distiller grain, cottonseed hulls, rumen-bypass protein, rumen-bypass fat, and grease. See Luhman (U.S. Publication US20150216817A1), Anderson et al. (U.S. Pat. No. 3,484,243), Porter and Luhman (U.S. Pat. No. 9,179,694B2), Iritani et al. (U.S. Pat. No. 6,090,416), Axelrod et al. (U.S. Publication US20060127530A1), and Katsumi et al. (U.S. Pat. No. 5,741,508) for animal feed and animal feed supplements capable of use in the present compositions and methods.

In some embodiments, feed occurs as a compound, which includes, in a mixed composition capable of meeting the basic dietary needs, the feed itself, vitamins, minerals, amino acids, and other necessary components. Compound feed may further comprise premixes.

In some embodiments, microbial compositions of the present disclosure may be mixed with animal feed, premix, and/or compound feed. Individual components of the animal feed may be mixed with the microbial compositions prior to feeding to beef cattle. The microbial compositions of the present disclosure may be applied into or on a premix, into or on a feed, and/or into or on a compound feed.

In some embodiments, microbial compositions of the present disclosure may be mixed with animal feed, premix, and/or compound feed at various stages of animal adaptation to the step-up or finishing diet.

In some embodiments, microbial compositions of the present disclosure are mixed with feed and microingredients. Microingredients include liquid fat blends, glycerin, rumensin, monensin, vitamins, tylan, optaflex, melengesterol acetate, minerals, and amino acids. In some embodiments, the mixing of feed, microbial compositions of the present disclosure, and microingredients is performed at the feedlot.

In some embodiments, cattle begin a step up or a starting ration. As used herein, a "step-up diet" or "starting ration" is a diet fed to feedlot cattle as a transition to the high grain content of the finishing diet. In some embodiments, the step-up diet may involve one or more step-up diets that ease the cattle into the transition to the finishing diet. In some embodiments, the step-up diet is formulated to slowly increase the amount of high energy feed in the diet while mitigating gastrointestinal distress and the effects of rapid onset acidosis. In some embodiments, the cattle are fed a single type of step-up diet. In some embodiments, the cattle are fed multiple varieties of step-up diets, increasing the amount of high energy feed with each iteration of the step up diet variety. In some embodiments, the cattle are fed at least one step up diet, wherein the subsequent diets are different from each of those step up diets that follow. In some embodiments, the cattle are fed at least two different step up diets. In some embodiments, the cattle are fed at least three different step up diets.

As used herein, a "finishing diet" is a concentrated high-energy diet (often high-grain) fed to cattle on a feedlot to rapidly bring the cattle up to get them to market weight by the time the cattle are rendered. In some embodiments, the finishing diet may result in liver disease, liver abscesses, and/or acidosis.

In some embodiments, the microbial compositions of the present disclosure are mixed with step-up diets. In some embodiments, the microbial compositions of the present disclosure are mixed with finishing diets.

Administration of Microbial Compositions

In some embodiments, the microbial compositions of the present disclosure are administered to cattle via the oral route. In some embodiments the microbial compositions are administered via a direct injection route into the gastrointestinal tract. In further embodiments, the direct injection administration delivers the microbial compositions directly to the rumen. In some embodiments, the microbial compositions of the present disclosure are administered to animals anally. In further embodiments, anal administration is in the form of an inserted suppository.

In some embodiments, the microbial composition is administered in a dose volume comprising a total of, or at least, 1 ml, 2 ml, 3 ml, 4 ml, 5 ml, 6 ml, 7 ml, 8 ml, 9 ml, 10 ml, 11ml, 12 ml, 13 ml, 14 ml, 15 ml, 16 ml, 17 ml, 18 ml, 19 ml, 20 ml, 21 ml, 22 ml, 23 ml, 24 ml, 25 ml, 26 ml, 27 ml, 28 ml, 29 ml, 30 ml, 31 ml, 32 ml, 33 ml, 34 ml, 35 ml, 36 ml, 37 ml, 38 ml, 39 ml, 40 ml, 41m, 42 ml, 43 ml, 44 ml, 45 ml, 46 ml, 47 ml, 48 ml, 49 ml, 50 ml, 60 ml, 70 ml, 80 ml, 90 ml, 100 ml, 200 ml, 300 ml, 400 ml, 500 ml, 600 ml, 700 ml, 800 ml, 900 ml, or 1,000 ml.

In some embodiments, the microbial composition is administered in a dose comprising a total of, or at least, $10^{18}$, $10^{17}$, $10^{16}$, $10^{15}$, $10^{14}$, $10^{13}$, $10^{12}$, $10^{11}$, $10^{10}$, $10^9$, $10^8$, $10^7$, $10^6$, $10^5$, $10^4$, $10^3$, or $10^2$ microbial cells.

In some embodiments, the microbial compositions are mixed with feed, and the administration occurs through the ingestion of the microbial compositions along with the feed.

In some embodiments, the dose of the microbial composition is administered such that there exists $10^2$ to $10^{12}$, $10^3$ to $10^{12}$, $10^4$ to $10^{12}$, $10^5$ to $10^{12}$, $10^6$ to $10^{12}$, $10^7$ to $10^{12}$, $10^8$ to $10^{12}$, $10^9$ to $10^{12}$, $10^{10}$ to $10^{12}$, $10^{11}$ to $10^{12}$, $10^2$ to $10^{11}$, $10^3$ to $10^{11}$, $10^4$ to $10^{11}$, $10^5$ to $10^{11}$, $10^6$ to $10^{11}$, $10^7$ to $10^{11}$, $10^8$ to $10^{11}$, $10^9$ to $10^{11}$, $10^{10}$ to $10^{11}$, $10^2$ to $10^{10}$, $10^3$ to $10^{10}$, $10^4$ to $10^{10}$, $10^5$ to $10^{10}$, $10^6$ to $10^{10}$, $10^7$ to $10^{10}$, $10^8$ to $10^{10}$, $10^9$ to $10^{10}$, $10^2$ to $10^9$, $10^3$ to $10^9$, $10^4$ to $10^9$, $10^5$ to $10^9$, $10^6$ to $10^9$, $10^7$ to $10^9$, $10^8$ to $10^9$, $10^2$ to $10^8$, $10^3$ to $10^8$, $10^4$ to $10^8$, $10^5$ to $10^8$, $10^6$ to $10^8$, $10^7$ to $10^8$, $10^2$ to $10^7$, $10^3$ to $10^7$, $10^4$ to $10^7$, $10^5$ to $10^7$, $10^6$ to $10^7$, $10^2$ to $10^6$, $10^3$ to $10^6$, $10^4$ to $10^6$, $10^5$ to $10^6$, $10^2$ to $10^5$, $10^3$ to $10^5$, $10^4$ to $10^5$, $10^2$ to $10^4$, $10^3$ to $10^4$, $10^2$ to $10^3$, $10^{12}$, $10^{11}$, $10^{10}$, $10^9$, $10^8$, $10^7$, $10^6$, $10^5$, $10^4$, $10^3$, or $10^2$ total microbial cells per gram or milliliter of the composition.

In some embodiments, the administered dose of the microbial composition comprises $10^2$ to $10^{18}$, $10^3$ to $10^{18}$, $10^4$ to $10^{18}$, $10^5$ to $10^{18}$, $10^6$ to $10^{18}$, $10^7$ to $10^{18}$, $10^8$ to $10^{18}$, $10^9$ to $10^{18}$, $10^{10}$ to $10^{18}$, $10^{11}$ to $10^{18}$, $10^{12}$ to $10^{18}$, $10^{13}$ to $10^{18}$, $10^{14}$ to $10^{18}$, $10^{15}$ to $10^{18}$, $10^{16}$ to $10^{18}$, $10^{17}$ to $10^{18}$, $10^2$ to $10^{12}$, $10^3$ to $10^{12}$, $10^4$ to $10^{12}$, $10^5$ to $10^{12}$, $10^6$ to $10^{12}$, $10^7$ to $10^{12}$, $10^8$ to $10^{12}$, $10^9$ to $10^{12}$, $10^{10}$ to $10^{12}$, $10^{11}$ to $10^{12}$, $10^2$ to $10^{11}$, $10^3$ to $10^{11}$, $10^4$ to $10^{11}$, $10^5$ to $10^{11}$, $10^6$ to $10^{11}$, $10^7$ to $10^{11}$, $10^8$ to $10^{11}$, $10^9$ to $10^{11}$, $10^{10}$ to $10^{11}$, $10^2$ to $10^{10}$, $10^3$ to $10^{10}$, $10^4$ to $10^{10}$, $10^5$ to $10^{10}$, $10^6$ to $10^{10}$, $10^7$ to $10^{10}$, $10^8$ to $10^{10}$, $10^9$ to $10^{10}$, $10^2$ to $10^9$, $10^3$ to $10^9$, $10^4$ to $10^9$, $10^5$ to $10^9$, $10^6$ to $10^9$, $10^7$ to $10^9$, $10^8$ to $10^9$, $10^2$ to $10^8$, $10^3$ to $10^8$, $10^4$ to $10^8$, $10^5$ to $10^8$, $10^6$ to $10^8$, $10^7$ to $10^8$, $10^2$ to $10^7$, $10^3$ to $10^7$, $10^4$ to $10^7$, $10^5$ to $10^7$, $10^6$ to $10^7$, $10^2$ to $10^6$, $10^3$ to $10^6$, $10^4$ to $10^6$, $10^5$ to $10^6$ $10^2$ to $10^5$, $10^3$ to $10^5$, $10^4$ to $10^5$, $10^2$ to $10^4$, $10^3$ to $10^4$, $10^2$ to $10^3$, $10^{18}$, $10^{17}$, $10^{16}$, $10^{15}$, $10^{14}$, $10^{13}$, $10^{12}$, $10^{11}$, $10^{10}$, $10^9$, $10^8$, $10^7$, $10^6$, $10^5$, $10^4$, $10^3$, or $10^2$ total microbial cells.

In some embodiments, the composition is administered 1 or more times per day. In some aspects, the composition is administered with food each time the animal is fed. In some embodiments, the composition is administered 1 to 10, 1 to 9, 1 to 8, 1 to 7, 1 to 6, 1 to 5, 1 to 4, 1 to 3, 1 to 2, 2 to 10, 2 to 9, 2 to 8, 2 to 7, 2 to 6, 2 to 5, 2 to 4, 2 to 3, 3 to 10, 3 to 9, 3 to 8, 3 to 7, 3 to 6, 3 to 5, 3 to 4, 4 to 10, 4 to 9, 4 to 8, 4 to 7, 4 to 6, 4 to 5, 5 to 10, 5 to 9, 5 to 8, 5 to 7, 5 to 6, 6 to 10, 6 to 9, 6 to 8, 6 to 7, 7 to 10, 7 to 9, 7 to 8, 8 to 10, 8 to 9, 9 to 10, 1, 2, 3, 4, 5, 6, 7, 8, 9, or 10 times per day.

In some embodiments, the microbial composition is administered 1 to 10, 1 to 9, 1 to 8, 1 to 7, 1 to 6, 1 to 5, 1 to 4, 1 to 3, 1 to 2, 2 to 10, 2 to 9, 2 to 8, 2 to 7, 2 to 6, 2 to 5, 2 to 4, 2 to 3, 3 to 10, 3 to 9, 3 to 8, 3 to 7, 3 to 6, 3 to 5, 3 to 4, 4 to 10, 4 to 9, 4 to 8, 4 to 7, 4 to 6, 4 to 5, 5 to 10, 5 to 9, 5 to 8, 5 to 7, 5 to 6, 6 to 10, 6 to 9, 6 to 8, 6 to 7, 7 to 10, 7 to 9, 7 to 8, 8 to 10, 8 to 9, 9 to 10, 1, 2, 3, 4, 5, 6, 7, 8, 9, or 10 times per week.

In some embodiments, the microbial composition is administered 1 to 10, 1 to 9, 1 to 8, 1 to 7, 1 to 6, 1 to 5, 1 to 4, 1 to 3, 1 to 2, 2 to 10, 2 to 9, 2 to 8, 2 to 7, 2 to 6, 2 to 5, 2 to 4, 2 to 3, 3 to 10, 3 to 9, 3 to 8, 3 to 7, 3 to 6, 3 to 5, 3 to 4, 4 to 10, 4 to 9, 4 to 8, 4 to 7, 4 to 6, 4 to 5, 5 to 10, 5 to 9, 5 to 8, 5 to 7, 5 to 6, 6 to 10, 6 to 9, 6 to 8, 6 to 7, 7 to 10, 7 to 9, 7 to 8, 8 to 10, 8 to 9, 9 to 10, 1, 2, 3, 4, 5, 6, 7, 8, 9, or 10 times per month.

In some embodiments, the microbial composition is administered 1 to 10, 1 to 9, 1 to 8, 1 to 7, 1 to 6, 1 to 5, 1 to 4, 1 to 3, 1 to 2, 2 to 10, 2 to 9, 2 to 8, 2 to 7, 2 to 6, 2 to 5, 2 to 4, 2 to 3, 3 to 10, 3 to 9, 3 to 8, 3 to 7, 3 to 6, 3 to 5, 3 to 4, 4 to 10, 4 to 9, 4 to 8, 4 to 7, 4 to 6, 4 to 5, 5 to 10, 5 to 9, 5 to 8, 5 to 7, 5 to 6, 6 to 10, 6 to 9, 6 to 8, 6 to 7, 7 to 10, 7 to 9, 7 to 8, 8 to 10, 8 to 9, 9 to 10, 1, 2, 3, 4, 5, 6, 7, 8, 9, or 10 times per year.

In some embodiments, the microbial composition is administered to animals throughout the entire time they are on the feedlot. In some embodiments, the microbial composition is administered to animals only during a portion of time while they are on the feedlot. In some embodiments, the microbial composition is administered only during the grower phase. In some embodiments, the microbial composition is administered only during the time when animals are in the receiving pen. In some embodiments, the microbial composition is administered only when the animals are receiving vaccinations and/or treatments. In some embodiments, the microbial composition is administered only when the animals are on a step up diet or when being adapted to a high grain diet. In some embodiments, the microbial composition is administered only when the animals are on a finisher diet or a high grain diet.

In some embodiments, the microbial composition is administered during the grower phase, when animals are in the receiving pen, when animals are receiving vaccinations and/or treatments, when animals are being adapted to a high grain diet or are on a step up diet, and/or when the animals are on a finisher diet or a high grain diet.

In some embodiments, an animal entering the feed lot receives at least one microbial composition prior to entering the feed lot. In some embodiments, an animal on the feed lot receives a microbial composition that is different from the first at least one microbial composition. In further embodiments, an animal on the feed lot receives a microbial composition that is different from the first and second at least one microbial composition.

In some embodiments, the type of diet fed to the animal corresponds with the type of microbial composition administered to the animal. In some embodiments, a grazing or grass/hay-fed animal will receive a first microbial composition. In further embodiments, the same animal fed a different diet will receive a second microbial composition, wherein the first microbial composition is different from the second microbial composition. In some embodiments, the same animal fed yet a different diet will receive a third microbial composition, wherein the first microbial composition is different from the second and third microbial compositions. In some embodiments, the same animal fed yet a different diet will receive a fourth microbial composition, wherein the first microbial composition is different from the second, third, and fourth microbial compositions. In some embodiments, the same animal fed yet a different diet will receive a fifth microbial composition, wherein the first microbial composition is different from the second, third, fourth, and fifth microbial compositions.

In some embodiments, the feed can be uniformly coated with one or more layers of the microbes and/or microbial compositions disclosed herein, using conventional methods of mixing, spraying, or a combination thereof through the use of treatment application equipment that is specifically designed and manufactured to accurately, safely, and efficiently apply coatings. Such equipment uses various types of coating technology such as rotary coaters, drum coaters, fluidized bed techniques, spouted beds, rotary mists, or a combination thereof. Liquid treatments such as those of the present disclosure can be applied via either a spinning "atomizer" disk or a spray nozzle, which evenly distributes the microbial composition onto the feed as it moves though the spray pattern. In some aspects, the feed is then mixed or tumbled for an additional period of time to achieve additional treatment distribution and drying.

In some embodiments, the feed coats of the present disclosure can be up to 10 µm, 20 µm, 30 µm, 40 µm, 50 µm, 60 µm, 70 µm, 80 µm, 90 µm, 100 µm, 110 µm, 120 µm, 130 µm, 140 µm, 150 µm, 160 µm, 170 µm, 180 µm, 190 µm, 200 µm, 210 µm, 220 µm, 230 µm, 240 µm, 250 µm, 260 µm, 270 µm, 280 µm, 290 µm, 300 µm, 310 µm, 320 µm, 330 µm, 340 µm, 350 µm, 360 µm, 370 µm, 380 µm, 390 µm, 400 µm, 410 µm, 420 µm, 430 µm, 440 µm, 450 µm, 460 µm, 470 µm, 480 µm, 490 µm, 500 µm, 510 µm, 520 µm, 530 µm, 540 µm, 550 µm, 560 µm, 570 µm, 580 µm, 590 µm, 600 µm, 610 µm, 620 µm, 630 µm, 640 µm, 650 µm, 660 µm, 670 µm, 680 µm, 690 µm, 700 µm, 710 µm, 720 µm, 730 µm, 740 µm, 750 µm, 760 µm, 770 µm, 780 µm, 790 µm, 800 µm, 810 µm, 820 µm, 830 µm, 840 µm, 850 µm, 860 µm, 870 µm, 880 µm, 890 µm, 900 µm, 910 µm, 920 µm, 930 µm, 940 µm, 950 µm, 960 µm, 970 µm, 980 µm, 990 µm, 1000 µm, 1010 µm, 1020 µm, 1030 µm, 1040 µm, 1050 µm, 1060 µm, 1070 µm, 1080 µm, 1090 µm, 1100 µm, 1110 µm, 1120 µm, 1130 µm, 1140 µm, 1150 µm, 1160 µm, 1170 µm, 1180 µm, 1190 µm, 1200 µm, 1210 µm, 1220 µm, 1230 µm, 1240 µm, 1250 µm, 1260 µm, 1270 µm, 1280 µm, 1290 µm, 1300 µm, 1310 µm, 1320 µm, 1330 µm, 1340 µm, 1350 µm, 1360 µm, 1370 µm, 1380 µm, 1390 µm, 1400 µm, 1410 µm, 1420 µm, 1430 µm, 1440 µm, 1450 µm, 1460 µm, 1470 µm, 1480 µm, 1490 µm, 1500 µm, 1510 µm, 1520 µm, 1530 µm, 1540 µm, 1550 µm, 1560 µm, 1570 µm, 1580 µm, 1590 µm, 1600 µm, 1610 µm, 1620 µm, 1630 µm, 1640 µm, 1650 µm, 1660 µm, 1670 µm, 1680 µm, 1690 µm, 1700 µm, 1710 µm, 1720 µm, 1730 µm, 1740 µm, 1750 µm, 1760 µm, 1770 µm, 1780 µm, 1790 µm, 1800 µm, 1810 µm, 1820 µm, 1830 µm, 1840 µm, 1850 µm, 1860 µm, 1870 µm, 1880 µm, 1890 µm, 1900 µm, 1910 µm, 1920 µm, 1930 µm, 1940 µm, 1950 µm, 1960 µm, 1970 µm, 1980 µm, 1990 µm, 2000 µm, 2010 µm, 2020 µm, 2030 µm, 2040 µm, 2050 µm, 2060 µm, 2070 µm, 2080 µm, 2090 µm, 2100 µm, 2110 µm, 2120 µm, 2130 µm, 2140 µm, 2150 µm, 2160 µm, 2170 µm, 2180 µm, 2190 µm, 2200 µm, 2210 µm, 2220 µm, 2230 µm, 2240 µm, 2250 µm, 2260 µm, 2270 µm, 2280 µm, 2290 µm, 2300 µm, 2310 µm, 2320 µm, 2330 µm, 2340 µm, 2350 µm, 2360 µm, 2370 µm, 2380 µm, 2390 µm, 2400 µm, 2410 µm, 2420 µm, 2430 µm, 2440 µm, 2450 µm, 2460 µm, 2470 µm, 2480 µm, 2490 µm, 2500 µm, 2510 µm, 2520 µm, 2530 µm, 2540 µm, 2550 µm, 2560 µm, 2570 µm, 2580 µm, 2590 µm, 2600 µm, 2610 µm, 2620 µm, 2630 µm, 2640 µm, 2650 µm, 2660 µm, 2670 µm, 2680 µm, 2690 µm, 2700 µm, 2710 µm, 2720 µm, 2730 µm, 2740 µm, 2750 µm, 2760 µm, 2770 µm, 2780 µm, 2790 µm, 2800 µm, 2810 µm, 2820 µm, 2830 µm, 2840 µm, 2850 µm, 2860 µm, 2870 µm, 2880 µm, 2890 µm, 2900 µm, 2910 µm, 2920 µm, 2930 µm, 2940 µm, 2950 µm, 2960 µm, 2970 µm, 2980 µm, 2990 µm, or 3000 µm thick.

In some embodiments, the microbial cells can be coated freely onto any number of compositions or they can be formulated in a liquid or solid composition before being coated onto a composition. For example, a solid composition comprising the microorganisms can be prepared by mixing a solid carrier with a suspension of the spores until the solid carriers are impregnated with the spore or cell suspension. This mixture can then be dried to obtain the desired particles.

In some other embodiments, it is contemplated that the solid or liquid microbial compositions of the present disclosure further contain functional agents e.g., activated carbon, minerals, vitamins, and other agents capable of improving the quality of the products or a combination thereof.

Methods of coating and compositions in use of said methods that are known in the art can be particularly useful when they are modified by the addition of one of the embodiments of the present disclosure. Such coating methods and apparatus for their application are disclosed in, for example: U.S. Pat. Nos. 8,097,245 and 7,998,502; and PCT Pat. App. Pub. Nos. WO 2008/076975, WO 2010/138522, WO 2011/094469, WO 2010/111347, and WO 2010/111565 each of which is incorporated by reference herein.

In some embodiments, the microbes or microbial compositions of the present disclosure exhibit a synergistic effect, on one or more of the traits described herein, in the presence of one or more of the microbes or microbial compositions coming into contact with one another. The synergistic effect obtained by the taught methods can be quantified, for example, according to Colby's formula (i.e., $(E)=X+Y-(X*Y/100)$). See Colby, R. S., "Calculating Synergistic and Antagonistic Responses of Herbicide Combinations," 1967. Weeds. Vol. 15, pp. 20-22, incorporated herein by reference in its entirety. Thus, "synergistic" is intended to reflect an outcome/parameter/effect that has been increased by more than an additive amount.

In some embodiments, the microbes or microbial compositions of the present disclosure may be administered via bolus. In one embodiment, a bolus (e.g., capsule containing the composition) is inserted into a bolus gun, and the bolus gun is inserted into the buccal cavity and/or esophagus of the animal, followed by the release/injection of the bolus into the animal's digestive tract. In one embodiment, the bolus gun/applicator is a BOVIKALC bolus gun/applicator. In another embodiment, the bolus gun/applicator is a QUADRICAL gun/applicator.

In some embodiments, the microbes or microbial compositions of the present disclosure may be administered via drench. In one embodiment, the drench is an oral drench. A drench administration comprises utilizing a drench kit/applicator/syringe that injects/releases a liquid comprising the microbes or microbial compositions into the buccal cavity and/or esophagus of the animal.

In some embodiments, the microbes or microbial compositions of the present disclosure may be administered in a time-released fashion. The composition may be coated in a chemical composition, or may be contained in a mechanical device or capsule that releases the microbes or microbial compositions over a period of time instead all at once. In one embodiment, the microbes or microbial compositions are administered to an animal in a time-release capsule. In one embodiment, the composition may be coated in a chemical composition, or may be contained in a mechanical device or capsule that releases the microbes or microbial compositions all at once a period of time hours post ingestion.

In some embodiments, one microbe composition is administered one or more times when the animals are on a step up diet, and a different microbe composition is administered one or more times when the animals are on a finishing diet. In some embodiments, one microbe composition is administered one or more times when the animals are on a step up diet, a different microbe composition is administered one or more times when the animals are on the first thirty days of the finishing diet, and yet a different microbe composition is administered one or more times when the animals have been on the finishing diet for greater than thirty days.

In some embodiments, one microbe composition is administered one or more times while the animals exhibit signs of acidosis, and different microbe composition is administered one or more times once the signs of acidosis have abated. In some embodiments, a microbe composition is administered to animals that do not exhibit signs of acidosis, and a different microbe composition is administered if the animals exhibit signs of acidosis.

In some embodiments, the microbes or microbial compositions are administered in a time-released fashion between 1 to 5, 1 to 10, 1 to 15, 1 to 20, 1 to 24, 1 to 25, 1 to 30, 1 to 35, 1 to 40, 1 to 45, 1 to 50, 1 to 55, 1 to 60, 1 to 65, 1 to 70, 1 to 75, 1 to 80, 1 to 85, 1 to 90, 1 to 95, or 1 to 100 hours.

In some embodiments, the microbes or microbial compositions are administered in a time-released fashion between 1 to 2, 1 to 3, 1 to 4, 1 to 5, 1 to 6, 1 to 7, 1 to 8, 1 to 9, 1 to 10, 1 to 11, 1 to 12, 1 to 13, 1 to 14, 1 to 15, 1 to 16, 1 to 17, 1 to 18, 1 to 19, 1 to 20, 1 to 21, 1 to 22, 1 to 23, 1 to 24, 1 to 25, 1 to 26, 1 to 27, 1 to 28, 1 to 29, or 1 to 30 days.

Microorganisms

As used herein the term "microorganism" should be taken broadly. It includes, but is not limited to, the two prokaryotic domains, Bacteria and Archaea, as well as eukaryotic fungi, protozoa, and viruses.

By way of example, the microorganisms may include species of the genera of: *Fibrobacter, Saccharofermentans, Bacillus, Spirochaeta, Bacteroides, Lachnospiracea incertae sedis, Clostridium XLVa, Ruminococcus, Butyricimonas, Olsenella, Acidaminococcus, Parabacteroides, Clostridium sensu stricto, Oribacterium, Pseudoflavonifractor, Treponema, Rhodobacter, Fluviicola, Succiniclasticum, Solobacterium, Veillonella, Cellulosimicrobium, Cupriavidus, Megasphaera, Succinivibrio, Oscillibacter, Pseudomonas, Corynebacterium, Adlercreutzia, Dorea, Roseburia, Anaerovibrio, Sporosarcina, Streptomyces, Syntrophococcus, Butyrivibrio, Lachnobacterium, Pyramidobacter, Coprococcus, Ruminobacter, Thermobifidia, Papillibacter, Aquimarina, Propioniciclava, Staphylococcus, Mogibacterium, Pseudobutyrivibrio, Asteroleplasma, Turicibacter, Aggregatibacter, Brevundimonas, Phascolarctobacterium,* and *Sphingobium.*

In certain embodiments, the microorganism is unculturable. This should be taken to mean that the microorganism is not known to be culturable or is difficult to culture using methods known to one skilled in the art.

In one embodiment, the microbes are obtained from animals (e.g., mammals, reptiles, birds, and the like), soil (e.g., rhizosphere), air, water (e.g., marine, freshwater, wastewater sludge), sediment, oil, plants (e.g., roots, leaves, stems), agricultural products, and extreme environments (e.g., acid mine drainage or hydrothermal systems). In a further embodiment, microbes obtained from marine or freshwater environments such as an ocean, river, or lake. In a further embodiment, the microbes can be from the surface of the body of water, or any depth of the body of water (e.g., a deep sea sample).

The microorganisms of the disclosure may be isolated in substantially pure or mixed cultures. They may be concentrated, diluted, or provided in the natural concentrations in which they are found in the source material. For example, microorganisms from saline sediments may be isolated for use in this disclosure by suspending the sediment in fresh water and allowing the sediment to fall to the bottom. The water containing the bulk of the microorganisms may be removed by decantation after a suitable period of settling and either administered to the GI tract of beef cattle, or concentrated by filtering or centrifugation, diluted to an appropriate concentration and administered to the GI tract of beef cattle with the bulk of the salt removed. By way of further example, microorganisms from mineralized or toxic sources may be similarly treated to recover the microbes for application to beef cattle to minimize the potential for damage to the animal.

In another embodiment, the microorganisms are used in a crude form, in which they are not isolated from the source material in which they naturally reside. For example, the microorganisms are provided in combination with the source material in which they reside; for example, fecal matter, rumen content, rumen fluid, or other composition found in the gastrointestinal tract. In this embodiment, the source material may include one or more species of microorganisms.

In some embodiments, a mixed population of microorganisms is used in the methods of the disclosure.

In embodiments of the disclosure where the microorganisms are isolated from a source material (for example, the material in which they naturally reside), any one or a combination of a number of standard techniques which will be readily known to skilled persons may be used. However, by way of example, these in general employ processes by which a solid or liquid culture of a single microorganism can be obtained in a substantially pure form, usually by physical separation on the surface of a solid microbial growth medium or by volumetric dilutive isolation into a liquid microbial growth medium. These processes may include isolation from dry material, liquid suspension, slurries or homogenates in which the material is spread in a thin layer over an appropriate solid gel growth medium, or serial dilutions of the material made into a sterile medium and inoculated into liquid or solid culture media.

While not essential, in one embodiment, the material containing the microorganisms may be pre-treated prior to the isolation process in order to either multiply all microorganisms in the material, remove certain microorganisms in the material, and/or shift the distribution of microorganisms in the material. Microorganisms can then be isolated from the enriched materials as disclosed above.

In certain embodiments, as mentioned herein before, the microorganism(s) may be used in crude form and need not be isolated from an animal or a media. For example, feces, or growth media which includes the microorganisms identified to be of benefit to increased feed efficiency may be obtained and used as a crude source of microorganisms for the next round of the method or as a crude source of microorganisms at the conclusion of the method. For example, fresh feces could be obtained and optionally processed.

Microbiome Shift and Abundance of Microbes

In some embodiments, the microbiome of beef cattle, including the rumen microbiome comprises a diverse arrive of microbes with a wide variety of metabolic capabilities. The microbiome is influenced by a range of factors including diet, variations in animal metabolism, and breed, among others. Most cattle diets are plant-based and rich in complex polysaccharides that enrich the gastrointestinal microbial community for microbes capable of breaking down specific polymeric components in the diet such as cellulose, hemicellulose, lignin, etc. The end products of primary degradation sustain a chain of microbes that ultimately produce a range of organic acids together with hydrogen and carbon dioxide. Because of the complex and interlinked nature of the microbiome, changing the diet and thus substrates for primary degradation may have a cascading effect on gut microbial metabolism, with changes in both the organic acid profiles and the methane levels produced, thus impacting the quality and quantity of animal production and or the products produced by the animal. See Menezes et al. (2011. *FEMS Microbiol. Ecol.* 78(2):256-265.)

In some aspects, the present disclosure is drawn to administering microbial compositions described herein to modulate or shift the microbiome of beef cattle.

In some embodiments, the microbiome is shifted through the administration of one or more microbes to one or more sections of the gastrointestinal tract. In some embodiments, the microbiome is shifted through the administration of one or more microbes to the rumen. In further embodiments, the one or more microbes are those selected from Table 1 and/or Table 2. In some embodiments, the microbiome shift or modulation includes a decrease or loss of specific microbes that were present prior to the administration of one or more microbes of the present disclosure. In some embodiments, the microbiome shift or modulation includes an increase in microbes that were present prior to the administration of one or more microbes of the present disclosure. In some embodiments, the microbiome shift or modulation includes a gain of one or more microbes that were not present prior to the administration of one or more microbes of the present disclosure. In a further embodiment, the gain of one or more microbes is a microbe that was not specifically included in the administered microbial composition.

In some embodiments, the administration of microbes of the present disclosure results in a sustained modulation of the microbiome such that the administered microbes are present in the microbiome for a period of at least 1 to 10, 1 to 9, 1 to 8, 1 to 7, 1 to 6, 1 to 5, 1 to 4, 1 to 3, 1 to 2, 2 to 10, 2 to 9, 2 to 8, 2 to 7, 2 to 6, 2 to 5, 2 to 4, 2 to 3, 3 to 10, 3 to 9, 3 to 8, 3 to 7, 3 to 6, 3 to 5, 3 to 4, 4 to 10, 4 to 9, 4 to 8, 4 to 7, 4 to 6, 4 to 5, 5 to 10, 5 to 9, 5 to 8, 5 to 7, 5 to 6, 6 to 10, 6 to 9, 6 to 8, 6 to 7, 7 to 10, 7 to 9, 7 to 8, 8 to 10, 8 to 9, 9 to 10, 1, 2, 3, 4, 5, 6, 7, 8, 9, or 10 days.

In some embodiments, the administration of microbes of the present disclosure results in a sustained modulation of the microbiome such that the administered microbes are present in the microbiome for a period of at least 1 to 10, 1 to 9, 1 to 8, 1 to 7, 1 to 6, 1 to 5, 1 to 4, 1 to 3, 1 to 2, 2 to 10, 2 to 9, 2 to 8, 2 to 7, 2 to 6, 2 to 5, 2 to 4, 2 to 3, 3 to 10, 3 to 9, 3 to 8, 3 to 7, 3 to 6, 3 to 5, 3 to 4, 4 to 10, 4 to 9, 4 to 8, 4 to 7, 4 to 6, 4 to 5, 5 to 10, 5 to 9, 5 to 8, 5 to 7, 5 to 6, 6 to 10, 6 to 9, 6 to 8, 6 to 7, 7 to 10, 7 to 9, 7 to 8, 8 to 10, 8 to 9, 9 to 10, 1, 2, 3, 4, 5, 6, 7, 8, 9, or 10 weeks.

In some embodiments, the administration of microbes of the present disclosure results in a sustained modulation of the microbiome such that the administered microbes are present in the microbiome for a period of at least 1 to 10, 1 to 9, 1 to 8, 1 to 7, 1 to 6, 1 to 5, 1 to 4, 1 to 3, 1 to 2, 2 to 10, 2 to 9, 2 to 8, 2 to 7, 2 to 6, 2 to 5, 2 to 4, 2 to 3, 3 to 10, 3 to 9, 3 to 8, 3 to 7, 3 to 6, 3 to 5, 3 to 4, 4 to 10, 4 to 9, 4 to 8, 4 to 7, 4 to 6, 4 to 5, 5 to 10, 5 to 9, 5 to 8, 5 to 7, 5 to 6, 6 to 10, 6 to 9, 6 to 8, 6 to 7, 7 to 10, 7 to 9, 7 to 8, 8 to 10, 8 to 9, 9 to 10, 1, 2, 3, 4, 5, 6, 7, 8, 9, 10, 11, or 12 months.

In some embodiments, the presence of the administered microbes are detected by sampling the gastrointestinal tract and using primers to amplify the 16S or 18S rDNA sequences, or the ITS rDNA sequences of the administered microbes. In some embodiments, the administered microbes are one or more of those selected from Table 1 and/or Table 2. In some embodiments, the administered microbes are one or more of those comprising rDNA sequences selected from SEQ ID NO: 1-5993.

In some embodiments, the microbiome of beef cattle is measured by amplifying polynucleotides collected from gastrointestinal samples, wherein the polynucleotides may be 16S or 18S rDNA fragments, or ITS rDNA fragments of microbial rDNA. In one embodiment, the microbiome is fingerprinted by a method of denaturing gradient gel electrophoresis (DGGE) wherein the amplified rDNA fragments are sorted by where they denature, and form a unique banding pattern in a gel that may be used for comparing the microbiome of the same beef cattle over time or the microbiomes of multiple. In another embodiment, the microbiome is fingerprinted by a method of terminal restriction fragment length polymorphism (T-RFLP), wherein labelled PCR fragments are digested using a restriction enzyme and then sorted by size. In a further embodiment, the data collected from the T-RFLP method is evaluated by nonmetric multidimensional scaling (nMDS) ordination and PERMANOVA statistics identify differences in microbiomes, thus allowing for the identification and measurement of shifts in the microbiome. See also Shanks et al. (2011. *Appl. Environ. Microbiol.* 77(9):2992-3001), Petri et al. (2013. *PLOS one.* 8(12):e83424), and Menezes et al. (2011. *FEMS Microbiol. Ecol.* 78(2):256-265.)

In some embodiments, administration of one or more microbial compositions results in a shift in the microbiome that increases the number and/or type of carbon dioxide fixing microbes. In some embodiments, administration of one or more microbial composition results in a shift in the microbiome that increases the number and/or type of carbon dioxide fixing microbes by at least 0.5%, at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 200%, at least 300%, at least 400%, at least 500%, at least 600%, or at least 700%. In some embodiments, administration of one or more microbial composition results in a shift in the microbiome that increases the number and/or type of carbon dioxide fixing microbes by at least about 0.5%, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 200%, at least about 300%, at least about 400%, at least about 500%, at least about 600%, or at least about 700%.

In some embodiments, administration of one or more microbial compositions results in a shift in the microbiome that decreases the number and/or type of methanogenic microbes. In some embodiments, administration of one or more microbial composition results in a shift in the microbiome that reduces the number and/or type of methanogenic microbes by at least 0.5%, at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. In some embodiments, administration of one or more microbial composition results in a shift in the microbiome that decreases the number and/or type of methanogenic microbes by at least about 0.5%, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%.

In some embodiments, administration of one or more microbial compositions results in a shift in the microbiome that decreases the number and/or type of lactate producing microbes. In some embodiments, administration of one or more microbial composition results in a shift in the microbiome that reduces the number and/or type of lactate producing microbes by at least 0.5%, at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. In some embodiments, administration of one or more microbial composition results in a shift in the microbiome that decreases the number and/or type of lactate producing microbes by at least about 0.5%, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%.

In some embodiments, administration of one or more microbial compositions results in a shift in the microbiome that increases the number and/or type of lactate degrading microbes. In some embodiments, administration of one or more microbial composition results in a shift in the microbiome that increases the number and/or type of lactate degrading microbes by at least 0.5%, at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 200%, at least 300%, at least 400%, at least 500%, at least 600%, or at least 700%. In some embodiments, administration of one or more microbial composition results in a shift in the microbiome that increases the number and/or type of lactate degrading microbes by at least about 0.5%, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 200%, at least about 300%, at least about 400%, at least about 500%, at least about 600%, or at least about 700%.

In some embodiments, administration of one or more microbial compositions results in a shift in the microbiome that increases the number and/or type of volatile fatty acid (VFA)-producing microbes. In some embodiments, the VFAs include acetate, butyrate, propionate, isobutyrate, isovalerate, and valerate. In some embodiments, administration of one or more microbial composition results in a shift in the microbiome that increases the number and/or type of VFA-producing microbes by at least 0.5%, at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 200%, at least 300%, at least 400%, at least 500%, at least 600%, or at least 700%. In some embodiments, administration of one or more microbial composition results in a shift in the microbiome that increases the number and/or type of VFA-producing microbes by at least about 0.5%, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 200%, at least about 300%, at least about 400%, at least about 500%, at least about 600%, or at least about 700%.

In some embodiments, administration of one or more microbial compositions results in a shift in the microbiome that increases the number and/or type of microbes that are utilized as protein sources for the animal. In some embodiments, administration of one or more microbial composition results in a shift in the microbiome that increases the number and/or type of microbes that are utilized as protein sources for the animal by at least 0.5%, at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 200%, at least 300%, at least 400%, at least 500%, at least 600%, or at least 700%. In some embodiments, administration of one or more microbial composition results in a shift in the microbiome that increases the number and/or type of microbes that are utilized as protein sources for the animal by at least about 0.5%, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 200%, at least about 300%, at least about 400%, at least about 500%, at least about 600%, or at least about 700%.

In some embodiments, administration of one or more microbial compositions results in a shift in the microbiome that increases the number and/or type of vitamin synthesizing microbes. In some embodiments, administration of one or more microbial composition results in a shift in the microbiome that increases the number and/or type of vitamin synthesizing microbes by at least 0.5%, at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 200%, at least 300%, at least 400%, at least 500%, at least 600%, or at least 700%. In some embodiments, administration of one or more microbial composition results in a shift in the microbiome that increases the number and/or type of vitamin synthesizing microbes by at least about 0.5%, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 200%, at least about 300%, at least about 400%, at least about 500%, at least about 600%, or at least about 700%.

In some embodiments, administration of one or more microbial compositions results in a shift in the microbiome that reduces the overall alpha diversity of the microbial community. In some embodiments, administration of one or more microbial composition results in a shift in the microbiome that reduces the overall alpha diversity of the microbial community by at least 0.5%, at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 200%, at least 300%, at least 400%, at least 500%, at least 600%, or at least 700%. In some embodiments, administration of one or more microbial composition results in a shift in the microbiome that reduces the overall alpha diversity of the microbial community by at least about 0.5%, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 200%, at least about 300%, at least about 400%, at least about 500%, at least about 600%, or at least about 700%.

In some embodiments, the administration of microbes of the present disclosure results in a modulation or shift of the microbiome which further results in a desired phenotype or improved trait.

Cattle Microbial Compositional Diversity

Bovine in a commercial settings have been found to exhibit a high degree of animal-to-animal variability in terms of the microbial diversity of the rumen. The increased variability of the microbial compositions of the rumen may lead to a lower ability to reach a stable microbial composition. Lower variability in turn results in a considerable difference in health, weight, and other attributes that affect commercial viability of the animal. See Shabat S K B et al. (ISME J 10:2958-2972.)

In some embodiments, the administration of one or more microbes and/or bioensembles of the present disclosure during feed transition in beef cattle decreases the variability of the rumen microbiome in cattle and further establishes a stable rumen microbiome.

In some embodiments, the variability of the rumen microbiome is measured as the total number of species present in the rumen at one or more locations.

In some embodiments, the administration of one or more microbes and/or bioensembles of the present disclosure reduces the amount of time required for the rumen microbiome to reach a stabilized state.

In some embodiments, the administration of one or more microbes and/or bioensembles of the present disclosure results in beef cattle of the present disclosure reaching a stabilized state of the rumen microbiome; a reduction in the variability of the rumen microbiome.

In some embodiments, the stabilized state of the rumen microbiome is reached when the rumen microbiome of beef cattle contains about 10, about 20, about, 30, about 40, about 50, about 60, about 70, about 80, about 90, about 100, about 120, about 130, about 140, about 150, about 160, about 170, about 180, about 190, about 200, about 250, about 300, about 400, about 500, about 600, about 700, about 800, about 900, about 1,000, about 1,500, about 2,000, about 2,500, about 3,000, about 3,500, about 4,000, about 4,500, about 5,000, about 5,500, about 6,000, about 6,500, about 7,000, about 7,500, about 8,000, about 8,500, about 9,000, about 9,500, or about 10,000 different species.

In some embodiments, the stabilized state of the rumen microbiome is reached when the rumen microbiome of beef cattle contains between about 10 to about 50, about 10 to about 100, about 50 to about 100, about 50 to about 200, about 100 to about 150, about 100 to about 200, about 100 to about 400, about 200 to about 500, about 200 to about 700, about 400 to about 800, about 500 to about 1,000, about 500 to about 2,000, about 1,000 to about 2,000, about 1,000 to about 5,000, about 5,000 to about 7,000, about 5,000 to about 10,000, or about 8,000 to about 10,000 different species.

In some embodiments, at least 5%, at least 10%, at least 20%, at least 30%, at least 40%, at least 50%, at least 60%, at least 70%, at least 80%, at least 90%, or at least 95% of the beef cattle in a feed transition reach a stabilized state after administration of one or more microbes and/or bioensembles of the present disclosure.

MIC Scoring

According to the methods provided herein, a sample is processed to detect the presence of one or more microorganism types in the sample (FIG. 1, 1001; FIG. 2, 2001). The absolute number of one or more microorganism organism type in the sample is determined (FIG. 1, 1002; FIG. 2, 2002). The determination of the presence of the one or more organism types and the absolute number of at least one organism type can be conducted in parallel or serially. For example, in the case of a sample comprising a microbial community comprising bacteria (i.e., one microorganism type) and fungi (i.e., a second microorganism type), the user in one embodiment detects the presence of one or both of the organism types in the sample (FIG. 1, 1001; FIG. 2, 2001). The user, in a further embodiment, determines the absolute number of at least one organism type in the sample—in the case of this example, the number of bacteria, fungi or combination thereof, in the sample (FIG. 1, 1002; FIG. 2, 2002).

In one embodiment, the sample, or a portion thereof is subjected to flow cytometry (FC) analysis to detect the presence and/or number of one or more microorganism types (FIG. 1, 1001, 1002; FIG. 2, 2001, 2002). In one flow cytometer embodiment, individual microbial cells pass through an illumination zone, at a rate of at least about $300*s^{-1}$, or at least about $500*s^{-1}$, or at least about $1000*s^{-1}$. However, one of ordinary skill in the art will recognize that this rate can vary depending on the type of instrument is employed. Detectors which are gated electronically measure the magnitude of a pulse representing the extent of light scattered. The magnitudes of these pulses are sorted electronically into "bins" or "channels," permitting the display of histograms of the number of cells possessing a certain quantitative property (e.g., cell staining property, diameter, cell membrane) versus the channel number. Such analysis allows for the determination of the number of cells in each "bin" which in embodiments described herein is an "microorganism type" bin, e.g., a bacteria, fungi, nematode, protozoan, archaea, algae, dinoflagellate, virus, viroid, etc.

In one embodiment, a sample is stained with one or more fluorescent dyes wherein a fluorescent dye is specific to a particular microorganism type, to enable detection via a flow cytometer or some other detection and quantification method that harnesses fluorescence, such as fluorescence microscopy. The method can provide quantification of the number of cells and/or cell volume of a given organism type in a sample. In a further embodiment, as described herein, flow cytometry is harnessed to determine the presence and quantity of a unique first marker and/or unique second marker of the organism type, such as enzyme expression, cell surface protein expression, etc. Two- or three-variable histograms or contour plots of, for example, light scattering versus fluorescence from a cell membrane stain (versus fluorescence from a protein stain or DNA stain) may also be generated, and thus an impression may be gained of the distribution of a variety of properties of interest among the cells in the population as a whole. A number of displays of such multiparameter flow cytometric data are in common use and are amenable for use with the methods described herein.

In one embodiment of processing the sample to detect the presence and number of one or more microorganism types, a microscopy assay is employed (FIG. 1, 1001, 1002). In one embodiment, the microscopy is optical microscopy, where visible light and a system of lenses are used to magnify images of small samples. Digital images can be captured by a charge-couple device (CCD) camera. Other microscopic techniques include, but are not limited to, scanning electron microscopy and transmission electron microscopy. Microorganism types are visualized and quantified according to the aspects provided herein.

In another embodiment of the disclosure, in order to detect the presence and number of one or more microorganism types, each sample, or a portion thereof is subjected to fluorescence microscopy. Different fluorescent dyes can be used to directly stain cells in samples and to quantify total cell counts using an epifluorescence microscope as well as flow cytometry, described above. Useful dyes to quantify microorganisms include but are not limited to acridine orange (AO), 4,6-di-amino-2 phenylindole (DAPI) and 5-cyano-2,3 Dytolyl Tetrazolium Chloride (CTC). Viable cells can be estimated by a viability staining method such as the LIVE/DEAD® Bacterial Viability Kit (Bac-Light™) which contains two nucleic acid stains: the green-fluorescent SYTO 9™ dye penetrates all membranes and the red-fluorescent propidium iodide (PI) dye penetrates cells with damaged membranes. Therefore, cells with compromised membranes will stain red, whereas cells with undamaged membranes will stain green. Fluorescent in situ hybridization (FISH) extends epifluorescence microscopy, allowing for the fast detection and enumeration of specific organisms. FISH uses fluorescent labelled oligonucleotides probes (usually 15-25 basepairs) which bind specifically to organism DNA in the sample, allowing the visualization of the cells using an epifluorescence or confocal laser scanning microscope (CLSM). Catalyzed reporter deposition fluorescence in situ hybridization (CARD-FISH) improves upon the FISH method by using oligonucleotide probes labelled with a horse radish peroxidase (HRP) to amplify the intensity of the signal obtained from the microorganisms being studied. FISH can be combined with other techniques to characterize microorganism communities. One combined technique is high affinity peptide nucleic acid (PNA)-FISH, where the probe has an enhanced capability to penetrate through the Extracellular Polymeric Substance (EPS) matrix. Another example is LIVE/DEAD-FISH which combines the cell viability kit with FISH and has been used to assess the efficiency of disinfection in drinking water distribution systems.

In another embodiment, each sample, or a portion thereof is subjected to Raman micro-spectroscopy in order to determine the presence of a microorganism type and the absolute number of at least one microorganism type (FIG. 1, 1001-1002; FIG. 2, 2001-2002). Raman micro-spectroscopy is a non-destructive and label-free technology capable of detecting and measuring a single cell Raman spectrum (SCRS). A typical SCRS provides an intrinsic biochemical "fingerprint" of a single cell. A SCRS contains rich information of the biomolecules within it, including nucleic acids, proteins, carbohydrates and lipids, which enables characterization of different cell species, physiological changes and cell phenotypes. Raman microscopy examines the scattering of laser light by the chemical bonds of different cell biomarkers. A SCRS is a sum of the spectra of all the biomolecules in one single cell, indicating a cell's phenotypic profile. Cellular phenotypes, as a consequence of gene expression, usually reflect genotypes. Thus, under identical growth conditions, different microorganism types give distinct SCRS corresponding to differences in their genotypes and can thus be identified by their Raman spectra.

In yet another embodiment, the sample, or a portion thereof is subjected to centrifugation in order to determine the presence of a microorganism type and the number of at least one microorganism type (FIG. 1, 1001-1002; FIG. 2, 2001-2002). This process sediments a heterogeneous mixture by using the centrifugal force created by a centrifuge. More dense components of the mixture migrate away from the axis of the centrifuge, while less dense components of the mixture migrate towards the axis. Centrifugation can allow fractionation of samples into cytoplasmic, membrane and extracellular portions. It can also be used to determine localization information for biological molecules of interest. Additionally, centrifugation can be used to fractionate total microbial community DNA. Different prokaryotic groups differ in their guanine-plus-cytosine (G+C) content of DNA, so density-gradient centrifugation based on G+C content is a method to differentiate organism types and the number of cells associated with each type. The technique generates a fractionated profile of the entire community DNA and indicates abundance of DNA as a function of G+C content. The total community DNA is physically separated into highly purified fractions, each representing a different G+C content that can be analyzed by additional molecular techniques such as denaturing gradient gel electrophoresis (DGGE)/amplified ribosomal DNA restriction analysis (AR-DRA) (see discussion herein) to assess total microbial community diversity and the presence/quantity of one or more microorganism types.

In another embodiment, the sample, or a portion thereof is subjected to staining in order to determine the presence of a microorganism type and the number of at least one microorganism type (FIG. 1, 1001-1002; FIG. 2, 2001-2002). Stains and dyes can be used to visualize biological tissues, cells or organelles within cells. Staining can be used in conjunction with microscopy, flow cytometry or gel electrophoresis to visualize or mark cells or biological molecules that are unique to different microorganism types. In vivo staining is the process of dyeing living tissues, whereas in vitro staining involves dyeing cells or structures that have been removed from their biological context. Examples of specific staining techniques for use with the methods described herein include, but are not limited to: gram staining to determine gram status of bacteria, endospore staining to identify the presence of endospores, Ziehl-Neelsen staining, haematoxylin and eosin staining to examine thin sections of tissue, papanicolaou staining to examine cell samples from various bodily secretions, periodic acid-Schiff staining of carbohydrates, Masson's trichome employing a three-color staining protocol to distinguish cells from the surrounding connective tissue, Romanowsky stains (or common variants that include Wright's stain, Jenner's stain, May-Grunwald stain, Leishman stain and Giemsa stain) to examine blood or bone marrow samples, silver staining to reveal proteins and DNA, Sudan staining for lipids and Conklin's staining to detect true endospores. Common biological stains include acridine orange for cell cycle determination; bismarck brown for acid mucins; carmine for glycogen; carmine alum for nuclei; Coomassie blue for proteins; Cresyl violet for the acidic components of the neuronal cytoplasm; Crystal violet for cell walls; DAPI for nuclei; eosin for cytoplasmic material, cell membranes, some extracellular structures and red blood cells; ethidium bromide for DNA; acid fuchsine for collagen, smooth muscle or mitochondria; haematoxylin for nuclei; Hoechst stains for DNA; iodine for starch; malachite green for bacteria in the Gimenez staining technique and for spores; methyl green for chromatin; methylene blue for animal cells; neutral red for Nissl substance; Nile blue for nuclei; Nile red for lipohilic entities; osmium tetroxide for lipids; rhodamine is used in fluorescence microscopy; safranin for nuclei. Stains are also used in transmission electron microscopy to enhance contrast and include phosphotungstic acid, osmium tetroxide, ruthenium tetroxide, ammonium molybdate, cadmium iodide, carbohydrazide, ferric chloride, hexamine, indium trichloride, lanthanum nitrate, lead acetate, lead citrate, lead(II) nitrate, periodic acid, phosphomolybdic acid, potassium ferricyanide, potassium ferrocyanide, ruthenium red, silver nitrate, silver proteinate, sodium chloroaurate, thallium nitrate, thiosemicarbazide, uranyl acetate, uranyl nitrate, and vanadyl sulfate.

In another embodiment, the sample, or a portion thereof is subjected to mass spectrometry (MS) in order to determine the presence of a microorganism type and the number of at least one microorganism type (FIG. 1, 1001-1002; FIG. 2, 2001-2002). MS, as discussed below, can also be used to detect the presence and expression of one or more unique markers in a sample (FIG. 1, 1003-1004; FIG. 2, 2003-2004). MS is used for example, to detect the presence and quantity of protein and/or peptide markers unique to microorganism types and therefore to provide an assessment of the number of the respective microorganism type in the sample. Quantification can be either with stable isotope labelling or label-free. De novo sequencing of peptides can also occur directly from MS/MS spectra or sequence tagging (produce a short tag that can be matched against a database). MS can also reveal post-translational modifications of proteins and identify metabolites. MS can be used in conjunction with chromatographic and other separation techniques (such as gas chromatography, liquid chromatography, capillary electrophoresis, ion mobility) to enhance mass resolution and determination.

In another embodiment, the sample, or a portion thereof is subjected to lipid analysis in order to determine the presence of a microorganism type and the number of at least one microorganism type (FIG. 1, 1001-1002; FIG. 2, 2001-2002). Fatty acids are present in a relatively constant proportion of the cell biomass, and signature fatty acids exist in microbial cells that can differentiate microorganism types within a community. In one embodiment, fatty acids are extracted by saponification followed by derivatization to give the respective fatty acid methyl esters (FAMEs), which are then analyzed by gas chromatography. The FAME profile in one embodiment is then compared to a reference FAME database to identify the fatty acids and their corresponding microbial signatures by multivariate statistical analyses.

In the aspects of the methods provided herein, the number of unique first makers in the sample, or portion thereof (e.g., sample aliquot) is measured, as well as the abundance of each of the unique first markers (FIG. 1, 1003; FIG. 2, 2003). A unique marker is a marker of a microorganism strain. It should be understood by one of ordinary skill in the art that depending on the unique marker being probed for and measured, the entire sample need not be analyzed. For example, if the unique marker is unique to bacterial strains, then the fungal portion of the sample need not be analyzed. As described above, in some embodiments, measuring the absolute abundance of one or more organism types in a sample comprises separating the sample by organism type, e.g., via flow cytometry.

Any marker that is unique to an organism strain can be employed herein. For example, markers can include, but are not limited to, small subunit ribosomal RNA genes (16S/18S rDNA), large subunit ribosomal RNA genes (23S/25S/28S rDNA), intercalary 5.8S gene, cytochrome c oxidase, beta-tubulin, elongation factor, RNA polymerase and internal transcribed spacer (ITS).

Ribosomal RNA genes (rDNA), especially the small subunit ribosomal RNA genes, i.e., 18S rRNA genes (18S rDNA) in the case of eukaryotes and 16S rRNA (16S rDNA) in the case of prokaryotes, have been the predominant target for the assessment of organism types and strains in a microbial community. However, the large subunit ribosomal RNA genes, 28S rDNAs, have been also targeted. rDNAs are suitable for taxonomic identification because: (i) they are ubiquitous in all known organisms; (ii) they possess both conserved and variable regions; (iii) there is an exponentially expanding database of their sequences available for comparison. In community analysis of samples, the conserved regions serve as annealing sites for the corresponding universal PCR and/or sequencing primers, whereas the variable regions can be used for phylogenetic differentiation. In addition, the high copy number of rDNA in the cells facilitates detection from environmental samples.

The internal transcribed spacer (ITS), located between the 18S rDNA and 28S rDNA, has also been targeted. The ITS is transcribed but spliced away before assembly of the ribosomes. The ITS region is composed of two highly variable spacers, ITS1 and ITS2, and the intercalary 5.8S gene. This rDNA operon occurs in multiple copies in genomes. Because the ITS region does not code for ribosome components, it is highly variable.

In one embodiment, the unique RNA marker can be an mRNA marker, an siRNA marker or a ribosomal RNA marker.

Protein-coding functional genes can also be used herein as a unique first marker. Such markers include but are not limited to: the recombinase A gene family (bacterial RecA, archaea RadA and RadB, eukaryotic Rad51 and Rad57, phage UvsX); RNA polymerase β subunit (RpoB) gene, which is responsible for transcription initiation and elongation; chaperonins. Candidate marker genes have also been identified for bacteria plus archaea: ribosomal protein S2 (rpsB), ribosomal protein S10 (rpsJ), ribosomal protein L1 (rplA), translation elongation factor EF-2, translation initiation factor IF-2, metalloendopeptidase, ribosomal protein L22, ffh signal recognition particle protein, ribosomal protein L4/L1e (rp1D), ribosomal protein L2 (rp1B), ribosomal protein S9 (rpsl), ribosomal protein L3 (rp1C), phenylalanyl-tRNA synthetase beta subunit, ribosomal protein L14b/L23e (rp1N), ribosomal protein S5, ribosomal protein S19 (rpsS), ribosomal protein S7, ribosomal protein L16/L10E (rp1P), ribosomal protein S13 (rpsM), phenylalanyl-tRNA synthetase α subunit, ribosomal protein L15, ribosomal protein L25/L23, ribosomal protein L6 (rp1F), ribosomal protein L11 (rp1K), ribosomal protein L5 (rp1E), ribosomal protein S12/S23, ribosomal protein L29, ribosomal protein S3 (rpsC), ribosomal protein S 11 (rpsK), ribosomal protein L10, ribosomal protein S8, tRNA pseudouridine synthase B, ribosomal protein L18P/L5E, ribosomal protein S15P/S13e, Porphobilinogen deaminase, ribosomal protein S17, ribosomal protein L13 (rp1M), phosphoribosylformylglycinamidine cyclo-ligase (rpsE), ribonuclease HII and ribosomal protein L24. Other candidate marker genes for bacteria include: transcription elongation protein NusA (nusA), rpoB DNA-directed RNA polymerase subunit beta (rpoB), GTP-binding protein EngA, rpoC DNA-directed RNA polymerase subunit beta', priA primosome assembly protein, transcription-repair coupling factor, CTP synthase (pyrG), secY preprotein translocase subunit SecY, GTP-binding protein Obg/CgtA, DNA polymerase I, rpsF 30S ribosomal protein S6, poA DNA-directed RNA polymerase subunit alpha, peptide chain release factor 1, rpII 50S ribosomal protein L9, polyribonucleotide nucleotidyltransferase, tsf elongation factor Ts (tsf), rplQ 50S ribosomal protein L17, tRNA (guanine-N(1)-)-methyltransferase (rp1S), rplY probable 50S ribosomal protein L25, DNA repair protein RadA, glucose-inhibited division protein A, ribosome-binding factor A, DNA mismatch repair protein MutL, smpB SsrA-binding protein (smpB), N-acetylglucosaminyl transferase, S-adenosyl-methyltransferase MraW, UDP-N-acetylmuramoylalanine-D-glutamate ligase, rplS 50S ribosomal protein L19, rp1T 50S ribosomal protein L20 (rp1T), ruvA Holliday junction DNA helicase, ruvB Holliday junction DNA helicase B, serS seryl-tRNA synthetase, rplU 50S ribosomal protein L21, rpsR 30S ribosomal protein S18, DNA mismatch repair protein MutS, rpsT 30S ribosomal protein S20, DNA repair protein RecN, frr ribosome recycling factor (frr), recombination protein RecR, protein of unknown function UPF0054, miaA tRNA isopentenyltransferase, GTP-binding protein YchF, chromosomal replication initiator protein DnaA, dephospho-CoA kinase, 16S rRNA processing protein RimM, ATP-cone domain protein, 1-deoxy-D-xylulose 5-phosphate reductoisomerase, 2C-methyl-D-erythritol 2,4-cyclodiphosphate synthase, fatty acid/phospholipid synthesis protein PlsX, tRNA(Ile)-lysidine synthetase, dnaG DNA primase (dnaG), ruvC Holliday junction resolvase, rpsP 30S ribosomal protein S16, Recombinase A recA, riboflavin biosynthesis protein RibF, glycyl-tRNA synthetase beta subunit, trmU tRNA (5-methylaminomethyl-2-thiouridylate)-methyltransferase, rpmI 50S ribosomal protein L35, hemE uroporphyrinogen decarboxylase, Rod shape-determining protein, rpmA 50S ribosomal protein L27 (rpmA), peptidyl-tRNA hydrolase, translation initiation factor IF-3 (infC), UDP-N-acetylmuramyl-tripeptide synthetase, rpmF 50S ribosomal protein L32, rplL 50S ribosomal protein L7/L12 (rpIL), leuS leucyl-tRNA synthetase, ligA NAD-dependent DNA ligase, cell division protein FtsA, GTP-binding protein TypA, ATP-dependent Clp protease, ATP-binding subunit ClpX, DNA replication and repair protein RecF and UDP-N-acetylenolpyruvoylglucosamine reductase.

Phospholipid fatty acids (PLFAs) may also be used as unique first markers according to the methods described herein. Because PLFAs are rapidly synthesized during microbial growth, are not found in storage molecules and degrade rapidly during cell death, it provides an accurate census of the current living community. All cells contain fatty acids (FAs) that can be extracted and esterified to form fatty acid methyl esters (FAMEs). When the FAMEs are analyzed using gas chromatography—mass spectrometry, the resulting profile constitutes a 'fingerprint' of the microorganisms in the sample. The chemical compositions of membranes for organisms in the domains Bacteria and Eukarya are comprised of fatty acids linked to the glycerol by an ester-type bond (phospholipid fatty acids (PLFAs)). In contrast, the membrane lipids of Archaea are composed of long and branched hydrocarbons that are joined to glycerol by an ether-type bond (phospholipid ether lipids (PLELs)). This is one of the most widely used non-genetic criteria to distinguish the three domains. In this context, the phospholipids derived from microbial cell membranes, characterized by different acyl chains, are excellent signature molecules, because such lipid structural diversity can be linked to specific microbial taxa.

As provided herein, in order to determine whether an organism strain is active, the level of expression of one or more unique second markers, which can be the same or different as the first marker, is measured (FIG. 1, 1004; FIG. 2, 2004). Unique first markers are described above. The unique second marker is a marker of microorganism activity. For example, in one embodiment, the mRNA or protein expression of any of the first markers described above is considered a unique second marker for the purposes of this disclosure.

In one embodiment, if the level of expression of the second marker is above a threshold level (e.g., a control level) or at a threshold level, the microorganism is considered to be active (FIG. 1, 1005; FIG. 2, 2005). Activity is determined in one embodiment, if the level of expression of the second marker is altered by at least about 5%, at least about 10%, at least about 15%, at least about 20%, at least about 25%, or at least about 30%, as compared to a threshold level, which in some embodiments, is a control level.

Second unique markers are measured, in one embodiment, at the protein, RNA or metabolite level. A unique second marker is the same or different as the first unique marker.

As provided above, a number of unique first markers and unique second markers can be detected according to the methods described herein. Moreover, the detection and quantification of a unique first marker is carried out according to methods known to those of ordinary skill in the art (FIG. 1, 1003-1004, FIG. 2, 2003-2004).

Nucleic acid sequencing (e.g., gDNA, cDNA, rRNA, mRNA) in one embodiment is used to determine absolute cell count of a unique first marker and/or unique second marker. Sequencing platforms include, but are not limited to, Sanger sequencing and high-throughput sequencing methods available from Roche/454 Life Sciences, Illumina/Solexa, Pacific Biosciences, Ion Torrent and Nanopore. The sequencing can be amplicon sequencing of particular DNA or RNA sequences or whole metagenome/transcriptome shotgun sequencing.

Traditional Sanger sequencing (Sanger et al. (1977) DNA sequencing with chain-terminating inhibitors. Proc Natl. Acad. Sci. USA, 74, pp. 5463-5467, incorporated by reference herein in its entirety) relies on the selective incorporation of chain-terminating dideoxynucleotides by DNA polymerase during in vitro DNA replication and is amenable for use with the methods described herein.

In another embodiment, the sample, or a portion thereof is subjected to extraction of nucleic acids, amplification of DNA of interest (such as the rRNA gene) with suitable primers and the construction of clone libraries using sequencing vectors. Selected clones are then sequenced by Sanger sequencing and the nucleotide sequence of the DNA of interest is retrieved, allowing calculation of the number of unique microorganism strains in a sample.

454 pyrosequencing from Roche/454 Life Sciences yields long reads and can be harnessed in the methods described herein (Margulies et al. (2005) Nature, 437, pp. 376-380; U.S. Pat. Nos. 6,274,320; 6,258,568; 6,210,891, each of which is herein incorporated in its entirety for all purposes). Nucleic acid to be sequenced (e.g., amplicons or nebulized genomic/metagenomic DNA) have specific adapters affixed on either end by PCR or by ligation. The DNA with adapters is fixed to tiny beads (ideally, one bead will have one DNA fragment) that are suspended in a water-in-oil emulsion. An emulsion PCR step is then performed to make multiple copies of each DNA fragment, resulting in a set of beads in which each bead contains many cloned copies of the same DNA fragment. Each bead is then placed into a well of a fiber-optic chip that also contains enzymes necessary for the sequencing-by-synthesis reactions. The addition of bases (such as A, C, G, or T) trigger pyrophosphate release, which produces flashes of light that are recorded to infer the sequence of the DNA fragments in each well. About 1 million reads per run with reads up to 1,000 bases in length can be achieved. Paired-end sequencing can be done, which produces pairs of reads, each of which begins at one end of a given DNA fragment. A molecular barcode can be created and placed between the adapter sequence and the sequence of interest in multiplex reactions, allowing each sequence to be assigned to a sample bioinformatically.

Illumina/Solexa sequencing produces average read lengths of about 25 basepairs (bp) to about 300 bp (Bennett et al. (2005) Pharmacogenomics, 6:373-382; Lange et al. (2014). BMC Genomics 15, p. 63; Fadrosh et al. (2014) Microbiome 2, p. 6; Caporaso et al. (2012) ISME J, 6, p. 1621-1624; Bentley et al. (2008) Accurate whole human genome sequencing using reversible terminator chemistry. Nature, 456:53-59). This sequencing technology is also sequencing-by-synthesis but employs reversible dye terminators and a flow cell with a field of oligos attached. DNA fragments to be sequenced have specific adapters on either end and are washed over a flow cell filled with specific oligonucleotides that hybridize to the ends of the fragments. Each fragment is then replicated to make a cluster of identical fragments. Reversible dye-terminator nucleotides are then washed over the flow cell and given time to attach. The excess nucleotides are washed away, the flow cell is imaged, and the reversible terminators can be removed so that the process can repeat and nucleotides can continue to be added in subsequent cycles. Paired-end reads that are 300 bases in length each can be achieved. An Illumina platform can produce 4 billion fragments in a paired-end fashion with 125 bases for each read in a single run. Barcodes can also be used for sample multiplexing, but indexing primers are used.

The SOLiD (Sequencing by Oligonucleotide Ligation and Detection, Life Technologies) process is a "sequencing-by-ligation" approach, and can be used with the methods described herein for detecting the presence and abundance of a first marker and/or a second marker (FIG. 1, 1003-1004; FIG. 2, 2003-2004) (Peckham et al. SOLiD™ Sequencing and 2-Base Encoding. San Diego, CA: American Society of Human Genetics, 2007; Mitra et al. (2013) Analysis of the intestinal microbiota using SOLiD 16S rRNA gene sequencing and SOLiD shotgun sequencing. BMC Genomics, 14(Suppl 5): S16; Mardis (2008) Next-generation DNA sequencing methods. Annu Rev Genomics Hum Genet, 9:387-402; each incorporated by reference herein in its entirety). A library of DNA fragments is prepared from the sample to be sequenced, and are used to prepare clonal bead populations, where only one species of fragment will be present on the surface of each magnetic bead. The fragments attached to the magnetic beads will have a universal P1 adapter sequence so that the starting sequence of every fragment is both known and identical. Primers hybridize to the P1 adapter sequence within the library template. A set of four fluorescently labelled di-base probes compete for ligation to the sequencing primer. Specificity of the di-base probe is achieved by interrogating every 1st and 2nd base in each ligation reaction. Multiple cycles of ligation, detection and cleavage are performed with the number of cycles determining the eventual read length. The SOLiD platform can produce up to 3 billion reads per run with reads that are 75 bases long. Paired-end sequencing is available and can be used herein, but with the second read in the pair being only 35 bases long. Multiplexing of samples is possible through a system akin to the one used by Illumina, with a separate indexing run.

The Ion Torrent system, like 454 sequencing, is amenable for use with the methods described herein for detecting the presence and abundance of a first marker and/or a second marker (FIG. 1, 1003-1004; FIG. 2, 2003-2004). It uses a plate of microwells containing beads to which DNA fragments are attached. It differs from all of the other systems, however, in the manner in which base incorporation is detected. When a base is added to a growing DNA strand, a proton is released, which slightly alters the surrounding pH. Microdetectors sensitive to pH are associated with the wells on the plate, and they record when these changes occur. The different bases (A, C, G, T) are washed sequentially through the wells, allowing the sequence from each well to be inferred. The Ion Proton platform can produce up to 50 million reads per run that have read lengths of 200 bases. The Personal Genome Machine platform has longer reads at 400 bases. Bidirectional sequencing is available. Multiplexing is possible through the standard in-line molecular barcode sequencing.

Pacific Biosciences (PacBio) SMRT sequencing uses a single-molecule, real-time sequencing approach and in one embodiment, is used with the methods described herein for detecting the presence and abundance of a first marker and/or a second marker (FIG. 1, 1003-1004; FIG. 2, 2003-2004). The PacBio sequencing system involves no amplification step, setting it apart from the other major next-generation sequencing systems. In one embodiment, the sequencing is performed on a chip containing many zero-mode waveguide (ZMW) detectors. DNA polymerases are attached to the ZMW detectors and phospholinked dye-labeled nucleotide incorporation is imaged in real time as DNA strands are synthesized. The PacBio system yields very long read lengths (averaging around 4,600 bases) and a very high number of reads per run (about 47,000). The typical "paired-end" approach is not used with PacBio, since reads are typically long enough that fragments, through CCS, can be covered multiple times without having to sequence from each end independently. Multiplexing with PacBio does not involve an independent read, but rather follows the standard "in-line" barcoding model.

In one embodiment, where the first unique marker is the ITS genomic region, automated ribosomal intergenic spacer analysis (ARISA) is used in one embodiment to determine the number and identity of microorganism strains in a sample (FIG. 1, 1003, FIG. 2, 2003) (Ranjard et al. (2003). Environmental Microbiology 5, pp. 1111-1120, incorporated by reference in its entirety for all purposes). The ITS region has significant heterogeneity in both length and nucleotide sequence. The use of a fluorescence-labeled forward primer and an automatic DNA sequencer permits high resolution of separation and high throughput. The inclusion of an internal standard in each sample provides accuracy in sizing general fragments.

In another embodiment, fragment length polymorphism (RFLP) of PCR-amplified rDNA fragments, otherwise known as amplified ribosomal DNA restriction analysis (ARDRA), is used to characterize unique first markers and the abundance of the same in samples (FIG. 1, 1003, FIG. 2, 2003) (for additional detail, see Massol-Deya et al. (1995). Mol. Microb. Ecol. Manual. 3.3.2, pp. 1-18, the entirety of which is herein incorporated by reference for all purposes). rDNA fragments are generated by PCR using general primers, digested with restriction enzymes, electrophoresed in agarose or acrylamide gels, and stained with ethidium bromide or silver nitrate.

One fingerprinting technique used in detecting the presence and abundance of a unique first marker is single-stranded-conformation polymorphism (SSCP) (see Lee et al. (1996). Appl Environ Microbiol 62, pp. 3112-3120; Scheinert et al. (1996). J. Microbiol. Methods 26, pp. 103-117; Schwieger and Tebbe (1998). Appl. Environ. Microbiol. 64, pp. 4870-4876, each of which is incorporated by reference herein in its entirety). In this technique, DNA fragments such as PCR products obtained with primers specific for the 16S rRNA gene, are denatured and directly electrophoresed on a non-denaturing gel. Separation is based on differences in size and in the folded conformation of single-stranded DNA, which influences the electrophoretic mobility. Reannealing of DNA strands during electrophoresis can be prevented by a number of strategies, including the use of one phosphorylated primer in the PCR followed by specific digestion of the phosphorylated strands with lambda exonuclease and the use of one biotinylated primer to perform magnetic separation of one single strand after denaturation. To assess the identity of the predominant populations in a given microbial composition, in one embodiment, bands are excised and sequenced, or SSCP-patterns can be hybridized with specific probes. Electrophoretic conditions, such as gel matrix, temperature, and addition of glycerol to the gel, can influence the separation.

In addition to sequencing based methods, other methods for quantifying expression (e.g., gene, protein expression) of a second marker are amenable for use with the methods provided herein for determining the level of expression of one or more second markers (FIG. 1, 1004; FIG. 2, 2004). For example, quantitative RT-PCR, microarray analysis, linear amplification techniques such as nucleic acid sequence based amplification (NASBA) are all amenable for use with the methods described herein, and can be carried out according to methods known to those of ordinary skill in the art.

In another embodiment, the sample, or a portion thereof is subjected to a quantitative polymerase chain reaction (PCR) for detecting the presence and abundance of a first marker and/or a second marker (FIG. 1, 1003-1004; FIG. 2, 2003-2004). Specific microorganism strains activity is measured by reverse transcription of transcribed ribosomal and/or messenger RNA (rRNA and mRNA) into complementary DNA (cDNA), followed by PCR (RT-PCR).

In another embodiment, the sample, or a portion thereof is subjected to PCR-based fingerprinting techniques to detect the presence and abundance of a first marker and/or a second marker (FIG. 1, 1003-1004; FIG. 2, 2003-2004). PCR products can be separated by electrophoresis based on the nucleotide composition. Sequence variation among the different DNA molecules influences the melting behavior, and therefore molecules with different sequences will stop migrating at different positions in the gel. Thus electrophoretic profiles can be defined by the position and the relative intensity of different bands or peaks and can be translated to numerical data for calculation of diversity indices. Bands can also be excised from the gel and subsequently sequenced to reveal the phylogenetic affiliation of the community members. Electrophoresis methods can include, but are not limited to: denaturing gradient gel electrophoresis (DGGE), temperature gradient gel electrophoresis (TGGE), single-stranded-conformation polymorphism (SSCP), restriction fragment length polymorphism analysis (RFLP) or amplified ribosomal DNA restriction analysis (ARDRA), terminal restriction fragment length polymorphism analysis (T-RFLP), automated ribosomal intergenic spacer analysis (ARISA), randomly amplified polymorphic DNA (RAPD), DNA amplification fingerprinting (DAF) and Bb-PEG electrophoresis.

In another embodiment, the sample, or a portion thereof is subjected to a chip-based platform such as microarray or microfluidics to determine the abundance of a unique first marker and/or presence/abundance of a unique second marker (FIG. 1, 1003-1004, FIG. 2, 2003-2004). The PCR products are amplified from total DNA in the sample and directly hybridized to known molecular probes affixed to microarrays. After the fluorescently labeled PCR amplicons are hybridized to the probes, positive signals are scored by the use of confocal laser scanning microscopy. The microarray technique allows samples to be rapidly evaluated with replication, which is a significant advantage in microbial community analyses. In general the hybridization signal intensity on microarrays can be directly proportional to the abundance of the target organism. The universal high-density 16S microarray (e.g., PHYLOCHIP) contains about 30,000 probes of 16SrRNA gene targeted to several cultured microbial species and "candidate divisions". These probes target all 121 demarcated prokaryotic orders and allow simultaneous detection of 8,741 bacterial and archaeal taxa. Another microarray in use for profiling microbial communities is the Functional Gene Array (FGA). Unlike PHYLOCHIPs, FGAs are designed primarily to detect specific metabolic groups of bacteria. Thus, FGA not only reveal the community structure, but they also shed light on the in situ community metabolic potential. FGA contain probes from genes with known biological functions, so they are useful in linking microbial community composition to ecosystem functions. An FGA termed GEOCHIP contains >24,000 probes from all known metabolic genes involved in various biogeochemical, ecological, and environmental processes such as ammonia oxidation, methane oxidation, and nitrogen fixation.

A protein expression assay, in one embodiment, is used with the methods described herein for determining the level of expression of one or more second markers (FIG. 1, 1004; FIG. 2, 2004). For example, in one embodiment, mass spectrometry or an immunoassay such as an enzyme-linked immunosorbant assay (ELISA) is utilized to quantify the level of expression of one or more unique second markers, wherein the one or more unique second markers is a protein.

In one embodiment, the sample, or a portion thereof is subjected to Bromodeoxyuridine (BrdU) incorporation to determine the level of a second unique marker (FIG. 1, 1004; FIG. 2, 2004). BrdU, a synthetic nucleoside analog of thymidine, can be incorporated into newly synthesized DNA of replicating cells. Antibodies specific for BRdU can then be used for detection of the base analog. Thus BrdU incorporation identifies cells that are actively replicating their DNA, a measure of activity of a microorganism according to one embodiment of the methods described herein. BrdU incorporation can be used in combination with FISH to provide the identity and activity of targeted cells.

In one embodiment, the sample, or a portion thereof is subjected to microautoradiography (MAR) combined with FISH to determine the level of a second unique marker (FIG. 1, 1004; FIG. 2, 2004). MAR-FISH is based on the incorporation of radioactive substrate into cells, detection of the active cells using autoradiography and identification of the cells using FISH. The detection and identification of active cells at single-cell resolution is performed with a microscope. MAR-FISH provides information on total cells, probe targeted cells and the percentage of cells that incorporate a given radiolabelled substance. The method provides an assessment of the in situ function of targeted microorganisms and is an effective approach to study the in vivo physiology of microorganisms. A technique developed for quantification of cell-specific substrate uptake in combination with MAR-FISH is known as quantitative MAR (QMAR).

In one embodiment, the sample, or a portion thereof is subjected to stable isotope Raman spectroscopy combined with FISH (Raman-FISH) to determine the level of a second unique marker (FIG. 1, 1004; FIG. 2, 2004). This technique combines stable isotope probing, Raman spectroscopy and FISH to link metabolic processes with particular organisms. The proportion of stable isotope incorporation by cells affects the light scatter, resulting in measurable peak shifts for labelled cellular components, including protein and mRNA components. Raman spectroscopy can be used to identify whether a cell synthesizes compounds including, but not limited to: oil (such as alkanes), lipids (such as triacylglycerols (TAG)), specific proteins (such as heme proteins, metalloproteins), cytochrome (such as P450, cytochrome c), chlorophyll, chromophores (such as pigments for light harvesting carotenoids and rhodopsins), organic polymers (such as polyhydroxyalkanoates (PHA), polyhydroxybutyrate (PHB)), hopanoids, steroids, starch, sulfide, sulfate and secondary metabolites (such as vitamin B12).

In one embodiment, the sample, or a portion thereof is subjected to DNA/RNA stable isotope probing (SIP) to determine the level of a second unique marker (FIG. 1, 1004; FIG. 2, 2004). SIP enables determination of the microbial diversity associated with specific metabolic pathways and has been generally applied to study microorganisms involved in the utilization of carbon and nitrogen compounds. The substrate of interest is labelled with stable isotopes (such as $^{13}C$ or $^{15}N$) and added to the sample. Only microorganisms able to metabolize the substrate will incorporate it into their cells. Subsequently, $^{13}C$-DNA and $^{15}N$-DNA can be isolated by density gradient centrifugation and used for metagenomic analysis. RNA-based SIP can be a responsive biomarker for use in SIP studies, since RNA itself is a reflection of cellular activity.

In one embodiment, the sample, or a portion thereof is subjected to isotope array to determine the level of a second unique marker (FIG. 1, 1004; FIG. 2, 2004). Isotope arrays allow for functional and phylogenetic screening of active microbial communities in a high-throughput fashion. The technique uses a combination of SIP for monitoring the substrate uptake profiles and microarray technology for determining the taxonomic identities of active microbial communities. Samples are incubated with a $^{14}C$-labeled substrate, which during the course of growth becomes incorporated into microbial biomass. The $^{14}C$-labeled rRNA is separated from unlabeled rRNA and then labeled with fluorochromes. Fluorescent labeled rRNA is hybridized to a phylogenetic microarray followed by scanning for radioactive and fluorescent signals. The technique thus allows simultaneous study of microbial community composition and specific substrate consumption by metabolically active microorganisms of complex microbial communities.

In one embodiment, the sample, or a portion thereof is subjected to a metabolomics assay to determine the level of a second unique marker (FIG. 1, 1004; FIG. 2, 2004). Metabolomics studies the metabolome which represents the collection of all metabolites, the end products of cellular processes, in a biological cell, tissue, organ or organism. This methodology can be used to monitor the presence of microorganisms and/or microbial mediated processes since it allows associating specific metabolite profiles with different microorganisms. Profiles of intracellular and extracellular metabolites associated with microbial activity can be obtained using techniques such as gas chromatography-mass spectrometry (GC-MS). The complex mixture of a metabolomic sample can be separated by such techniques as gas chromatography, high performance liquid chromatography and capillary electrophoresis. Detection of metabolites can be by mass spectrometry, nuclear magnetic resonance (NMR) spectroscopy, ion-mobility spectrometry, electrochemical detection (coupled to HPLC) and radiolabel (when combined with thin-layer chromatography).

According to the embodiments described herein, the presence and respective number of one or more active microorganism strains in a sample are determined (FIG. 1, 1006; FIG. 2, 2006). For example, strain identity information obtained from assaying the number and presence of first markers is analyzed to determine how many occurrences of a unique first marker are present, thereby representing a unique microorganism strain (e.g., by counting the number of sequence reads in a sequencing assay). This value can be represented in one embodiment as a percentage of total sequence reads of the first maker to give a percentage of unique microorganism strains of a particular microorganism type. In a further embodiment, this percentage is multiplied by the number of microorganism types (obtained at step 1002 or 2002, see FIG. 1 and FIG. 2) to give the absolute abundance of the one or more microorganism strains in a sample and a given volume.

The one or more microorganism strains are considered active, as described above, if the level of second unique marker expression is at a threshold level, higher than a threshold value, e.g., higher than at least about 5%, at least about 10%, at least about 20% or at least about 30% over a control level.

In another aspect of the disclosure, a method for determining the absolute abundance of one or more microorganism strains is determined in a plurality of samples (FIG. 2, see in particular, 2007). For a microorganism strain to be classified as active, it need only be active in one of the samples. The samples can be taken over multiple time points from the same source, or can be from different environmental sources (e.g., different animals).

The absolute abundance values over samples are used in one embodiment to relate the one or more active microorganism strains, with an environmental parameter (FIG. 2, 2008). In one embodiment, the environmental parameter is the presence of a second active microorganism strain. Relating the one or more active microorganism strains to the environmental parameter, in one embodiment, is carried out by determining the co-occurrence of the strain and parameter by correlation or by network analysis.

In one embodiment, determining the co-occurrence of one or more active microorganism strains with an environmental parameter comprises a network and/or cluster analysis method to measure connectivity of strains or a strain with an environmental parameter within a network, wherein the network is a collection of two or more samples that share a common or similar environmental parameter. In another embodiment, the network and/or cluster analysis method may be applied to determining the co-occurrence of two or more active microorganism strains in a sample (FIG. 2, 2008). In another embodiment, the network analysis comprises nonparametric approaches including mutual information to establish connectivity between variables. In another embodiment, the network analysis comprises linkage analysis, modularity analysis, robustness measures, betweenness measures, connectivity measures, transitivity measures, centrality measures or a combination thereof (FIG. 2, 2009). In another embodiment, the cluster analysis method comprises building a connectivity model, subspace model, distribution model, density model, or a centroid model and/or using community detection algorithms such as the Louvain, Bron-Kerbosch, Girvan-Newman, Clauset-Newman-Moore, Pons-Latapy, and Wakita-Tsurumi algorithms (FIG. 2, 2010).

In one embodiment, the cluster analysis method is a heuristic method based on modularity optimization. In a further embodiment, the cluster analysis method is the Louvain method (See, e.g., the method described by Blondel et al. (2008) Fast unfolding of communities in large networks. Journal of Statistical Mechanics: Theory and Experiment, Volume 2008, October 2008, incorporated by reference herein in its entirety for all purposes).

In another embodiment, the network analysis comprises predictive modeling of network through link mining and prediction, collective classification, link-based clustering, relational similarity, or a combination thereof. In another embodiment, the network analysis comprises differential equation based modeling of populations. In another embodiment, the network analysis comprises Lotka-Volterra modeling.

In one embodiment, relating the one or more active microorganism strains to an environmental parameter (e.g., determining the co-occurrence) in the sample comprises creating matrices populated with linkages denoting environmental parameter and microorganism strain associations.

In one embodiment, the multiple sample data obtained at step 2007 (e.g., over two or more samples which can be collected at two or more time points where each time point corresponds to an individual sample) is compiled. In a further embodiment, the number of cells of each of the one or more microorganism strains in each sample is stored in an association matrix (which can be in some embodiments, an abundance matrix). In one embodiment, the association matrix is used to identify associations between active microorganism strains in a specific time point sample using rule mining approaches weighted with association (e.g., abundance) data. Filters are applied in one embodiment to remove insignificant rules.

In one embodiment, the absolute abundance of one or more, or two or more active microorganism strains is related to one or more environmental parameters (FIG. 2, 2008), e.g., via co-occurrence determination. Environmental parameters are chosen by the user depending on the sample (s) to be analyzed and are not restricted by the methods described herein. The environmental parameter can be a parameter of the sample itself, e.g., pH, temperature, amount of protein in the sample. Alternatively, the environmental parameter is a parameter that affects a change in the identity of a microbial community (i.e., where the "identity" of a microbial community is characterized by the type of microorganism strains and/or number of particular microorganism strains in a community), or is affected by a change in the identity of a microbial community. For example, an environmental parameter in one embodiment, is the food intake of an animal. In one embodiment, the environmental parameter is the presence, activity and/or abundance of a second microorganism strain in the microbial community, present in the same sample.

In some embodiments described herein, an environmental parameter is referred to as a metadata parameter.

Other examples of metadata parameters include but are not limited to genetic information from the host from which the sample was obtained (e.g., DNA mutation information), sample pH, sample temperature, expression of a particular protein or mRNA, nutrient conditions (e.g., level and/or identity of one or more nutrients) of the surrounding environment/ecosystem), susceptibility or resistance to disease, onset or progression of disease, susceptibility or resistance of the sample to toxins, efficacy of xenobiotic compounds (pharmaceutical drugs), biosynthesis of natural products, or a combination thereof.

For example, according to one embodiment, microorganism strain number changes are calculated over multiple samples according to the method of FIG. 2 (i.e., at 2001-2007). Strain number changes of one or more active strains over time is compiled (e.g., one or more strains that have initially been identified as active according to step 2006), and the directionality of change is noted (i.e., negative values denoting decreases, positive values denoting increases). The number of cells over time is represented as a network, with microorganism strains representing nodes and the abundance weighted rules representing edges. Markov chains and random walks are leveraged to determine connectivity between nodes and to define clusters. Clusters in one embodiment are filtered using metadata in order to identify clusters associated with desirable metadata (FIG. 2, 2008).

In a further embodiment, microorganism strains are ranked according to importance by integrating cell number changes over time and strains present in target clusters, with the highest changes in cell number ranking the highest.

Network Analysis

Network and/or cluster analysis method in one embodiment, is used to measure connectivity of the one or more strains within a network, wherein the network is a collection of two or more samples that share a common or similar environmental parameter. In one embodiment, network analysis comprises linkage analysis, modularity analysis, robustness measures, betweenness measures, connectivity measures, transitivity measures, centrality measures or a combination thereof. In another embodiment, network analysis comprises predictive modeling of network through link mining and prediction, social network theory, collective classification, link-based clustering, relational similarity, or a combination thereof. In another embodiment, network analysis comprises differential equation based modeling of populations. In yet another embodiment, network analysis comprises Lotka-Volterra modeling.

Cluster analysis method comprises building a connectivity model, subspace model, distribution model, density model, or a centroid model.

Network and cluster based analysis, for example, to carry out method step 2008 of FIG. 2, can be carried out via a module. As used herein, a component and/or module can be, for example, any assembly, instructions and/or set of operatively-coupled electrical components, and can include, for example, a memory, a processor, electrical traces, optical connectors, software (executing in hardware) and/or the like.

Cattle Pathogen Resistance and Clearance

In some aspects, the present disclosure is drawn to administering one or more microbial compositions described herein to beef cattle to clear the gastrointestinal tract of pathogenic microbes. In some embodiments, the present disclosure is further drawn to administering microbial compositions described herein to prevent colonization of pathogenic microbes in the gastrointestinal tract. In some embodiments, the administration of microbial compositions described herein further clear pathogens from the integument and the respiratory tract of beef cattle, and/or prevent colonization of pathogens on the integument and in the respiratory tract. In some embodiments, the administration of microbial compositions described herein reduce leaky gut/intestinal permeability, levels of histamine, production of lipopolysaccharides (LPS), inflammation, ketosis, laminitis, respiratory and metabolic acidosis, rumen acidosis, bloat, abomasal dysplasia, liver abscesses, and/or incidence of liver disease.

In some embodiments, the microbial compositions of the present disclosure comprise one or more microbes that are present in the gastrointestinal tract of beef cattle at a relative abundance of less than 15%, 14%, 13%, 12%, 11%, 10%, 9%, 8%, 7%, 6%, 5%, 4%, 3%, 2%, 1%, 0.5%, 0.1%, or 0.01%.

In some embodiments, after administration of microbial compositions of the present disclosure the one or more microbes are present in the gastrointestinal tract of the beef cattle at a relative abundance of at least 0.5%, 1%, 5%, 10%, 15%, 20%, 25%, 30%, 35%, 40%, 45%, 50%, 55%, 60%, 65%, 70%, 75%, 80%, 85%, 90%, or 95%.

Pathogenic microbes of beef cattle include the following: *Clostridium perfringens*, *Clostridium botulinum*, *Salmonella typi*, *Salmonella typhimurium*, *Salmonella enterica*, *Salmonella pullorum*, *Erysipelothrix insidiosa*, *Campylobacter jejuni*, *Campylobacter coli*, *Campylobacter lari*, *Listeria monocytogenes*, *Streptococcus agalactiae*, *Streptococcus dysgalactiae*, *Corynebacterium bovis*, *Mycoplasma* sp., *Citrobacter* sp., *Enterobacter* sp., *Pseudomonas aeruginosa*, *Pasteurella* sp., *Bacillus cereus*, *Bacillus licheniformis*, *Streptococcus uberis*, *Staphylococcus aureus*, and pathogenic strains of enteropathogenic, enteroinvasive, or enterohemorrhagic *Escherichia coli*, *Staphylococcus aureus*, *Pasteurella multocida*, *Mannheimia haemolytica*, *Histophilus somni*, *Mycoplasma bovis*, and *Aspergillus* sp.

In some embodiments, the pathogenic microbes include viral pathogens. In some embodiments, the pathogenic microbes are pathogenic to both beef cattle and humans. In some embodiments, the pathogenic microbes are pathogenic to either beef cattle or humans.

In some embodiments, the administration of compositions of the present disclosure to beef cattle modulate the makeup of the gastrointestinal microbiome such that the administered microbes outcompete microbial pathogens present in the gastrointestinal tract. In some embodiments, the administration of compositions of the present disclosure to beef cattle harboring microbial pathogens outcompetes the pathogens and clears the beef cattle of the pathogens. In some embodiments, the administration of compositions of the present disclosure stimulate host immunity, and aids in clearance of the microbial pathogens. In some embodiments, the administration of compositions of the present disclosure introduce microbes that produce bacteriostatic and/or bactericidal components that decrease or clear the beef cattle of the microbial pathogens. (U.S. Pat. No. 8,345,010).

In some embodiments, challenging beef cattle with a microbial colonizer or microbial pathogen after administering one or more compositions of the present disclosure prevents the microbial colonizer or microbial pathogen from growing to a relative abundance of greater than 15%, 14%, 13%, 12%, 11%, 10%, 9%, 8%, 7%, 6%, 5%, 4%, 3%, 2%, 1%, 0.5%, 0.1%, or 0.01%. In further embodiments, challenging beef cattle with a microbial colonizer or microbial pathogen after administering one or more compositions of the present disclosure prevents the microbial colonizer or microbial pathogen from colonizing beef cattle.

In some embodiments, clearance of the microbial colonizer or microbial pathogen occurs occurs in less than 25 days, less than 24 days, less than 23 days, less than 22 days, less than 21 days, less than 20 days, less than 19 days, less than 18 days, less than 17 days, less than 16 days, less than 15 days, less than 14 days, less than 13 days, less than 12 days, less than 11 days, less than 10 days, less than 9 days, less than 8 days, less than 7 days, less than 6 days, less than 5 days, less than 4 days, less than 3 days, or less than 2 days post administration of the one or more compositions of the present disclosure.

In some embodiments, clearance of the microbial colonizer or microbial pathogen occurs within 1-30 days, 1-25 days, 1-20 day, 1-15 days, 1-10 days, 1-5 days, 5-30 days, 5-25 days, 5-20 days, 5-15 days, 5-10 days, 10-30 days, 10-25 days, 10-20 days, 10-15 days, 15-30 days, 15-25 days, 15-20 days, 20-30 days, 20-25 days, or 25-30 days post administration of the one or more compositions of the present disclosure.

Improved Traits

Figure 3:
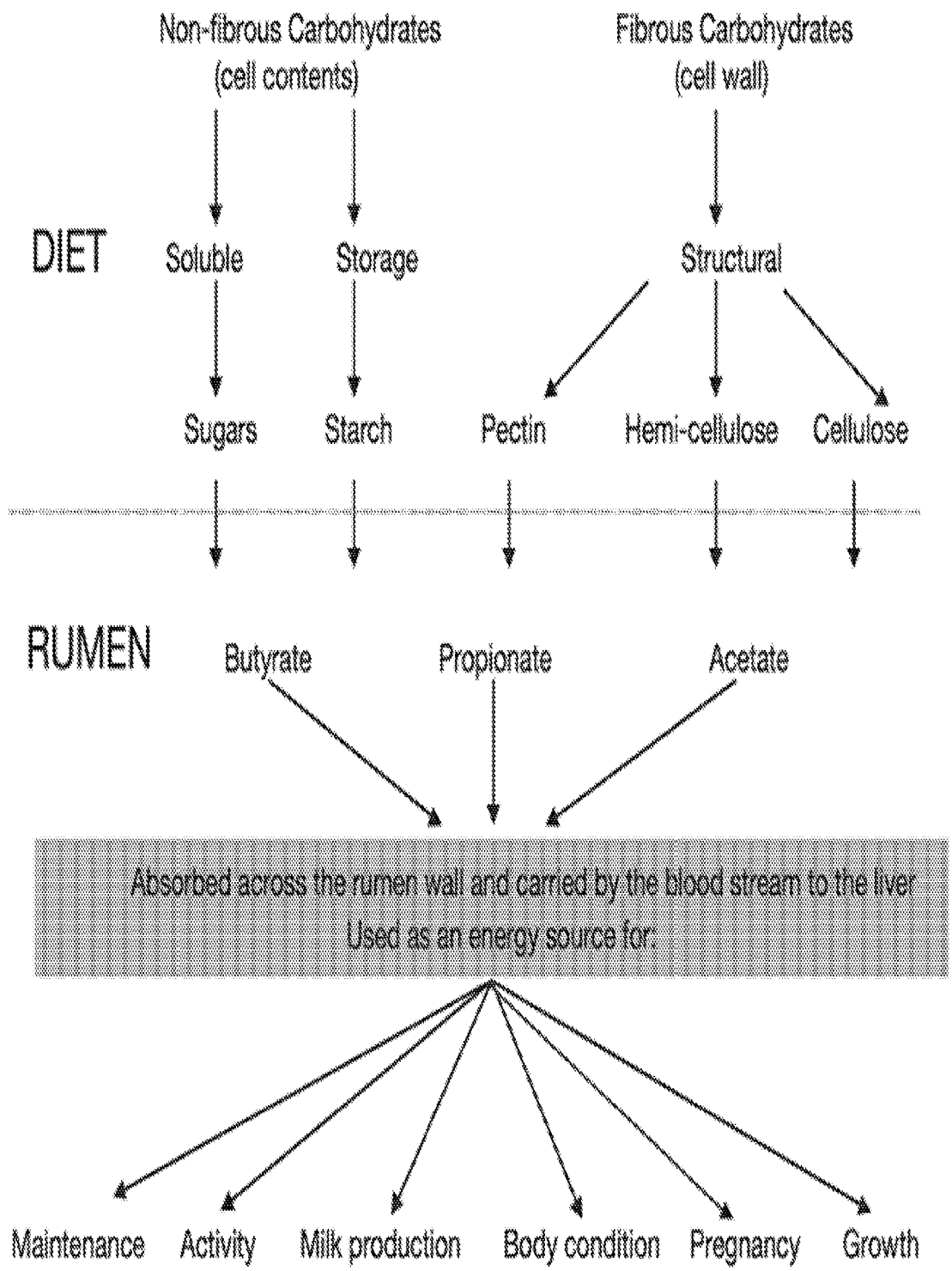
FIG. 3 depicts a diagram that exemplifies how the diet influences the production of volatile fatty acids which in turn modulate milk production, body condition, growth, etc. Reproduced from Moran, 2005. Tropical dairy farming: feeding management for small holder dairy farmers in the humic tropics (Chapter 5), Landlinks Press, 312 pp.

The rumen is a specialized stomach dedicated to the digestion of feed components in ruminants. A diverse microbial population inhabits the rumen, where their primary function revolves around converting the fibrous and non-fibrous carbohydrate components into useable sources of energy and protein (FIG. 3). Cellulose, in particular, forms up to 40% of plant biomass and is considered indigestible by mammals. It also is tightly associated with other structural carbohydrates, including hemicellulose, pectin, and lignin. The cellulolytic microbes in the rumen leverage extensive enzymatic activity in order break these molecules down into simple sugars and volatile fatty acids. This enzymatic activity is critical to the extraction of energy from feed, and more efficient degradation ultimately provides more energy to the animal. The soluble sugars found in the non-fibrous portion of the feed are also fermented into gases and volatile fatty acids such as butyrate, propionate, and acetate. Volatile fatty acids arising from the digestion of both the fibrous and non-fibrous components of feed are ultimately the main source of energy of the ruminant.

In some aspects, the present disclosure is drawn to administering microbial compositions described herein to beef cattle to improve one or more traits through the modulation of aspects of weight, musculature, digestive chemistry, efficiency of feed utilization and digestibility, fecal output, prevention of colonization of pathogenic microbes, and clearance of pathogenic microbes.

In some embodiments, the at least one improved trait is selected from the group consisting of: an increase in weight; an increase of musculature; an increase of fatty acid concentration in the gastrointestinal tract; an increase of fatty acid production in the gastrointestinal tract; an increase of fatty acid concentration in the rumen; a decrease in lactate concentration in the rumen; an improved efficiency in feed utilization and digestibility; an improved feed efficiency; an improved average daily weight gain; an increased final body weight; an improved dry matter intake; an increase in polysaccharide and lignin degradation; an increase in fat, starch, and/or protein digestion; an increase in fatty acid concentration in the rumen; pH balance in the rumen, an increase in vitamin availability; an increase in mineral availability; an increase in amino acid availability; an increase in milk production, a reduction in methane and/or nitrous oxide emissions; a reduction in manure production; an improved efficiency of nitrogen utilization; an improved efficiency of phosphorous utilization; an increased resistance to colonization of pathogenic microbes that colonize cattle; reduced mortality; increased production of antimicrobials; increased clearance of pathogenic microbes; increased resistance to colonization of pathogenic microbes that colonize cattle; increased resistance to colonization of pathogenic microbes that infect humans; and any combination thereof; reduced incidence and/or prevalence of acidosis or bloat; reduced incidence of abomasal dysplasia; reduced body temperature; reduction in the concentration of $CO_2$ (dissolved or otherwise) in the rumen; increase in $CO_2$ fixation; reduction in microbial methanogenic populations; increase in $CO_2$ fixing microbes; increasing the concentration of B vitamins in the rumen; an increase in mammalian and/or microbial synthesis of vitamins; reducing alpha diversity of the microbiome residing in the rumen; reducing histamine and LPS production; reducing leaky gut and permeability of the gastrointestinal lining; reduction in respiratory and metabolic acidosis; reduction in laminitis; reduction in ketosis; reduction of the incidence of liver disease and/or liver abscesses; reducing lactate concentrations in the rumen; increasing degradation of lactate in the rumen; increasing microbial lactate-degrading populations; wherein said increase or reduction is determined by comparing against an animal not having been administered said composition.

In some embodiments, the [$CO_2$] (dissolved or otherwise) is reduced by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an animal not having been administered a composition of the present disclosure.

In some embodiments, the [$CO_2$] (dissolved or otherwise) in the rumen is reduced by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an animal not having been administered a composition of the present disclosure.

In some embodiments, the ruminal pH is increased by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an animal not having been administered a composition of the present disclosure.

In some embodiments, the ruminal pH has an increased buffering capacity by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an animal not having been administered a composition of the present disclosure.

In some embodiments, the [carbonic acid] is reduced by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an animal not having been administered a composition of the present disclosure.

In some embodiments, the [carbonic acid] in the rumen is reduced by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an animal not having been administered a composition of the present disclosure.

In some embodiments, the fecal output is reduced by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an animal not having been administered a composition of the present disclosure. In some embodiments, the fecal output is reduced by less than 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an animal not having been administered a composition of the present disclosure.

In some embodiments, the incidence of liver disease or liver abscesses is reduced by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an animal not having been administered a composition of the present disclosure.

In some embodiments, the incidence of bloat is reduced by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an animal not having been administered a composition of the present disclosure.

In some embodiments, the synthesis of one or more volatile fatty acids is increased by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an animal not having been administered a composition of the present disclosure.

In some embodiments, the final body weight of the animals is increased by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an animal not having been administered a composition of the present disclosure.

In some embodiments, the rate of weight gain of the animals is increased by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an animal not having been administered a composition of the present disclosure.

In some embodiments, the lipopolysaccharide production in the animals is decreased by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an animal not having been administered a composition of the present disclosure.

In some embodiments, improving the efficiency and digestibility of animal feed is desirable. In some embodiments, increasing the degradation of lignocellulosic components from animal feed is desirable. Lignocellulosic components include lignin, cellulose, and hemicellulose.

In some embodiments, increasing the concentration of fatty acids in the gastrointestinal tract is desirable. Fatty acids include acetic acid, propionic acid, and butyric acid. In some embodiments, maintaining the pH balance in the gastrointestinal tract to prevent destruction of beneficial microbial compositions is desirable.

In some embodiments, decreasing the amount of methane and manure produced by beef cattle is desirable In some embodiments, a decrease in the amount of total manure produced is desirable. In further embodiments, a decrease in the total amount of phosphorous and/or nitrogen in the total manure produced is desirable.

In some embodiments, improving the dry matter intake is desirable. In some embodiments, improving the feed intake is desirable. In some embodiments, improving the efficiency of nitrogen utilization of the feed and/or dry matter ingested by beef cattle is desirable.

In some embodiments, the improved traits of the present disclosure are the result of the administration of the presently described microbial compositions. It is thought that the microbial compositions modulate the microbiome of beef cattle such that the biochemistry of the rumen is changed in such a way that the gastrointestinal liquid and solid substratum are more efficiently and more completely degraded into subcomponents and metabolites than the gastrointestinal tract of beef cattle not having been administered microbial compositions of the present disclosure.

In some embodiments, the increase in efficiency and the increase of degradation of the gastrointestinal substratum result in an increase in improved traits of the present disclosure.

In some embodiments, the administration of one or more compositions of the present disclosure result in an improved feed efficiency of grain intensive and/or energy intensive diets. In some embodiments, the improved feed efficiency measured as a decrease in the amount/volume of feces while maintaining or increasing the intake of the feed. In further embodiments, the grain intensive diet is that which contains 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, or 40% grains.

In some embodiments, the administration of one or more compositions of the present disclosure result in an improved feed efficiency in the presence or absence of antibiotic agents.

In some embodiments, the administration of one or more compositions of the present disclosure result in an increase in the average daily weight gain of ruminants, as compared to those not having been administered the one or more compositions.

In some embodiments, the administration of one or more compositions of the present disclosure result in an increase in the dry matter intake of ruminants, as compared to those not having been administered the one or more compositions.

In some embodiments, the administration of one or more compositions of the present disclosure result in a reduced incidence and/or prevalence of acidosis or bloat in ruminants, as compared to those not having been administered the one or more compositions.

In some embodiments, the administration of one or more compositions of the present disclosure result in a reduced body temperature in ruminants, as compared to those not having been administered the one or more compositions. In further embodiments, the reduction in temperature is at least 0.2° F., at least 0.4° F., at least 0.6° F., at least 0.8° F., at least 1° F., at least 1.2° F., at least 1.4° F., at least 1.6° F., at least 1.8° F., at least 2° F., at least 2.2° F., at least 2.4° F., at least 2.6° F., at least 2.8° F., at least 3° F., at least 3.2° F., at least 3.4° F., at least 3.6° F., at least 3.8° F., at least 4° F., at least 4.2° F., at least 4.4° F., at least 4.6° F., at least 4.8° F., at least 5° F., at least 5.2° F., at least 5.4° F., at least 5.6° F., at least 5.8° F., or at least 6° F.

In further embodiments, the reduction in temperature is at about 0.2° F., about 0.4° F., about 0.6° F., about 0.8° F., about 1° F., about 1.2° F., about 1.4° F., about 1.6° F., about 1.8° F., about 2° F., about 2.2° F., about 2.4° F., about 2.6° F., about 2.8° F., about 3° F., about 3.2° F., about 3.4° F., about 3.6° F., about 3.8° F., about 4° F., about 4.2° F., about 4.4° F., about 4.6° F., about 4.8° F., about 5° F., about 5.2° F., about 5.4° F., about 5.6° F., about 5.8° F., or about 6° F.

In some embodiments, the administration of one or more compositions of the present disclosure result in an increase in the quality grade of the resulting beef, as set forth by the USDA Beef Quality and Yield Grades. In further embodiments, the increase in the quality grade is an increase or upgrade to USDA Prime, USDA Choice, or USDA Select quality grades, as compared to those not having been administered the one or more compositions. In some embodiments, the increase in the quality grade is an increase in the amount of meat per ruminant that is labelled as USDA Prime, USDA Choice, or USDA Select.

In some embodiments, the administration of one or more compositions of the present disclosure result in an increase in the amount of marbling (intramuscular fat) in the resulting meat of the ruminants. In further embodiments, the increase in the amount of marbling is an increase in marbling grade to Prime+, Prime°, Prime−, Choice+, Choice°, Choice−, Select+, Select−, Standard+, Standard°, Standard−, as compared to those not having been administered the one or more compositions.

In some embodiments, the administration of one of more compositions of the present disclosure result in an increase or decrease in the red color of the resulting meat from the ruminant. In some embodiments, the increase in the red color of the meat is an increase to light cherry red to slightly dark red, moderately light red to moderately dark red, moderately dark red to dark red, dark red to very dark red, as compared to those not having been administered the one or more compositions. In some embodiments, the decrease in the red color of the meat is a decrease to light cherry red, light cherry red to slightly dark red, moderately light red to moderately dark red, or moderately dark red to dark red, as compared to those not having been administered the one or more compositions.

In some embodiments, the administration of one or more compositions of the present disclosure result in an increase or decrease in the texture of the resulting meat from the ruminant. In some embodiments, the decrease in the texture is from coarse to slightly coarse, moderately fine, fine, or very fine, as compared to those not having been administered the one or more compositions. In some embodiments, the increase in the texture is very fine, fine, moderately fine, slightly coarse, or coarse.

In some embodiments, the administration of one or more compositions of the present disclosure result in an increase or decrease in the concentration and/or amount of the following volatile components which are known to modulate the flavor and/or aroma of the resulting meat from the ruminants: pentanal, hexanal, heptanal, nonanal, methional, 12-methyltridecanal, nona-2(E)-enal, deca-2(E),4(E)-dienal, butanoic acid, hexanoic acid, delta-nonalactone, decan-2-one, 3-hydroxy-2-butanone, 2,3-octanedione, 1-octene-3-ol, 2-pentyl furan, 2-methyl-3-[methylthio]furan, 4-hydroxy-5-methyl-3(2H)-furanone (HMF), methylpyrazine,2,5-dimethylpyrazine, methylpyrazine,2,6-dimethylpyrazine, pyrazines, glycine, alanine, lysine, cysteine, methionine, glutamine, succinic acid, lactic acid, inosinic acid, orthophosphoric acid, pyrrolidone carboxylic acid, glucose, fructose, ribose, aspartic acid, histidine, asparagine, pyrrolidone carboxylic, carnosine, anserine, hypoxanthine, arginine, leucine, tryptophan, monosodium glutamate (MSG), inosine monophosphate (IMP), guanosine monophosphate (GMP), bis(2-methyl-3-furyl) disulfide, and 2-methyl-3-furanthiol.

In some embodiments, the increase of any one or more of the traits of the present disclosure is an increase of about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% relative to an animal not having been administered one or more microbial compositions of the present disclosure.

In some embodiments, the increase of any one or more of the traits of the present disclosure is an increase of at least 0.1%, at least 0.2%, at least 0.3%, at least 0.4%, at least 0.5%, at least 0.6%, at least 0.7%, at least 0.8%, at least 0.9%, at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% relative to an animal not having been administered one or more microbial compositions of the present disclosure.

In some embodiments, the decrease of any one or more of the traits of the present disclosure is a decrease of about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% relative to an animal not having been administered one or more microbial compositions of the present disclosure.

In some embodiments, the decrease of any one or more of the traits of the present disclosure is a decrease of at least 0.1%, at least 0.2%, at least 0.3%, at least 0.4%, at least 0.5%, at least 0.6%, at least 0.7%, at least 0.8%, at least 0.9%, at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% relative to an animal not having been administered one or more microbial compositions of the present disclosure.

Network Analysis

A network and/or cluster analysis method, in one embodiment, is used to measure connectivity of the one or more strains within a network, wherein the network is a collection of two or more samples that share a common or similar environmental parameter. In one embodiment, network analysis comprises linkage analysis, modularity analysis, robustness measures, betweenness measures, connectivity measures, transitivity measures, centrality measures or a combination thereof. In another embodiment, network analysis comprises predictive modeling of network through link mining and prediction, social network theory, collective classification, link-based clustering, relational similarity, or a combination thereof. In another embodiment, network analysis comprises mutual information, maximal information coefficient (MIC) calculations, or other nonparametric methods between variables to establish connectivity. In another embodiment, network analysis comprises differential equation based modeling of populations. In yet another embodiment, network analysis comprises Lotka-Volterra modeling.

The environmental parameter can be a parameter of the sample itself, e.g., pH, temperature, amount of protein in the sample. Alternatively, the environmental parameter is a parameter that affects a change in the identity of a microbial community (i.e., where the "identity" of a microbial community is characterized by the type of microorganism strains and/or number of particular microorganism strains in a community), or is affected by a change in the identity of a microbial community. For example, an environmental parameter in one embodiment, is the food intake of an animal. In one embodiment, the environmental parameter is the presence, activity and/or abundance of a second microorganism strain in the microbial community, present in the same sample. In some embodiments, an environmental parameter is referred to as a metadata parameter.

Other examples of metadata parameters include but are not limited to genetic information from the host from which the sample was obtained (e.g., DNA mutation information), sample pH, sample temperature, expression of a particular protein or mRNA, nutrient conditions (e.g., level and/or identity of one or more nutrients) of the surrounding environment/ecosystem), susceptibility or resistance to disease, onset or progression of disease, susceptibility or resistance of the sample to toxins, efficacy of xenobiotic compounds (pharmaceutical drugs), biosynthesis of natural products, or a combination thereof.

Diagnostics

In some embodiments, a sample (serum, fecal, rumen, tissue, blood, etc.) is collected from a ruminant. In some embodiments, the sample is assayed for the presence and/or quantity of one or more chemical substances. In some embodiments the presence or absence of the one or more chemical substances are diagnostic of a desirable trait described in the present disclosure.

In some embodiments, the one or more chemical substances may be selected from pantothenate, homocysteine, glutamine, carnitine, D-gluconate, hypoxanthine, orotate, succinate, methylmalonate, aconitate, 2-hydroxy-2-methyl succinate, allantoin, homocysteic acid, homocysteine, citrate, isocitrate, and cytosine.

In some embodiments, the increase of any one of the following chemical substances in the blood or blood serum at greater than 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3. 2.4, 2.5, 2.6, 2.7, 2.8, 2.9, 3.0, 3.1, 3.2, 3.3, 3.4, 3.5, 3.6, 3.7, 3.8, 3.9 or 4.0 fold is predictive of the rumen bacterial community composition comprising bacteria from class Flavobacteriia.

In some embodiments, the increase of at least 0.7 fold of pantothenate in the blood or blood serum is predictive of the rumen bacterial community composition comprising a higher proportion of bacteria from class Flavobacteriia.

In some embodiments, the increase of at least 0.7 fold of pantothenate in the blood or blood serum is predictive of the animal having a low residual feed intake (RFI), as compared to an animal without at least a 0.7 fold increase of pantothenate.

In some embodiments, the present disclosure is drawn to a method of determining the RFI of an animal. In some embodiments, the method comprises collecting a first sample of blood or blood serum at a first time point and collecting a second sample of blood or blood serum at a second time point, assaying the samples for the presence and concentration of pantothenate in the blood or blood serum, wherein the animal is indicated to possess low RFI if the pantothenate exhibits a fold increase of at least 0.7 between the first sample and the second sample.

EXAMPLES

Example I. Determination of Feed Efficiency in Beef Cattle

The objective of the study was to document and quantify the feed efficiency of steers fed finishing diets.

A total of 50 steers were adjusted to trial rations during a pretest adjustment period of at least 15 days. This initial adjustment period enabled the animals to acclimate to the GROWSAFE (model 4000E, GrowSafe Systems Ltd., Airdrie, AB, Canada) feeding units and test rations. Steers were fed a step up diet for approximately 21 days before receiving a high concentrate finishing diet, as presented below. Rumensin was added to the finishing diet at a rate of 96 mg/hd/d. At the end of the first period, a 60 day trial was conducted with a minimum of 50 steers for which RFI was determined using the GROWSAFE feed intake system. Residual feed intakes for steers was ranked together, and animals were classified as low RFI (highly efficient), mid RFI, or high RFI (lowly efficient) by dividing them in thirds. From this classification, the low and high RFI steers were selected for further study.

TABLE 10

Finishing diet defined by crude protein (CP), total digestible nutrients (TDN), and dry matter (DM).

| | CP (%) | TDN (%) | % of diet (DM) |
|---|---|---|---|
| Corn | 9.00 | 87.60 | 75.00 |
| Sorghum Sudan Hay | 8.33 | 54.00 | 15.00 |
| 44% CP Supplement | 44.00 | 73.00 | 10.00 |

Total Diet Nutrient Composition: 12.4% CP, 81.1% TDN. Rumensin was added at a rate of 96 mg/hd/d Example II. Characterization of Microbial Communities of Steers that Differ in RFI On day 1 and weekly throughout a 60 trial period, rumen content samples were collected via esophageal tubing. The rumen content was collected while the steer was in a chute by passing the tubing through a Frick speculum placed in the mouth and a rubber bulb was manipulated to provide a suction once the tube was in the rumen to collect three rumen samples. A first sample consisted of 20 ml of rumen content. A second sample consisted of rumen content that was added to a 15 ml conical tube prefilled with stabilization solution and stored at 4° C. immediately after. The conical tube was filled to the top with rumen content. A third sample consisted of 20 ml of rumen content that was added to a conical tube prefilled with stop solution. After adding the rumen content to the stop solution, the solution was mixed via inversion several times and stored at 4° C. immediately after. Samples 2 and 3 were shipped to Ascus overnight on ice the day of or the day following sample collection. In addition, up to 10 ml of venous blood was collected directly after rumen content collection.

Immediately after rumen sampling, rumen pH was measured using an electronic pH meter. Subsamples were frozen to stop microbial fermentation and stored at −20° C. for subsequent volatile fatty acids (acetate, propionate, butyrate, isobutyrate, and valerate) analyses. Ammonia-nitrogen (NH3-N) was analyzed according to the colorimetric technique described by Chaney and Marbach (1962. Clin. Chem. 8(2):130-132). Flash frozen (liquid nitrogen and storage at −80° C.) and live rumen content samples were utilized to determine the abundances of bacterial species utilizing next-generation sequencing of the 16S rRNA, 16S rDNA, and/or ITS sequences on the Illumina MiSeq sequencing platform (Illumina, Inc., San Diego, CA). Body weight, dry matter intake, and average daily gain for each animal was also measured at the time of rumen sampling.

Example III. Dynamics Mediating Feed Efficiency in Cattle

Rumen microbes produce metabolites that are released into the rumen lumen and can be absorbed through the rumen epithelium or through the epithelium in the lower gastrointestinal tract. (See Hungate. The Rumen and Its Microbes, Elsevier. 1966.). The rumen microbes are responsible for the production of approximately 70% of the energy supply to the ruminant, including production of organic acids such as acetate and propionate. (See Seymour et al. Animal Feed Sci. Tech. 2005. 119:155-169). Differences in the production of these metabolites as well as variation in rate and quantity of absorption can contribute to divergences in nutrient utilization and efficiency of the ruminants, and may lead to physiological or phenotypic changes. (See Huntington. Reproduction Nutrition Development. 1990. 30:35-47; Okine and Mathison. Journal of Animal Science. 1991. 69:3435-3445). However, it can be difficult to distinguish the origin of many metabolites between those of endogenous origin and metabolites of microbial origin. Although associations between the rumen microbiome and physiological changes in the host have been identified, it has yet to be determined the mechanisms driving these changes and whether foundational, or keystone, species are responsible for the divergences in feed efficiency and other phenotypes. (See Hungate. The Rumen Microbial Ecosystem. Annual Review of Ecology and Systematics. 1975. 39-66).

In order to address these critical knowledge gaps, a combination of microbial genomics, metabolomics, and bioinformatics were utilized to further define variations in feed efficiency as determined by the divergences in residual feed intake (RFI). Determination of the complex associations and networks between the rumen microbiome, host metabolome, and differences in host phenotype can be facilitated by novel utilization of bioinformatics and machine learning to discover physiological patterns and identifying microbial factors. This example examines the relationship among RFI, the rumen microbial community, and serum metabolome in order to identify potential biomarkers for feed efficiency in beef/feedlot cattle.

Fifty weaned steers of approximately 7 months of age were housed at the Plateau Research and Education Center in Crossville, TN Animals weighed 264±2.7 kg at the beginning of the study and transitioned to a backgrounding diet (11.57% crude protein and 76.93% total digestible nutrients with 28 mg monensin/kg on a dry matter basis) for 14 days prior to the start of the trial. Steers were adapted to the GROWSAFE system during that adaptation period. Body weight (BW) was measured at 7 day intervals and daily feed intake measured using the GROWSAFE system for the length of the 70 day feed efficiency trial. Feed efficiency was determined using RFI. (See Koch et al. Journal of Animal Science. 1963. 22:486-494). At the conclusion of the trial, steers were ranked based on RFI. Low- or high-RFI was determined as 0.5 SD below or above the mean RFI, respectively Approximately 9 mL of blood was sampled weekly via venipuncture from the coccygeal vein into serum separator tubes (Corvac, Kendall Health Care, St. Louis, MO). Blood samples were centrifuged at 2,000×g for 20 min at 4° C. Serum was decanted into 5 mL plastic culture tubes and stored at −80° C. for further analyses Rumen samples were centrifuged at 4,000 rpm for 15 min, and the nucleic acids were isolated using the POWERVIRAL Environmental RNA/DNA Isolation Kit (Mo Bio Laboratories, Inc., Carlsbad, CA, USA). The 16S rRNA gene was amplified. (See Lane. 16S/23S rRNA sequencing. Nucleic acid techniques in bacterial systematics. 1991; Muyzer et al. Applied and Environmental Microbiology. 1993. 59:695-700). Following amplification, PCR products were verified with a 2% agarose gel electrophoresis and purified using AMPure XP bead (Beckman Coulter, Brea, CA, USA). The purified amplicon library was quantified and sequenced on the MiSeq Platform (Illumina, San Diego, CA, USA) according to standard protocols. (See Flores et al. Genome Biology. 2014. 15:531). Raw fastq reads were de-multiplexed on the MiSeq Platform (Illumina, San Diego, CA, USA)

All raw sequencing data was trimmed of adapter sequences and phred33 quality filtered using Trim Galore (See Krueger and Galore. A wrapper tool around Cutadapt and FastQC to consistently apply quality and adapter trimming to FastQ files. 2015). 16S taxonomic sequence clustering and classification was performed on filtered sequence data with the RDP 16S rRNA database. (See Edgar. SINTAX: a simple non-Bayesian taxonomy classifier for 16S amplicon reads. BioRxiv. 2016. 074161; Edgar and Flyvbjerg. Bioinformatics. 2015. 31:3476-3482; and Cole et al. Nucleic Acids Research. 2013. 42:D633-D642).

Serum samples (50 µL) from each steer were extracted for metabolomic analysis using 0.1% formic acid in acetonitrile:water:methanol (2:2:1), as described previous. (See Kamphorst et al. Analytical Chemistry. 2011. 83:9114-9122). Metabolites were separated using a Synergy Hydro-RP column (100×2 mm, 2.5 µm particle size). Mobile phases consisted of A: 97:3 H2O:MeOH with 11 mM tributylamine and 15 mM acetic acid and B: MeOH. The gradient consisted of the following: 0.0 min, 0% B; 2.5 min 0% B; 5.0 min, 20% B; 7.5 min, 20% B; 13 min, 55% B; 15.5 min, 95% B; 18.5 min, 95% B; 19 min, 0% B, and 25 min, 0% B. Flow rate was set to a constant 0.200 mL/min and the column temperature remained at 25° C. The autosampler tray was maintained at 4° C. and 10 µL of sample was injected into the Dionex UltiMate 3000 UPLC system (Thermo Fisher Scientific, Waltham, MA). Electrospray ionization was used to introduce the samples into an Exactive Plus Orbitrap MS (Thermo Fisher Scientific, Waltham, MA), using an established method. (See Kamphorst et al. Analytical Chemistry. 2011. 83:9114-9122; and Lu et al. Analytical Chemistry. 2010. 82:3212-3221).

Raw files obtained from Xcalibur MS software (Thermo Electron Corp., Waltham, MA) were converted into the mzML format using ProteoWizard. (See Chambers et al. Nature Biotechnology. 2012. 30:918). The converted files were imported into MAVEN (Metabolomic Analysis and Visualization Engine for LC-MS Data), a software package. (See Clasquin et al. Current Protocols in Bioinformatics. 2012. 14.11.1-14.11.23). Peaks for the known metabolites were picked in MAVEN, which automatically performs non-linear retention time correction and calculates peak areas across samples, using a preliminary mass error of ±20 ppm and retention time window of five min. The UTK Biological and Small Molecule Mass Spectrometry Core (BSMMSC) has replicated and expanded the method of Rabinowitz and coworkers and final metabolite annotations were made using a library of 263 retention time-accurate m/z pairs taken from MS1 spectra. (See Lu et al. Analytical Chemistry. 2010. 82:3212-3221). The annotation parameters were verified previously with pure standards as part of establishing the method. For a metabolite to be annotated as a known compound, the eluted peak had to be found within two min of the expected retention time, and the metabolite mass had to be within ±5 ppm of the expected value. Metabolite identities were confirmed using the MAVEN software package, and peak areas for each compound were integrated using the Quan Browser function of the Xcalibur MS Software (Thermo Electron Corp., Waltham, MA).

Downstream analysis was performed in python. PCoA was performed on Bray-Curtis distances and statistical significance was assessed through Analysis of Similarities (ANOSIM). (See Clarke. Austral Ecology. 1993. 18:117-143). Alpha diversity was measured both in dominance and singletons. (See Hammer et al. Palaeontol Electronica. 2001. 4:1-9). Regression based analysis was performed through Ordinary Least Squares (OLS) regression. (See Shi et al. The Annals of Applied Statistics. 2016. 10:1019-1040). Feature selection and supervised machine learning was performed on completed data through Random Forests. (See Breiman. Machine Learning. 2001. 45:5-32).

Other measurements of $\alpha$-diversity, including equitability, Simpson's Evenness E, Shannon's Diversity Index, and Observed OTU, were assessed for normality using SAS 9.4 (SAS Institute, Cary, NC). All variables were found to follow a non-normal distribution, and were analyzed using Wilcoxon Rank Sum and Kruskal Wallis test.

Figure 10A:
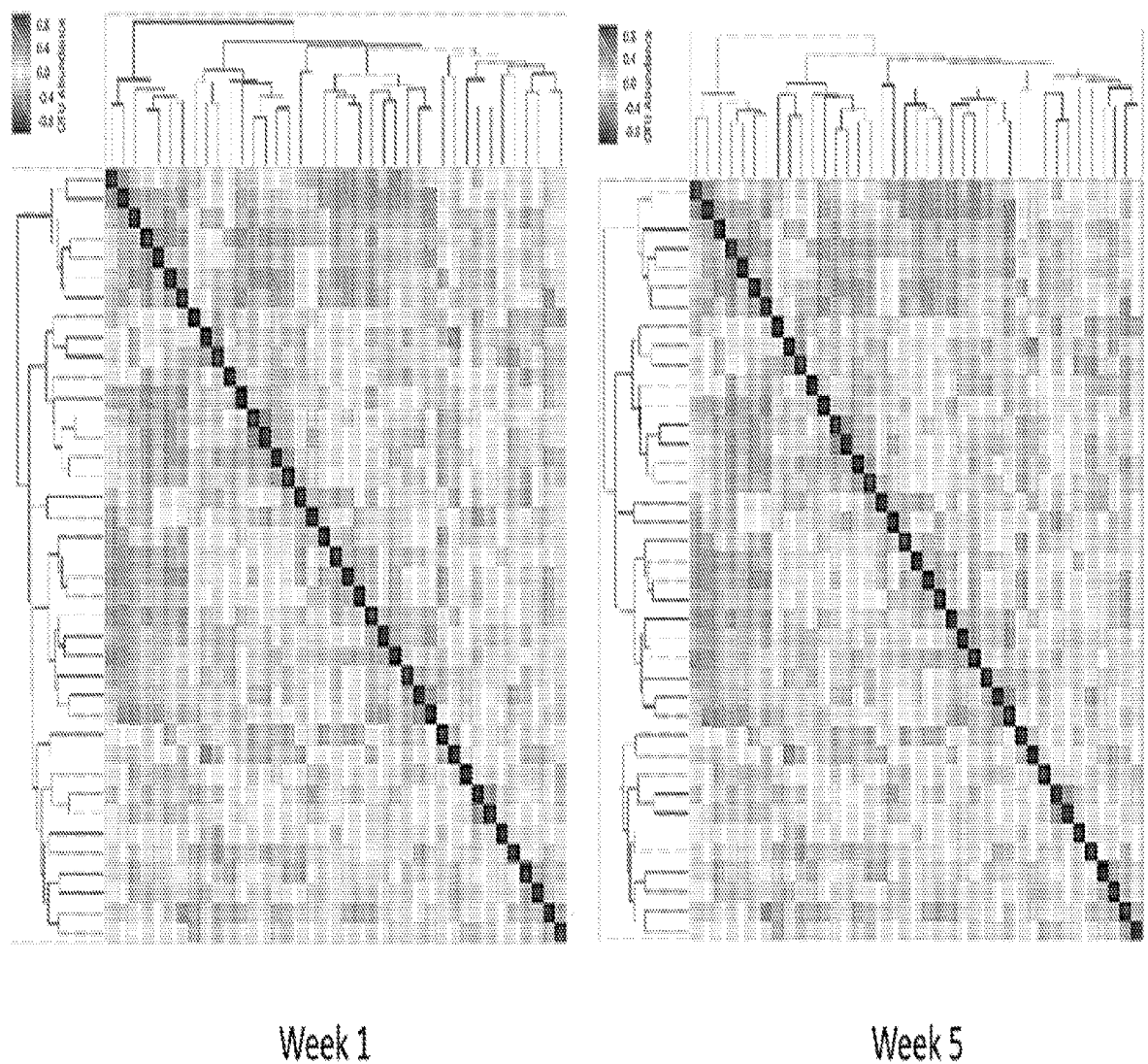
FIG. 10A and FIG. 10B depict the phylogenetic diversity of rumen bacterial communities across samples at week 1 and week 5 of the study (FIG. 10A) and across samples at week 7 and week 10 of the study (FIG. 10B).
Figure 10B:
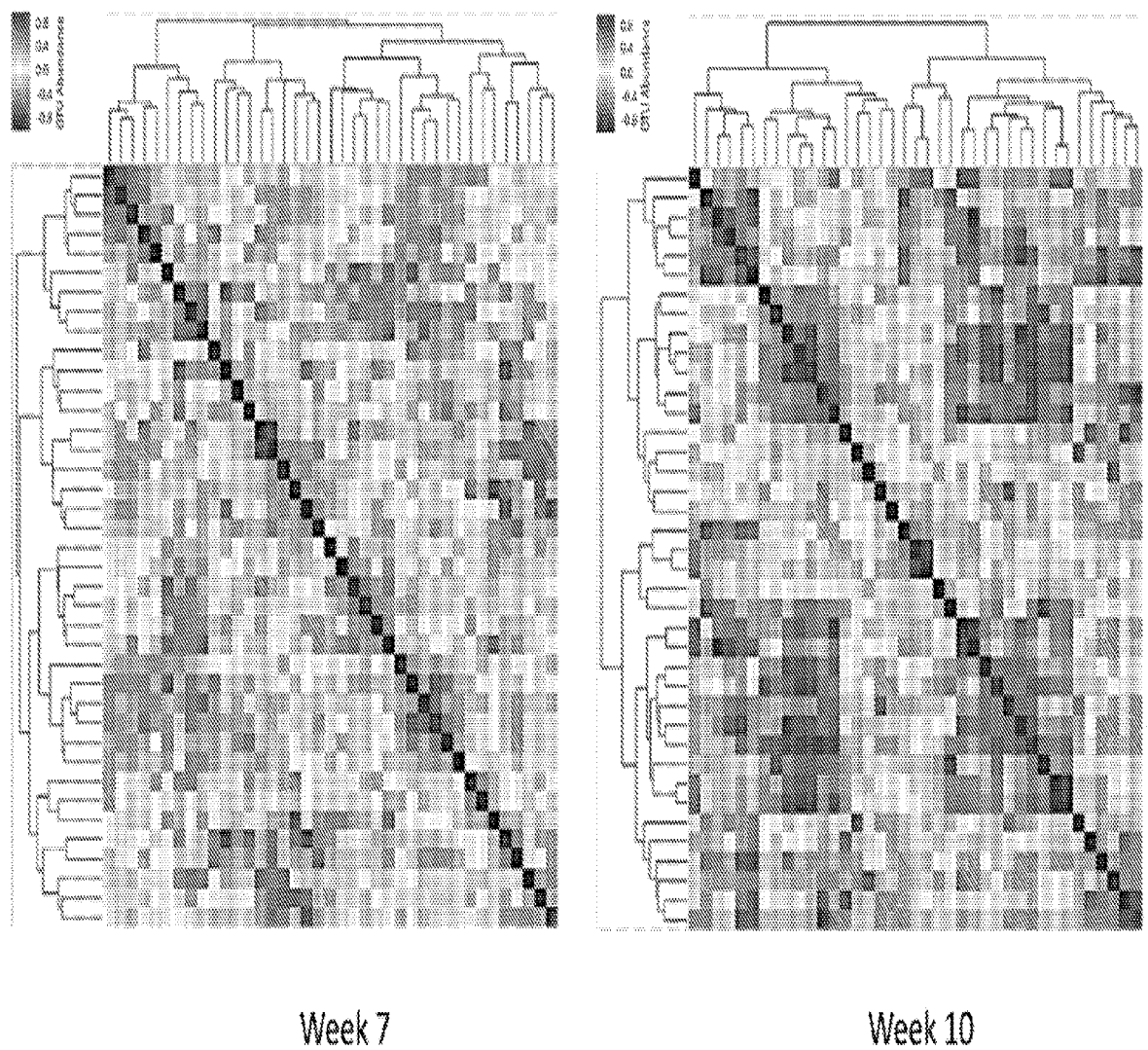

Alpha-diversity was measured by number of singletons, equitability, Simpson's Evenness, observed OTU, Good's coverage, chao1, and Shannon's Diversity Index. With the exception of number of singletons, $\alpha$-diversity metrics did not differ between low- and high-RFI steers at the end of the study. Other $\alpha$-diversity metrics did not differ between high- and low-RFI steers, including equitability (p=0.24), Simpson's Evenness (p=0.19), Observed OTU (p=0.78), Good's coverage (p=0.14), chao1 (p=0.78), and Shannon's Diversity Index (p=0.07). Phylogenetic diversity of the rumen bacterial communities also occurred over time with two distinct communities arising (FIG. 10A and FIG. 10B).

Figure 11A:
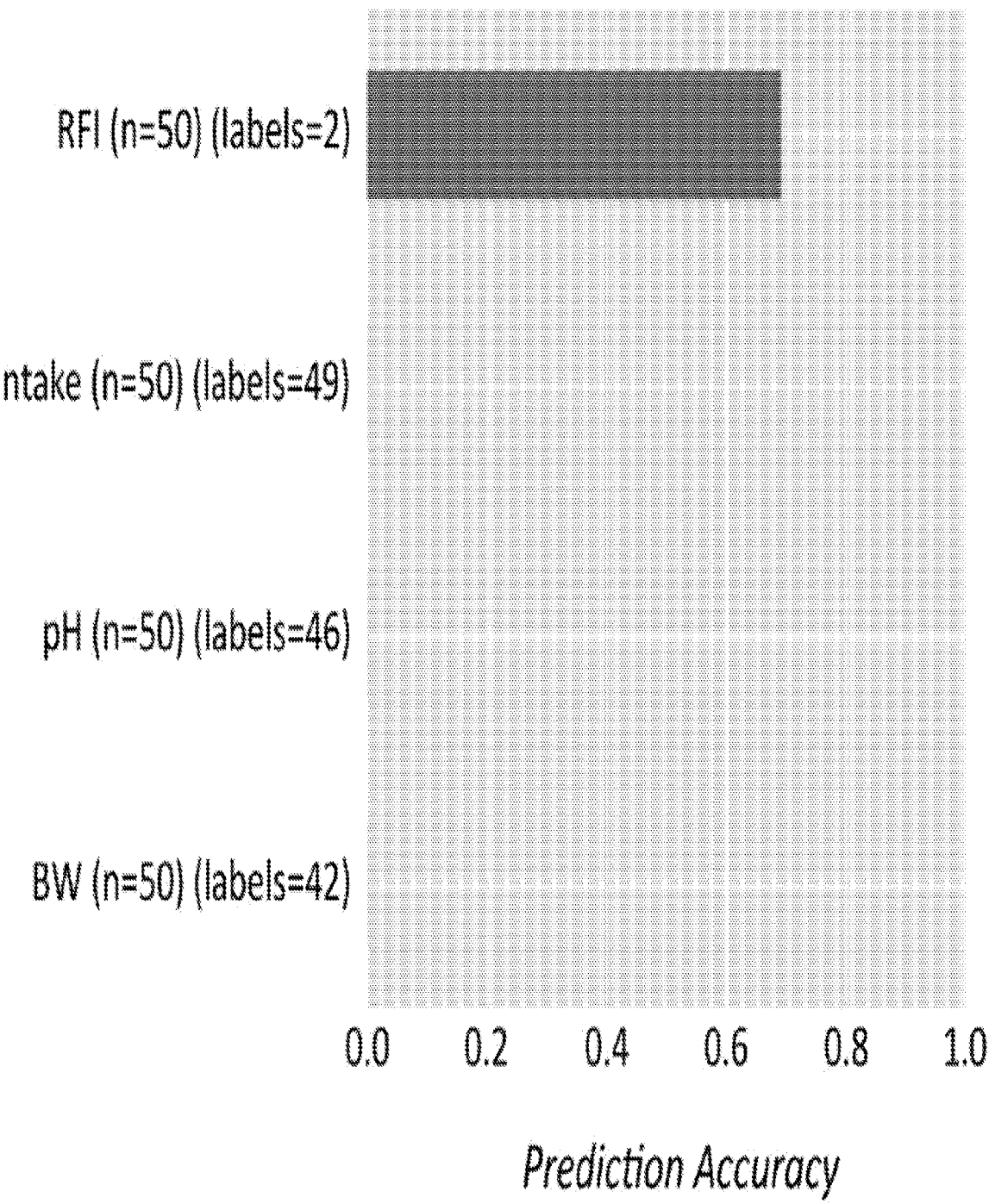
FIG. 11A and FIG. 11B depict the machine learning prediction accuracy utilized in the study. The residual feed intake (RFI) is predictive of serum metabolic signature (FIG. 11A) and the RFI is predictive of rumen microbiome signature (FIG. 11B).
Figure 11B:
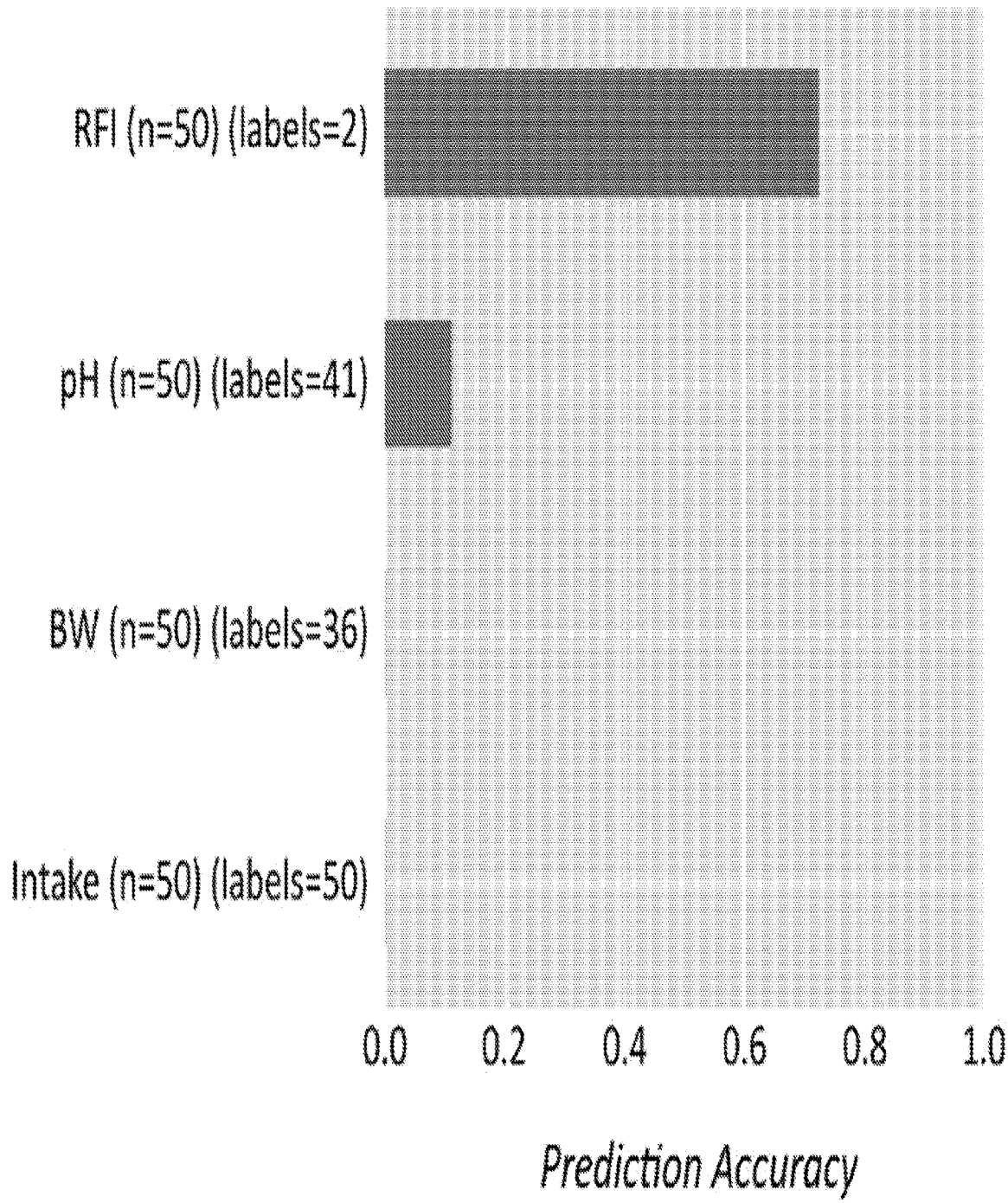
Figure 12:
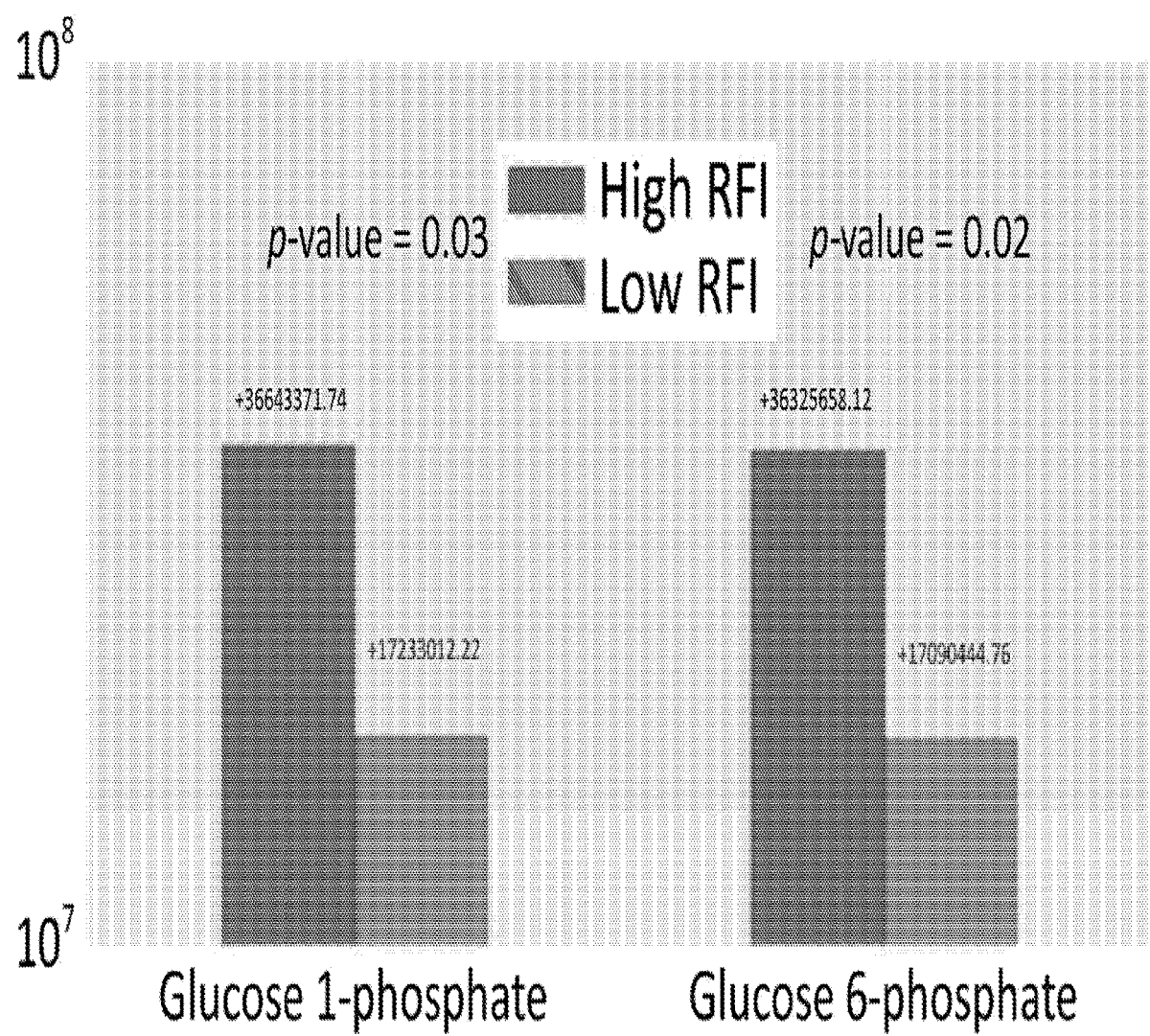
FIG. 12 depicts the mean predictive compounds between low-RFI and high-RFI. The greater the abundance of glucose-1-phosphate and/or glucose-6-phosphate is indicative of high-RFI.
Figure 13:
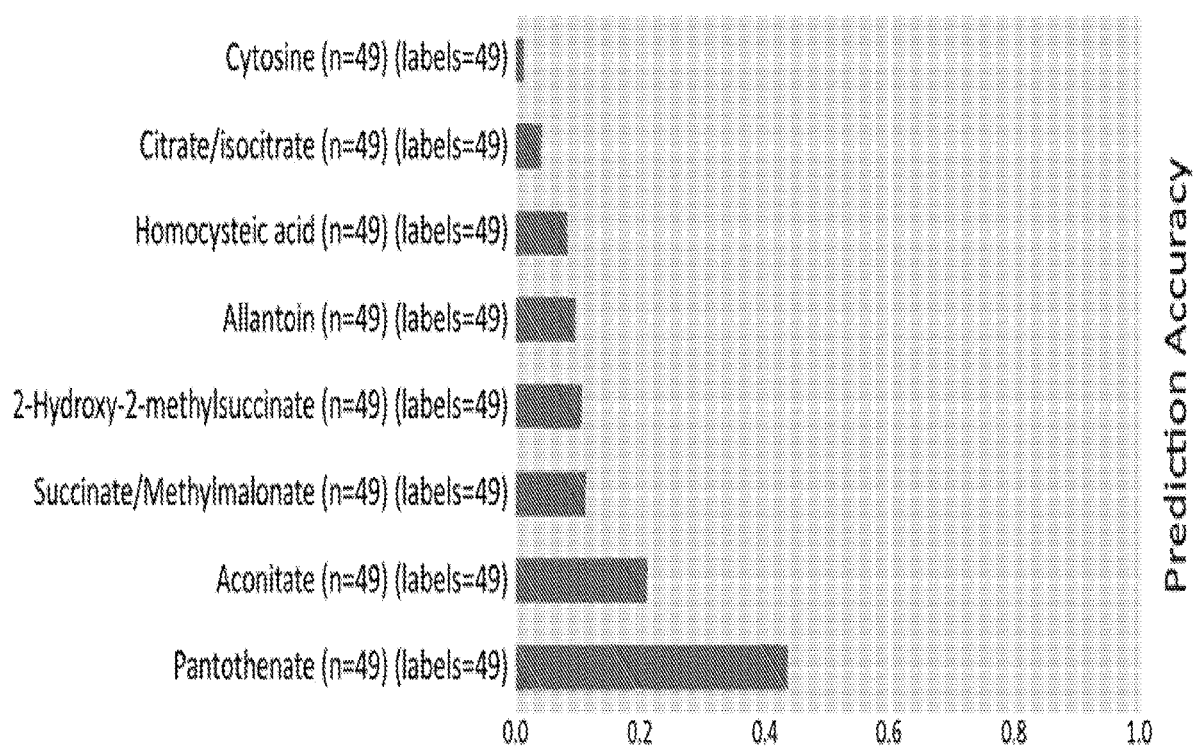
FIG. 13 depicts the serum metabolic signatures correlated to week 10 bacterial community composition.
Figure 14A:
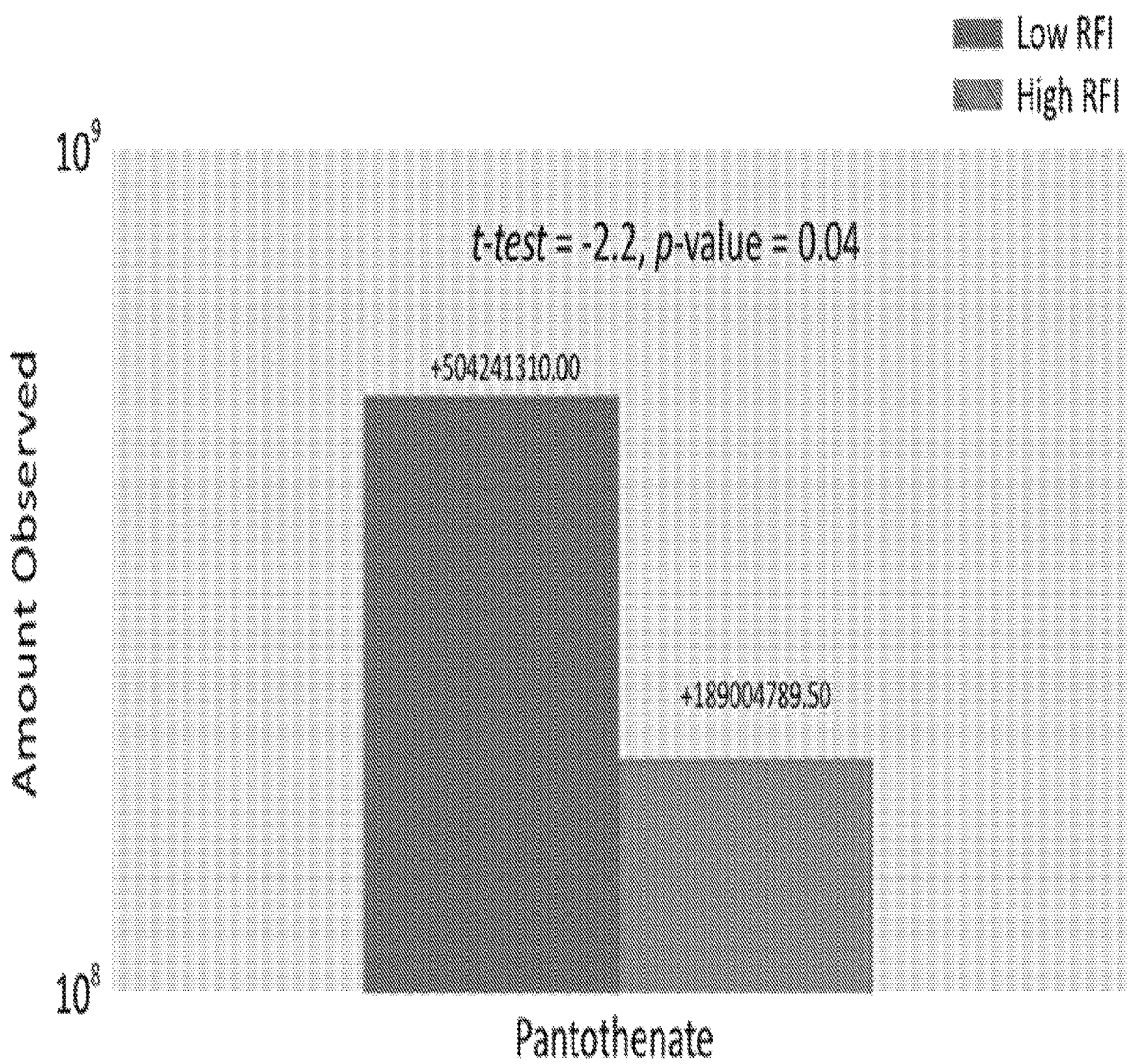
FIG. 14A and FIG. 14B depict the week 10 rumen microbial community correlations to serum metabolome. The mean serum pantothenate abundance differs between low-RFI and high-RFI steers (FIG. 14A). The mean Flavobacteria abundance is associated with high pantothenate abundance (FIG. 14B).

A total of 109 known metabolites were identified. Residual feed intake was predictive of serum metabolomic signature and rumen microbial community signature at week 10 (FIG. 11A and FIG. 11B). Glucose-1-phosphate (p=0.03; FIG. 12) and glucose-6-phosphate (p=0.02; FIG. 12) differed between low- and high-RFI steers. Several other serum metabolites were predictive of rumen bacterial community structure, including pantothenate, aconitate, succinate, 2-hydroxy-2-methylsuccinate, allantoin, homocysteic acid, citate/isocitrate, and cytosine (FIG. 13). Serum pantothenate abundance was the greatest predictor of the rumen bacterial community composition, and was also found to be significantly different between low- and high-RFI steers (p=0.04; FIG. 13; FIG. 14A).

Figure 14B:
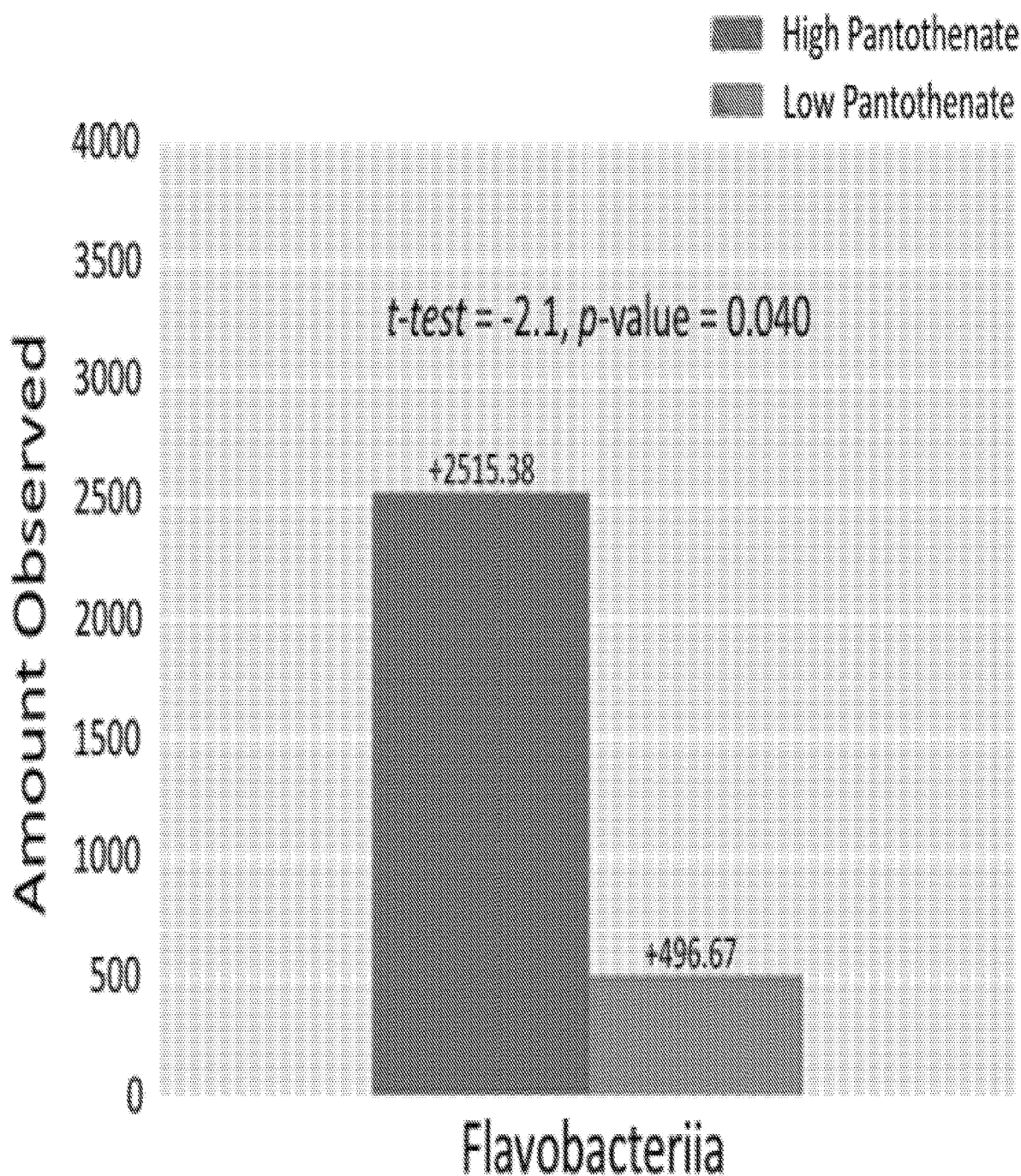
Figure 15:
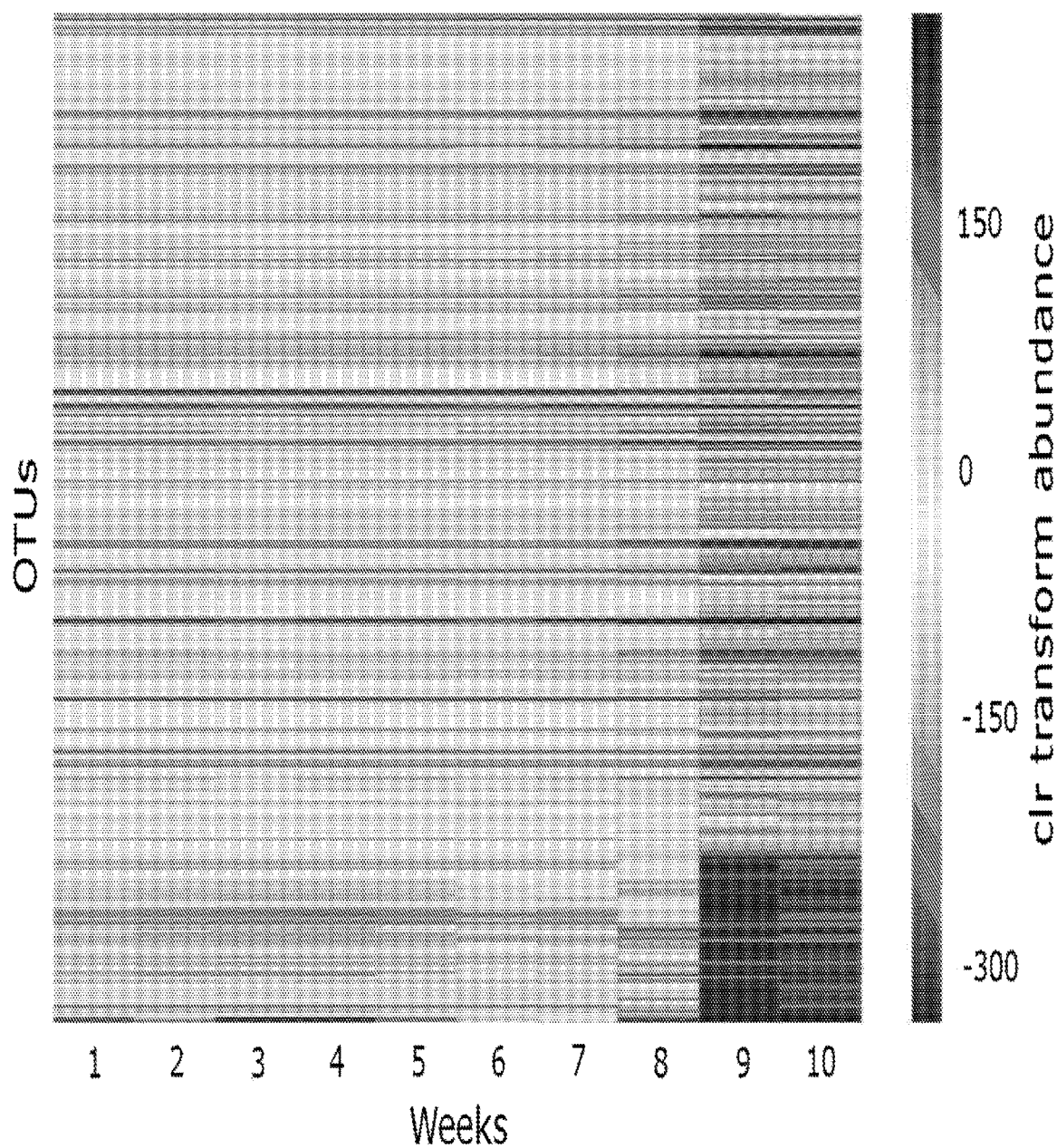
FIG. 15 depicts spectral coclustering of composite average of OTU over time, indicating major microbial successions throughout the study in the rumen microbial community.
Figure 16:
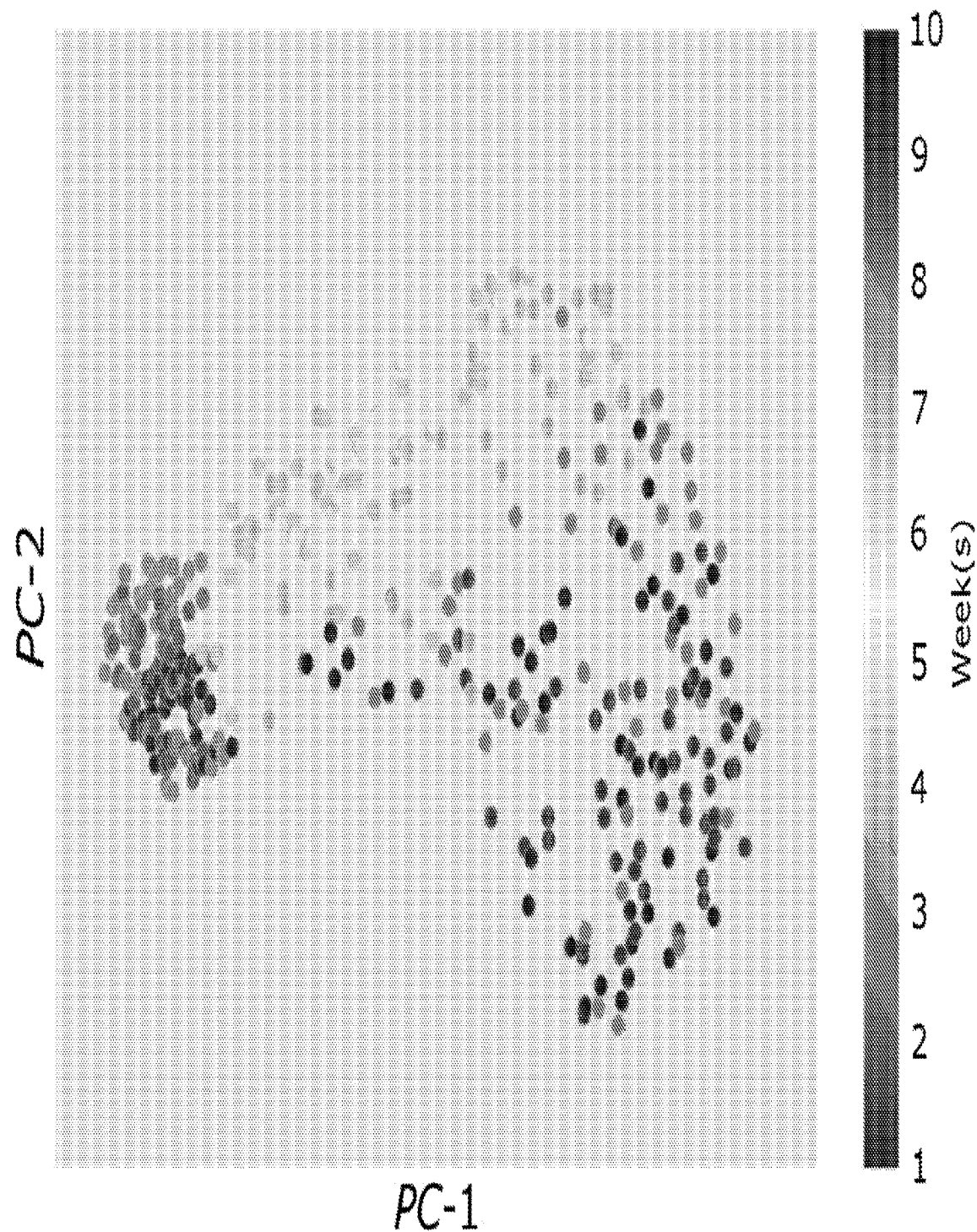
FIG. 16 depicts a principal coordinate analysis (PCoA) based on Bray-Curtis distances among the ruminal bacterial communities throughout the study.

In addition to serum pantothenate abundance as a predictor of rumen bacterial community composition, panothenate abundances were also associated with a class of rumen bacteria, Flavobacteriia. Flavobacteriia were predictive of pantothenate abundance in serum Mean Flavobacteriia abundance differed between steers with low and high pantothenate abundances (p=0.04; FIG. 14B).

While a number of singletons in the rumen bacteria differed between low- and high-RFI steers, other measurements of $\alpha$-diversity did not differ between the two groups. The data presented in this study suggest that $\alpha$-diversity may not be a significant contributing factor to feed efficiency phenotypes in stable microbial communities in growing beef steers.

Glucose-1-phosphate and glucose-6-phosphate are both intermediate metabolites of the pentose phosphate pathway in which G6P undergoes several enzymatic reactions to generate NADPH, and is most common in pathways involved in fatty acid and steroid production. (See Cori et al. Journal of Biological Chemistry. 1939. 129:629-639). Glucose-6-phosphate dehydrogenase, the first enzyme of the pentose phosphate pathway, is the rate limiting enzyme of this pathway (See Laliotis et al. Comparative Biochemistry and Physiology Part B: Biochemistry and Molecular Biology. 2007. 147:627-634), which is estimated to supply 50 to 80% of the NADPH required to perform fatty acid synthesis in ruminants. (See Vernon. Lipid Metabolism in Ruminant Animals, Pergamon. 1981. P. 279-362; and Belk et al. Journal of Animal Science. 1993. 71:1796-1804). Accumulation of G6P and G1P in less efficient animals may indicate less enzymatic activity or efficiency of the pentose phosphate pathway, which would decrease NADPH concentrations, resulting in less adipose accumulation. Both G1P and G6P in serum could potentially serve as biomarkers for feed efficiency, as increased concentrations are both are associated with decreased feed efficiency.

The rumen microbiome produces several vital nutrients for the host animals, including organic acids that serve as glucogenic precursors, as well as proteins and vitamins. (See Hungate. The Rumen and its Microbes. Elsevier. 1966). A nutrient produced by the rumen microbiota is pantothenate. Pantothenate plays a significant role in the metabolism of fatty acids in ruminants and other species. (See Smith et al. Metabolism. 1987. 36:115-121; Palanker. Journal of Lipid Research. 2016. 57:380-387). In this example, pantothenate was not only associated with greater feed efficiency, but was also predictive of rumen bacterial community composition. Pantothenate is a key component of coenzyme A (CoA), which is required to perform a variety of functions in intermediary metabolism of ruminants. (See Ragaller et al. Journal of Animal Physiology and Animal Nutrition. 2011. 95:6-16). Namely, CoA is responsible for transfer of fatty acid components into and out of the mitochondria. (See Ball. Vitamins in Foods. Analysis, Bioavailability, and Stability. Boca Raton: CRC Press. 2006). Pantothenate is produced by several species of bacteria in the rumen, and can then be released into the rumen lumen to be absorbed by the host animal. One class of bacteria that can generate pantothenate in the rumen are Flavobacteriia. It was found in this example that greater Flavobacteriia abundances were associated with greater pantothenate abundances, and Flavobacteriia abundances were predictive of pantothenate quantities, supporting that more efficient steers may have greater abundances of Flavobacteriia, which may lead to increased abundance of pantothenate.

As with G1P and G6P, pantothenate can be identified through serum; however, whereas G1P and G6P may serve as indicators of lower feed efficiency, pantothenate may indicate greater feed efficiency. The relationship between pantothenate and Flavobacteriia can not only provide insight as to mechanisms accounting for some variability in feed efficiency, but also serve as biochemical and microbial biomarkers in the serum and rumen, respectively. These biomarkers could allow producers to identify and select animals of greater feed efficiency. Metabolites and microbes predictive of efficiency phenotypes in cattle are not only imperative to partially explaining divergences in feed efficiency, but also to the selection of microbial communities related to efficient animals. These insights may also lead to the ability to select for an optimal rumen microbiome.

This example identified potential microbial and biochemical biomarkers that were used to determine extremes in feed efficiency in steers. Although, notable correlations between G1P and G6P and feed efficiency were identified, linking, and perhaps predicting, the functional capacity of the rumen and its microbiome, specifically Flavobacteriia, through serum pantothenate offers the potential to use serum biochemistry as an indicator in identification of feed efficient cattle. Additionally, although it has yet to be determined to what degree the rumen microbiome influences the host, or the host influences the rumen microbiome, the present example identified several key physiological elements that may impact or predict microbial community structure (e.g. RFI), or predictive of RFI (i.e. the serum metabolome and rumen microbial community).

Example IV. Dynamics Mediating Feed Efficiency in Cattle

The majority of research aimed at determining the influence of the microbiome on cattle production or the influence of cattle production on the ruminal microbiome has been conducted by examining short-term, end point sampling or single periods of sample collection. These single-point analyses have provided valuable insight to the influence of the rumen microbiome on livestock production but may confound the interpretation of study results and conclusions. Variation of the ruminal microbiota between animals is considerable (See Ross et al. 2012. BMC genetics 13(1):53; and Myer et al. 2015. PLOS ONE 10(6): e0129174), end point samples may not be satisfactory to adequately define an existing state within a population. Studies examining bovine nutrition with regard to the ruminal microbiome routinely rely on differences in diet or diet transitions, where the length of the study is defined by traditional nutritional parameters and historical data, not taking into account microbial acclimation to the study ration. The ruminal microbial temporal stability following such perturbations has yet to be determined. Thus, diet acclimation prior to experiments, diet re-acclimation among experimental periods, and other dietary changes in cattle gut microbiome studies may confound microbial characterization when temporal variation and stability are not taken into consideration. These patterns of variation may have significant implications when aiming to determine relationships between the gut microbiome and nutrition in cattle.

Fifty steers of approximately seven months of were obtained. The steers weighed 264±2.7 kg at the beginning of the trial. The steers grazed on cool-season grasses until being transferred to the GROWSAFE system for a 14d adaptation period. Animals were placed on a step-up diet during the 14d adaptation period and transitioned to a growing diet (11.57% crude protein and 76.93% total digestible nutrients on a dry matter basis) with 28 mg monensin/kg DM. A 70d feed efficiency trial was administered following the acclimation period. Weekly, body weight (BW) via chute scale, rumen fluid samples via gastric tubing, and blood samples via coccygeal venipuncture were collected. (See Krysl and Hess. 1993. Journal of Animal Science 71(9): 2546-2555). Approximately 100 mL of rumen content were transferred to 50 mL conical tubes, rumen content pH determined, and samples stored at −80° C. Feed intake was continually monitored via the GROWSAFE system throughout the 70d feed efficiency trial.

Rumen samples were centrifuged at 4,000 rpm for 15 min, were isolated using the POWERVIRAL Environmental RNA/DNA Isolation Kit (Mo Bio Laboratories, Inc., Carlsbad, CA, USA). The 16S rRNA gene was amplified for Illumina sequencing. Following amplification, PCR products were verified with a standard agarose gel electrophoresis and purified using AMPure XP bead (Beckman Coulter, Brea, CA, USA). The purified amplicon library was quantified and sequenced on the MiSeq Platform (Illumina, San Diego, CA, USA) according to standard protocols (Flores, Caporaso et al. 2014). Raw fastq read were de-multiplexed on the MiSeq Platform (Illumina, San Diego, CA, USA).

All raw sequencing data was trimmed of adapter sequences and phred33 quality filtered using Trim Galore (See Krueger and Galore. A wrapper tool around Cutadapt and FastQC to consistently apply quality and adapter trimming to FastQ files. 2015). 16S taxonomic sequence clustering and classification was performed on filtered sequencing data with the RDP 16S rRNA database. (See Edgar. SINTAX: a simple non-Bayesian taxonomy classifier for 16S amplicon reads. BioRxiv. 2016. 074161; Edgar and Flyvbjerg. Bioinformatics. 2015. 31:3476-3482; and Cole et al. Nucleic Acids Research. 2013. 42:D633-D642).

Downstream analysis was performed in python. PCoA was performed on Bray-Curtis distances and statistical significance was assessed through Analysis of Similarities (ANOSIM). (See Clarke. Austral Ecology. 1993. 18:117-143). Alpha diversity was measured both in dominance and singletons. (See Hammer et al. Palaeontol Electronica. 2001. 4:1-9). Regression based analysis was performed through Ordinary Least Squares (OLS) regression. (See Shi et al. The Annals of Applied Statistics. 2016. 10:1019-1040). Feature selection and supervised machine learning was performed on completed data through Random Forests. (See Breiman. Machine Learning. 2001. 45:5-32).

Other measurements of α-diversity, including equitability, Simpson's Evenness E, Shannon's Diversity Index, and Observed OTU, were assessed for normality using SAS 9.4 using the PROC UNIVARIATE command (SAS Institute, Cary, NC). All variables were found to follow a non-normal distribution, and were analyzed using Wilcoxon Rank Sum and Kruskal Wallis test.

Figure 4:
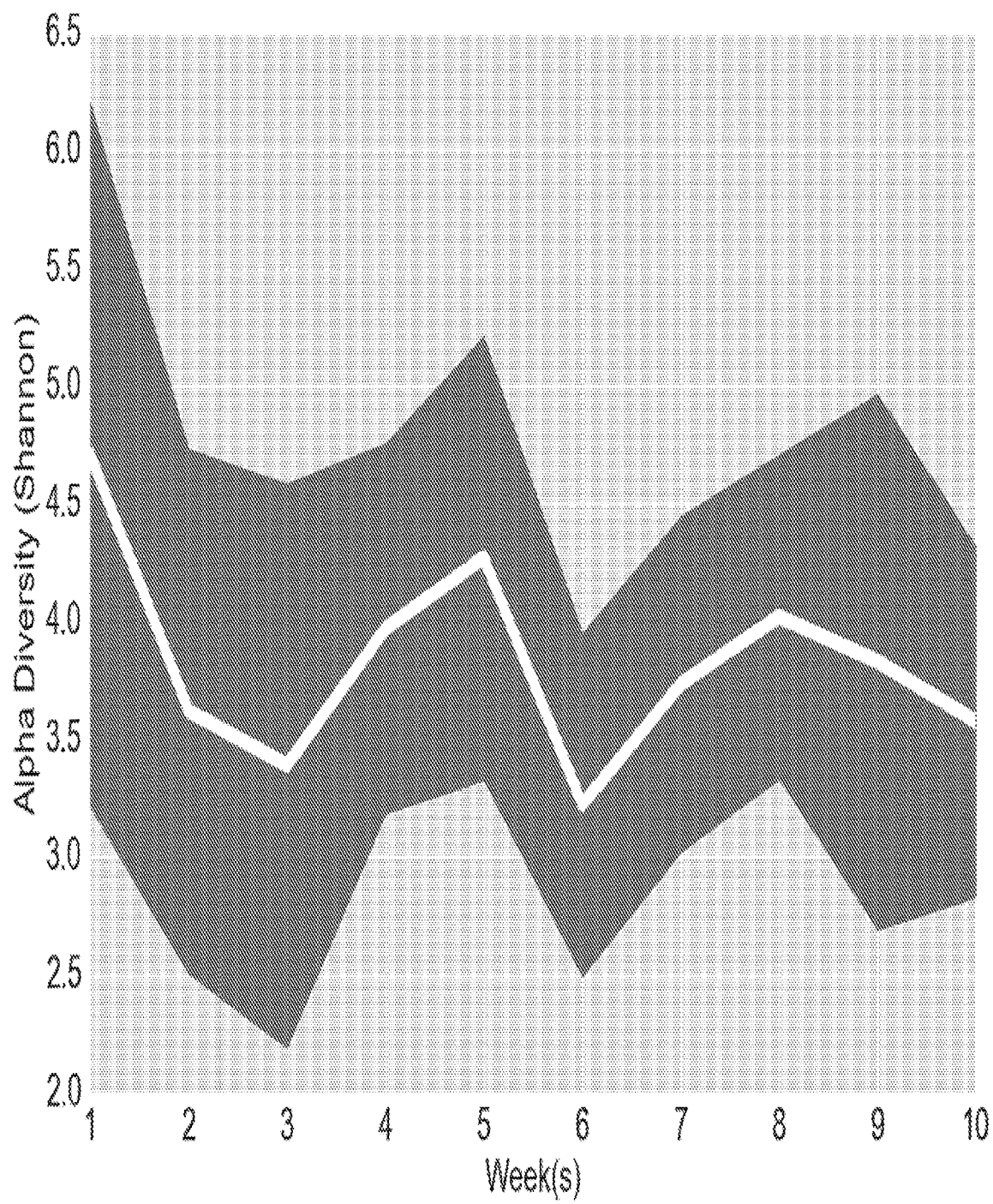
FIG. 4 depicts the large change in microbial alpha-diversity as an animal continues to be fed a finishing diet.
Figure 5:
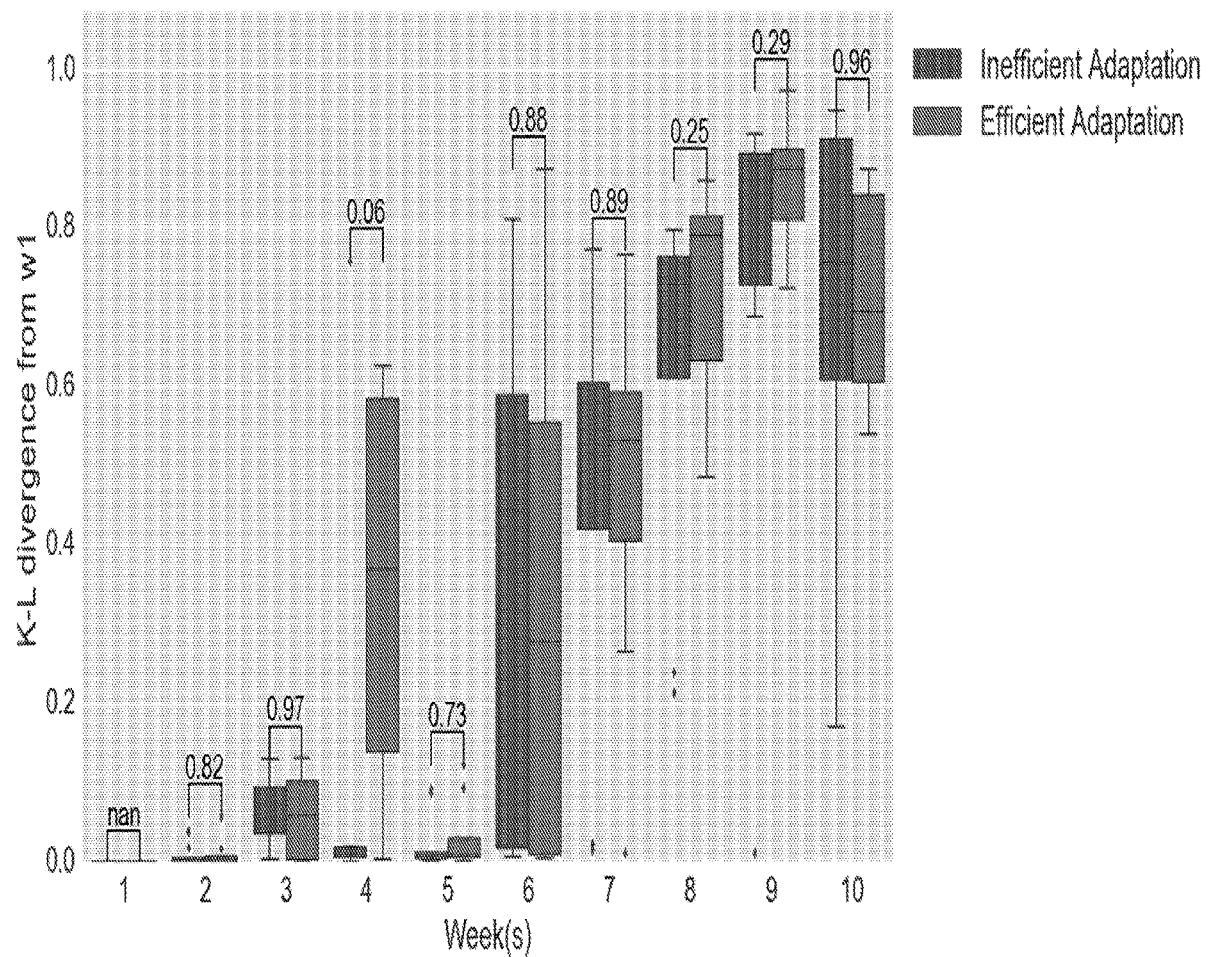
FIG. 5 depicts the importance of the speed of microbial successions into a streamlined microbial ensemble related to animal efficiency. Furthermore, the large shift in the rumen microbiome on week 4 is most significant when related to efficiency.
Figure 25:
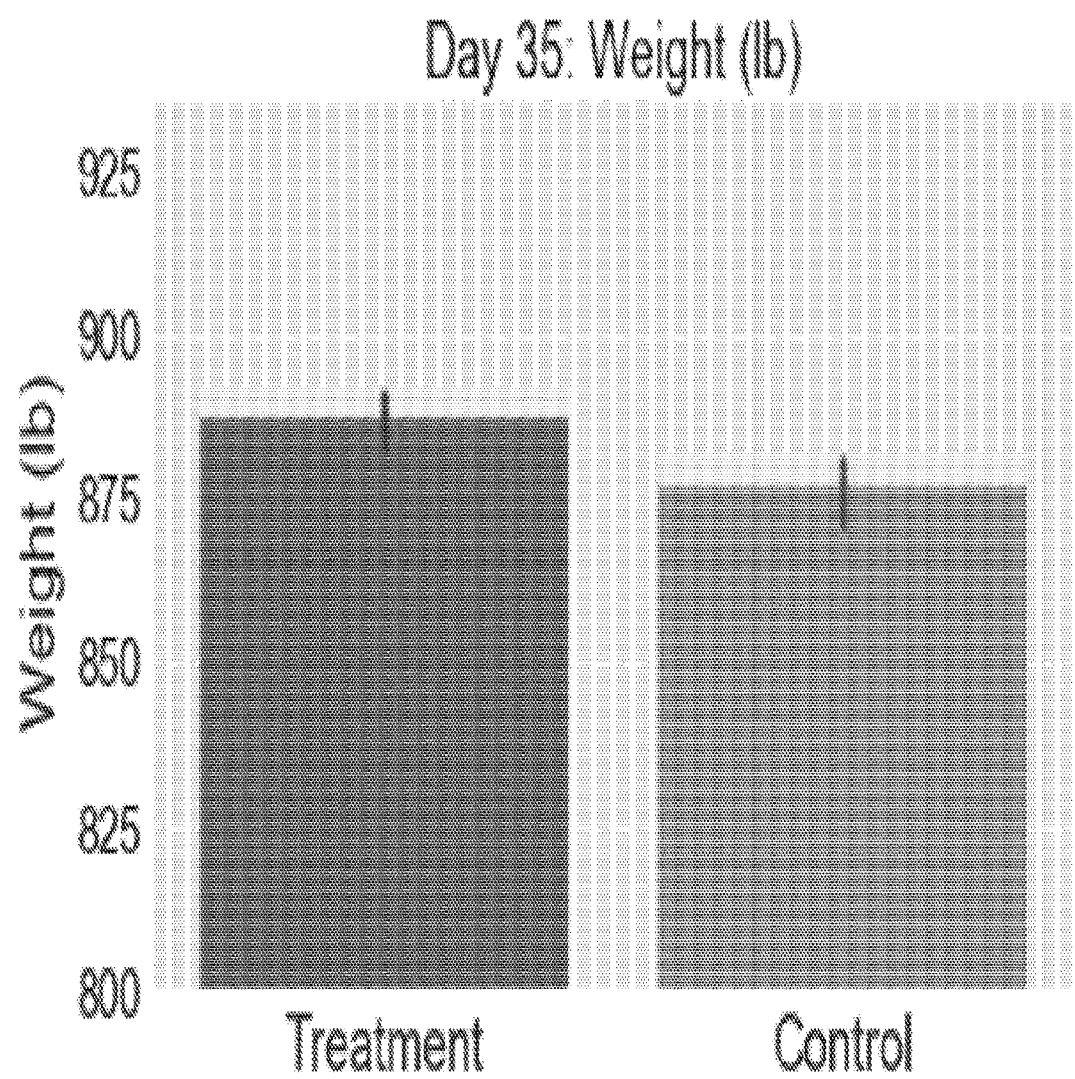
FIG. 25 depicts the evaluation of the microbes of the present disclosure and their ability to modulate weight in the animal, particularly the ability to increase the weight of the animal.

Alpha-diversity was measured using, equitability, Simpson's Evenness, chao1, Shannon's Diversity Index, and observed OTU. Good's coverage was also measured to ensure satisfactory coverage of OTU for each week. Shannon's Diversity Index was greatest at the beginning of the trial (4.66±0.32), but decreased overall by the end of the trial (3.61±0.14; P<0.0001). Observed OTU also was greater during the first week (160.14±12.83) compared to the final week (57.9±2.5; P<0.0001). Equitability was greatest during week 1 of the trial (0.66±0.03), fluctuated throughout the trial, but was lower at week 10 (0.61±0.02; P<0.0001). Whereas several metrics related to richness increased from week 1 to week 10, overall evenness fluctuated greatly (P<0.0001) but was numerically similar by the end of the trial (0.12±0.02) to the first week of the trial (0.13±0.01). Greater phylogenetic diversity was observed at week 5 compared to week 1, but decreased by week 10 as evidence by spatial co-clustering. The rumen microbial community began to shift at week and reached stabilization by week 10. Three orders were identified as changing significantly during the shift to the final microbial community, including Pasteurellales, Aeromonadales, and Bacteriodales. The shift to the final bacterial community composition began to occur at week 4 (FIG. 4). Several physiological factors were predictive of the rumen microbial community. Rumen pH was correlated with α-diversity (P=0.005; FIG. 4) at week 5 and predictive of rumen microbial community signature at week 10 (FIG. 25).

The diversity of the rumen bacterial community was greatest at the start of the trial, following a field-standard two week adaptation period to the growing diet and was greatly variable throughout much of the trial. Rumen bacterial community diversity was lowest by the end of the trial, at ten weeks following the adaptation period. The rumen bacterial diversity was greatest at the start of the trial following the adaptation period, but reached stability by ten weeks. The transition from a predominantly forage-based diet to a diet incorporating concentrates causes a shift in bacterial taxa due to changes in substrate type (See Tajima et al. 2001. Applied and Environmental Microbiology 67(6): 2766-2774). These differences in nutrient availability to the microbes may have resulted in a state of microbial community dysbiosis as bacterial populations competed for nutritional sources, increased functional redundancy occurred, and the physical environment of the rumen, such as pH, changed (See Whittaker. 1972. Taxon 21(2/3): 213-251).

Dietary transitions, adaptation periods, and wash-out periods are often incorporated into nutritional studies, including those involving the rumen microbiome adaptation and wash-out periods have historically spanned anywhere from several days to four weeks, which previous studies have suggested is adequate time for acclimation, as reviewed by (See Brown et al. 2006. Journal of Animal Science 84(13_suppl): E25-E33) and supported by recent nutritional microbial studies (See Anderson et al. 2016. Journal of applied microbiology 120(3): 588-599). However, in this study, it took approximately ten weeks for the rumen microbial community to stabilize, a time frame much longer than traditionally utilized for adaptation or wash-out periods. Although cattle may physically acclimate to feed within a two week period, the results of this study suggest the rumen microbiome requires additional time to stabilize.

At week 4 of this study, three orders appeared to drive the shift to a stable bacterial community composition, including Aeromonadales, Pasteurellales, and Bacteroidales. Two of these orders, Aeromonadales and Pasteurellales, belong to the phylum Proteobacteria, and Bacteroidales belongs to the phylum Bacteroidetes. Proteobacteria and Bacteroidetes are typically two of the three most prevalent bacterial phyla found in the rumen but bacteria belonging to the phylum Firmicutes are frequently found to be the most abundant in the rumen, followed by Bacteroidetes and Proteobacteria in cattle on a primarily forage-based diet. However, as cattle transition to incorporate more readily-fermentable feedstuffs, Bacteroidetes becomes the dominant phylum.

The changes in abundances of these orders also provides additional insight given their function in the rumen. At week 4, relative abundance of Aeromonadales sharply decreased, whereas Bacteroidales and Pasteurellales both increased at week 4. Some rumen microbes belonging to Aeromonadales, including Ruminobacter and Succinovibrio, are fibrolytic in nature and found in conjunction with high-fiber diets, which may account for the decrease in abundance of those microbes as the rumen microbiome adapted to the more readily digestible diet. Genera found in Bacteroidales and Pasteurellales, including *Prevotella* and *Actinobacillus*, respectively, are important for digestion of protein and carbohydrates. Rapid production of byproducts of metabolism, such as organic acids, by Bacteroidales and Pasteurellales may be responsible for the shift in pH seen in week 5, which was also indicative of rumen microbiome signature. The diet fed in this study included feedstuffs that are more readily fermentable, which can cause decreases in rumen pH due to increased production of organic acids such as lactate. This can shift the bacterial community composition towards those bacteria that are more tolerant of low pH, including those in Bacteroidales and Pasteurellales (See Fernando et al. 2010. Applied and Environmental Microbiology 76(22): 7482-7490).

Example V. Dynamics Mediating Efficiency with a High Corn Diet

The lactate and other acids produced in the rumen are generally considered the main drivers of acidosis and feed inefficiency in high corn or grain intensive diets, like those provided in beef/cattle feedlots. Many in the art believe that higher concentrations of volatile fatty acids (VFAs) induce acidosis, and that lactate producers dominate the rumen microbiome during acidosis, dropping the pH faster than other fermentation acids. Many believe that bringing acidotic feedlot cattle back to a healthy state requires increasing the ruminal pH by reducing lactate and VFA concentration, or through the use of feed additives such as buffers for pH stability or ionophores to inhibit lactate producers.

The table that occurs in FIG. 6 identifies the ruminal VFA concentrations and pH of Blank Angus steers between high RFI and low RFI at week 10. The low RFI animals tended to have a higher production of VFAs compared to the high RFI animals, and the pH is similar for both groups.

The pH is measured by taking the $pK_a$ plus the log of $HCO_3-$ divided by dissolved $CO_2$ ($dCO_2$). $CO_2$ is known to play a key role in respiration and blood buffering, and it likely plays a large role in pH regulation of the rumen. In the rumen, $CO_2$ is present in the rumen gas cap and the rumen liquid. Most is in the rumen liquid as $dCO_2$ as a base (bicarbonate) or as an acid (carbonic acid). The $CO_2$ in the liquid transforms into carbonic acid (~1%), which quickly dissociates to bicarbonate, the primary base in the rumen fluid. (See Laporte-Uribe. 2016. Animal Feed Science and Technology. 219:268-279). Thus, as fermentation progresses, $dCO_2$ becomes the main species, which may lead to pH decline. High levels of $CO_2$ reduce the buffering capability of the rumen.

There are many different microbial pathways that utilize carbon dioxide. Three different bacterial carbon fixation pathways exist in nature: (1) the Calvin cycle, (2) the Wood-Ljungdahl pathway, and the reductive TCA.

High partial pressures of $CO_2$ in the rumen favors carbon dioxide fixers and the utilization of these pathways.

Figure 7:
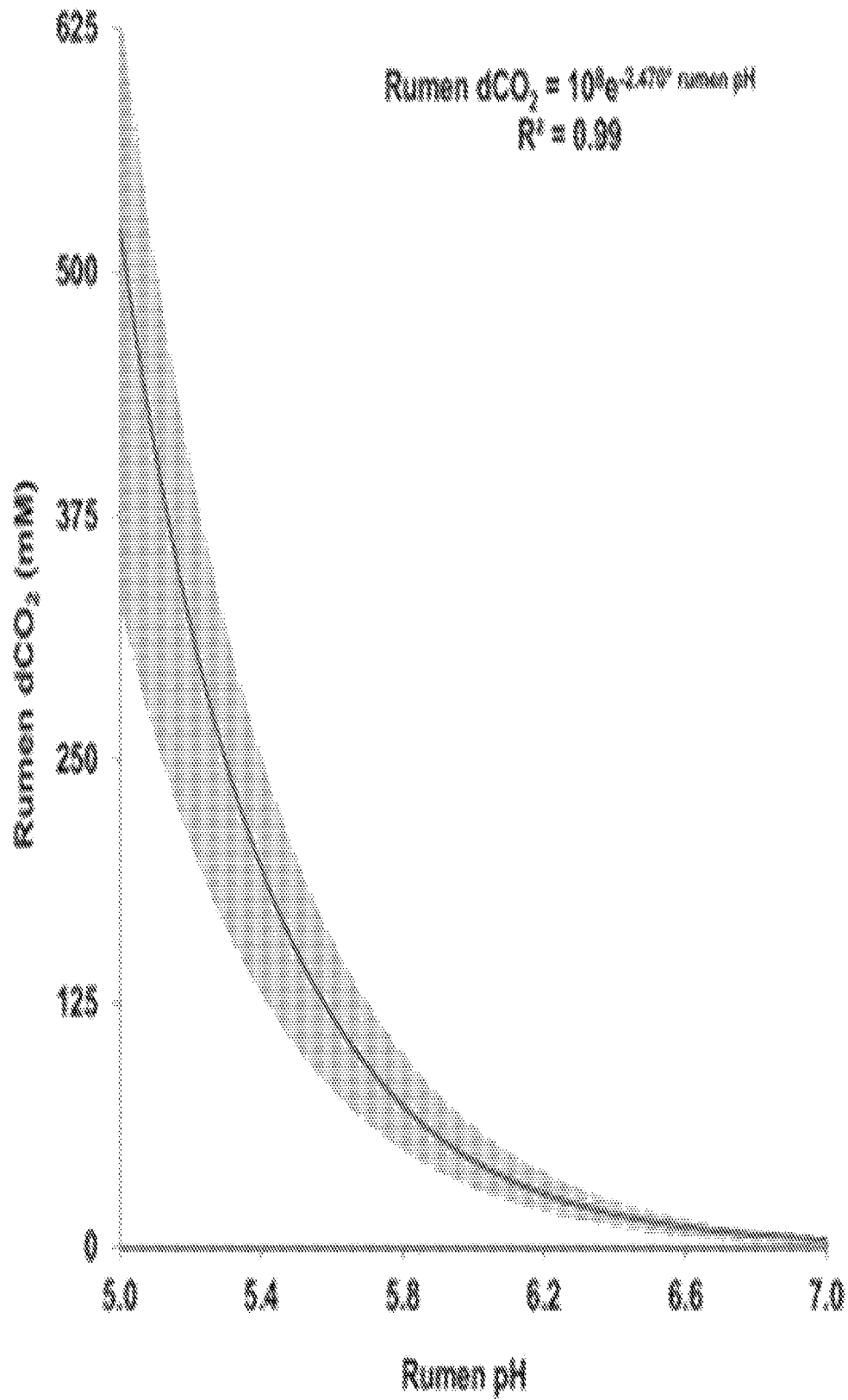
FIG. 7 depicts the theoretical concentrations of dissolved $CO_2$ with respect to rumen pH. Reproduced from Laporte-Uribe, 2016.
Figure 8:
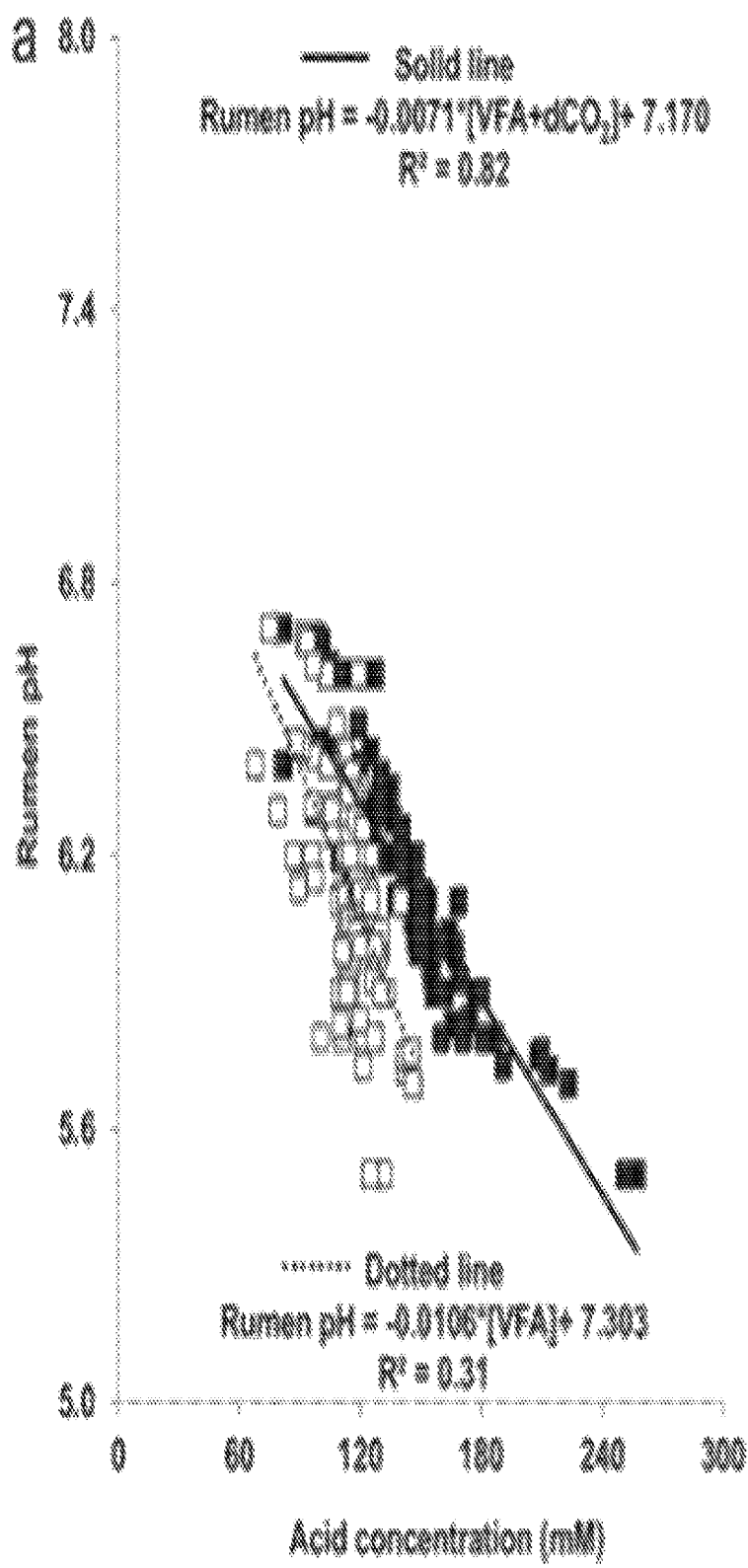
FIG. 8 depicts the theorized pH of the rumen based on both VFA concentrations and $dCO_2$ concentrations (filled squares), and VFA concentrations alone (open squares). Including $dCO_2$ better predicts pH than VFAs alone. Reproduced from Laporte-Uribe, 2016.

Although previously deemed negligible, modeling suggests that $dCO_2$ concentrations can be very high, and a better predictor of ruminal pH. FIG. 7 depicts the theoretical concentrations of dissolved $CO_2$ with respect to rumen pH. FIG. 8 depicts the theorized pH of the rumen when taking into account both VFA concentrations and $dCO_2$ concentrations and VFA concentrations alone. The inclusion of $dCO_2$ in the pH prediction is more accurate than utilizing VFAs alone. Modeling and extrapolation of existing data shows that as pH declines, $dCO_2$ concentration values could increase above the theoretical maximum of 50 mM. Morgante et al. (2009. Comparative Clinical Pathology. 18(3): 229-232) support these models and extrapolations.

Figure 9:
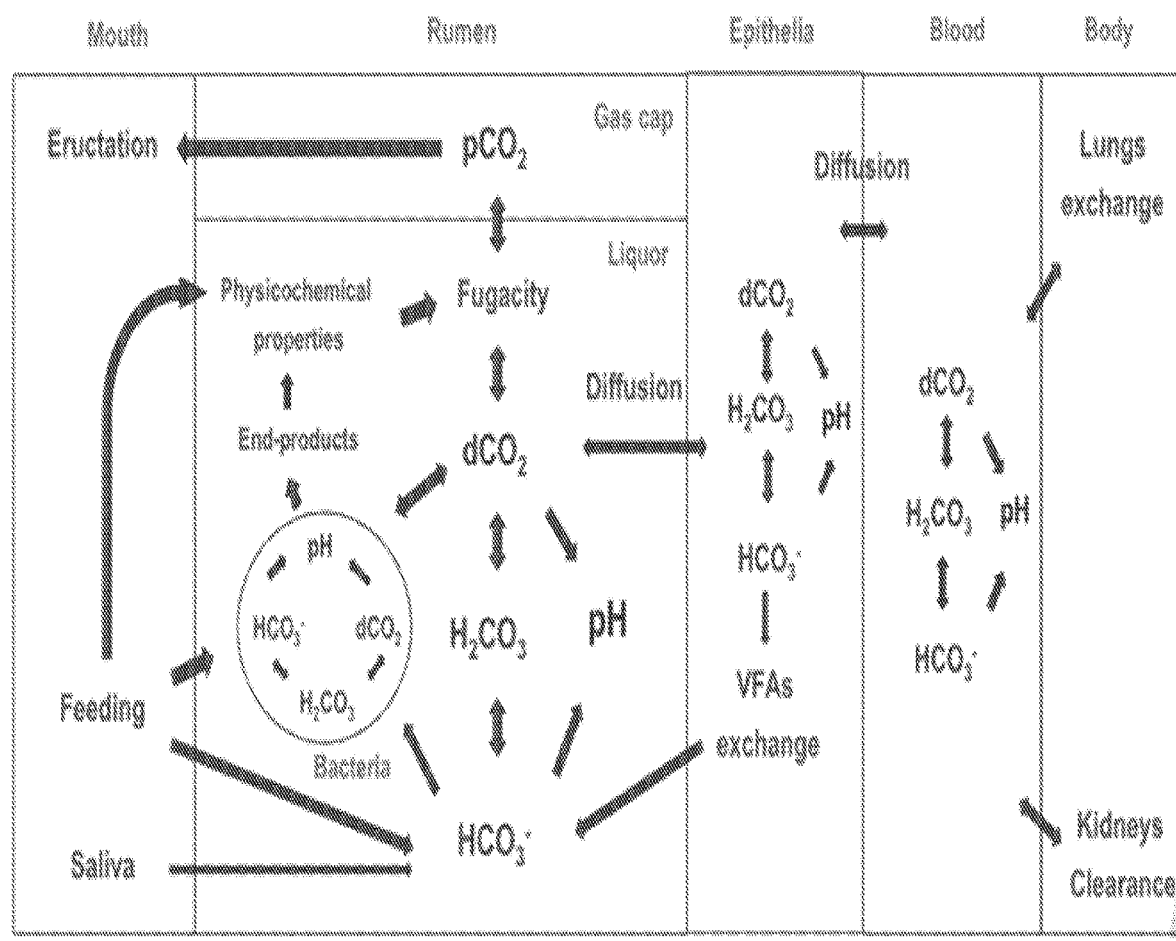
FIG. 9 depicts the potential path ruminal CO2 may follow to impact the physiology of a ruminant. Reproduced from Laporte-Uribe, 2016.
Figure 17:
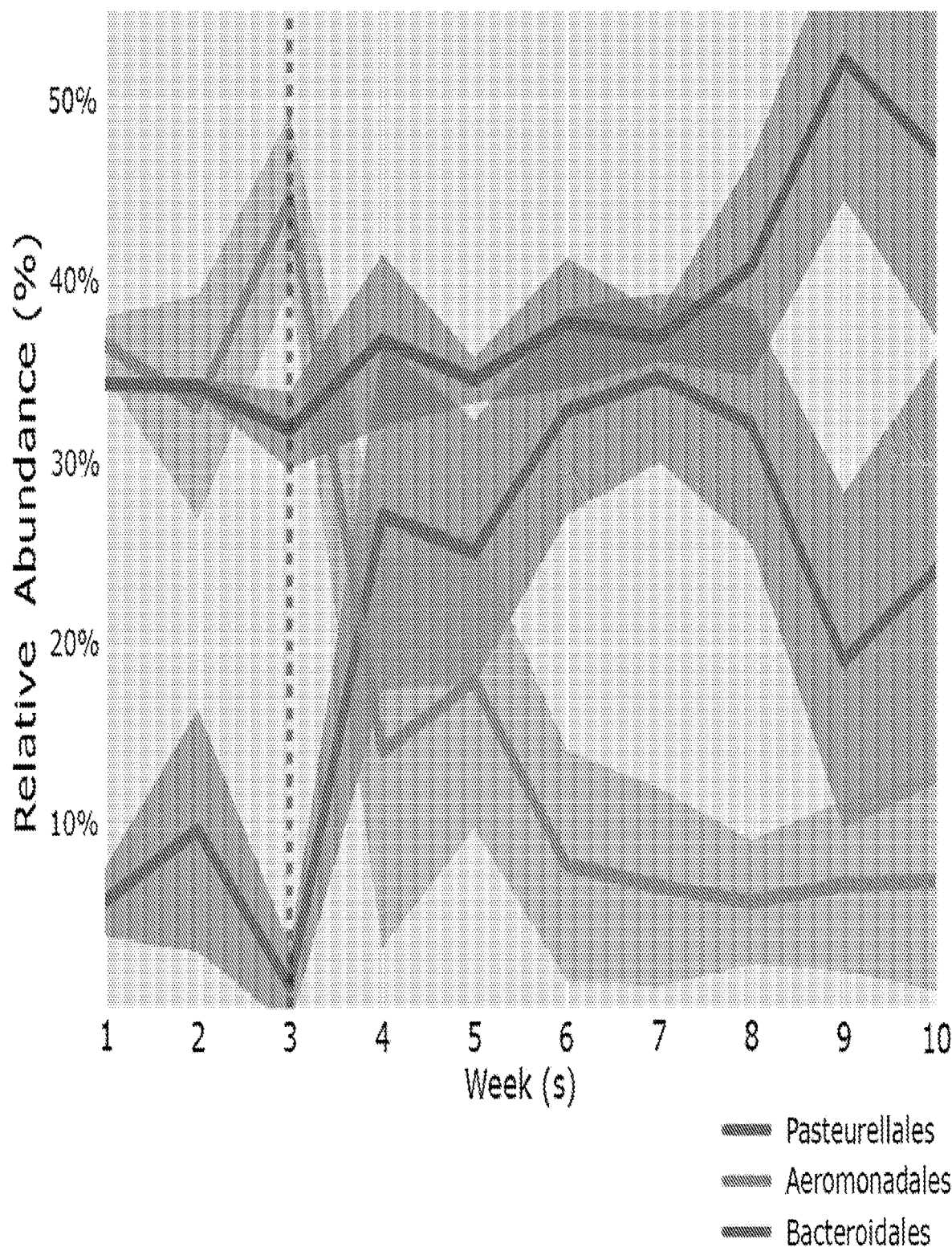
FIG. 17 depicts the relative abundance of three bacterial orders driving the shift in bacterial community composition throughout the 10-week trial. Shaded regions indicate SEM. These three order are important to RFI. A major microbial succession occurs in week 4.
Figure 18A:
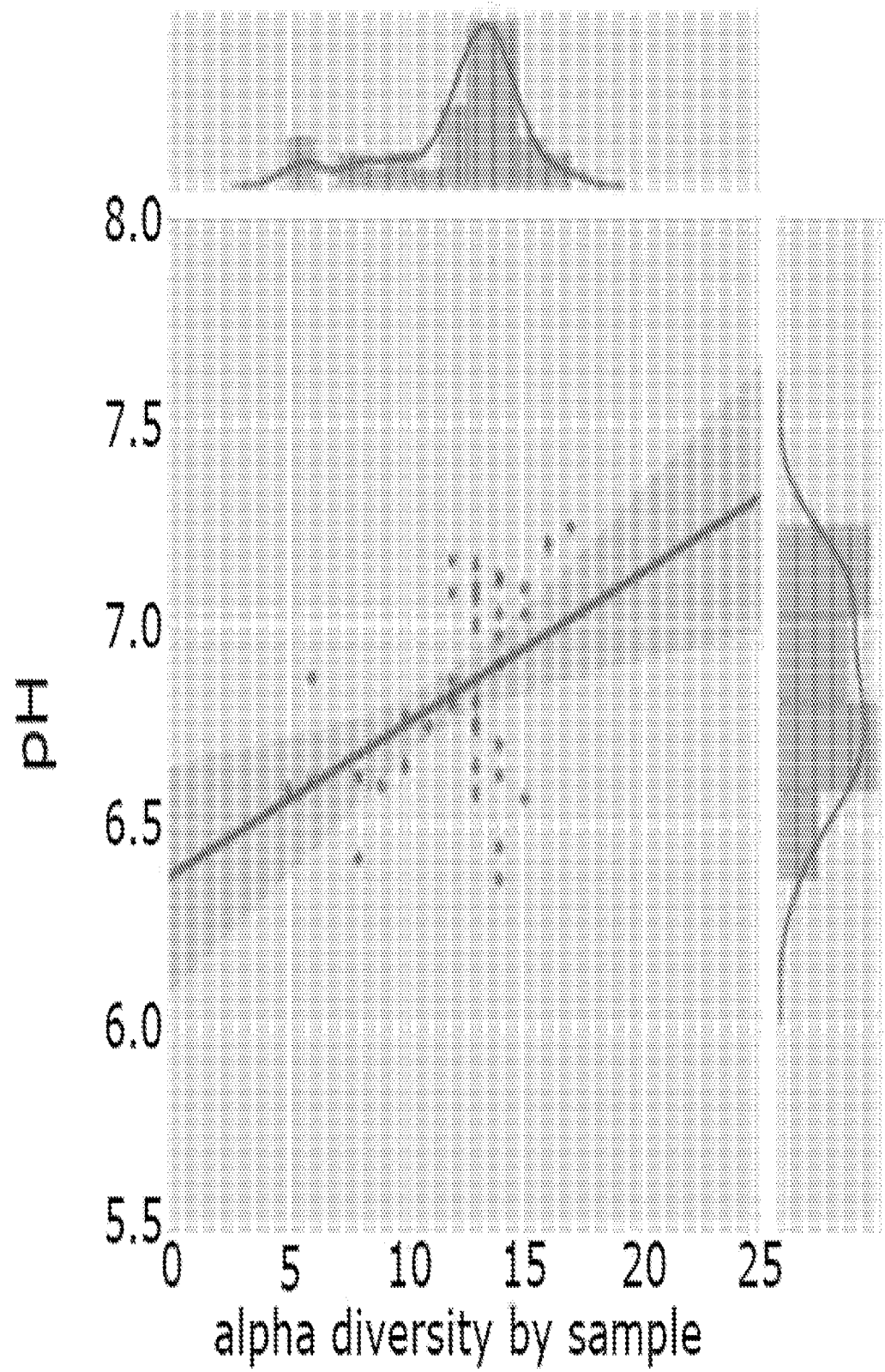
FIG. 18A and FIG. 18B depicts the microbial differentiation over pH between animals on week 5 following the large microbial succession in the rumen on week 4. Rumen alpha-diversity correlated with pH (Pearson R=0.44; P=0.0051) (FIG. 18A). Rumen pH is predictive of bacterial community structure at week 5 ($R^2$=0.48; P=0.04) (FIG. 18B). PC=Principle Component.
Figure 18B:
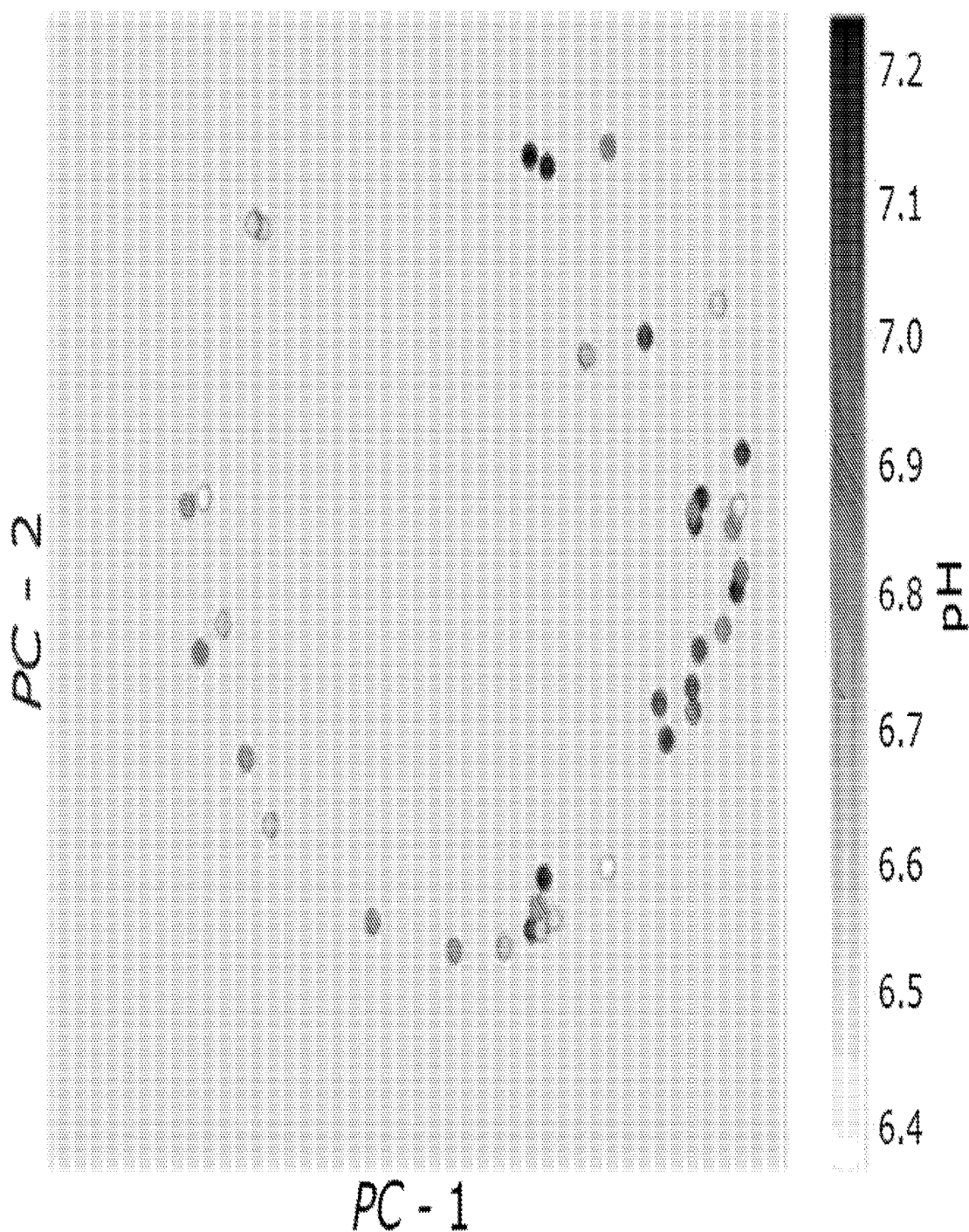
Figure 19:
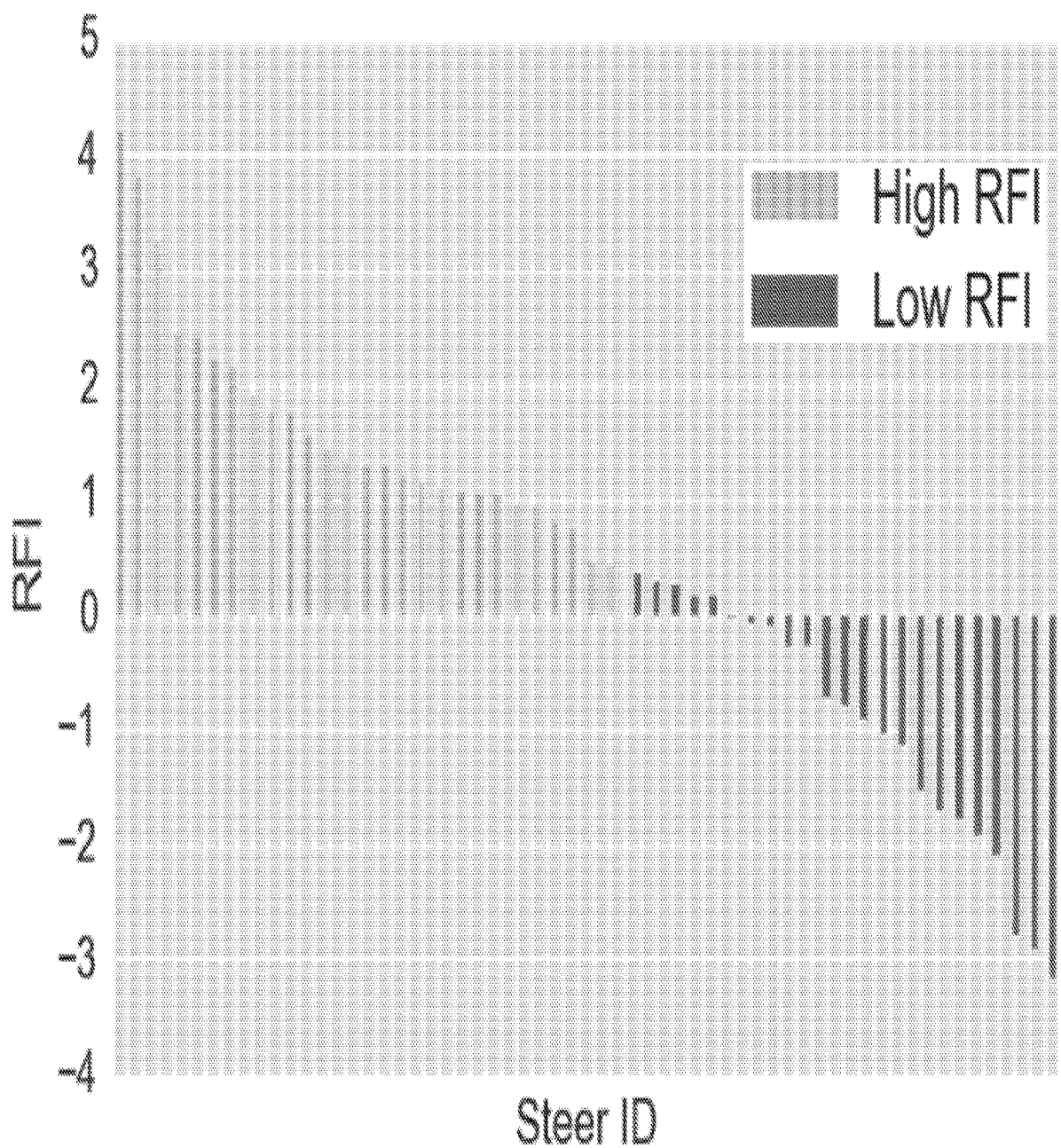
FIG. 19 depicts the plot of the residual feed intake (RFI) of the 50 steers.
Figure 20:
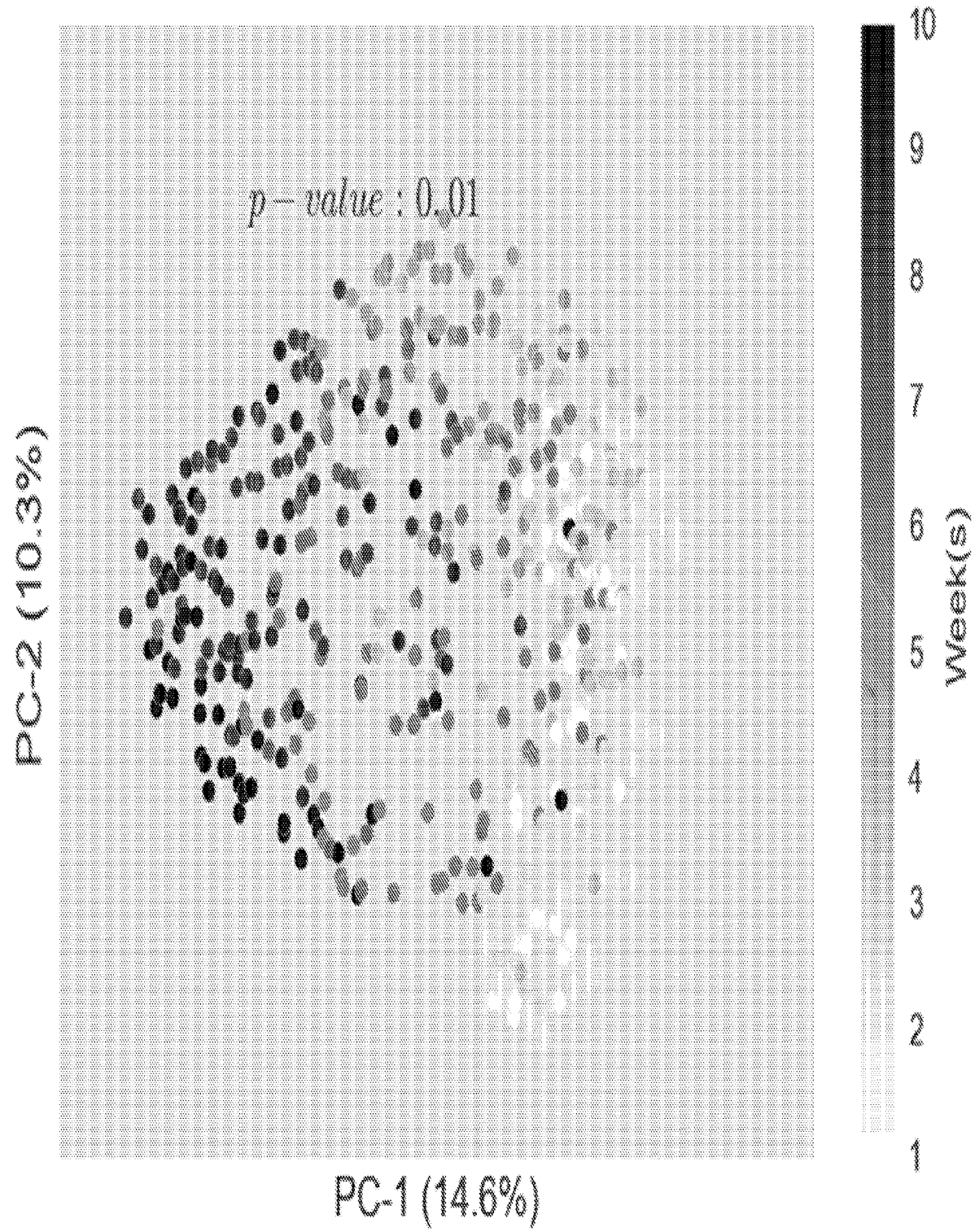
FIG. 20 depicts a principal coordinate analysis (PCoA) of all samples throughout the study. Each dot represents a rumen sample's bacterial community, and the distance between dots represents the difference between those communities. The shading of each dot represents the time in weeks when the sample was taken.
Figure 21:
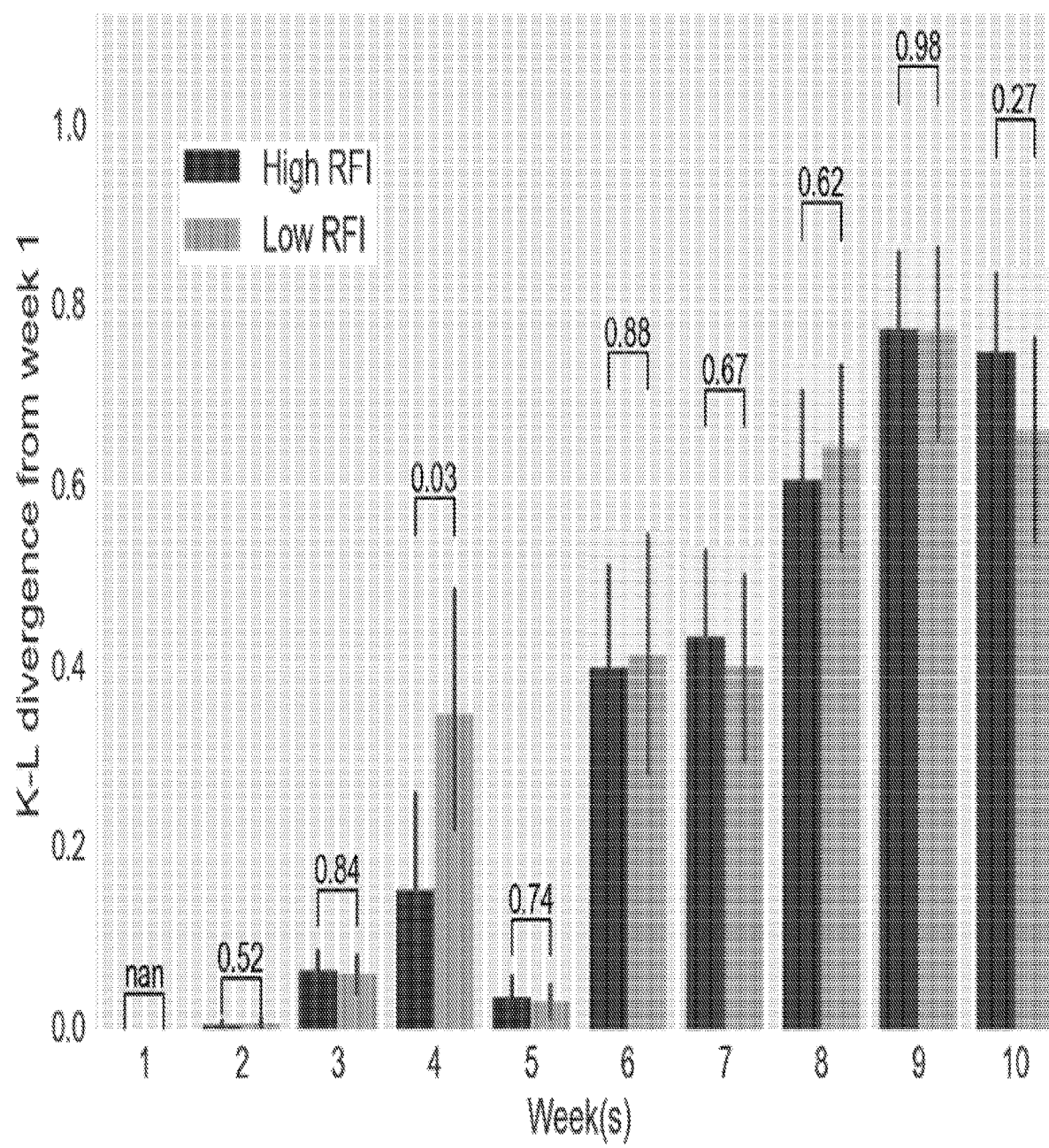
FIG. 21 depicts a Kullback-Leibler (K-L) divergence. The K-L divergence is a method for determining the commotional distance between two sets (i.e., difference between two sample's microbial communities).
Figure 22:
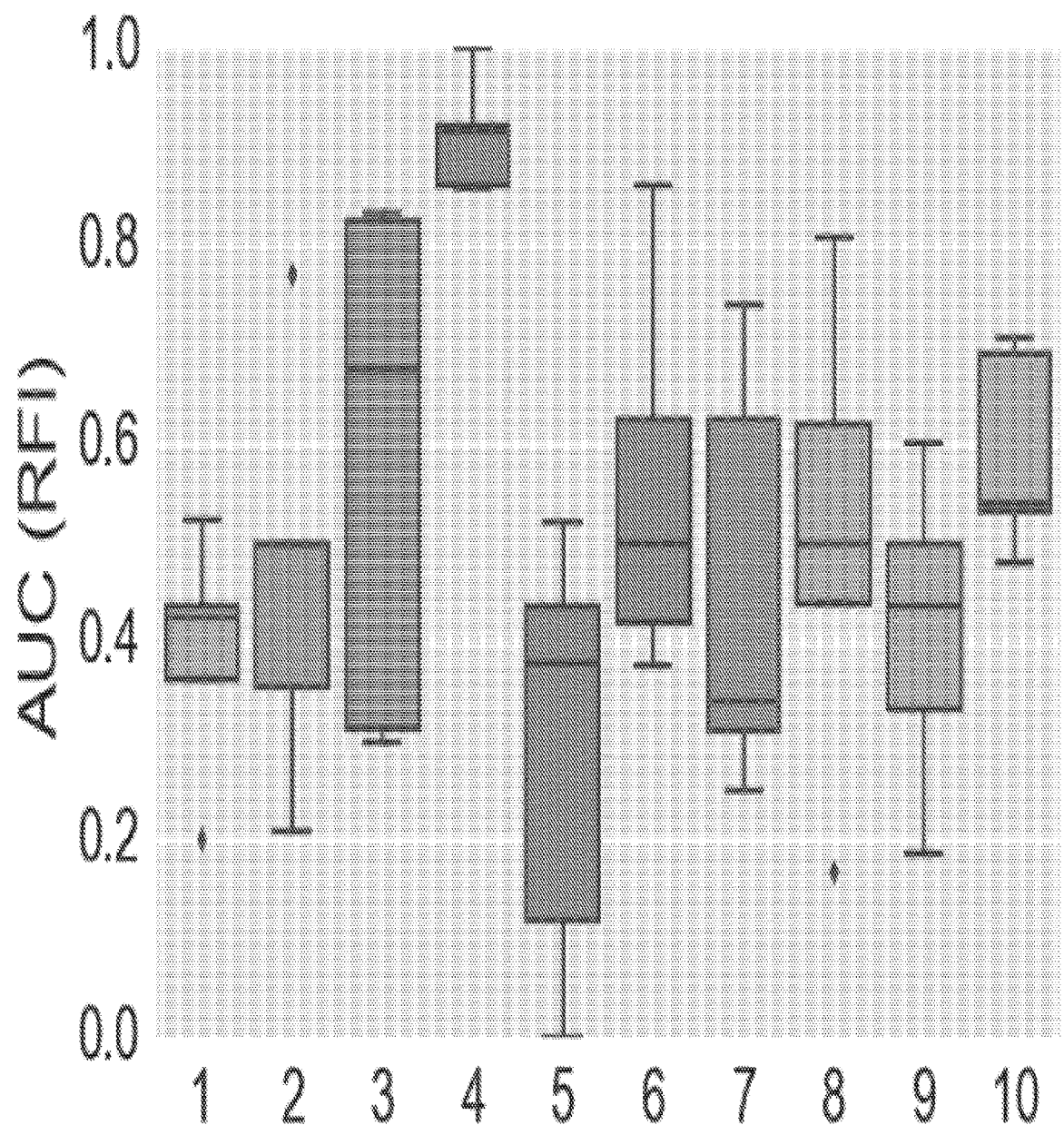
FIG. 22 depicts the AUC for the residual feed intake. Random Forests machine learning was used to predict the RFI on any given week given the microbial community composition. The microbial community is most predictive of RFI at week four.
Figure 23:
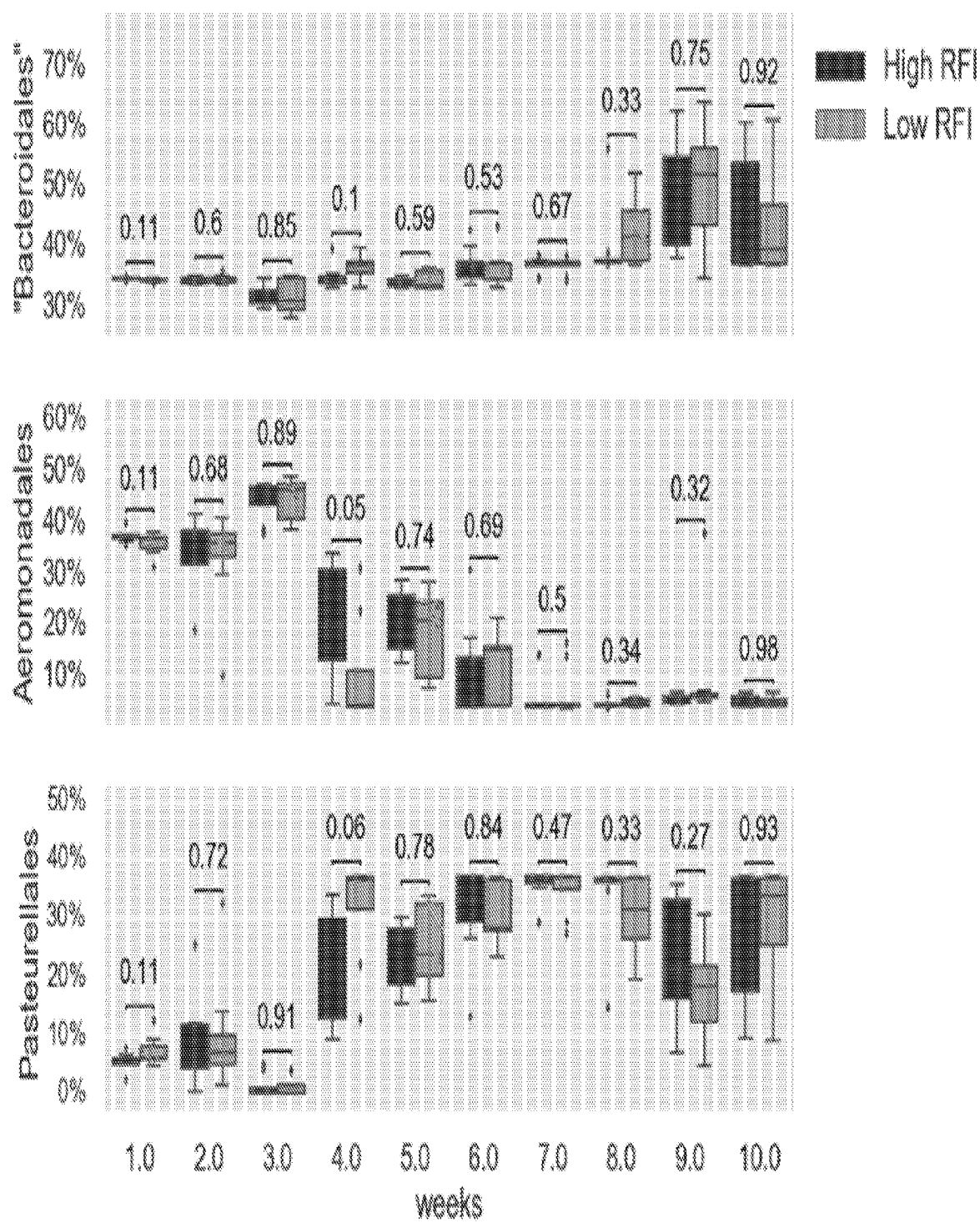
FIG. 23 depicts the abundance of three taxonomic orders by week separated by RFI, which indicates the taxa that are having a direct correlation with RFI and at what time. The figure shows that week four is important for Aeromonadales and Pasteurellales populations in relation to RFI.
Figure 24:
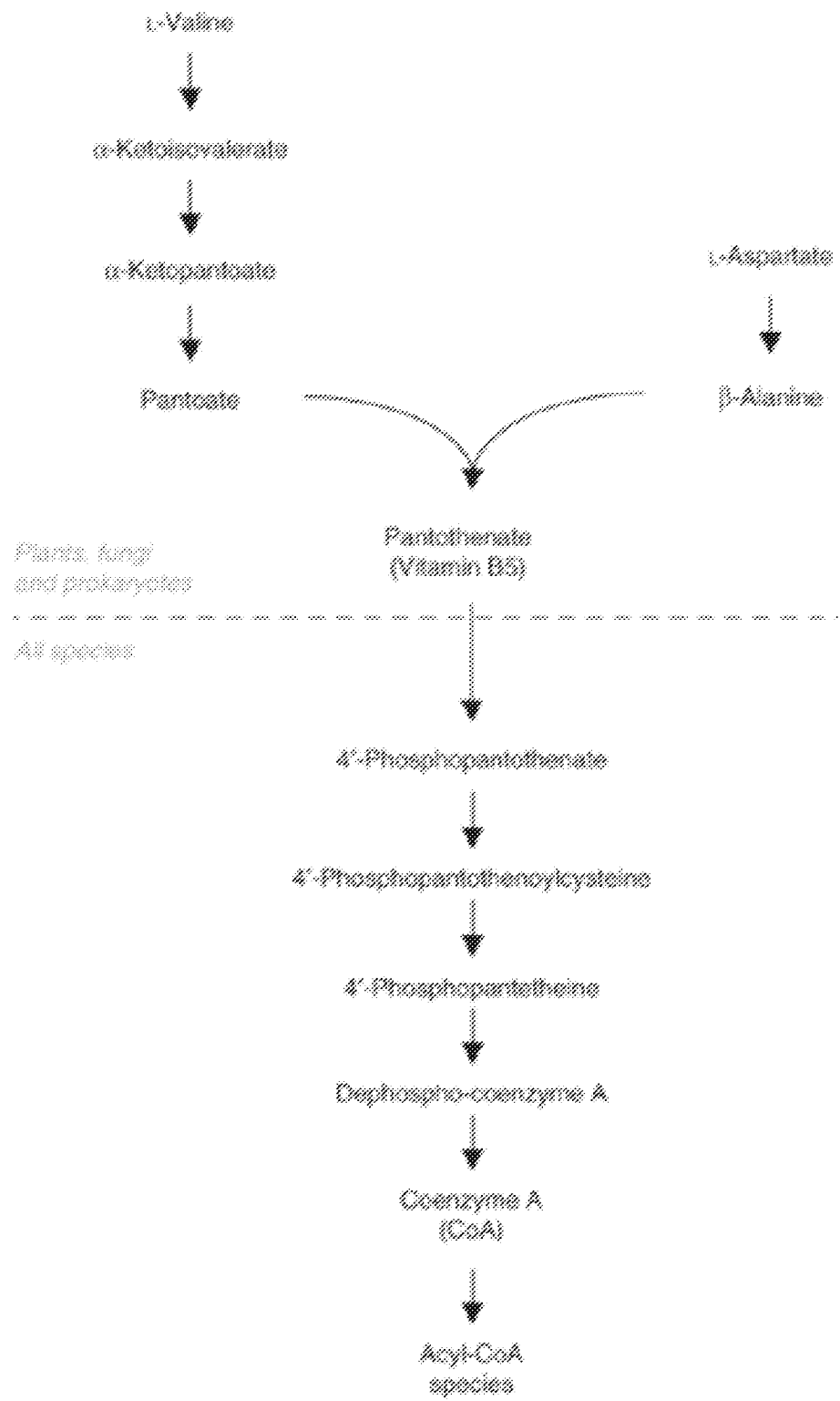
FIG. 24 depicts a flow chart for the synthesis of Vitamin B or pantothenate, and the intermediate products produced to arrive at Acyl-CoA species. Reproduced from Basu and Blair. 2012. Nature Protocols. 7:1-11.

The high $CO_2$ concentrations in the rumen create systemic physiological health problems for the animal. (See FIG. 9). The ruminal microbial metabolism can shift due to changes in the stoichiometry for VFA concentrations that can result in lactate production, and further increase histamine and LPS production. Nutritional diseases related to high $dCO_2$ concentrations cause issues in the rumen due to foaming and high viscosity. High $dCO_2$ concentrations result in rumen acidosis, increased bloat, and abomasal dysplasia. Nutritional diseases related to rumen $dCO_2$ and high $dCO_2$ diffusion include respiratory and metabolic acidosis, modulated immune responses, laminitis, ketosis, liver disease, and liver abscesses. Fat and cholesterol can also mobilize to reduce $dCO_2$ absorption, creating other deleterious physiological health problems for the animal. FIG. 17 indicates that many $CO_2$ related microbes become abundant throughout the survey experiment. Many Clostridia, *Prevotella* (Bacteroidales), and other acetogens utilize $CO_2$ and hydrogen to produce acetate.

Example VI. Acidosis Challenge

Sixteen heifers are cannulated, eight controls and eight experimental. The experimental group is to receive six types of rumen microbes directly administered to the rumen daily.

The treatments are run as a 2×2 cross-over design with two 28 day periods. There are 4-6 weeks for adaptation/step up. A 28 day acidosis challenge uses elevates step-up concentrations in the diet. There is a fourteen day covariate between the periods.

The ruminal pH is measured daily using an eCow eBolus. The rumen content is sampled. 10 mL of venous blood is sampled for oximetry. The weight, contractions of the rumen, and intakes are sampled. The rumen samples are assayed for microbial analysis, VFA analysis, and $dCO_2$.

The diet is as follows:

| Item, % of DM | Control Diet | Acidosis Challenge |
| --- | --- | --- |
| Dry-rolled corn | 66 | 74 |
| Dried distiller's grains | 20 | 20 |
| Corn silage | 10 | 2 |
| Premix | 4 | 4 |

The heifers that received microbes daily are expected to tolerate the acidosis challenge more adeptly than heifers not administered the microbes. The heifers that received the microbes are expected to exhibit (1) a higher ruminal and/or systemic pH during the challenge, (2) lower concentrations of ruminal carbon dioxide, (3) increased feed intake (more consistent intake and greater number of pounds of feed eaten, (4) greater average daily weight gain, and (5) greater final weight; as compared to heifers not having been administered the microbes.

Example VII. Effects of Native Rumen Microorganism Supplementation on the Ability of Heifers to Tolerate High-Grain Diets Experimental Design: Sixteen heifers were cannulated and blocked into two different groups: 8 control animals, and 8 experimental animals. The experimental group received live cells of six different rumen bacterial strains: Ascusbbf_24302, Ascusbbf_4, Ascusbbf_14146, Ascusbbf_154, Ascusbbf_1085, and Ascusbbf_876. Fresh cultures of each strain were prepared, and whole cells suspended in saline were directly administered to the rumen via cannula daily at a dose of 1E9 cells/strain/dose. Control animals received an equivalent volume of of saline daily via cannula.

The ruminal pH was measured daily using an eCow eBolus. Animal weight was measured weekly and feed intakes were measured daily. Rumen content was sampled weekly to determine concentrations of VFAs and carbon dioxide in the rumen, and to determine colonization of administered strains. Venous blood was sampled for oximetry.

Animals were stepped up to the final ration diet over 4 weeks, using 4 intermediate step-up diets that gradually replaced corn silage with dry-rolled corn. The first two weeks (first two step up diets) were used to create a baseline for blocking the animals. After these two weeks, the animals were assigned into either the experimental or control group. Microbe administration began on day 14 and continued until day 35 (21 days of microbe administration).

The diet is as follows:

| Item, % of DM | Final ration |
| --- | --- |
| Dry-rolled corn | 66 |
| Dried distiller's grains | 20 |
| Corn silage | 10 |
| Premix | 4 |

The diet also included a small amount of premix to add micronutrients, Rumensin, and Tylosin.

Figure 26:
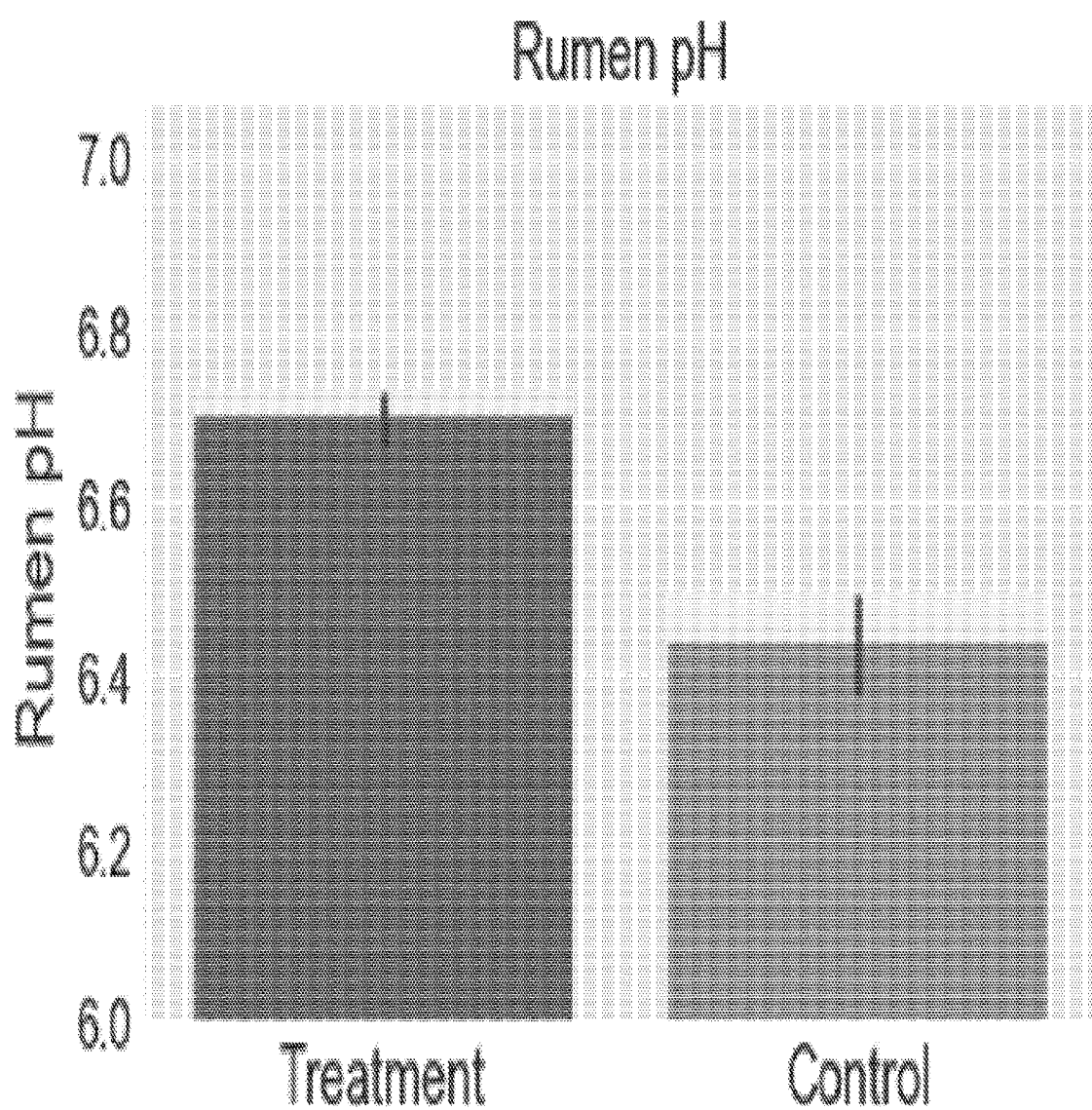
FIG. 26 depicts the evaluation of the microbes of the present disclosure and their ability to modulate pH in the rumen, particularly the ability to increase the pH in the rumen while the animal is being fed a high grain diet.
Figure 27:
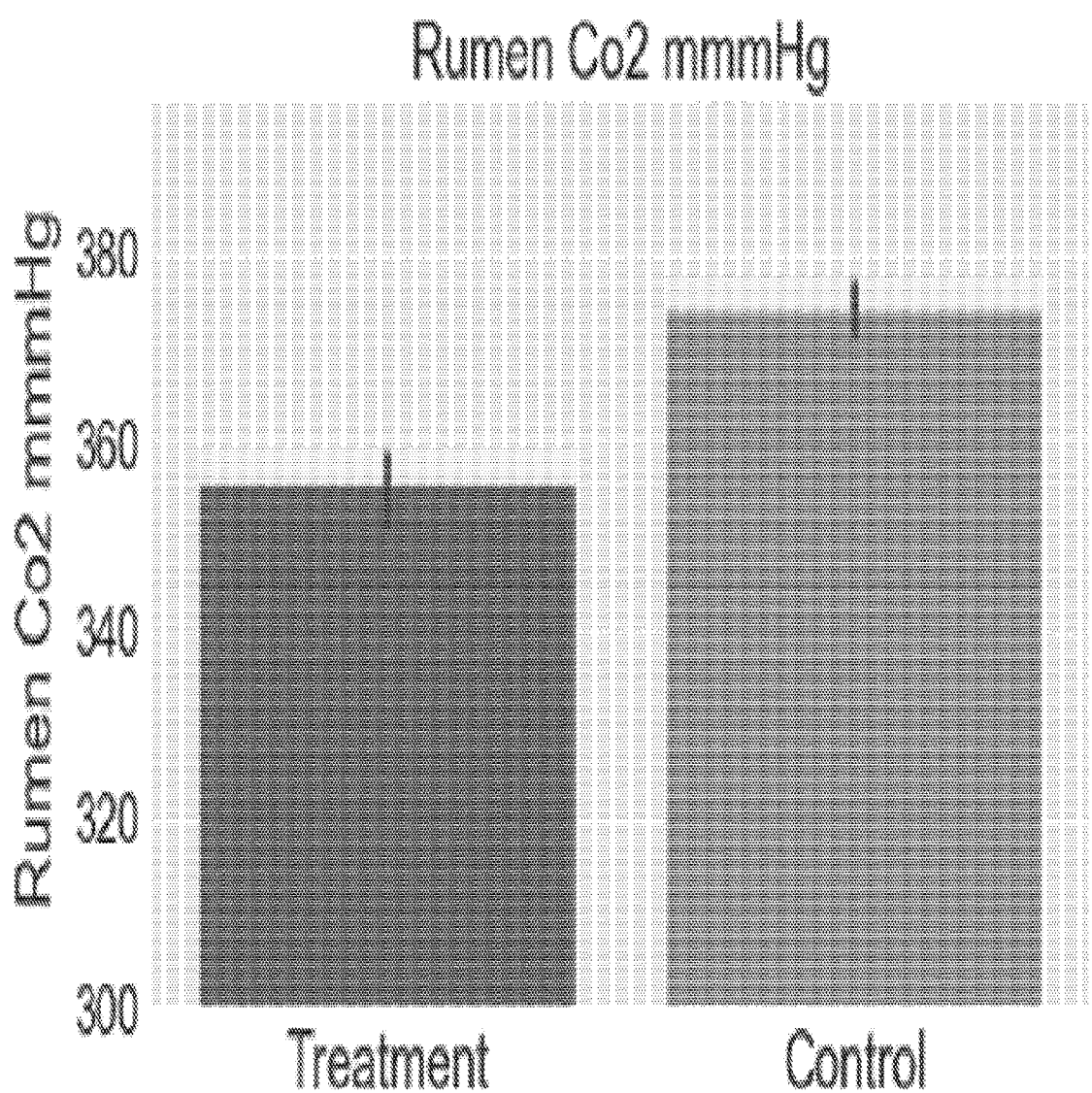
FIG. 27 depicts the evaluation of the microbes of the present disclosure and their ability to decrease CO2 in the rumen.
Figure 28:
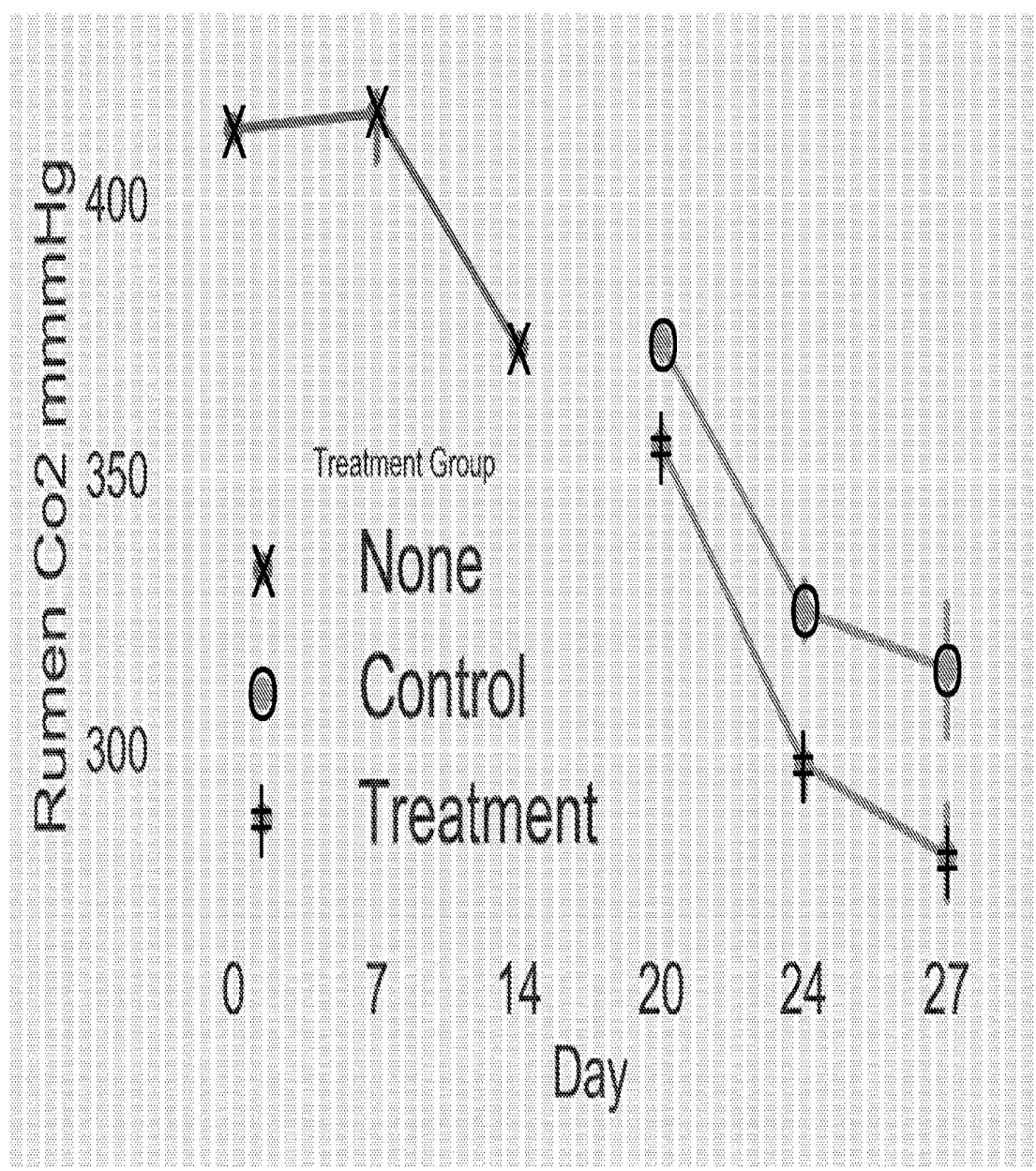
FIG. 28 depicts the evaluation of the microbes of the present disclosure and their ability to modulate CO2 in the rumen, particularly the ability to decrease CO2 in the rumen while the animal is being fed a high grain diet.

Results: Administration of microbes to heifers had a clear impact on the performance of the animal. Animals that received microbes exhibited higher final weights (FIG. 25), and higher rumen pH (FIG. 26) by day 35 of the experiment. Experimental animals also showed lower concentrations of rumen $CO_2$ (FIG. 227) as compared to control animals. As can be seen from FIG. 28, although rumen $CO_2$ concentrations dropped in both groups, $CO_2$ concentrations in the experimental group dropped more rapidly than the control group.

Example VIII. Carbon Fixation Pathways

The whole genomes of ten microbial strains were sequenced, annotated, and analyzed for carbon fixation-related genes.

The reductive citric acid cycle is used by some bacteria to produce carbon compounds from carbon dioxide and water. The cycle contains three critical enzymes in the pathway: 2-oxoglutarate/2-oxoacid ferredoxin oxidoreductase (EC 1.2.7.3), ATP citrate ligase (EC 2.3.3.8), and fumarate reductase (EC 1.3.4.5, 1.3.5.1, 1.3.1.6, and 1.3.4.1 in KEGG carbon fixation pathways). Ascusbbf_1010 and Ascusbbf_14146 contain EC 1.3.5.1. Furthermore, Ascusbbf_14146 and Ascusbbf_154 contain EC 1.3.5.4.

Figure 30:
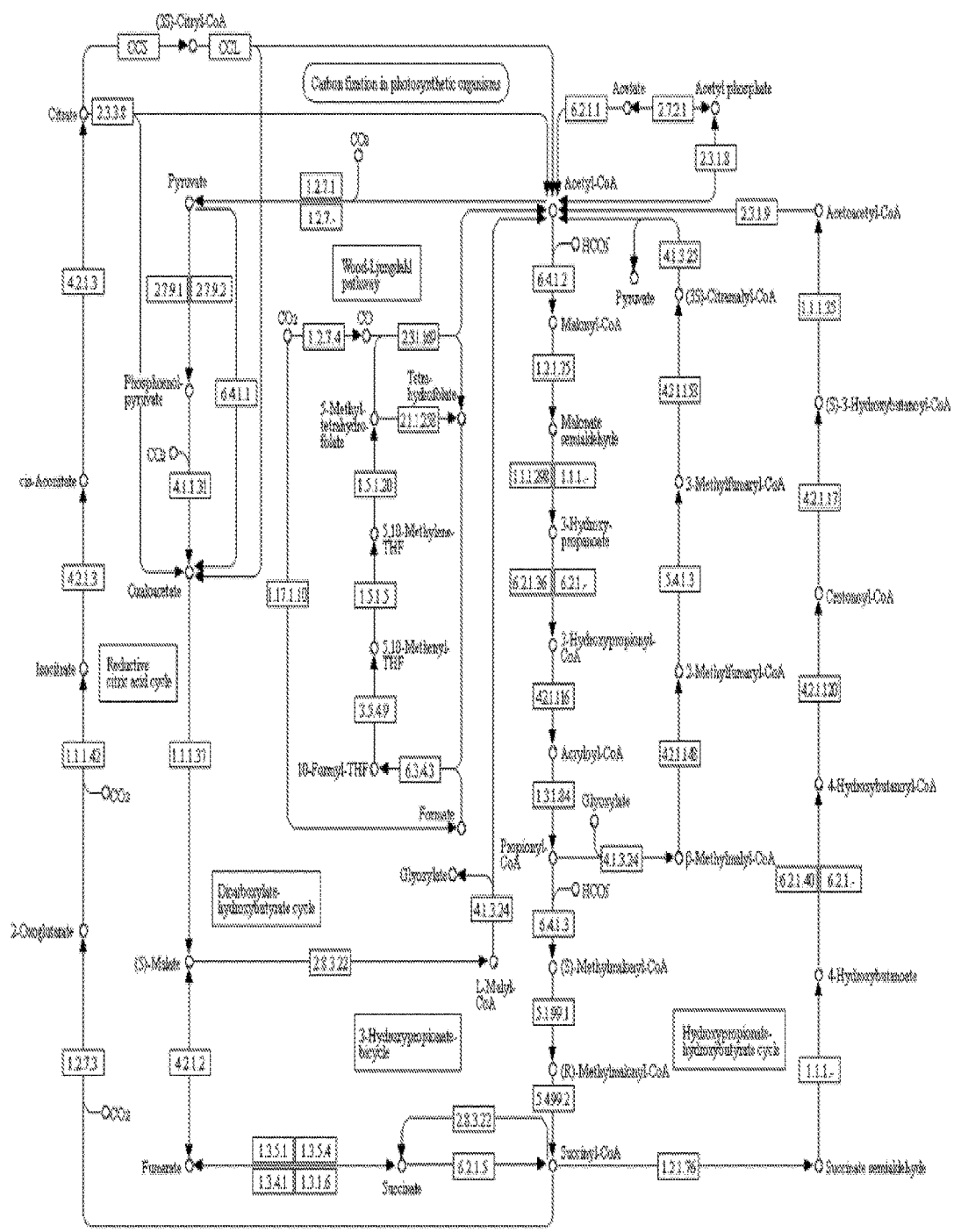
FIG. 30 depicts the KEGG carbon dioxide fixation pathways in prokaryotes.

The Wood-Ljungdahl pathway, also known as the reductive acetyl-coenzyme A pathway enables some bacteria to utilize hydrogen as an electron donor and carbon dioxide as an electron acceptor and as a building block for biosynthesis. The pathway contains three critical enzymes: carbon-monoxide dehydrogenase (EC 1.2.7.4), acetyl-CoA synthase (EC 2.3.1.169), and formate dehydrogenase (EC 1.71.1.10 KEGG and 1.2.1.43 PATRIC). Ascusbbf_1085 and Ascusbbf_876 both contain 1.2.7.4 and 2.3.1.169. See FIG. 30.

Figure 31:
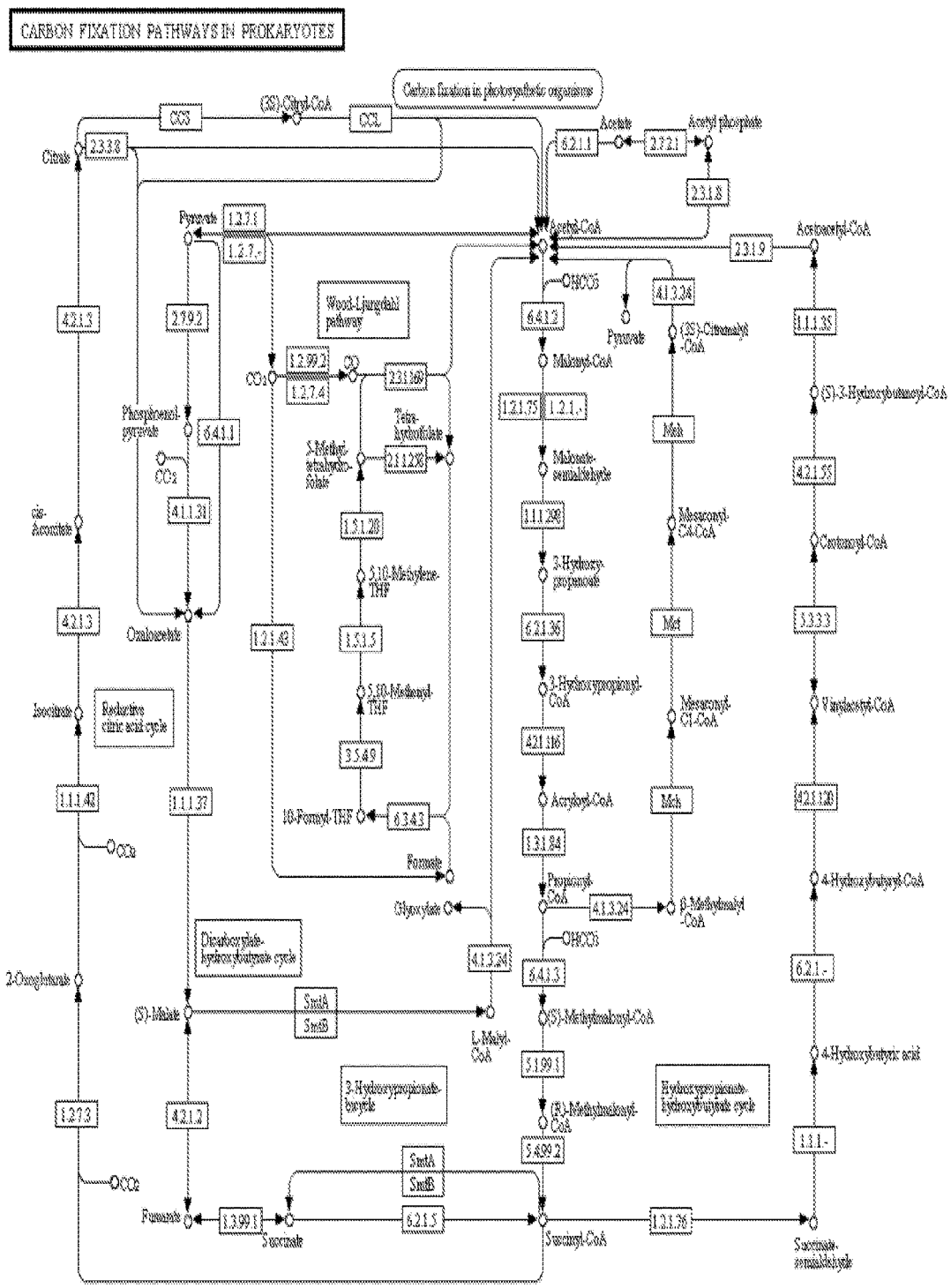
FIG. 31 depicts the PATRIC carbon dioxide fixation pathways in prokaryotes.

The Hydroxypropionate-hydroxybutyrate cycle contains three critical enzymes: succinyl-CoA reductase (EC 1.2.1.76), acetyl-CoA C-acetyltransferase (2.3.1.9), and MalCoA lyase (4.1.3.25 KEGG and 4.1.3.24 PATRIC). The ten sequenced genomes did not contain 1.2.1.76, 4.1.3.25 KEGG, or 4.1.3.24 PATRIC, so it is unlikely that the strains are utilizing this pathway. See FIG. 31.

Several genomes suggested that the strains may be fixing carbon dioxide in conjunction with a carbohydrate, such as glucose. The strains may be fixing carbon during the conversion of: acetyl-CoA+$CO_2$+2 reduced ferredoxin+$2H^+$ →pyruvate+CoA=2 oxidized ferredoxin.

Example IX. Mode of Action—Highly Fermentable Diet Tolerance in Ruminants

The rumen is a specialized stomach dedicated to the digestion of feed components in ruminants. A diverse microbial population inhabits the rumen, where their primary function revolves around converting the fibrous and non-fibrous carbohydrate components into useable sources of energy and protein (FIG. 3). In typical commercial ruminant diets, cellulose and other plant-related structural carbohydrates (e.g. hemicellulose, pectin, lignin, etc.) are one component of the feed ration. This portion of the ration is considered indigestible by mammals' native metabolism, and must be degraded by microorganisms inhabiting the rumen. The cellulolytic microbes in the rumen leverage extensive enzymatic activity in order break these molecules down into simple sugars and volatile fatty acids. This enzymatic activity is critical to the extraction of energy from feed, and more efficient degradation ultimately provides more energy to the animal. The soluble sugars found in the non-fibrous portion of the feed are also fermented into gases and volatile fatty acids such as butyrate, propionate, and acetate. Volatile fatty acids arising from the digestion of both the fibrous and non-fibrous components of feed are ultimately the main source of energy of the ruminant.

In a feedlot setting, ruminants receive a diet with much higher levels of concentrate and readily digestible soluble sugars to increase weight gain of the animal more rapidly. Because of the highly fermentable nature of the feed, the physiology of the rumen microbial metabolism shifts dramatically (as compared to the rumen microbial metabolism of an animal on a more balanced diet), creating many health issues for the host animal. High levels of fermentation will increase the build-up of fermentation by-products. These by-products include various acids (e.g. lactic acid, volatile fatty acids, succinic acid, citric acid, etc.), alcohols (e.g. ethanol, propanol, etc.) and gases (e.g. hydrogen, carbon dioxide, methane, hydrogen sulfide, etc.).

Accumulation of these by-products in the rumen can lead to: acidosis, bloat, panting, abomasal dysplasia, reduced buffering capacity in the rumen, leaky gut, increased permeability of the gastrointestinal lining, increased histamine and LPS production, respiratory acidosis, metabolic acidosis, laminitis, ketosis, liver disease, and liver abscesses.

Microorganisms strains used as products may be utilizing a variety of metabolic and physiological processes to maintain a more healthy rumen state in the host animal. These microbes ultimately counter the increased fermentation and accompanying physiological side effects. The function of microorganisms in the animals that are most productive/most tolerant of a highly fermentable diet in a feedlot setting encourage one or more of the following:

Reduction or sequestration of carbon dioxide due to excess fermentation within the rumen. Microorganisms leverage a variety of different pathways to utilize bicarbonate produced by the animal and carbon dioxide produced from fermentation within the rumen. Carbon fixation pathways include the Calvin cycle, Wood-Ljundahl Pathway, Reductive TCA cycle, and variations thereof.

Reduction of the methanogen population within the rumen. Hydrogenotrophic methanogens convert $CO_2$ and hydrogen to methane, which is subsequently lost to the environment due to cattle flatulence. Microbial strains that compete with methanogens and convert $CO_2$ into a form usable by the animal (e.g. acetate) maximize the amount of energy assimilated by the animal.

Increase production of volatile fatty acids. Volatile fatty acids are the primary energy source for ruminants. More efficient animals tend of have higher concentrations of these acids in their rumen. Although overall acid production increases due to the increased amount of fermentation, biasing acid production towards energetically useful acids for the animal promotes productivity.

Increase de novo synthesis/provide vitamin B, K, and other relevant vitamins as a prebiotic. Due to the severe composition shift of the rumen microbial community, vitamins typically synthesized by the microbial community may be insufficient for both animal and microbial nutritional requirements.

Reduction of alpha diversity in the rumen microbiome. More efficient animals have lower numbers of microbial species in their rumen microbial population.

Addition of the appropriate microbial strains as a product can ameliorate the effects of rapid rumen microbial fermentation and by-product accumulation, ultimately enhancing the productivity and health of the ruminant. Potential product microorganisms were assayed in vitro for their ability to degrade various carbohydrates, and to identify the acids produced from the degradation of these carbohydrates. (See Example XII and corresponding table). Genomic information was also mined to identify the strains' metabolic potential to fix $CO_2$ and synthesize various vitamins.

Example X. Comparative Analysis of MIC Scores from Published Work of Other Groups Utilizing Ascus Biosciences' technology, the performance of currently available microbial feed additive products was predicted.

Figure 29:
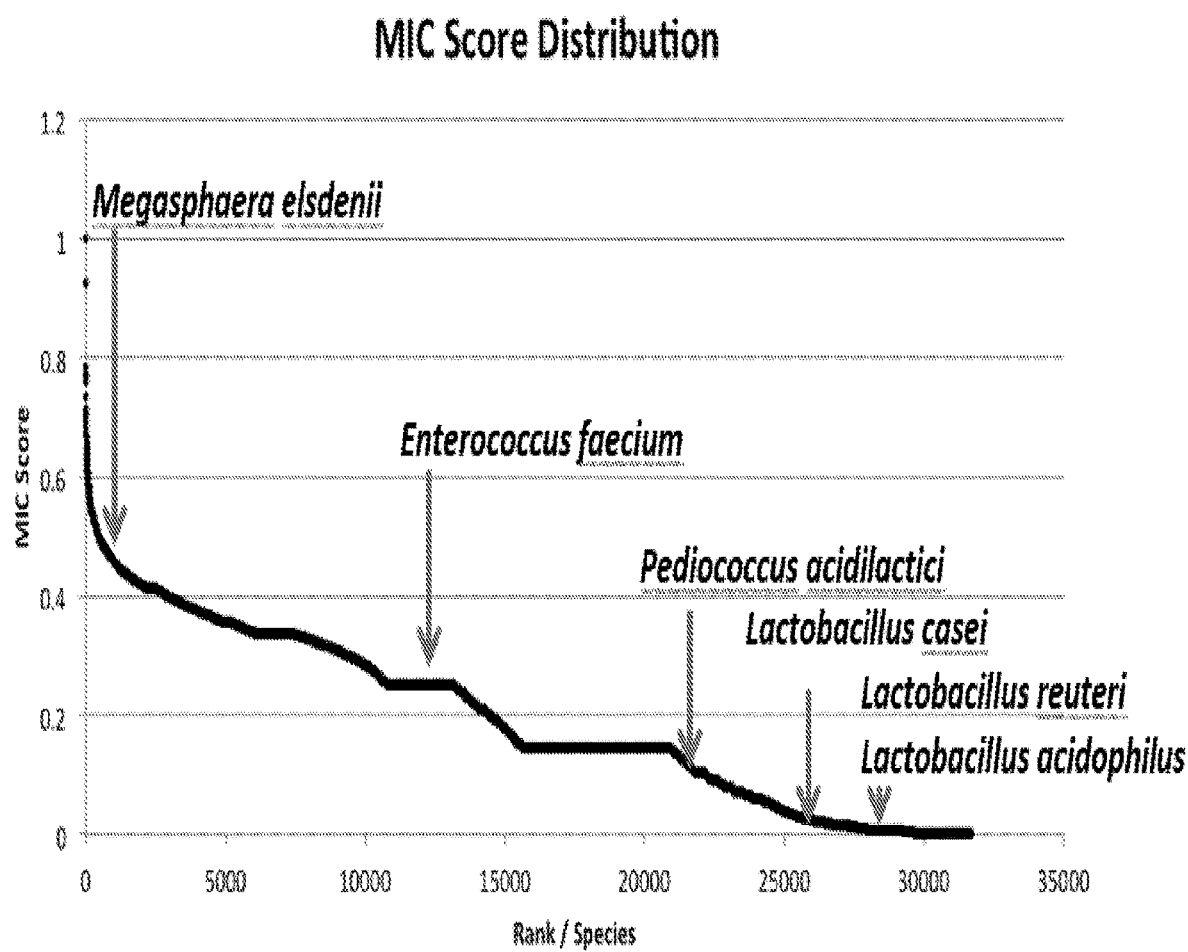
FIG. 29 depicts the MIC score distribution for common performance parameters including average daily weight gain, weight gain, feed intake, and feed efficiency with six species of bacteria, in which many of the species have been evaluated in $3^{rd}$ party studies. The lower the MIC score, the less likely the species/strains associated with that MIC score are capable of positively modulating the aforementioned performance parameters.

Direct-fed microbial products that claim to enhance cattle performance and prevent acidosis are available on the market. A few of these products contain microorganism strains that are native rumen microorganisms (*Megasphaera elsdenii*), or are within 97% sequence similarity of native rumen microorganisms. Here, we've identified the species that are used in these products, and determined their platform score with respect to common performance parameters: average daily gain, weight gain, feed intake, and feed efficiency (FIG. 29). As can be seen from the curve, all but one of the currently available strains fall below the threshold (~0.4) used to define "useful" and "non-useful" strains. The one strain above the cutoff, *Megasphaera elsdenii*, has shown a positive effect in a few studies. Other common strains used in direct fed microbial products, such as *Lactobacillus animalis* and *Propionibacterium freudenreichii*, were not similar to any native rumen microorganisms. Thus, scores could not be generated for these microorganisms.

*Lactobacillus casei*: MIC 0.04587

No change in performance during finishing. Impact of a mixed culture of *Lactobacillus casei* and *L. lactis* on in vitro ruminal fermentation and the growth of feedlot steers fed barley-based diets. Baah et al. 2009.

*Megasphaera elsdenii*: MIC 0.54494

Small increase in hot carcass weight. *M. elsdenii* on the performance of steers adapting to a high-concentrate diet, using three or five transition diets. Drouillard et al. 2012.

Higher rumen pH after carbohydrate challenge. The effects of dosing feedlot cattle with *M. elsdenii* strain NCIMB 41125 prior to the introduction of a grain-rich diet. McDaniel et al. 2007.

No effect, slight shift of acetate led to propionate production. Rumen pH and fermentation characteristics in dairy cows supplemented with *M. elsdenii* NCIMB 41125 in early lactation. Aikman et al. 2011.

Higher feed intakes and improved ADG. Effect of ruminal administration of the lactate-utilizing strain *M. elsdenii* MCIMB 41125 on abrupt or gradual transition from forage to concentrate diets. Henning et al. 2010.

Higher carcass weights when used with 30 kg/ton roughage diet. Effects of virginiamycin and monensin administered alone or together with *M. elsdenii* strain NCIMB 41125 on in vitro production of lactate and VFA and the effects of monensin and *M. elsdenii* strain NCIMB 41125 on health and performance of feedlot steers. Leeuw et al. 2015.

*Lactobacillus acidophilus*: MIC 0.04839

No change in performance, but may decrease *E. coli* levels. Prevalence of *Escherichia coli* 0157:H7 and Performance by Beef Feedlot Cattle Given *Lactobacillus* Direct-Fed Microbials. Brashears et al. 2003.

Slightly improved overall gain—127 kg to 130 kg (2.3%). Performance and carcass characteristics of commercial feedlot cattle from a study of vaccine and direct-fed microbial effects on *Escherichia coli* O157:H7 fecal shedding. Cull et al. 2015.

No effect on performance. Direct-fed microbials containing lactate-producing bacteria influence ruminal fermentation but not lactate utilization in steers fed a high-concentrate diet. Kenney et al. 2015.

No effect. Effect of Direct-Fed Microbial Dosage on the Fecal Concentrations of Enterohemorrhagic *Escherichia coli* in Feedlot Cattle. Luedtke et al. 2016.

No effect on performance. Effect of *Lactobacillus acidophilus* Strain NP51 on *Escherichia coli* O157:H7 Fecal Shedding and Finishing Performance in Beef Feedlot Cattle. Peterson et al. 2007.

No effect. Evaluation of *Lactobacillus* Fermentation Cultures in Calf Feeding Systems. Higginbotham et al. 1992.

*Pediococcus acidilactici*: MIC 0.14609

No effect on performance. Direct-fed microbials containing lactate-producing bacteria influence ruminal fermentation but not lactate utilization in steers fed a high-concentrate diet. Kenney et al. 2015.

*Enterococcus faecium*: MIC 0.37215

No effect on acidosis/tolerance of high grain diet. Effects of bacterial direct-fed microbials and yeast on site and extent of digestion, blood chemistry, and subclinical ruminal acidosis in feedlot cattle. Beauchemin et al. 2003.

No effect on ruminal pH, blood pH, or DMI. Effects of bacterial direct-fed microbials on ruminal fermentation, blood variables, and the microbial populations of feedlot cattle. Ghorbani et al. 2002.

No effect on performance. Direct-fed microbials containing lactate-producing bacteria influence ruminal fermentation but not lactate utilization in steers fed a high-concentrate diet. Kenney et al. 2015.

*Lactobacillus reuteri*: MIC 0.06366 May help reduce *E. coli*, no mention of performance improvements. *Lactobacillus reuteri* suppresses *E. coli* O157:H7 in bovine ruminal fluid: Toward a pre-slaughter strategy to improve food safety. Bertin et al. 2017.

*Propionibacterium freudenreichii*: MIC not Detected

Slightly improved overall gain—127 kg to 130 kg (2.3%). Performance and carcass characteristics of commercial feedlot cattle from a study of vaccine and direct-fed microbial effects on *Escherichia coli* O157:H7 fecal shedding. Cull et al. 2015.

No effect on performance or carcass characteristics. Effects of live culture of *Lactobacillus acidophilus* (strains NP45 and NP51) and *Propionibacterium freudenreichii* on performance, carcass, and intestinal characteristics, and *Escherichia coli* strain 0157 shedding of finishing beef steers. Elam et al. 2013.

No effect on ruminal pH, blood pH, or DMI. Effects of bacterial direct-fed microbials on ruminal fermentation, blood variables, and the microbial populations of feedlot cattle. Ghorbani et al. 2002.

No effect on performance. Direct-fed microbials containing lactate-producing bacteria influence ruminal fermentation but not lactate utilization in steers fed a high-concentrate diet. Kenney et al. 2015.

No effect: Effect of Direct-Fed Microbial Dosage on the Fecal Concentrations of Enterohemorrhagic *Escherichia coli* in Feedlot Cattle. Luedtke et al. 2016.

No effect on performance. Effects of increasing dose of live cultures of *Lactobacillus acidophilus* (Strain NP 51) combined with a single dose of *Propionibacterium freudenreichii* (Strain NP 24) on performance and carcass characteristics of finishing beef steers. Vasconcelos et al. 2008.

*Lactobacillus* Animals: MIC not Detected

No effect on performance or carcass characteristics. Effects of live culture of *Lactobacillus acidophilus* (strains NP45 and NP51) and *Propionibacterium freudenreichii* on performance, carcass, and intestinal characteristics, and *Escherichia coli* strain 0157 shedding of finishing beef steers. Elam et al. 2003. *L. acidophilus* NP51 has been reclassified as *Lactobacillus animalis*.

No effect on performance. Effects of increasing dose of live cultures of *Lactobacillus acidophilus* (Strain NP 51) combined with a single dose of *Propionibacterium freudenreichii* (Strain NP 24) on performance and carcass characteristics of finishing beef steers. Vasconcelos et al. 2008.

*Lactobacillus plantarum*: MIC not Detected

No effect on performance. Direct-fed microbials containing lactate-producing bacteria influence ruminal fermentation but not lactate utilization in steers fed a high-concentrate diet. Kenney et al. 2015.

*Bacillus subtilis*: MIC not Detected

No effect. Evaluation of a Direct-Fed Microbial Product Effect on the Prevalence and Load of *Escherichia coli* O157:H7 in Feedlot Cattle. Arthur et al. 2010.

Example XI. Beef Enrichment Media Compositions

Kreb's Yeast Lactate Medium

| Component | g/L |
| --- | --- |
| Yeast Extract | 10.0 |
| NaNO$_3$ | 1.7 |
| Sodium Lactate | 46.7 |
| KH$_2$PO$_4$ | 1 |
| Na$_2$HPO$_4$ | 2.4 |
| Resazurin | 1 mL |
| Agar/Gelrite/Gellan Gum | 15 |
| DI H2O | 1 L |

Place the above components into a flask 2× larger than the volume being prepared. pH to 6.8-7.0. Autoclave at 121° C. for 15 minutes, liquid cycle. Place in 47° C. for 30 minutes MRS Medium (Originally from BD Difco Lactobacilli MR)

| Component | g/1000 mL |
| --- | --- |
| Proteose Peptone No. 3 | 10.0 |
| Beef Extract | 10.0 |
| Yeast Extract | 5.0 |
| Glucose | 20.0 |
| Tween 80 | 1.0 mL |
| Sodium Acetate | 5.0 |
| Ammonium citrate | 2.0 |
| Magnesium Sulfate | 0.1 |
| Manganese Sulfate | 0.05 |
| Agar | 15.0 |
| L-Cysteine HCl | 0.5 |
| 0.1% Rezasurin | 1.0 mL |
| DI H2O | 1000 mL |

Place the aforementioned components into a flask 2× larger than the volume being prepared. Adjust pH to 6.8 with HCl or NaOH. Autoclave at 121° C. for 15 minutes, liquid cycle.

M2 Salts

| Component | g/L |
| --- | --- |
| (NH$_4$)$_2$SO$_4$ | 0.674 |
| MgSO$_4$ 7H$_2$O | 0.035 |
| K$_2$HPO$_4$ | 0.348 |
| KH$_2$PO$_4$ | 0.347 |
| 0.1% Resazurin | 1 mL |
| DI H$_2$O | Up to 1 L |

Place the aforementioned components into a flask 2× larger than the volume being prepared. Adjust pH to 6.8. Place in 47° C. for 30 minutes. Add L-cysteine hydrochloride (100 mM) to liquid media. Sterile filter any additives from the following list to create amended medias.

| Component | Molarity (mM) | g/L |
| --- | --- | --- |
| Fructose | 13.9 | 2.5 |
| Arabinose | 16.7 | 2.5 |
| Cellulose | 7.3 | 2.5 |
| Xylose | 79.9 | 12.0 |
| Maltose | 2.86 | 0.978 |
| Galactose | 13.88 | 2.5 |
| Cellobiose | 10 | 3.42 |
| Ground Corn** | — | 0.5 |
| Sodium Lactate (60% Soln) | 233.8 | 20 mLs |

| Component | Molarity (mM) | g/L |
| --- | --- | --- |
| Amino Acid Soln 1 | — | 100 mLs |
| Fatty Acid Soln 2 | — | 20 mLs |
| Wolfes Mineral Solution | — | 1.0 mL |

**Add to media before autoclaving

Amino Acid Solution 1 (50 mL)

| Component | Molarity (mM) | g/50 mL |
| --- | --- | --- |
| Glutamine | 100.0 | .731 |
| Glycine | 100.0 | .375 |
| Proline | 100.0 | .576 |
| DI H$_2$O | — | Up to 50 mL |

Fatty Acid Solution 2 (50 mL)

| Component | 1.1 - Molarity (mM) | uL/50 mL |
| --- | --- | --- |
| Propionic Acid | 9.40 | 35.0 |
| Isovaleric Acid | 0.906 | 5.0 |
| Methylbutyric ACid | 0.916 | 5.0 |
| DI H$_2$O | — | Up to 50 mL |

Wolfe's Mineral Solution

| Component | g/L |
| --- | --- |
| MgSO$_4$ 7H$_2$O | 3.0 |
| Nitrilotriacetic acid | 1.5 |
| NaCl | 1.0 |
| MnSO$_4$ H$_2$O | 0.5 |
| CaCl$_2$ | 0.1 |
| CoCl$_2$ 6H$_2$O | 0.1 |
| FeSO$_4$ 7H$_2$O | 0.1 |
| ZnSO$_4$ 7H$_2$O | 0.1 |
| AlK(SO$_4$)$_2$ 12H$_2$O | 0.01 |
| CuSO$_4$ 5H$_2$O | 0.01 |
| H$_3$BO$_3$ | 0.01 |
| NaMoO$_4$ 2H$_2$O | 0.01 |
| DI H2O | To 1 L |

MBM

| Component | g/L |
| --- | --- |
| 100x Wolfes Minerals | 1.0 mL |
| Ammonium Sulfate | 0.90 |
| Cellobiose | 4.0 |
| Sodium Bicarbonate | 7.5 |
| Sodium Carbonate | 4.0 |
| 0.1% Resazurin | 1 mL |
| VFA Soln | 48 mL |
| DI H2O | 1 L |

Place the aforementioned components into a flask 2× the size of the volume being made.

To create modified MBM (MBM mod) media, add the following components:

| Component | g/L |
| --- | --- |
| KH$_2$PO$_4$ | 1.0 |
| K$_2$HPO$_4$ | 1.0 | pH to 6.8-7.0. Autoclave at 121° C. for 15 minutes, liquid cycle. Place in 47° C. water bath for 30 minutes. Sterile filter any of the following additives to create amended media:

| Component | Molarity (mM) | g/L |
|---|---|---|
| Xylan | 30.0 | 4.98 |
| Fructose | 13.88 | 2.5 |
| Cellulose | 7.30 | 2.5 |

VFA Solution

| Component | g/L |
|---|---|
| Acetic Acid | 40 mL |
| Isobutyric Acid | 2 mL |
| Isovaleric Acid | 2 mL |
| Valeric Acid | 2 mL |
| 2-Methylbutyric acid | 2 mL |

RCM
BD Difco Dehydrated Culture Media: Reinforced Clostridial Medium

| Component | g/L |
|---|---|
| Peptone | 10 |
| Beef Extract | 10 |
| Yeast Extract | 3 |
| Dextrose | 5 |
| Sodium Chloride | 5 |
| Soluble Starch | 1 |
| Cysteine HCl | 0.5 |
| Sodium Acetate | 3 |
| Agar | 0.5 |

Place the aforementioned components into a flask 2× larger than the volume being made. pH to 6.8-7.0. Autoclave at 121° C. for 15 minutes, liquid cycle.

Trypic Soy Broth (TSB)

Add the following components into a flask 2× larger than the volume being made. Add 500 mL of deionized water. Add stir bar to flask and place on stir plate. Stir while adding 30 g/L of Tryptic Soy Broth (Sigma Aldrich T8907). Top off to 850 mL with deionized water. Add 1 mL of 0.01% resazurin indicator. Autoclave at 121° C. for 15 minutes, liquid cycle. Place flask in hot bath at 47° C. for 30 minutes.

TSBHK

Sterile filter (0.2 micrometer) 10 mL hemin (0.05%) and 0.2 mL vitamin K1 solution.

To create stock solutions:

| Hemin Solution (100 mLs) | |
|---|---|
| Component | grams/volumes |
| Hemin (Sigma Aldrich H9039) | 50 mg |
| 1M NaOH | 1.0 mLs |
| dI H2O | 99 mLs |

| Vitamin K1 Solution (30 mLs) | |
|---|---|
| Component | mLs |
| Vitamin K1 (Sigma Aldrich V3501) | 0.15 |
| 95% EtOH | 30 |

TSB+5% Sheep's Blood

Add 50 mL of defibrinated sheep's blood to 950 mL of TSB.

VL55/BC (Modified DSMZ 1266)

Place the following components into a flask 2× larger than the volume being made.

| Component | mL/L |
|---|---|
| 2-Morpholinoethanesulfonic Acid (MES) | 1.95 g |
| 20 mM $MgSO_4$ | 10.0 |
| 30 mM $CaCl_2$ | 10.0 |
| 20 mM $(NH_4)_2HPO_4$ | 10.0 |
| Selenite-Tungstate Soln | 1.0 |
| Trace Element Soln SL10 | 1.0 |
| 0.1% Resazurin | 1.0 |
| Di $H_2O$ | 960 |

Once all components are in solution, aliquot 50 mL into separate 120 mL serum vials. Each vial is bubbled under $N_2$ gas for 3 minutes at 15 psi. All vials are stoppered with grey stops and crimped with aluminum tear off crimps. Head space of every vial is sparged, needle in/out, for 2 minutes under $N_2$ gas. All vials are labeled and autoclaved at 121° C. for 20 minutes under fast cycle. When vials have finished autoclaving and cooled, the following three sets of components are added at the following concentration to every vial, via syringe, syringe filter 0.2 micrometers, and needle.

| Component | mL/L |
|---|---|
| 100× Wolfe's Minerals | 10.0 |
| 1000× Wolfe's Vitamins | 1.0 |
| BC Solution | 40.0 |
| 5% $Na_2S$ | 10.0 |
| NaOH | 10.0 |
| $Na_2SeO \times 5H_2O$ | 1.0 |
| $Na_2WO_4 \times 2H_2O$ | 10.0 |
| Di $H_2O$ | 1000 |

| Component | mg/L |
|---|---|
| HCl (25%; 7.7M) | 10.0 mLs |
| $FeCl_2 \times 4H_2O$ | 1.50 g |
| $ZnCl_2$ | 70.0 |
| $MnCl_2 \times 4H_2O$ | 100.0 |
| $H_3BO_3$ | 6.0 |
| $CoCl_2 \times 6H_2O$ | 190.0 |
| $CuCl_2 \times 2H_2O$ | 2.0 |
| $NiCl_2 \times 6H_2O$ | 24.0 |
| $Na_2MoO_4 \times 2H_2O$ | 36.0 |
| Di $H_2O$ | 990.0 |

First dissolved $FeCl_2$ in the HCL, then dilute in water, add and dissolve the other salts. Finally make up to volume.

| Component | g/50 mLs |
|---|---|
| Bile Salts | 1.0 g |
| Creatine | .282 |

Rumen Winogradsky Column
Clarified Rumen Fluid Creation
(a) Obtain approximately 2 L of unfiltered rumen fluid.
(b) Aliquot into 250 mL conicals.
(c) Spin at 4300 RPM for 30 minutes at 4° C.
   (i) Remove the supernatant (1× Clarified Rumen Fluid) in an anaerobic chamber with 5:20:75, $H_2:CO_2:N_2$ gas. Store half the 1× Clarified Rumen Fluid in an airtight container at 4° C. until ready to use.

(ii) Remove the pellet (Rumen solids) from all conicals and store in an airtight container at 4° C. until ready to use.
(d) Aliquot the 1× Clarified Rumen Fluid into 50 mL conicals.
(e) Spin 1× Clarified Rumen Fluid at 13200 RPM for 30 minutes
  (i) Remove supernatant (2× Clarified Rumen Fluid) in an anaerobic chamber and store in an airtight container at 4° C. until ready to use.
  (ii) Discard the pellet.
Creation of Column
(a) Bring sterile Winogradsky Column, fresh beef Total Mixed Ration (TMR), Beef Rumen Sample, Rumen Solids, 1× Clarified Rumen Fluid and 2× Clarified Rumen Fluid into an anaerobic chamber.
(b) Tightly pack approximately 100-mLs of Rumen Solids into the bottom of the column.
(c) Pour approximately 150-mLs 1× Clarified Rumen Fluid on top of the Rumen Solids.
(d) Pour Approximately 150-mLs 2× Clarified Rumen Fluid on top of the 1× Rumen Fluid.
(e) Seed column with approximately 10-mLs raw beef rumen sample.
(f) Add 50-mLs TMR to the top of the column.
(g) Incubate at 39° C. in a well ventilated incubator.
Basal Salts Medium with Sodium Sulfate (BSMS)
Prepare the following solutions and filter sterilize and then store at 4° C.
Solution I

| Component | g/L |
|---|---|
| $Na_2SO_4$ | 5.0 |
| NaCl | 2.0 |
| $(NH_4)_2SO_4$ | 3.0 |
| $KH_2PO_4$ | 3.0 |
| $CaCl_2\ 2H_2O$ | 0.6 |
| $MgSO_4\ 7H_2O$ | 0.6 |

Solution II

| | |
|---|---|
| $K_2HPO_4$ | 3.0 |

Media Preparation

| Component | g/L |
|---|---|
| Solution I | 150 mL |
| Solution II | 150 mL |
| Yeast extract | 1.50 |
| Sodium Bicarbonate | 6.0 |

Bring up to 1 L. Adjust pH to 7.0+/−0.05. Autoclave for 15 minutes at 121° C. under slow exhaust. After autoclave, add sterile L-cysteine (100 micromolar).

RAMM Salts with Vitamins, Minerals, and Sodium Sulfide

| Component | g/500 mL |
|---|---|
| $KH_2PO_4$ | 0.11 |
| $K_2HPO_4$ | 0.08 |
| $NH_4Cl$ | 0.265 |
| $NaHCO_3$ | 0.6 |
| $DIH_2O$ | 500 mL |

After autoclaving, add 5 mL of 100× Wolfe's vitamin mix. 5 mL of 5% sodium sulfide.

Example XII. Analysis of Rumen Microbes for Volatile Fatty Acid Production and Carbon Source Use A. Carbon Source Use To assess the ability of the strains to metabolize various carbon sources, OD600 was used to measure the growth of strains over time in both minimal and rich media. Minimal media conditions demonstrate what compounds a strain can use as its sole carbon source, while the rich media iteration shows which carbon sources a strain can use under ideal, rumen-like conditions.

A single colony from each of the desired strains (on anaerobic agar plates) was inoculated into 1 ml of anaerobic RAMM salts. This was vortexed briefly and 10 μL was inoculated into a rich and minimal media, spiked with a chosen carbon source.

Strains were inoculated anaerobically into 1 mL of media in the 2 ml well of a 96 well plate. Carbon sources included arabinose, fructose, dextrose, galactose, xylose, cellobiose and starch. Carbon sources for the minimal media conditions were made at a 20 g/L concentration in RAMM salts, and filter sterilized through a 0.22 μm polyethersulfone membrane. Starch was prepared at a concentration of 2 g/L and autoclaved. Carbon sources for the rich media conditions were made in RAMM salts at a 200 g/L concentration and 100 μl of sterile carbon source was added to 900 μl of rich media.

Plates were incubated in the dark anaerobically at 37° C. 100 μL aliquots of each well were periodically read at 600 nm over a two-week period on a "Synergy H4 hybrid plate reader". Strain ID was confirmed prior to inoculation with Illumina sequencing. Duplicate entries represent strains within 97% of the listed strain ID.

| strain id | Minimal Arabinose | Fructose | Starch | Dextrose | Galactose | Xylose | Cellobiose |
|---|---|---|---|---|---|---|---|
| Ascusbbf_24302 | + | N/A | − | + | + | + | + |
| Ascusbbf_24302 | + | N/A | − | + | + | + | + |
| Ascusbbf_10712 | − | N/A | − | − | − | − | − |
| Ascusbbf_4 | − | N/A | − | − | − | − | − |
| Ascusbbf_4 | − | N/A | − | − | − | − | − |
| Ascusbbf_951 | − | N/A | − | − | − | − | − |
| Ascusbbf_951 | − | − | N/A | − | − | − | − |
| Ascusbbf_951 | − | N/A | − | − | − | − | − |
| Ascusbbf_14146 | + | N/A | − | + | + | + | + |

-continued

| strain id | Minimal Arabinose | Fructose | Starch | Dextrose | Galactose | Xylose | Cellobiose |
|---|---|---|---|---|---|---|---|
| Ascusbbf_14146 | − | N/A | − | + | − | − | − |
| Ascusbbf_14146 | − | − | N/A | − | − | − | − |
| Ascusbbf_154 | − | N/A | − | − | − | − | − |
| Ascusbbf_1010 | + | N/A | + | + | + | + | − |
| Ascusbbf_154 | − | N/A | − | − | − | − | − |
| Ascusbbf_24302 | + | N/A | + | + | + | + | + |
| Ascusbbf_24302 | + | N/A | + | + | + | + | + |
| Ascusbbf_1085 | − | N/A | − | − | − | − | − |
| Ascusbbf_14146 | − | N/A | + | + | + | + | − |
| Ascusbbf_951 | − | N/A | − | − | − | − | − |
| Ascusbbf_951 | − | N/A | − | − | − | − | − |
| Ascusbbf_951 | − | N/A | − | − | − | − | − |
| Ascusbbf_1085 | − | N/A | − | − | − | − | − |
| Ascusbbf_876 | − | N/A | − | − | − | − | − |
| Ascusbbf_10712 | − | N/A | − | − | − | − | − |
| Ascusbbf_10712 | − | N/A | − | − | − | − | − |
| Ascusbbf_10109 | − | − | N/A | − | − | − | − |

| strain id | Rich Arabinose | Fructose | Dextrose | Galactose | Xylose | Cellobiose |
|---|---|---|---|---|---|---|
| Ascusbbf_24302 | + | + | + | + | + | + |
| Ascusbbf_24302 | + | + | + | + | + | + |
| Ascusbbf_10712 | − | + | + | − | − | − |
| Ascusbbf_4 | N/A | N/A | N/A | N/A | N/A | N/A |
| Ascusbbf_4 | − | − | − | + | − | − |
| Ascusbbf_951 | N/A | N/A | N/A | N/A | N/A | N/A |
| Ascusbbf_951 | + | + | + | + | − | + |
| Ascusbbf_951 | − | + | + | − | − | − |
| Ascusbbf_14146 | N/A | N/A | N/A | N/A | N/A | N/A |
| Ascusbbf_14146 | N/A | N/A | N/A | N/A | N/A | N/A |
| Ascusbbf_14146 | − | + | − | − | − | − |
| Ascusbbf_154 | N/A | N/A | N/A | N/A | N/A | N/A |
| Ascusbbf_1010 | + | + | + | + | − | − |
| Ascusbbf_154 | + | + | + | + | + | + |
| Ascusbbf_24302 | + | + | + | + | + | + |
| Ascusbbf_24302 | + | + | + | + | + | + |
| Ascusbbf_1085 | − | + | − | + | − | − |
| Ascusbbf_14146 | N/A | N/A | N/A | N/A | N/A | N/A |
| Ascusbbf_951 | − | − | − | − | − | − |
| Ascusbbf_951 | − | − | − | − | − | − |
| Ascusbbf_951 | − | − | − | − | − | − |
| Ascusbbf_1085 | − | + | + | + | − | + |
| Ascusbbf_876 | − | − | − | − | − | − |
| Ascusbbf_10712 | − | + | + | − | − | − |
| Ascusbbf_10712 | − | + | + | − | − | − |
| Ascusbbf_10109 | + | − | − | − | − | − |

B. Volatile Fatty Acid (VFA) Production

To assess the ability of the strains or enrichments to produce volatile fatty acids, HPLC was used to measure the concentrations of acetate, butyrate, and propionate in spent media.

For pure isolates, a single colony from each of the desired strains (on solid anaerobic media) was inoculated into the strain's preferred rich media. Enrichments were inoculated from fresh rumen sample into a desired media.

Cultures and medium blanks were incubated at their optimal conditions until significant growth was visible in the cultures. Absorbance reads were taken at 600 and 420 nm to determine the growth of each culture.

Pure culture strain IDs were confirmed with Illumina sequencing. Enrichments and their corresponding rumen sample inocula were Illumina sequenced to determine the presence or absence of target strains. These sequencing datasets were integrated with cell count data to determine if target strains grew in vitro.

An aliquot of each culture was sterile filtered through 0.22 micrometer polyethersulfone membrane into a sterile acid washed 15 mL glass sample vial to be analyzed by HPLC. HPLC reactions were performed at Michigan State University Bioeconomy Institute. Concentrations of acetate, butyrate, and propionate were quantified for the cultures and media blanks. HPLC parameters: The column is BioRad Aminex HPX-87H, 60° C., 0.5 mL/min mobile phase 0.00325 N $H_2SO_4$, 500 psi, 35C RI detector, 45 min run time, injection volume 5 μL.

| Strain ID | pyruvic | glucose | succinic | lactic | glycerol | acetic | propionic | butyric | ethanol | 1-Butanol |
|---|---|---|---|---|---|---|---|---|---|---|
| Ascusbbf_1007A | 0 | 0 | 0 | 0 | 0 | + | + | + | − | 0 |
| Ascusbbf_100A | 0 | − | + | − | + | + | + | 0 | 0 | 0 |
| Ascusbbf_100A | 0 | 0 | 0 | 0 | + | − | 0 | 0 | + | 0 |
| Ascusbbf_100A | 0 | − | + | − | − | + | − | + | − | 0 |
| Ascusbbf_100A | 0 | 0 | 0 | + | 0 | + | 0 | 0 | 0 | 0 |
| Ascusbbf_100B | 0 | 0 | 0 | 0 | − | − | 0 | + | 0 | 0 |
| Ascusbbf_100B | 0 | − | + | 0 | 0 | + | + | + | + | 0 |
| Ascusbbf_100C | 0 | − | + | − | + | + | + | 0 | 0 | 0 |
| Ascusbbf_100C | 0 | 0 | 0 | 0 | − | − | 0 | + | 0 | 0 |
| Ascusbbf_100C | 0 | 0 | 0 | 0 | + | + | 0 | + | + | 0 |
| Ascusbbf_100C | 0 | − | + | 0 | 0 | + | + | 0 | + | 0 |
| Ascusbbf_100C | 0 | 0 | 0 | 0 | + | − | 0 | 0 | + | 0 |
| Ascusbbf_100C | 0 | 0 | 0 | 0 | 0 | + | 0 | 0 | 0 | 0 |
| Ascusbbf_100C | 0 | 0 | 0 | + | 0 | + | 0 | 0 | 0 | 0 |
| Ascusbbf_100D | 0 | − | + | − | + | + | + | 0 | 0 | 0 |
| Ascusbbf_100D | 0 | 0 | 0 | 0 | − | − | 0 | + | 0 | 0 |
| Ascusbbf_100D | 0 | 0 | 0 | 0 | 0 | + | + | + | − | 0 |
| Ascusbbf_100D | 0 | − | + | − | − | + | − | + | − | 0 |
| Ascusbbf_100E | 0 | − | + | − | + | + | + | 0 | 0 | 0 |
| Ascusbbf_100E | 0 | 0 | 0 | 0 | − | − | 0 | + | 0 | 0 |
| Ascusbbf_100E | 0 | 0 | 0 | 0 | + | + | 0 | + | + | 0 |
| Ascusbbf_100E | 0 | − | + | 0 | 0 | + | + | 0 | + | 0 |
| Ascusbbf_100E | 0 | 0 | 0 | 0 | + | − | 0 | 0 | + | 0 |
| Ascusbbf_100E | 0 | 0 | 0 | 0 | 0 | + | 0 | 0 | 0 | 0 |
| Ascusbbf_100F | 0 | 0 | 0 | 0 | 0 | + | + | + | − | 0 |
| Ascusbbf_100G | 0 | − | + | 0 | 0 | + | + | 0 | + | 0 |
| Ascusbbf_10109A | + | − | + | − | 0 | + | + | + | − | 0 |
| Ascusbbf_10109B | + | − | + | − | 0 | + | + | + | − | 0 |
| Ascusbbf_10109C | 0 | − | + | − | + | + | + | 0 | 0 | 0 |
| Ascusbbf_10109C | 0 | 0 | 0 | 0 | + | − | 0 | 0 | + | 0 |
| Ascusbbf_10109D | 0 | 0 | 0 | 0 | + | − | 0 | 0 | + | 0 |
| Ascusbbf_10109E | 0 | 0 | 0 | 0 | + | − | 0 | 0 | + | 0 |
| Ascusbbf_10109E | 0 | − | + | 0 | − | + | − | + | − | 0 |
| Ascusbbf_10109F | 0 | 0 | 0 | 0 | + | − | 0 | 0 | + | 0 |
| Ascusbbf_10109G | 0 | 0 | 0 | 0 | + | − | 0 | 0 | + | 0 |
| Ascusbbf_10109G | 0 | − | + | + | − | + | + | + | − | 0 |
| Ascusbbf_10109H | 0 | 0 | 0 | 0 | + | − | 0 | 0 | + | 0 |
| Ascusbbf_10109H | 0 | − | + | − | − | + | − | + | − | 0 |
| Ascusbbf_10109I | 0 | − | + | − | − | + | − | + | − | 0 |
| Ascusbbf_1010A | + | − | + | − | 0 | + | + | + | − | 0 |
| Ascusbbf_1010A | + | − | 0 | + | − | + | + | 0 | + | 0 |
| Ascusbbf_1010B | 0 | − | + | − | + | + | + | 0 | 0 | 0 |
| Ascusbbf_1010B | 0 | 0 | 0 | 0 | − | − | 0 | + | 0 | 0 |
| Ascusbbf_1010B | 0 | 0 | 0 | 0 | + | + | 0 | + | + | 0 |
| Ascusbbf_1010B | 0 | − | + | 0 | 0 | + | + | + | + | 0 |
| Ascusbbf_1010B | 0 | 0 | 0 | 0 | + | − | 0 | 0 | + | 0 |
| Ascusbbf_1010B | 0 | 0 | 0 | 0 | 0 | + | 0 | 0 | 0 | 0 |
| Ascusbbf_1010B | 0 | 0 | + | + | + | + | + | 0 | + | 0 |
| Ascusbbf_1010B | 0 | 0 | 0 | + | 0 | + | 0 | 0 | + | 0 |
| Ascusbbf_1010C | 0 | 0 | 0 | 0 | − | − | 0 | + | 0 | 0 |
| Ascusbbf_1010C | 0 | 0 | 0 | 0 | + | + | 0 | + | + | 0 |
| Ascusbbf_1010C | 0 | − | + | 0 | 0 | + | + | + | + | 0 |
| Ascusbbf_1010C | 0 | 0 | 0 | 0 | + |   | 0 | 0 | + | 0 |
| Ascusbbf_1010C | 0 | 0 | 0 | 0 | 0 | + | 0 | 0 | 0 | 0 |
| Ascusbbf_1010C | 0 | 0 | + | + | + | + | + | 0 | + | 0 |
| Ascusbbf_1010C | 0 | 0 | 0 | + | 0 | + | 0 | 0 | 0 | 0 |
| Ascusbbf_1010D | 0 | − | + | − | + | + | + | 0 | 0 | 0 |
| Ascusbbf_1010D | 0 | 0 | 0 | 0 | − | − | 0 | + | 0 | 0 |
| Ascusbbf_1010D | 0 | 0 | 0 | 0 | + | + | 0 | + | + | 0 |
| Ascusbbf_1010D | 0 | − | + | 0 | 0 | + | + | + | + | 0 |
| Ascusbbf_1010D | 0 | 0 | 0 | 0 | + | − | 0 | 0 | + | 0 |
| Ascusbbf_1010D | 0 | − | + | + | + | + | 0 | 0 | + | 0 |
| Ascusbbf_1010D | 0 | 0 | + | + | + | + | + | 0 | + | 0 |
| Ascusbbf_1010D | 0 | 0 | 0 | + | 0 | + | 0 | 0 | 0 | 0 |
| Ascusbbf_1010E | 0 | − | + | − | + | + | + | 0 | 0 | 0 |
| Ascusbbf_1010E | 0 | 0 | 0 | 0 | − | − | 0 | + | 0 | 0 |
| Ascusbbf_1010E | 0 | 0 | 0 | 0 | 0 | + | + | + | − | 0 |
| Ascusbbf_1010E | 0 | − | + | − | + | + | + | + | + | 0 |
| Ascusbbf_1010E | 0 | 0 | 0 | + | 0 | + | 0 | 0 | 0 | 0 |
| Ascusbbf_1010F | 0 | − | + | − | + | + | + | 0 | 0 | 0 |
| Ascusbbf_1010F | 0 | 0 | 0 | 0 | − | − | 0 | + | 0 | 0 |
| Ascusbbf_1010F | 0 | 0 | 0 | 0 | 0 | + | + | + | − | 0 |
| Ascusbbf_1010F | 0 | 0 | 0 | + | 0 | + | 0 | 0 | 0 | 0 |
| Ascusbbf_1010G | 0 | − | + | − | + | + | + | 0 | 0 | 0 |
| Ascusbbf_1010G | 0 | 0 | 0 | 0 | − | − | 0 | + | 0 | 0 |
| Ascusbbf_1010G | 0 | 0 | 0 | 0 | + | + | 0 | + | + | 0 |
| Ascusbbf_1010G | 0 | − | + | 0 | 0 | + | + | + | + | 0 |
| Ascusbbf_1010G | 0 | 0 | 0 | 0 | + | − | 0 | 0 | + | 0 |
| Ascusbbf_1010G | 0 | − | + | + | + | + | 0 | 0 | + | 0 |

-continued

| Strain ID | pyruvic | glucose | succinic | lactic | glycerol | acetic | propionic | butyric | ethanol | 1-Butanol |
|---|---|---|---|---|---|---|---|---|---|---|
| Ascusbbf__1010G | 0 | 0 | + | + | + | + | + | 0 | + | 0 |
| Ascusbbf__1010G | 0 | 0 | 0 | + | 0 | + | 0 | 0 | 0 | 0 |
| Ascusbbf__1010H | 0 | − | + | − | + | + | + | 0 | 0 | 0 |
| Ascusbbf__1010H | 0 | 0 | 0 | 0 | 0 | + | + | + | − | 0 |
| Ascusbbf__1010I | 0 | − | + | − | + | + | + | 0 | 0 | 0 |
| Ascusbbf__1010I | 0 | 0 | 0 | 0 | 0 | + | + | + | − | 0 |
| Ascusbbf__1010I | 0 | 0 | + | + | + | + | + | 0 | + | 0 |
| Ascusbbf__1010J | 0 | 0 | 0 | 0 | + | + | 0 | + | + | 0 |
| Ascusbbf__1010J | 0 | 0 | 0 | 0 | 0 | + | 0 | 0 | 0 | 0 |
| Ascusbbf__1010J | 0 | 0 | 0 | + | 0 | + | 0 | 0 | 0 | 0 |
| Ascusbbf__1034A | 0 | 0 | 0 | + | 0 | + | 0 | 0 | + | 0 |
| Ascusbbf__1034A | 0 | 0 | 0 | + | 0 | + | 0 | 0 | + | 0 |
| Ascusbbf__1034B | 0 | 0 | 0 | + | 0 | + | 0 | 0 | + | 0 |
| Ascusbbf__1034B | 0 | 0 | 0 | + | 0 | + | 0 | 0 | + | 0 |
| Ascusbbf__104A | 0 | 0 | 0 | − | 0 | + | 0 | 0 | + | − |
| Ascusbbf__104B | 0 | 0 | 0 | 0 | − | − | 0 | + | 0 | 0 |
| Ascusbbf__104B | 0 | − | + | 0 | 0 | + | + | + | + | 0 |
| Ascusbbf__104B | 0 | 0 | 0 | 0 | + | − | 0 | 0 | + | 0 |
| Ascusbbf__104B | 0 | − | + | − | − | + | − | + | − | 0 |
| Ascusbbf__104C | 0 | 0 | 0 | 0 | − | − | 0 | + | 0 | 0 |
| Ascusbbf__104C | 0 | − | + | 0 | 0 | + | + | + | + | 0 |
| Ascusbbf__104C | 0 | 0 | 0 | 0 | + | − | 0 | 0 | + | 0 |
| Ascusbbf__104C | 0 | − | + | − | − | + | − | + | − | 0 |
| Ascusbbf__104D | 0 | 0 | 0 | 0 | − | − | 0 | + | 0 | 0 |
| Ascusbbf__104E | 0 | 0 | 0 | 0 | − | − | 0 | + | 0 | 0 |
| Ascusbbf__104E | 0 | 0 | 0 | 0 | 0 | + | + | + | − | 0 |
| Ascusbbf__104E | 0 | − | + | 0 | 0 | + | + | + | + | 0 |
| Ascusbbf__104F | 0 | − | + | − | + | + | + | 0 | + | 0 |
| Ascusbbf__104F | 0 | − | + | 0 | 0 | + | + | + | + | 0 |
| Ascusbbf__104G | 0 | − | + | − | − | + | − | + | − | 0 |
| Ascusbbf__104H | 0 | − | + | − | + | + | + | + | + | 0 |
| Ascusbbf__104I | 0 | − | + | − | + | + | + | + | + | 0 |
| Ascusbbf__10576A | 0 | 0 | 0 | 0 | + | − | 0 | 0 | + | 0 |
| Ascusbbf__10576A | 0 | − | + | − | − | + | − | + | − | 0 |
| Ascusbbf__10576A | 0 | 0 | + | + | + | + | + | 0 | + | 0 |
| Ascusbbf__10576B | 0 | 0 | 0 | 0 | + | − | 0 | 0 | + | 0 |
| Ascusbbf__10576B | 0 | − | + | − | − | + | − | + | − | 0 |
| Ascusbbf__10576B | 0 | 0 | + | + | + | + | + | 0 | + | 0 |
| Ascusbbf__10576B | 0 | 0 | 0 | + | 0 | + | 0 | 0 | 0 | 0 |
| Ascusbbf__10576C | 0 | 0 | 0 | 0 | + | − | 0 | 0 | + | 0 |
| Ascusbbf__10576C | 0 | − | + | − | − | + | − | + | − | 0 |
| Ascusbbf__10576C | 0 | 0 | + | + | + | + | + | 0 | + | 0 |
| Ascusbbf__10576D | 0 | 0 | 0 | 0 | + | − | 0 | 0 | + | 0 |
| Ascusbbf__10576E | 0 | 0 | + | + | + | + | + | 0 | + | 0 |
| Ascusbbf__106863A | 0 | 0 | 0 | + | 0 | + | 0 | 0 | + | 0 |
| Ascusbbf__106863A | 0 | 0 | 0 | + | 0 | + | 0 | 0 | + | 0 |
| Ascusbbf__106863B | 0 | 0 | 0 | + | 0 | + | 0 | 0 | + | 0 |
| Ascusbbf__106863B | 0 | 0 | 0 | + | 0 | + | 0 | 0 | + | 0 |
| Ascusbbf__10712A | 0 | − | + | − | + | + | + | 0 | 0 | 0 |
| Ascusbbf__10712A | 0 | − | + | 0 | 0 | + | + | + | + | 0 |
| Ascusbbf__10712A | 0 | − | + | + | + | + | 0 | 0 | + | 0 |
| Ascusbbf__10712A | + | − | + | − | 0 | + | + | + | − | 0 |
| Ascusbbf__10712B | + | − | + | − | 0 | + | + | + | − | 0 |
| Ascusbbf__10712C | 0 | − | + | − | + | + | + | 0 | 0 | 0 |
| Ascusbbf__10712C | 0 | − | + | 0 | 0 | + | + | 0 | + | 0 |
| Ascusbbf__10712C | 0 | 0 | 0 | 0 | + | − | 0 | 0 | + | 0 |
| Ascusbbf__10712D | 0 | − | + | − | + | + | + | 0 | 0 | 0 |
| Ascusbbf__10712D | 0 | − | + | 0 | 0 | + | + | + | + | 0 |
| Ascusbbf__10712E | 0 | − | + | 0 | 0 | + | + | + | + | 0 |
| Ascusbbf__10712E | 0 | 0 | 0 | 0 | + | − | 0 | 0 | + | 0 |
| Ascusbbf__10712F | 0 | − | + | − | + | + | + | 0 | 0 | 0 |
| Ascusbbf__10712F | 0 | − | 0 | − | − | 0 | 0 | + | + | 0 |
| Ascusbbf__10712F | 0 | − | + | 0 | 0 | + | + | + | + | 0 |
| Ascusbbf__10712F | 0 | − | + | − | − | + | − | + | − | 0 |
| Ascusbbf__10712F | 0 | − | 0 | − | − | 0 | 0 | + | + | 0 |
| Ascusbbf__10712G | 0 | − | + | − | + | + | + | 0 | 0 | 0 |
| Ascusbbf__10712G | 0 | − | + | 0 | 0 | + | + | + | + | 0 |
| Ascusbbf__10712G | 0 | 0 | 0 | 0 | + | − | 0 | 0 | + | 0 |
| Ascusbbf__10712G | 0 | − | + | − | − | + | − | + | − | 0 |
| Ascusbbf__10712G | 0 | − | 0 | − | − | 0 | 0 | + | + | 0 |
| Ascusbbf__10712H | 0 | − | + | − | + | + | + | 0 | 0 | 0 |
| Ascusbbf__10712H | 0 | − | + | 0 | 0 | + | + | + | + | 0 |
| Ascusbbf__10712H | 0 | 0 | 0 | 0 | + | − | 0 | 0 | + | 0 |
| Ascusbbf__10712H | 0 | − | + | − | − | + | − | + | − | 0 |
| Ascusbbf__10712H | 0 | 0 | 0 | + | 0 | + | 0 | 0 | 0 | 0 |
| Ascusbbf__10712I | 0 | − | + | 0 | 0 | + | + | + | + | 0 |
| Ascusbbf__10712I | 0 | − | + | + | + | + | 0 | 0 | + | 0 |

-continued

| Strain ID | pyruvic | glucose | succinic | lactic | glycerol | acetic | propionic | butyric | ethanol | 1-Butanol |
|---|---|---|---|---|---|---|---|---|---|---|
| Ascusbbf_1085A | 0 | − | + | − | + | + | + | 0 | 0 | 0 |
| Ascusbbf_1085A | 0 | 0 | 0 | 0 | 0 | + | + | + | − | 0 |
| Ascusbbf_1085A | 0 | 0 | 0 | 0 | + | − | 0 | 0 | + | 0 |
| Ascusbbf_1085A | 0 | 0 | 0 | 0 | 0 | + | 0 | 0 | 0 | 0 |
| Ascusbbf_1085A | + | − | + | − | 0 | + | + | + | − | 0 |
| Ascusbbf_1085A | + | − | 0 | + | − | + | 0 | + | − | 0 |
| Ascusbbf_1085B | 0 | − | + | − | + | + | + | 0 | 0 | 0 |
| Ascusbbf_1085B | 0 | − | + | − | + | + | + | + | + | 0 |
| Ascusbbf_1085B | 0 | 0 | 0 | 0 | 0 | + | 0 | 0 | 0 | 0 |
| Ascusbbf_1085B | 0 | 0 | + | + | + | + | + | 0 | + | 0 |
| Ascusbbf_1085B | + | − | 0 | + | 0 | + | 0 | + | + | 0 |
| Ascusbbf_1085C | 0 | − | + | − | + | + | + | 0 | 0 | 0 |
| Ascusbbf_1085C | 0 | 0 | 0 | 0 | − | − | 0 | + | 0 | 0 |
| Ascusbbf_1085C | 0 | 0 | 0 | 0 | 0 | + | + | + | − | 0 |
| Ascusbbf_1085C | 0 | − | + | 0 | 0 | + | + | 0 | + | 0 |
| Ascusbbf_1085C | 0 | 0 | 0 | 0 | + | − | 0 | 0 | + | 0 |
| Ascusbbf_1085C | 0 | 0 | 0 | 0 | 0 | + | 0 | 0 | 0 | 0 |
| Ascusbbf_1085C | 0 | 0 | 0 | + | 0 | + | 0 | 0 | + | 0 |
| Ascusbbf_1085C | 0 | 0 | 0 | + | 0 | + | 0 | 0 | + | 0 |
| Ascusbbf_1085D | 0 | 0 | 0 | 0 | − | − | 0 | + | 0 | 0 |
| Ascusbbf_1085D | 0 | 0 | 0 | 0 | 0 | + | + | + | − | 0 |
| Ascusbbf_1085D | 0 | − | + | 0 | 0 | + | + | + | + | 0 |
| Ascusbbf_1085D | 0 | 0 | 0 | 0 | + | − | 0 | 0 | + | 0 |
| Ascusbbf_1085D | 0 | 0 | 0 | 0 | 0 | + | 0 | 0 | 0 | 0 |
| Ascusbbf_1085D | 0 | 0 | 0 | + | 0 | + | 0 | 0 | 0 | 0 |
| Ascusbbf_1085E | 0 | − | + | − | + | + | + | 0 | 0 | 0 |
| Ascusbbf_1085E | 0 | 0 | 0 | 0 | − | − | 0 | + | 0 | 0 |
| Ascusbbf_1085E | 0 | 0 | 0 | 0 | 0 | + | + | + | − | 0 |
| Ascusbbf_1085E | 0 | − | + | 0 | 0 | + | + | + | + | 0 |
| Ascusbbf_1085E | 0 | 0 | 0 | 0 | + | − | 0 | 0 | + | 0 |
| Ascusbbf_1085E | 0 | 0 | 0 | 0 | 0 | + | 0 | 0 | 0 | 0 |
| Ascusbbf_1085E | 0 | 0 | 0 | + | 0 | + | 0 | 0 | 0 | 0 |
| Ascusbbf_1085E | + | − | 0 | + | 0 | + | 0 | + | + | 0 |
| Ascusbbf_1085F | 0 | − | + | − | + | + | + | 0 | 0 | 0 |
| Ascusbbf_1085F | 0 | 0 | 0 | 0 | + | − | 0 | 0 | + | 0 |
| Ascusbbf_1085F | 0 | 0 | 0 | + | 0 | + | 0 | 0 | + | 0 |
| Ascusbbf_1085F | 0 | 0 | 0 | + | 0 | + | 0 | 0 | + | 0 |
| Ascusbbf_1085G | 0 | − | + | − | + | + | + | 0 | 0 | 0 |
| Ascusbbf_1085G | 0 | − | + | − | − | + | − | + | − | 0 |
| Ascusbbf_1085H | 0 | − | + | − | + | + | + | 0 | 0 | 0 |
| Ascusbbf_1085H | 0 | − | + | − | − | + | − | + | − | 0 |
| Ascusbbf_1085I | 0 | − | + | − | + | + | + | 0 | 0 | 0 |
| Ascusbbf_1085I | 0 | − | + | − | − | + | − | + | − | 0 |
| Ascusbbf_1085J | 0 | − | + | − | + | + | + | 0 | 0 | 0 |
| Ascusbbf_1085J | 0 | − | + | − | + | + | + | + | + | 0 |
| Ascusbbf_1085K | 0 | − | + | − | + | + | + | + | + | 0 |
| Ascusbbf_1103A | 0 | − | + | − | + | + | + | 0 | 0 | 0 |
| Ascusbbf_1103A | 0 | 0 | 0 | 0 | + | + | 0 | + | + | 0 |
| Ascusbbf_1103B | 0 | 0 | 0 | 0 | 0 | + | + | + | − | 0 |
| Ascusbbf_1103B | 0 | 0 | + | + | + | + | + | 0 | + | 0 |
| Ascusbbf_1103B | 0 | 0 | 0 | + | 0 | + | 0 | 0 | + | 0 |
| Ascusbbf_1103C | 0 | 0 | 0 | 0 | 0 | + | + | + | − | 0 |
| Ascusbbf_1103C | 0 | 0 | 0 | + | 0 | + | 0 | 0 | + | 0 |
| Ascusbbf_1103C | 0 | 0 | 0 | + | 0 | + | 0 | 0 | + | 0 |
| Ascusbbf_1103D | 0 | 0 | 0 | 0 | + | + | 0 | + | + | 0 |
| Ascusbbf_1103D | 0 | − | + | 0 | 0 | + | + | 0 | + | 0 |
| Ascusbbf_1103D | 0 | 0 | 0 | + | 0 | + | 0 | 0 | + | 0 |
| Ascusbbf_1103D | 0 | 0 | 0 | + | 0 | + | 0 | 0 | + | 0 |
| Ascusbbf_1103E | 0 | 0 | 0 | 0 | + | + | 0 | + | + | 0 |
| Ascusbbf_1103E | 0 | 0 | + | + | + | + | + | 0 | + | 0 |
| Ascusbbf_1103E | 0 | 0 | 0 | + | 0 | + | 0 | 0 | + | 0 |
| Ascusbbf_1103F | 0 | 0 | 0 | + | 0 | + | 0 | 0 | + | 0 |
| Ascusbbf_1103G | 0 | 0 | 0 | + | 0 | + | 0 | 0 | + | 0 |
| Ascusbbf_1103G | 0 | 0 | 0 | + | 0 | + | 0 | 0 | + | 0 |
| Ascusbbf_1103H | 0 | 0 | 0 | + | 0 | + | 0 | 0 | + | 0 |
| Ascusbbf_1103H | 0 | 0 | 0 | + | 0 | + | 0 | 0 | + | 0 |
| Ascusbbf_1103I | 0 | 0 | + | + | + | + | + | 0 | + | 0 |
| Ascusbbf_1103I | 0 | 0 | 0 | + | 0 | + | 0 | 0 | + | 0 |
| Ascusbbf_113152A | 0 | − | + | − | − | + | − | + | − | 0 |
| Ascusbbf_1136A | 0 | 0 | 0 | 0 | − | − | 0 | + | 0 | 0 |
| Ascusbbf_1136A | 0 | 0 | 0 | 0 | + | + | 0 | + | + | 0 |
| Ascusbbf_1136A | 0 | 0 | + | 0 | 0 | + | + | + | + | 0 |
| Ascusbbf_1136A | 0 | 0 | 0 | 0 | 0 | + | − | 0 | + | 0 |
| Ascusbbf_1136A | 0 | − | + | − | − | + | − | + | − | 0 |
| Ascusbbf_1136B | 0 | 0 | 0 | 0 | − | − | 0 | + | 0 | 0 |
| Ascusbbf_1136B | 0 | 0 | 0 | 0 | 0 | + | + | + | − | 0 |
| Ascusbbf_1136B | 0 | − | + | 0 | 0 | + | + | 0 | + | 0 |

-continued

| Strain ID | pyruvic | glucose | succinic | lactic | glycerol | acetic | propionic | butyric | ethanol | 1-Butanol |
|---|---|---|---|---|---|---|---|---|---|---|
| Ascusbbf_1136B | 0 | 0 | 0 | 0 | + | − | 0 | 0 | + | 0 |
| Ascusbbf_1136B | 0 | − | + | − | − | + | − | + | − | 0 |
| Ascusbbf_1136B | 0 | 0 | 0 | + | 0 | + | 0 | 0 | 0 | 0 |
| Ascusbbf_1136C | 0 | − | + | − | + | + | + | 0 | 0 | 0 |
| Ascusbbf_1136C | 0 | 0 | 0 | 0 | − | − | 0 | + | 0 | 0 |
| Ascusbbf_1136C | 0 | 0 | 0 | 0 | 0 | + | + | + | − | 0 |
| Ascusbbf_1136C | 0 | − | + | 0 | 0 | + | + | + | + | 0 |
| Ascusbbf_1136C | 0 | 0 | 0 | 0 | + | − | 0 | 0 | + | 0 |
| Ascusbbf_1136C | 0 | − | + | − | − | + | − | + | − | 0 |
| Ascusbbf_1136D | 0 | 0 | 0 | 0 | − | − | 0 | + | 0 | 0 |
| Ascusbbf_1136D | 0 | 0 | 0 | 0 | + | + | 0 | + | + | 0 |
| Ascusbbf_1136D | 0 | − | + | 0 | 0 | + | + | + | + | 0 |
| Ascusbbf_1136D | 0 | 0 | 0 | 0 | + | − | 0 | 0 | + | 0 |
| Ascusbbf_1136D | 0 | 0 | 0 | 0 | 0 | + | 0 | 0 | 0 | 0 |
| Ascusbbf_1136D | 0 | 0 | 0 | + | 0 | + | 0 | 0 | 0 | 0 |
| Ascusbbf_1136E | 0 | 0 | 0 | 0 | − | − | 0 | + | 0 | 0 |
| Ascusbbf_1136E | 0 | 0 | 0 | 0 | + | + | 0 | + | + | 0 |
| Ascusbbf_1136E | 0 | 0 | 0 | 0 | + | − | 0 | 0 | + | 0 |
| Ascusbbf_1136E | 0 | − | + | − | − | + | − | + | − | 0 |
| Ascusbbf_1136F | 0 | − | + | 0 | 0 | + | + | + | + | 0 |
| Ascusbbf_11823A | 0 | 0 | 0 | 0 | 0 | + | + | + | − | 0 |
| Ascusbbf_11823B | 0 | 0 | 0 | 0 | 0 | + | + | + | − | 0 |
| Ascusbbf_11823B | 0 | − | + | − | + | + | + | + | + | 0 |
| Ascusbbf_11823B | 0 | 0 | 0 | 0 | + | − | 0 | 0 | + | 0 |
| Ascusbbf_11823C | 0 | − | + | − | − | + | − | + | − | 0 |
| Ascusbbf_118A | 0 | 0 | 0 | 0 | + | − | 0 | 0 | + | 0 |
| Ascusbbf_118A | 0 | 0 | 0 | + | 0 | + | 0 | 0 | + | 0 |
| Ascusbbf_118A | 0 | 0 | 0 | + | 0 | + | 0 | 0 | + | 0 |
| Ascusbbf_118B | 0 | 0 | 0 | + | 0 | + | 0 | 0 | + | 0 |
| Ascusbbf_118B | 0 | 0 | 0 | + | 0 | + | 0 | 0 | + | 0 |
| Ascusbbf_118C | 0 | 0 | 0 | + | 0 | + | 0 | 0 | + | 0 |
| Ascusbbf_118C | 0 | 0 | 0 | + | 0 | + | 0 | 0 | + | 0 |
| Ascusbbf_1207A | 0 | − | + | − | + | + | + | 0 | 0 | 0 |
| Ascusbbf_1207A | 0 | − | + | 0 | 0 | + | + | 0 | + | 0 |
| Ascusbbf_1207A | 0 | 0 | 0 | 0 | + | − | 0 | 0 | + | 0 |
| Ascusbbf_1207A | 0 | − | + | − | − | + | − | + | − | 0 |
| Ascusbbf_1207B | 0 | − | + | − | + | + | + | 0 | 0 | 0 |
| Ascusbbf_1207B | 0 | − | + | − | + | + | + | + | + | 0 |
| Ascusbbf_1207C | 0 | − | + | − | + | + | + | 0 | 0 | 0 |
| Ascusbbf_1207D | 0 | 0 | 0 | 0 | − | − | 0 | + | 0 | 0 |
| Ascusbbf_1207D | 0 | 0 | 0 | 0 | 0 | + | + | + | − | 0 |
| Ascusbbf_1207E | 0 | 0 | 0 | 0 | − | − | 0 | + | 0 | 0 |
| Ascusbbf_1207E | 0 | 0 | 0 | 0 | 0 | + | + | + | − | 0 |
| Ascusbbf_1207F | 0 | 0 | 0 | 0 | − | − | 0 | + | 0 | 0 |
| Ascusbbf_1207F | 0 | 0 | 0 | 0 | 0 | + | + | + | − | 0 |
| Ascusbbf_1207F | 0 | − | + | 0 | 0 | + | + | 0 | + | 0 |
| Ascusbbf_1207G | 0 | − | + | − | + | + | + | 0 | 0 | 0 |
| Ascusbbf_1207G | 0 | 0 | 0 | 0 | − | − | 0 | + | 0 | 0 |
| Ascusbbf_1207G | 0 | 0 | 0 | 0 | + | + | 0 | + | + | 0 |
| Ascusbbf_1207G | 0 | − | + | 0 | 0 | + | + | 0 | + | 0 |
| Ascusbbf_1207G | 0 | 0 | 0 | 0 | + | − | 0 | 0 | + | 0 |
| Ascusbbf_1207G | 0 | 0 | 0 | 0 | 0 | + | 0 | 0 | 0 | 0 |
| Ascusbbf_1207G | 0 | 0 | 0 | + | 0 | + | 0 | 0 | 0 | 0 |
| Ascusbbf_1207H | 0 | − | + | − | + | + | + | 0 | 0 | 0 |
| Ascusbbf_1207H | 0 | 0 | 0 | 0 | − | − | 0 | + | 0 | 0 |
| Ascusbbf_1207I | 0 | − | + | − | + | + | + | 0 | 0 | 0 |
| Ascusbbf_1207I | 0 | 0 | 0 | 0 | − | − | 0 | + | 0 | 0 |
| Ascusbbf_1207I | 0 | 0 | 0 | 0 | + | + | 0 | + | + | 0 |
| Ascusbbf_1207I | 0 | 0 | 0 | 0 | + | − | 0 | 0 | + | 0 |
| Ascusbbf_1207I | 0 | 0 | 0 | 0 | 0 | + | 0 | 0 | 0 | 0 |
| Ascusbbf_1207J | 0 | − | + | − | + | + | + | 0 | 0 | 0 |
| Ascusbbf_1207J | 0 | − | + | 0 | 0 | + | + | 0 | + | 0 |
| Ascusbbf_1207J | 0 | 0 | 0 | 0 | + | − | 0 | 0 | + | 0 |
| Ascusbbf_1207K | 0 | − | + | − | + | + | + | 0 | 0 | 0 |
| Ascusbbf_1207K | 0 | 0 | 0 | 0 | + | − | 0 | 0 | + | 0 |
| Ascusbbf_1207K | 0 | − | + | − | − | + | − | + | − | 0 |
| Ascusbbf_1207L | 0 | 0 | 0 | 0 | + | − | 0 | 0 | + | 0 |
| Ascusbbf_120A | 0 | 0 | + | + | + | + | + | 0 | + | 0 |
| Ascusbbf_120B | 0 | 0 | + | + | + | + | + | 0 | + | 0 |
| Ascusbbf_120C | 0 | 0 | + | + | + | + | + | 0 | + | 0 |
| Ascusbbf_121971A | 0 | 0 | 0 | 0 | 0 | + | + | + | − | 0 |
| Ascusbbf_1238A | 0 | − | + | − | + | + | + | 0 | 0 | 0 |
| Ascusbbf_1238A | 0 | 0 | 0 | 0 | − | − | 0 | + | 0 | 0 |
| Ascusbbf_1238A | 0 | 0 | 0 | 0 | + | + | 0 | + | + | 0 |
| Ascusbbf_1238A | 0 | 0 | 0 | 0 | 0 | + | 0 | 0 | 0 | 0 |
| Ascusbbf_1238A | 0 | 0 | + | + | + | + | + | 0 | + | 0 |
| Ascusbbf_1238A | 0 | 0 | 0 | + | 0 | + | 0 | 0 | 0 | 0 |

-continued

| Strain ID | pyruvic | glucose | succinic | lactic | glycerol | acetic | propionic | butyric | ethanol | 1-Butanol |
|---|---|---|---|---|---|---|---|---|---|---|
| Ascusbbf_1238B | 0 | 0 | 0 | 0 | − | − | 0 | + | 0 | 0 |
| Ascusbbf_1238B | 0 | 0 | 0 | 0 | + | + | 0 | + | + | 0 |
| Ascusbbf_1238B | 0 | 0 | 0 | 0 | 0 | + | 0 | 0 | 0 | 0 |
| Ascusbbf_1238B | 0 | 0 | 0 | + | 0 | + | 0 | 0 | 0 | 0 |
| Ascusbbf_1238C | 0 | − | + | − | + | + | + | 0 | 0 | 0 |
| Ascusbbf_1238C | 0 | 0 | 0 | 0 | − | − | 0 | + | 0 | 0 |
| Ascusbbf_1238C | 0 | 0 | 0 | 0 | + | + | 0 | + | + | 0 |
| Ascusbbf_1238C | 0 | − | + | 0 | 0 | + | + | + | + | 0 |
| Ascusbbf_1238C | 0 | 0 | 0 | 0 | 0 | + | 0 | 0 | 0 | 0 |
| Ascusbbf_1238C | 0 | 0 | + | + | + | + | + | 0 | + | 0 |
| Ascusbbf_1238C | 0 | 0 | 0 | + | 0 | + | 0 | 0 | 0 | 0 |
| Ascusbbf_1238D | 0 | − | + | − | + | + | + | 0 | + | 0 |
| Ascusbbf_1238D | 0 | 0 | + | + | + | + | + | 0 | + | 0 |
| Ascusbbf_1238D | 0 | 0 | 0 | + | 0 | + | 0 | 0 | 0 | 0 |
| Ascusbbf_1273A | 0 | 0 | 0 | 0 | + | − | 0 | 0 | + | 0 |
| Ascusbbf_1273A | 0 | 0 | + | + | + | + | + | 0 | + | 0 |
| Ascusbbf_1273A | 0 | 0 | 0 | + | 0 | + | 0 | 0 | + | 0 |
| Ascusbbf_1273B | 0 | 0 | 0 | + | 0 | + | 0 | 0 | + | 0 |
| Ascusbbf_1273C | 0 | 0 | + | + | + | + | + | 0 | + | 0 |
| Ascusbbf_1273C | 0 | 0 | 0 | + | 0 | + | 0 | 0 | + | 0 |
| Ascusbbf_1273D | 0 | 0 | + | + | + | + | + | 0 | + | 0 |
| Ascusbbf_1273D | 0 | 0 | 0 | + | 0 | + | 0 | 0 | + | 0 |
| Ascusbbf_130A | 0 | 0 | 0 | 0 | + | − | 0 | 0 | + | 0 |
| Ascusbbf_130A | 0 | − | + | − | − | + | − | + | − | 0 |
| Ascusbbf_130A | 0 | 0 | 0 | + | 0 | + | 0 | 0 | + | 0 |
| Ascusbbf_130A | 0 | 0 | 0 | + | 0 | + | 0 | 0 | + | 0 |
| Ascusbbf_130B | 0 | 0 | 0 | 0 | + | − | 0 | 0 | + | 0 |
| Ascusbbf_130C | 0 | 0 | 0 | 0 | + | − | 0 | 0 | + | 0 |
| Ascusbbf_130C | 0 | − | + | − | − | + | − | + | − | 0 |
| Ascusbbf_130D | 0 | 0 | 0 | 0 | + | − | 0 | 0 | + | 0 |
| Ascusbbf_130D | 0 | − | + | − | − | + | − | + | − | 0 |
| Ascusbbf_130E | 0 | 0 | 0 | 0 | + | − | 0 | 0 | + | 0 |
| Ascusbbf_130F | 0 | 0 | 0 | 0 | + | − | 0 | 0 | + | 0 |
| Ascusbbf_130F | 0 | − | + | − | − | + | − | + | − | 0 |
| Ascusbbf_130G | 0 | 0 | + | + | + | + | + | 0 | + | 0 |
| Ascusbbf_1325058A | 0 | 0 | 0 | 0 | 0 | + | + | + | − | 0 |
| Ascusbbf_1325058A | 0 | 0 | 0 | 0 | + | − | 0 | 0 | + | 0 |
| Ascusbbf_1325058A | 0 | 0 | 0 | + | 0 | + | 0 | 0 | + | 0 |
| Ascusbbf_1325058A | 0 | 0 | 0 | + | 0 | + | 0 | 0 | + | 0 |
| Ascusbbf_1325058B | 0 | 0 | 0 | 0 | + | + | 0 | + | + | 0 |
| Ascusbbf_1325058B | 0 | − | + | 0 | 0 | + | + | 0 | + | 0 |
| Ascusbbf_1325058B | 0 | 0 | 0 | 0 | + | − | 0 | 0 | + | 0 |
| Ascusbbf_1325058B | 0 | − | + | − | − | + | − | + | − | 0 |
| Ascusbbf_1325058B | 0 | 0 | + | + | + | + | + | 0 | + | 0 |
| Ascusbbf_1325058C | 0 | 0 | 0 | 0 | + | − | 0 | 0 | + | 0 |
| Ascusbbf_1325058D | 0 | 0 | 0 | 0 | + | − | 0 | 0 | + | 0 |
| Ascusbbf_1325058E | 0 | − | + | − | − | + | − | + | − | 0 |
| Ascusbbf_1325058F | 0 | 0 | + | + | + | + | + | 0 | + | 0 |
| Ascusbbf_13543A | 0 | − | + | − | + | + | + | 0 | 0 | 0 |
| Ascusbbf_13543B | 0 | 0 | 0 | 0 | + | + | 0 | + | + | 0 |
| Ascusbbf_13543B | 0 | 0 | 0 | 0 | 0 | + | 0 | 0 | 0 | 0 |
| Ascusbbf_13543C | 0 | 0 | 0 | 0 | + | + | 0 | + | + | 0 |
| Ascusbbf_13543C | 0 | − | + | 0 | 0 | + | + | 0 | + | 0 |
| Ascusbbf_13543C | 0 | 0 | 0 | 0 | 0 | + | 0 | 0 | 0 | 0 |
| Ascusbbf_13543C | 0 | 0 | 0 | + | 0 | + | 0 | 0 | + | 0 |
| Ascusbbf_13543C | 0 | 0 | 0 | + | 0 | + | 0 | 0 | + | 0 |
| Ascusbbf_13543D | 0 | 0 | 0 | 0 | + | + | 0 | + | + | 0 |
| Ascusbbf_13543D | 0 | 0 | 0 | 0 | 0 | + | 0 | 0 | 0 | 0 |
| Ascusbbf_13543E | 0 | − | + | − | + | + | + | 0 | 0 | 0 |
| Ascusbbf_13543E | 0 | 0 | 0 | 0 | + | + | 0 | + | + | 0 |
| Ascusbbf_13543E | 0 | − | + | 0 | 0 | + | + | 0 | + | 0 |
| Ascusbbf_13543E | 0 | 0 | 0 | + | 0 | + | 0 | 0 | + | 0 |
| Ascusbbf_13543E | 0 | 0 | 0 | + | 0 | + | 0 | 0 | + | 0 |
| Ascusbbf_13717A | 0 | 0 | + | + | + | + | + | 0 | + | 0 |
| Ascusbbf_13717A | 0 | 0 | 0 | + | 0 | + | 0 | 0 | + | 0 |
| Ascusbbf_13717B | 0 | 0 | + | + | + | + | + | 0 | + | 0 |
| Ascusbbf_13717B | 0 | 0 | 0 | + | 0 | + | 0 | 0 | + | 0 |
| Ascusbbf_13717C | 0 | 0 | + | + | + | + | + | 0 | + | 0 |
| Ascusbbf_13717C | 0 | 0 | 0 | + | 0 | + | 0 | 0 | + | 0 |
| Ascusbbf_1372985A | 0 | 0 | 0 | 0 | 0 | + | + | + | − | 0 |
| Ascusbbf_1372985A | + | − | + | − | 0 | + | + | + | − | 0 |
| Ascusbbf_1372985B | 0 | − | + | − | + | + | + | 0 | 0 | 0 |
| Ascusbbf_1372985B | 0 | 0 | 0 | 0 | 0 | + | + | + | − | 0 |
| Ascusbbf_1372985B | 0 | − | + | 0 | + | + | + | 0 | + | 0 |
| Ascusbbf_1372985C | 0 | − | + | − | + | + | + | 0 | 0 | 0 |
| Ascusbbf_1372985C | 0 | 0 | 0 | 0 | 0 | + | + | + | − | 0 |
| Ascusbbf_1372985D | 0 | 0 | 0 | 0 | − | − | 0 | + | 0 | 0 |

-continued

| Strain ID | pyruvic | glucose | succinic | lactic | glycerol | acetic | propionic | butyric | ethanol | 1-Butanol |
|---|---|---|---|---|---|---|---|---|---|---|
| Ascusbbf_1372985D | 0 | 0 | 0 | 0 | + | + | 0 | + | + | 0 |
| Ascusbbf_1372985D | 0 | − | + | 0 | 0 | + | + | + | + | 0 |
| Ascusbbf_1372985D | 0 | 0 | 0 | 0 | + | | 0 | 0 | + | 0 |
| Ascusbbf_1372985D | 0 | 0 | 0 | 0 | 0 | + | 0 | 0 | 0 | 0 |
| Ascusbbf_1372985E | 0 | 0 | 0 | 0 | − | − | 0 | + | 0 | 0 |
| Ascusbbf_1372985E | 0 | 0 | 0 | 0 | + | + | 0 | + | + | 0 |
| Ascusbbf_1372985E | 0 | 0 | 0 | 0 | + | − | 0 | 0 | + | 0 |
| Ascusbbf_1372985E | 0 | 0 | 0 | 0 | 0 | + | 0 | 0 | 0 | 0 |
| Ascusbbf_1372985F | 0 | 0 | 0 | 0 | 0 | + | + | + | − | 0 |
| Ascusbbf_1372985I | 0 | − | + | − | + | + | + | 0 | 0 | 0 |
| Ascusbbf_1372985I | 0 | 0 | 0 | 0 | 0 | + | + | + | − | 0 |
| Ascusbbf_1372985L | 0 | 0 | 0 | 0 | 0 | + | + | + | − | 0 |
| Ascusbbf_1372985M | 0 | 0 | 0 | 0 | 0 | + | + | + | − | 0 |
| Ascusbbf_1372985N | 0 | 0 | 0 | 0 | 0 | + | + | + | − | 0 |
| Ascusbbf_1372985O | 0 | 0 | 0 | 0 | 0 | + | + | + | − | 0 |
| Ascusbbf_1372985P | 0 | 0 | 0 | 0 | 0 | + | + | + | − | 0 |
| Ascusbbf_1372985Q | 0 | 0 | 0 | 0 | 0 | + | + | + | − | 0 |
| Ascusbbf_1372985R | 0 | 0 | 0 | 0 | 0 | + | + | + | − | 0 |
| Ascusbbf_1372985S | 0 | 0 | 0 | 0 | + | + | 0 | + | + | 0 |
| Ascusbbf_1372985S | 0 | 0 | 0 | 0 | + | − | 0 | 0 | + | 0 |
| Ascusbbf_1372985S | 0 | 0 | 0 | 0 | 0 | + | 0 | 0 | 0 | 0 |
| Ascusbbf_1372985T | 0 | 0 | 0 | 0 | + | + | 0 | + | + | 0 |
| Ascusbbf_1372985T | 0 | 0 | 0 | 0 | + | − | 0 | 0 | + | 0 |
| Ascusbbf_1372985T | 0 | 0 | 0 | 0 | 0 | + | 0 | 0 | 0 | 0 |
| Ascusbbf_14146A | 0 | − | + | − | + | + | + | 0 | 0 | 0 |
| Ascusbbf_14146A | 0 | 0 | 0 | 0 | 0 | + | + | + | − | 0 |
| Ascusbbf_14146A | 0 | − | + | 0 | 0 | + | + | + | + | 0 |
| Ascusbbf_14146A | 0 | 0 | + | + | + | + | + | 0 | + | 0 |
| Ascusbbf_14146A | 0 | 0 | 0 | + | 0 | + | 0 | 0 | 0 | 0 |
| Ascusbbf_14146A | + | − | + | − | 0 | + | + | + | − | 0 |
| Ascusbbf_14146A | + | − | + | + | 0 | + | 0 | 0 | − | 0 |
| Ascusbbf_14146A | + | − | + | + | − | + | 0 | 0 | 0 | + |
| Ascusbbf_14146A | + | − | + | − | + | + | + | 0 | − | 0 |
| Ascusbbf_14146B | 0 | − | + | − | + | + | + | 0 | 0 | 0 |
| Ascusbbf_14146B | 0 | 0 | 0 | 0 | + | + | 0 | + | + | 0 |
| Ascusbbf_14146B | 0 | − | + | 0 | 0 | + | + | + | + | 0 |
| Ascusbbf_14146B | 0 | 0 | + | + | + | + | + | 0 | + | 0 |
| Ascusbbf_14146B | 0 | 0 | 0 | + | 0 | + | 0 | 0 | 0 | 0 |
| Ascusbbf_14146C | 0 | 0 | 0 | 0 | 0 | + | + | + | − | 0 |
| Ascusbbf_14146D | 0 | − | + | − | + | + | + | 0 | 0 | 0 |
| Ascusbbf_14146D | 0 | 0 | 0 | 0 | 0 | + | + | + | − | 0 |
| Ascusbbf_14146D | 0 | − | + | − | + | + | + | + | + | 0 |
| Ascusbbf_14146D | 0 | 0 | + | + | + | + | + | 0 | + | 0 |
| Ascusbbf_14146D | 0 | 0 | 0 | + | 0 | + | 0 | 0 | 0 | 0 |
| Ascusbbf_14146E | 0 | − | + | − | + | + | + | 0 | 0 | 0 |
| Ascusbbf_14146E | 0 | 0 | 0 | 0 | 0 | + | + | + | − | 0 |
| Ascusbbf_14146F | 0 | 0 | 0 | 0 | 0 | + | + | + | − | 0 |
| Ascusbbf_14146G | 0 | − | + | − | + | + | + | + | + | 0 |
| Ascusbbf_14146G | 0 | 0 | 0 | + | 0 | + | 0 | 0 | + | 0 |
| Ascusbbf_14146G | 0 | 0 | 0 | + | 0 | + | 0 | 0 | + | 0 |
| Ascusbbf_148A | 0 | 0 | 0 | 0 | + | − | 0 | 0 | + | 0 |
| Ascusbbf_148A | 0 | 0 | + | + | + | + | + | 0 | + | 0 |
| Ascusbbf_148A | 0 | 0 | 0 | + | 0 | + | 0 | 0 | + | 0 |
| Ascusbbf_148B | 0 | 0 | 0 | 0 | + | − | 0 | 0 | + | 0 |
| Ascusbbf_148B | 0 | 0 | + | + | + | + | + | 0 | + | 0 |
| Ascusbbf_148B | 0 | 0 | 0 | + | 0 | + | 0 | 0 | + | 0 |
| Ascusbbf_148C | 0 | 0 | 0 | 0 | + | − | 0 | 0 | + | 0 |
| Ascusbbf_148C | 0 | − | + | − | − | + | − | + | − | 0 |
| Ascusbbf_148C | 0 | 0 | + | + | + | + | + | 0 | + | 0 |
| Ascusbbf_148C | 0 | 0 | 0 | + | 0 | + | 0 | 0 | + | 0 |
| Ascusbbf_148D | 0 | 0 | + | + | + | + | + | 0 | + | 0 |
| Ascusbbf_148D | 0 | 0 | 0 | + | 0 | + | 0 | 0 | + | 0 |
| Ascusbbf_148E | 0 | 0 | 0 | + | 0 | + | 0 | 0 | + | 0 |
| Ascusbbf_148F | 0 | 0 | 0 | + | 0 | + | 0 | 0 | + | 0 |
| Ascusbbf_148F | 0 | 0 | 0 | + | 0 | + | 0 | 0 | + | 0 |
| Ascusbbf_148G | 0 | 0 | 0 | + | 0 | + | 0 | 0 | + | 0 |
| Ascusbbf_148G | 0 | 0 | 0 | + | 0 | + | 0 | 0 | + | 0 |
| Ascusbbf_148H | 0 | 0 | 0 | + | 0 | + | 0 | 0 | + | 0 |
| Ascusbbf_148H | 0 | 0 | 0 | + | 0 | + | 0 | 0 | + | 0 |
| Ascusbbf_1517A | 0 | − | + | − | + | + | + | 0 | 0 | 0 |
| Ascusbbf_1517A | 0 | 0 | 0 | 0 | − | − | 0 | + | 0 | 0 |
| Ascusbbf_1517A | 0 | 0 | 0 | 0 | + | + | 0 | + | + | 0 |
| Ascusbbf_1517A | 0 | − | + | 0 | 0 | + | + | + | 0 | 0 |
| Ascusbbf_1517A | 0 | 0 | 0 | + | 0 | + | 0 | 0 | + | 0 |
| Ascusbbf_1517A | 0 | 0 | 0 | + | 0 | + | 0 | 0 | 0 | 0 |
| Ascusbbf_1517B | 0 | 0 | 0 | 0 | − | − | 0 | + | 0 | 0 |
| Ascusbbf_1517B | 0 | 0 | 0 | 0 | + | + | 0 | + | + | 0 |

-continued

| Strain ID | pyruvic | glucose | succinic | lactic | glycerol | acetic | propionic | butyric | ethanol | 1-Butanol |
|---|---|---|---|---|---|---|---|---|---|---|
| Ascusbbf_1517B | 0 | − | + | 0 | 0 | + | + | + | + | 0 |
| Ascusbbf_1517B | 0 | 0 | + | + | + | + | + | 0 | + | 0 |
| Ascusbbf_1517B | 0 | 0 | 0 | + | 0 | + | 0 | 0 | 0 | 0 |
| Ascusbbf_1517C | 0 | 0 | 0 | 0 | − | − | 0 | + | 0 | 0 |
| Ascusbbf_1517C | 0 | − | + | 0 | 0 | + | + | 0 | + | 0 |
| Ascusbbf_1517C | 0 | 0 | 0 | 0 | + | − | 0 | 0 | + | 0 |
| Ascusbbf_1517C | 0 | − | + | − | − | + | − | + | − | 0 |
| Ascusbbf_1517C | 0 | 0 | 0 | + | 0 | + | 0 | 0 | + | 0 |
| Ascusbbf_1517C | 0 | 0 | 0 | + | 0 | + | 0 | 0 | + | 0 |
| Ascusbbf_1517D | 0 | − | + | − | + | + | + | 0 | 0 | 0 |
| Ascusbbf_1517D | 0 | 0 | 0 | 0 | − | − | 0 | + | 0 | 0 |
| Ascusbbf_1517D | 0 | − | + | 0 | 0 | + | + | + | + | 0 |
| Ascusbbf_1517D | 0 | 0 | 0 | 0 | + | − | 0 | 0 | + | 0 |
| Ascusbbf_1517D | 0 | − | + | − | − | + | − | + | − | 0 |
| Ascusbbf_1517D | 0 | 0 | 0 | + | 0 | + | 0 | 0 | + | 0 |
| Ascusbbf_1517D | 0 | 0 | 0 | + | 0 | + | 0 | 0 | 0 | 0 |
| Ascusbbf_1517E | 0 | − | + | − | + | + | + | 0 | 0 | 0 |
| Ascusbbf_1517E | 0 | 0 | 0 | 0 | + | + | 0 | + | + | 0 |
| Ascusbbf_1517E | 0 | 0 | 0 | 0 | 0 | + | 0 | 0 | 0 | 0 |
| Ascusbbf_1517F | 0 | − | + | 0 | 0 | + | + | 0 | + | 0 |
| Ascusbbf_1517G | 0 | − | + | 0 | 0 | + | + | 0 | + | 0 |
| Ascusbbf_1517H | 0 | − | + | 0 | 0 | + | + | + | + | 0 |
| Ascusbbf_1517I | 0 | 0 | 0 | 0 | + | − | 0 | 0 | + | 0 |
| Ascusbbf_152A | 0 | 0 | + | + | + | + | + | 0 | + | 0 |
| Ascusbbf_152B | 0 | 0 | + | + | + | + | + | 0 | + | 0 |
| Ascusbbf_152C | 0 | 0 | + | + | + | + | + | 0 | + | 0 |
| Ascusbbf_154A | + | − | + | − | 0 | + | + | + | − | 0 |
| Ascusbbf_154A | + | − | + | + | + | + | 0 | 0 | + | + |
| Ascusbbf_154B | 0 | − | + | − | + | + | + | + | + | 0 |
| Ascusbbf_154B | 0 | 0 | 0 | 0 | + | − | 0 | 0 | + | 0 |
| Ascusbbf_154B | 0 | − | + | − | − | + | − | + | − | 0 |
| Ascusbbf_154B | 0 | 0 | 0 | + | 0 | + | 0 | 0 | + | 0 |
| Ascusbbf_154B | + | − | + | + | + | + | 0 | 0 | + | + |
| Ascusbbf_154D | 0 | 0 | 0 | 0 | − | − | 0 | + | 0 | 0 |
| Ascusbbf_154D | 0 | 0 | 0 | 0 | 0 | + | + | + | − | 0 |
| Ascusbbf_154D | 0 | − | + | − | + | + | + | + | + | 0 |
| Ascusbbf_154D | 0 | 0 | 0 | + | 0 | + | 0 | 0 | + | 0 |
| Ascusbbf_154D | 0 | 0 | 0 | + | 0 | + | 0 | 0 | + | 0 |
| Ascusbbf_154E | 0 | 0 | 0 | 0 | − | − | 0 | + | 0 | 0 |
| Ascusbbf_154E | 0 | 0 | 0 | 0 | + | + | 0 | + | + | 0 |
| Ascusbbf_154E | 0 | 0 | 0 | 0 | + | − | 0 | 0 | + | 0 |
| Ascusbbf_154E | 0 | 0 | 0 | 0 | 0 | + | 0 | 0 | 0 | 0 |
| Ascusbbf_154E | 0 | 0 | 0 | + | 0 | + | 0 | 0 | 0 | 0 |
| Ascusbbf_154F | 0 | − | + | − | + | + | + | 0 | 0 | 0 |
| Ascusbbf_154F | 0 | 0 | 0 | 0 | − | − | 0 | + | 0 | 0 |
| Ascusbbf_154F | 0 | 0 | 0 | 0 | + | + | 0 | + | + | 0 |
| Ascusbbf_154F | 0 | − | + | 0 | 0 | + | + | 0 | + | 0 |
| Ascusbbf_154F | 0 | 0 | 0 | 0 | + | − | 0 | 0 | + | 0 |
| Ascusbbf_154F | 0 | 0 | 0 | + | 0 | + | 0 | 0 | 0 | 0 |
| Ascusbbf_154G | 0 | − | + | − | + | + | + | 0 | 0 | 0 |
| Ascusbbf_154G | 0 | 0 | 0 | 0 | 0 | + | + | + | − | 0 |
| Ascusbbf_154G | 0 | − | + | − | + | + | + | + | + | 0 |
| Ascusbbf_154G | 0 | 0 | 0 | 0 | + | − | 0 | 0 | + | 0 |
| Ascusbbf_154G | 0 | − | + | − | − | + | − | + | − | 0 |
| Ascusbbf_154G | 0 | 0 | 0 | + | 0 | + | 0 | 0 | + | 0 |
| Ascusbbf_154G | 0 | 0 | 0 | + | 0 | + | 0 | 0 | + | 0 |
| Ascusbbf_154G | 0 | − | 0 | + | + | + | − | 0 | + | 0 |
| Ascusbbf_154H | 0 | 0 | 0 | 0 | + | − | 0 | 0 | + | 0 |
| Ascusbbf_154H | 0 | − | + | − | − | + | − | + | − | 0 |
| Ascusbbf_154I | 0 | 0 | 0 | 0 | + | − | 0 | 0 | + | 0 |
| Ascusbbf_154I | 0 | − | + | − | − | + | − | + | − | 0 |
| Ascusbbf_154M | 0 | − | + | − | + | + | + | + | + | 0 |
| Ascusbbf_15806A | 0 | 0 | 0 | 0 | + | − | 0 | 0 | + | 0 |
| Ascusbbf_15806B | 0 | 0 | 0 | 0 | + | − | 0 | 0 | + | 0 |
| Ascusbbf_15806B | 0 | 0 | 0 | + | 0 | + | 0 | 0 | + | 0 |
| Ascusbbf_15806B | 0 | 0 | 0 | + | 0 | + | 0 | 0 | + | 0 |
| Ascusbbf_1629A | 0 | − | + | − | + | + | + | 0 | 0 | 0 |
| Ascusbbf_1629B | 0 | 0 | 0 | 0 | − | − | 0 | + | 0 | 0 |
| Ascusbbf_1629B | 0 | 0 | 0 | 0 | 0 | + | + | + | − | 0 |
| Ascusbbf_1629C | 0 | 0 | 0 | 0 | − | − | 0 | + | 0 | 0 |
| Ascusbbf_1629C | 0 | 0 | 0 | 0 | + | + | 0 | + | + | 0 |
| Ascusbbf_1629C | 0 | − | + | 0 | 0 | + | + | 0 | + | 0 |
| Ascusbbf_1629C | 0 | 0 | 0 | 0 | + | − | 0 | 0 | + | 0 |
| Ascusbbf_1629C | 0 | 0 | 0 | 0 | 0 | + | 0 | 0 | 0 | 0 |
| Ascusbbf_1629D | 0 | − | + | − | + | + | + | 0 | 0 | 0 |

-continued

| Strain ID | pyruvic | glucose | succinic | lactic | glycerol | acetic | propionic | butyric | ethanol | 1-Butanol |
|---|---|---|---|---|---|---|---|---|---|---|
| Ascusbbf_1629D | 0 | 0 | 0 | 0 | − | − | 0 | + | 0 | 0 |
| Ascusbbf_1629D | 0 | 0 | 0 | 0 | + | + | 0 | + | + | 0 |
| Ascusbbf_1629D | 0 | 0 | 0 | 0 | + | − | 0 | 0 | + | 0 |
| Ascusbbf_1629D | 0 | 0 | 0 | 0 | 0 | + | 0 | 0 | 0 | 0 |
| Ascusbbf_1629E | 0 | 0 | 0 | 0 | + | + | 0 | + | + | 0 |
| Ascusbbf_1629E | 0 | 0 | 0 | 0 | 0 | + | 0 | 0 | 0 | 0 |
| Ascusbbf_1629F | 0 | − | + | − | − | + | − | + | − | 0 |
| Ascusbbf_1629G | 0 | 0 | 0 | 0 | 0 | + | 0 | 0 | 0 | 0 |
| Ascusbbf_1697A | 0 | 0 | 0 | 0 | + | − | 0 | 0 | + | 0 |
| Ascusbbf_1697B | 0 | − | + | − | − | + | − | + | − | 0 |
| Ascusbbf_1697C | 0 | 0 | + | 0 | − | + | − | + | − | 0 |
| Ascusbbf_1821A | 0 | 0 | 0 | 0 | + | − | 0 | 0 | + | 0 |
| Ascusbbf_1821B | 0 | 0 | 0 | 0 | + | − | 0 | 0 | + | 0 |
| Ascusbbf_1821B | 0 | − | + | − | − | + | − | + | − | 0 |
| Ascusbbf_1821C | 0 | 0 | 0 | 0 | + | − | 0 | 0 | + | 0 |
| Ascusbbf_1821C | 0 | − | + | − | − | + | − | + | − | 0 |
| Ascusbbf_1821D | 0 | 0 | 0 | 0 | + | − | 0 | 0 | + | 0 |
| Ascusbbf_1821D | 0 | − | + | − | − | + | − | + | − | 0 |
| Ascusbbf_19022A | 0 | − | + | − | + | + | + | 0 | 0 | 0 |
| Ascusbbf_19022A | 0 | 0 | 0 | 0 | − | − | 0 | + | 0 | 0 |
| Ascusbbf_19022A | 0 | 0 | 0 | 0 | 0 | + | + | + | − | 0 |
| Ascusbbf_19022B | 0 | 0 | 0 | 0 | − | − | 0 | + | 0 | 0 |
| Ascusbbf_19022B | 0 | 0 | 0 | 0 | + | + | 0 | + | + | 0 |
| Ascusbbf_19022B | 0 | − | + | − | + | + | + | + | + | 0 |
| Ascusbbf_19022B | 0 | 0 | 0 | 0 | 0 | + | 0 | 0 | 0 | 0 |
| Ascusbbf_19022C | 0 | − | + | − | + | + | + | + | + | 0 |
| Ascusbbf_19022C | 0 | 0 | 0 | + | 0 | + | 0 | 0 | 0 | 0 |
| Ascusbbf_1A | 0 | 0 | 0 | 0 | − | − | 0 | + | 0 | 0 |
| Ascusbbf_1A | 0 | 0 | 0 | 0 | 0 | + | + | + | − | 0 |
| Ascusbbf_1A | 0 | − | + | 0 | 0 | + | + | 0 | + | 0 |
| Ascusbbf_1A | 0 | 0 | 0 | + | 0 | + | 0 | 0 | 0 | 0 |
| Ascusbbf_1B | 0 | 0 | 0 | 0 | − | − | 0 | + | 0 | 0 |
| Ascusbbf_1B | 0 | 0 | 0 | 0 | + | + | 0 | + | + | 0 |
| Ascusbbf_1B | 0 | − | + | 0 | 0 | + | + | 0 | + | 0 |
| Ascusbbf_1B | 0 | 0 | 0 | 0 | + | − | 0 | 0 | + | 0 |
| Ascusbbf_1B | 0 | 0 | 0 | 0 | 0 | + | 0 | 0 | 0 | 0 |
| Ascusbbf_1B | 0 | 0 | 0 | + | 0 | + | 0 | 0 | 0 | 0 |
| Ascusbbf_1C | 0 | 0 | 0 | 0 | − | − | 0 | + | 0 | 0 |
| Ascusbbf_1C | 0 | 0 | 0 | 0 | + | + | 0 | + | + | 0 |
| Ascusbbf_1C | 0 | − | + | 0 | 0 | + | + | 0 | + | 0 |
| Ascusbbf_1C | 0 | 0 | 0 | 0 | 0 | + | 0 | 0 | 0 | 0 |
| Ascusbbf_1D | 0 | − | + | − | + | + | + | 0 | 0 | 0 |
| Ascusbbf_1D | 0 | 0 | 0 | 0 | − | − | 0 | + | 0 | 0 |
| Ascusbbf_1D | 0 | 0 | 0 | 0 | + | + | 0 | + | + | 0 |
| Ascusbbf_1D | 0 | − | + | 0 | 0 | + | + | 0 | + | 0 |
| Ascusbbf_1D | 0 | 0 | 0 | 0 | + | − | 0 | 0 | + | 0 |
| Ascusbbf_1D | 0 | 0 | 0 | 0 | 0 | + | 0 | 0 | 0 | 0 |
| Ascusbbf_1D | 0 | 0 | + | + | + | + | + | 0 | + | 0 |
| Ascusbbf_1D | 0 | 0 | 0 | + | 0 | + | 0 | 0 | 0 | 0 |
| Ascusbbf_1E | 0 | − | + | − | + | + | + | 0 | 0 | 0 |
| Ascusbbf_1E | 0 | 0 | 0 | 0 | − | − | 0 | + | 0 | 0 |
| Ascusbbf_1E | 0 | − | + | − | + | + | + | + | + | 0 |
| Ascusbbf_1F | 0 | − | + | − | + | + | + | 0 | 0 | 0 |
| Ascusbbf_1F | 0 | 0 | 0 | 0 | − | − | 0 | + | 0 | 0 |
| Ascusbbf_1F | 0 | 0 | 0 | 0 | 0 | + | + | + | − | 0 |
| Ascusbbf_1F | 0 | − | + | 0 | 0 | + | + | + | + | 0 |
| Ascusbbf_1F | 0 | 0 | 0 | 0 | 0 | + | 0 | 0 | + | 0 |
| Ascusbbf_1F | 0 | 0 | 0 | + | 0 | + | 0 | 0 | + | 0 |
| Ascusbbf_1F | 0 | 0 | 0 | + | 0 | + | 0 | 0 | + | 0 |
| Ascusbbf_1G | 0 | − | + | − | + | + | + | 0 | 0 | 0 |
| Ascusbbf_1G | 0 | 0 | 0 | 0 | − | − | 0 | + | 0 | 0 |
| Ascusbbf_1G | 0 | 0 | 0 | 0 | + | + | 0 | + | + | 0 |
| Ascusbbf_1G | 0 | − | + | 0 | 0 | + | + | + | + | 0 |
| Ascusbbf_1G | 0 | 0 | 0 | 0 | + | − | 0 | 0 | + | 0 |
| Ascusbbf_1G | 0 | 0 | 0 | 0 | 0 | + | 0 | 0 | 0 | 0 |
| Ascusbbf_1G | 0 | 0 | 0 | + | 0 | + | 0 | 0 | 0 | 0 |
| Ascusbbf_1H | 0 | − | + | − | + | + | + | 0 | 0 | 0 |
| Ascusbbf_1H | 0 | 0 | 0 | 0 | − | − | 0 | + | 0 | 0 |
| Ascusbbf_1H | 0 | 0 | 0 | 0 | + | + | 0 | + | + | 0 |
| Ascusbbf_1H | 0 | 0 | 0 | 0 | 0 | + | 0 | 0 | 0 | 0 |
| Ascusbbf_1I | 0 | − | + | − | + | + | − | 0 | 0 | 0 |
| Ascusbbf_1I | 0 | 0 | 0 | 0 | − | − | 0 | + | 0 | 0 |
| Ascusbbf_1I | 0 | 0 | 0 | 0 | + | + | 0 | + | + | 0 |
| Ascusbbf_1I | 0 | − | + | 0 | 0 | + | + | + | + | 0 |
| Ascusbbf_1I | 0 | 0 | 0 | 0 | 0 | + | 0 | 0 | 0 | 0 |
| Ascusbbf_1I | 0 | 0 | 0 | + | 0 | + | 0 | 0 | 0 | 0 |
| Ascusbbf_1J | 0 | − | + | − | + | + | + | 0 | 0 | 0 |

-continued

| Strain ID | pyruvic | glucose | succinic | lactic | glycerol | acetic | propionic | butyric | ethanol | 1-Butanol |
|---|---|---|---|---|---|---|---|---|---|---|
| Ascusbbf_1J | 0 | 0 | 0 | 0 | − | − | 0 | + | 0 | 0 |
| Ascusbbf_1J | 0 | 0 | 0 | 0 | 0 | + | + | + | − | 0 |
| Ascusbbf_1J | 0 | − | + | 0 | 0 | + | + | 0 | + | 0 |
| Ascusbbf_1J | 0 | 0 | 0 | 0 | + | − | 0 | 0 | + | 0 |
| Ascusbbf_1J | 0 | 0 | 0 | 0 | 0 | + | 0 | 0 | 0 | 0 |
| Ascusbbf_1K | 0 | 0 | 0 | 0 | + | + | 0 | + | + | 0 |
| Ascusbbf_1K | 0 | − | + | 0 | 0 | + | + | + | + | 0 |
| Ascusbbf_1K | 0 | 0 | 0 | 0 | + | − | 0 | 0 | + | 0 |
| Ascusbbf_1K | 0 | 0 | 0 | 0 | 0 | + | 0 | 0 | 0 | 0 |
| Ascusbbf_201A | 0 | − | + | − | + | + | + | + | + | 0 |
| Ascusbbf_201B | 0 | 0 | 0 | 0 | + | + | 0 | + | + | 0 |
| Ascusbbf_201B | 0 | − | + | 0 | + | + | + | + | + | 0 |
| Ascusbbf_201B | 0 | 0 | 0 | 0 | 0 | + | 0 | 0 | 0 | 0 |
| Ascusbbf_201B | 0 | 0 | 0 | + | 0 | + | 0 | 0 | + | 0 |
| Ascusbbf_201B | 0 | 0 | 0 | + | 0 | + | 0 | 0 | + | 0 |
| Ascusbbf_201C | 0 | − | + | − | + | + | + | 0 | 0 | 0 |
| Ascusbbf_201D | 0 | − | + | − | + | + | + | 0 | 0 | 0 |
| Ascusbbf_201D | 0 | 0 | 0 | 0 | + | + | 0 | + | + | 0 |
| Ascusbbf_201D | 0 | − | + | 0 | 0 | + | + | 0 | + | 0 |
| Ascusbbf_201D | 0 | 0 | 0 | + | 0 | + | 0 | 0 | + | 0 |
| Ascusbbf_201D | 0 | 0 | 0 | + | 0 | + | 0 | 0 | + | 0 |
| Ascusbbf_201E | 0 | 0 | 0 | 0 | − | − | 0 | + | 0 | 0 |
| Ascusbbf_201E | 0 | 0 | 0 | 0 | + | + | 0 | + | + | 0 |
| Ascusbbf_201F | 0 | 0 | 0 | 0 | − | − | 0 | + | 0 | 0 |
| Ascusbbf_201G | 0 | − | + | − | + | + | + | 0 | 0 | 0 |
| Ascusbbf_201G | 0 | 0 | 0 | 0 | 0 | + | + | + | − | 0 |
| Ascusbbf_201G | 0 | 0 | 0 | 0 | 0 | + | 0 | 0 | 0 | 0 |
| Ascusbbf_201H | 0 | − | + | − | + | + | + | 0 | 0 | 0 |
| Ascusbbf_201H | 0 | 0 | 0 | 0 | + | + | 0 | + | + | 0 |
| Ascusbbf_201H | 0 | − | + | 0 | 0 | + | + | 0 | + | 0 |
| Ascusbbf_201H | 0 | 0 | 0 | 0 | 0 | + | 0 | 0 | 0 | 0 |
| Ascusbbf_201I | 0 | − | + | − | + | + | + | 0 | 0 | 0 |
| Ascusbbf_201I | 0 | 0 | 0 | 0 | + | + | 0 | + | + | 0 |
| Ascusbbf_201I | 0 | − | + | 0 | 0 | + | + | 0 | + | 0 |
| Ascusbbf_201I | 0 | 0 | 0 | 0 | 0 | + | 0 | 0 | 0 | 0 |
| Ascusbbf_201I | 0 | 0 | 0 | + | 0 | + | 0 | 0 | + | 0 |
| Ascusbbf_201I | 0 | 0 | 0 | + | 0 | + | 0 | 0 | 0 | 0 |
| Ascusbbf_201J | 0 | − | + | − | + | + | + | 0 | 0 | 0 |
| Ascusbbf_201J | 0 | − | + | 0 | 0 | + | + | 0 | + | 0 |
| Ascusbbf_201J | 0 | 0 | 0 | 0 | + | − | 0 | 0 | + | 0 |
| Ascusbbf_201K | 0 | − | + | 0 | 0 | + | + | 0 | + | 0 |
| Ascusbbf_201K | 0 | 0 | 0 | 0 | + | − | 0 | 0 | + | 0 |
| Ascusbbf_201K | 0 | 0 | 0 | + | 0 | + | 0 | 0 | + | 0 |
| Ascusbbf_201K | 0 | 0 | 0 | + | 0 | + | 0 | 0 | 0 | 0 |
| Ascusbbf_201L | 0 | − | + | − | + | + | + | + | + | 0 |
| Ascusbbf_201L | 0 | 0 | 0 | + | 0 | + | 0 | 0 | + | 0 |
| Ascusbbf_20584A | 0 | 0 | 0 | 0 | + | − | 0 | 0 | + | 0 |
| Ascusbbf_20584B | 0 | 0 | 0 | + | 0 | + | 0 | 0 | + | 0 |
| Ascusbbf_20584B | 0 | 0 | 0 | + | 0 | + | 0 | 0 | + | 0 |
| Ascusbbf_22558A | 0 | 0 | 0 | + | 0 | + | 0 | 0 | + | 0 |
| Ascusbbf_22558A | 0 | 0 | 0 | + | 0 | + | 0 | 0 | + | 0 |
| Ascusbbf_22558B | 0 | 0 | + | + | + | + | + | 0 | + | 0 |
| Ascusbbf_22558B | 0 | 0 | 0 | + | 0 | + | 0 | 0 | + | 0 |
| Ascusbbf_2297A | 0 | 0 | 0 | 0 | + | − | 0 | 0 | + | 0 |
| Ascusbbf_2297A | 0 | − | + | − | − | + | − | + | − | 0 |
| Ascusbbf_2297A | 0 | 0 | 0 | + | 0 | + | 0 | 0 | + | 0 |
| Ascusbbf_2297A | 0 | 0 | 0 | + | 0 | + | 0 | 0 | + | 0 |
| Ascusbbf_2297B | 0 | 0 | 0 | 0 | + | − | 0 | 0 | + | 0 |
| Ascusbbf_2297B | 0 | 0 | 0 | + | 0 | + | 0 | 0 | + | 0 |
| Ascusbbf_2297B | 0 | 0 | 0 | + | 0 | + | 0 | 0 | + | 0 |
| Ascusbbf_2297C | 0 | 0 | 0 | 0 | + | − | 0 | 0 | + | 0 |
| Ascusbbf_2297C | 0 | 0 | 0 | + | 0 | + | 0 | 0 | + | 0 |
| Ascusbbf_2297C | 0 | 0 | 0 | + | 0 | + | 0 | 0 | + | 0 |
| Ascusbbf_2297D | 0 | 0 | 0 | 0 | + | − | 0 | 0 | + | 0 |
| Ascusbbf_2297D | 0 | 0 | + | + | + | + | + | 0 | + | 0 |
| Ascusbbf_2297D | 0 | 0 | 0 | + | 0 | + | 0 | 0 | + | 0 |
| Ascusbbf_2297E | 0 | 0 | 0 | 0 | + | − | 0 | 0 | + | 0 |
| Ascusbbf_2297E | 0 | 0 | 0 | + | 0 | + | 0 | 0 | + | 0 |
| Ascusbbf_2297E | 0 | 0 | 0 | + | 0 | + | 0 | 0 | + | 0 |
| Ascusbbf_2297F | 0 | 0 | + | + | + | + | + | 0 | + | 0 |
| Ascusbbf_2297F | 0 | 0 | 0 | + | 0 | + | 0 | 0 | + | 0 |
| Ascusbbf_2297G | 0 | 0 | + | + | + | + | + | 0 | + | 0 |
| Ascusbbf_2297G | 0 | 0 | 0 | + | 0 | + | 0 | 0 | + | 0 |
| Ascusbbf_2297H | 0 | 0 | 0 | + | 0 | + | 0 | 0 | + | 0 |
| Ascusbbf_2297H | 0 | 0 | 0 | + | 0 | + | 0 | 0 | + | 0 |
| Ascusbbf_23033A | 0 | 0 | 0 | + | 0 | + | 0 | 0 | + | 0 |
| Ascusbbf_23033A | 0 | 0 | 0 | + | 0 | + | 0 | 0 | + | 0 |

-continued

| Strain ID | pyruvic | glucose | succinic | lactic | glycerol | acetic | propionic | butyric | ethanol | 1-Butanol |
|---|---|---|---|---|---|---|---|---|---|---|
| Ascusbbf_23033B | 0 | 0 | 0 | + | 0 | + | 0 | 0 | + | 0 |
| Ascusbbf_23033B | 0 | 0 | 0 | + | 0 | + | 0 | 0 | + | 0 |
| Ascusbbf_23033C | 0 | 0 | 0 | + | 0 | + | 0 | 0 | + | 0 |
| Ascusbbf_23033C | 0 | 0 | 0 | + | 0 | + | 0 | 0 | + | 0 |
| Ascusbbf_23033D | 0 | 0 | 0 | + | 0 | + | 0 | 0 | + | 0 |
| Ascusbbf_23033D | 0 | 0 | 0 | + | 0 | + | 0 | 0 | + | 0 |
| Ascusbbf_23134A | 0 | 0 | 0 | 0 | + | − | 0 | 0 | + | 0 |
| Ascusbbf_23A | 0 | 0 | 0 | + | 0 | + | 0 | 0 | + | 0 |
| Ascusbbf_23A | 0 | 0 | 0 | + | 0 | + | 0 | 0 | + | 0 |
| Ascusbbf_24302A | 0 | 0 | 0 | 0 | 0 | + | + | + | − | 0 |
| Ascusbbf_24302A | 0 | − | + | + | + | + | 0 | 0 | + | 0 |
| Ascusbbf_24302A | − | − | − | + | − | + | 0 | + | − | + |
| Ascusbbf_24302A | 0 | − | 0 | − | 0 | 0 | − | + | − | 0 |
| Ascusbbf_24302B | 0 | − | + | − | + | + | + | 0 | 0 | 0 |
| Ascusbbf_24302B | 0 | 0 | 0 | 0 | − | − | 0 | + | 0 | 0 |
| Ascusbbf_24302B | 0 | 0 | 0 | 0 | 0 | + | + | + | − | 0 |
| Ascusbbf_24302B | 0 | 0 | 0 | 0 | + | − | 0 | 0 | + | 0 |
| Ascusbbf_24302B | − | − | − | − | − | + | 0 | + | − | + |
| Ascusbbf_24302C | 0 | − | + | − | + | + | + | 0 | 0 | 0 |
| Ascusbbf_24302C | 0 | 0 | 0 | 0 | − | − | 0 | + | 0 | 0 |
| Ascusbbf_24302C | 0 | 0 | 0 | 0 | 0 | + | + | + | − | 0 |
| Ascusbbf_24302C | 0 | 0 | 0 | + | 0 | + | 0 | 0 | + | 0 |
| Ascusbbf_24302C | 0 | 0 | 0 | + | 0 | + | 0 | 0 | 0 | 0 |
| Ascusbbf_24302C | 0 | − | + | + | + | − | + | + | + | 0 |
| Ascusbbf_24302D | 0 | 0 | 0 | 0 | 0 | + | + | + | − | 0 |
| Ascusbbf_24302D | 0 | 0 | 0 | 0 | + | − | 0 | 0 | + | 0 |
| Ascusbbf_24302E | 0 | − | + | − | + | + | + | 0 | 0 | 0 |
| Ascusbbf_24302E | 0 | 0 | 0 | 0 | 0 | + | + | + | − | 0 |
| Ascusbbf_24302E | 0 | − | 0 | − | 0 | + | − | + | + | 0 |
| Ascusbbf_24302F | 0 | − | + | − | + | + | + | 0 | 0 | 0 |
| Ascusbbf_24302F | 0 | 0 | 0 | 0 | 0 | + | + | + | − | 0 |
| Ascusbbf_24302F | 0 | − | + | 0 | 0 | + | + | 0 | + | 0 |
| Ascusbbf_24302F | 0 | 0 | 0 | 0 | + | − | 0 | 0 | + | 0 |
| Ascusbbf_24302F | 0 | − | + | − | − | + | − | + | − | 0 |
| Ascusbbf_24302F | 0 | 0 | 0 | + | 0 | + | 0 | 0 | 0 | 0 |
| Ascusbbf_24302G | 0 | − | + | − | + | + | + | 0 | 0 | 0 |
| Ascusbbf_24302G | 0 | 0 | 0 | 0 | 0 | + | + | + | − | 0 |
| Ascusbbf_24302G | 0 | 0 | 0 | 0 | + | − | 0 | 0 | + | 0 |
| Ascusbbf_24302G | 0 | − | + | + | + | + | 0 | 0 | + | 0 |
| Ascusbbf_24302G | 0 | 0 | 0 | + | 0 | + | 0 | 0 | + | 0 |
| Ascusbbf_24302G | 0 | 0 | 0 | + | 0 | + | 0 | 0 | + | 0 |
| Ascusbbf_24302H | 0 | 0 | 0 | 0 | + | + | 0 | + | + | 0 |
| Ascusbbf_24302H | 0 | 0 | 0 | + | 0 | + | 0 | 0 | 0 | 0 |
| Ascusbbf_24302I | 0 | 0 | 0 | 0 | + | + | 0 | + | + | 0 |
| Ascusbbf_24302I | 0 | − | + | + | + | + | 0 | 0 | + | 0 |
| Ascusbbf_24302I | 0 | 0 | 0 | + | 0 | + | 0 | 0 | + | 0 |
| Ascusbbf_24302I | 0 | 0 | 0 | + | 0 | + | 0 | 0 | 0 | 0 |
| Ascusbbf_24302J | 0 | 0 | + | + | + | + | + | 0 | + | 0 |
| Ascusbbf_24302J | 0 | 0 | 0 | + | 0 | + | 0 | 0 | 0 | 0 |
| Ascusbbf_24422A | 0 | 0 | 0 | + | 0 | + | 0 | 0 | + | 0 |
| Ascusbbf_24422A | 0 | 0 | 0 | + | 0 | + | 0 | 0 | + | 0 |
| Ascusbbf_2600A | + | − | + | − | 0 | + | + | + | − | 0 |
| Ascusbbf_2600B | 0 | − | + | − | + | + | + | 0 | 0 | 0 |
| Ascusbbf_2600B | 0 | 0 | 0 | 0 | − | − | 0 | + | 0 | 0 |
| Ascusbbf_2600B | 0 | 0 | 0 | 0 | + | + | 0 | + | + | 0 |
| Ascusbbf_2600B | 0 | − | + | 0 | 0 | + | + | + | + | 0 |
| Ascusbbf_2600C | 0 | − | + | − | + | + | + | 0 | 0 | 0 |
| Ascusbbf_2600C | 0 | 0 | 0 | 0 | − | − | 0 | + | 0 | 0 |
| Ascusbbf_2600C | 0 | 0 | 0 | 0 | + | + | 0 | + | + | 0 |
| Ascusbbf_2600C | 0 | − | + | 0 | 0 | + | + | 0 | + | 0 |
| Ascusbbf_2600D | 0 | 0 | 0 | 0 | 0 | + | + | + | − | 0 |
| Ascusbbf_2600E | 0 | − | + | − | + | + | + | 0 | 0 | 0 |
| Ascusbbf_2600E | 0 | 0 | 0 | 0 | 0 | + | + | + | − | 0 |
| Ascusbbf_2600F | 0 | − | + | − | + | + | + | 0 | 0 | 0 |
| Ascusbbf_2600F | 0 | 0 | 0 | 0 | 0 | + | + | + | − | 0 |
| Ascusbbf_2600G | 0 | 0 | 0 | 0 | 0 | + | + | + | 0 | 0 |
| Ascusbbf_2600H | 0 | − | + | 0 | 0 | + | + | 0 | + | 0 |
| Ascusbbf_2624A | 0 | − | + | − | + | + | + | 0 | 0 | 0 |
| Ascusbbf_2624A | 0 | 0 | 0 | 0 | 0 | + | + | + | − | 0 |
| Ascusbbf_2624A | 0 | − | + | 0 | + | + | + | 0 | + | 0 |
| Ascusbbf_2624A | 0 | 0 | + | + | + | + | + | 0 | + | 0 |
| Ascusbbf_2624A | 0 | 0 | 0 | + | 0 | + | 0 | 0 | + | 0 |
| Ascusbbf_2624B | 0 | 0 | 0 | 0 | 0 | + | + | + | − | 0 |
| Ascusbbf_2624B | 0 | − | + | − | + | + | + | + | + | 0 |
| Ascusbbf_2624B | 0 | − | + | − | − | + | − | + | − | 0 |
| Ascusbbf_2624B | 0 | 0 | + | + | + | + | + | 0 | + | 0 |
| Ascusbbf_2624B | 0 | 0 | 0 | + | 0 | + | 0 | 0 | + | 0 |

-continued

| Strain ID | pyruvic | glucose | succinic | lactic | glycerol | acetic | propionic | butyric | ethanol | 1-Butanol |
|---|---|---|---|---|---|---|---|---|---|---|
| Ascusbbf_2624C | 0 | − | + | − | + | + | + | + | + | 0 |
| Ascusbbf_2624C | 0 | 0 | 0 | + | 0 | + | 0 | 0 | + | 0 |
| Ascusbbf_2624C | 0 | 0 | 0 | + | 0 | + | 0 | 0 | + | 0 |
| Ascusbbf_2624D | 0 | − | + | − | + | + | + | + | + | 0 |
| Ascusbbf_2624D | 0 | 0 | + | + | + | + | + | 0 | + | 0 |
| Ascusbbf_2624D | 0 | 0 | 0 | + | 0 | + | 0 | 0 | + | 0 |
| Ascusbbf_2624E | 0 | − | + | − | + | + | + | + | + | 0 |
| Ascusbbf_2624E | 0 | 0 | + | + | + | + | + | 0 | + | 0 |
| Ascusbbf_2624F | 0 | 0 | + | + | + | + | + | 0 | + | 0 |
| Ascusbbf_2624F | 0 | 0 | 0 | + | 0 | + | 0 | 0 | + | 0 |
| Ascusbbf_2624G | 0 | 0 | + | + | + | + | + | 0 | + | 0 |
| Ascusbbf_2624G | 0 | 0 | 0 | + | 0 | + | 0 | 0 | + | 0 |
| Ascusbbf_269A | 0 | − | + | − | + | + | + | 0 | 0 | 0 |
| Ascusbbf_269A | 0 | 0 | 0 | 0 | + | + | 0 | + | + | 0 |
| Ascusbbf_269A | 0 | − | + | − | + | + | + | + | + | 0 |
| Ascusbbf_269A | 0 | 0 | 0 | 0 | 0 | + | 0 | 0 | 0 | 0 |
| Ascusbbf_269B | 0 | − | + | − | + | + | + | 0 | 0 | 0 |
| Ascusbbf_269C | 0 | − | + | − | + | + | + | 0 | 0 | 0 |
| Ascusbbf_269C | 0 | − | + | − | + | + | + | + | + | 0 |
| Ascusbbf_269D | 0 | 0 | 0 | 0 | + | + | 0 | + | + | 0 |
| Ascusbbf_269D | 0 | 0 | 0 | 0 | 0 | + | 0 | 0 | 0 | 0 |
| Ascusbbf_269E | 0 | − | + | − | + | + | + | 0 | 0 | 0 |
| Ascusbbf_269E | 0 | 0 | 0 | 0 | + | + | 0 | + | + | 0 |
| Ascusbbf_269E | 0 | 0 | 0 | 0 | 0 | + | 0 | 0 | 0 | 0 |
| Ascusbbf_269F | 0 | − | + | − | + | + | + | 0 | 0 | 0 |
| Ascusbbf_269G | 0 | − | + | − | + | + | + | 0 | 0 | 0 |
| Ascusbbf_2770A | 0 | − | + | 0 | 0 | + | + | 0 | + | 0 |
| Ascusbbf_2770A | 0 | 0 | 0 | 0 | + | − | 0 | 0 | + | 0 |
| Ascusbbf_2770A | 0 | − | + | − | − | + | − | + | − | 0 |
| Ascusbbf_2770A | 0 | 0 | + | + | + | + | + | 0 | + | 0 |
| Ascusbbf_2770B | 0 | 0 | 0 | 0 | + | − | 0 | 0 | + | 0 |
| Ascusbbf_2770B | 0 | − | + | − | − | + | − | + | − | 0 |
| Ascusbbf_2770C | 0 | 0 | 0 | 0 | + | − | 0 | 0 | + | 0 |
| Ascusbbf_27932A | 0 | 0 | 0 | 0 | − | − | 0 | + | 0 | 0 |
| Ascusbbf_27932B | 0 | 0 | 0 | 0 | − | − | 0 | + | 0 | 0 |
| Ascusbbf_27932B | 0 | 0 | 0 | 0 | + | + | 0 | + | + | 0 |
| Ascusbbf_27932B | 0 | 0 | 0 | 0 | 0 | + | 0 | 0 | 0 | 0 |
| Ascusbbf_27932C | 0 | 0 | 0 | 0 | − | − | 0 | + | 0 | 0 |
| Ascusbbf_27932C | 0 | 0 | 0 | 0 | + | − | 0 | 0 | + | 0 |
| Ascusbbf_27932C | 0 | 0 | 0 | + | 0 | + | 0 | 0 | 0 | 0 |
| Ascusbbf_28350A | 0 | 0 | 0 | 0 | + | + | 0 | + | + | 0 |
| Ascusbbf_28350A | 0 | 0 | 0 | 0 | 0 | + | 0 | 0 | 0 | 0 |
| Ascusbbf_28350B | 0 | 0 | 0 | 0 | + | + | 0 | + | + | 0 |
| Ascusbbf_28350B | 0 | 0 | 0 | 0 | 0 | + | 0 | 0 | 0 | 0 |
| Ascusbbf_28350C | 0 | 0 | 0 | 0 | + | + | 0 | + | + | 0 |
| Ascusbbf_28350C | 0 | 0 | 0 | 0 | 0 | + | 0 | 0 | 0 | 0 |
| Ascusbbf_29797A | 0 | 0 | 0 | + | 0 | + | 0 | 0 | + | 0 |
| Ascusbbf_29797A | 0 | 0 | 0 | + | 0 | + | 0 | 0 | + | 0 |
| Ascusbbf_318A | 0 | 0 | 0 | 0 | + | − | 0 | 0 | + | 0 |
| Ascusbbf_318A | 0 | − | + | − | − | + | − | + | − | 0 |
| Ascusbbf_318B | 0 | 0 | 0 | 0 | + | − | 0 | 0 | + | 0 |
| Ascusbbf_318C | 0 | 0 | 0 | 0 | + | − | 0 | 0 | + | 0 |
| Ascusbbf_318C | 0 | − | + | − | − | + | − | + | − | 0 |
| Ascusbbf_318D | 0 | − | + | − | + | + | + | + | + | 0 |
| Ascusbbf_318D | 0 | − | + | − | − | + | − | + | − | 0 |
| Ascusbbf_318D | 0 | 0 | + | + | + | + | + | 0 | + | 0 |
| Ascusbbf_318D | 0 | 0 | 0 | + | 0 | + | 0 | 0 | + | 0 |
| Ascusbbf_318E | 0 | − | + | − | + | + | + | + | + | 0 |
| Ascusbbf_318E | 0 | − | + | − | − | + | − | + | − | 0 |
| Ascusbbf_318E | 0 | 0 | 0 | + | 0 | + | 0 | 0 | + | 0 |
| Ascusbbf_318E | 0 | 0 | 0 | + | 0 | + | 0 | 0 | 0 | 0 |
| Ascusbbf_32877A | + | − | + | − | 0 | + | + | + | − | 0 |
| Ascusbbf_3427A | 0 | 0 | 0 | 0 | + | + | 0 | + | + | 0 |
| Ascusbbf_3427A | 0 | 0 | 0 | 0 | + | − | 0 | 0 | + | 0 |
| Ascusbbf_3427A | 0 | 0 | 0 | 0 | 0 | + | 0 | 0 | 0 | 0 |
| Ascusbbf_3427B | 0 | 0 | 0 | 0 | + | + | 0 | + | + | 0 |
| Ascusbbf_3427B | 0 | − | + | 0 | 0 | + | + | 0 | + | 0 |
| Ascusbbf_3427B | 0 | 0 | 0 | 0 | + | − | 0 | 0 | + | 0 |
| Ascusbbf_3427B | 0 | 0 | 0 | 0 | 0 | + | 0 | 0 | 0 | 0 |
| Ascusbbf_3427B | 0 | 0 | 0 | + | 0 | + | 0 | 0 | + | 0 |
| Ascusbbf_3427B | 0 | 0 | 0 | + | 0 | + | 0 | 0 | + | 0 |
| Ascusbbf_3427C | 0 | 0 | + | 0 | + | + | + | + | + | 0 |
| Ascusbbf_3427C | 0 | 0 | 0 | 0 | + | − | 0 | 0 | + | 0 |
| Ascusbbf_3427C | 0 | − | + | − | − | + | − | + | − | 0 |
| Ascusbbf_3427C | 0 | 0 | 0 | + | 0 | + | 0 | 0 | + | 0 |
| Ascusbbf_3427C | 0 | 0 | 0 | + | 0 | + | 0 | 0 | + | 0 |
| Ascusbbf_3427D | 0 | − | + | − | − | + | − | + | − | 0 |

-continued

| Strain ID | pyruvic | glucose | succinic | lactic | glycerol | acetic | propionic | butyric | ethanol | 1-Butanol |
|---|---|---|---|---|---|---|---|---|---|---|
| Ascusbbf_3427E | 0 | 0 | 0 | + | 0 | + | 0 | 0 | 0 | 0 |
| Ascusbbf_372A | 0 | − | + | − | + | + | + | 0 | 0 | 0 |
| Ascusbbf_372A | 0 | 0 | 0 | 0 | − | − | 0 | + | 0 | 0 |
| Ascusbbf_372A | 0 | 0 | 0 | 0 | + | + | 0 | + | + | 0 |
| Ascusbbf_372A | 0 | − | + | 0 | 0 | + | + | + | + | 0 |
| Ascusbbf_372A | 0 | 0 | 0 | 0 | + | − | 0 | 0 | + | 0 |
| Ascusbbf_372A | 0 | 0 | 0 | 0 | 0 | + | 0 | 0 | 0 | 0 |
| Ascusbbf_372A | 0 | 0 | 0 | + | 0 | + | 0 | 0 | 0 | 0 |
| Ascusbbf_372B | 0 | − | + | − | + | + | + | 0 | 0 | 0 |
| Ascusbbf_372C | 0 | 0 | 0 | 0 | − | − | 0 | + | 0 | 0 |
| Ascusbbf_372C | 0 | 0 | 0 | 0 | + | + | 0 | + | + | 0 |
| Ascusbbf_372C | 0 | 0 | 0 | 0 | + | − | 0 | 0 | + | 0 |
| Ascusbbf_372C | 0 | 0 | 0 | 0 | 0 | + | 0 | 0 | 0 | 0 |
| Ascusbbf_372D | 0 | − | + | − | + | + | + | 0 | 0 | 0 |
| Ascusbbf_372D | 0 | 0 | 0 | 0 | − | − | 0 | + | 0 | 0 |
| Ascusbbf_372D | 0 | 0 | 0 | 0 | 0 | + | + | + | − | 0 |
| Ascusbbf_372E | 0 | − | + | − | + | + | + | 0 | 0 | 0 |
| Ascusbbf_372E | 0 | 0 | 0 | 0 | − | − | 0 | + | 0 | 0 |
| Ascusbbf_372E | 0 | 0 | 0 | 0 | + | + | 0 | + | + | 0 |
| Ascusbbf_372E | 0 | − | + | 0 | + | + | + | + | + | 0 |
| Ascusbbf_372E | 0 | 0 | 0 | 0 | + | − | 0 | 0 | + | 0 |
| Ascusbbf_372E | 0 | 0 | 0 | 0 | 0 | + | 0 | 0 | 0 | 0 |
| Ascusbbf_372F | 0 | − | + | − | + | + | + | 0 | 0 | 0 |
| Ascusbbf_372F | 0 | 0 | 0 | 0 | 0 | + | + | + | − | 0 |
| Ascusbbf_372F | 0 | 0 | 0 | 0 | 0 | + | 0 | 0 | 0 | 0 |
| Ascusbbf_372G | 0 | − | + | − | + | + | + | 0 | 0 | 0 |
| Ascusbbf_372G | 0 | − | + | − | + | + | + | + | + | 0 |
| Ascusbbf_374A | 0 | 0 | + | + | + | + | + | 0 | + | 0 |
| Ascusbbf_374A | 0 | 0 | 0 | + | 0 | + | 0 | 0 | + | 0 |
| Ascusbbf_374B | 0 | 0 | + | + | + | + | + | 0 | + | 0 |
| Ascusbbf_374B | 0 | 0 | 0 | + | 0 | + | 0 | 0 | + | 0 |
| Ascusbbf_374C | 0 | 0 | + | + | + | + | + | 0 | + | 0 |
| Ascusbbf_374C | 0 | 0 | 0 | + | 0 | + | 0 | 0 | + | 0 |
| Ascusbbf_3819A | + | − | 0 | + | + | + | + | 0 | − | 0 |
| Ascusbbf_3819A | 0 | 0 | 0 | + | 0 | + | 0 | 0 | + | 0 |
| Ascusbbf_3875A | 0 | − | + | − | + | + | + | 0 | 0 | 0 |
| Ascusbbf_3875A | 0 | 0 | 0 | 0 | + | + | 0 | + | + | 0 |
| Ascusbbf_3875A | 0 | − | + | 0 | 0 | + | + | 0 | + | 0 |
| Ascusbbf_3875B | 0 | 0 | 0 | 0 | − | − | 0 | + | 0 | 0 |
| Ascusbbf_3875B | 0 | − | + | 0 | 0 | + | + | + | + | 0 |
| Ascusbbf_3875C | 0 | − | + | − | + | + | + | 0 | 0 | 0 |
| Ascusbbf_3875C | 0 | 0 | 0 | 0 | 0 | + | + | + | − | 0 |
| Ascusbbf_3875D | 0 | 0 | 0 | 0 | 0 | + | + | + | − | 0 |
| Ascusbbf_39159A | 0 | 0 | 0 | 0 | 0 | + | + | + | − | 0 |
| Ascusbbf_39159B | 0 | 0 | 0 | 0 | 0 | + | + | + | − | 0 |
| Ascusbbf_39159C | 0 | − | + | − | − | + | − | + | − | 0 |
| Ascusbbf_39159D | 0 | − | + | − | + | + | + | + | + | 0 |
| Ascusbbf_3A | 0 | − | + | − | + | + | + | 0 | 0 | 0 |
| Ascusbbf_3A | 0 | 0 | 0 | 0 | − | − | 0 | + | 0 | 0 |
| Ascusbbf_3A | 0 | 0 | 0 | 0 | + | + | 0 | + | + | 0 |
| Ascusbbf_3A | 0 | 0 | 0 | 0 | + | − | 0 | 0 | + | 0 |
| Ascusbbf_3A | 0 | 0 | 0 | 0 | 0 | + | 0 | 0 | 0 | 0 |
| Ascusbbf_3A | 0 | 0 | 0 | + | 0 | + | 0 | 0 | 0 | 0 |
| Ascusbbf_3B | 0 | 0 | 0 | 0 | − | − | 0 | + | 0 | 0 |
| Ascusbbf_3B | 0 | 0 | 0 | 0 | + | + | 0 | + | + | 0 |
| Ascusbbf_3B | 0 | 0 | 0 | 0 | + | − | 0 | 0 | + | 0 |
| Ascusbbf_3B | 0 | 0 | 0 | 0 | 0 | + | 0 | 0 | 0 | 0 |
| Ascusbbf_3B | 0 | 0 | 0 | + | 0 | + | 0 | 0 | 0 | 0 |
| Ascusbbf_3C | 0 | 0 | 0 | 0 | − | − | 0 | + | 0 | 0 |
| Ascusbbf_3C | 0 | 0 | 0 | 0 | + | + | 0 | + | + | 0 |
| Ascusbbf_3C | 0 | 0 | 0 | 0 | + | − | 0 | 0 | + | 0 |
| Ascusbbf_3C | 0 | 0 | 0 | 0 | 0 | + | 0 | 0 | 0 | 0 |
| Ascusbbf_3D | 0 | 0 | 0 | 0 | − | − | 0 | + | 0 | 0 |
| Ascusbbf_3E | 0 | − | + | 0 | 0 | + | + | 0 | + | 0 |
| Ascusbbf_3F | 0 | − | + | 0 | 0 | + | + | + | + | 0 |
| Ascusbbf_3G | 0 | 0 | 0 | 0 | 0 | + | 0 | 0 | 0 | 0 |
| Ascusbbf_41015A | 0 | − | + | − | + | + | + | 0 | 0 | 0 |
| Ascusbbf_41015A | 0 | 0 | 0 | 0 | + | + | 0 | + | + | 0 |
| Ascusbbf_41015A | 0 | 0 | 0 | 0 | 0 | + | 0 | 0 | 0 | 0 |
| Ascusbbf_41015B | 0 | − | + | − | + | + | + | 0 | 0 | 0 |
| Ascusbbf_41015C | 0 | 0 | 0 | 0 | 0 | + | + | + | − | 0 |
| Ascusbbf_41015D | 0 | − | + | 0 | + | + | + | + | 0 | 0 |
| Ascusbbf_41015E | 0 | − | + | − | + | + | + | + | + | 0 |
| Ascusbbf_416A | 0 | 0 | 0 | 0 | + | − | 0 | 0 | + | 0 |
| Ascusbbf_416B | 0 | 0 | 0 | 0 | + | − | 0 | 0 | + | 0 |
| Ascusbbf_416B | 0 | 0 | + | + | + | + | + | 0 | + | 0 |
| Ascusbbf_416B | 0 | 0 | 0 | + | 0 | + | 0 | 0 | + | 0 |

-continued

| Strain ID | pyruvic | glucose | succinic | lactic | glycerol | acetic | propionic | butyric | ethanol | 1-Butanol |
|---|---|---|---|---|---|---|---|---|---|---|
| Ascusbbf_416C | 0 | 0 | 0 | 0 | + | − | 0 | 0 | + | 0 |
| Ascusbbf_416C | 0 | − | + | − | − | + | − | + | − | 0 |
| Ascusbbf_416D | 0 | 0 | 0 | 0 | + | − | 0 | 0 | + | 0 |
| Ascusbbf_416D | 0 | − | + | − | − | + | − | + | − | 0 |
| Ascusbbf_416E | 0 | 0 | 0 | 0 | + | − | 0 | 0 | + | 0 |
| Ascusbbf_416F | 0 | 0 | 0 | 0 | + | − | 0 | 0 | + | 0 |
| Ascusbbf_416F | 0 | 0 | + | + | + | + | + | 0 | + | 0 |
| Ascusbbf_416F | 0 | 0 | 0 | + | 0 | + | 0 | 0 | + | 0 |
| Ascusbbf_416G | 0 | − | + | − | − | + | − | + | − | 0 |
| Ascusbbf_4317A | 0 | 0 | 0 | 0 | 0 | + | + | + | − | 0 |
| Ascusbbf_4317B | 0 | 0 | 0 | 0 | 0 | + | + | + | − | 0 |
| Ascusbbf_4317C | 0 | − | + | 0 | 0 | + | + | 0 | + | 0 |
| Ascusbbf_4317D | 0 | 0 | 0 | + | 0 | + | 0 | 0 | + | 0 |
| Ascusbbf_4317D | 0 | 0 | 0 | + | 0 | + | 0 | 0 | + | 0 |
| Ascusbbf_4317E | 0 | 0 | + | + | + | + | + | 0 | + | 0 |
| Ascusbbf_4317E | 0 | 0 | 0 | + | 0 | + | 0 | 0 | + | 0 |
| Ascusbbf_4323A | 0 | 0 | 0 | + | 0 | + | 0 | 0 | + | 0 |
| Ascusbbf_4323A | 0 | 0 | 0 | + | 0 | + | 0 | 0 | + | 0 |
| Ascusbbf_4323B | 0 | 0 | 0 | + | 0 | + | 0 | 0 | + | 0 |
| Ascusbbf_4323B | 0 | 0 | 0 | + | 0 | + | 0 | 0 | + | 0 |
| Ascusbbf_4323C | 0 | 0 | 0 | + | 0 | + | 0 | 0 | + | 0 |
| Ascusbbf_4323C | 0 | 0 | 0 | + | 0 | + | 0 | 0 | + | 0 |
| Ascusbbf_4323D | 0 | 0 | 0 | + | 0 | + | 0 | 0 | + | 0 |
| Ascusbbf_4323D | 0 | 0 | 0 | + | 0 | + | 0 | 0 | + | 0 |
| Ascusbbf_43679A | 0 | 0 | 0 | 0 | − | − | 0 | + | 0 | 0 |
| Ascusbbf_43679A | 0 | 0 | 0 | 0 | + | + | 0 | + | + | 0 |
| Ascusbbf_43679A | 0 | 0 | 0 | 0 | 0 | + | 0 | 0 | 0 | 0 |
| Ascusbbf_43679B | 0 | 0 | 0 | 0 | 0 | + | + | + | − | 0 |
| Ascusbbf_43679C | 0 | 0 | 0 | 0 | 0 | + | + | + | − | 0 |
| Ascusbbf_43679D | 0 | 0 | 0 | 0 | 0 | + | + | + | − | 0 |
| Ascusbbf_43679E | 0 | 0 | 0 | 0 | + | + | 0 | + | + | 0 |
| Ascusbbf_43679E | 0 | 0 | 0 | 0 | 0 | + | 0 | 0 | 0 | 0 |
| Ascusbbf_43679F | 0 | − | + | − | − | + | − | + | − | 0 |
| Ascusbbf_4691A | 0 | − | + | − | − | + | − | + | − | 0 |
| Ascusbbf_4691A | 0 | 0 | 0 | + | 0 | + | 0 | 0 | + | 0 |
| Ascusbbf_4691A | 0 | 0 | 0 | + | 0 | + | 0 | 0 | + | 0 |
| Ascusbbf_4691B | 0 | 0 | 0 | + | 0 | + | 0 | 0 | + | 0 |
| Ascusbbf_4691B | 0 | 0 | 0 | + | 0 | + | 0 | 0 | + | 0 |
| Ascusbbf_4691C | 0 | 0 | 0 | + | 0 | + | 0 | 0 | + | 0 |
| Ascusbbf_4691C | 0 | 0 | 0 | + | 0 | + | 0 | 0 | + | 0 |
| Ascusbbf_4883A | 0 | − | + | 0 | 0 | + | + | 0 | + | 0 |
| Ascusbbf_4883A | 0 | 0 | 0 | 0 | + | − | 0 | 0 | + | 0 |
| Ascusbbf_4883B | 0 | 0 | 0 | 0 | + | − | 0 | 0 | + | 0 |
| Ascusbbf_4883B | 0 | 0 | 0 | + | 0 | + | 0 | 0 | + | 0 |
| Ascusbbf_4883B | 0 | 0 | 0 | + | 0 | + | 0 | 0 | + | 0 |
| Ascusbbf_4883C | 0 | 0 | 0 | 0 | + | − | 0 | 0 | + | 0 |
| Ascusbbf_4883C | 0 | − | + | − | − | + | − | + | − | 0 |
| Ascusbbf_4883C | 0 | 0 | + | + | + | + | + | 0 | + | 0 |
| Ascusbbf_4883D | 0 | 0 | 0 | 0 | + | − | 0 | 0 | + | 0 |
| Ascusbbf_4883D | 0 | − | + | − | − | + | − | + | − | 0 |
| Ascusbbf_4883D | 0 | 0 | + | + | + | + | + | 0 | + | 0 |
| Ascusbbf_4883E | 0 | − | + | − | − | + | − | + | − | 0 |
| Ascusbbf_4936A | 0 | 0 | 0 | 0 | + | + | 0 | + | + | 0 |
| Ascusbbf_4936A | 0 | 0 | 0 | 0 | 0 | + | 0 | 0 | 0 | 0 |
| Ascusbbf_4936B | 0 | 0 | 0 | 0 | + | + | 0 | + | + | 0 |
| Ascusbbf_4A | 0 | + | − | + | − | 0 | + | + | + | − | 0 |
| Ascusbbf_4A | 0 | + | − | + | − | 0 | + | + | 0 | + | 0 |
| Ascusbbf_4B | 0 | 0 | 0 | 0 | − | − | 0 | + | 0 | 0 |
| Ascusbbf_4B | 0 | 0 | 0 | 0 | + | + | 0 | + | + | 0 |
| Ascusbbf_4B | 0 | − | + | 0 | 0 | + | + | + | + | 0 |
| Ascusbbf_4B | 0 | 0 | 0 | 0 | + | − | 0 | 0 | + | 0 |
| Ascusbbf_4B | 0 | − | + | + | + | + | 0 | 0 | + | 0 |
| Ascusbbf_4B | 0 | 0 | 0 | + | 0 | + | 0 | 0 | 0 | 0 |
| Ascusbbf_4C | 0 | 0 | 0 | 0 | 0 | + | + | + | − | 0 |
| Ascusbbf_4C | 0 | 0 | + | + | + | + | + | 0 | + | 0 |
| Ascusbbf_4D | 0 | 0 | 0 | 0 | − | − | 0 | + | 0 | 0 |
| Ascusbbf_4D | 0 | 0 | 0 | 0 | + | + | 0 | + | + | 0 |
| Ascusbbf_4D | 0 | − | + | − | + | + | + | + | + | 0 |
| Ascusbbf_4D | 0 | − | + | + | + | + | 0 | 0 | + | 0 |
| Ascusbbf_4D | 0 | 0 | + | + | + | + | + | 0 | + | 0 |
| Ascusbbf_4D | 0 | 0 | 0 | 0 | + | 0 | + | 0 | 0 | 0 |
| Ascusbbf_4E | 0 | 0 | 0 | 0 | 0 | − | 0 | + | 0 | 0 |
| Ascusbbf_4E | 0 | 0 | 0 | 0 | + | + | 0 | + | + | 0 |
| Ascusbbf_4E | 0 | 0 | 0 | 0 | 0 | + | 0 | 0 | 0 | 0 |
| Ascusbbf_4E | 0 | 0 | 0 | + | 0 | + | 0 | 0 | 0 | 0 |
| Ascusbbf_4F | 0 | − | + | − | + | + | + | 0 | 0 | 0 |
| Ascusbbf_4F | 0 | 0 | 0 | 0 | − | − | 0 | + | 0 | 0 |

-continued

| Strain ID | pyruvic | glucose | succinic | lactic | glycerol | acetic | propionic | butyric | ethanol | 1-Butanol |
|---|---|---|---|---|---|---|---|---|---|---|
| Ascusbbf_4F | 0 | 0 | 0 | 0 | + | + | 0 | + | + | 0 |
| Ascusbbf_4F | 0 | − | + | 0 | 0 | + | + | 0 | + | 0 |
| Ascusbbf_4F | 0 | − | + | + | + | + | 0 | 0 | + | 0 |
| Ascusbbf_4F | 0 | 0 | + | + | + | + | + | 0 | + | 0 |
| Ascusbbf_4F | 0 | 0 | 0 | + | 0 | + | 0 | 0 | 0 | 0 |
| Ascusbbf_4F | 0 | − | + | + | − | + | 0 | 0 | 0 | 0 |
| Ascusbbf_4G | 0 | 0 | 0 | 0 | + | + | 0 | + | + | 0 |
| Ascusbbf_4G | 0 | − | + | 0 | 0 | + | + | + | + | 0 |
| Ascusbbf_4G | 0 | 0 | 0 | 0 | + | − | 0 | 0 | + | 0 |
| Ascusbbf_4G | 0 | 0 | 0 | 0 | 0 | + | 0 | 0 | 0 | 0 |
| Ascusbbf_4G | 0 | 0 | 0 | + | 0 | + | 0 | 0 | + | 0 |
| Ascusbbf_4G | 0 | 0 | 0 | + | 0 | + | 0 | 0 | 0 | 0 |
| Ascusbbf_4H | 0 | 0 | 0 | 0 | + | + | 0 | + | + | 0 |
| Ascusbbf_4H | 0 | − | + | 0 | 0 | + | + | 0 | + | 0 |
| Ascusbbf_4H | 0 | 0 | 0 | 0 | + | − | 0 | 0 | + | 0 |
| Ascusbbf_4H | 0 | 0 | 0 | 0 | 0 | + | 0 | 0 | 0 | 0 |
| Ascusbbf_4H | 0 | 0 | 0 | + | 0 | + | 0 | 0 | + | 0 |
| Ascusbbf_4H | 0 | 0 | 0 | + | 0 | + | 0 | 0 | + | 0 |
| Ascusbbf_4I | 0 | 0 | 0 | 0 | + | + | 0 | + | + | 0 |
| Ascusbbf_4I | 0 | 0 | 0 | 0 | + | − | 0 | 0 | + | 0 |
| Ascusbbf_4I | 0 | 0 | 0 | 0 | 0 | + | 0 | 0 | 0 | 0 |
| Ascusbbf_4I | 0 | 0 | 0 | + | 0 | + | 0 | 0 | 0 | 0 |
| Ascusbbf_4J | 0 | 0 | 0 | 0 | + | + | 0 | + | + | 0 |
| Ascusbbf_4J | 0 | 0 | 0 | 0 | 0 | + | 0 | 0 | 0 | 0 |
| Ascusbbf_4K | 0 | 0 | + | + | + | + | + | 0 | + | 0 |
| Ascusbbf_5005A | 0 | 0 | 0 | 0 | + | − | 0 | 0 | + | 0 |
| Ascusbbf_5005A | 0 | − | + | − | − | + | − | + | − | 0 |
| Ascusbbf_5005A | 0 | 0 | 0 | + | 0 | + | 0 | 0 | + | 0 |
| Ascusbbf_5005A | 0 | 0 | 0 | + | 0 | + | 0 | 0 | + | 0 |
| Ascusbbf_5005B | 0 | − | + | − | − | + | − | + | − | 0 |
| Ascusbbf_50658A | 0 | − | + | − | − | + | − | + | − | 0 |
| Ascusbbf_5131A | 0 | 0 | 0 | 0 | + | − | 0 | 0 | + | 0 |
| Ascusbbf_5131A | 0 | − | + | − | − | + | − | + | − | 0 |
| Ascusbbf_5131A | 0 | 0 | 0 | + | 0 | + | 0 | 0 | + | 0 |
| Ascusbbf_5131A | 0 | 0 | 0 | + | 0 | + | 0 | 0 | + | 0 |
| Ascusbbf_5131B | 0 | 0 | 0 | 0 | + | − | 0 | 0 | + | 0 |
| Ascusbbf_5131B | 0 | 0 | + | + | + | + | + | 0 | + | 0 |
| Ascusbbf_5131C | 0 | 0 | 0 | 0 | + | − | 0 | 0 | + | 0 |
| Ascusbbf_5131C | 0 | 0 | 0 | + | 0 | + | 0 | 0 | + | 0 |
| Ascusbbf_5131C | 0 | 0 | 0 | + | 0 | + | 0 | 0 | + | 0 |
| Ascusbbf_5131D | 0 | 0 | 0 | 0 | + | − | 0 | 0 | + | 0 |
| Ascusbbf_5131D | 0 | 0 | 0 | + | 0 | + | 0 | 0 | + | 0 |
| Ascusbbf_5131D | 0 | 0 | 0 | + | 0 | + | 0 | 0 | + | 0 |
| Ascusbbf_5131E | 0 | 0 | 0 | + | 0 | + | 0 | 0 | + | 0 |
| Ascusbbf_5131F | 0 | 0 | + | + | + | + | + | 0 | + | 0 |
| Ascusbbf_5131G | 0 | 0 | + | + | + | + | + | 0 | + | 0 |
| Ascusbbf_5131G | 0 | 0 | 0 | + | 0 | + | 0 | 0 | + | 0 |
| Ascusbbf_5131H | 0 | 0 | + | + | + | + | + | 0 | + | 0 |
| Ascusbbf_5131H | 0 | 0 | 0 | + | 0 | + | 0 | 0 | + | 0 |
| Ascusbbf_52330A | 0 | − | + | − | + | + | + | 0 | 0 | 0 |
| Ascusbbf_5251A | 0 | − | + | − | + | + | + | 0 | 0 | 0 |
| Ascusbbf_5251A | 0 | 0 | 0 | 0 | + | − | 0 | 0 | + | 0 |
| Ascusbbf_5251A | 0 | − | + | − | − | + | − | + | − | 0 |
| Ascusbbf_5251B | 0 | − | + | − | + | + | + | 0 | 0 | 0 |
| Ascusbbf_5251B | 0 | 0 | 0 | 0 | 0 | + | + | + | − | 0 |
| Ascusbbf_5251C | 0 | 0 | 0 | 0 | 0 | + | + | + | − | 0 |
| Ascusbbf_5251C | 0 | 0 | 0 | 0 | + | − | 0 | 0 | + | 0 |
| Ascusbbf_5251C | 0 | − | + | − | − | + | − | + | − | 0 |
| Ascusbbf_5251C | 0 | 0 | + | + | + | + | + | 0 | + | 0 |
| Ascusbbf_5251C | 0 | 0 | 0 | + | 0 | + | 0 | 0 | + | 0 |
| Ascusbbf_5251D | 0 | − | + | − | + | + | + | 0 | 0 | 0 |
| Ascusbbf_5251D | 0 | 0 | 0 | 0 | 0 | + | + | + | − | 0 |
| Ascusbbf_5251D | 0 | 0 | 0 | 0 | + | − | 0 | 0 | + | 0 |
| Ascusbbf_5251E | 0 | 0 | 0 | 0 | + | − | 0 | 0 | + | 0 |
| Ascusbbf_5251E | 0 | − | + | − | − | + | − | + | − | 0 |
| Ascusbbf_5251E | 0 | 0 | 0 | + | 0 | + | 0 | 0 | + | 0 |
| Ascusbbf_5251E | 0 | 0 | 0 | + | 0 | + | 0 | 0 | + | 0 |
| Ascusbbf_5251F | 0 | 0 | 0 | + | 0 | + | 0 | 0 | + | 0 |
| Ascusbbf_5251G | 0 | 0 | + | + | + | + | + | 0 | + | 0 |
| Ascusbbf_5251G | 0 | 0 | 0 | + | 0 | + | 0 | 0 | + | 0 |
| Ascusbbf_52548A | 0 | 0 | 0 | + | 0 | + | 0 | 0 | + | 0 |
| Ascusbbf_52548A | 0 | 0 | 0 | + | 0 | + | 0 | 0 | + | 0 |
| Ascusbbf_52548B | 0 | 0 | 0 | + | 0 | + | 0 | 0 | + | 0 |
| Ascusbbf_52548B | 0 | 0 | 0 | + | 0 | + | 0 | 0 | 0 | 0 |
| Ascusbbf_54068A | + | − | + | − | 0 | + | + | + | − | 0 |
| Ascusbbf_54068B | 0 | − | + | − | + | + | + | 0 | 0 | 0 |
| Ascusbbf_54068C | 0 | − | + | − | + | + | + | 0 | 0 | 0 |

-continued

| Strain ID | pyruvic | glucose | succinic | lactic | glycerol | acetic | propionic | butyric | ethanol | 1-Butanol |
|---|---|---|---|---|---|---|---|---|---|---|
| Ascusbbf_54068C | 0 | 0 | 0 | 0 | − | − | 0 | + | 0 | 0 |
| Ascusbbf_54068C | 0 | 0 | 0 | 0 | + | + | 0 | + | + | 0 |
| Ascusbbf_54068C | 0 | − | + | 0 | 0 | + | + | + | + | 0 |
| Ascusbbf_54068C | 0 | 0 | 0 | 0 | + | − | 0 | 0 | + | 0 |
| Ascusbbf_54068D | 0 | − | + | − | + | + | + | 0 | 0 | 0 |
| Ascusbbf_54068D | 0 | 0 | 0 | 0 | + | + | 0 | + | + | 0 |
| Ascusbbf_54068D | 0 | − | + | 0 | 0 | + | + | 0 | + | 0 |
| Ascusbbf_54068D | 0 | 0 | 0 | 0 | + | − | 0 | 0 | + | 0 |
| Ascusbbf_54068D | 0 | − | + | − | − | + | − | + | − | 0 |
| Ascusbbf_5429A | 0 | 0 | 0 | 0 | − | − | 0 | + | 0 | 0 |
| Ascusbbf_5429A | 0 | 0 | 0 | 0 | + | + | 0 | + | + | 0 |
| Ascusbbf_5429A | 0 | 0 | 0 | 0 | + | − | 0 | 0 | + | 0 |
| Ascusbbf_5429A | 0 | 0 | 0 | 0 | 0 | + | 0 | 0 | 0 | 0 |
| Ascusbbf_5429A | 0 | 0 | 0 | + | 0 | + | 0 | 0 | 0 | 0 |
| Ascusbbf_5429B | 0 | 0 | 0 | 0 | − | − | 0 | + | 0 | 0 |
| Ascusbbf_5429B | 0 | 0 | 0 | 0 | + | + | 0 | + | + | 0 |
| Ascusbbf_5429B | 0 | 0 | 0 | 0 | + | − | 0 | 0 | + | 0 |
| Ascusbbf_5429B | 0 | 0 | 0 | 0 | 0 | + | 0 | 0 | 0 | 0 |
| Ascusbbf_5429B | 0 | 0 | 0 | + | 0 | + | 0 | 0 | 0 | 0 |
| Ascusbbf_5429C | 0 | − | + | − | + | + | + | 0 | 0 | 0 |
| Ascusbbf_5429C | 0 | − | + | 0 | 0 | + | + | 0 | + | 0 |
| Ascusbbf_5429D | 0 | 0 | 0 | 0 | + | − | 0 | 0 | + | 0 |
| Ascusbbf_5575A | + | − | + | − | 0 | + | + | + | − | 0 |
| Ascusbbf_5575A | 0 | − | 0 | 0 | 0 | + | 0 | + | + | 0 |
| Ascusbbf_5575B | + | − | + | − | 0 | + | + | + | − | 0 |
| Ascusbbf_5575B | 0 | − | 0 | 0 | 0 | + | 0 | + | + | 0 |
| Ascusbbf_5575C | 0 | − | + | − | + | + | + | 0 | 0 | 0 |
| Ascusbbf_5575C | 0 | − | + | 0 | 0 | + | + | + | + | 0 |
| Ascusbbf_5575C | 0 | 0 | 0 | 0 | 0 | + | 0 | 0 | 0 | 0 |
| Ascusbbf_5575D | 0 | − | + | − | − | 0 | 0 | + | + | 0 |
| Ascusbbf_5575D | 0 | − | + | 0 | 0 | + | + | + | + | 0 |
| Ascusbbf_5575D | 0 | − | + | + | + | + | 0 | 0 | + | 0 |
| Ascusbbf_5575D | 0 | − | + | − | − | 0 | 0 | + | + | 0 |
| Ascusbbf_5575E | 0 | − | + | − | + | + | + | 0 | 0 | 0 |
| Ascusbbf_5575E | 0 | − | + | 0 | 0 | + | + | + | + | 0 |
| Ascusbbf_5575E | 0 | 0 | 0 | 0 | + | − | 0 | 0 | + | 0 |
| Ascusbbf_5575E | 0 | 0 | 0 | + | 0 | + | 0 | 0 | 0 | 0 |
| Ascusbbf_5575F | 0 | − | + | − | + | + | + | 0 | 0 | 0 |
| Ascusbbf_5575F | 0 | − | + | 0 | 0 | + | + | + | + | 0 |
| Ascusbbf_5575F | 0 | 0 | 0 | 0 | + | − | 0 | 0 | + | 0 |
| Ascusbbf_5575G | 0 | − | + | − | + | + | + | 0 | 0 | 0 |
| Ascusbbf_5575G | 0 | − | + | 0 | 0 | + | + | + | + | 0 |
| Ascusbbf_5575G | 0 | 0 | 0 | 0 | + | − | 0 | 0 | + | 0 |
| Ascusbbf_5575G | 0 | − | + | + | + | + | 0 | 0 | + | 0 |
| Ascusbbf_5575H | 0 | − | + | − | + | + | + | 0 | 0 | 0 |
| Ascusbbf_5575H | 0 | − | + | 0 | 0 | + | + | + | + | 0 |
| Ascusbbf_5575H | 0 | − | + | − | − | + | − | + | − | 0 |
| Ascusbbf_5588A | 0 | 0 | 0 | 0 | − | − | 0 | + | 0 | 0 |
| Ascusbbf_5588A | 0 | 0 | 0 | 0 | 0 | + | + | + | − | 0 |
| Ascusbbf_5588A | 0 | − | + | 0 | 0 | + | + | 0 | + | 0 |
| Ascusbbf_5588A | 0 | 0 | 0 | 0 | + | − | 0 | 0 | + | 0 |
| Ascusbbf_5588A | 0 | − | + | − | − | + | − | + | − | 0 |
| Ascusbbf_5588B | 0 | 0 | 0 | 0 | − | − | 0 | + | 0 | 0 |
| Ascusbbf_5588B | 0 | − | + | 0 | 0 | + | + | 0 | + | 0 |
| Ascusbbf_5588C | 0 | 0 | 0 | 0 | − | − | 0 | + | 0 | 0 |
| Ascusbbf_5588C | 0 | 0 | 0 | 0 | 0 | + | + | + | − | 0 |
| Ascusbbf_5588C | 0 | − | + | 0 | 0 | + | + | 0 | + | 0 |
| Ascusbbf_5588C | 0 | 0 | 0 | 0 | + | − | 0 | 0 | + | 0 |
| Ascusbbf_5588C | 0 | − | + | − | − | + | − | + | − | 0 |
| Ascusbbf_5588C | 0 | 0 | 0 | + | 0 | + | 0 | 0 | + | 0 |
| Ascusbbf_5588C | 0 | 0 | 0 | + | 0 | + | 0 | 0 | + | 0 |
| Ascusbbf_5588D | 0 | 0 | 0 | 0 | − | − | 0 | + | 0 | 0 |
| Ascusbbf_5588D | 0 | 0 | 0 | 0 | + | + | 0 | + | + | 0 |
| Ascusbbf_5588D | 0 | − | + | 0 | 0 | + | + | 0 | + | 0 |
| Ascusbbf_5588D | 0 | 0 | 0 | 0 | + | − | 0 | 0 | + | 0 |
| Ascusbbf_5588D | 0 | 0 | 0 | 0 | 0 | + | 0 | 0 | + | 0 |
| Ascusbbf_5588D | 0 | 0 | + | + | + | + | + | 0 | + | 0 |
| Ascusbbf_5588D | 0 | 0 | 0 | + | 0 | + | 0 | 0 | 0 | 0 |
| Ascusbbf_5588E | 0 | − | + | 0 | 0 | + | + | 0 | + | 0 |
| Ascusbbf_5588F | 0 | − | + | 0 | 0 | + | + | 0 | + | 0 |
| Ascusbbf_5588G | 0 | − | + | 0 | 0 | + | + | 0 | + | 0 |
| Ascusbbf_5588H | 0 | 0 | 0 | 0 | + | − | 0 | 0 | + | 0 |
| Ascusbbf_5588H | 0 | 0 | + | + | + | + | + | 0 | + | 0 |
| Ascusbbf_56782A | 0 | − | + | − | + | + | + | 0 | 0 | 0 |
| Ascusbbf_56782A | 0 | 0 | 0 | 0 | + | + | 0 | + | + | 0 |
| Ascusbbf_56782A | 0 | − | + | 0 | 0 | + | + | + | + | 0 |
| Ascusbbf_56782A | 0 | 0 | 0 | 0 | + | − | 0 | 0 | + | 0 |

-continued

| Strain ID | pyruvic | glucose | succinic | lactic | glycerol | acetic | propionic | butyric | ethanol | 1-Butanol |
|---|---|---|---|---|---|---|---|---|---|---|
| Ascusbbf_56782A | 0 | 0 | 0 | 0 | 0 | + | 0 | 0 | 0 | 0 |
| Ascusbbf_56782A | 0 | 0 | 0 | + | 0 | + | 0 | 0 | + | 0 |
| Ascusbbf_56782A | 0 | 0 | 0 | + | 0 | + | 0 | 0 | + | 0 |
| Ascusbbf_56782B | 0 | 0 | + | + | + | + | + | 0 | + | 0 |
| Ascusbbf_56782C | 0 | 0 | + | + | + | + | + | 0 | + | 0 |
| Ascusbbf_5699A | 0 | 0 | 0 | 0 | + | − | 0 | 0 | + | 0 |
| Ascusbbf_5699A | 0 | − | + | − | − | + | − | + | − | 0 |
| Ascusbbf_5699B | 0 | 0 | 0 | 0 | + | − | 0 | 0 | + | 0 |
| Ascusbbf_5699B | 0 | − | + | − | − | + | − | + | − | 0 |
| Ascusbbf_5699C | 0 | 0 | 0 | 0 | + | − | 0 | 0 | + | 0 |
| Ascusbbf_5699C | 0 | − | + | − | − | + | − | + | − | 0 |
| Ascusbbf_5699D | 0 | − | + | − | − | + | − | + | − | 0 |
| Ascusbbf_5699D | 0 | 0 | + | + | + | + | + | 0 | + | 0 |
| Ascusbbf_57294A | 0 | 0 | 0 | 0 | + | + | 0 | + | + | 0 |
| Ascusbbf_57294A | + | − | + | − | 0 | + | + | + | − | 0 |
| Ascusbbf_57294B | 0 | − | + | − | + | + | + | 0 | 0 | 0 |
| Ascusbbf_57294B | 0 | 0 | 0 | 0 | 0 | + | 0 | 0 | 0 | 0 |
| Ascusbbf_57294C | 0 | − | + | − | + | + | + | 0 | 0 | 0 |
| Ascusbbf_57294C | 0 | 0 | 0 | + | 0 | + | 0 | 0 | 0 | 0 |
| Ascusbbf_6012A | + | − | + | − | 0 | + | + | + | − | 0 |
| Ascusbbf_6012B | 0 | 0 | 0 | 0 | − | − | 0 | + | 0 | 0 |
| Ascusbbf_6012B | 0 | 0 | 0 | 0 | 0 | + | + | + | − | 0 |
| Ascusbbf_6012B | 0 | 0 | 0 | 0 | + | − | 0 | 0 | + | 0 |
| Ascusbbf_6012B | 0 | 0 | 0 | 0 | 0 | + | 0 | 0 | 0 | 0 |
| Ascusbbf_6012C | 0 | 0 | 0 | 0 | − | − | 0 | + | 0 | 0 |
| Ascusbbf_6012C | 0 | 0 | 0 | 0 | + | + | 0 | + | + | 0 |
| Ascusbbf_6012C | 0 | 0 | 0 | 0 | + | − | 0 | 0 | + | 0 |
| Ascusbbf_6012C | 0 | − | + | − | − | + | − | + | − | 0 |
| Ascusbbf_6012D | 0 | 0 | 0 | 0 | 0 | + | + | + | − | 0 |
| Ascusbbf_6012D | 0 | 0 | 0 | 0 | + | − | 0 | 0 | + | 0 |
| Ascusbbf_6012E | 0 | 0 | 0 | 0 | 0 | + | + | + | − | 0 |
| Ascusbbf_6087A | 0 | 0 | 0 | + | 0 | + | 0 | 0 | + | 0 |
| Ascusbbf_6087A | 0 | 0 | 0 | + | 0 | + | 0 | 0 | + | 0 |
| Ascusbbf_6087B | 0 | 0 | 0 | + | 0 | + | 0 | 0 | + | 0 |
| Ascusbbf_6087B | 0 | 0 | 0 | + | 0 | + | 0 | 0 | + | 0 |
| Ascusbbf_6087C | 0 | 0 | 0 | + | 0 | + | 0 | 0 | + | 0 |
| Ascusbbf_6087C | 0 | 0 | 0 | + | 0 | + | 0 | 0 | + | 0 |
| Ascusbbf_6115A | 0 | − | + | − | + | + | + | 0 | 0 | 0 |
| Ascusbbf_6115A | 0 | 0 | 0 | 0 | 0 | + | + | + | − | 0 |
| Ascusbbf_6115B | 0 | 0 | 0 | 0 | + | + | 0 | + | + | 0 |
| Ascusbbf_6115B | 0 | 0 | 0 | 0 | 0 | + | 0 | 0 | 0 | 0 |
| Ascusbbf_6115C | 0 | 0 | 0 | 0 | + | + | 0 | + | + | 0 |
| Ascusbbf_6115C | 0 | 0 | 0 | 0 | 0 | + | 0 | 0 | 0 | 0 |
| Ascusbbf_6115D | 0 | 0 | 0 | 0 | + | + | 0 | + | + | 0 |
| Ascusbbf_6176A | 0 | 0 | 0 | 0 | 0 | + | + | + | − | 0 |
| Ascusbbf_6176A | 0 | − | + | 0 | 0 | + | + | 0 | + | 0 |
| Ascusbbf_6176A | 0 | 0 | 0 | 0 | + | − | 0 | 0 | + | 0 |
| Ascusbbf_6176A | 0 | − | + | − | − | + | − | + | − | 0 |
| Ascusbbf_6176A | 0 | 0 | 0 | + | 0 | + | 0 | 0 | + | 0 |
| Ascusbbf_6176A | 0 | 0 | 0 | + | 0 | + | 0 | 0 | + | 0 |
| Ascusbbf_6176B | 0 | 0 | 0 | 0 | 0 | + | + | + | − | 0 |
| Ascusbbf_6176B | 0 | − | + | 0 | 0 | + | + | 0 | + | 0 |
| Ascusbbf_6176B | 0 | 0 | 0 | 0 | + | − | 0 | 0 | + | 0 |
| Ascusbbf_6176B | 0 | − | + | − | − | + | − | + | − | 0 |
| Ascusbbf_6176B | 0 | 0 | 0 | + | 0 | + | 0 | 0 | + | 0 |
| Ascusbbf_6176B | 0 | 0 | 0 | + | 0 | + | 0 | 0 | + | 0 |
| Ascusbbf_6176C | 0 | 0 | 0 | 0 | + | + | 0 | + | + | 0 |
| Ascusbbf_6176C | 0 | 0 | 0 | 0 | + | − | 0 | 0 | + | 0 |
| Ascusbbf_6176C | 0 | 0 | 0 | 0 | 0 | + | 0 | 0 | 0 | 0 |
| Ascusbbf_6176D | 0 | 0 | 0 | 0 | + | − | 0 | 0 | + | 0 |
| Ascusbbf_6176D | 0 | 0 | 0 | + | 0 | + | 0 | 0 | + | 0 |
| Ascusbbf_6176D | 0 | 0 | 0 | + | 0 | + | 0 | 0 | + | 0 |
| Ascusbbf_6176E | 0 | 0 | 0 | 0 | + | − | 0 | 0 | + | 0 |
| Ascusbbf_6176E | 0 | 0 | 0 | + | 0 | + | 0 | 0 | + | 0 |
| Ascusbbf_6176E | 0 | 0 | 0 | + | 0 | + | 0 | 0 | + | 0 |
| Ascusbbf_6176F | 0 | 0 | 0 | 0 | + | − | 0 | 0 | + | 0 |
| Ascusbbf_6176G | 0 | 0 | 0 | 0 | + | − | 0 | 0 | + | 0 |
| Ascusbbf_6176G | 0 | − | + | − | − | + | − | + | − | 0 |
| Ascusbbf_6176G | 0 | 0 | 0 | + | 0 | + | 0 | 0 | + | 0 |
| Ascusbbf_6176G | 0 | 0 | 0 | + | 0 | + | 0 | 0 | 0 | 0 |
| Ascusbbf_6176H | 0 | 0 | 0 | 0 | + | − | 0 | 0 | + | 0 |
| Ascusbbf_6176H | 0 | 0 | 0 | + | 0 | + | 0 | 0 | + | 0 |
| Ascusbbf_6176H | 0 | 0 | 0 | + | 0 | + | 0 | 0 | + | 0 |
| Ascusbbf_6176I | 0 | − | + | − | − | + | − | + | − | 0 |
| Ascusbbf_6176I | 0 | 0 | 0 | + | 0 | + | 0 | 0 | + | 0 |
| Ascusbbf_6176I | 0 | 0 | 0 | + | 0 | + | 0 | 0 | + | 0 |
| Ascusbbf_63954A | 0 | 0 | 0 | 0 | + | − | 0 | 0 | + | 0 |

-continued

| Strain ID | pyruvic | glucose | succinic | lactic | glycerol | acetic | propionic | butyric | ethanol | 1-Butanol |
|---|---|---|---|---|---|---|---|---|---|---|
| Ascusbbf_667A | 0 | − | + | − | + | + | + | + | + | 0 |
| Ascusbbf_667A | 0 | 0 | 0 | 0 | + | − | 0 | 0 | + | 0 |
| Ascusbbf_667A | 0 | − | + | − | − | + | − | + | − | 0 |
| Ascusbbf_667A | 0 | 0 | 0 | + | 0 | + | 0 | 0 | 0 | 0 |
| Ascusbbf_667B | 0 | − | + | − | + | + | + | + | + | 0 |
| Ascusbbf_667B | 0 | 0 | 0 | 0 | + | − | 0 | 0 | + | 0 |
| Ascusbbf_6906A | 0 | 0 | + | + | + | + | + | 0 | + | 0 |
| Ascusbbf_6906A | 0 | 0 | 0 | + | 0 | + | 0 | 0 | + | 0 |
| Ascusbbf_6906B | 0 | 0 | + | + | + | + | + | 0 | + | 0 |
| Ascusbbf_6906C | 0 | 0 | + | + | + | + | + | 0 | + | 0 |
| Ascusbbf_6906C | 0 | 0 | 0 | + | 0 | + | 0 | 0 | + | 0 |
| Ascusbbf_6906D | 0 | 0 | + | + | + | + | + | 0 | + | 0 |
| Ascusbbf_6906E | 0 | 0 | + | + | + | + | + | 0 | + | 0 |
| Ascusbbf_6906E | 0 | 0 | 0 | + | 0 | + | 0 | 0 | + | 0 |
| Ascusbbf_69A | 0 | − | + | − | + | + | + | 0 | 0 | 0 |
| Ascusbbf_69A | 0 | 0 | 0 | 0 | − | − | 0 | + | 0 | 0 |
| Ascusbbf_69A | 0 | 0 | 0 | 0 | + | + | 0 | + | + | 0 |
| Ascusbbf_69A | 0 | − | + | 0 | 0 | + | + | 0 | + | 0 |
| Ascusbbf_69A | 0 | 0 | 0 | 0 | + | − | 0 | 0 | + | 0 |
| Ascusbbf_69A | 0 | 0 | 0 | 0 | 0 | + | 0 | 0 | 0 | 0 |
| Ascusbbf_69A | 0 | 0 | + | + | + | + | + | 0 | + | 0 |
| Ascusbbf_69A | 0 | 0 | 0 | + | 0 | + | 0 | 0 | + | 0 |
| Ascusbbf_69B | 0 | − | + | − | + | + | + | 0 | 0 | 0 |
| Ascusbbf_69B | 0 | 0 | 0 | 0 | − | − | 0 | + | 0 | 0 |
| Ascusbbf_69B | 0 | 0 | 0 | 0 | + | + | 0 | + | + | 0 |
| Ascusbbf_69B | 0 | − | + | 0 | 0 | + | + | 0 | + | 0 |
| Ascusbbf_69B | 0 | 0 | 0 | 0 | + | − | 0 | 0 | + | 0 |
| Ascusbbf_69B | 0 | − | + | − | − | + | − | + | − | 0 |
| Ascusbbf_69B | 0 | 0 | 0 | + | 0 | + | 0 | 0 | + | 0 |
| Ascusbbf_69B | 0 | 0 | 0 | + | 0 | + | 0 | 0 | + | 0 |
| Ascusbbf_69C | 0 | − | + | − | + | + | + | 0 | 0 | 0 |
| Ascusbbf_69C | 0 | 0 | 0 | 0 | − | − | 0 | + | 0 | 0 |
| Ascusbbf_69C | 0 | 0 | 0 | 0 | + | + | 0 | + | + | 0 |
| Ascusbbf_69C | 0 | − | + | 0 | 0 | + | + | 0 | + | 0 |
| Ascusbbf_69C | 0 | 0 | 0 | 0 | + | − | 0 | 0 | + | 0 |
| Ascusbbf_69C | 0 | 0 | 0 | 0 | 0 | + | 0 | 0 | 0 | 0 |
| Ascusbbf_69C | 0 | 0 | + | + | + | + | + | 0 | + | 0 |
| Ascusbbf_69C | 0 | 0 | 0 | + | 0 | + | 0 | 0 | + | 0 |
| Ascusbbf_69D | 0 | − | + | − | + | + | + | 0 | 0 | 0 |
| Ascusbbf_69D | 0 | 0 | 0 | 0 | − | − | 0 | + | 0 | 0 |
| Ascusbbf_69D | 0 | 0 | 0 | 0 | + | + | 0 | + | + | 0 |
| Ascusbbf_69D | 0 | 0 | 0 | 0 | + | − | 0 | 0 | + | 0 |
| Ascusbbf_69D | 0 | 0 | 0 | 0 | 0 | + | 0 | 0 | 0 | 0 |
| Ascusbbf_69D | 0 | 0 | + | + | + | + | + | 0 | + | 0 |
| Ascusbbf_69D | 0 | 0 | 0 | + | 0 | + | 0 | 0 | + | 0 |
| Ascusbbf_69E | 0 | − | + | − | + | + | + | 0 | 0 | 0 |
| Ascusbbf_69E | 0 | 0 | 0 | 0 | − | − | 0 | + | 0 | 0 |
| Ascusbbf_69E | 0 | 0 | 0 | 0 | + | + | 0 | + | + | 0 |
| Ascusbbf_69E | 0 | − | + | 0 | 0 | + | + | + | + | 0 |
| Ascusbbf_69E | 0 | 0 | 0 | 0 | + | − | 0 | 0 | + | 0 |
| Ascusbbf_69E | 0 | 0 | 0 | 0 | 0 | + | 0 | 0 | 0 | 0 |
| Ascusbbf_69E | 0 | 0 | + | + | + | + | + | 0 | + | 0 |
| Ascusbbf_69E | 0 | 0 | 0 | + | 0 | + | 0 | 0 | + | 0 |
| Ascusbbf_69F | 0 | − | + | − | + | + | + | 0 | 0 | 0 |
| Ascusbbf_69F | 0 | 0 | 0 | 0 | − | − | 0 | + | 0 | 0 |
| Ascusbbf_69F | 0 | 0 | 0 | 0 | + | + | 0 | + | + | 0 |
| Ascusbbf_69F | 0 | − | + | 0 | 0 | + | + | + | + | 0 |
| Ascusbbf_69F | 0 | 0 | 0 | 0 | + | − | 0 | 0 | + | 0 |
| Ascusbbf_69F | 0 | 0 | 0 | 0 | 0 | + | 0 | 0 | 0 | 0 |
| Ascusbbf_69F | 0 | 0 | + | + | + | + | + | 0 | + | 0 |
| Ascusbbf_69F | 0 | 0 | 0 | + | 0 | + | 0 | 0 | + | 0 |
| Ascusbbf_69G | 0 | − | + | − | + | + | + | 0 | 0 | 0 |
| Ascusbbf_69G | 0 | 0 | 0 | 0 | + | + | 0 | + | + | 0 |
| Ascusbbf_69G | 0 | − | + | 0 | 0 | + | + | 0 | + | 0 |
| Ascusbbf_69G | 0 | 0 | 0 | 0 | + | − | 0 | 0 | + | 0 |
| Ascusbbf_69G | 0 | 0 | 0 | 0 | 0 | + | 0 | 0 | 0 | 0 |
| Ascusbbf_69G | 0 | 0 | + | + | + | + | + | 0 | + | 0 |
| Ascusbbf_69G | 0 | 0 | 0 | + | 0 | + | 0 | 0 | 0 | 0 |
| Ascusbbf_69H | 0 | − | + | − | + | + | + | 0 | 0 | 0 |
| Ascusbbf_69H | 0 | 0 | 0 | 0 | + | + | 0 | + | + | 0 |
| Ascusbbf_69H | 0 | − | + | 0 | 0 | + | + | + | + | 0 |
| Ascusbbf_69H | 0 | 0 | 0 | 0 | + | − | 0 | 0 | + | 0 |
| Ascusbbf_69H | 0 | 0 | 0 | 0 | 0 | + | 0 | 0 | 0 | 0 |
| Ascusbbf_69H | 0 | 0 | 0 | + | 0 | + | 0 | 0 | + | 0 |
| Ascusbbf_69H | 0 | 0 | 0 | + | 0 | + | 0 | 0 | + | 0 |
| Ascusbbf_69I | 0 | − | + | − | + | + | + | 0 | 0 | 0 |
| Ascusbbf_69I | 0 | 0 | 0 | 0 | + | + | 0 | + | + | 0 |

-continued

| Strain ID | pyruvic | glucose | succinic | lactic | glycerol | acetic | propionic | butyric | ethanol | 1-Butanol |
|---|---|---|---|---|---|---|---|---|---|---|
| Ascusbbf_69I | 0 | − | + | 0 | 0 | + | + | 0 | + | 0 |
| Ascusbbf_69I | 0 | 0 | 0 | 0 | + | − | 0 | 0 | + | 0 |
| Ascusbbf_69I | 0 | 0 | + | + | + | + | + | 0 | + | 0 |
| Ascusbbf_69I | 0 | 0 | 0 | + | 0 | + | 0 | 0 | + | 0 |
| Ascusbbf_69J | 0 | − | + | − | + | + | + | 0 | 0 | 0 |
| Ascusbbf_69J | 0 | − | + | − | + | + | + | + | + | 0 |
| Ascusbbf_69J | 0 | 0 | 0 | + | 0 | + | 0 | 0 | + | 0 |
| Ascusbbf_69J | 0 | 0 | 0 | + | 0 | + | 0 | 0 | 0 | 0 |
| Ascusbbf_69K | 0 | − | + | − | + | + | + | 0 | 0 | 0 |
| Ascusbbf_69K | 0 | − | + | − | + | + | + | + | + | 0 |
| Ascusbbf_69L | 0 | − | + | − | + | + | + | 0 | 0 | 0 |
| Ascusbbf_69L | 0 | − | + | − | + | + | + | + | + | 0 |
| Ascusbbf_69M | 0 | − | + | − | + | + | + | 0 | 0 | 0 |
| Ascusbbf_69M | 0 | − | + | − | + | + | + | + | + | 0 |
| Ascusbbf_69N | 0 | − | + | − | + | + | + | 0 | 0 | 0 |
| Ascusbbf_69N | 0 | − | + | − | + | + | + | + | + | 0 |
| Ascusbbf_69O | 0 | − | + | − | + | + | + | 0 | 0 | 0 |
| Ascusbbf_69O | 0 | − | + | − | + | + | + | + | + | 0 |
| Ascusbbf_69P | 0 | − | + | − | + | + | + | 0 | 0 | 0 |
| Ascusbbf_6A | 0 | 0 | 0 | 0 | − | − | 0 | + | 0 | 0 |
| Ascusbbf_6A | 0 | 0 | 0 | 0 | + | + | 0 | + | + | 0 |
| Ascusbbf_6A | 0 | 0 | 0 | 0 | + | − | 0 | 0 | + | 0 |
| Ascusbbf_6A | 0 | 0 | 0 | 0 | 0 | + | 0 | 0 | 0 | 0 |
| Ascusbbf_6A | 0 | 0 | 0 | + | 0 | + | 0 | 0 | 0 | 0 |
| Ascusbbf_6B | 0 | 0 | 0 | 0 | − | − | 0 | + | 0 | 0 |
| Ascusbbf_6B | 0 | 0 | 0 | 0 | 0 | + | + | + | − | 0 |
| Ascusbbf_6B | 0 | − | + | − | + | + | + | + | + | 0 |
| Ascusbbf_6B | 0 | 0 | 0 | 0 | + | − | 0 | 0 | + | 0 |
| Ascusbbf_6B | 0 | − | + | − | − | + | − | + | − | 0 |
| Ascusbbf_6B | 0 | 0 | 0 | + | 0 | + | 0 | 0 | 0 | 0 |
| Ascusbbf_6B | 0 | − | 0 | + | + | + | 0 | + | − | 0 |
| Ascusbbf_6C | 0 | 0 | 0 | 0 | − | − | 0 | + | 0 | 0 |
| Ascusbbf_6C | 0 | 0 | 0 | 0 | 0 | + | + | + | − | 0 |
| Ascusbbf_6C | 0 | − | + | − | + | + | + | + | + | 0 |
| Ascusbbf_6C | 0 | 0 | 0 | 0 | + | − | 0 | 0 | + | 0 |
| Ascusbbf_6C | 0 | − | + | − | − | + | − | + | − | 0 |
| Ascusbbf_6C | 0 | 0 | 0 | + | 0 | 0 | 0 | 0 | 0 | 0 |
| Ascusbbf_6D | 0 | 0 | 0 | 0 | − | − | 0 | + | 0 | 0 |
| Ascusbbf_6D | 0 | 0 | 0 | 0 | + | + | 0 | + | + | 0 |
| Ascusbbf_6D | 0 | 0 | 0 | 0 | 0 | + | 0 | 0 | 0 | 0 |
| Ascusbbf_6D | 0 | 0 | 0 | + | 0 | + | 0 | 0 | 0 | 0 |
| Ascusbbf_6E | 0 | 0 | 0 | 0 | − | − | 0 | + | 0 | 0 |
| Ascusbbf_6E | 0 | 0 | 0 | 0 | 0 | + | + | + | − | 0 |
| Ascusbbf_6E | 0 | − | + | 0 | 0 | + | + | + | + | 0 |
| Ascusbbf_6E | 0 | 0 | 0 | 0 | + | − | 0 | 0 | + | 0 |
| Ascusbbf_6E | 0 | − | + | − | − | + | − | + | − | 0 |
| Ascusbbf_6E | 0 | 0 | 0 | + | 0 | + | 0 | 0 | 0 | 0 |
| Ascusbbf_6F | 0 | 0 | 0 | 0 | − | − | 0 | + | 0 | 0 |
| Ascusbbf_6F | 0 | 0 | 0 | + | 0 | + | 0 | 0 | 0 | 0 |
| Ascusbbf_6G | 0 | 0 | 0 | 0 | − | − | 0 | + | 0 | 0 |
| Ascusbbf_6G | 0 | 0 | 0 | 0 | 0 | + | + | + | − | 0 |
| Ascusbbf_6G | 0 | − | + | − | + | + | + | + | + | 0 |
| Ascusbbf_6G | 0 | 0 | 0 | 0 | + | − | 0 | 0 | + | 0 |
| Ascusbbf_6G | 0 | − | + | − | − | + | − | + | − | 0 |
| Ascusbbf_6G | 0 | 0 | 0 | + | 0 | + | 0 | 0 | 0 | 0 |
| Ascusbbf_6H | 0 | 0 | 0 | 0 | 0 | + | + | + | − | 0 |
| Ascusbbf_6H | 0 | − | + | 0 | 0 | + | + | + | + | 0 |
| Ascusbbf_6H | 0 | − | + | − | − | + | − | + | − | 0 |
| Ascusbbf_6I | 0 | 0 | 0 | 0 | + | + | 0 | + | + | 0 |
| Ascusbbf_6I | 0 | 0 | 0 | 0 | 0 | + | 0 | 0 | 0 | 0 |
| Ascusbbf_6J | 0 | 0 | 0 | 0 | + | + | 0 | + | + | 0 |
| Ascusbbf_6J | 0 | 0 | 0 | 0 | 0 | + | 0 | 0 | 0 | 0 |
| Ascusbbf_6K | 0 | − | + | 0 | 0 | + | + | 0 | + | 0 |
| Ascusbbf_6L | 0 | − | + | 0 | 0 | + | + | 0 | + | 0 |
| Ascusbbf_7003A | + | − | + | − | 0 | + | + | + | − | 0 |
| Ascusbbf_7003C | 0 | − | + | 0 | + | + | + | 0 | 0 | 0 |
| Ascusbbf_7046A | 0 | 0 | 0 | 0 | 0 | + | 0 | 0 | 0 | 0 |
| Ascusbbf_707A | 0 | 0 | 0 | 0 | + | − | 0 | 0 | + | 0 |
| Ascusbbf_707A | 0 | − | + | − | + | − | + | − | 0 |  |
| Ascusbbf_707A | 0 | 0 | + | + | + | + | + | 0 | + | 0 |
| Ascusbbf_707A | 0 | 0 | 0 | + | 0 | + | 0 | 0 | + | 0 |
| Ascusbbf_707B | 0 | 0 | 0 | 0 | + | − | 0 | 0 | + | 0 |
| Ascusbbf_707B | 0 | − | + | − | − | + | − | + | − | 0 |
| Ascusbbf_707B | 0 | 0 | 0 | + | 0 | + | 0 | 0 | + | 0 |
| Ascusbbf_707B | 0 | 0 | 0 | + | 0 | + | 0 | 0 | 0 | 0 |
| Ascusbbf_707C | 0 | 0 | 0 | 0 | + | − | 0 | 0 | + | 0 |
| Ascusbbf_707C | 0 | − | + | − | − | + | − | + | − | 0 |

-continued

| Strain ID | pyruvic | glucose | succinic | lactic | glycerol | acetic | propionic | butyric | ethanol | 1-Butanol |
|---|---|---|---|---|---|---|---|---|---|---|
| Ascusbbf_707D | 0 | 0 | 0 | 0 | + | − | 0 | 0 | + | 0 |
| Ascusbbf_707D | 0 | 0 | 0 | + | 0 | + | 0 | 0 | + | 0 |
| Ascusbbf_707D | 0 | 0 | 0 | + | 0 | + | 0 | 0 | + | 0 |
| Ascusbbf_707E | 0 | 0 | 0 | 0 | + | − | 0 | 0 | + | 0 |
| Ascusbbf_707E | 0 | 0 | 0 | + | 0 | + | 0 | 0 | + | 0 |
| Ascusbbf_707E | 0 | 0 | 0 | + | 0 | + | 0 | 0 | + | 0 |
| Ascusbbf_707F | 0 | 0 | 0 | 0 | + | − | 0 | 0 | + | 0 |
| Ascusbbf_707F | 0 | − | + | − | − | + | − | + | − | 0 |
| Ascusbbf_707F | 0 | 0 | + | + | + | + | + | 0 | + | 0 |
| Ascusbbf_707F | 0 | 0 | 0 | + | 0 | + | 0 | 0 | + | 0 |
| Ascusbbf_707G | 0 | 0 | 0 | 0 | + | − | 0 | 0 | + | 0 |
| Ascusbbf_707G | 0 | − | + | − | − | + | − | + | − | 0 |
| Ascusbbf_707G | 0 | 0 | 0 | + | 0 | + | 0 | 0 | + | 0 |
| Ascusbbf_707G | 0 | 0 | 0 | + | 0 | + | 0 | 0 | + | 0 |
| Ascusbbf_707H | 0 | 0 | 0 | 0 | + | − | 0 | 0 | + | 0 |
| Ascusbbf_707H | 0 | − | + | − | − | + | − | + | − | 0 |
| Ascusbbf_707H | 0 | 0 | 0 | + | 0 | + | 0 | 0 | + | 0 |
| Ascusbbf_707H | 0 | 0 | 0 | + | 0 | + | 0 | 0 | 0 | 0 |
| Ascusbbf_707I | 0 | 0 | + | + | + | + | + | 0 | + | 0 |
| Ascusbbf_707J | 0 | 0 | + | + | + | + | + | 0 | + | 0 |
| Ascusbbf_721A | 0 | 0 | + | + | + | + | + | 0 | + | 0 |
| Ascusbbf_721A | 0 | 0 | 0 | + | 0 | + | 0 | 0 | + | 0 |
| Ascusbbf_721B | 0 | 0 | 0 | + | 0 | + | 0 | 0 | + | 0 |
| Ascusbbf_721B | 0 | 0 | 0 | + | 0 | + | 0 | 0 | + | 0 |
| Ascusbbf_721C | 0 | 0 | 0 | + | 0 | + | 0 | 0 | + | 0 |
| Ascusbbf_721C | 0 | 0 | 0 | + | 0 | + | 0 | 0 | + | 0 |
| Ascusbbf_72889A | 0 | 0 | 0 | + | 0 | + | 0 | 0 | + | 0 |
| Ascusbbf_72889A | 0 | 0 | 0 | + | 0 | + | 0 | 0 | + | 0 |
| Ascusbbf_72889B | 0 | 0 | 0 | + | 0 | + | 0 | 0 | + | 0 |
| Ascusbbf_72889B | 0 | 0 | 0 | + | 0 | + | 0 | 0 | + | 0 |
| Ascusbbf_729A | 0 | 0 | 0 | 0 | + | − | 0 | 0 | + | 0 |
| Ascusbbf_729A | 0 | 0 | + | + | + | + | + | 0 | + | 0 |
| Ascusbbf_729A | 0 | 0 | 0 | + | 0 | + | 0 | 0 | + | 0 |
| Ascusbbf_729B | 0 | 0 | + | + | + | + | + | 0 | + | 0 |
| Ascusbbf_729B | 0 | 0 | 0 | + | 0 | + | 0 | 0 | + | 0 |
| Ascusbbf_729C | 0 | 0 | 0 | + | 0 | + | 0 | 0 | + | 0 |
| Ascusbbf_729C | 0 | 0 | 0 | + | 0 | + | 0 | 0 | + | 0 |
| Ascusbbf_729D | 0 | 0 | 0 | + | 0 | + | 0 | 0 | + | 0 |
| Ascusbbf_729D | 0 | 0 | 0 | + | 0 | + | 0 | 0 | + | 0 |
| Ascusbbf_729E | 0 | 0 | 0 | + | 0 | + | 0 | 0 | + | 0 |
| Ascusbbf_729E | 0 | 0 | 0 | + | 0 | + | 0 | 0 | + | 0 |
| Ascusbbf_729F | 0 | 0 | + | + | + | + | + | 0 | + | 0 |
| Ascusbbf_729F | 0 | 0 | 0 | + | 0 | + | 0 | 0 | + | 0 |
| Ascusbbf_7586A | 0 | 0 | 0 | 0 | 0 | + | + | + | − | 0 |
| Ascusbbf_7586B | 0 | 0 | 0 | 0 | + | + | 0 | + | + | 0 |
| Ascusbbf_7586B | 0 | − | + | 0 | 0 | + | + | + | + | 0 |
| Ascusbbf_7586B | 0 | 0 | 0 | 0 | 0 | + | 0 | 0 | 0 | 0 |
| Ascusbbf_7586C | 0 | 0 | 0 | 0 | + | + | 0 | + | + | 0 |
| Ascusbbf_7586C | 0 | − | + | 0 | 0 | + | + | 0 | + | 0 |
| Ascusbbf_7586C | 0 | 0 | 0 | 0 | 0 | + | 0 | 0 | 0 | 0 |
| Ascusbbf_7586D | 0 | − | + | − | + | + | + | + | + | 0 |
| Ascusbbf_775A | 0 | 0 | 0 | 0 | + | − | 0 | 0 | + | 0 |
| Ascusbbf_775A | 0 | − | + | − | − | + | − | + | − | 0 |
| Ascusbbf_775A | 0 | 0 | 0 | + | 0 | + | 0 | 0 | + | 0 |
| Ascusbbf_775A | 0 | 0 | 0 | + | 0 | + | 0 | 0 | + | 0 |
| Ascusbbf_775B | 0 | 0 | 0 | + | 0 | + | 0 | 0 | + | 0 |
| Ascusbbf_775B | 0 | 0 | 0 | + | 0 | + | 0 | 0 | + | 0 |
| Ascusbbf_8082A | 0 | − | + | − | + | + | + | 0 | 0 | 0 |
| Ascusbbf_8082A | 0 | 0 | 0 | 0 | − | − | 0 | + | 0 | 0 |
| Ascusbbf_8082A | 0 | 0 | 0 | 0 | + | + | 0 | + | + | 0 |
| Ascusbbf_8082A | 0 | − | + | 0 | 0 | + | + | 0 | + | 0 |
| Ascusbbf_8082A | 0 | 0 | 0 | + | 0 | + | 0 | 0 | 0 | 0 |
| Ascusbbf_8082B | 0 | 0 | 0 | 0 | − | − | 0 | + | 0 | 0 |
| Ascusbbf_8082B | 0 | 0 | 0 | 0 | 0 | + | + | + | − | 0 |
| Ascusbbf_8082B | 0 | − | + | 0 | 0 | + | + | 0 | + | 0 |
| Ascusbbf_8082B | 0 | 0 | 0 | 0 | 0 | + | 0 | 0 | 0 | 0 |
| Ascusbbf_8082C | 0 | − | + | − | + | + | + | 0 | 0 | 0 |
| Ascusbbf_8082C | 0 | 0 | 0 | 0 | − | − | 0 | + | 0 | 0 |
| Ascusbbf_8082C | 0 | 0 | 0 | 0 | + | + | 0 | + | + | 0 |
| Ascusbbf_8082C | 0 | − | + | 0 | 0 | + | + | 0 | + | 0 |
| Ascusbbf_8082C | 0 | 0 | 0 | + | 0 | + | 0 | 0 | 0 | 0 |
| Ascusbbf_8082D | 0 | − | + | − | + | + | + | 0 | 0 | 0 |
| Ascusbbf_8082D | 0 | 0 | 0 | 0 | − | − | 0 | + | 0 | 0 |
| Ascusbbf_8082D | 0 | 0 | 0 | 0 | + | + | 0 | + | + | 0 |
| Ascusbbf_8082D | 0 | − | + | 0 | 0 | + | + | + | + | 0 |

-continued

| Strain ID | pyruvic | glucose | succinic | lactic | glycerol | acetic | propionic | butyric | ethanol | 1-Butanol |
|---|---|---|---|---|---|---|---|---|---|---|
| Ascusbbf_8082D | 0 | 0 | 0 | 0 | 0 | + | 0 | 0 | 0 | 0 |
| Ascusbbf_8082D | 0 | 0 | 0 | + | 0 | + | 0 | 0 | 0 | 0 |
| Ascusbbf_8082E | 0 | − | + | − | + | + | + | 0 | 0 | 0 |
| Ascusbbf_8082E | 0 | 0 | 0 | 0 | 0 | + | + | + | − | 0 |
| Ascusbbf_8082F | 0 | − | + | − | + | + | + | 0 | 0 | 0 |
| Ascusbbf_8082F | 0 | 0 | 0 | 0 | + | + | 0 | + | + | 0 |
| Ascusbbf_8082F | 0 | − | + | 0 | 0 | + | + | 0 | + | 0 |
| Ascusbbf_8082G | 0 | − | + | − | + | + | + | 0 | 0 | 0 |
| Ascusbbf_8082G | 0 | − | + | 0 | 0 | + | + | 0 | + | 0 |
| Ascusbbf_8082H | 0 | − | + | − | + | + | + | 0 | 0 | 0 |
| Ascusbbf_8082H | 0 | − | + | 0 | 0 | + | + | 0 | + | 0 |
| Ascusbbf_8082I | 0 | − | + | − | + | + | + | 0 | 0 | 0 |
| Ascusbbf_8118A | 0 | 0 | 0 | + | 0 | + | 0 | 0 | + | 0 |
| Ascusbbf_8118B | 0 | 0 | + | + | + | + | + | 0 | + | 0 |
| Ascusbbf_8118B | 0 | 0 | 0 | + | 0 | + | 0 | 0 | + | 0 |
| Ascusbbf_8414A | 0 | 0 | 0 | + | 0 | + | 0 | 0 | + | 0 |
| Ascusbbf_8414A | 0 | 0 | 0 | + | 0 | + | 0 | 0 | + | 0 |
| Ascusbbf_8480A | 0 | 0 | + | + | + | + | + | 0 | + | 0 |
| Ascusbbf_8480A | 0 | 0 | 0 | + | 0 | + | 0 | 0 | + | 0 |
| Ascusbbf_8480B | 0 | 0 | + | + | + | + | + | 0 | + | 0 |
| Ascusbbf_850A | + | − | + | − | 0 | + | + | + | − | 0 |
| Ascusbbf_850B | 0 | − | + | − | + | + | + | 0 | 0 | 0 |
| Ascusbbf_850C | 0 | − | + | − | + | + | + | 0 | 0 | 0 |
| Ascusbbf_850C | 0 | 0 | 0 | 0 | − | − | 0 | + | 0 | 0 |
| Ascusbbf_850C | 0 | 0 | 0 | 0 | + | + | 0 | 0 | + | 0 |
| Ascusbbf_850C | 0 | 0 | 0 | 0 | + | − | 0 | 0 | + | 0 |
| Ascusbbf_850C | 0 | 0 | 0 | 0 | 0 | + | 0 | 0 | 0 | 0 |
| Ascusbbf_850D | 0 | 0 | 0 | 0 | − | − | 0 | + | 0 | 0 |
| Ascusbbf_850E | 0 | 0 | 0 | 0 | − | − | 0 | + | 0 | 0 |
| Ascusbbf_850E | 0 | 0 | 0 | 0 | + | + | 0 | + | + | 0 |
| Ascusbbf_850E | 0 | − | + | 0 | 0 | + | + | 0 | + | 0 |
| Ascusbbf_850E | 0 | 0 | 0 | 0 | + | − | 0 | 0 | + | 0 |
| Ascusbbf_850E | 0 | 0 | 0 | 0 | 0 | + | 0 | 0 | 0 | 0 |
| Ascusbbf_850F | 0 | − | + | − | + | + | + | 0 | 0 | 0 |
| Ascusbbf_850F | 0 | 0 | 0 | 0 | − | − | 0 | + | 0 | 0 |
| Ascusbbf_850F | 0 | 0 | 0 | 0 | + | + | 0 | + | + | 0 |
| Ascusbbf_850F | 0 | − | 0 | − | + | + | + | + | + | 0 |
| Ascusbbf_850F | 0 | 0 | 0 | 0 | + | − | 0 | 0 | + | 0 |
| Ascusbbf_850F | 0 | 0 | 0 | 0 | 0 | + | 0 | 0 | 0 | 0 |
| Ascusbbf_850G | 0 | − | + | − | + | + | + | 0 | 0 | 0 |
| Ascusbbf_850G | 0 | 0 | 0 | 0 | − | − | 0 | + | 0 | 0 |
| Ascusbbf_850G | 0 | 0 | 0 | 0 | + | + | 0 | + | + | 0 |
| Ascusbbf_850G | 0 | 0 | 0 | 0 | + | − | 0 | 0 | + | 0 |
| Ascusbbf_850G | 0 | 0 | 0 | 0 | 0 | + | 0 | 0 | 0 | 0 |
| Ascusbbf_850H | 0 | − | + | − | + | + | + | 0 | 0 | 0 |
| Ascusbbf_850H | 0 | 0 | 0 | 0 | 0 | + | + | + | − | 0 |
| Ascusbbf_850H | 0 | − | + | − | − | + | − | + | − | 0 |
| Ascusbbf_850I | 0 | − | + | − | + | + | + | 0 | 0 | 0 |
| Ascusbbf_850I | 0 | − | + | − | − | + | − | + | − | 0 |
| Ascusbbf_850J | 0 | − | + | − | + | + | + | 0 | 0 | 0 |
| Ascusbbf_850J | 0 | − | + | − | + | + | + | + | + | 0 |
| Ascusbbf_8600A | 0 | 0 | + | + | + | + | + | 0 | + | 0 |
| Ascusbbf_8600B | 0 | 0 | + | + | + | + | + | 0 | + | 0 |
| Ascusbbf_873A | 0 | − | + | − | + | + | + | 0 | 0 | 0 |
| Ascusbbf_873B | 0 | − | + | − | + | + | + | 0 | 0 | 0 |
| Ascusbbf_873B | 0 | 0 | 0 | 0 | + | + | 0 | + | + | 0 |
| Ascusbbf_873B | 0 | − | + | 0 | 0 | + | + | 0 | + | 0 |
| Ascusbbf_873B | 0 | 0 | 0 | 0 | + | − | 0 | 0 | + | 0 |
| Ascusbbf_873B | 0 | 0 | 0 | 0 | 0 | + | 0 | 0 | 0 | 0 |
| Ascusbbf_873B | 0 | 0 | 0 | + | 0 | + | 0 | 0 | 0 | 0 |
| Ascusbbf_873C | 0 | 0 | 0 | 0 | − | − | 0 | + | 0 | 0 |
| Ascusbbf_873C | 0 | 0 | 0 | 0 | + | + | 0 | + | + | 0 |
| Ascusbbf_873C | 0 | − | + | 0 | 0 | + | + | 0 | + | 0 |
| Ascusbbf_873C | 0 | − | + | − | − | + | − | + | − | 0 |
| Ascusbbf_873D | 0 | 0 | 0 | 0 | + | + | 0 | + | + | 0 |
| Ascusbbf_873D | 0 | − | + | − | + | + | + | + | + | 0 |
| Ascusbbf_873D | 0 | 0 | 0 | 0 | 0 | + | 0 | 0 | 0 | 0 |
| Ascusbbf_873E | 0 | − | + | − | + | + | + | 0 | 0 | 0 |
| Ascusbbf_873E | 0 | 0 | 0 | 0 | + | + | 0 | + | + | 0 |
| Ascusbbf_873E | 0 | − | + | 0 | 0 | + | + | 0 | + | 0 |
| Ascusbbf_873E | 0 | 0 | 0 | 0 | + | − | 0 | 0 | + | 0 |
| Ascusbbf_873E | 0 | 0 | 0 | 0 | 0 | + | 0 | 0 | 0 | 0 |
| Ascusbbf_873F | 0 | − | + | − | + | + | + | 0 | 0 | 0 |
| Ascusbbf_873F | 0 | 0 | 0 | 0 | + | + | 0 | + | + | 0 |
| Ascusbbf_873F | 0 | − | + | 0 | 0 | + | + | 0 | + | 0 |
| Ascusbbf_873F | 0 | 0 | 0 | + | 0 | + | 0 | 0 | 0 | 0 |
| Ascusbbf_873G | 0 | − | + | − | + | + | + | + | + | 0 |

-continued

| Strain ID | pyruvic | glucose | succinic | lactic | glycerol | acetic | propionic | butyric | ethanol | 1-Butanol |
|---|---|---|---|---|---|---|---|---|---|---|
| Ascusbbf_876A | 0 | − | + | + | 0 | 0 | − | 0 | + | 0 |
| Ascusbbf_876A | + | − | + | − | 0 | + | + | + | − | 0 |
| Ascusbbf_876A | + | + | + | + | 0 | + | 0 | 0 | + | 0 |
| Ascusbbf_876B | 0 | − | + | 0 | 0 | + | + | 0 | + | 0 |
| Ascusbbf_876C | 0 | − | + | − | + | + | + | 0 | 0 | 0 |
| Ascusbbf_876C | 0 | 0 | 0 | 0 | − | − | 0 | + | 0 | 0 |
| Ascusbbf_876C | 0 | 0 | 0 | 0 | + | + | 0 | + | + | 0 |
| Ascusbbf_876C | 0 | − | + | 0 | 0 | + | + | + | + | 0 |
| Ascusbbf_876C | 0 | 0 | 0 | 0 | 0 | + | 0 | 0 | 0 | 0 |
| Ascusbbf_876D | 0 | − | + | − | + | + | + | 0 | 0 | 0 |
| Ascusbbf_876D | 0 | 0 | 0 | 0 | − | − | 0 | + | 0 | 0 |
| Ascusbbf_876D | 0 | 0 | 0 | 0 | + | + | 0 | + | + | 0 |
| Ascusbbf_876D | 0 | − | + | 0 | 0 | + | + | + | + | 0 |
| Ascusbbf_876D | 0 | 0 | 0 | 0 | 0 | + | 0 | 0 | 0 | 0 |
| Ascusbbf_876D | 0 | 0 | 0 | + | 0 | + | 0 | 0 | 0 | 0 |
| Ascusbbf_876F | 0 | − | + | − | + | + | + | 0 | 0 | 0 |
| Ascusbbf_876F | 0 | 0 | 0 | 0 | − | − | 0 | + | 0 | 0 |
| Ascusbbf_876F | 0 | 0 | 0 | 0 | + | + | 0 | + | + | 0 |
| Ascusbbf_876F | 0 | − | + | 0 | 0 | + | + | 0 | + | 0 |
| Ascusbbf_876F | 0 | 0 | 0 | + | 0 | + | 0 | 0 | 0 | 0 |
| Ascusbbf_876G | 0 | − | + | − | + | + | + | 0 | 0 | 0 |
| Ascusbbf_876G | 0 | − | + | − | + | + | + | + | + | 0 |
| Ascusbbf_8941A | 0 | 0 | 0 | + | 0 | + | 0 | 0 | + | 0 |
| Ascusbbf_8941A | 0 | 0 | 0 | + | 0 | + | 0 | 0 | + | 0 |
| Ascusbbf_9031A | 0 | 0 | 0 | 0 | + | − | 0 | 0 | + | 0 |
| Ascusbbf_9031B | 0 | 0 | 0 | 0 | + | − | 0 | 0 | + | 0 |
| Ascusbbf_9031C | 0 | 0 | 0 | 0 | + | − | 0 | 0 | + | 0 |
| Ascusbbf_9031D | 0 | 0 | 0 | 0 | + | − | 0 | 0 | + | 0 |
| Ascusbbf_9031D | 0 | − | + | − | − | + | − | + | − | 0 |
| Ascusbbf_9031E | 0 | 0 | 0 | 0 | + | − | 0 | 0 | + | 0 |
| Ascusbbf_9031E | 0 | − | + | − | − | + | − | + | − | 0 |
| Ascusbbf_9031F | 0 | 0 | 0 | 0 | + | − | 0 | 0 | + | 0 |
| Ascusbbf_9031F | 0 | − | + | − | − | + | − | + | − | 0 |
| Ascusbbf_9031G | 0 | − | + | − | − | + | − | + | − | 0 |
| Ascusbbf_915A | 0 | 0 | 0 | + | 0 | + | 0 | 0 | + | 0 |
| Ascusbbf_915A | 0 | 0 | 0 | + | 0 | + | 0 | 0 | + | 0 |
| Ascusbbf_92A | 0 | 0 | 0 | 0 | − | − | 0 | + | 0 | 0 |
| Ascusbbf_92A | 0 | − | + | − | − | + | − | + | − | 0 |
| Ascusbbf_92B | 0 | 0 | 0 | 0 | − | − | 0 | + | 0 | 0 |
| Ascusbbf_92B | 0 | 0 | 0 | 0 | + | + | 0 | + | + | 0 |
| Ascusbbf_92B | 0 | 0 | 0 | 0 | + | − | 0 | 0 | + | 0 |
| Ascusbbf_92B | 0 | 0 | 0 | 0 | 0 | + | 0 | 0 | 0 | 0 |
| Ascusbbf_92C | 0 | 0 | 0 | 0 | − | − | 0 | + | 0 | 0 |
| Ascusbbf_92C | 0 | − | + | − | − | + | − | + | − | 0 |
| Ascusbbf_92D | 0 | 0 | 0 | 0 | − | − | 0 | + | 0 | 0 |
| Ascusbbf_92D | 0 | 0 | 0 | 0 | + | − | 0 | 0 | + | 0 |
| Ascusbbf_92D | 0 | 0 | 0 | 0 | 0 | + | 0 | 0 | 0 | 0 |
| Ascusbbf_92E | 0 | 0 | 0 | 0 | − | − | 0 | + | 0 | 0 |
| Ascusbbf_92F | 0 | 0 | 0 | 0 | − | − | 0 | + | 0 | 0 |
| Ascusbbf_92F | 0 | 0 | 0 | 0 | + | − | 0 | 0 | + | 0 |
| Ascusbbf_92F | 0 | 0 | 0 | 0 | 0 | + | 0 | 0 | 0 | 0 |
| Ascusbbf_92H | 0 | 0 | 0 | 0 | 0 | + | + | + | − | 0 |
| Ascusbbf_92H | 0 | 0 | 0 | 0 | + | − | 0 | 0 | + | 0 |
| Ascusbbf_92K | 0 | 0 | 0 | 0 | 0 | + | + | + | − | 0 |
| Ascusbbf_92K | 0 | 0 | + | + | + | + | + | 0 | + | 0 |
| Ascusbbf_92K | 0 | 0 | 0 | + | 0 | + | 0 | 0 | 0 | 0 |
| Ascusbbf_92L | 0 | − | + | − | − | + | − | + | − | 0 |
| Ascusbbf_930A | 0 | 0 | + | + | + | + | + | 0 | + | 0 |
| Ascusbbf_930A | 0 | 0 | 0 | + | 0 | + | 0 | 0 | 0 | 0 |
| Ascusbbf_930B | 0 | 0 | + | + | + | + | + | 0 | + | 0 |
| Ascusbbf_930B | 0 | 0 | 0 | + | 0 | + | 0 | 0 | + | 0 |
| Ascusbbf_944A | 0 | − | + | − | 0 | + | + | + | − | 0 |
| Ascusbbf_944B | 0 | 0 | 0 | 0 | + | + | 0 | + | + | 0 |
| Ascusbbf_944B | 0 | 0 | 0 | 0 | + | − | 0 | + | + | 0 |
| Ascusbbf_944B | 0 | 0 | + | 0 | + | + | + | 0 | + | 0 |
| Ascusbbf_944B | 0 | 0 | 0 | + | 0 | + | 0 | 0 | + | 0 |
| Ascusbbf_944C | 0 | 0 | 0 | 0 | + | − | 0 | 0 | + | 0 |
| Ascusbbf_944C | 0 | 0 | + | + | + | + | + | 0 | + | 0 |
| Ascusbbf_944D | 0 | 0 | 0 | 0 | + | − | 0 | 0 | + | 0 |
| Ascusbbf_944D | 0 | − | + | − | − | + | − | + | − | 0 |
| Ascusbbf_944E | 0 | 0 | 0 | 0 | + | − | 0 | 0 | + | 0 |
| Ascusbbf_944F | 0 | 0 | 0 | 0 | + | − | 0 | 0 | + | 0 |
| Ascusbbf_944G | 0 | 0 | 0 | 0 | + | − | 0 | 0 | + | 0 |
| Ascusbbf_944G | 0 | 0 | 0 | + | 0 | + | 0 | 0 | + | 0 |
| Ascusbbf_944G | 0 | 0 | 0 | + | 0 | + | 0 | 0 | + | 0 |
| Ascusbbf_951A | 0 | − | + | − | + | + | + | + | + | 0 |

-continued

| Strain ID | pyruvic | glucose | succinic | lactic | glycerol | acetic | propionic | butyric | ethanol | 1-Butanol |
|---|---|---|---|---|---|---|---|---|---|---|
| Ascusbbf_951A | + | − | + | − | 0 | + | + | + | − | 0 |
| Ascusbbf_951A | 0 | − | 0 | + | + | + | 0 | 0 | + | 0 |
| Ascusbbf_951B | 0 | − | + | − | + | + | + | 0 | 0 | 0 |
| Ascusbbf_951B | 0 | 0 | 0 | 0 | − | − | 0 | + | 0 | 0 |
| Ascusbbf_951B | 0 | 0 | 0 | 0 | + | + | 0 | + | + | 0 |
| Ascusbbf_951B | 0 | − | + | 0 | 0 | + | + | 0 | + | 0 |
| Ascusbbf_951B | 0 | 0 | 0 | 0 | + | − | 0 | 0 | + | 0 |
| Ascusbbf_951B | 0 | − | + | + | + | + | 0 | 0 | + | 0 |
| Ascusbbf_951B | 0 | 0 | 0 | + | 0 | + | 0 | 0 | + | 0 |
| Ascusbbf_951B | 0 | 0 | 0 | + | 0 | + | 0 | 0 | 0 | 0 |
| Ascusbbf_951B | − | − | − | + | − | + | + | + | − | 0 |
| Ascusbbf_951B | 0 | − | 0 | + | 0 | 0 | 0 | 0 | + | 0 |
| Ascusbbf_951B | 0 | − | 0 | + | 0 | 0 | 0 | 0 | + | 0 |
| Ascusbbf_951C | 0 | − | + | − | + | + | + | 0 | 0 | 0 |
| Ascusbbf_951C | 0 | 0 | 0 | 0 | − | − | 0 | + | 0 | 0 |
| Ascusbbf_951C | 0 | 0 | 0 | 0 | + | + | 0 | + | + | 0 |
| Ascusbbf_951C | 0 | − | + | 0 | 0 | + | + | 0 | + | 0 |
| Ascusbbf_951C | 0 | 0 | 0 | 0 | + | − | 0 | 0 | + | 0 |
| Ascusbbf_951C | 0 | − | + | + | + | + | 0 | 0 | + | 0 |
| Ascusbbf_951C | 0 | 0 | 0 | + | 0 | + | 0 | 0 | + | 0 |
| Ascusbbf_951C | 0 | 0 | 0 | + | 0 | + | 0 | 0 | 0 | 0 |
| Ascusbbf_951D | 0 | − | + | − | + | + | + | 0 | 0 | 0 |
| Ascusbbf_951D | 0 | 0 | 0 | 0 | − | − | 0 | + | 0 | 0 |
| Ascusbbf_951D | 0 | 0 | 0 | 0 | 0 | + | + | + | − | 0 |
| Ascusbbf_951D | 0 | − | + | 0 | 0 | + | + | + | + | 0 |
| Ascusbbf_951D | 0 | 0 | 0 | 0 | + | − | 0 | 0 | + | 0 |
| Ascusbbf_951E | 0 | − | + | − | + | + | + | 0 | 0 | 0 |
| Ascusbbf_951E | 0 | − | + | − | + | + | + | + | + | 0 |
| Ascusbbf_951E | 0 | 0 | 0 | + | 0 | + | 0 | 0 | + | 0 |
| Ascusbbf_951E | 0 | 0 | 0 | + | 0 | + | 0 | 0 | + | 0 |
| Ascusbbf_951F | 0 | − | + | − | + | + | + | 0 | 0 | 0 |
| Ascusbbf_951G | 0 | − | + | − | + | + | + | 0 | 0 | 0 |
| Ascusbbf_95A | 0 | 0 | 0 | 0 | + | − | 0 | 0 | + | 0 |
| Ascusbbf_95A | 0 | − | + | − | − | + | − | + | − | 0 |
| Ascusbbf_95B | 0 | 0 | 0 | 0 | + | − | 0 | 0 | + | 0 |
| Ascusbbf_95B | 0 | − | + | − | − | + | − | + | − | 0 |
| Ascusbbf_95B | 0 | 0 | + | + | + | + | + | 0 | + | 0 |
| Ascusbbf_95B | 0 | 0 | 0 | + | 0 | + | 0 | 0 | + | 0 |
| Ascusbbf_95C | 0 | 0 | 0 | 0 | + | − | 0 | 0 | + | 0 |
| Ascusbbf_95C | 0 | − | + | − | − | + | − | + | − | 0 |
| Ascusbbf_95D | 0 | 0 | 0 | 0 | + | − | 0 | 0 | + | 0 |
| Ascusbbf_95D | 0 | − | + | − | − | + | − | + | − | 0 |
| Ascusbbf_95D | 0 | 0 | + | + | + | + | + | 0 | + | 0 |
| Ascusbbf_95D | 0 | 0 | 0 | + | 0 | + | 0 | 0 | + | 0 |
| Ascusbbf_95E | 0 | 0 | 0 | + | 0 | + | 0 | 0 | + | 0 |
| Ascusbbf_95E | 0 | 0 | 0 | + | 0 | + | 0 | 0 | + | 0 |
| Ascusbbf_95F | 0 | 0 | 0 | + | 0 | + | 0 | 0 | + | 0 |
| Ascusbbf_95F | 0 | 0 | 0 | + | 0 | + | 0 | 0 | + | 0 |
| Ascusbbf_95G | 0 | 0 | 0 | + | 0 | + | 0 | 0 | + | 0 |
| Ascusbbf_95G | 0 | 0 | 0 | + | 0 | + | 0 | 0 | + | 0 |
| Ascusbbf_95H | 0 | 0 | 0 | + | 0 | + | 0 | 0 | + | 0 |
| Ascusbbf_95H | 0 | 0 | 0 | + | 0 | + | 0 | 0 | + | 0 |
| Ascusbbf_9770A | 0 | 0 | 0 | 0 | + | + | 0 | + | + | 0 |
| Ascusbbf_9770A | 0 | − | + | 0 | 0 | + | + | 0 | + | 0 |
| Ascusbbf_9770A | 0 | 0 | 0 | 0 | + | − | 0 | 0 | + | 0 |
| Ascusbbf_9770A | 0 | 0 | 0 | 0 | 0 | + | 0 | 0 | 0 | 0 |
| Ascusbbf_9770B | 0 | 0 | 0 | 0 | + | + | 0 | + | + | 0 |
| Ascusbbf_9770B | 0 | 0 | 0 | 0 | + | − | 0 | 0 | + | 0 |
| Ascusbbf_9770B | 0 | 0 | 0 | 0 | 0 | + | 0 | 0 | 0 | 0 |
| Ascusbbf_9770C | 0 | 0 | 0 | 0 | + | − | 0 | 0 | + | 0 |
| Ascusbbf_9770C | 0 | 0 | 0 | + | 0 | + | 0 | 0 | + | 0 |
| Ascusbbf_9770C | 0 | 0 | 0 | + | 0 | + | 0 | 0 | + | 0 |
| Ascusbbf_9770D | 0 | 0 | 0 | 0 | + | − | 0 | 0 | + | 0 |
| Ascusbbf_9770D | 0 | − | + | − | − | + | − | + | − | 0 |
| Ascusbbf_9770E | 0 | 0 | 0 | 0 | + | − | 0 | 0 | + | 0 |
| Ascusbbf_9770E | 0 | − | + | − | − | + | − | + | − | 0 |
| Ascusbbf_9770F | 0 | 0 | 0 | 0 | + | − | 0 | 0 | + | 0 |
| Ascusbbf_9770F | 0 | − | + | − | − | + | − | + | − | 0 |
| Ascusbbf_9770G | 0 | 0 | 0 | 0 | + | − | 0 | 0 | + | 0 |
| Ascusbbf_9770G | 0 | − | + | − | − | + | − | + | − | 0 |
| Ascusbbf_9770H | 0 | 0 | 0 | 0 | + | − | 0 | 0 | + | 0 |
| Ascusbbf_9770H | 0 | − | + | − | − | + | − | + | − | 0 |
| Ascusbbf_9770H | 0 | 0 | 0 | + | 0 | + | 0 | 0 | + | 0 |
| Ascusbbf_9770H | 0 | 0 | 0 | + | 0 | + | 0 | 0 | + | 0 |
| Ascusbbf_983757A | 0 | 0 | 0 | + | 0 | + | 0 | 0 | + | 0 |
| Ascusbbf_983757A | 0 | 0 | 0 | + | 0 | + | 0 | 0 | + | 0 |
| Ascusbbf_983757B | 0 | 0 | 0 | + | 0 | + | 0 | 0 | + | 0 |

-continued

| Strain ID | pyruvic | glucose | succinic | lactic | glycerol | acetic | propionic | butyric | ethanol | 1-Butanol |
|---|---|---|---|---|---|---|---|---|---|---|
| Ascusbbf_983757B | 0 | 0 | 0 | + | 0 | + | 0 | 0 | + | 0 |
| Ascusbbf_983757C | 0 | 0 | 0 | + | 0 | + | 0 | 0 | + | 0 |
| Ascusbbf_983757C | 0 | 0 | 0 | + | 0 | + | 0 | 0 | + | 0 |

Example XIII. Effects of Native Rumen Microorganism Supplementation on Feed Conversion Ratio of Heifers on High-Grain Diets Experimental Design: Sixteen heifers were cannulated and blocked into two different groups: 8 control animals, and 8 experimental animals. The experimental group received live cells of six different rumen bacterial strains: Ascusbbf_24302, Ascusbbf_4, Ascusbbf_14146, Ascusbbf_154, Ascusbbf_1085, and Ascusbbf_876. Fresh cultures of each strain were prepared, and whole cells suspended in saline were directly administered to the rumen via cannula daily at a dose of 1E9 cells/strain/dose. Control animals received an equivalent volume of saline daily via cannula.

The ruminal pH was measured daily using an eCow eBolus. Animal weight was measured weekly and feed intakes were measured daily. Rumen content was sampled weekly to determine concentrations of VFAs and carbon dioxide in the rumen, and to determine colonization of administered strains. Venous blood was sampled for oximetry. Feed conversion ratio was calculated by dividing weight gain by the amount of feed consumed.

Animals were stepped up to the final ration diet over 4 weeks, using 4 intermediate step-up diets that gradually replaced corn silage with dry-rolled corn. The first two weeks (first two step up diets) were used to create a baseline for blocking the animals. After these two weeks, the animals were assigned into either the experimental or control group. Microbe administration began on day 14 and continued until day 56 (42 days of microbe administration). On day 48, all heifers underwent an acidosis challenge for 8 days. The acidosis challenge was induced by increasing the amount of corn in the diet of the animals.

The diet is as follows:

| Item, % of DM | Control Diet | Acidosis Challenge |
|---|---|---|
| Dry-rolled corn | 66 | 74 |
| Dried distiller's grains | 20 | 20 |
| Corn silage | 10 | 2 |
| Premix | 4 | 4 |

The diet also included a small amount of premix to add micronutrients, Rumensin, and Tylosin.

Results

Figure 32:
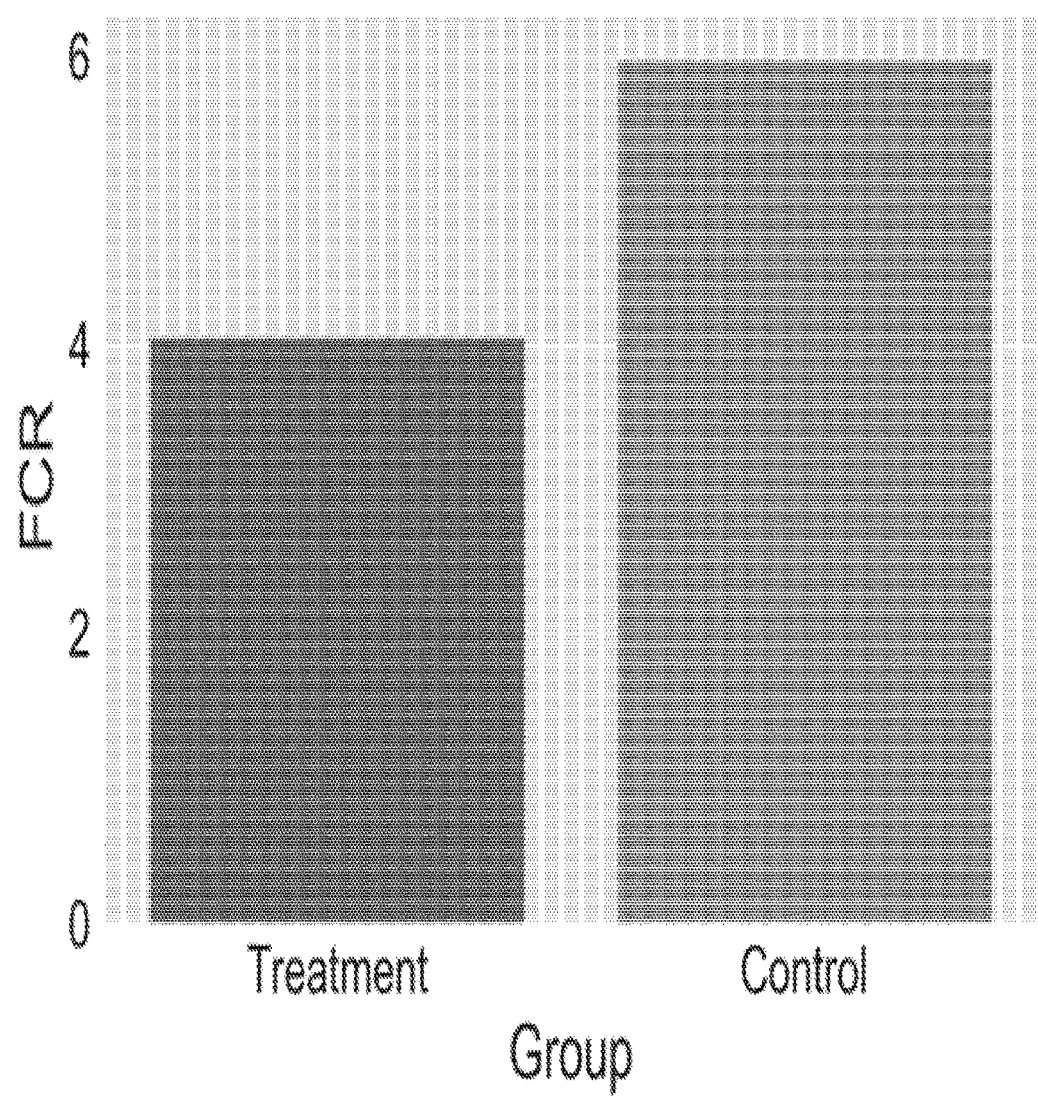
FIG. 32 depicts the feed conversion ratio (FCR) for animals that received microbes vs. animals that did not receive microbes.

Administration of microbes to heifers had a clear impact on the performance of the animal. Intakes and weights of the animals were measured throughout the step up and acidosis challenge. Feed conversion ratio (FCR) was calculated by dividing the amount of feed consumed by the animal over a specific amount of time by the weight gain of the animal over the same time period. Animals that received microbes exhibited improved feed conversion during the last phase of step up and the acidosis challenge as compared to control animals (FIG. 32). Animals in the control group required roughly 6 lbs of feed to create 1 lb of body weight, while experimental animals required roughly 4 lbs of feed to create 1 lb of body weight.

Numbered Embodiments of the Disclosure

1. A microbial composition comprising at least one microbial strain selected from Table 1 and/or Table 2.

2. A microbial composition comprising at least one microbial strain, wherein the at least one microbial strain comprises a 16S rRNA sequence selected from SEQ ID NOs: 1-100.

3. The microbial composition of claim 2, wherein the at least one microbial strain comprises Ascusbbf_6176.

4. The microbial composition of claim 2, wherein the at least one microbial strain comprises Ascusbbf_22143.

5. The microbial composition of claim 2, wherein the at least one microbial strain comprises Ascusbbf_4483.

6. The microbial composition of claim 2, wherein the at least one microbial strain comprises Ascusbbf_13543.

7. The microbial composition of claim 2, wherein the at least one microbial strain comprises Ascusbbf_152.

8. The microbial composition of claim 2, wherein the at least one microbial strain comprises Ascusbbf_707 and Ascusbbf_1238.

9. The microbial composition of claim 2, wherein the at least one microbial strain comprises Ascusbbf_4691, Ascusbbf_5588, and Ascusbbf_1238.

10. The microbial composition of any one of claims 1-9, wherein said microbial composition is encapsulated.

11. A composition comprising:
    (a) a microbial composition of any one of claims 1-10, and
    (b) an acceptable carrier.

12. The composition of claim 11, wherein the microbial composition is encapsulated.

13. The composition of claim 11, wherein the encapsulated microbial composition comprises a polymer selected from a saccharide polymer, agar polymer, agarose polymer, protein polymer, and lipid polymer.

14. The composition of claim 11, wherein the acceptable carrier is selected from the group consisting of: edible feed grade material, mineral mixture, water, glycol, molasses, and corn oil.

15. The composition of claim 11, wherein the at least two microbial strains forming the microbial composition are present in the composition at 102 to 1015 cells per gram of said composition.

16. The composition of claim 11, wherein said composition is (a) mixed with animal feed, (b) mixed with animal drinking water, or (c) administered onto animal feed.

17. A method of imparting at least one improved trait upon an animal, said method comprising administering the composition of claim 11 to said animal.

18. The method of claim 17, wherein said animal is a ruminant.

19. The method of claim 17, wherein said steer is an Angus breed of cattle, or a hybrid or cross thereof.

20. The method of claim 18, wherein the administration comprises (a) injecting the composition into rumen of the animal, (b) administering a bolus of the composition, or (c) drenching the animal with the composition.

21. The method of claim 17, wherein said composition is administered at least once per month.

22. The method of claim 21, wherein said composition is administered at least once per week.

23. The method of claim 22, wherein said composition is administered at least once per day.

24. The method of claim 17, wherein the administration occurs each time the animal is fed.

25. The method of claim 17, wherein the administration is a rectal administration.

26. The method of claim 25, wherein the rectal administration comprises inserting a suppository comprising the composition into the rectum of the animal.

27. The method of claim 17, wherein the administration is an oral administration.

28. The method of claim 27, wherein the oral administration comprises administering the composition in combination with the animal's feed, water, medicine, or vaccination.

29. The method of claim 27, wherein the oral administration comprises applying the composition in a gel or viscous solution to a body part of the animal, wherein the animal ingests the composition.

30. The method of claim 17, wherein the administration comprises spraying the composition onto the animal feed, and wherein the animal ingests the animal feed.

31. The method of claim 17, wherein said at least one improved trait is selected from the group consisting of: an increase in weight; an increase of musculature; an increase of fatty acid concentration in the gastrointestinal tract; an increase of fatty acid concentration in the rumen; a decrease in lactate concentration in the rumen; an improved efficiency in feed utilization and digestibility; an improved feed efficiency; an improved average daily gain; an improved dry matter intake; an increase in polysaccharide and lignin degradation; an increase in fat, starch, and/or protein digestion; an increase in fatty acid concentration in the rumen; pH balance in the rumen, an increase in vitamin availability; an increase in mineral availability; an increase in amino acid availability; a reduction in methane and/or nitrous oxide emissions; a reduction in manure production; an improved efficiency of nitrogen utilization; an improved efficiency of phosphorous utilization; an increased resistance to colonization of pathogenic microbes that colonize cattle; reduced mortality; increased production of antimicrobials; increased clearance of pathogenic microbes; increased resistance to colonization of pathogenic microbes that colonize cattle; increased resistance to colonization of pathogenic microbes that infect humans; and any combination thereof; reduced incidence and/or prevalence of acidosis or bloat; reduced body temperature; improved rumen wall integrity; faster adaptation to a high grain diet; improved tolerance of a high grain diet; wherein said increase or reduction is determined by comparing against an animal not having been administered said composition.

32. The method of claim 31, wherein said increase in weight is an increase by at least 0.1%.

33. The method of claim 31, wherein said reduction in manure production is a reduction by at least 0.1%.

34. The method of claim 31, wherein said increase in polysaccharide degradation is an increase in the degradation of lignin, cellulose, and/or hemicellulose.

35. The method of claim 31, wherein said increase in fatty acid concentration is an increase in acetic acid, propionic acid, and/or butyric acid.

36. The composition of claim 11, wherein the at least one microbial strain exhibit an increased utility that is not exhibited when said at least one microbial strain occurs alone, or when said at least one microbial strain is present at naturally occurring concentrations.

37. The composition of claim 11, wherein the at least one microbial strain exhibits a synergistic effect on imparting at least one improved trait in an animal.

38. A feedlot cattle feed supplement capable of increasing a desirable phenotypic trait in feedlot cattle, the feed supplement comprising:
  (a) a microbial composition of any one of claims 1-9 present at a concentration that does not occur naturally in said cattle, and
  (b) an acceptable carrier.

39. The feedlot cattle feed supplement of claim 38, wherein the microbial composition is encapsulated.

40. An isolated microbial strain selected from any one of the microbial strains in Table 1 and/or Table 2.

41. An isolated microbial strain selected from the group consisting of:
  (a) Ascusbbf_6176 deposited as ATCC Accession Deposit No. PTA-_____;
  (b) Ascusbbf_22143 deposited as ATCC Accession Deposit No. PTA-_____;
  (c) Ascusbbf_4883 deposited as ATCC Accession Deposit No. PTA-_____;
  (d) Ascusbbf_13543 deposited as ATCC Accession Deposit No. PTA-_____;
  (e) Ascusbbf_152 deposited as ATCC Accession Deposit No. PTA-_____;
  (f) Ascusbbf_707 deposited as ATCC Accession Deposit No. PTA-_____;
  (g) Ascusbbf_1238 deposited as ATCC Accession Deposit No. PTA-_____;
  (h) Ascusbbf_5588 deposited as ATCC Accession Deposit No. PTA-_____; and
  (i) Ascusbbf_4691 deposited as ATCC Accession Deposit No. PTA-_____.

42. An isolated microbial strain comprising a polynucleotide sequence sharing at least 90% sequence identity with any one of SEQ ID NOs:1-100.

43. A substantially pure culture of an isolated microbial strain according to any one of claims 40 to 42.

44. A method of modulating the microbiome of a cow, the method comprising administering the composition of claim 12.

45. The method of claim 44, wherein the administration of the composition imparts at least one improved trait upon the steer, bull, cow, or heifer.

46. The method of claim 45, wherein the at least one improved trait is selected from the group consisting of: an increase in weight; an increase of musculature; an increase of fatty acid concentration in the gastrointestinal tract; an increase of fatty acid concentration in the rumen; a decrease in lactate concentration in the rumen; an improved efficiency in feed utilization and digestibility; an improved feed efficiency; an improved average daily gain; an improved dry matter intake; an increase in polysaccharide and lignin degradation; an increase in fat, starch, and/or protein digestion; an increase in fatty acid concentration in the rumen; pH balance in the rumen, an increase in vitamin availability; an increase in mineral availability; an increase in amino acid availability; a reduction in methane and/or nitrous oxide emissions; a reduction in manure production; an improved efficiency of nitrogen utilization; an improved efficiency of phosphorous utilization; an increased resistance to colonization of pathogenic microbes that colonize cattle; reduced mortality; increased production of antimicrobials; increased clearance of pathogenic microbes; increased resistance to colonization of pathogenic microbes that colonize cattle; increased resistance to colonization of pathogenic microbes that infect humans; and any combination thereof; reduced incidence and/or prevalence of acidosis or bloat; reduced body temperature; improved rumen wall integrity; faster adaptation to a high grain diet; improved tolerance of a high grain diet; wherein said increase or reduction is determined by comparing against an animal not having been administered said composition.

47. The method of claim 46, wherein said increase in weight is an increase by at least 0.1%.

48. The method of claim 46, wherein said increase in feed efficiency is an increase by at least 0.1%.

49. The method of claim 46, wherein said increase in polysaccharide degradation is an increase in the degradation of lignin, cellulose, and/or hemicellulose.

50. The method of claim 46, wherein said increase in fat digestion, starch digestion, and/or protein digestion is an increase by at least 0.1%.

51. The method of claim 46, wherein said increase in fatty acid concentration is an increase in acetic acid, propionic acid, and/or butyric acid.

52. The method of claim 45, wherein the modulation of the microbiome is an increase in the proportion of the at least one microbial strain of the microbiome, wherein the increase is measured relative to a steer, bull, cow, or heifer that did not have the at least one microbial strain administered.

53. The method of claim 45, wherein the modulation of the microbiome is a decrease in the proportion of the microbial strains present in the microbiome prior to the administration of the composition, wherein the decrease is measured relative to the microbiome of the steer, bull, cow, or heifer prior to the administration of the composition.

54. A method of increasing resistance of cattle to the colonization of pathogenic microbes, the method comprising the administration of the composition of claim 11, wherein the pathogen is unable to colonize the gastrointestinal tract of the steer, bull, cow, or heifer.

55. The method of treating cattle for the presence of at least one pathogenic microbe, the method comprising the administration of the composition of claim 11.

56. The method of claim 55, wherein after administration of the composition the relative abundance of the at least one pathogenic microbe decreases to less than 5% relative abundance in the gastrointestinal tract.

57. The method of claim 56, wherein the relative abundance of the at least one pathogenic microbe decreases to least than 0.1% relative abundance in the gastrointestinal tract.

58. The method of claim 56, wherein the at least one pathogenic microbe is undetectable in the gastrointestinal tract.

59. The method of claim 58, wherein less than 10 days post administration of the composition the at least one pathogenic microbe is undetectable in the gastrointestinal tract.

60. The method of claim 58, wherein within 5-15 days post administration of the composition the at least one pathogenic microbe is undetectable in the gastrointestinal tract.

61. The method of any one of claims 54-61, wherein the at least one pathogenic microbe is selected from: *Clostridium perfringens, Clostridium botulinum, Salmonella typhimurium, Salmonella enterica, Salmonella typi, Salmonella pullorum, Erysipelothrix insidiosa, Campylobacter jejuni, Campylobacter coli, Campylobacter lari, Listeria monocytogenes, Streptococcus agalactiae, Streptococcus dysgalactiae, Corynebacterium bovis, Mycoplasma* sp., *Citrobacter* sp., *Enterobacter* sp., *Pseudomonas aeruginosa, Pasteurella* sp., *Bacillus cereus, Bacillus licheniformis, Streptococcus uberis, Staphylococcus aureus*, and pathogenic strains of enteropathogenic, enteroinvasive, or enterohemorrhagic *Escherichia coli*, and *Staphylococcus aureus*.

62. The method of claim 61, wherein the at least one pathogenic microbe is selected from enteropathogenic *E. coli*, enteroinvasive *E. coli*, or enterohemorrhagic *E. coli*.

64. The method of claim 17, wherein said composition is administered to the animal in a high grain diet adaptation phase.

65. The method of claim 17, wherein said composition is administered to the animal on a feed lot diet.

67. The method of claim 17, wherein said composition is administered to the animal on a grain intensive diet.

In aspects, the aforementioned microbial species—that is, a purified microbial population that comprises a bacteria with a 16S nucleic acid sequence, and/or a fungi with an ITS nucleic acid sequence, which is at least about 97% identical to a nucleic acid sequence selected from the group consisting of: SEQ ID NOs: 1-5,368—are members of a Markush group, as the present disclosure illustrates that the members belong to a class of microbes characterized by various physical and functional attributes, which can include any of the following: a) the ability to convert a carbon source into a volatile fatty acid such as acetate, butyrate, propionate, or combinations thereof; b) the ability to degrade a soluble or insoluble carbon source; c) the ability to impart a decreased methane output in feedlot cattle administered the microbe(s); d) the ability to modulate the microbiome of the gastrointestinal tract of feedlot cattle administered the microbe; e) the ability to be formulated into a shelf-stable composition; f) the ability to exhibit a decrease in feed conversion ratio and/or increase the weight gain, and/or increase the average daily gain in feedlot cattle having been administered the microbe(s); g) the ability to impart a decrease in pathogen-associated lesion formation in the gastrointestinal tract; h) the ability to impart a decrease in pathogenic microbes in the gastrointestinal tract; i) possessing a MIC score of at least about 0.4 if a bacteria. j) the ability to reduce acidosis and/or bloat in feedlot cattle administered the microbe; k) the ability to reduce carbon dioxide concentrations in the rumen of feedlot cattle administered the microbe; l) the ability to increase pH and/or improve the buffering capability of the rumen of feedlot cattle administered the microbe; and/or m) reduce lactate concentrations in the rumen of feedlot cattle administered the microbe. Thus, the members of the Markush group possess at least one property in common, which can be responsible for their function in the claimed relationship.

As used herein "shelf-stable" refers to a functional attribute and new utility acquired by the microbes formulated according to the disclosure, which enable said microbes to exist in a useful/active state outside of their natural environment in the gastrointestinal tract (i.e. a markedly different characteristic). Thus, shelf-stable is a functional attribute created by the formulations/compositions of the disclosure and denoting that the microbe formulated into a shelf-stable composition can exist outside the gastrointestinal tract and under ambient conditions for a period of time that can be determined depending upon the particular formulation utilized, but in general means that the microbes can be formulated to exist in a composition that is stable under ambient conditions for at least a few days and generally at least one week. Accordingly, a "shelf-stable feedlot cattle supplement" is a composition comprising one or more microbes of the disclosure, said microbes formulated in a composition, such that the composition is stable under ambient conditions for at least one week, meaning that the microbes comprised in the composition (e.g. whole cell, spore, or lysed cell) are able to impart one or more beneficial phenotypic properties to feedlot cattle when administered (e.g. increased weight gain, improved gastrointestinal health, and/or modulation of the gastrointestinal microbiome).

In some embodiments, the isolated microbial strains of the present disclosure further encompass mutants thereof. In some embodiments, the present disclosure further contemplates microbial strains having all of the identifying characteristics of the presently disclosed microbial strains.

TABLE 11

Budapest Treaty Deposits of the Disclosure

| Depository | Accession Number | Date of Deposit |
|---|---|---|
| NRRL | B-67550 | Feb. 7, 2018 |
| NRRL | B-67551 | Feb. 7, 2018 |
| NRRL | B-67552 | Feb. 7, 2018 |
| NRRL | B-67553 | Feb. 7, 2018 |
| NRRL | B-67554 | Feb. 7, 2018 |
| NRRL | B-67555 | Feb. 7, 2018 |
| ATCC | PTA-12942 | Feb. 14, 2018 |
| ATCC | PTA-125033 | Mar. 22, 2018 |

TABLE 11-continued

Budapest Treaty Deposits of the Disclosure

| Depository | Accession Number | Date of Deposit |
|---|---|---|
| ATCC | PTA-125040 | Mar. 29, 2018 |
| ATCC | PTA-125041 | Mar. 29, 2018 |
| ATCC | PTA-125042 | Mar. 29, 2018 |
| ATCC | PTA-125049 | Apr. 4, 2018 |
| ATCC | PTA-125050 | Apr. 4, 2018 |
| ATCC | PTA-125051 | Apr. 5, 2018 |
| ATCC | PTA-125052 | Apr. 5, 2018 |

INCORPORATION BY REFERENCE

All references, articles, publications, patents, patent publications, and patent applications cited herein are incorporated by reference in their entireties for all purposes.

However, mention of any reference, article, publication, patent, patent publication, and patent application cited herein is not, and should not be taken as, an acknowledgment or any form of suggestion that they constitute valid prior art or form part of the common general knowledge in any country in the world.

Ascus Biosciences, Inc. is the assignee/applicant of the following patents and/or patent publications that relate generally to the subject matter of microbial compositions, microbial ensembles, methods of making the compositions and ensembles, and methods of administering such: PCT Publication Nos. WO2016210251A1, WO2017120495A1, and WO2017181203A1; U.S. Pat. Nos. 9,540,676 and 9,938,558; and U.S. Pregrant Publication Nos. US20170342457A1, US20160376627A1, US20170107557A1, US20170196922A1, and US20170196921A1.

SEQUENCE LISTING

The patent contains a lengthy sequence listing. A copy of the sequence listing is available in electronic form from the USPTO web site (https://seqdata.uspto.gov/?pageRequest=docDetail&DocID=US11871767B2). An electronic copy of the sequence listing will also be available from the USPTO upon request and payment of the fee set forth in 37 CFR 1.19(b)(3).

The invention claimed is:

1. A method for improving one or more desirable traits in a ruminant, the method comprising administering to the ruminant an effective amount of a microbial composition comprising:
  (a) a purified population of bacteria comprising a 16S nucleic acid sequence that shares at least 97% sequence identity to SEQ ID NO: 75; and
  (b) a carrier suitable for ruminant administration.

2. The method of claim 1, wherein the microbial composition further comprises a purified population of one or more bacteria sharing at least 97% sequence identity to a 16S nucleic acid sequence selected from: SEQ ID NOs: 1-74 and 76-5993.

3. The method of claim 2, wherein the purified population of one or more bacteria comprises: a bacterium comprising a 16S nucleic acid sequence that shares at least 97% sequence identity to SEQ ID NO: 17; and/or a bacterium comprising a 16S nucleic acid sequence that shares at least 97% sequence identity to SEQ ID NO: 86.

4. The method of claim 2, wherein the purified population of one or more bacteria comprises: a bacterium comprising a 16S nucleic acid sequence that shares at least 98% sequence identity to SEQ ID NO: 17; and/or a bacterium comprising a 16S nucleic acid sequence that shares at least 98% sequence identity to SEQ ID NO: 86.

5. The method of claim 2, wherein the purified population of one or more bacteria comprises: a bacterium comprising a 16S nucleic acid sequence of SEQ ID NO: 5457; a bacterium comprising a 16S nucleic acid sequence of SEQ ID NO: 5644; and/or a bacterium comprising a 16S nucleic acid sequence of SEQ ID NO: 5709.

6. The method of claim 2, wherein the purified population of one or more bacteria comprises: a bacterium comprising a 16S nucleic acid sequence of SEQ ID NO: 5457; a bacterium comprising a 16S nucleic acid sequence of SEQ ID NO: 5644; and a bacterium comprising a 16S nucleic acid sequence of SEQ ID NO: 5709.

7. The method of claim 2, wherein the purified population of one or more bacteria comprises: a bacterium comprising a 16S nucleic acid sequence of SEQ ID NO: 5457; and a bacterium comprising a 16S nucleic acid sequence of SEQ ID NO: 5644.

8. The method of claim 2, wherein the purified population of one or more bacteria comprises: a bacterium comprising a 16S nucleic acid sequence of SEQ ID NO: 5457; and a bacterium comprising a 16S nucleic acid sequence of SEQ ID NO: 5709.

9. The method of claim 2, wherein the purified population of one or more bacteria comprises: a bacterium comprising a 16S nucleic acid sequence of SEQ ID NO: 5644; and a bacterium comprising a 16S nucleic acid sequence of SEQ ID NO: 5709.

10. The method of claim 2, wherein the purified population of one or more bacteria comprises: a bacterium comprising a 16S nucleic acid sequence of SEQ ID NO: 5457.

11. The method of claim 2, wherein the purified population of one or more bacteria comprises: a bacterium comprising a 16S nucleic acid sequence of SEQ ID NO: 5644.

12. The method of claim 2, wherein the purified population of one or more bacteria comprises: a bacterium comprising a 16S nucleic acid sequence of SEQ ID NO: 5709.

13. The method of claim 2, wherein the purified population of one or more bacteria comprises: a bacterium deposited as B-67553; a bacterium deposited as B-67550; and/or a bacterium deposited as B-67552.

14. The method of claim 2, wherein the one or more bacteria are in the form of spores.

15. The method of claim 1, wherein the microbial composition further comprises a purified population of one or more bacteria sharing at least 97% sequence identity to a 16S nucleic acid sequence selected from: SEQ ID NOs:1-74, 76-136, 5369-5378, 5398, 5425, 5450, 5460, 5462, 5473, 5474, 5483, 5502, 5511, 5517, 5519, 5526, 5576, 5582, 5589, 5598, 5614, 5619, 5621, 5627, 5629, 5631, 5663, 5670, 5726, 5746, 5757, 5764, 5777, 5797, 5802, 5868, 5872, 5930, 5947, 5949, 5955, 5956, 5971, 5973, 5977, 5989, and 5991.

16. The method of claim 1, wherein the microbial composition is a tablet, a capsule, a pill, a feed additive, a powder, a food ingredient, a food preparation, a food supplement, a water additive, a thermostable-additive, a moisture-resistant additive, a pre-pelleted feed additive, a pelleted feed additive, a post-pelleting-applied feed additive, a consumable solution, a consumable spray additive, a consumable solid, a consumable gel, an injection, a suppository, a drench, a bolus, or combinations thereof.

17. The method of claim 1, wherein the bacteria are encapsulated.

18. The method of claim 17, wherein the bacteria are encapsulated in one or more of a polymer, carbohydrate, sugar, sugar alcohol, surfactant, plastic, glass, polysaccharide, lipid, wax, oil, fatty acid, amino acid, or glyceride.

19. The method of claim 1, wherein the bacteria comprise at least $10^2$ cells.

20. The method of claim 1, wherein the microbial composition is stable under ambient conditions for at least one week.

21. The method of claim 1, wherein the microbial composition is orally administered to the ruminant.

22. The method of claim 21, wherein the microbial composition is fed to the ruminant.

23. The method of claim 22, wherein the ruminant is fed a step-up diet or a finishing diet comprising the microbial composition.

24. The method of claim 1, wherein the ruminant administered the effective amount of the microbial composition exhibits a shift in the microbiome of the rumen.

25. The method of claim 1, wherein the one or more desirable traits are selected from the group consisting of: a decrease in the incidence and/or prevalence of acidosis or bloat, a decrease in the amount of carbon dioxide and/or carbonic acid in the rumen, an increase in the amount of meat marbling, an increase in feed efficiency, an increase in feed utilization, an increase in feed digestibility, a decrease in manure production, an increase in performance, an increase in weight, an increase in musculature, a decrease in nitrous oxide production and emission, a decrease in methane production and emission, improved gastrointestinal health, and a decrease in mortality.

26. The method of claim 25, wherein the one or more desirable traits is an increase in performance.

27. The method of claim 25, wherein the one or more desirable traits is an increase in feed efficiency.

28. The method of claim 25, wherein the one or more desirable traits is a decrease in the incidence and/or prevalence of acidosis or bloat in the ruminant.

* * * * *